(12) United States Patent
Reed et al.

(10) Patent No.: US 6,592,877 B1
(45) Date of Patent: Jul. 15, 2003

(54) COMPOUNDS AND METHODS FOR IMMUNOTHERAPY AND DIAGNOSIS OF TUBERCULOSIS

(75) Inventors: Steven G. Reed, Bellevue; Yasir A. W. Skeiky, Seattle; Davin C. Dillon, Redmond; Antonio Campos-Neto, Bainbridge Island; Raymond Houghton, Bothell; Thomas S. Vedvick, Federal Way; Daniel R. Twardzik, Bainbridge Island; Michael J. Lodes; Ronald C. Hendrickson, both of Seattle, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/072,967

(22) Filed: May 5, 1998

Related U.S. Application Data

(63) Continuation-in-part of application No. 09/025,197, filed on Feb. 18, 1998, now abandoned, which is a continuation-in-part of application No. 08/942,578, filed on Oct. 1, 1997, now abandoned, which is a continuation-in-part of application No. 08/818,112, filed on Mar. 13, 1997, now Pat. No. 6,290,969, which is a continuation-in-part of application No. 08/730,510, filed as application No. PCT/US96/14674 on Aug. 30, 1996, now abandoned, and a continuation-in-part of application No. 08/680,574, filed on Jul. 12, 1996, now abandoned, which is a continuation-in-part of application No. 08/659,683, filed on Jun. 5, 1996, now abandoned, which is a continuation-in-part of application No. 08/620,874, filed on Mar. 22, 1996, now abandoned, which is a continuation-in-part of application No. 08/533,634, filed on Sep. 22, 1995, now abandoned, which is a continuation-in-part of application No. 08/523,436, filed on Sep. 1, 1995, now abandoned.

(51) Int. Cl.[7] .................. A61K 39/04; A61K 39/00; A61K 39/385; C12N 1/12; C07H 21/04
(52) U.S. Cl. ................... 424/248.1; 424/185.1; 424/192.1; 424/194.1; 435/253.1; 530/350; 536/23.4; 536/23.7
(58) Field of Search ................ 424/185.1, 192.1, 424/194.1, 248.1; 435/253.1; 530/350; 536/23.4, 23.7

(56) References Cited

U.S. PATENT DOCUMENTS

| 3,943,119 A | | 3/1976 | Tsumita et al. ....... 260/112.5 R |
| 4,952,395 A | * | 8/1990 | Shinnick et al. ............... 424/92 |
| 5,108,745 A | | 4/1992 | Horwitz ....................... 424/92 |

FOREIGN PATENT DOCUMENTS

| EP | 419 355 A1 | 3/1991 |
| WO | WO 88/05823 | 8/1988 |
| WO | WO 91/04272 | 4/1991 |
| WO | WO 91/14448 | 10/1991 |
| WO | WO 92/04049 | 3/1992 |
| WO | WO 92/14823 | 9/1992 |
| WO | WO 92/21758 | 12/1992 |
| WO | WO 94/00493 | 1/1994 |
| WO | WO 95/01440 | 1/1995 |
| WO | WO 95/01441 | 1/1995 |
| WO | WO 95/14713 | 6/1995 |
| WO | WO 95/31216 | 11/1995 |
| WO | WO 96/15241 | 5/1996 |
| WO | WO 96/23885 | 8/1996 |
| WO | WO 97/09429 | 3/1997 |
| WO | WO 97/09728 | 3/1997 |

OTHER PUBLICATIONS

Andersen and Hansen, "Structure and Mapping of Antigenic Domains of Protein Antigen b, a 38,000–Molecular–Weight Protein of *Mycobacterium tuberculosis*," *Infection and Immunity* 37(8):2481–2488, 1989.

Andersen et al., "Identifcation of Immunodominant Antigens during Infection with *Mycobacterium tuberculosis*," *Scand. J. Immunol*. 36:832–831, 1992.

Andersen, P., "Effective Vaccination of Mice against *Mycobacterium tuberculosis* Infection with a Soluble Mixture of Secreted Mycobacterial Proteins," *Infection and Immunity* 62(6):2536–2544, 1994.

Ausebel et al., "Isolation of Proteins for Microsequence Analysis," in Current Protocols in Molecular Biology, Wiley & Sons, New York, 1993, pp. 10.19.1–10.19.12.

Barnes et al., "Immunoreactivity of a 10–kDa Antigen of *Mycobacterium tuberculosis*," *The Journal of Immunology* 148(6):1835–1840, 1992.

Boesen et al., "Human T–Cell Responses to Secreted Antigen Fractions of *Mycobacterium tuberculosis*," *Infection and Immunity* 63(4):1491–1497, 1995.

Borremans et al., "Cloning, Sequencing Determination, and Expression of a 32–Kilodalton–Protein Gene of *Mycobacterium tuberculosis*," *Infection and Immunity* 57(10):3123–3130, 1989.

Content et al., "The Genes Coding for the Antigen 85 Complexes of *Mycobacterium tuberculosis* and *Mycobacterium bovis* BCG Are Members of a Gene Family: Cloning, Sequence Determination, and Genomic Orginization of the Gene Coding for Antigen 85–C of *M. tuberculosis*," *Infection and Immunity* 59:3205–3212, 1991.

Horowitz et al., "Protective immunity against tuberculosis induced by vaccination with major extracellular proteins of *Mycobacterium tuberculosis*," *Proc. Natl. Acad. Sci. USA* 92:1530–1534, 1995.

(List continued on next page.)

*Primary Examiner*—Rodney P Swartz
(74) *Attorney, Agent, or Firm*—Townsend and Townsend and Crew LLP

(57) ABSTRACT

Compounds and methods for inducing protective immunity against tuberculosis are disclosed. The compounds provided include polypeptides that contain at least one immunogenic portion of one or more *M. tuberculosis* proteins and DNA molecules encoding such polypeptides. Such compounds may be formulated into vaccines and/or pharmaceutical compositions for immunization against *M. tuberculosis* infection, or may be used for the diagnosis of tuberculosis.

11 Claims, 19 Drawing Sheets

OTHER PUBLICATIONS

Lowrie et al., "Towards a DNA vaccine against tuberculosis," *Vaccine* 12(16):1537–1540, 1994.

Matsumoto et al., "Cloning and Sequencing of a Unique Antigen MPT70 from *Mycobacterium tuberculosis* H37Rv and Expression in BCG Using *E. coli*–Mycobacteria Shuttle Vector," *Scand. J. Immunol.* 41:281–287, 1995.

Nagai et al., "Isolation and Partial Characterization of Major Protein Antigens in the Culture Fluid of *Mycobacterium tuberculosis*," *Infection and Immunity* 59(1):372–382, 1991.

Oettinger and Andersen, "Cloning and B–Cell–Epitope Mapping of MPT64 from *Mycobacterium tuberculosis* H37Rv," *Infection and Immunity* 62(5):2058–2064, 1994.

Pal and Horwitz, "Immunization with Extracellular Proteins of *Mycobacterium tuberculosis* Induces Cell–Mediated Immune Responses and Substantial Protective Immunity in a Guinea Pig Model of Pulmonary Tuberculosis," *Infection and Immunity* 60(1):4781–4792, 1992.

Romain et al., "Isolation of a proline–rich mycobacterial protein elicting delayed–type hypersensitivity reactions only in guinea pigs immunized with living mycobacteria," *Proc. Natl. Acad. Sci. USA* 90:5322–5326, 1993.

Romain et al., "Preparation of Tuberculin Antigen L," *Ann. Inst. Pasteur/Microbiol.* 136B:235–248, 1985.

Wallis et al., "Identification of Antigens of *Mycobacterium tuberculosis* Using Human Monoclonal Antibodies," *J. Clin. Invest.* 84:214–219, 1989.

Wiker and Haboe, "The Antigen 85 Complex: a Major Secretion Product of *Mycobacterium tuberculosis*," *Microbiological Reviews* 56(4):648–661, 1992.

Yamaguchi et al., "Cloning and Characterization of the Gene for Immunogenic Protein MPB64 of *Mycobacterium bovis* BCG," *Infection and Immunity* 57(1):283–288, 1989.

Young et al., "Screening of a Recombinant Mycobacterial DNA Library with Polyclonal Antiserum and Molecular Weight Analysis of Expressed Antigens," *Infection and Immunity* 55(6):1421–1425, 1987.

* cited by examiner

COMPOUNDS AND METHODS FOR IMMUNOTHERAPY AND DIAGNOSIS OF TUBERCULOSIS

CROSS-REFERENCE TO RELATED APPLICATIONS

This application is a continuation-in-part of U.S. application Ser. No. 09/025,197, filed Feb. 18, 1998, now abandoned; which is a continuation-in-part of U.S. application Ser. No. 08/942,578, filed Oct. 1, 1997, now abandoned; which is a continuation-in-part of U.S. application Ser. No. 08/818,112, filed Mar. 13, 1997, now U.S. Pat. No. 6,290,969, which is a continuation-in-part of U.S. application Ser. No. 08/730,510, filed Oct. 11, 1996, now abandoned; which national stage from PCT Application Ser. No. PCT/US 96/14674, filed Aug. 30, 1996; and is a continuation-in-part of U.S. application Ser. No. 08/680,574, filed Jul. 12, 1996, now abandoned; which is a continuation-in-part of U.S. application Ser. No. 08/659,683, filed Jun. 5, 1996, now abandoned; which is a continuation-in-part of U.S. application Ser. No. 08/620,874, filed Mar. 22, 1996, now abandoned; which is a continuation-in-part of U.S. application Ser. No. 08/533,634, filed Sep. 22, 1995, now abandoned; which is a continuation-in-part of U.S. application Ser. No. 08/523,436, filed Sep. 1, 1995, now abandoned.

TECHNICAL FIELD

The present invention relates generally to detecting, treating and preventing *Mycobacterium tuberculosis* infection. The invention is more particularly related to polypeptides comprising a *Mycobacterium tuberculosis* antigen, or a portion or other variant thereof, and the use of such polypeptides for diagnosing and vaccinating against *Mycobacterium tuberculosis* infection.

BACKGROUND OF THE INVENTION

Tuberculosis is a chronic, infectious disease, that is generally caused by infection with *Mycobacterium tuberculosis*. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If left untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

Inhibiting the spread of tuberculosis requires effective vaccination and accurate, early diagnosis of the disease. Currently, vaccination with live bacteria is the most efficient method for inducing protective immunity. The most common Mycobacterium employed for this purpose is Bacillus Calmette-Guerin (BCG), an avirulent strain of *Mycobacterium bovis*. However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable induration at the injection site by 48–72 hours after injection, which indicates exposure to Mycobacterial antigens. Sensitivity and specificity have, however, been a problem with this test, and individuals vaccinated with BCG cannot be distinguished from infected individuals.

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. Mycobacterium-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, IL-12 has been shown to play a role in stimulating resistance to *M. tuberculosis* infection. For a review of the immunology of *M. tuberculosis* infection see Chan and Kaufmann in *Tuberculosis: Pathogenesis, Protection and Control*, Bloom (ed.), ASM Press, Washington, D.C., 1994.

Accordingly, there is a need in the art for improved vaccines and methods for preventing, treating and detecting tuberculosis. The present invention fulfills these needs and further provides other related advantages.

SUMMARY OF THE INVENTION

Briefly stated, this invention provides compounds and methods for preventing and diagnosing tuberculosis. In one aspect, polypeptides are provided comprising an immunogenic portion of a soluble *M. tuberculosis* antigen, or a variant of such an antigen that differs only in conservative substitutions and/or modifications. In one embodiment of this aspect, the soluble antigen has one of the following N-terminal sequences:

(a) Asp-Pro-Val-Asp-Ala-Val-Ile-Asn-Thr-Thr-Cys-Asn-Tyr-Gly-Gln-Val-Val-Ala-Ala-Leu; (SEQ ID No. 120)

(b) Ala-Val-Glu-Ser-Gly-Met-Leu-Ala-Leu-Gly-Thr-Pro-Ala-Pro-Ser; (SEQ ID No. 121)

(c) Ala-Ala-Met-Lys-Pro-Arg-Thr-Gly-Asp-Gly-Pro-Leu-Glu-Ala-Ala-Lys-Glu-Gly-Arg; (SEQ ID No. 122)

(d) Tyr-Tyr-Trp-Cys-Pro-Gly-Gln-Pro-Phe-Asp-Pro-Ala-Trp-Gly-Pro; (SEQ ID No. 123)

(e) Asp-Ile-Gly-Ser-Glu-Ser-Thr-Glu-Asp-Gln-Gln-Xaa-Ala-Val; (SEQ ID No. 124)

(f) Ala-Glu-Glu-Ser-Ile-Ser-Thr-Xaa-Glu-Xaa-Ile-Val-Pro; (SEQ ID No. 125)

(g) Asp-Pro-Glu-Pro-Ala-Pro-Pro-Val-Pro-Thr-Thr-Ala-Ala-Ser-Pro-Pro-Ser; (SEQ ID No. 126)

(h) Ala-Pro-Lys-Thr-Tyr-Xaa-Glu-Glu-Leu-Lys-Gly-Thr-Asp-Thr-Gly; (SEQ ID No. 127)

(i) Asp-Pro-Ala-Ser-Ala-Pro-Asp-Val-Pro-Thr-Ala-Ala-Gln-Leu-Thr-Ser-Leu-Leu-Asn-Ser-Leu-Ala-Asp-Pro-Asn-Val-Ser-Phe-Ala-Asn; (SEQ ID No. 128)

(j) Xaa-Asp-Ser-Glu-Lys-Ser-Ala-Thr-Ile-Lys-Val-Thr-Asp-Ala-Ser; (SEQ ID No. 134)

(k) Ala-Gly-Asp-Thr-Xaa-Ile-Tyr-Ile-Val-Gly-Asn-Leu-Thr-Ala-Asp; (SEQ ID No. 135) or (l) Ala-Pro-Glu-Ser-Gly-Ala-Gly-Leu-Gly-Gly-Thr-Val-Gln-Ala-Gly; (SEQ ID No. 136)

wherein Xaa may be any amino acid.

In a related aspect, polypeptides are provided comprising an immunogenic portion of an *M. tuberculosis* antigen, or a variant of such an antigen that differs only in conservative substitutions and/or modifications, the antigen having one of the following N-terminal sequences:

(m) Xaa-Tyr-Ile-Ala-Tyr-Xaa-Thr-Thr-Ala-Gly-Ile-Val-Pro-Gly-Lys-Ile-Asn-Val-His-Leu-Val; (SEQ ID No. 137) or (n) Asp-Pro-Pro-Asp-Pro-His-Gln-Xaa-Asp-Met-Thr-Lys-Gly-Tyr-Tyr-Pro-Gly-Gly-Arg-Arg-Xaa-Phe; (SEQ ID No. 129)

wherein Xaa may be any amino acid.

In another embodiment, the soluble *M. tuberculosis* antigen comprises an amino acid sequence encoded by a DNA sequence selected from the group consisting of the sequences recited in SEQ ID Nos.: 1, 2, 4–10, 13–25, 52, 99 and 101, the complements of said sequences, and DNA sequences that hybridize to a sequence recited in SEQ ID Nos.: 1, 2, 4–10, 13–25, 52, 99 and 101 or a complement thereof under moderately stringent conditions.

In a related aspect, the polypeptides comprise an immunogenic portion of a *M. tuberculosis* antigen, or a variant of such an antigen that differs only in conservative substitutions and/or modifications, wherein the antigen comprises an amino acid sequence encoded by a DNA sequence selected from the group consisting of the sequences recited in SEQ ID Nos.: 26–51, 138, 139, 163–183, 201, 240, 242–247, 253–256, 295–298, 309, 316, 318–320, 322, 324, 328, 339, 333, 335, 337, 339 and 341, the complements of said sequences, and DNA sequences that hybridize to a sequence recited in SEQ ID Nos.: 26–51, 138, 139, 163–183, 201, 240, 242–247, 253–256, 295–298, 309, 316, 318–320, 322, 324, 328, 329, 333, 335, 337, 339 and 341 or a complement thereof under moderately stringent conditions.

In related aspects, DNA sequences encoding the above polypeptides, expression vectors comprising these DNA sequences and host cells transformed or transfected with such expression vectors are also provided.

In another aspect, the present invention provides fusion proteins comprising a first and a second inventive polypeptide or, alternatively, an inventive polypeptide and a known *M. tuberculosis* antigen.

Within other aspects, the present invention provides pharmaceutical compositions that comprise one or more of the above polypeptides, or a DNA molecule encoding such polypeptides, and a physiologically acceptable carrier. The invention also provides vaccines comprising one or more of the polypeptides as described above and a non-specific immune response enhancer, together with vaccines comprising one or more DNA sequences encoding such polypeptides and a non-specific immune response enhancer.

In yet another aspect, methods are provided for inducing protective immunity in a patient, comprising administering to a patient an effective amount of one or more of the above polypeptides.

In further aspects of this invention, methods and diagnostic kits are provided for detecting tuberculosis in a patient. The methods comprise contacting dermal cells of a patient with one or more of the above polypeptides and detecting an immune response on the patient's skin. The diagnostic kits comprise one or more of the above polypeptides in combination with an apparatus sufficient to contact the polypeptide with the dermal cells of a patient.

In yet other aspects, methods are provided for detecting tuberculosis in a patient, such methods comprising contacting dermal cells of a patient with one or more polypeptides encoded by a DNA sequence selected from the group consisting of SEQ ID Nos.: 3, 11, 12, 140, 141, 156–160, 189–193, 199,200, 203, 215–225, 237, 239, 261–276, 292, 293, 303–308, 310–315, 317, 321, 323, 325–327, 330–332, 334, 336, 338, 340 and 342–347, the complements of said sequences, and DNA sequences that hybridize to a sequence recited in SEQ ID Nos.: 3, 11, 12, 140, 141, 156–160, 189–193, 199, 200, 203, 215–225, 237, 239, 261–276, 292, 293, 303–308, 310–315, 317, 321, 323, 325–327, 330–332, 334, 336, 338, 340 and 342–347; and detecting an immune response on the patient's skin. Diagnostic kits for use in such methods are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

FIGS. 1A, B, C, and D illustrate the stimulation of proliferation and interferon-γ production in T cells derived from a first and a second *M. tuberculosis*-immune donor, respectively, by the 14 Kd, 20 Kd and 26 Kd antigens described in Example 1.

FIG. 2 illustrates the stimulation of proliferation and interferon-γ production in T cells derived from an *M. tuberculosis*-immune individual by the two representative polypeptides TbRa3 and TbRa9.

FIGS. 3A–D illustrate the reactivity of antisera raised against secretory *M. tuberculosis* proteins, the known *M. tuberculosis* antigen 85b and the inventive antigens Tb38-1 and TbH-9, respectively, with *M. tuberculosis* lysate (lane 2), *M. tuberculosis* secretory proteins (lane 3), recombinant Tb38-1 (lane 4), recombinant TbH-9 (lane 5) and recombinant 85b (lane 5).

Figure 5A:
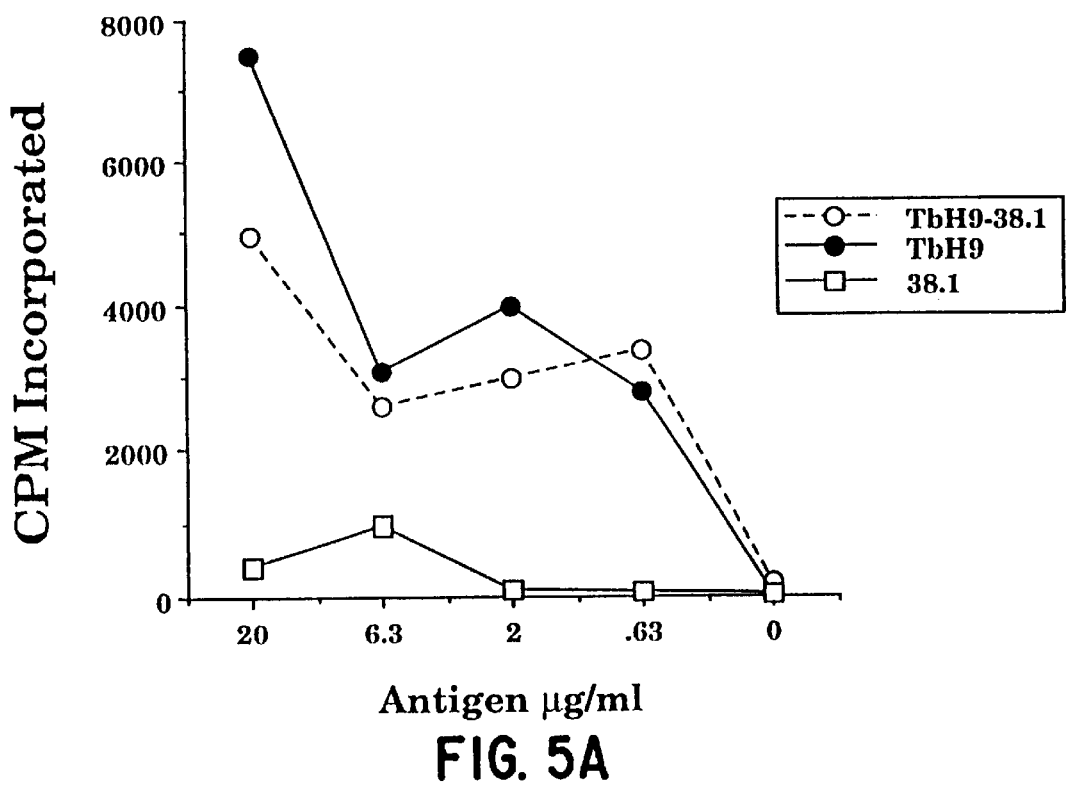

FIGS. 5A and B illustrate the stimulation of proliferation and interferon-γ production in TbH9-specific T cells by the fusion protein TbH9-Tb38-1.

Figure 6A:
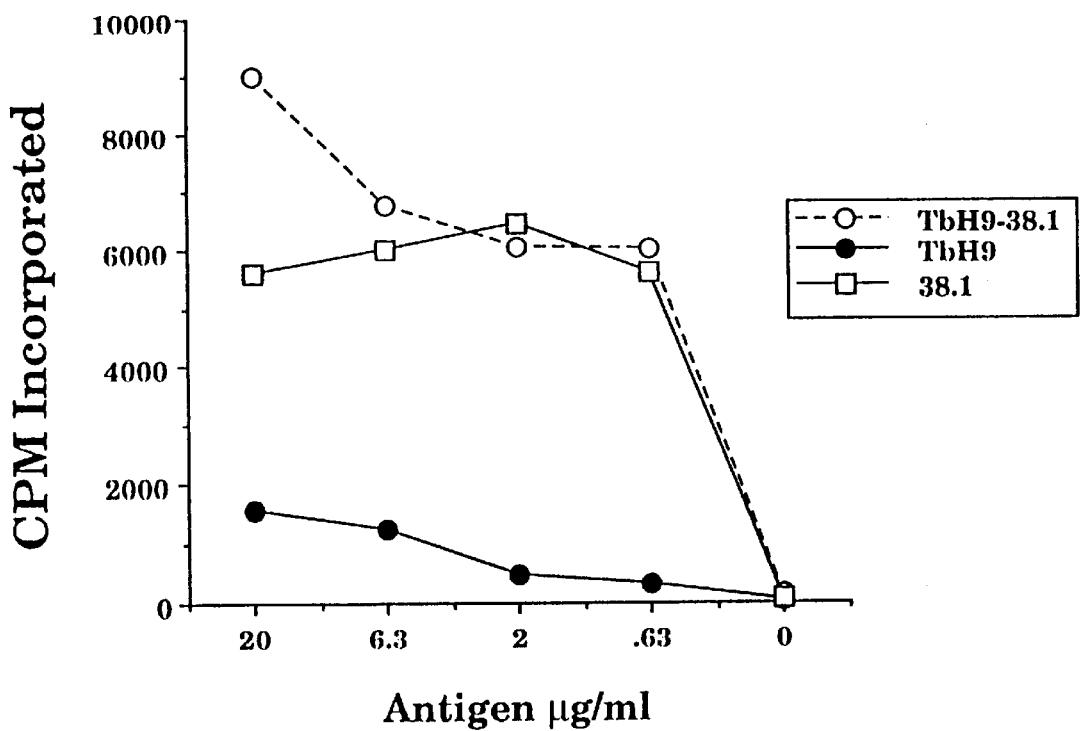

FIGS. 6A and B illustrate the stimulation of proliferation and interferon-γ production in Tb38-1-specific T cells by the fusion protein TbH9-Tb38-1.

Figure 7A:
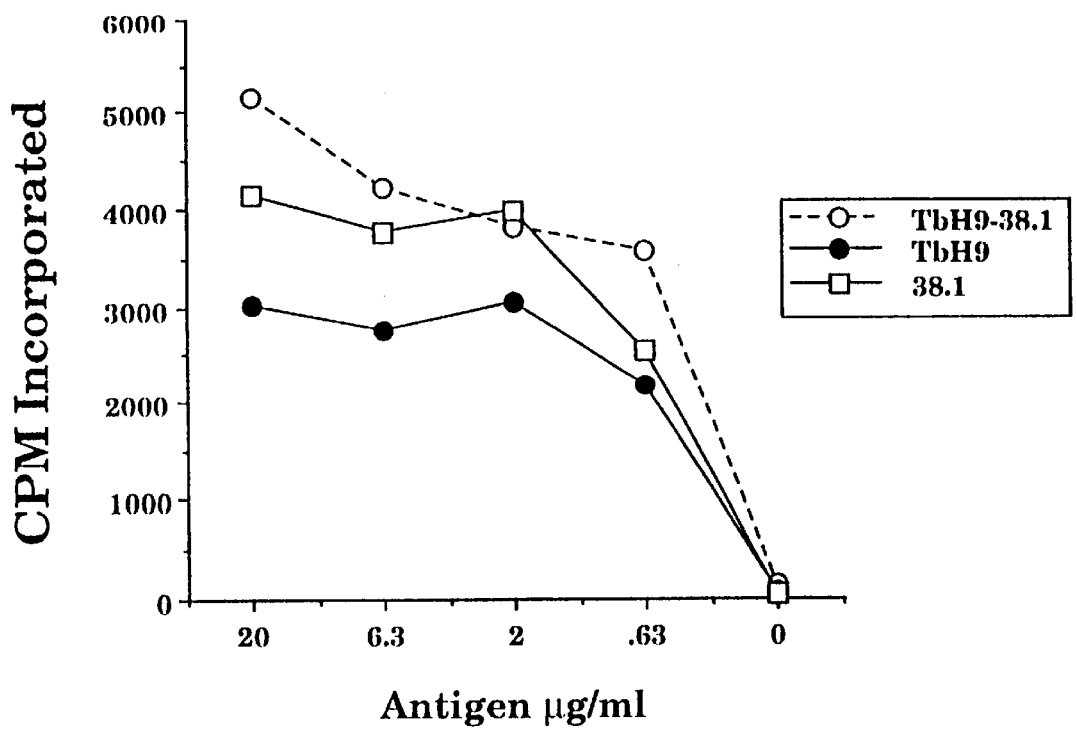

FIGS. 7A and B illustrate the stimulation of proliferation and interferon-γ production in T cells previously shown to respond to both TbH-9 and Tb38-1 by the fusion protein TbH9-Tb38-1.

Figure 8A:
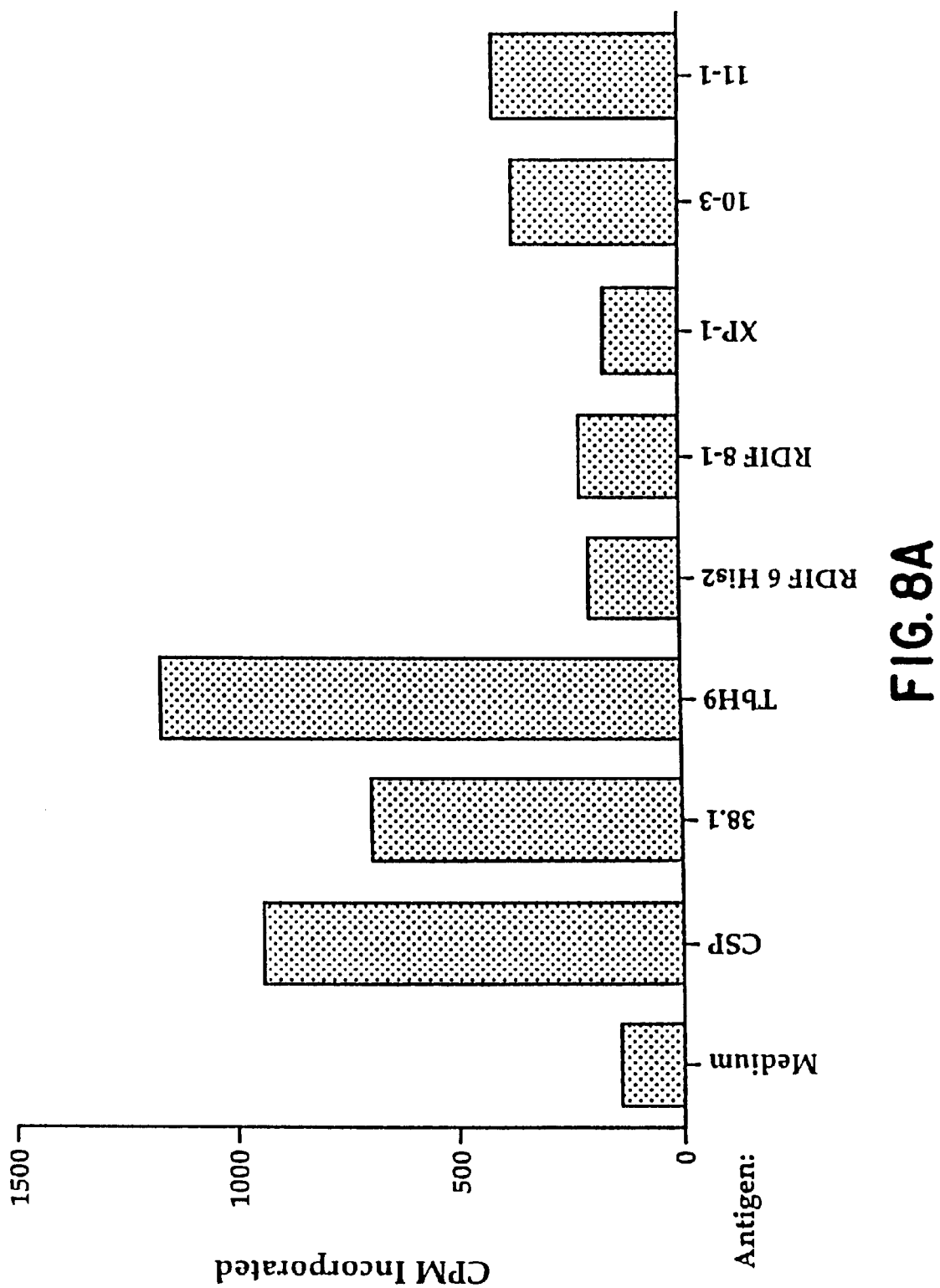
Figure 8B:
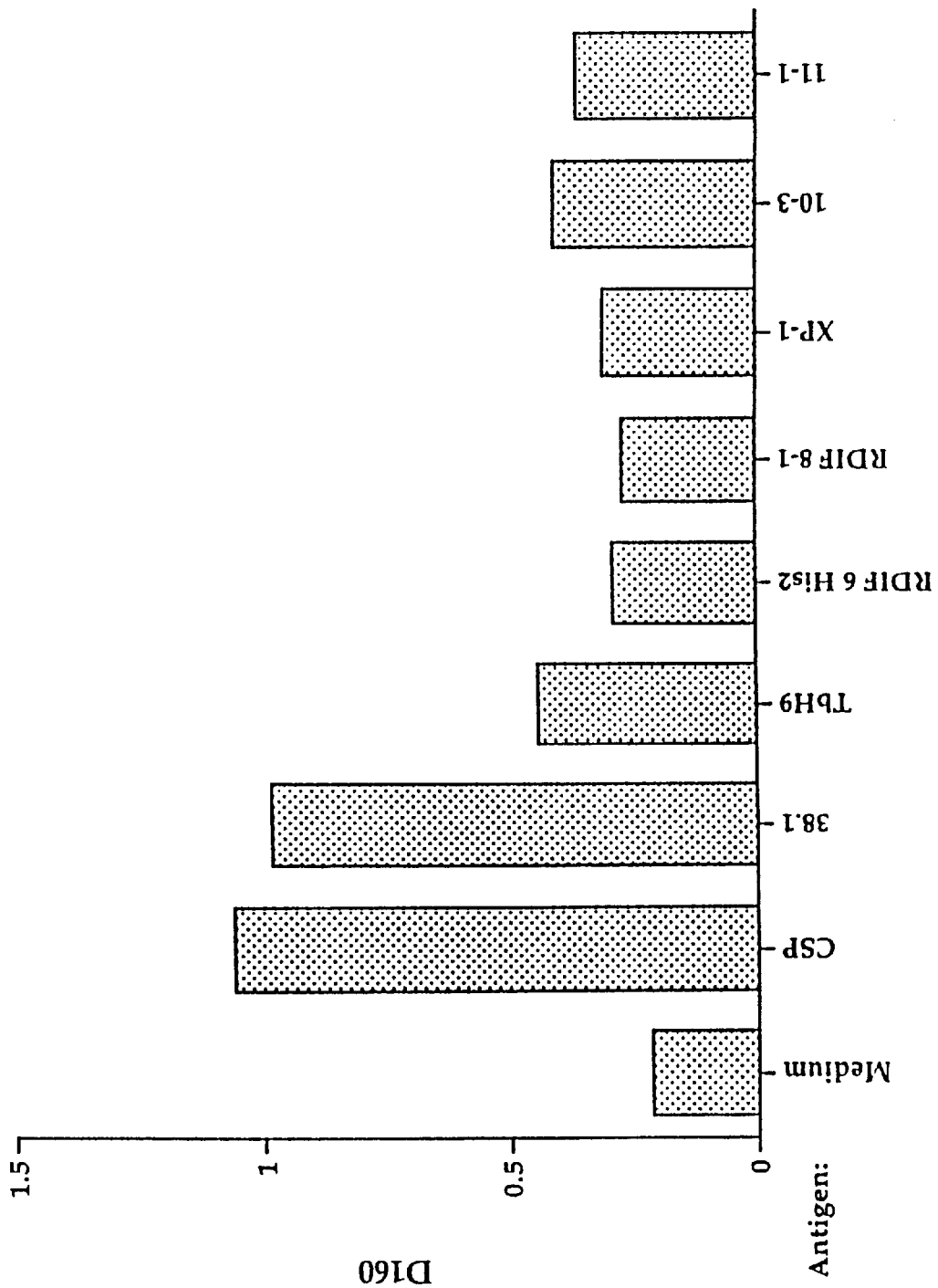

FIGS. 8A and B illustrate the stimulation of proliferation and interferon-γ production in T cells derived from a first *M. tuberculosis*-immune individual by the representative polypeptides XP-1, RDIF6, RDIF8, RDIF10 and RDIF11.

Figure 9A:
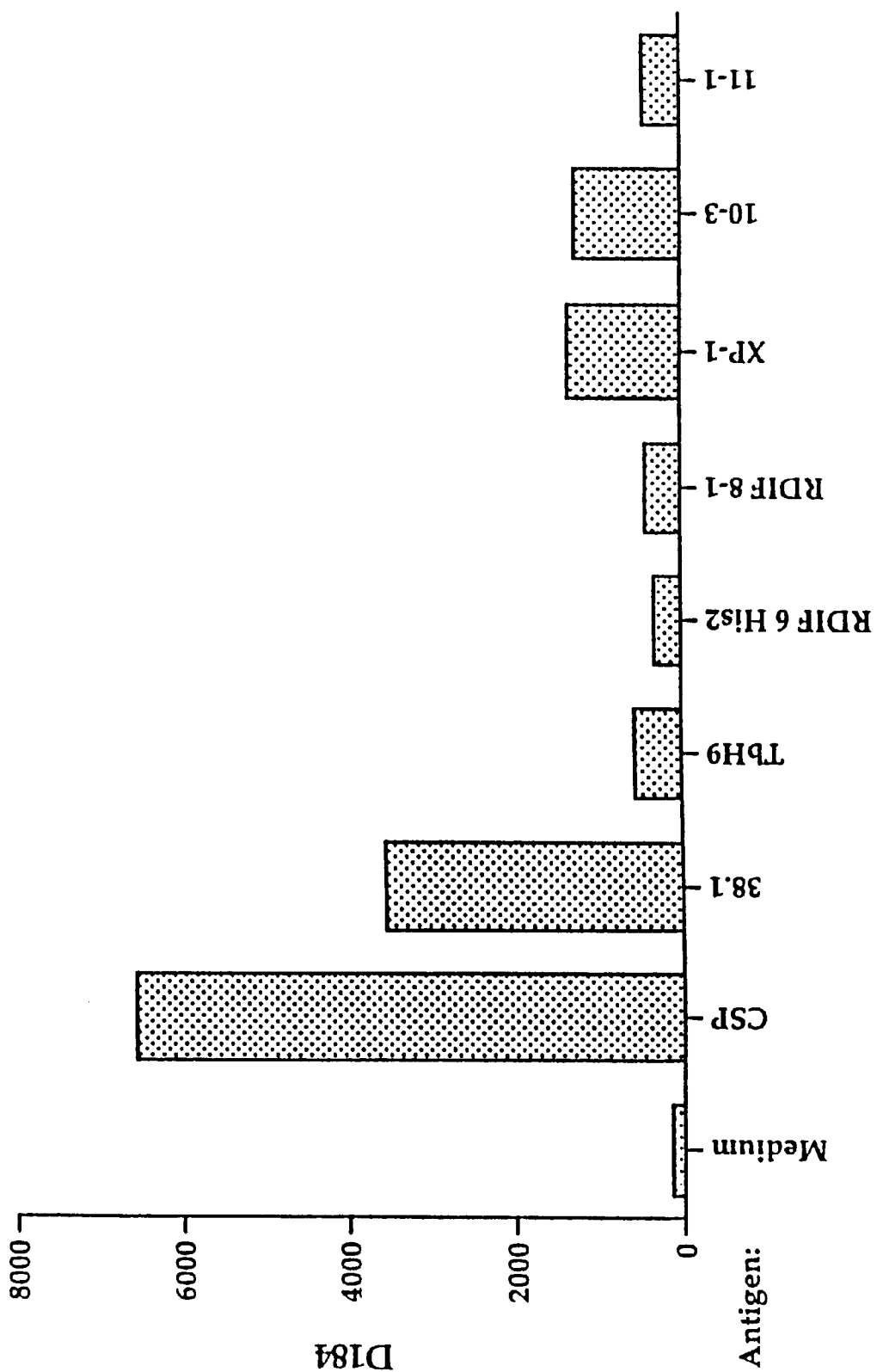
Figure 9B:
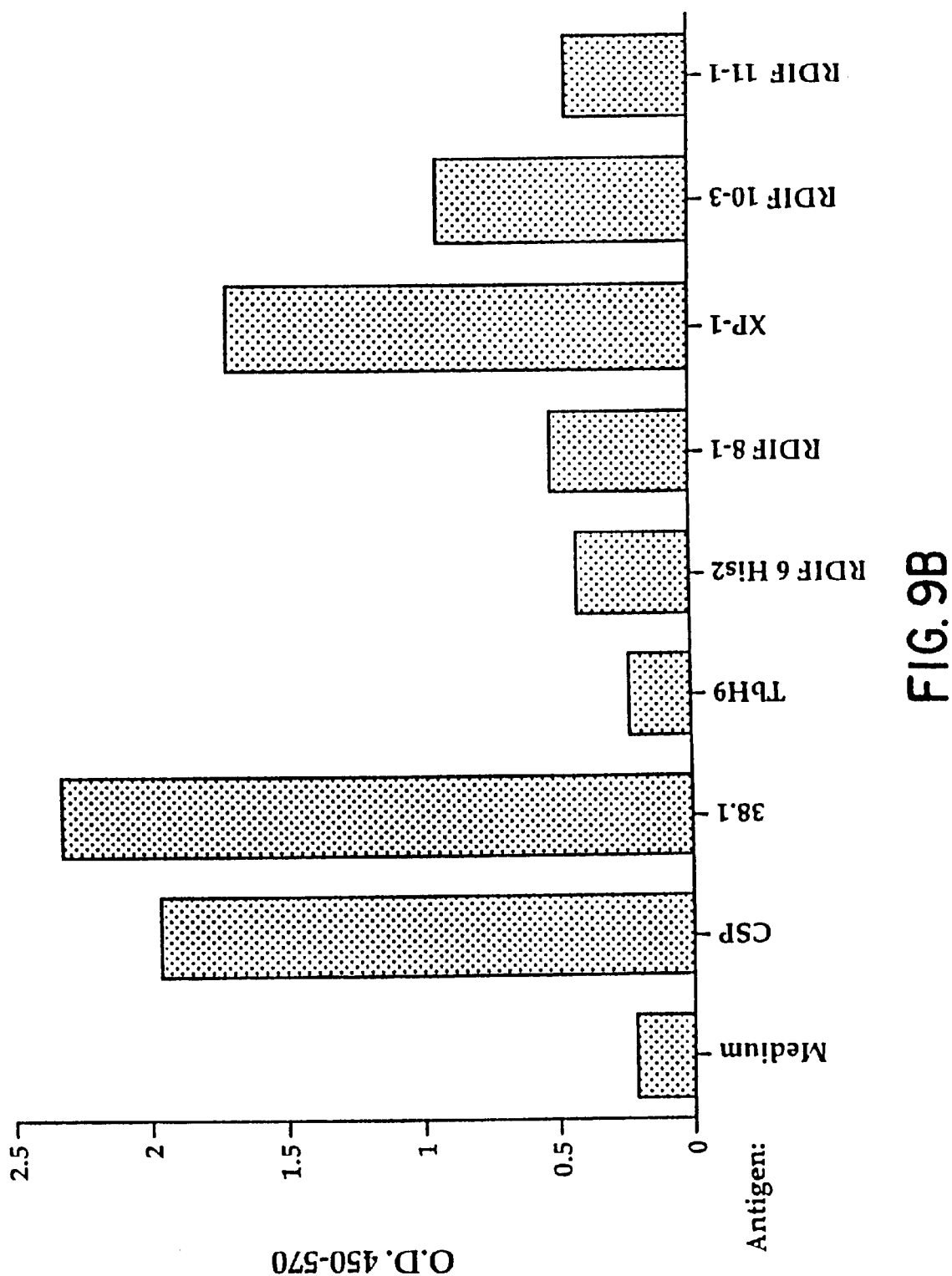

FIGS. 9A and B illustrate the stimulation of proliferation and interferon-γ production in T cells derived from a second *M. tuberculosis*-immune individual by the representative polypeptides XP-1, RDIF6, RDIF8, RDIF10 and RDIF11.

Figure 10:
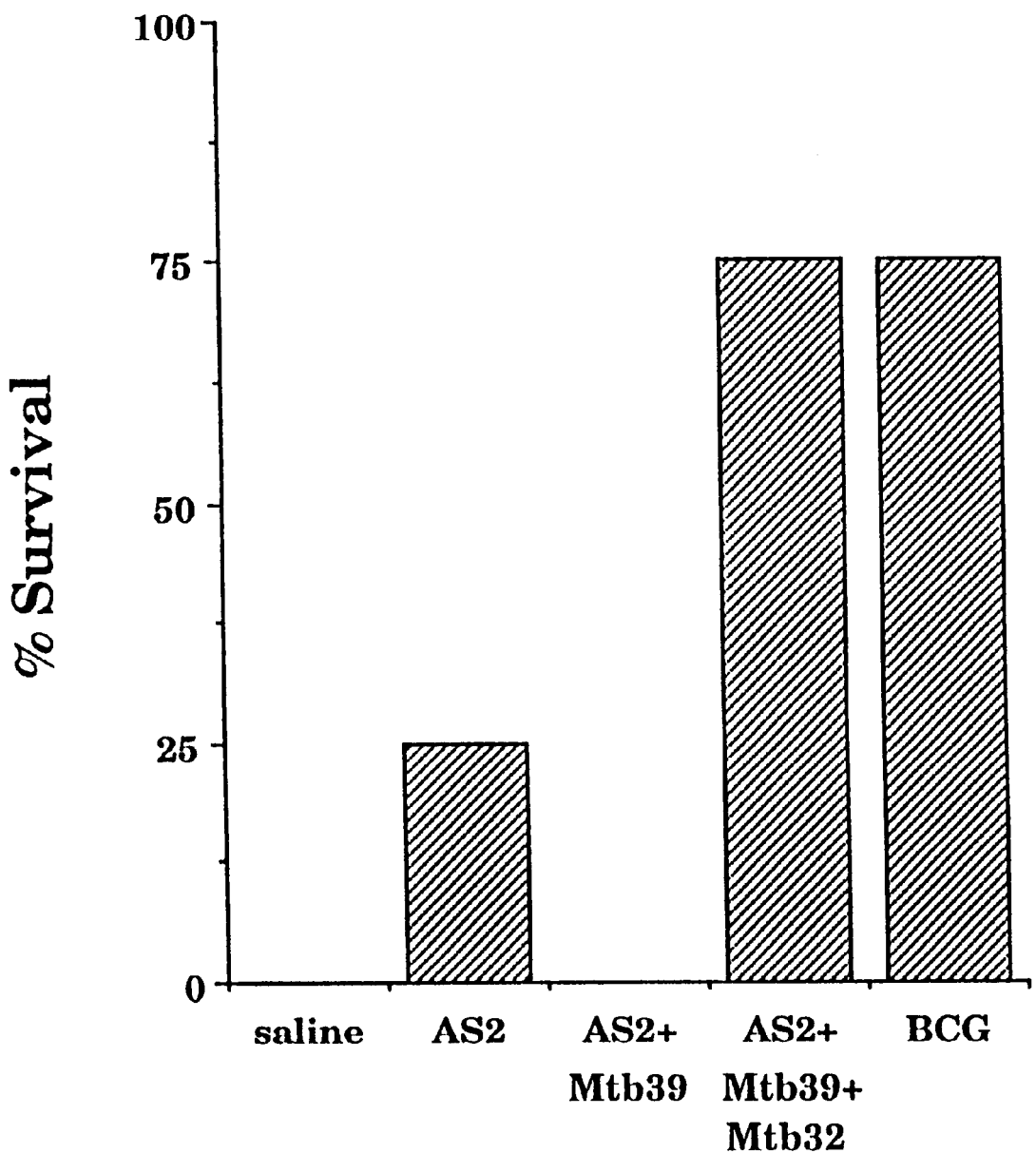

FIG. 10 illustrates the percent survival after administration of saline, AS2, AS2+Mtb39, AS2+Mtb39+Mtb32, or BCG.

Figure 11A:
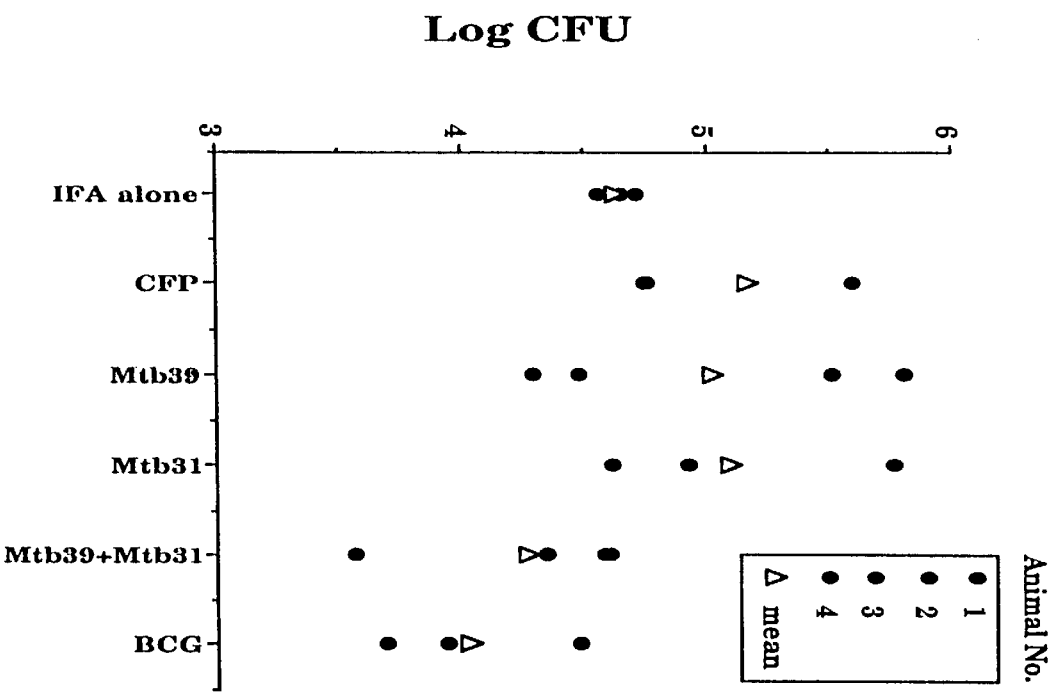
Figure 11B:
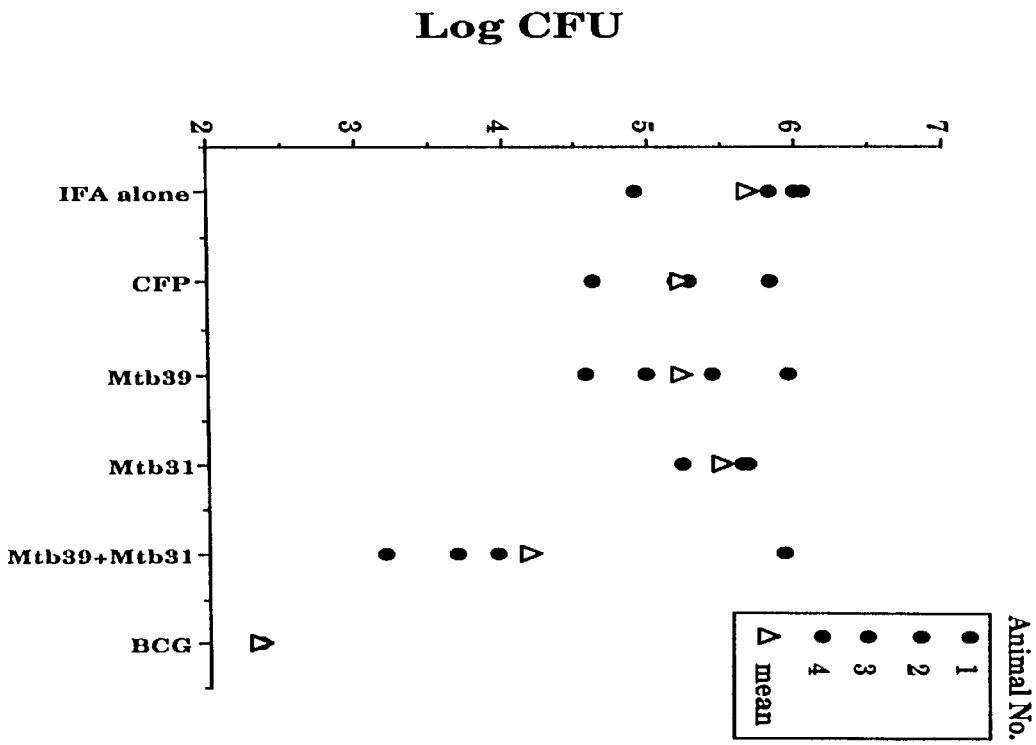

FIGS. 11A and B show the results of aerosol TB challenge of vaccinated guinea pigs.

Figure 12:
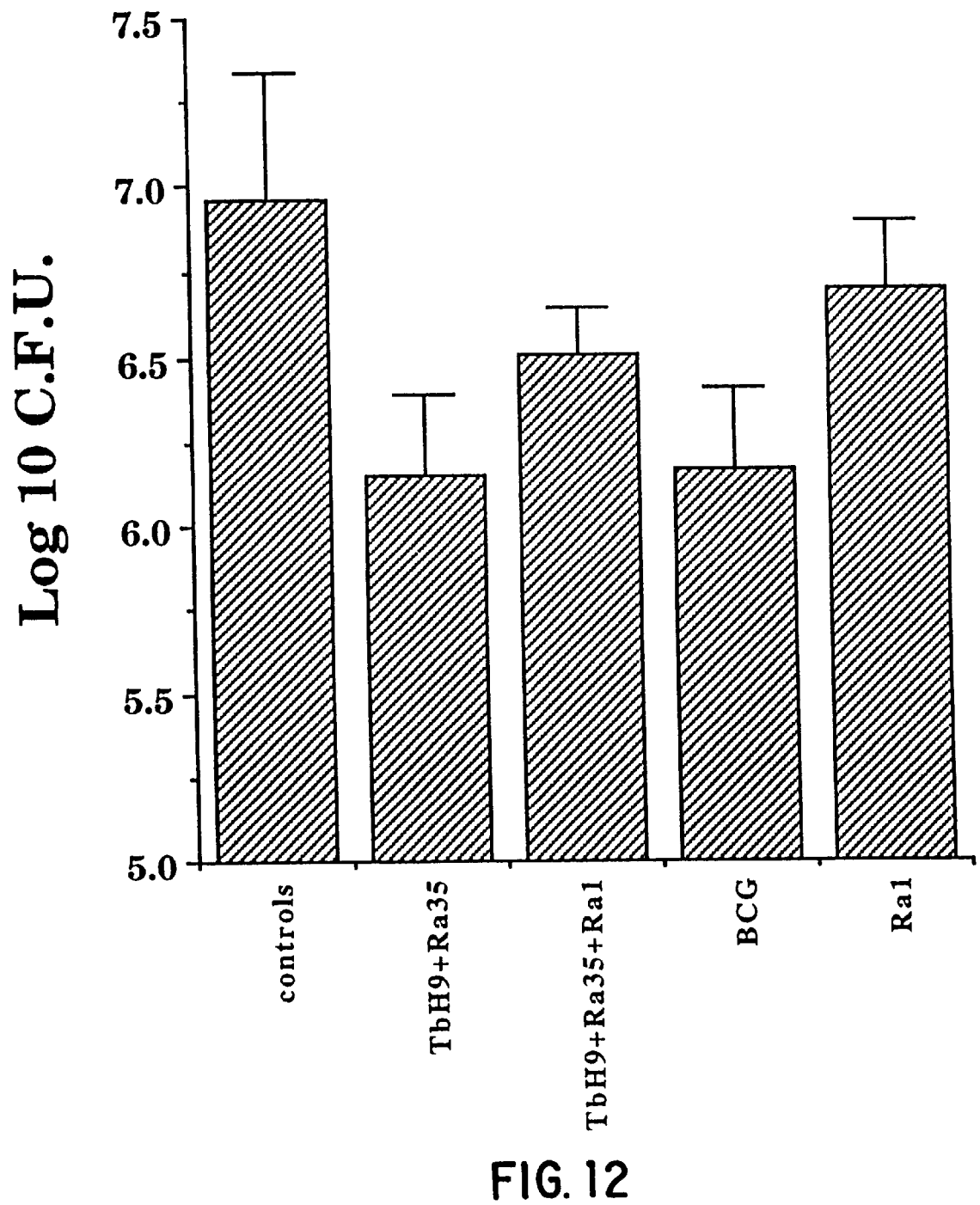

FIG. 12 shows the results of DNA immunized mice challenged with aerosol TB (lung CFU).

SEQ. ID NO. 1 is the DNA sequence of TbRa1.
SEQ. ID NO. 2 is the DNA sequence of TbRa10.
SEQ. ID NO. 3 is the DNA sequence of TbRa11.
SEQ. ID NO. 4 is the DNA sequence of TbRa12.
SEQ. ID NO. 5 is the DNA sequence of TbRa13.
SEQ. ID NO. 6 is the DNA sequence of TbRa16.
SEQ. ID NO. 7 is the DNA sequence of TbRa17.
SEQ. ID NO. 8 is the DNA sequence of TbRa18.
SEQ. ID NO. 9 is the DNA sequence of TbRa19.
SEQ. ID NO. 10 is the DNA sequence of TbRa24.
SEQ. ID NO. 11 is the DNA sequence of TbRa26.
SEQ. ID NO. 12 is the DNA sequence of TbRa28.
SEQ. ID NO. 13 is the DNA sequence of TbRa29.
SEQ. ID NO. 14 is the DNA sequence of TbRa2A.
SEQ. ID NO. 15 is the DNA sequence of TbRa3.
SEQ. ID NO. 16 is the DNA sequence of TbRa32.
SEQ. ID NO. 17 is the DNA sequence of TbRa35.
SEQ. ID NO. 18 is the DNA sequence of TbRa36.
SEQ. ID NO. 19 is the DNA sequence of TbRa4.
SEQ. ID NO. 20 is the DNA sequence of TbRa9.
SEQ. ID NO. 21 is the DNA sequence of TbRaB.
SEQ. ID NO. 22 is the DNA sequence of TbRaC.
SEQ. ID NO. 23 is the DNA sequence of TbRaD.
SEQ. ID NO. 24 is the DNA sequence of YYWCPG.
SEQ. ID NO. 25 is the DNA sequence of AAMK.
SEQ. ID NO. 26 is the DNA sequence of TbL-23.
SEQ. ID NO. 27 is the DNA sequence of TbL-24.
SEQ. ID NO. 28 is the DNA sequence of TbL-25.
SEQ. ID NO. 29 is the DNA sequence of TbL-28.
SEQ. ID NO. 30 is the DNA sequence of TbL-29.
SEQ. ID NO. 31 is the DNA sequence of TbH-5.
SEQ. ID NO. 32 is the DNA sequence of TbH-8.
SEQ. ID NO. 33 is the DNA sequence of TbH-9.
SEQ. ID NO. 34 is the DNA sequence of TbM-1.
SEQ. ID NO. 35 is the DNA sequence of TbM-3.
SEQ. ID NO. 36 is the DNA sequence of TbM-6.
SEQ. ID NO. 37 is the DNA sequence of TbM-7.
SEQ. ID NO. 38 is the DNA sequence of TbM-9.
SEQ. ID NO. 39 is the DNA sequence of TbM-12.
SEQ. ID NO. 40 is the DNA sequence of TbM-13.
SEQ. ID NO. 41 is the DNA sequence of TbM-14.
SEQ. ID NO. 42 is the DNA sequence of TbM-15.
SEQ. ID NO. 43 is the DNA sequence of TbH-4.
SEQ. ID NO. 44 is the DNA sequence of TbH-4-FWD.
SEQ. ID NO. 45 is the DNA sequence of TbH-12.
SEQ. ID NO. 46 is the DNA sequence of Tb38-1.
SEQ. ID NO. 47 is the DNA sequence of Tb38-4.
SEQ. ID NO. 48 is the DNA sequence of TbL-17.
SEQ. ID NO. 49 is the DNA sequence of TbL-20.
SEQ. ID NO. 50 is the DNA sequence of TbL-21.
SEQ. ID NO. 51 is the DNA sequence of TbH-16.
SEQ. ID NO. 52 is the DNA sequence of DPEP.
SEQ. ID NO. 53 is the deduced amino acid sequence of DPEP.
SEQ. ID NO. 54 is the protein sequence of DPV N-terminal Antigen.
SEQ. ID NO. 55 is the protein sequence of AVGS N-terminal Antigen.
SEQ. ID NO. 56 is the protein sequence of AAMK N-terminal Antigen.
SEQ. ID NO. 57 is the protein sequence of YYWC N-terminal Antigen.
SEQ. ID NO. 58 is the protein sequence of DIGS N-terminal Antigen.
SEQ. ID NO. 59 is the protein sequence of AEES N-terminal Antigen.
SEQ. ID NO. 60 is the protein sequence of DPEP N-terminal Antigen.
SEQ. ID NO. 61 is the protein sequence of APKT N-terminal Antigen.
SEQ. ID NO. 62 is the protein sequence of DPAS N-terminal Antigen.
SEQ. ID NO. 63 is the deduced amino acid sequence of TbRa1.
SEQ. ID NO. 64 is the deduced amino acid sequence of TbRa10.
SEQ. ID NO. 65 is the deduced amino acid sequence of TbRa11.
SEQ. ID NO. 66 is the deduced amino acid sequence of TbRa12.
SEQ. ID NO. 67 is the deduced amino acid sequence of TbRa13.
SEQ. ID NO. 68 is the deduced amino acid sequence of TbRa16.
SEQ. ID NO. 69 is the deduced amino acid sequence of TbRa17.
SEQ. ID NO. 70 is the deduced amino acid sequence of TbRa18.
SEQ. ID NO. 71 is the deduced amino acid sequence of TbRa19.
SEQ. ID NO. 72 is the deduced amino acid sequence of TbRa24.
SEQ. ID NO. 73 is the deduced amino acid sequence of TbRa26.
SEQ. ID NO. 74 is the deduced amino acid sequence of TbRa28.
SEQ. ID NO. 75 is the deduced amino acid sequence of TbRa29.
SEQ. ID NO. 76 is the deduced amino acid sequence of TbRa2A.
SEQ. ID NO. 77 is the deduced amino acid sequence of TbRa3.
SEQ. ID NO. 78 is the deduced amino acid sequence of TbRa32.
SEQ. ID NO. 79 is the deduced amino acid sequence of TbRa35.
SEQ. ID NO. 80 is the deduced amino acid sequence of TbRa36.
SEQ. ID NO. 81 is the deduced amino acid sequence of TbRa4.
SEQ. ID NO. 82 is the deduced amino acid sequence of TbRa9.
SEQ. ID NO. 83 is the deduced amino acid sequence of TbRaB.
SEQ. ID NO. 84 is the deduced amino acid sequence of TbRaC.
SEQ. ID NO. 85 is the deduced amino acid sequence of TbRaD.

SEQ. ID NO. 86 is the deduced amino acid sequence of YYWCPG.

SEQ. ID NO. 87 is the deduced amino acid sequence of TbAAMK.

SEQ. ID NO. 88 is the deduced amino acid sequence of Tb38-1.

SEQ. ID NO. 89 is the deduced amino acid sequence of TbH-4.

SEQ. ID NO. 90 is the deduced amino acid sequence of TbH-8.

SEQ. ID NO. 91 is the deduced amino acid sequence of TbH-9.

SEQ. ID NO. 92 is the deduced amino acid sequence of TbH-12.

SEQ. ID NO. 93 is the amino acid sequence of Tb38-1 Peptide 1.

SEQ. ID NO. 94 is the amino acid sequence of Tb38-1 Peptide 2.

SEQ. ID NO. 95 is the amino acid sequence of Tb38-1 Peptide 3.

SEQ. ID NO. 96 is the amino acid sequence of Tb38-1 Peptide 4.

SEQ. ID NO. 97 is the amino acid sequence of Tb38-1 Peptide 5.

SEQ. ID NO. 98 is the amino acid sequence of Tb38-1 Peptide 6.

SEQ. ID NO. 99 is the DNA sequence of DPAS.

SEQ. ID NO. 100 is the deduced amino acid sequence of DPAS.

SEQ. ID NO. 101 is the DNA sequence of DPV.

SEQ. ID NO. 102 is the deduced amino acid sequence of DPV.

SEQ. ID NO. 103 is the DNA sequence of ESAT-6.

SEQ. ID NO. 104 is the deduced amino acid sequence of ESAT-6.

SEQ. ID NO. 105 is the DNA sequence of TbH-8-2.

SEQ. ID NO. 106 is the DNA sequence of TbH-9FL.

SEQ. ID NO. 107 is the deduced amino acid sequence of TbH-9FL.

SEQ. ID NO. 108 is the DNA sequence of TbH-9-1.

SEQ. ID NO. 109 is the deduced amino acid sequence of TbH-9-1.

SEQ. ID NO. 110 is the DNA sequence of TbH-9-4.

SEQ. ID NO. 111 is the deduced amino acid sequence of TbH-9-4.

SEQ. ID NO. 112 is the DNA sequence of Tb38-1F2 IN.

SEQ. ID NO. 113 is the DNA sequence of Tb38-2F2 RP.

SEQ. ID NO. 114 is the deduced amino acid sequence of Tb37-FL.

SEQ. ID NO. 115 is the deduced amino acid sequence of Tb38-IN.

SEQ. ID NO. 116 is the DNA sequence of Tb38-1 RF3.

SEQ. ID NO. 117 is the deduced amino acid sequence of Tb38-1F3.

SEQ. ID NO. 118 is the DNA sequence of T38-1F5.

SEQ. ID NO. 119 is the DNA sequence of Tb38-1F6.

SEQ. ID NO. 120 is the deduced N-terminal amino acid sequence of DPV.

SEQ. ID NO. 121 is the deduced N-terminal amino acid sequence of AVGS.

SEQ. ID NO. 122 is the deduced N-terminal amino acid sequence of AAMK.

SEQ. ID NO. 123 is the deduced N-terminal amino acid sequence of YYWC.

SEQ. ID NO. 124 is the deduced N-terminal amino acid sequence of DIGS.

SEQ. ID NO. 125 is the deduced N-terminal amino acid sequence of AEES.

SEQ. ID NO. 126 is the deduced N-terminal amino acid sequence of DPEP.

SEQ. ID NO. 127 is the deduced N-terminal amino acid sequence of APKT.

SEQ. ID NO. 128 is the deduced amino acid sequence of DPAS.

SEQ. ID NO. 129 is the protein sequence of DPPD N-terminal Antigen.

SEQ ID NO. 130–133 are the protein sequences of four DPPD cyanogen bromide fragments.

SEQ ID NO. 134 is the N-terminal protein sequence of XDS antigen.

SEQ ID NO. 135 is the N-terminal protein sequence of AGD antigen.

SEQ ID NO. 136 is the N-terminal protein sequence of APE antigen.

SEQ ID NO. 137 is the N-terminal protein sequence of XYI antigen.

SEQ ID NO. 138 is the DNA sequence of TbH-29.

SEQ ID NO. 139 is the DNA sequence of TbH-30.

SEQ ID NO. 140 is the DNA sequence of TbH-32.

SEQ ID NO. 141 is the DNA sequence of TbH-33.

SEQ ID NO. 142 is the predicted amino acid sequence of TbH-29.

SEQ ID NO. 143 is the predicted amino acid sequence of TbH-30.

SEQ ID NO. 144 is the predicted amino acid sequence of TbH-32.

SEQ ID NO. 145 is the predicted amino acid sequence of TbH-33.

SEQ ID NO: 146–151 are PCR primers used in the preparation of a fusion protein containing TbRa3, 38 kD and Tb38-1.

SEQ ID NO: 152 is the DNA sequence of the fusion protein containing TbRa3, 38 kD and Tb38-1.

SEQ ID NO: 153 is the amino acid sequence of the fusion protein containing TbRa3, 38 kD and Tb38-1.

SEQ ID NO: 154 is the DNA sequence of the *M. tuberculosis* antigen 38 kD.

SEQ ID NO: 155 is the amino acid sequence of the *M. tuberculosis* antigen 38 kD.

SEQ ID NO: 156 is the DNA sequence of XP14.

SEQ ID NO: 157 is the DNA sequence of XP24.

SEQ ID NO: 158 is the DNA sequence of XP31.

SEQ ID NO: 159 is the 5' DNA sequence of XP32.

SEQ ID NO: 160 is the 3' DNA sequence of XP32.

SEQ ID NO: 161 is the predicted amino acid sequence of XP 14.

SEQ ID NO: 162 is the predicted amino acid sequence encoded by the reverse complement of XP 14.

SEQ ID NO: 163 is the DNA sequence of XP27.

SEQ ID NO: 164 is the DNA sequence of XP36.

SEQ ID NO: 165 is the 5' DNA sequence of XP4.

SEQ ID NO: 166 is the 5' DNA sequence of XP5.
SEQ ID NO: 167 is the 5' DNA sequence of XP17.
SEQ ID NO: 168 is the 5' DNA sequence of XP30.
SEQ ID NO: 169 is the 5' DNA sequence of XP2.
SEQ ID NO: 170 is the 3' DNA sequence of XP2.
SEQ ID NO: 171 is the 5' DNA sequence of XP3.
SEQ ID NO: 172 is the 3' DNA sequence of XP3.
SEQ ID NO: 173 is the 5' DNA sequence of XP6.
SEQ ID NO: 174 is the 3' DNA sequence of XP6.
SEQ ID NO: 175 is the 5' DNA sequence of XP18.
SEQ ID NO: 176 is the 3' DNA sequence of XP18.
SEQ ID NO: 177 is the 5' DNA sequence of XP19.
SEQ ID NO: 178 is the 3' DNA sequence of XP19.
SEQ ID NO: 179 is the 5' DNA sequence of XP22.
SEQ ID NO: 180 is the 3' DNA sequence of XP22.
SEQ ID NO: 181 is the 5' DNA sequence of XP25.
SEQ ID NO: 182 is the 3' DNA sequence of XP25.
SEQ ID NO: 183 is the full-length DNA sequence of TbH4-XP1.
SEQ ID NO: 184 is the predicted amino acid sequence of TbH4-XP1.
SEQ ID NO: 185 is the predicted amino acid sequence encoded by the reverse complement of TbH4-XP1.
SEQ ID NO: 186 is a first predicted amino acid sequence encoded by XP36.
SEQ ID NO: 187 is a second predicted amino acid sequence encoded by XP36.
SEQ ID NO: 188 is the predicted amino acid sequence encoded by the reverse complement of XP36.
SEQ ID NO: 189 is the DNA sequence of RDIF2.
SEQ ID NO: 190 is the DNA sequence of RDIF5.
SEQ ID NO: 191 is the DNA sequence of RDIF8.
SEQ ID NO: 192 is the DNA sequence of RDIF10.
SEQ ID NO: 193 is the DNA sequence of RDIF11.
SEQ ID NO: 194 is the predicted amino acid sequence of RDIF2.
SEQ ID NO: 195 is the predicted amino acid sequence of RDIF5.
SEQ ID NO: 196 is the predicted amino acid sequence of RDIF8.
SEQ ID NO: 197 is the predicted amino acid sequence of RDIF10.
SEQ ID NO: 198 is the predicted amino acid sequence of RDIF 11.
SEQ ID NO: 199 is the 5' DNA sequence of RDIF12.
SEQ ID NO: 200 is the 3' DNA sequence of RDIF12.
SEQ ID NO: 201 is the DNA sequence of RDIF7.
SEQ ID NO: 202 is the predicted amino acid sequence of RDIF7.
SEQ ID NO: 203 is the DNA sequence of DIF2-1.
SEQ ID NO: 204 is the predicted amino acid sequence of DIF2-1.
SEQ ID NO: 205–212 are PCR primers used in the preparation of a fusion protein containing TbRa3, 38 kD, Tb38-1 and DPEP (hereinafter referred to as TbF-2).
SEQ ID NO: 213 is the DNA sequence of the fusion protein TbF-2.
SEQ ID NO: 214 is the amino acid sequence of the fusion protein TbF-2.
SEQ ID NO: 215 is the 5' DNA sequence of MO-1.
SEQ ID NO: 216 is the 5' DNA sequence for MO-2
SEQ ID NO: 217 is the 5' DNA sequence for MO-4.
SEQ ID NO: 218 is the 5' DNA sequence for MO-8.
SEQ ID NO: 219 is the 5' DNA sequence for MO-9.
SEQ ID NO: 220 is the 5' DNA sequence for MO-26.
SEQ ID NO: 221 is the 5' DNA sequence for MO-28.
SEQ ID NO: 222 is the 5' DNA sequence for MO-29.
SEQ ID NO: 223 is the 5' DNA sequence for MO-30.
SEQ ID NO: 224 is the 5' DNA sequence for MO-34.
SEQ ID NO: 225 is the 5' DNA sequence for MO-35.
SEQ ID NO: 226 is the predicted amino acid sequence for MO-1.
SEQ ID NO: 227 is the predicted amino acid sequence for MO-2.
SEQ ID NO: 228 is the predicted amino acid sequence for MO-4.
SEQ ID NO: 229 is the predicted amino acid sequence for MO-8.
SEQ ID NO: 230 is the predicted amino acid sequence for MO-9.
SEQ ID NO: 231 is the predicted amino acid sequence for MO-26.
SEQ ID NO: 232 is the predicted amino acid sequence for MO-28.
SEQ ID NO: 233 is the predicted amino acid sequence for MO-29.
SEQ ID NO: 234 is the predicted amino acid sequence for MO-30.
SEQ ID NO: 235 is the predicted amino acid sequence for MO-34.
SEQ ID NO: 236 is the predicted amino acid sequence for MO-35.
SEQ ID NO: 237 is the determined DNA sequence for MO-10.
SEQ ID NO: 238 is the predicted amino acid sequence for MO-10.
SEQ ID NO: 239 is the 3' DNA sequence for MO-27.
SEQ ID NO: 240 is the full-length DNA sequence for DPPD.
SEQ ID NO: 241 is the predicted full-length amino acid sequence for DPPD.
SEQ ID NO: 242 is the determined 5' cDNA sequence for LSER-10
SEQ ID NO: 243 is the determined 5' cDNA sequence for LSER-1
SEQ ID NO: 244 is the determined 5' cDNA sequence for LSER-12
SEQ ID NO: 245 is the determined 5' cDNA sequence for LSER-13
SEQ ID NO: 246 is the determined 5' cDNA sequence for LSER-16
SEQ ID NO: 247 is the determined 5' cDNA sequence for LSER-25
SEQ ID NO: 248 is the predicted amino acid sequence for LSER-10
SEQ ID NO: 249 is the predicted amino acid sequence for LSER-12
SEQ ID NO: 250 is the predicted amino acid sequence for LSER-13

SEQ ID NO: 251 is the predicted amino acid sequence for LSER-16

SEQ ID NO: 252 is the predicted amino acid sequence for LSER-25

SEQ ID NO: 253 is the determined cDNA sequence for LSER-18

SEQ ID NO: 254 is the determined cDNA sequence for LSER-23

SEQ ID NO: 255 is the determined cDNA sequence for LSER-24

SEQ ID NO: 256 is the determined cDNA sequence for LSER-27

SEQ ID NO: 257 is the predicted amino acid sequence for LSER-18

SEQ ID NO: 258 is the predicted amino acid sequence for LSER-23

SEQ ID NO: 259 is the predicted amino acid sequence for LSER-24

SEQ ID NO: 260 is the predicted amino acid sequence for LSER-27

SEQ ID NO: 261 is the determined 5' cDNA sequence for LSER-1

SEQ ID NO: 262 is the determined 5' cDNA sequence for LSER-3

SEQ ID NO: 263 is the determined 5' cDNA sequence for LSER-4

SEQ ID NO: 264 is the determined 5' cDNA sequence for LSER-5

SEQ ID NO: 265 is the determined 5' CDNA sequence for LSER-6

SEQ ID NO: 266 is the determined 5' cDNA sequence for LSER-8

SEQ ID NO: 267 is the determined 5' cDNA sequence for LSER-14

SEQ ID NO: 268 is the determined 5' cDNA sequence for LSER-15

SEQ ID NO: 269 is the determined 5' cDNA sequence for LSER-17

SEQ ID NO: 270 is the determined 5' cDNA sequence for LSER-19

SEQ ID NO: 271 is the determined 5' cDNA sequence for LSER-20

SEQ ID NO: 272 is the determined 5' cDNA sequence for LSER-22

SEQ ID NO: 273 is the determined 5' cDNA sequence for LSER-26

SEQ ID NO: 274 is the determined 5' cDNA sequence for LSER-28

SEQ ID NO: 275 is the determined 5' cDNA sequence for LSER-29

SEQ ID NO: 276 is the determined 5' cDNA sequence for LSER-30

SEQ ID NO: 277 is the predicted amino acid sequence for LSER-28

SEQ ID NO: 278 is the predicted amino acid sequence for LSER-3

SEQ ID NO: 279 is the predicted amino acid sequence for LSER-5

SEQ ID NO: 280 is the predicted amino acid sequence for LSER-6

SEQ ID NO: 281 is the predicted amino acid sequence for LSER-8

SEQ ID NO: 282 is the predicted amino acid sequence for LSER-14

SEQ ID NO: 283 is the predicted amino acid sequence for LSER-15

SEQ ID NO: 284 is the predicted amino acid sequence for LSER-17

SEQ ID NO: 285 is the predicted amino acid sequence for LSER-19

SEQ ID NO: 286 is the predicted amino acid sequence for LSER-20

SEQ ID NO: 287 is the predicted amino acid sequence for LSER-22

SEQ ID NO: 288 is the predicted amino acid sequence for LSER-26

SEQ ID NO: 289 is the predicted amino acid sequence for LSER-28

SEQ ID NO: 290 is the predicted amino acid sequence for LSER-29

SEQ ID NO: 291 is the predicted amino acid sequence for LSER-30

SEQ ID NO: 292 is the determined cDNA sequence for LSER-9

SEQ ID NO: 293 is the determined cDNA sequence for the reverse complement of LSER-6

SEQ ID NO: 294 is the predicted amino acid sequence for the reverse complement of LSER-6

SEQ ID NO: 295 is the determined 5' cDNA sequence for MO-12

SEQ ID NO: 296 is the determined 5' cDNA sequence for MO-13

SEQ ID NO: 297 is the determined 5' cDNA sequence for MO-19

SEQ ID NO: 298 is the determined 5' cDNA sequence for MO-39

SEQ ID NO: 299 is the predicted amino acid sequence for MO-12

SEQ ID NO: 300 is the predicted amino acid sequence for MO-13

SEQ ID NO: 301 is the predicted amino acid sequence for MO-19

SEQ ID NO: 302 is the predicted amino acid sequence for MO-39

SEQ ID NO: 303 is the determined 5' cDNA sequence for Erdsn-1

SEQ ID NO: 304 is the determined 5' cDNA sequence for Erdsn-2

SEQ ID NO: 305 is the determined 5' cDNA sequence for Erdsn-4

SEQ ID NO: 306 is the determined 5' cDNA sequence for Erdsn-5

SEQ ID NO: 307 is the determined 5' cDNA sequence for Erdsn-6

SEQ ID NO: 308 is the determined 5' cDNA sequence for Erdsn-7

SEQ ID NO: 309 is the determined 5' cDNA sequence for Erdsn-8

SEQ ID NO: 310 is the determined 5' cDNA sequence for Erdsn-9

SEQ ID NO: 311 is the determined 5' cDNA sequence for Erdsn-10

SEQ ID NO: 312 is the determined 5' cDNA sequence for Erdsn-12

SEQ ID NO: 313 is the determined 5' cDNA sequence for Erdsn-13

SEQ ID NO: 314 is the determined 5' cDNA sequence for Erdsn-14

SEQ ID NO: 315 is the determined 5' cDNA sequence for Erdsn-15

SEQ ID NO: 316 is the determined 5' cDNA sequence for Erdsn-16

SEQ ID NO: 317 is the determined 5' cDNA sequence for Erdsn-17

SEQ ID NO: 318 is the determined 5' cDNA sequence for Erdsn-18

SEQ ID NO: 319 is the determined 5' cDNA sequence for Erdsn-21

SEQ ID NO: 320 is the determined 5' cDNA sequence for Erdsn-22

SEQ ID NO: 321 is the determined 5' cDNA sequence for Erdsn-23

SEQ ID NO: 322 is the determined 5' cDNA sequence for Erdsn-25

SEQ ID NO: 323 is the determined 3' cDNA sequence for Erdsn-1

SEQ ID NO: 324 is the determined 3' cDNA sequence for Erdsn-2

SEQ ID NO: 325 is the determined 3' cDNA sequence for Erdsn-4

SEQ ID NO: 326 is the determined 3' cDNA sequence for Erdsn-5

SEQ ID NO: 327 is the determined 3' cDNA sequence for Erdsn-7

SEQ ID NO: 328 is the determined 3' cDNA sequence for Erdsn-8

SEQ ID NO: 329 is the determined 3' cDNA sequence for Erdsn-9

SEQ ID NO: 330 is the determined 3' cDNA sequence for Erdsn-10

SEQ ID NO: 331 is the determined 3' cDNA sequence for Erdsn-12

SEQ ID NO: 332 is the determined 3' cDNA sequence for Erdsn-13

SEQ ID NO: 333 is the determined 3' cDNA sequence for Erdsn-14

SEQ ID NO: 334 is the determined 3° CDNA sequence for Erdsn-15

SEQ ID NO: 335 is the determined 3' cDNA sequence for Erdsn-16

SEQ ID NO: 336 is the determined 3' cDNA sequence for Erdsn-17

SEQ ID NO: 337 is the determined 3' cDNA sequence for Erdsn-18

SEQ ID NO: 338 is the determined 3' cDNA sequence for Erdsn-21

SEQ ID NO: 339 is the determined 3' cDNA sequence for Erdsn-22

SEQ ID NO: 340 is the determined 3' cDNA sequence for Erdsn-23

SEQ ID NO: 341 is the determined 3' cDNA sequence for Erdsn-25

SEQ ID NO: 342 is the determined cDNA sequence for Erdsn-24

SEQ ID NO: 343 is the determined amino acid sequence for a *M. tuberculosis* 85b precursor homolog SEQ ID NO: 344 is the determined amino acid sequence for spot 1

SEQ ID NO: 345 is a determined amino acid sequence for spot 2

SEQ ID NO: 346 is a determined amino acid sequence for spot 2

SEQ ID NO: 347 is the determined amino acid seq for spot 4

SEQ ID NO: 348 is the sequence of primer PDM-157

SEQ ID NO: 349 is the sequence of primer PDM-160

SEQ ID NO: 350 is the DNA sequence of the fusion protein TbF-6

SEQ ID NO: 351 is the amino acid sequence of fusion protein TbF-6

SEQ ID NO: 352 is the sequence of primer PDM-176

SEQ ID NO: 353 is the sequence of primer PDM-175

SEQ ID NO: 354 is the DNA sequence of the fusion protein TbF-8

SEQ ID NO: 355 is the amino acid sequence of the fusion protein TbF-8

DETAILED DESCRIPTION OF THE INVENTION

As noted above, the present invention is generally directed to compositions and methods for preventing, treating and diagnosing tuberculosis. The compositions of the subject invention include polypeptides that comprise at least one immunogenic portion of a *M. tuberculosis* antigen, or a variant of such an antigen that differs only in conservative substitutions and/or modifications. Polypeptides within the scope of the present invention include, but are not limited to, immunogenic soluble *M. tuberculosis* antigens. A "soluble *M. tuberculosis* antigen" is a protein of *M. tuberculosis* origin that is present in *M. tuberculosis* culture filtrate. As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native *M. tuberculosis* antigen or may be heterologous, and such sequences may (but need not) be immunogenic.

"Immunogenic," as used herein, refers to the ability to elicit an immune response (e.g., cellular) in a patient, such as a human, and/or in a biological sample. In particular, antigens that are immunogenic (and immunogenic portions or other variants of such antigens) are capable of stimulating cell proliferation, interleukin-12 production and/or interferon-γ production in biological samples comprising one or more cells selected from the group of T cells, NK cells, B cells and macrophages, where the cells are derived from an *M. tuberculosis*-immune individual. Polypeptides comprising at least an immunogenic portion of one or more *M. tuberculosis* antigens may generally be used to detect tuberculosis or to induce protective immunity against tuberculosis in a patient.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. For polypeptides with immunoreactive properties, variants may, alternatively, be identified by modifying the amino acid sequence of one of the above polypeptides, and evaluating the immunoreactivity of the modified polypeptide. For polypeptides useful for the generation of diagnostic binding agents, a variant may be identified by evaluating a modified polypeptide for the ability to generate antibodies that detect the presence or absence of tuberculosis. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. Such variant nucleotide sequences will generally hybridize to the recite nucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

In a related aspect, combination polypeptides are disclosed. A "combination polypeptide" is a polypeptide comprising at least one of the above immunogenic portions and one or more additional immunogenic *M. tuberculosis* sequences, which are joined via a peptide linkage into a single amino acid chain. The sequences may be joined directly (i.e., with no intervening amino acids) or may be joined by way of a linker sequence (e.g., Gly-Cys-Gly) that does not significantly diminish the immunogenic properties of the component polypeptides.

In general, *M. tuberculosis* antigens, and DNA sequences encoding such antigens, may be prepared using any of a variety of procedures. For example, soluble antigens may be isolated from *M. tuberculosis* culture filtrate by procedures known to those of ordinary skill in the art, including anion-exchange and reverse phase chromatography. Purified antigens are then evaluated for their ability to elicit an appropriate immune response (e.g., cellular) using, for example, the representative methods described herein. Immunogenic antigens may then be partially sequenced using techniques such as traditional Edman chemistry. See Edman and Berg, *Eur. J. Biochem.* 80:116–132, 1967.

Immunogenic antigens may also be produced recombinantly using a DNA sequence that encodes the antigen, which has been inserted into an expression vector and expressed in an appropriate host. DNA molecules encoding soluble antigens may be isolated by screening an appropriate *M. tuberculosis* expression library with anti-sera (e.g., rabbit) raised specifically against soluble *M. tuberculosis* antigens. DNA sequences encoding antigens that may or may not be soluble may be identified by screening an appropriate *M. tuberculosis* genomic or cDNA expression library with sera obtained from patients infected with *M. tuberculosis*. Such screens may generally be performed using techniques well known to those of ordinary skill in the art, such as those described in Sambrook et al., *Molecular Cloning: A Laboratory Manual*, Cold Spring Harbor Laboratories, Cold Spring Harbor, N.Y., 1989.

DNA sequences encoding soluble antigens may also be obtained by screening an appropriate *M. tuberculosis* cDNA or genomic DNA library for DNA sequences that hybridize to degenerate oligonucleotides derived from partial amino acid sequences of isolated soluble antigens. Degenerate oligonucleotide sequences for use in such a screen may be designed and synthesized, and the screen may be performed, as described (for example) in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Alternatively, genomic or cDNA libraries derived from *M. tuberculosis* may be screened directly using peripheral blood mononuclear cells (PBMCs) or T cell lines or clones derived from one or more *M. tuberculosis*-immune individuals. In general, PBMCs and/or T cells for use in such screens may be prepared as described below. Direct library screens may generally be performed by assaying pools of expressed recombinant proteins for the ability to induce proliferation and/or interferon-γ production in T cells derived from an *M. tuberculosis*-immune individual. Alternatively, potential T cell antigens may be first selected based on antibody reactivity, as described above.

Regardless of the method of preparation, the antigens (and immunogenic portions thereof) described herein (which may or may not be soluble) have the ability to induce an immunogenic response. More specifically, the antigens have the ability to induce proliferation and/or cytokine production (i.e., interferon-γ and/or interleukin-12 production) in T cells, NK cells, B cells and/or macrophages derived from an *M. tuberculosis*-immune individual. The selection of cell type for use in evaluating an immunogenic response to a antigen will, of course, depend on the desired response. For example, interleukin-12 production is most readily evaluated using preparations containing B cells and/or macrophages. An *M. tuberculosis*-immune individual is one who is considered to be resistant to the development of tuberculosis by virtue of having mounted an effective T cell response to *M. tuberculosis* (i.e., substantially free of disease symptoms). Such individuals may be identified based on a strongly positive (i.e., greater than about 10 mm diameter induration) intradermal skin test response to tuberculosis proteins (PPD) and an absence of any signs or symptoms of tuberculosis disease. T cells, NK cells, B cells and macrophages derived from *M. tuberculosis*-immune individuals may be prepared using methods known to those of ordinary skill in the art. For example, a preparation of PBMCs (i.e., peripheral blood mononuclear cells) may be employed without further separation of component cells. PBMCs may generally be prepared, for example, using density centrifugation through Ficoll™ (Winthrop Laboratories, NY). T cells for use in the assays described herein may also be purified directly from PBMCs. Alternatively, an enriched T cell line reactive against mycobacterial proteins, or T cell clones reactive to individual mycobacterial proteins, may be employed. Such T cell clones may be generated by, for example, culturing PBMCs from *M. tuberculosis*-immune individuals with mycobacterial proteins for a period of 2–4 weeks. This allows expansion of only the mycobacterial protein-specific T cells, resulting in a line composed solely of such cells. These cells may then be cloned and tested with individual proteins, using methods known to those of ordinary skill in the art, to more accurately define individual T cell specificity. In general, antigens that test positive in assays for proliferation and/or cytokine production (i.e., interferon-γ and/or interleukin-12 production) performed using T cells, NK cells, B cells and/or macrophages derived from an *M. tuberculosis*-immune individual are considered immunogenic. Such assays may be performed, for example, using the representative procedures described below. Immunogenic portions of such antigens may be identified using similar assays, and may be present within the polypeptides described herein.

The ability of a polypeptide (e.g., an immunogenic antigen, or a portion or other variant thereof) to induce cell proliferation is evaluated by contacting the cells (e.g., T cells and/or NK cells) with the polypeptide and measuring the proliferation of the cells. In general, the amount of polypeptide that is sufficient for evaluation of about $10^5$ cells ranges from about 10 ng/mL to about 100 μg/mL and preferably is about 10 μg/mL. The incubation of polypeptide with cells is typically performed at 37° C. for about six days. Following incubation with polypeptide, the cells are assayed for a proliferative response, which may be evaluated by methods known to those of ordinary skill in the art, such as exposing cells to a pulse of radiolabeled thymidine and measuring the incorporation of label into cellular DNA. In general, a polypeptide that results in at least a three fold increase in proliferation above background (i.e., the proliferation observed for cells cultured without polypeptide) is considered to be able to induce proliferation.

The ability of a polypeptide to stimulate the production of interferon-γ and/or interleukin-12 in cells may be evaluated by contacting the cells with the polypeptide and measuring the level of interferon-γ or interleukin-12 produced by the cells. In general, the amount of polypeptide that is sufficient for the evaluation of about $10^5$ cells ranges from about 10 ng/mL to about 100 μg/mL and preferably is about 10 μg/mL. The polypeptide may, but need not, be immobilized on a solid support, such as a bead or a biodegradable microsphere, such as those described in U.S. Pat. Nos. 4,897,268 and 5,075,109. The incubation of polypeptide with the cells is typically performed at 37° C. for about six days. Following incubation with polypeptide, the cells are assayed for interferon-γ and/or interleukin-12 (or one or more subunits thereof), which may be evaluated by methods known to those of ordinary skill in the art, such as an enzyme-linked immunosorbent assay (ELISA) or, in the case of IL-12 P70 subunit, a bioassay such as an assay measuring proliferation of T cells. In general, a polypeptide that results in the production of at least 50 pg of interferon-γ per mL of cultured supernatant (containing $10^4$–$10^5$ T cells per mL) is considered able to stimulate the production of interferon-γ. A polypeptide that stimulates the production of at least 10 pg/mL of IL-12 P70 subunit, and/or at least 100 pg/mL of IL-12 P40 subunit, per $10^5$ macrophages or B cells (or per $3\times10^5$ PBMC) is considered able to stimulate the production of IL-12.

In general, immunogenic antigens are those antigens that stimulate proliferation and/or cytokine production (i.e., interferon-γ and/or interleukin-12 production) in T cells, NK cells, B cells and/or macrophages derived from at least about 25% of *M. tuberculosis*-immune individuals. Among these immunogenic antigens, polypeptides having superior therapeutic properties may be distinguished based on the magnitude of the responses in the above assays and based on the percentage of individuals for which a response is observed. In addition, antigens having superior therapeutic properties will not stimulate proliferation and/or cytokine production in vitro in cells derived from more than about 25% of individuals that are not *M. tuberculosis*-immune, thereby eliminating responses that are not specifically due to *M. tuberculosis*-responsive cells. Those antigens that induce a response in a high percentage of T cell, NK cell, B cell and/or macrophage preparations from *M. tuberculosis*-immune individuals (with a low incidence of responses in cell preparations from other individuals) have superior therapeutic properties.

Antigens with superior therapeutic properties may also be identified based on their ability to diminish the severity of *M. tuberculosis* infection in experimental animals, when administered as a vaccine. Suitable vaccine preparations for use on experimental animals are described in detail below. Efficacy may be determined based on the ability of the antigen to provide at least about a 50% reduction in bacterial numbers and/or at least about a 40% decrease in mortality following experimental infection. Suitable experimental animals include mice, guinea pigs and primates.

Antigens having superior diagnostic properties may generally be identified based on the ability to elicit a response in an intradermal skin test performed on an individual with active tuberculosis, but not in a test performed on an individual who is not infected with *M. tuberculosis*. Skin tests may generally be performed as described below, with a response of at least 5 mm induration considered positive.

Immunogenic portions of the antigens described herein may be prepared and identified using well known techniques, such as those summarized in Paul, Fundamental Immunology, 3d ed., Raven Press, 1993, pp. 243–247 and references cited therein. Such techniques include screening polypeptide portions of the native antigen for immunogenic properties. The representative proliferation and cytokine production assays described herein may generally be employed in these screens. An immunogenic portion of a polypeptide is a portion that, within such representative assays, generates an immune response (e.g., proliferation, interferon-γ production and/or interleukin-12 production) that is substantially similar to that generated by the full length antigen. In other words, an immunogenic portion of an antigen may generate at least about 20%, and preferably about 100%, of the proliferation induced by the full length antigen in the model proliferation assay described herein. An immunogenic portion may also, or alternatively, stimulate the production of at least about 20%, and preferably about 100%, of the interferon-γ and/or interleukin-12 induced by the full length antigen in the model assay described herein.

Portions and other variants of *M. tuberculosis* antigens may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc., Foster City, Calif., and may be operated according to the manufacturer's instructions. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides of this invention.

Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner may encode naturally occurring antigens, portions of naturally occurring antigens, or other variants thereof.

In general, regardless of the method of preparation, the polypeptides disclosed herein are prepared in substantially pure form. Preferably, the polypeptides are at least about 80% pure, more preferably at least about 90% pure and most preferably at least about 99% pure. In certain preferred embodiments, described in detail below, the substantially pure polypeptides are incorporated into pharmaceutical compositions or vaccines for use in one or more of the methods disclosed herein.

In certain specific embodiments, the subject invention discloses polypeptides comprising at least an immunogenic portion of a soluble *M. tuberculosis* antigen having one of the following N-terminal sequences, or a variant thereof that differs only in conservative substitutions and/or modifications:

(a) Asp-Pro-Val-Asp-Ala-Val-Ile-Asn-Thr-Thr-Cys-Asn-Tyr-Gly-Gln-Val-Val-Ala-Ala-Leu; (SEQ ID No. 120)

(b) Ala-Val-Glu-Ser-Gly-Met-Leu-Ala-Leu-Gly-Thr-Pro-Ala-Pro-Ser; (SEQ ID No. 121)

(c) Ala-Ala-Met-Lys-Pro-Arg-Thr-Gly-Asp-Gly-Pro-Leu-Glu-Ala-Ala-Lys-Glu-Gly-Arg; (SEQ ID No. 122)

(d) Tyr-Tyr-Trp-Cys-Pro-Gly-Gln-Pro-Phe-Asp-Pro-Ala-Trp-Gly-Pro; (SEQ ID No. 123)

(e) Asp-Ile-Gly-Ser-Glu-Ser-Thr-Glu-Asp-Gln-Gln-Xaa-Ala-Val; (SEQ ID No. 124)

(f) Ala-Glu-Glu-Ser-Ile-Ser-Thr-Xaa-Glu-Xaa-Ile-Val-Pro; (SEQ ID No. 125)

(g) Asp-Pro-Glu-Pro-Ala-Pro-Pro-Val-Pro-Thr-Ala-Ala-Ala-Ser-Pro-Pro-Ser; (SEQ ID No. 126)

(h) Ala-Pro-Lys-Thr-Tyr-Xaa-Glu-Glu-Leu-Lys-Gly-Thr-Asp-Thr-Gly; (SEQ ID No. 127)

(i) Asp-Pro-Ala-Ser-Ala-Pro-Asp-Val-Pro-Thr-Ala-Ala-Gln-Leu-Thr-Ser-Leu-Leu-Asn-Ser-Leu-Ala-Asp-Pro-Asn-Val-Ser-Phe-Ala-Asn; (SEQ ID No. 128)

(j) Xaa-Asp-Ser-Glu-Lys-Ser-Ala-Thr-Ile-Lys-Val-Thr-Asp-Ala-Ser; (SEQ ID No. 134)

(k) Ala-Gly-Asp-Thr-Xaa-Ile-Tyr-Ile-Val-Gly-Asn-Leu-Thr-Ala-Asp; (SEQ ID No. 135) or (l) Ala-Pro-Glu-Ser-Gly-Ala-Gly-Leu-Gly-Gly-Thr-Val-Gln-Ala-Gly; (SEQ ID No. 136)

wherein Xaa may be any amino acid, preferably a cysteine residue. A DNA sequence encoding the antigen identified as (g) above is provided in SEQ ID No. 52, and the polypeptide encoded by SEQ ID No. 52 is provided in SEQ ID No. 53. A DNA sequence encoding the antigen defined as (a) above is provided in SEQ ID No. 101; its deduced amino acid sequence is provided in SEQ ID No. 102. A DNA sequence corresponding to antigen (d) above is provided in SEQ ID No. 24 a DNA sequence corresponding to antigen (c) is provided in SEQ ID No. 25 and a DNA sequence corresponding to antigen (i) is provided in SEQ ID No. 99; its deduced amino acid sequence is provided in SEQ ID No. 100.

In a further specific embodiment, the subject invention discloses polypeptides comprising at least an immunogenic portion of an *M. tuberculosis* antigen having one of the following N-terminal sequences, or a variant thereof that differs only in conservative substitutions and/or modifications:

(m) Xaa-Tyr-Ile-Ala-Tyr-Xaa-Thr-Thr-Ala-Gly-Ile-Val-Pro-Gly-Lys-Ile-Asn-Val-His-Leu-Val; (SEQ ID No 137) or (n) Asp-Pro-Pro-Asp-Pro-His-Gln-Xaa-Asp-Met-Thr-Lys-Gly-Tyr-Tyr-Pro-Gly-Gly-Arg-Arg-Xaa-Phe; (SEQ ID No. 129)

wherein Xaa may be any amino acid, preferably a cysteine residue.

In other specific embodiments, the subject invention discloses polypeptides comprising at least an immunogenic portion of a soluble *M. tuberculosis* antigen (or a variant of such an antigen) that comprises one or more of the amino acid sequences encoded by (a) the DNA sequences of SEQ ID Nos.: 1, 2, 4–10, 13–25 and 52; (b) the complements of such DNA sequences, or (c) DNA sequences substantially homologous to a sequence in (a) or (b).

In further specific embodiments, the subject invention discloses polypeptides comprising at least an immunogenic portion of a *M. tuberculosis* antigen (or a variant of such an antigen), which may or may not be soluble, that comprises one or more of the amino acid sequences encoded by (a) the DNA sequences of SEQ ID Nos.: 26–51, 138, 139, 163–183, 189–193, 199, 200, 201, 203, 215–225, 239, 240, 242–247, 253–256, 261–276, 292, 293, 295–298 and 303–342, (b) the complements of such DNA sequences or (c) DNA sequences substantially homologous to a sequence in (a) or (b).

In the specific embodiments discussed above, the *M. tuberculosis* antigens include variants that are encoded by DNA sequences which are substantially homologous to one or more of DNA sequences specifically recited herein. "Substantial homology," as used herein, refers to DNA sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the case of cross-species homology at 45° C., 0.5×SSC; followed by washing twice at 65° C. for 20 minutes with each of 2×, 0.5× and 0.2×SSC containing 0.1% SDS). Such hybridizing DNA sequences are also within the scope of this invention, as are nucleotide sequences that, due to code degeneracy, encode an immunogenic polypeptide that is encoded by a hybridizing DNA sequence.

In a related aspect, the present invention provides fusion proteins comprising a first and a second inventive polypeptide or, alternatively, a polypeptide of the present invention and a known *M. tuberculosis* antigen, such as the 38 kD antigen described in Andersen and Hansen, *Infect. Immun.* 57:2481–2488, 1989, (Genbank Accession No. M30046) or ESAT-6 (SEQ ID Nos. 103 and 104), together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

In another aspect, the present invention provides methods for using one or more of the above polypeptides or fusion proteins (or DNA molecules encoding such polypeptides) to induce protective immunity against tuberculosis in a patient. As used herein, a "patient" refers to any warm-blooded animal, preferably a human. A patient may be afflicted with a disease, or may be free of detectable disease and/or infection. In other words, protective immunity may be induced to prevent or treat tuberculosis.

In this aspect, the polypeptide, fusion protein or DNA molecule is generally present within a pharmaceutical composition and/or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response enhancer, such as an adjuvant or a liposome (into which the polypeptide is incorporated). Such pharmaceutical compositions and vaccines may also contain other *M. tuberculosis* antigens, either incorporated into a combination polypeptide or present within a separate polypeptide.

Alternatively, a vaccine may contain DNA encoding one or more polypeptides as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In a related aspect, a DNA vaccine as described above may be administered simultaneously with or sequentially to either a polypeptide of the present invention or a known *M. tuberculosis* antigen, such as the 38 kD antigen described above. For example, administration of DNA encoding a polypeptide of the present invention, either "naked" or in a delivery system as described above, may be followed by administration of an antigen in order to enhance the protective immune effect of the vaccine.

Routes and frequency of administration, as well as dosage, will vary from individual to individual and may parallel those currently being used in immunization using BCG. In general, the pharmaceutical compositions and vaccines may be administered by injection (e.g., intracutaneous, intramuscular, intravenous or subcutaneous), intranasally (e.g., by aspiration) or orally.

Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from *M. tuberculosis* infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed.

Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Suitable adjuvants are commercially available as, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A and quil A.

In another aspect, this invention provides methods for using one or more of the polypeptides described above to diagnose tuberculosis using a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 48–72 hours.

The DTH reaction is a cell-mediated immune response, which is greater in patients that have been exposed previously to the test antigen (i.e., the immunogenic portion of the polypeptide employed, or a variant thereof). The response may be measured visually, using a ruler. In general, a response that is greater than about 0.5 cm in diameter, preferably greater than about 1.0 cm in diameter, is a positive response, indicative of tuberculosis infection, which may or may not be manifested as an active disease.

The polypeptides of this invention are preferably formulated, for use in a skin test, as pharmaceutical compositions containing a polypeptide and a physiologically acceptable carrier, as described above. Such compositions typically contain one or more of the above polypeptides in an amount ranging from about 1 $\mu$g to about 100 $\mu$g, preferably from about 10 $\mu$g to about 50 $\mu$g in a volume of 0.1 mL. Preferably, the carrier employed in such pharmaceutical compositions is a saline solution with appropriate preservatives, such as phenol and/or Tween 80™.

In a preferred embodiment, a polypeptide employed in a skin test is of sufficient size such that it remains at the site of injection for the duration of the reaction period. In general, a polypeptide that is at least 9 amino acids in length is sufficient. The polypeptide is also preferably broken down by macrophages within hours of injection to allow presentation to T-cells. Such polypeptides may contain repeats of one or more of the above sequences and/or other immunogenic or nonimmunogenic sequences.

The following Examples are offered by way of illustration and not by way of limitation.

EXAMPLES

Example 1

Purification and Characterization of Polypeptides from *M. Tuberculosis* Culture Filtrate This example illustrates the preparation of *M. tuberculosis* soluble polypeptides from culture filtrate. Unless otherwise noted, all percentages in the following example are weight per volume.

*M. tuberculosis* (either H37Ra, ATCC No. 25177, or H37Rv, ATCC No. 25618) was cultured in sterile GAS media at 37° C. for fourteen days. The media was then vacuum filtered (leaving the bulk of the cells) through a 0.45$\mu$ filter into a sterile 2.5 L bottle. The media was next filtered through a 0.2$\mu$ filter into a sterile 4 L bottle and $NaN_3$ was added to the culture filtrate to a concentration of 0.04%. The bottles were then placed in a 4° C. cold room.

The culture filtrate was concentrated by placing the filtrate in a 12 L reservoir that had been autoclaved and feeding the filtrate into a 400 ml Amiconi stir cell which had been rinsed with ethanol and contained a 10,000 kDa MWCO membrane. The pressure was maintained at 60 psi using nitrogen gas. This procedure reduced the 12 L volume to approximately 50 ml.

The culture filtrate was dialyzed into 0.1% ammonium bicarbonate using a 8,000 kDa MWCO cellulose ester membrane, with two changes of ammonium bicarbonate solution. Protein concentration was then determined by a commercially available BCA assay (Pierce, Rockford, Ill.).

The dialyzed culture filtrate was then lyophilized, and the polypeptides resuspended in distilled water. The polypeptides were dialyzed against 0.01 mM 1,3 bis[tris (hydroxymethyl)-methylamino]propane, pH 7.5 (Bis-Tris propane buffer), the initial conditions for anion exchange chromatography. Fractionation was performed using gel profusion chromatography on a POROS 146 II Q/M anion exchange column 4.6 mm×100 mm (Perseptive BioSystems, Framingham, Mass.) equilibrated in 0.01 mM Bis-Tris propane buffer pH 7.5. Polypeptides were eluted with a linear 0–0.5 M NaCl gradient in the above buffer system. The column eluent was monitored at a wavelength of 220 nm.

The pools of polypeptides eluting from the ion exchange column were dialyzed against distilled water and lyophilized. The resulting material was dissolved in 0.1% trifluoroacetic acid (TFA) pH 1.9 in water, and the polypeptides were purified on a Delta-Pak C18 column (Waters, Milford, Mass.) 300 Angstrom pore size, 5 micron particle size (3.9×150 mm). The polypeptides were eluted from the column with a linear gradient from 0–60% dilution buffer (0.1% TFA in acetonitrile). The flow rate was 0.75 ml/minute and the HPLC eluent was monitored at 214 nm. Fractions containing the eluted polypeptides were collected to maximize the purity of the individual samples. Approximately 200 purified polypeptides were obtained.

The purified polypeptides were then screened for the ability to induce T-cell proliferation in PBMC preparations. The PBMCs from donors known to be PPD skin test positive and whose T-cells were shown to proliferate in response to PPD and crude soluble proteins from MTB were cultured in medium comprising RPMI 1640 supplemented with 10% pooled human serum and 50 µg/ml gentamicin. Purified polypeptides were added in duplicate at concentrations of 0.5 to 10 µg/mL. After six days of culture in 96-well round-bottom plates in a volume of 200 μl, 50 μl of medium was removed from each well for determination of IFN-γ levels, as described below. The plates were then pulsed with 1 μCi/well of tritiated thymidine for a further 18 hours, harvested and tritium uptake determined using a gas scintillation counter. Fractions that resulted in proliferation in both replicates three fold greater than the proliferation observed in cells cultured in medium alone were considered positive.

IFN-γ was measured using an enzyme-linked immunosorbent assay (ELISA). ELISA plates were coated with a mouse monoclonal antibody directed to human IFN-γ (PharMingen, San Diego, Calif.) in PBS for four hours at room temperature. Wells were then blocked with PBS containing 5% (W/V) non-fat dried milk for 1 hour at room temperature. The plates were then washed six times in PBS/0.2% TWEEN-20 and samples diluted 1:2 in culture medium in the ELISA plates were incubated overnight at room temperature. The plates were again washed and a polyclonal rabbit anti-human IFN-γ serum diluted 1:3000 in PBS/10% normal goat serum was added to each well. The plates were then incubated for two hours at room temperature, washed and horseradish peroxidase-coupled anti-rabbit IgG (Sigma Chemical So., St. Louis, Mo.) was added at a 1:2000 dilution in PBS/5% non-fat dried milk. After a further two hour incubation at room temperature, the plates were washed and TMB substrate added. The reaction was stopped after 20 min with 1 N sulfuric acid. Optical density was determined at 450 nm using 570 nm as a reference wavelength. Fractions that resulted in both replicates giving an OD two fold greater than the mean OD from cells cultured in medium alone, plus 3 standard deviations, were considered positive.

For sequencing, the polypeptides were individually dried onto Biobrene TM (Perkin Elmer/Applied BioSystems Division, Foster City, Calif.) treated glass fiber filters. The filters with polypeptide were loaded onto a Perkin Elmer/Applied BioSystems Division Procise 492 protein sequencer. The polypeptides were sequenced from the amino terminal and using traditional Edman chemistry. The amino acid sequence was determined for each polypeptide by comparing the retention time of the PTH amino acid derivative to the appropriate PTH derivative standards.

Using the procedure described above, antigens having the following N-terminal sequences were isolated:

(a) Asp-Pro-Val-Asp-Ala-Val-Ile-Asn-Thr-Thr-Xaa-Asn-Tyr-Gly-Gln-Val-Val-Ala-Ala-Leu; (SEQ ID No. 54)

(b) Ala-Val-Glu-Ser-Gly-Met-Leu-Ala-Leu-Gly-Thr-Pro-Ala-Pro-Ser; (SEQ ID No. 55)

(c) Ala-Ala-Met-Lys-Pro-Arg-Thr-Gly-Asp-Gly-Pro-Leu-Glu-Ala-Ala-Lys-Glu-Gly-Arg; (SEQ ID No. 56)

(d) Tyr-Tyr-Trp-Cys-Pro-Gly-Gln-Pro-Phe-Asp-Pro-Ala-Trp-Gly-Pro; (SEQ ID No. 57)

(e) Asp-Ile-Gly-Ser-Glu-Ser-Thr-Glu-Asp-Gln-Gln-Xaa-Ala-Val; (SEQ ID No. 58)

(f) Ala-Glu-Glu-Ser-Ile-Ser-Thr-Xaa-Glu-Xaa-Ile-Val-Pro; (SEQ ID No. 59)

(g) Asp-Pro-Glu-Pro-Ala-Pro-Pro-Val-Pro-Thr-Ala-Ala-Ala-Ala-Pro-Pro-Ala; (SEQ ID No. 60) and (h) Ala-Pro-Lys-Thr-Tyr-Xaa-Glu-Glu-Leu-Lys-Gly-Thr-Asp-Thr-Gly; (SEQ ID No. 61)

wherein Xaa may be any amino acid.

An additional antigen was isolated employing a microbore HPLC purification step in addition to the procedure described above. Specifically, 20 μl of a fraction comprising a mixture of antigens from the chromatographic purification step previously described, was purified on an Aquapore C18 column (Perkin Elmer/Applied Biosystems Division, Foster City, Calif.) with a 7 micron pore size, column size 1 mm×100 mm, in a Perkin Elmer/Applied Biosystems Division Model 172 HPLC. Fractions were eluted from the column with a linear gradient of 1%/minute of acetonitrile (containing 0.05% TFA) in water (0.05% TFA) at a flow rate of 80 μl/minute. The eluent was monitored at 250 nm. The original fraction was separated into 4 major peaks plus other smaller components and a polypeptide was obtained which was shown to have a molecular weight of 12.054 Kd (by mass spectrometry) and the following N-terminal sequence:

(i) Asp-Pro-Ala-Ser-Ala-Pro-Asp-Val-Pro-Thr-Ala-Ala-Gln-Gln-Thr-Ser-Leu-Leu-Asn-Asn-Leu-Ala-Asp-Pro-Asp-Val-Ser-Phe-Ala-Asp (SEQ ID No. 62).

This polypeptide was shown to induce proliferation and IFN-γ production in PBMC preparations using the assays described above.

Additional soluble antigens were isolated from *M. tuberculosis* culture filtrate as follows. *M. tuberculosis* culture filtrate was prepared as described above. Following dialysis against Bis-Tris propane buffer, at pH 5.5, fractionation was performed using anion exchange chromatography on a Poros QE column 4.6×100 mm (Perseptive Biosystems) equilibrated in Bis-Tris propane buffer pH 5.5. Polypeptides were eluted with a linear 0–1.5 M NaCl gradient in the above buffer system at a flow rate of 10 ml/min. The column eluent was monitored at a wavelength of 214 mn.

The fractions eluting from the ion exchange column were pooled and subjected to reverse phase chromatography using a Poros R2 column 4.6×100 mm (Perseptive Biosystems). Polypeptides were eluted from the column with a linear gradient from 0–100% acetonitrile (0.1% TFA) at a flow rate of 5 ml/min. The eluent was monitored at 214 nm.

Fractions containing the eluted polypeptides were lyophilized and resuspended in 80 μl of aqueous 0.1% TFA and further subjected to reverse phase chromatography on a Vydac C4 column 4.6×150 mm (Western Analytical, Temecula, Calif.) with a linear gradient of 0–100% acetonitrile (0.1% TFA) at a flow rate of 2 ml/min. Eluent was monitored at 214 nm.

The fraction with biological activity was separated into one major peak plus other smaller components. Western blot of this peak onto PVDF membrane revealed three major bands of molecular weights 14 Kd, 20 Kd and 26 Kd. These polypeptides were determined to have the following N-terminal sequences, respectively:

(j) Xaa-Asp-Ser-Glu-Lys-Ser-Ala-Thr-Ile-Lys-Val-Thr-Asp-Ala-Ser; (SEQ ID No. 134)

(k) Ala-Gly-Asp-Thr-Xaa-Ile-Tyr-Ile-Val-Gly-Asn-Leu-Thr-Ala-Asp; (SEQ ID No. 135) and (l) Ala-Pro-Glu-Ser-Gly-Ala-Gly-Leu-Gly-Gly-Thr-Val-Gln-Ala-Gly; (SEQ ID No. 136), wherein Xaa may be any amino acid.

Figure 1A:
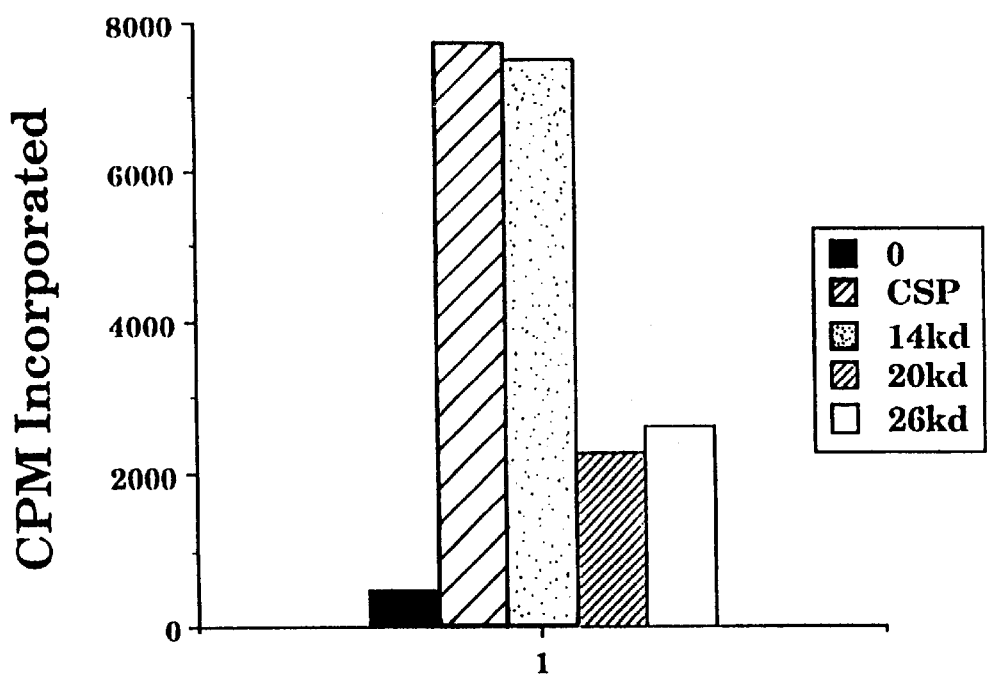
Figure 1B:
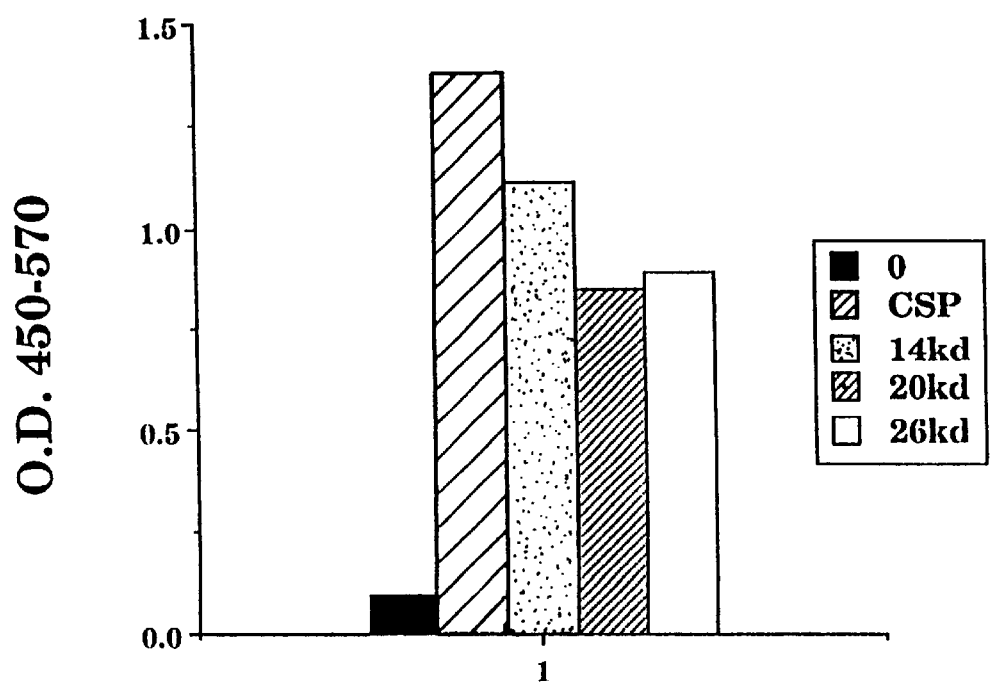
Figure 1C:
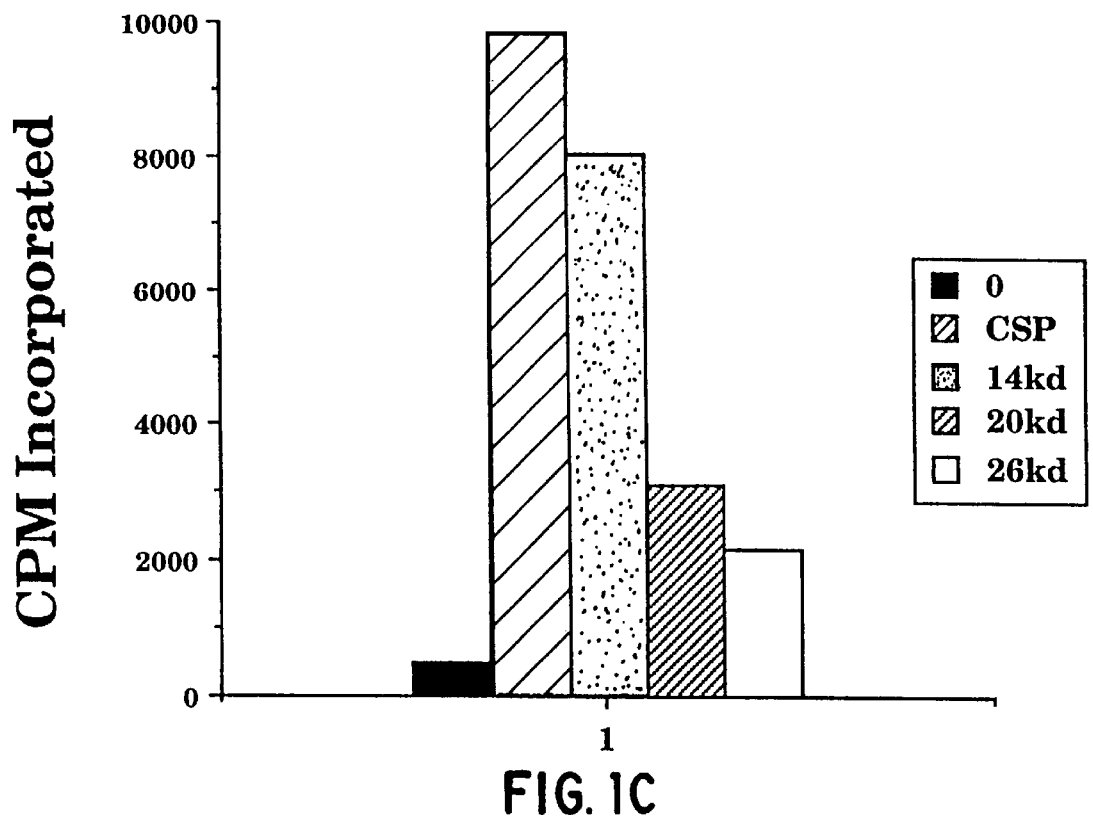
Figure 1D:
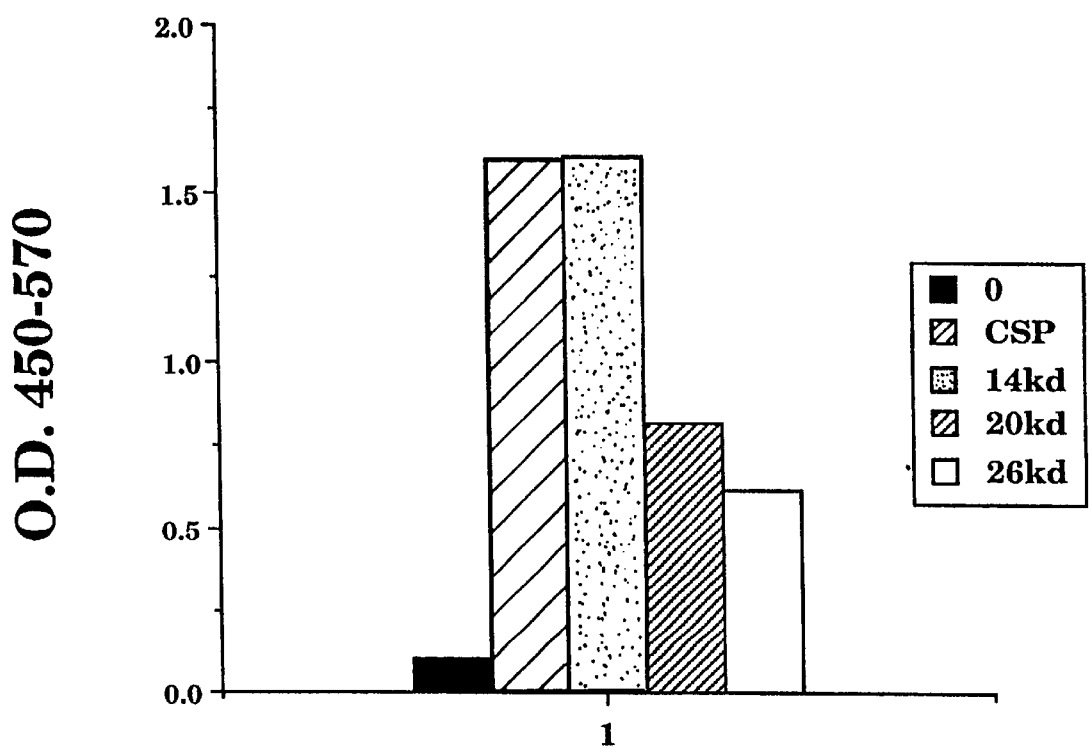
Figure 2A:
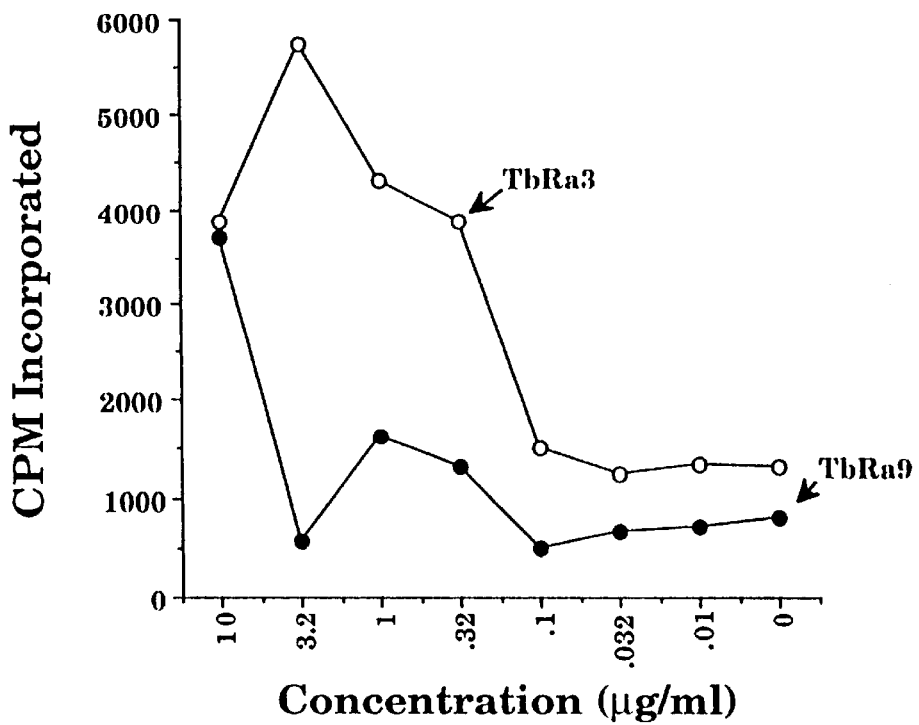
Figure 2B:
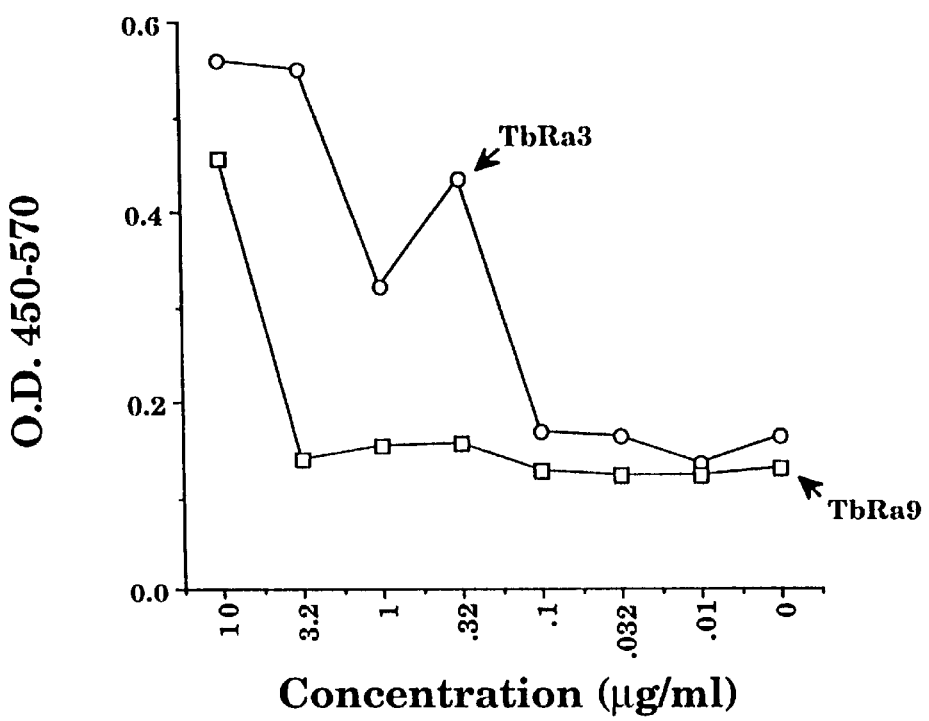

Using the assays described above, these polypeptides were shown to induce proliferation and IFN-γ production in PBMC preparations. FIGS. 1A and B show the results of such assays using PBMC preparations from a first and a second donor, respectively.

DNA sequences that encode the antigens designated as (a), (c), (d) and (g) above were obtained by screening a genomic M. tuberculosis library using $^{32}$P end labeled degenerate oligonucleotides corresponding to the N-terminal sequence and containing M. tuberculosis codon bias. The screen performed using a probe corresponding to antigen (a) above identified a clone having the sequence provided in SEQ ID No. 101. The polypeptide encoded by SEQ ID No. 101 is provided in SEQ ID No. 102. The screen performed using a probe corresponding to antigen (g) above identified a clone having the sequence provided in SEQ ID No. 52. The polypeptide encoded by SEQ ID No. 52 is provided in SEQ ID No. 53. The screen performed using a probe corresponding to antigen (d) above identified a clone having the sequence provided in SEQ ID No. 24, and the screen performed with a probe corresponding to antigen (c) identified a clone having the sequence provided in SEQ ID No: 25.

The above amino acid sequences were compared to known amino acid sequences in the gene bank using the DNA STAR system. The database searched contains some 173,000 proteins and is a combination of the Swiss, PIR databases along with translated protein sequences (Version 87). No significant homologies to the amino acid sequences for antigens (a)–(h) and (l) were detected.

The amino acid sequence for antigen (i) was found to be homologous to a sequence from M. leprae. The full length M. leprae sequence was amplified from genomic DNA using the sequence obtained from GENBANK. This sequence was then used to screen the M. tuberculosis library described below in Example 2 and a full length copy of the M. tuberculosis homologue was obtained (SEQ ID No. 99).

The amino acid sequence for antigen (j) was found to be homologous to a known M. tuberculosis protein translated from a DNA sequence. To the best of the inventors' knowledge, this protein has not been previously shown to possess T-cell stimulatory activity. The amino acid sequence for antigen (k) was found to be related to a sequence from M. leprae.

In the proliferation and IFN-γ assays described above, using three PPD positive donors, the results for representative antigens provided above are presented in Table 1:

TABLE 1

RESULTS OF PBMC PROLIFERATION AND IFN-γ ASSAYS

| Sequence | Proliferation | IFN-γ |
|---|---|---|
| (a) | + | − |
| (c) | +++ | +++ |
| (d) | ++ | ++ |
| (g) | +++ | +++ |
| (h) | +++ | +++ |

In Table 1, responses that gave a stimulation index (SI) of between 2 and 4 (compared to cells cultured in medium alone) were scored as +, an SI of 4–8 or 2–4 at a concentration of 1 µg or less was scored as ++ and an SI of greater than 8 was scored as +++. The antigen of sequence (i) was found to have a high SI (+++) for one donor and lower SI (++ and +) for the two other donors in both proliferation and IFN-γ assays. These results indicate that these antigens are capable of inducing proliferation and/or interferon-γ production.

Example 2

Use of Patient Sera to Isolate M. Tuberculosis Antigens

This example illustrates the isolation of antigens from M. tuberculosis lysate by screening with serum from M. tuberculosis-infected individuals.

Dessicated M. tuberculosis H37Ra (Difco Laboratories) was added to a 2% NP40 solution, and alternately homogenized and sonicated three times. The resulting suspension was centrifuged at 13,000 rpm in microfuge tubes and the supernatant put through a 0.2 micron syringe filter. The filtrate was bound to Macro Prep DEAE beads (BioRad, Hercules, Calif.). The beads were extensively washed with 20 mM Tris pH 7.5 and bound proteins eluted with 1M NaCl. The 1M NaCl elute was dialyzed overnight against 10 mM Tris, pH 7.5. Dialyzed solution was treated with DNase and RNase at 0.05 mg/ml for 30 min. at room temperature and then with α-D-mannosidase, 0.5 U/mg at pH 4.5 for 3–4 hours at room temperature. After returning to pH 7.5, the material was fractionated via FPLC over a Bio Scale-Q-20 column (BioRad). Fractions were combined into nine pools, concentrated in a Centriprep 10 (Amicon, Beverley, Mass.) and then screened by Western blot for serological activity using a serum pool from M. tuberculosis-infected patients which was not immunoreactive with other antigens of the present invention.

The most reactive fraction was run in SDS-PAGE and transferred to PVDF. A band at approximately 85 Kd was cut out yielding the sequence:

(m) Xaa-Tyr-Ile-Ala-Tyr-Xaa-Thr-Thr-Ala-Gly-Ile-Val-Pro-Gly-Lys-Ile-Asn-Val-His-Leu-Val; (SEQ ID No. 137), wherein Xaa may be any amino acid.

Comparison of this sequence with those in the gene bank as described above, revealed no significant homologies to known sequences.

A DNA sequence that encodes the antigen designated as (m) above was obtained by screening a genomic M. tuberculosis Erdman strain library using labeled degenerate oligonucleotides corresponding to the N-terminal sequence of SEQ ID NO:137. A clone was identified having the DNA sequence provided in SEQ ID NO: 203. This sequence was found to encode the amino acid sequence provided in SEQ ID NO: 204. Comparison of these sequences with those in the genebank revealed some similarity to sequences previously identified in M. tuberculosis and M. bovis.

Example 3

Preparation of DNA Sequences Encoding M. Tuberculosis Antigens

This example illustrates the preparation of DNA sequences encoding M. tuberculosis antigens by screening a M. tuberculosis expression library with sera obtained from patients infected with M. tuberculosis, or with anti-sera raised against soluble M. tuberculosis antigens.

A. Preparation of M. Tuberculosis Soluble Antigens Using Rabbit Anti-sera Raised Against M. Tuberculosis Supernatant Genomic DNA was isolated from the *M. tuberculosis* strain H37Ra. The DNA was randomly sheared and used to construct an expression library using the Lambda ZAP expression system (Stratagene, La Jolla, Calif.). Rabbit anti-sera was generated against secretory proteins of the *M. tuberculosis* strains H37Ra, H37Rv and Erdman by immunizing a rabbit with concentrated supernatant of the M tuberculosis cultures. Specifically, the rabbit was first immunized subcutaneously with 200 μg of protein antigen in a total volume of 2 ml containing 10 μg muramyl dipeptide (Calbiochem, La Jolla, Calif.) and 1 ml of incomplete Freund's adjuvant. Four weeks later the rabbit was boosted subcutaneously with 100 μg antigen in incomplete Freund's adjuvant. Finally, the rabbit was immunized intravenously four weeks later with 50 μg protein antigen. The anti-sera were used to screen the expression library as described in Sambrook et al., *Molecular Cloning: A Laboratory Manual*, Cold Spring Harbor Laboratories, Cold Spring Harbor, N.Y., 1989. Bacteriophage plaques expressing immunoreactive antigens were purified. Phagemid from the plaques was rescued and the nucleotide sequences of the *M. tuberculosis* clones deduced.

Thirty two clones were purified. Of these, 25 represent sequences that have not been previously identified in human *M. tuberculosis*. Recombinant antigens were expressed and purified antigens used in the immunological analysis described in Example 1. Proteins were induced by IPTG and purified by gel elution, as described in Skeiky et al., *J. Exp. Med.* 181:1527–1537, 1995. Representative sequences of DNA molecules identified in this screen are provided in SEQ ID Nos.: 1–25. The corresponding predicted amino acid sequences are shown in SEQ ID Nos. 63–87.

On comparison of these sequences with known sequences in the gene bank using the databases described above, it was found that the clones referred to hereinafter as TbRA2A, TbRA16, TbRA18, and TbRA29 (SEQ ID Nos. 76, 68, 70, 75) show some homology to sequences previously identified in *Mycobacterium leprae* but not in *M. tuberculosis*. TbRA2A was found to be a lipoprotein, with a six residue lipidation sequence being located adjacent to a hydrophobic secretory sequence. TbRA11, TbRA26, TbRA28 and TbDPEP (SEQ ID Nos.: 65, 73, 74, 53) have been previously identified in *M. tuberculosis*. No significant homologies were found to TbRA1, TbRA3, TbRA4, TbRA9, TbRA10, TbRA13, TbRA17, TbRa19, TbRA29, TbRA32, TbRA36 and the overlapping clones TbRA35 and TbRA12 (SEQ ID Nos. 63, 77, 81, 82, 64, 67, 69, 71, 75, 78, 80, 79, 66). The clone TbRa24 is overlapping with clone TbRa29.

The results of PBMC proliferation and interferon-γ assays performed on representative recombinant antigens, and using T-cell preparations from several different *M. tuberculosis*-immune patients, are presented in Tables 2 and 3, respectively.

TABLE 2

RESULTS OF PBMC PROLIFERATION TO REPRESENTATIVE SOLUBLE ANTIGENS

| | Patient | | | | | | | | | | | | |
|---|---|---|---|---|---|---|---|---|---|---|---|---|---|
| Antigen | 1 | 2 | 3 | 4 | 5 | 6 | 7 | 8 | 9 | 10 | 11 | 12 | 13 |
| TbRa1 | – | – | ± | ++ | – | – | ± | ± | – | – | + | ± | – |
| TbRa3 | – | ± | ++ | – | ± | – | – | ++ | ± | – | – | – | – |
| TbRa9 | – | – | nt | nt | ++ | ++ | nt | nt | nt | nt | nt | nt | nt |
| TbRa10 | – | – | ± | ± | ± | + | nt | ± | – | + | ± | ± | – |
| TbRa11 | ± | ± | + | ++ | ++ | + | nt | – | ++ | ++ | ++ | ± | nt |
| TbRa12 | – | – | + | + | ± | ++ | + | ± | ± | – | + | – | – |
| TbRa16 | nt | nt | nt | nt | – | + | nt | nt | nt | nt | nt | nt | nt |
| TbRa24 | nt | nt | nt | nt | – | – | nt | nt | nt | nt | nt | nt | nt |
| TbRa26 | – | + | nt | nt | – | – | nt | nt | nt | nt | nt | nt | nt |
| TbRa29 | nt | nt | nt | nt | – | – | nt | nt | nt | nt | nt | nt | nt |
| TbRa35 | ++ | nt | ++ | ++ | ++ | ++ | nt | ++ | ++ | ++ | ++ | ++ | nt |
| TbRaB | nt | nt | nt | nt | – | – | nt | nt | nt | nt | nt | nt | nt |
| TbRaC | nt | nt | nt | nt | – | – | nt | nt | nt | nt | nt | nt | nt |
| TbRaD | nt | nt | nt | nt | – | – | nt | nt | nt | nt | nt | nt | nt |
| AAMK | – | – | ± | – | – | – | nt | – | – | – | nt | ± | nt |
| YY | – | – | – | – | – | – | nt | – | – | – | nt | + | nt |
| DPEP | – | + | – | ++ | – | – | nt | ++ | ± | + | ± | ± | nt |
| Control | – | – | – | – | – | – | – | – | – | – | – | – | – | nt = not tested

TABLE 3

RESULTS OF PBMC INTERFERON-γ PRODUCTION TO REPRESENTATIVE SOLUBLE ANTIGENS

| | Patient | | | | | | | | | | | | |
|---|---|---|---|---|---|---|---|---|---|---|---|---|---|
| Antigen | 1 | 2 | 3 | 4 | 5 | 6 | 7 | 8 | 9 | 10 | 11 | 12 | 13 |
| TbRa1 | + | ++ | | +++ | + | – | | ± | – | – | + | ± | – |
| TbRa3 | – | ± | ++ | – | ± | – | – | ++ | ± | – | – | – | – |
| TbRa9 | ++ | + | nt | nt | ++ | – | nt | nt | nt | nt | nt | nt | nt |
| TbRa10 | + | + | ± | ± | ± | + | nt | ± | – | + | ± | ± | – |
| TbRa11 | | ± | + | ++ | ++ | + | nt | – | ++ | ++ | ++ | ± | nt |
| TbRa12 | – | – | + | + | ± | +++ | + | ± | ± | – | + | – | – |
| TbRa16 | nt | nt | nt | nt | + | + | nt | nt | nt | nt | nt | nt | nt |
| TbRa24 | nt | nt | nt | nt | + | – | nt | nt | nt | nt | nt | nt | nt |
| TbRa26 | ++ | ++ | nt | nt | + | + | nt | nt | nt | nt | nt | nt | nt |
| TbRa29 | nt | nt | nt | nt | + | – | nt | nt | nt | nt | nt | nt | nt |
| TbRa35 | ++ | nt | ++ | ++ | +++ | +++ | nt | ++ | ++ | +++ | +++ | ++ | nt |
| TbRaB | nt | nt | nt | nt | ++ | + | nt | nt | nt | nt | nt | nt | nt |
| TbRaC | nt | nt | nt | nt | + | + | nt | nt | nt | nt | nt | nt | nt |
| TbRaD | nt | nt | nt | nt | + | + | nt | nt | nt | nt | nt | nt | nt |
| AAMK | – | – | ± | – | – | – | nt | – | – | – | nt | ± | nt |
| YY | – | – | – | – | – | – | nt | – | – | – | nt | + | nt |
| DPEP | + | + | + | +++ | + | – | nt | +++ | ± | + | ± | ± | nt |
| Control | – | – | – | – | – | – | – | – | – | – | – | – | – |

In Tables 2 and 3, responses that gave a stimulation index (SI) of between 1.2 and 2 (compared to cells cultured in medium alone) were scored as +, a SI of 2–4 was scored as +, as SI of 4–8 or 2–4 at a concentration of 1 μg or less was scored as ++ and an SI of greater than 8 was scored as +++. In addition, the effect of concentration on proliferation and interferon-γ production is shown for two of the above antigens in the attached Figure. For both proliferation and interferon-γ production, TbRa3 was scored as ++ and TbRa9 as +.

These results indicate that these soluble antigens can induce proliferation and/or interferon-γ production in T-cells derived from an *M. tuberculosis*-immune individual.

B. Use of Sera from Patients Having Pulmonary or Pleural Tuberculosis to Identify DNA Sequences Encoding *M. Tuberculosis* Antigens The genomic DNA library described above, and an additional H37Rv library, were screened using pools of sera obtained from patients with active tuberculosis. To prepare the H37Rv library, *M. tuberculosis* strain H37Rv genomic DNA was isolated, subjected to partial Sau3A digestion and used to construct an expression library using the Lambda Zap expression system (Stratagene, La Jolla, Calif.). Three different pools of sera, each containing sera obtained from three individuals with active pulmonary or pleural disease, were used in the expression screening. The pools were designated TbL, ThM and TbH, referring to relative reactivity with H37Ra lysate (i.e., TbL=low reactivity, TbM=medium reactivity and TbH=high reactivity) in both ELISA and immunoblot format. A fourth pool of sera from seven patients with active pulmonary tuberculosis was also employed. All of the sera lacked increased reactivity with the recombinant 38 kD *M. tuberculosis* H37Ra phosphate-binding protein.

All pools were pre-adsorbed with *E. coli* lysate and used to screen the H37Ra and H37Rv expression libraries, as described in Sambrook et al., *Molecular Cloning: A Laboratory Manual*, Cold Spring Harbor Laboratories, Cold Spring Harbor, N.Y., 1989. Bacteriophage plaques expressing immunoreactive antigens were purified. Phagemid from the plaques was rescued and the nucleotide sequences of the *M. tuberculosis* clones deduced.

Thirty two clones were purified. Of these, 31 represented sequences that had not been previously identified in human *M. tuberculosis*. Representative sequences of the DNA molecules identified are provided in SEQ ID Nos.: 26–51 and 105. Of these, TbH-8-2 (SEQ. ID NO. 105) is a partial clone of TbH-8, and TbH-4 (SEQ. ID NO. 43) and TbH-4-FWD (SEQ. ID NO. 44) are non-contiguous sequences from the same clone. Amino acid sequences for the antigens hereinafter identified as Tb38-1, TbH-4, TbH-8, TbH-9, and TbH-12 are shown in SEQ ID Nos.: 88–92. Comparison of these sequences with known sequences in the gene bank using the databases identified above revealed no significant homologies to TbH-4, TbH-8, TbH-9 and TbM-3, although weak homologies were found to TbH-9. TbH-12 was found to be homologous to a 34 kD antigenic protein previously identified in *M. paratuberculosis* (Acc. No. S28515). Tb38-1 was found to be located 34 base pairs upstream of the open reading frame for the antigen ESAT-6 previously identified in *M. bovis* (Acc. No. U34848) and in *M. tuberculosis* (Sorensen et al., *Infec. Immun.* 63:1710–1717, 1995).

Probes derived from Tb38-1 and TbH-9, both isolated from an H37Ra library, were used to identify clones in an H37Rv library. Tb38-1 hybridized to Tb38-1F2, Tb38-1F3, Tb38-1F5 and Tb38-1F6 (SEQ. ID NOS. 112, 113, 116, 118, and 119). (SEQ ID NOS. 112 and 113 are non-contiguous sequences from clone Tb38-1F2.) Two open reading frames were deduced in Tb38-IF2; one corresponds to Tb37FL (SEQ. ID. NO. 114), the second, a partial sequence, may be the homologue of Tb38-1 and is called Tb38-IN (SEQ. ID NO. 115). The deduced amino acid sequence of Tb38-1F3 is presented in SEQ. ID. NO. 117. A TbH-9 probe identified three clones in the H37Rv library: TbH-9-FL (SEQ. ID NO. 106), which may be the homologue of TbH-9 (R37Ra), TbH-9-1 (SEQ. ID NO. 108), and TbH-9-4 (SEQ. ID NO. 110), all of which are highly related sequences to TbH-9. The deduced amino acid sequences for these three clones are presented in SEQ ID NOS. 107, 109 and 111.

Further screening of the *M. tuberculosis* genomic DNA library, as described above, resulted in the recovery of ten additional reactive clones, representing seven different genes. One of these genes was identified as the 38 Kd antigen discussed above, one was determined to be identical to the 14 Kd alpha crystallin heat shock protein previously shown to be present in *M. tuberculosis*, and a third was determined to be identical to the antigen TbH-8 described above. The determined DNA sequences for the remaining five clones (hereinafter referred to as TbH-29, TbH-30, TbH-32 and TbH-33) are provided in SEQ ID NO: 138–141, respectively, with the corresponding predicted amino acid sequences being provided in SEQ ID NO: 142–145, respectively. The DNA and amino acid sequences for these antigens were compared with those in the gene bank as described above. No homologies were found to the 5' end of TbH-29 (which contains the reactive open reading frame), although the 3' end of TbH-29 was found to be identical to the *M. tuberculosis* cosmid Y227. TbH-32 and TbH-33 were found to be identical to the previously identified *M. tuberculosis* insertion element IS6110 and to the *M. tuberculosis* cosmid Y50, respectively. No significant homologies to TbH-30 were found.

Positive phagemid from this additional screening were used to infect *E. coli* XL-1 Blue MRF', as described in Sambrook et al., supra. Induction of recombinant protein was accomplished by the addition of IPTG. Induced and uninduced lysates were run in duplicate on SDS-PAGE and transferred to nitrocellulose filters. Filters were reacted with human *M. tuberculosis* sera (1:200 dilution) reactive with TbH and a rabbit sera (1:200 or 1:250 dilution) reactive with the N-terminal 4 Kd portion of lacZ. Sera incubations were performed for 2 hours at room temperature. Bound antibody was detected by addition of $^{125}$I-labeled Protein A and subsequent exposure to film for variable times ranging from 16 hours to 11 days. The results of the immunoblots are summarized in Table 4.

TABLE 4

| Antigen | Human M. tb Sera | Anti-lacZ Sera |
|---|---|---|
| TbH-29 | 45 Kd | 45 Kd |
| TbH-30 | No reactivity | 29 Kd |
| TbH-32 | 12 Kd | 12 Kd |
| TbH-33 | 16 Kd | 16 Kd |

Positive reaction of the recombinant human *M. tuberculosis* antigens with both the human *M. tuberculosis* sera and anti-lacZ sera indicate that reactivity of the human *M. tuberculosis* sera is directed towards the fusion protein. Antigens reactive with the anti-lacZ sera but not with the human *M. tuberculosis* sera may be the result of the human *M. tuberculosis* sera recognizing conformational epitopes, or the antigen-antibody binding kinetics may be such that the 2 hour sera exposure in the immunoblot is not sufficient.

The results of T-cell assays performed on Tb38-1, ESAT-6 and other representative recombinant antigens are presented in Tables 5A, B and 6, respectively, below:

TABLE 5A

RESULTS OF PBMC PROLIFERATION TO REPRESENTATIVE ANTIGENS

| Antigen | Donor | | | | | | | | | | |
|---|---|---|---|---|---|---|---|---|---|---|---|
|  | 1 | 2 | 3 | 4 | 5 | 6 | 7 | 8 | 9 | 10 | 11 |
| Tb38.1 | +++ | + | – | – | – | ++ | – | + | – | ++ | +++ |
| ESAT-6 | +++ | + | + | + | – | + | – | + | + | ++ | +++ |
| TbH-9 | ++ | ++ | – | ++ | ± | ± | ++ | ++ | ++ | ++ | ++ |

TABLE 5B

RESULTS OF PBMC INTERFERON-γ PRODUCTION TO REPRESENTATIVE ANTIGENS

| Antigen | Donor | | | | | | | | | | |
|---|---|---|---|---|---|---|---|---|---|---|---|
|  | 1 | 2 | 3 | 4 | 5 | 6 | 7 | 8 | 9 | 10 | 11 |
| Tb38.1 | +++ | + | – | + | + | +++ | – | ++ | – | +++ | +++ |
| ESAT-6 | +++ | + | + | + | + | + | – | + | + | +++ | +++ |
| TbH-9 | ++ | ++ | – | +++ | ± | ± | +++ | +++ | ++ | +++ | ++ |

TABLE 6

SUMMARY OF T-CELL RESPONSES TO REPRESENTATIVE ANTIGENS

| Antigen | Proliferation | | | Interferon-γ | | | |
|---|---|---|---|---|---|---|---|
|  | patient 4 | patient 5 | patient 6 | patient 4 | patient 5 | patient 6 | total |
| TbH9 | ++ | ++ | ++ | +++ | ++ | ++ | 13 |
| TbM7 | – | + | – | ++ | + | – | 4 |
| TbH5 | – | + | + | ++ | ++ | ++ | 8 |
| TbL23 | – | + | ± | ++ | ++ | + | 7.5 |
| TbH4 | – | ++ | ± | ++ | ++ | ± | 7 |
| control | – | – | – | – | – | – | 0 |

Figure 3A:
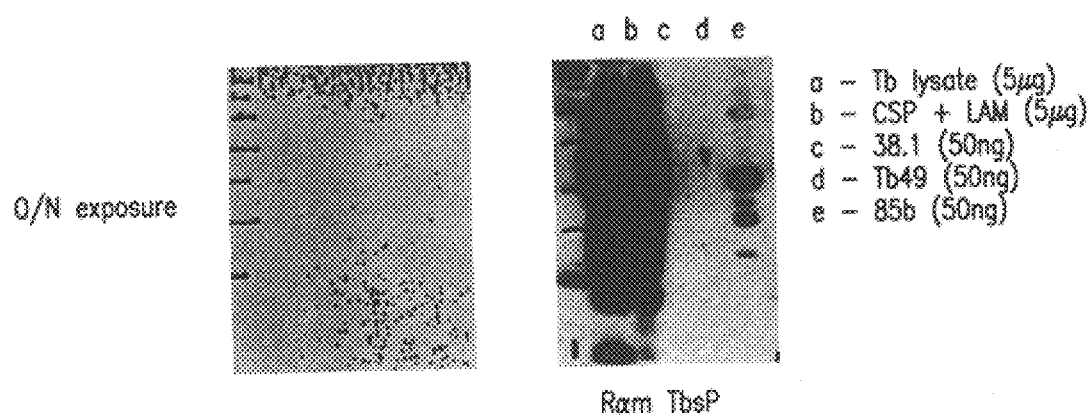
Figure 3B:
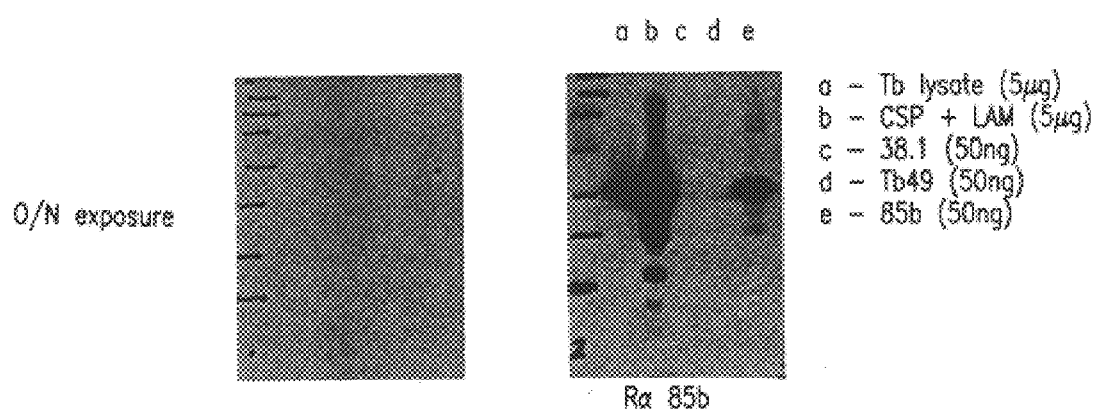
Figure 3C:
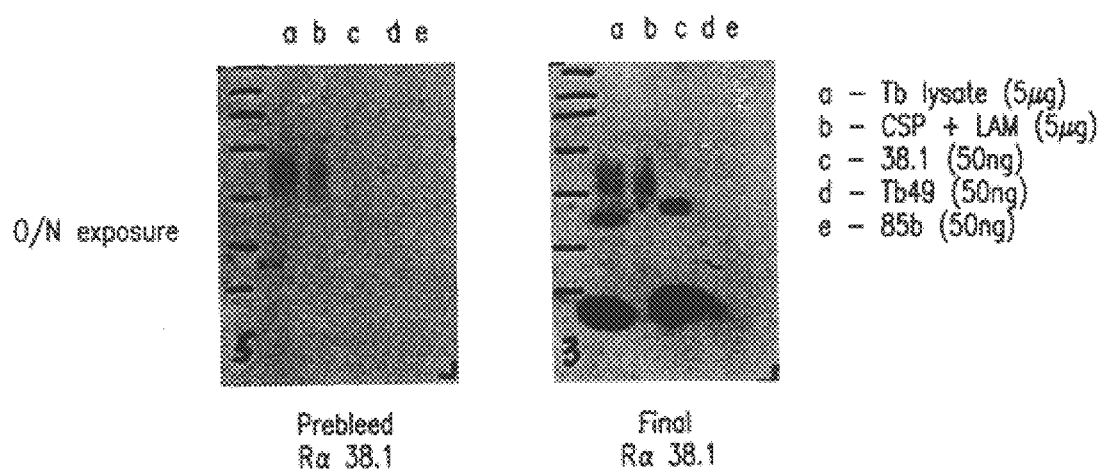
Figure 3D:
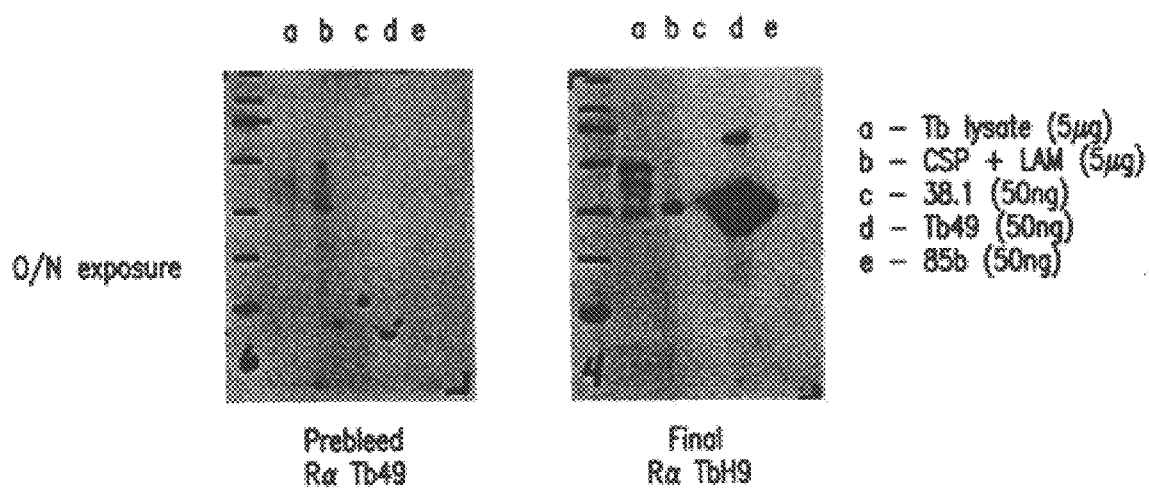

These results indicate that both the inventive *M. tuberculosis* antigens and ESAT-6 can induce proliferation and/or interferon-γ production in T-cells derived from an *M. tuberculosis*-immune individual. To the best of the inventors' knowledge, ESAT-6 has not been previously shown to stimulate human immune responses A set of six overlapping peptides covering the amino acid sequence of the antigen Tb38-1 was constructed using the method described in Example 6. The sequences of these peptides, hereinafter referred to as pep1–6, are provided in SEQ ID Nos. 93–98, respectively. The results of T-cell assays using these peptides are shown in Tables 7 and 8. These results confirm the existence, and help to localize T-cell epitopes within Tb38-1 capable of inducing proliferation and interferon-γ production in T-cells derived from an *M. tuberculosis* immune individual.

TABLE 7

RESULTS OF PBMC PROLIFERATION TO TB38-1 PEPTIDES

| | Patient | | | | | | | | | | | | |
|---|---|---|---|---|---|---|---|---|---|---|---|---|---|
| Peptide | 1 | 2 | 3 | 4 | 5 | 6 | 7 | 8 | 9 | 10 | 11 | 12 | 13 |
| pep1 | − | − | − | − | ± | − | − | − | − | ± | − | − | + |
| pep2 | ± | − | − | − | ± | − | − | − | ± | ± | − | − | + |
| pep3 | − | − | − | − | − | − | − | − | ± | − | − | − | ± |
| pep4 | ++ | − | − | − | − | − | + | − | ± | ± | − | − | + |
| pep5 | ++ | ± | − | − | − | − | + | − | ± | − | − | − | + |
| pep6 | − | ++ | − | − | − | − | ± | − | ± | + | − | − | + |
| Control | − | − | − | − | − | − | − | − | − | − | − | − | − |

TABLE 8

RESULTS OF PBMC INTERFERON-γ PRODUCTION TO TB38-1 PEPTIDES

| | Patient | | | | | | | | | | | | |
|---|---|---|---|---|---|---|---|---|---|---|---|---|---|
| Peptide | 1 | 2 | 3 | 4 | 5 | 6 | 7 | 8 | 9 | 10 | 11 | 12 | 13 |
| pep1 | + | − | − | − | ± | − | − | − | − | ± | − | − | + |
| pep2 | | − | − | − | ± | − | − | − | ± | ± | − | − | + |
| pep3 | − | − | − | − | − | − | − | − | ± | − | − | − | ± |
| pep4 | ++ | − | − | − | − | − | + | − | ± | ± | − | − | + |
| pep5 | ++ | ± | − | − | − | − | + | − | ± | − | − | − | + |
| pep6 | + | ++ | − | − | − | − | ± | − | ± | + | − | − | + |
| Control | − | − | − | − | − | − | − | − | − | − | − | − | − |

Studies were undertaken to determine whether the antigens TbH-9 and Tb38-1 represent cellular proteins or are secreted into *M. tuberculosis* culture media. In the first study, rabbit sera were raised against A) secretory proteins of *M. tuberculosis*, B) the known secretory recombinant *M. tuberculosis* antigen 85b, C) recombinant Tb38-1 and D) recombinant TbH-9, using protocols substantially the same as that as described in Example 3A. Total *M. tuberculosis* lysate, concentrated supernatant of *M. tuberculosis* cultures and the recombinant antigens 85b, TbH-9 and Tb38-1 were resolved on denaturing gels, immobilized on nitrocellulose membranes and duplicate blots were probed using the rabbit sera described above.

The results of this analysis using control sera (panel I) and antisera (panel II) against secretory proteins, recombinant 85b, recombinant Tb38-1 and recombinant TbH-9 are shown in FIGS. 3A–D, respectively, wherein the lane designations are as follows: 1) molecular weight protein standards; 2) 5 μg of *M. tuberculosis* lysate; 3) 5 μg secretory proteins; 4) 50 ng recombinant Tb38-1; 5) 50 ng recombinant TbH-9; and 6) 50 ng recombinant 85b. The recombinant antigens were engineered with six terminal histidine residues and would therefore be expected to migrate with a mobility approximately 1 kD larger that the native protein. In FIG. 3D, recombinant TbH-9 is lacking approximately 10 kD of the full-length 42 kD antigen, hence the significant difference in the size of the immunoreactive native TbH-9 antigen in the lysate lane (indicated by an arrow). These results demonstrate that Tb38-1 and TbH-9 are intracellular antigens and are not actively secreted by M. tuberculosis.

Figure 4A:
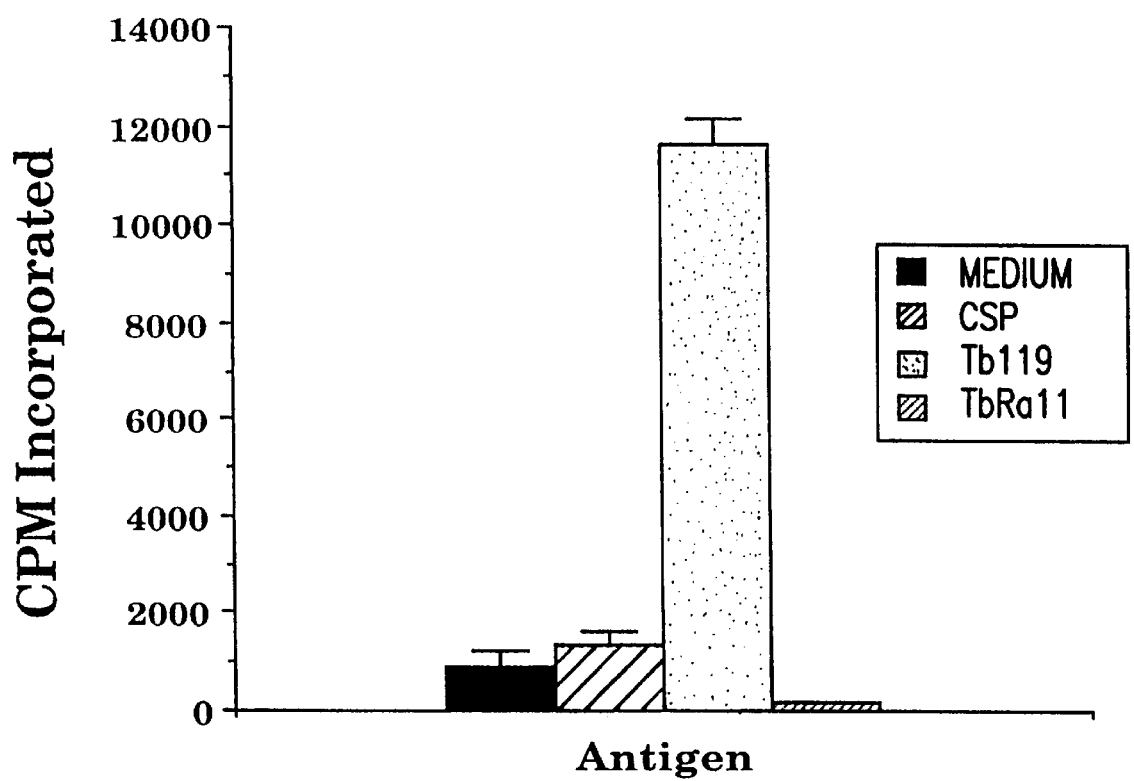
FIG. 4A illustrates the stimulation of proliferation in a TbH-9-specific T cell clone by secretory *M. tuberculosis* proteins, recombinant TbH-9 and a control antigen, TbRa11.
Figure 4B:
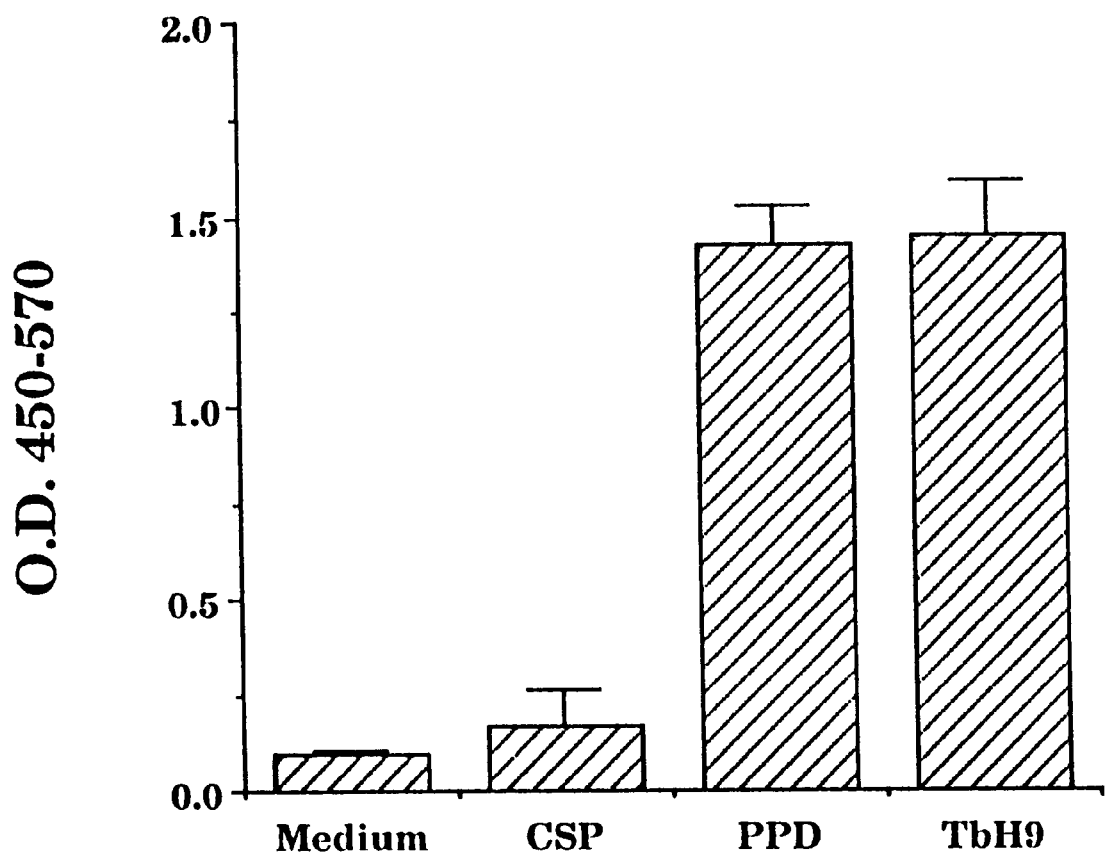
FIG. 4B illustrates the stimulation of interferon-γ production in a TbH-9-specific T cell clone by secretory *M. tuberculosis* proteins, PPD and recombinant TbH-9.

The finding that TbH-9 is an intracellular antigen was confirmed by determining the reactivity of TbH-9-specific human T cell clones to recombinant TbH-9, secretory M. tuberculosis proteins and PPD. A TbH-9-specific T cell clone (designated 131TbH-9) was generated from PBMC of a healthy PPD-positive donor. The proliferative response of 131TbH-9 to secretory proteins, recombinant TbH-9 and a control M. tuberculosis antigen, TbRa11, was determined by measuring uptake of tritiated thymidine, as described in Example 1. As shown in FIG. 4A, the clone 131TbH-9 responds specifically to TbH-9, showing that TbH-9 is not a significant component of M. tuberculosis secretory proteins. FIG. 4B shows the production of IFN-γ by a second TbH-9-specific T cell clone (designated PPD 800–10) prepared from PBMC from a healthy PPD-positive donor, following stimulation of the T cell clone with secretory proteins, PPD or recombinant TbH-9. These results further confirm that TbH-9 is not secreted by M. tuberculosis.

C. Use of Sera from Patients Having Extrapulmonary Tuberculosis to Identify DNA Sequences Encoding M. Tuberculosis Antigens Genomic DNA was isolated from M. tuberculosis Erdman strain, randomly sheared and used to construct an expression library employing the Lambda ZAP expression system (Stratagene, La Jolla, Calif.). The resulting library was screened using pools of sera obtained from individuals with extrapulmonary tuberculosis, as described above in Example 3B, with the secondary antibody being goat anti-human IgG+A+M (H+L) conjugated with alkaline phosphatase.

Eighteen clones were purified. Of these, 4 clones (hereinafter referred to as XP14, XP24, XP31 and XP32) were found to bear some similarity to known sequences. The determined DNA sequences for XP14, XP24 and XP31 are provided in SEQ ID Nos.: 156–158, respectively, with the 5' and 3' DNA sequences for XP32 being provided in SEQ ID Nos.: 159 and 160, respectively. The predicted amino acid sequence for XP14 is provided in SEQ ID No: 161. The reverse complement of XP14 was found to encode the amino acid sequence provided in SEQ ID No.: 162.

Comparison of the sequences for the remaining 14 clones (hereinafter referred to as XP1–XP6, XP17–XP19, XP22, XP25, XP27, XP30 and XP36) with those in the genebank as described above, revealed no homologies with the exception of the 3' ends of XP2 and XP6 which were found to bear some homology to known M. tuberculosis cosmids. The DNA sequences for XP27 and XP36 are shown in SEQ ID Nos.: 163 and 164, respectively, with the 5' sequences for XP4, XP5, XP17 and XP30 being shown in SEQ ID Nos: 165–168, respectively, and the 5' and 3' sequences for XP2, XP3, XP6, XP18, XP19, XP22 and XP25 being shown in SEQ ID Nos: 169 and 170; 171 and 172; 173 and 174; 175 and 176; 177 and 178; 179 and 180; and 181 and 182, respectively. XP1 was found to overlap with the DNA sequences for TbH4, disclosed above. The full-length DNA sequence for TbH4-XP1 is provided in SEQ ID No.: 183. This DNA sequence was found to contain an open reading frame encoding the amino acid sequence shown in SEQ ID No: 184. The reverse complement of TbH4-XP1 was found to contain an open reading frame encoding the amino acid sequence shown in SEQ ID No.: 185. The DNA sequence for XP36 was found to contain two open reading frames encoding the amino acid sequence shown in SEQ ID Nos.: 186 and 187, with the reverse complement containing an open reading frame encoding the amino acid sequence shown in SEQ ID No.: 188.

Recombinant XPI protein was prepared as described above in Example 3B, with a metal ion affinity chromatography column being employed for purification. As illustrated in FIGS. 8A–B and 9A–B, using the assays described herein, recombinant XP1 was found to stimulate cell proliferation and IFN-γ production in T cells isolated from an M. tuberculosis-immune donors.

D. Use of a Lysate Positive Serum Pool from Patients Having Tuberculosis to Identify DNA Sequences Encoding M. Tuberculosis Antigens Genomic DNA was isolated from M. tuberculosis Erdman strain, randomly sheared and used to construct an expression library employing the Lambda Screen expression system (Novagen, Madison, Wis.), as described below in Example 6. Pooled serum obtained from M. tuberculosis-infected patients and that was shown to react with M. tuberculosis lysate but not with the previously expressed proteins 38 kD, Tb38-1, TbRa3, TbH4, DPEP and TbRa11, was used to screen the expression library as described above in Example 3B, with the secondary antibody being goat anti-human IgG+A+M (H+L) conjugated with alkaline phosphatase.

Twenty-seven clones were purified. Comparison of the determined cDNA sequences for these clones revealed no significant homologies to 10 of the clones (hereinafter referred to as LSER-10, LSER-11, LSER-12, LSER-13, LSER-16, LSER-18, LSER-23, LSER-24, LSER-25 and LSER-27). The determined 5' cDNA sequences for LSER-10, LSER-11, LSER-12, LSER-13, LSER-16 and LSER-25 are provided in SEQ ID NO: 242–247, respectively, with the corresponding predicted amino acid sequences for LSER-10, LSER-12, LSER-13, LSER-16 and LSER-25 being provided in SEQ ID NO: 248–252, respectively. The determined full-length cDNA sequences for LSER-18, LSER-23, LSER-24 and LSER-27 are shown in SEQ ID NO: 253–256, respectively, with the corresponding predicted amino acid sequences being provided in SEQ ID NO: 257–260. The remaining seventeen clones were found to show similarities to unknown sequences previously identified in M. tuberculosis. The determined 5' CDNA sequences for sixteen of these clones (hereinafter referred to as LSER-1, LSER-3, LSER-4, LSER-5, LSER-6, LSER-8, LSER-14, LSER-15, LSER-17, LSER-19, LSER-20, LSER-22, LSER-26, LSER-28, LSER-29 and LSER-30) are provided in SEQ ID NO: 261–276, respectively, with the corresponding predicted amino acid sequences for LSER-1, LSER-3, LSER-5, LSER-6, LSER-8, LSER-14, LSER-15, LSER-17, LSER-19, LSER-20, LSER-22, LSER-26, LSER-28, LSER-29 and LSER-30 being provided in SEQ ID NO: 277–291, respectively. The determined full-length cDNA sequence for the clone LSER-9 is provided in SEQ ID NO: 292. The reverse complement of LSER-6 (SEQ ID NO: 293) was found to encode the predicted amino acid sequence of SEQ ID NO: 294.

E. Preparation of M. Tuberculosis Soluble Antigens Using Rabbit Anti-Sera Raised Against M. Tuberculosis Fractionated Proteins M. tuberculosis lysate was prepared as described above in Example 2. The resulting material was fractionated by HPLC and the fractions screened by Western blot for serological activity with a serum pool from M. tuberculosis-infected patients which showed little or no immunoreactivity with other antigens of the present invention. Rabbit anti-sera was generated against the most reactive fraction using the method described in Example 3A. The anti-sera was used to screen an *M. tuberculosis* Erdman strain genomic DNA expression library prepared as described above. Bacteriophage plaques expressing immunoreactive antigens were purified. Phagemid from the plaques was rescued and the nucleotide sequences of the *M. tuberculosis* clones determined.

Ten different clones were purified. Of these, one was found to be TbRa35, described above, and one was found to be the previously identified *M. tuberculosis* antigen, HSP60. Of the remaining eight clones, seven (hereinafter referred to as RDIF2, RDIF5, RDIF8, RDIF10, RDIF 11 and RDIF12) were found to bear some similarity to previously identified *M. tuberculosis* sequences. The determined DNA sequences for RDIF2, RDIF5, RDIF8, RDIF10 and RDIF11 are provided in SEQ ID Nos.: 189–193, respectively, with the corresponding predicted amino acid sequences being provided in SEQ ID Nos: 194–198, respectively. The 5' and 3' DNA sequences for RDIF12 are provided in SEQ ID Nos.: 199 and 200, respectively. No significant homologies were found to the antigen RDIF-7. The determined DNA and predicted amino acid sequences for RDIF7 are provided in SEQ ID Nos.: 201 and 202, respectively. One additional clone, referred to as RDIF6 was isolated, however, this was found to be identical to RDIF5.

Recombinant RDIF6, RDIF8, RDIF10 and RDIF11 were prepared as described above. As shown in FIGS. 8A–B and 9A–B, these antigens were found to stimulate cell proliferation and IFN-γ production in T cells isolated from *M. tuberculosis*-immune donors.

Example 4

Purification and Characterization of a Polypeptide from Tuberculin Purified Protein Derivative An *M. tuberculosis* polypeptide was isolated from tuberculin purified protein derivative (PPD) as follows.

PPD was prepared as published with some modification (Seibert, F. et al., Tuberculin purified protein derivative. Preparation and analyses of a large quantity for standard. *The American Review of Tuberculosis* 44:9–25, 1941).

*M. tuberculosis* Rv strain was grown for 6 weeks in synthetic medium in roller bottles at 37° C. Bottles containing the bacterial growth were then heated to 100° C. in water vapor for 3 hours. Cultures were sterile filtered using a 0.22μ filter and the liquid phase was concentrated 20 times using a 3 kD cut-off membrane. Proteins were precipitated once with 50% ammonium sulfate solution and eight times with 25% ammonium sulfate solution. The resulting proteins (PPD) were fractionated by reverse phase liquid chromatography (RP-HPLC) using a C18 column (7.8×300 mM; Waters, Milford, Mass.) in a Biocad HPLC system (Perseptive Biosystems, Framingham, Mass.). Fractions were eluted from the column with a linear gradient from 0–100% buffer (0.1% TFA in acetonitrile). The flow rate was 10 ml/minute and eluent was monitored at 214 nm and 280 nm.

Six fractions were collected, dried, suspended in PBS and tested individually in *M. tuberculosis*-infected guinea pigs for induction of delayed type hypersensitivity (DTH) reaction. One fraction was found to induce a strong DTH reaction and was subsequently fractionated further by RP-HPLC on a microbore Vydac C18 column (Cat. No. 218TP5115) in a Perkin Elmer/Applied Biosystems Division Model 172 HPLC. Fractions were eluted with a linear gradient from 5–100% buffer (0.05% TFA in acetonitrile) with a flow rate of 80 μl/minute. Eluent was monitored at 215 nm. Eight fractions were collected and tested for induction of DTH in *M. tuberculosis*-infected guinea pigs. One fraction was found to induce strong DTH of about 16 mm induration. The other fractions did not induce detectable DTH. The positive fraction was submitted to SDS-PAGE gel electrophoresis and found to contain a single protein band of approximately 12 kD molecular weight.

This polypeptide, herein after referred to as DPPD, was sequenced from the amino terminal using a Perkin Elmer/Applied Biosystems Division Procise 492 protein sequencer as described above and found to have the N-terminal sequence shown in SEQ ID No.: 129. Comparison of this sequence with known sequences in the gene bank as described above revealed no known homologies. Four cyanogen bromide fragments of DPPD were isolated and found to have the sequences shown in SEQ ID Nos.: 130–133. A subsequent search of the *M. tuberculosis* genome database released by the Institute for Genomic Research revealed a match of the DPPD partial amino acid sequence with a sequence present within the *M. tuberculosis* cosmid MTY21C12. An open reading frame of 336 bp was identified. The full-length DNA sequence for DPPD is provided in SEQ ID NO: 240, with the corresponding full-length amino acid sequence being provided in SEQ ID NO: 241.

The ability of the antigen DPPD to stimulate human PBMC to proliferate and to produce IFN-γ was assayed as described in Example 1. As shown in Table 9, DPPD was found to stimulate proliferation and elicit production of large quantities of IFN-γ; more than that elicited by commercial PPD.

TABLE 9

RESULTS OF PROLIFERATION AND INTERFERON-γ ASSAYS TO DPPD

| PBMC Donor | Stimulator | Proliferation (CPM) | IFN-γ ($OD_{450}$) |
|---|---|---|---|
| A | Medium | 1,089 | 0.17 |
| | PPD (commercial) | 8,394 | 1.29 |
| | DPPD | 13,451 | 2.21 |
| B | Medium | 450 | 0.09 |
| | PPD (commercial) | 3,929 | 1.26 |
| | DPPD | 6,184 | 1.49 |
| C | Medium | 541 | 0.11 |
| | PPD (commercial) | 8,907 | 0.76 |
| | DPPD | 23,024 | >2.70 |

Example 5

Use of Sera from Tuberculosis-Infected Monkeys to Identify DNA Sequences Encoding *M. Tuberculosis* Antigens Genomic DNA was isolated from *M. tuberculosis* Erdman strain, randomly sheared and used to construct an expression library employing the Lambda ZAP expression system (Stratagene, La Jolla, Calif.). Serum samples were obtained from a cynomolgous monkey 18, 33, 51 and 56 days following infection with *M. tuberculosis* Erdman strain. These samples were pooled and used to screen the *M. tuberculosis* genomic DNA expression library using the procedure described above in Example 3C. Twenty clones were purified. The determined 5' DNA sequences for the clones referred to as MO-1, MO-2, MO-4, MO-8, MO-9, MO-26, MO-28, MO-29, MO-30, MO-34 and MO-35 are provided in SEQ ID NO: 215–225, respectively, with the corresponding predicted amino acid sequences being provided in SEQ ID NO: 226–236. The full-length DNA sequence of the clone MO-10 is provided in SEQ ID NO: 237, with the corresponding predicted amino acid sequence being provided in SEQ ID NO: 238. The 3' DNA sequence for the clone MO-27 is provided in SEQ ID NO: 239.

Clones MO-1, MO-30 and MO-35 were found to show a high degree of relatedness and showed some homology to a previously identified unknown *M. tuberculosis* sequence and to cosmid MTCI237. MO-2 was found to show some homology to aspartokinase from *M. tuberculosis*. Clones MO-3, MO-7 and MO-27 were found to be identical and to show a high degree of relatedness to MO-5. All four of these clones showed some homology to *M. tuberculosis* heat shock protein 70. MO-27 was found to show some homology to *M. tuberculosis* cosmid MTCY339. MO-4 and MO-34 were found to show some homology to cosmid SCY21B4 and *M. smegmatis* integration host factor, and were both found to show some homology to a previously identified, unknown *M. tuberculosis* sequence. MO-6 was found to show some homology to *M. tuberculosis* heat shock protein 65. MO-8, MO-9, MO-10, MO-26 and MO-29 were found to be highly related to each other and to show some homology to *M. tuberculosis* dihydrolipamide succinyltransferase. MO-28, MO-31 and MO-32 were found to be identical and to show some homology to a previously identified *M. tuberculosis* protein. MO-33 was found to show some homology to a previously identified 14 kDa *M. tuberculosis* heat shock protein.

Further studies using the above protocol resulted in the isolation of an additional four clones, hereinafter referred to as MO-12, MO-13, MO-19 and MO-39. The determined 5' cDNA sequences for these clones are provided in SEQ ID NO: 295–298, respectively, with the corresponding predicted protein sequences being provided in SEQ ID NO: 299–302, respectively. Comparison of these sequences with those in the gene bank as described above revealed no significant homologies to MO-39. MO-1 2, MO-13 and MO-19 were found to show some homologies to unknown sequences previously isolated from *M. tuberculosis*.

Example 6

Isolation of DNA Sequences Encoding *M. Tuberculosis* Antigens by Screening of a Novel Expression Library This example illustrates isolation of DNA sequences encoding *M. tuberculosis* antigens by screening of a novel expression library with sera from *M. tuberculosis*-infected patients that were shown to be unreactive with a panel of the recombinant *M. tuberculosis* antigens TbRa11, TbRa3, Tb38-1, TbH4, TbF and 38 kD.

Genomic DNA from *M. tuberculosis* Erdman strain was randomly sheared to an average size of 2 kb, and blunt ended with Klenow polymerase, followed by the addition of EcoRI adaptors. The insert was subsequently ligated into the Screen phage vector (Novagen, Madison, Wis.) and packaged in vitro using the PhageMaker extract (Novagen). The resulting library was screened with sera from several *M. tuberculosis* donors that had been shown to be negative on a panel of previously identified *M. tuberculosis* antigens as described above in Example 3B.

A total of 22 different clones were isolated. By comparison, screening of the λ Zap library described above using the same sera did not result in any positive hits. One of the clones was found to represent TbRa11, described above. The determined 5' cDNA sequences for 19 of the remaining 21 clones (hereinafter referred to as Erdsn1, Erdsn2, Erdsn4–Erdsn10, Erdsn12–18, Erdsn21–Erdsn23 and Erdsn25) are provided in SEQ ID NO: 303–322, respectively, with the determined 3' cDNA sequences for Erdsn1, Erdsn2, Erdsn4, Erdsn-5, Erdsn-7–Erdsn10, Erdsn12–18, Erdsn21–Erdsn23 and Erdsn25 being provided in SEQ ID NO: 323–341, respectively. The complete cDNA insert sequence for the clone Erdsn24 is provided in SEQ ID NO: 342. Comparison of the determined cDNA sequences with those in the gene bank revealed no significant homologies to the sequences provided in SEQ ID NO: 309, 316, 318–320, 322, 324, 328, 329, 333, 335, 337, 339 and 341. The sequences of SEQ ID NO: 303–308, 310–315, 317, 321, 323, 325–327, 330–332, 334, 336, 338, 340 and 342 were found to show some homology to unknown sequences previously identified in *M. tuberculosis*.

Example 7

Isolation of Soluble *M. Tuberculosis* Antigens Using Mass Spectrometry

This example illustrates the use of mass spectrometry to identify soluble *M. tuberculosis* antigens.

In a first approach, *M. tuberculosis* culture filtrate was screened by Western analysis using serum from a tuberculosis-infected individual. The reactive bands were excised from a silver stained gel and the amino acid sequences determined by mass spectrometry. The determined amino acid sequence for one of the isolated antigens is provided in SEQ ID NO: 343. Comparison of this sequence with those in the gene bank revealed homology to the 85b precursor antigen previously identified in *M. tuberculosis*.

In a second approach, the high molecular weight region of *M. tuberculosis* culture supernatant was studied. This area may contain immunodominant antigens which may be useful in the diagnosis of *M. tuberculosis* infection. Two known monoclonal antibodies, IT42 and IT57 (available from the Center for Disease Control, Atlanta, Ga.), show reactivity by Western analysis to antigens in this vicinity, although the identity of the antigens remains unknown. In addition, unknown high-molecular weight proteins have been described as containing a surrogate marker for *M. tuberculosis* infection in HIV-positive individuals (*Jnl. Infect. Dis.*, 176:133–143, 1997). To determine the identity of these antigens, two-dimensional gel electrophoresis and two-dimensional Western analysis were performed using the antibodies IT57 and IT42. Five protein spots in the high molecular weight region were identified, individually excised, enzymatically digested and subjected to mass spectrometric analysis.

The determined amino acid sequences for three of these spots (referred to as spots 1, 2 and 4) are provided in SEQ ID NO: 344, 345–346 and 347, respectively. Comparison of these sequences with those in the gene bank revealed that spot 1 is the previously identified PcK-1, a phosphoenolpyruvate kinase. The two sequences isolated from spot 2 were determined to be from two DNAks, previously identified in *M. tuberculosis* as heat shock proteins. Spot 4 was determined to be the previously identified *M. tuberculosis* protein Kat G. To the best of the inventors' knowledge, neither PcK-1 nor the two DNAks have previously been shown to have utility in the diagnosis of M. tuberculosis infection.

Example 8

Use of Representative Antigens for Diagnosis of Tuberculosis

This example illustrates the effectiveness of several representative polypeptides in skin tests for the diagnosis of M. tuberculosis infection.

Individuals were injected intradermnally with 100 μl of either PBS or PBS plus Tween 20™ containing either 0.1 μg of protein (for TbH-9 and TbRa35) or 1.0 μg of protein (for TbRa38-1). Induration was measured between 5–7 days after injection, with a response of 5 mm or greater being considered positive. Of the 20 individuals tested, 2 were PPD negative and 18 were PPD positive. Of the PPD positive individuals, 3 had active tuberculosis, 3 had been previously infected with tuberculosis and 9 were healthy. In a second study, 13 PPD positive individuals were tested with 0.1 μg TbRa11 in either PBS or PBS plus Tween 20™ as described above. The results of both studies are shown in Table 10.

TABLE 10

RESULTS OF DTH TESTING WITH REPRESENTATIVE ANTIGENS

|  | TbH-9 Pos/Total | Tb38-1 Pos/Total | TbRa35 Pos/Total | Cumulative Pos/Total | TbRa11 Pos/Total |
|---|---|---|---|---|---|
| PPD negative | 0/2 | 0/2 | 0/2 | 0/2 | |
| PPD positive | | | | | |
| healthy | 5/9 | 4/9 | 4/9 | 6/9 | 1/4 |
| prior TB | 3/5 | 2/5 | 2/5 | 4/5 | 3/5 |
| active | 3/4 | 3/4 | 0/4 | 4/4 | 1/4 |
| TOTAL | 11/18 | 9/18 | 6/18 | 14/18 | 5/13 |

Example 9

Synthesis of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

Example 10

Preparation and Characterization of M. Tuberculosis Fusion Proteins

A fusion protein containing TbRa3, the 38 kD antigen and Tb38-1 was prepared as follows.

Each of the DNA constructs TbRa3, 38 kD and Tb38-1 were modified by PCR in order to facilitate their fusion and the subsequent expression of the fusion protein TbRa3-38 kD-Tb38-1. TbRa3, 38 kD and Tb38-1 DNA was used to perform PCR using the primers PDM-64 and PDM-65 (SEQ ID NO: 146 and 147), PDM-57 and PDM-58 (SEQ ID NO: 148 and 149), and PDM-69 and PDM-60 (SEQ ID NO: 150 and 151), respectively. In each case, the DNA amplification was performed using 10 μl 10×Pfu buffer, 2 μl 10 mM dNTPs, 2 μl each of the PCR primers at 10 μM concentration, 81.5 μl water, 1.5 μl Pfu DNA polymerase (Stratagene, La Jolla, Calif.) and 1 μl DNA at either 70 ng/μl (for TbRa3) or 50 ng/μl (for 38 kD and Tb38-1). For TbRa3, denaturation at 94° C. was performed for 2 min, followed by 40 cycles of 96° C. for 15 sec and 72° C. for 1 min, and lastly by 72° C. for 4 min. For 38 kD, denaturation at 96° C. was performed for 2 min, followed by 40 cycles of 96° C. for 30 sec, 68° C. for 15 sec and 72° C. for 3 min, and finally by 72° C. for 4 min. For Tb38-1 denaturation at 94° C. for 2 min was followed by 10 cycles of 96° C. for 15 sec, 68° C. for 15 sec and 72° C. for 1.5 min, 30 cycles of 96° C. for 15 sec, 64° C. for 15 sec and 72° C. for 1.5, and finally by 72° C. for 4 min.

The TbRa3 PCR fragment was digested with NdeI and EcoRI and cloned directly into pT7^L2 IL 1 vector using NdeI and EcoRi sites. The 38 kD PCR fragment was digested with Sse8387I, treated with T4 DNA polymerase to make blunt ends and then digested with EcoRI for direct cloning into the pT7^L2Ra3-1 vector which was digested with StuI and EcoRI. The 38-1 PCR fragment was digested with Eco47III and EcoRI and directly subcloned into pT7^L2Ra3/38 kD-17 digested with the same enzymes. The whole fusion was then transferred to pET28b—using NdeI and EcoRI sites. The fusion construct was confirmed by DNA sequencing.

The expression construct was transformed into BLR pLys S E. coli (Novagen, Madison, Wis.) and grown overnight in LB broth with kanamycin (30 μg/ml) and chloramphenicol (34 μg/ml). This culture (12 ml) was used to inoculate 500 ml 2×YT with the same antibiotics and the culture was induced with IPTG at an OD560 of 0.44 to a final concentration of 1.2 mM. Four hours post-induction, the bacteria were harvested and sonicated in 20 mM Tris (8.0), 100 mM NaCl, 0.1% DOC, 20 μg/ml Leupeptin, 20 mM PMSF followed by centrifugation at 26,000×g. The resulting pellet was resuspended in 8 M urea, 20 mM Tris (8.0), 100 mM NaCl and bound to Pro-bond nickel resin (Invitrogen, Carlsbad, Calif.). The column was washed several times with the above buffer then eluted with an imidazole gradient (50 mM, 100 mM, 500 mM imidazole was added to 8 M urea, 20 mM Tris (8.0), 100 mM NaCl). The eluates containing the protein of interest were then dialyzed against 10 mM Tris (8.0).

The DNA and amino acid sequences for the resulting fusion protein (hereinafter referred to as TbRa3-38 kD-Tb38-1) are provided in SEQ ID NO: 152 and 153, respectively.

A fusion protein containing the two antigens TbH-9 and Tb38-1 (hereinafter referred to as TbH9-Tb38-1) without a hinge sequence, was prepared using a similar procedure to that described above. The DNA sequence for the TbH9-Tb38-1 fusion protein is provided in SEQ ID NO: 156.

Figure 5B:
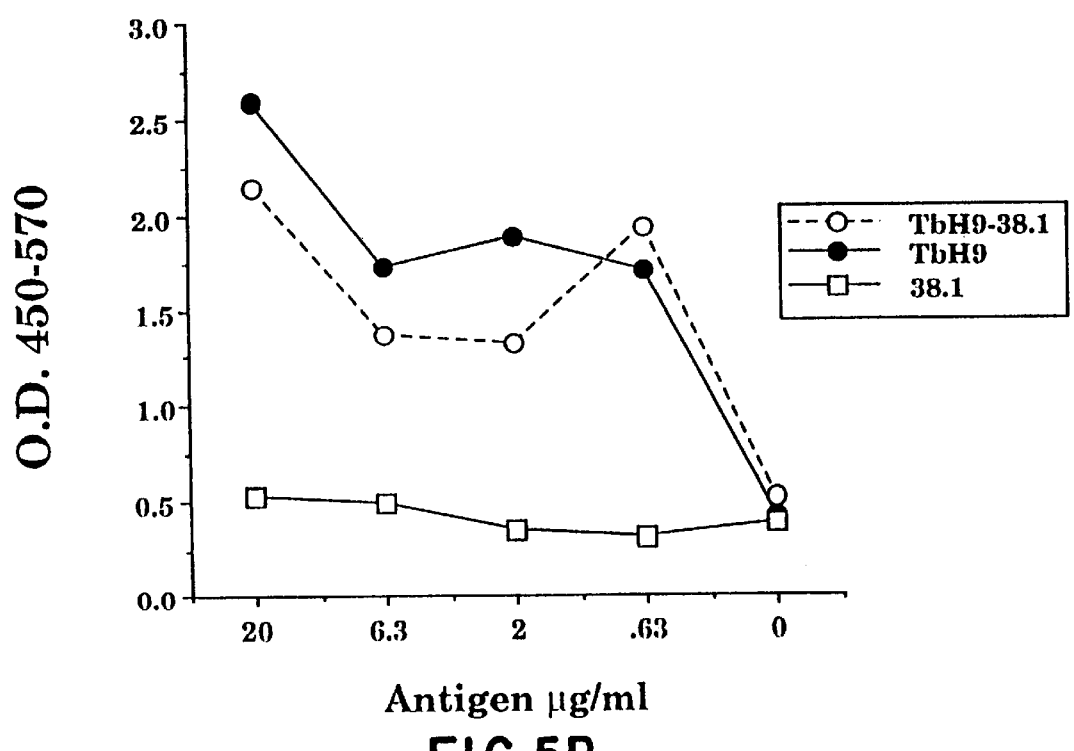
Figure 6B:
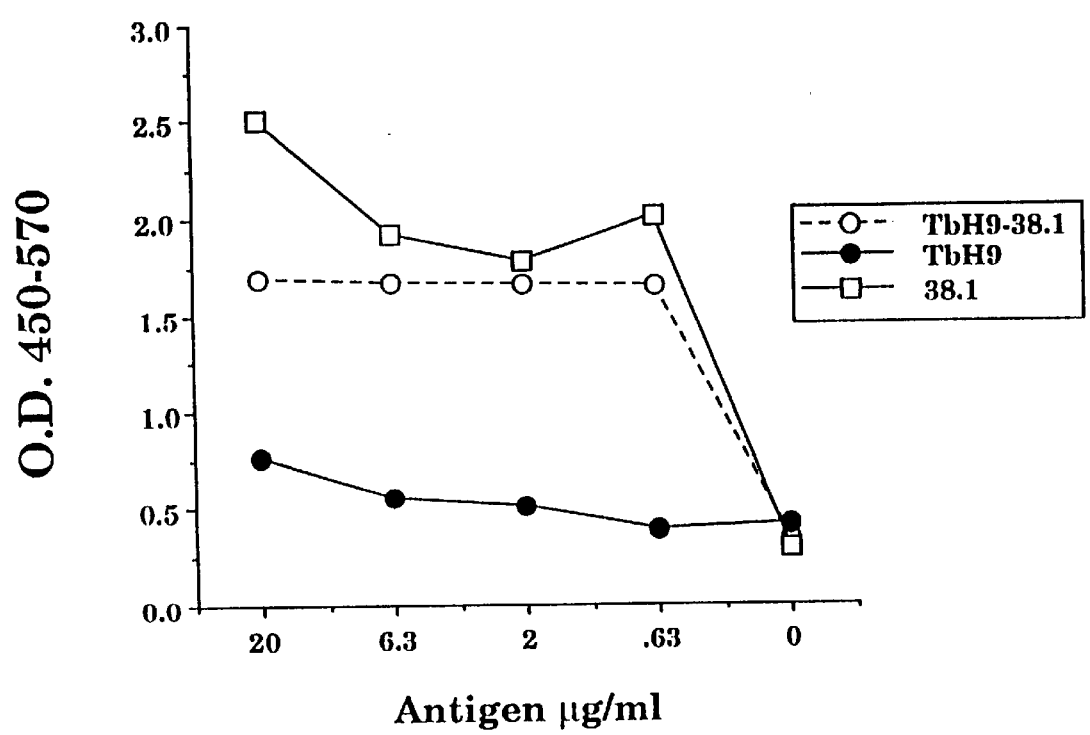
Figure 7B:
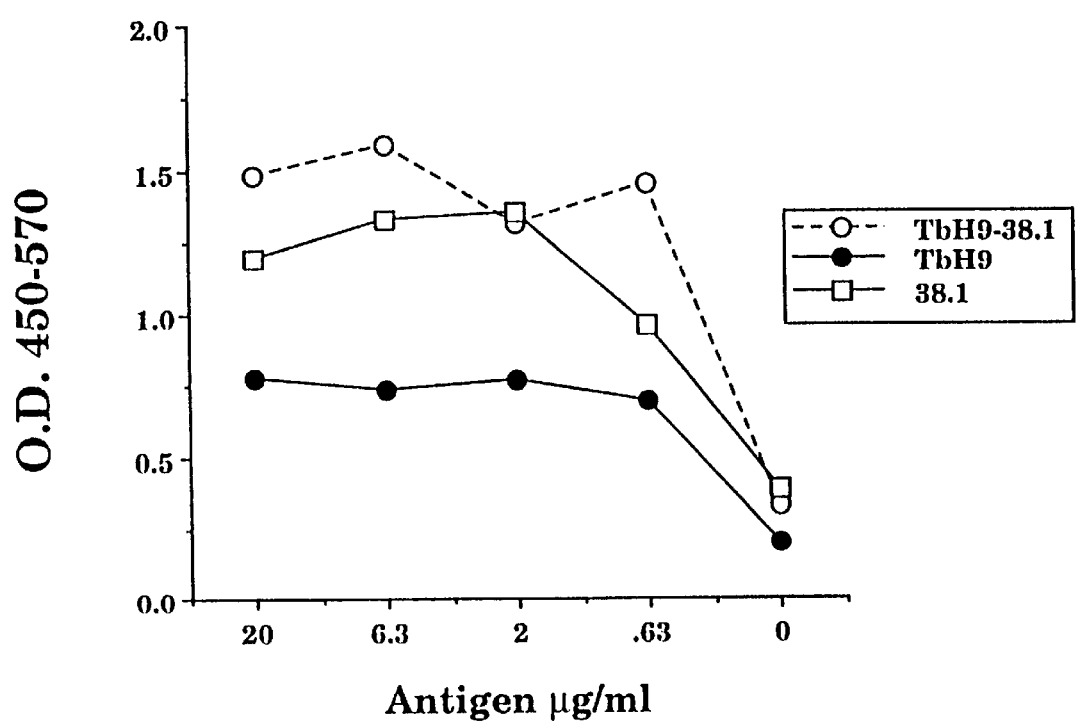

The ability of the fusion protein TbH9-Tb38-1 to induce T cell proliferation and IFN-γ production in PBMC preparations was examined using the protocol described above in Example 1. PBMC from three donors were employed: one who had been previously shown to respond to TbH9 but not Tb38-1 (donor 131); one who had been shown to respond to Tb38-1 but not TbH9 (donor 184); and one who had been shown to respond to both antigens (donor 201). The results of these studies (FIGS. 5–7, respectively) demonstrate the functional activity of both the antigens in the fusion protein.

A fusion protein containing TbRa3, the antigen 38 kD, Tb38-1 and DPEP was prepared as follows.

Each of the DNA constructs TbRa3, 38 kD and Tb38-1 were modified by PCR and cloned into vectors essentially as described above, with the primers PDM-69 (SEQ ID NO:150 and PDM-83 (SEQ ID NO: 205) being used for amplification of the Tb38-1A fragment. Tb38-1A differs from Tb38-1 by a DraI site at the 3' end of the coding region that keeps the final amino acid intact while creating a blunt restriction site that is in frame. The TbRa3/38 kD/Tb38-1A fusion was then transferred to pET28b using NdeI and EcoRl sites.

DPEP DNA was used to perform PCR using the primers PDM-84 and PDM-85 (SEQ ID NO: 206 and 207, respectively) and 1 µl DNA at 50 ng/µl. Denaturation at 94° C. was performed for 2 min, followed by 10 cycles of 96° C. for 15 sec, 68° C. for 15 sec and 72° C. for 1.5 min; 30 cycles of 96° C. for 15 sec, 64° C. for 15 sec and 72° C. for 1.5 min; and finally by 72° C. for 4 min. The DPEP PCR fragment was digested with EcoRI and Eco72I and clones directly into the pET28Ra3/38 kD/38-1A construct which was digested with DraI and EcoRI. The fusion construct was confirmed to be correct by DNA sequencing. Recombinant protein was prepared as described above. The DNA and amino acid sequences for the resulting fusion protein (hereinafter referred to as TbF-2) are provided in SEQ ID NO: 208 and 209, respectively.

The reactivity of the fusion protein TbF-2 with sera from M. tuberculosis-infected patients was examined by ELISA using the protocol described above. The results of these studies (Table 11) demonstrate that all four antigens function independently in the fusion protein.

TABLE 11

REACTIVITY OF TBF-2 FUSION RECOMBINANT WITH TB AND NORMAL SERA

| | | TbF | | TbF-2 | | ELISA Reactivity | | | |
|---|---|---|---|---|---|---|---|---|---|
| Serum ID | Status | OD450 | Status | OD450 | Status | 38 kD | TbRa3 | Tb38-1 | DPEP |
| B931-40 | TB | 0.57 | + | 0.321 | + | − | + | − | + |
| B931-41 | TB | 0.601 | + | 0.396 | + | + | + | + | − |
| B931-109 | TB | 0.494 | + | 0.404 | + | + | + | ± | − |
| B931-132 | TB | 1.502 | + | 1.292 | + | + | + | + | ± |
| 5004 | TB | 1.806 | + | 1.666 | + | ± | ± | + | − |
| 15004 | TB | 2.862 | + | 2.468 | + | + | + | + | − |
| 39004 | TB | 2.443 | + | 1.722 | + | + | + | + | − |
| 68004 | TB | 2.871 | + | 2.575 | + | + | + | + | − |
| 99004 | TB | 0.691 | + | 0.971 | + | − | ± | + | − |
| 107004 | TB | 0.875 | + | 0.732 | + | − | ± | + | − |
| 92004 | TB | 1.632 | + | 1.394 | + | + | ± | ± | − |
| 97004 | TB | 1.491 | + | 1.979 | + | + | ± | − | + |
| 118004 | TB | 3.182 | + | 3.045 | + | + | ± | − | − |
| 173004 | TB | 3.644 | + | 3.578 | + | + | + | + | − |
| 175004 | TB | 3.332 | + | 2.916 | + | + | + | − | − |
| 274004 | TB | 3.696 | + | 3.716 | + | − | + | − | + |
| 276004 | TB | 3.243 | + | 2.56 | + | − | − | + | − |
| 282004 | TB | 1.249 | + | 1.234 | + | + | − | − | − |
| 289004 | TB | 1.373 | + | 1.17 | + | − | + | − | − |
| 308004 | TB | 3.708 | + | 3.355 | + | − | − | + | − |
| 314004 | TB | 1.663 | + | 1.399 | + | − | − | + | − |
| 317004 | TB | 1.163 | + | 0.92 | + | + | − | − | − |
| 312004 | TB | 1.709 | + | 1.453 | + | − | + | − | − |
| 380004 | TB | 0.238 | − | 0.461 | + | − | ± | − | + |
| 451004 | TB | 0.18 | − | 0.2 | − | − | − | − | ± |
| 478004 | TB | 0.188 | − | 0.469 | + | − | − | − | ± |
| 410004 | TB | 0.384 | + | 2.392 | + | ± | − | − | + |
| 411004 | TB | 0.306 | + | 0.874 | + | − | + | − | + |
| 421004 | TB | 0.357 | + | 1.456 | + | − | + | − | + |
| 528004 | TB | 0.047 | − | 0.196 | − | − | − | − | + |
| A6-87 | Normal | 0.094 | − | 0.063 | − | − | − | − | − |
| A6-88 | Normal | 0.214 | − | 0.19 | − | − | − | − | − |
| A6-89 | Normal | 0.248 | − | 0.125 | − | − | − | − | − |
| A6-90 | Normal | 0.179 | − | 0.206 | − | − | − | − | − |
| A6-91 | Normal | 0.135 | − | 0.151 | − | − | − | − | − |
| A6-92 | Normal | 0.064 | − | 0.097 | − | − | − | − | − |
| A6-93 | Normal | 0.072 | − | 0.098 | − | − | − | − | − |
| A6-94 | Normal | 0.072 | − | 0.064 | − | − | − | − | − |
| A6-95 | Normal | 0.125 | − | 0.159 | − | − | − | − | − |
| A6-96 | Normal | 0.121 | − | 0.12 | − | − | − | − | − |
| Cut-off | | 0.284 | | 0.266 | | | | | |

A fusion protein containing TbRa3, the antigen 38 kD, Tb38-1 and TbH4 was prepared as follows.

Genomic *M. tuberculosis* DNA was used to PCR full-length TbH4 (FL TbH4) with the primers PDM-157 and PDM-160 (SEQ ID NO: 348 and 349, respectively) and 2 μl DNA at 100 ng/μl. Denaturation at 96° C. was performed for 2 min, followed by 40 cycles of 96° C. for 30 sec, 61° C. for 20 sec and 72° C. for 5 min; and finally by annealing at 72° C. for 10 min. The FL TbH4 PCR fragment was digested with EcoRI and Sca I (New England Biolabs.) and cloned directly into the pET28Ra3/38 kD/38-1A construct described above which was digested with DraI and EcoRI. The fusion construct was confirmed to be correct by DNA sequencing. Recombinant protein was prepared as described above. The DNA and amino acid sequences for the resulting fusion protein (hereinafter referred to as TbF-6) are provided in SEQ ID NO: 350 and 351, respectively.

A fusion protein containing the antigen 38 kD and DPEP separated by a linker was prepared as follows.

38 kD DNA was used to perform PCR using the primers PDM-1 76 and PDM-175 (SEQ ID NO: 352 and 353, respectively), and 1 μl PET28Ra3/38 kD/38-1/Ra2A-12 DNA at 110 ng/μl. Denaturation at 96° C. was performed for 2 min, followed by 40 cycles of 96° C. for 30 sec, 71° C. for 15 sec and 72° C. for 5 min and 40 sec; and finally by annealing at 72° C. for 4 min. The two sets of primers PDM-171, PDM-172, and PDM-173, PDM-174 were annealed by heating to 95° C. for 2 min and then ramping down to 25° C. slowly at 0.1° C./sec. DPEP DNA was used to perform PCR as described above. The 38 kD fragment was digested with Eco RI (New England Biolabs) and cloned into a modified pT7ΔL2 vector which was cut with Eco 72 I (Promega) and Eco RI. The modified pT7ΔL2 construct was designed to have a MGHHHHHH amino acid coding region in frame just 5' of the Eco 72 I site. The construct was digested with Kpn 2I (Gibco, BRL) and Pst I (New England Biolabs) and the annealed sets of phosphorylated primers (PDM-171, PDM-172 and PDM-173, PDM-174) were cloned in. The DPEP PCR fragment was digested with Eco RI and Eco 72 I and cloned into this second construct which was digested with Eco 47 III (New England Biolabs) and Eco RI. Ligations were done with a ligation kit from Panvera (Madison, Wis.). The resulting construct was digested with NdeI (New England Biolabs) and Eco RI, and transferred to a modified pET28 vector. The fusion construct was confirmed to be correct by DNA sequencing.

Recombinant protein was prepared essentially as described above. The DNA and amino acid sequences for the resulting fusion protein (hereinafter referred to as TbF-8) are provided in SEQ ID NO: 354 and 355, respectively.

One of skill in the art will appreciate that the order of the individual antigens within the fusion protein may be changed and that comparable activity would be expected provided each of the epitopes is still functionally available. In addition, truncated forms of the proteins containing active epitopes may be used in the construction of fusion proteins.

From the foregoing, it will be appreciated that, although specific embodiments of the invention have been described herein for the purpose of illustration, various modifications may be made without deviating from the spirit and scope of the invention.

What is claimed is:

1. An isolated fusion protein comprising four polypleptides, wherein
    the first polypeptide comprises a *M. tuberculosis* antigen having an amino acid sequence of TbRa3 (SEQ ID NO:77) or an immunogenic portion thereof;
    the second polypeptide comprises a *M. tuberculosis* antigen having an amino acid sequence of Tb38-1 (SEQ ID NO:88) or an immunogenic portion thereof;
    the third polypeptide comprises a *M. tuberculosis* antigen having an amino acid sequence of TbH4 (SEQ ID NO:89) or an immunogenic portion thereof; and
    the fourth polypeptide comprises a *M. tuberculosis* antigen having an amino acid sequence of 38 kD (SEQ ID NO:155) or an immunogenic portion thereof.

2. The fusion protein of claim 1, the protein comprising four polypeptides, wherein
    the first polypeptide comprises an amino acid sequence of TbRa3 (SEQ ID NO:77);
    the second polypeptide comprises an amino acid sequence of Tb38-1 (SEQ ID NO:88);
    the third polypeptide comprises an amino acid sequence of TbH4 (SEQ ID NO:89); and
    the fourth polypeptide comprises an amino acid sequence of 38 kD (SEQ ID NO:155).

3. The fusion protein of claim 1, wherein the first, second, third, and fourth polypeptides are directly fused to each other.

4. The fusion protein of claim 1, wherein the first, second, third, and fourth polypeptides are fused to each other via amino acid linkers.

5. The fusion protein of claim 1, the protein comprising four polypeptides, the polypeptides comprising amino acid sequences, fused in the following order from N- to C-terminus, of TbRa3 (SEQ ID NO:77), 38 kD (SEQ ID NO:155), Tb38-1 (SEQ ID NO:88), and TbH4 (SEQ ID NO:89).

6. The fusion protein of claim 1, the protein consisting of four polypeptides, the polypeptides consisting of amino acid sequences, fused in the following order from N- to C-terminus, of TbRa3 (SEQ ID NO:77), 38 kD (SEQ ID NO:155), Tb38-1 (SEQ ID NO:88), and TbH4 (SEQ ID NO:89).

7. The fusion protein of claim 1, the protein comprising an amino acid sequence of TbF6 (SEQ ID NO:351).

8. The fusion protein of claim 1, the protein consisting of an amino acid sequence of TbF6 (SEQ ID NO:351).

9. The fusion protein of claim 1, the protein encoded by a nucleotide sequence of TbF6 (SEQ ID NO:350).

10. A composition comprising the isolated fusion protein of claim 1.

11. The composition of claim 10, further comprising an adjuvant.

* * * * *

SEQUENCE LISTING

```
(1) GENERAL INFORMATION:

(iii) NUMBER OF SEQUENCES: 355

(2) INFORMATION FOR SEQ ID NO:1:

(i) SEQUENCE CHARACTERISTICS:
          (A) LENGTH: 766 base pairs
          (B) TYPE: nucleic acid
          (C) STRANDEDNESS: single
          (D) TOPOLOGY: linear (xi) SEQUENCE DESCRIPTION: SEQ ID NO:1:

CGAGGCACCG GTAGTTTGAA CCAAACGCAC AATCGACGGG CAAACGAACG GAAGAACACA     60

ACCATGAAGA TGGTGAAATC GATCGCCGCA GGTCTGACCG CCGCGGCTGC AATCGGCGCC    120

GCTGCGGCCG GTGTGACTTC GATCATGGCT GGCGGCCCGG TCGTATACCA GATGCAGCCG    180

GTCGTCTTCG GCGCGCCACT GCCGTTGGAC CCGGCATCCG CCCCTGACGT CCCGACCGCC    240

GCCCAGTTGA CCAGCCTGCT CAACAGCCTC GCCGATCCCA ACGTGTCGTT TGCGAACAAG    300

GGCAGTCTGG TCGAGGGCGG CATCGGGGGC ACCGAGGCGC GCATCGCCGA CCACAAGCTG    360

AAGAAGGCCG CCGAGCACGG GGATCTGCCG CTGTCGTTCA GCGTGACGAA CATCCAGCCG    420

GCGGCCGCCG GTTCGGCCAC CGCCGACGTT TCCGTCTCGG GTCCGAAGCT CTCGTCGCCG    480

GTCACGCAGA ACGTCACGTT CGTGAATCAA GGCGGCTGGA TGCTGTCACG CGCATCGGCG    540

ATGGAGTTGC TGCAGGCCGC AGGGNAACTG ATTGGCGGGC CGGNTTCAGC CCGCTGTTCA    600
```

```
GCTACGCCGC CCGCCTGGTG ACGCGTCCAT GTCGAACACT CGCGCGTGTA GCACGGTGCG    660

GTNTGCGCAG GGNCGCACGC ACCGCCCGGT GCAAGCCGTC CTCGAGATAG GTGGTGNCTC    720

GNCACCAGNG ANCACCCCCN NNTCGNCNNT TCTCGNTGNT GNATGA                   766
```

(2) INFORMATION FOR SEQ ID NO:2:

(i) SEQUENCE CHARACTERISTICS:
        (A) LENGTH: 752 base pairs
        (B) TYPE: nucleic acid
        (C) STRANDEDNESS: single
        (D) TOPOLOGY: linear (xi) SEQUENCE DESCRIPTION: SEQ ID NO:2:

```
ATGCATCACC ATCACCATCA CGATGAAGTC ACGGTAGAGA CGACCTCCGT CTTCCGCGCA     60

GACTTCCTCA GCGAGCTGGA CGCTCCTGCG CAAGCGGGTA CGGAGAGCGC GGTCTCCGGG    120

GTGGAAGGGC TCCCGCCGGG CTCGGCGTTG CTGGTAGTCA AACGAGGCCC CAACGCCGGG    180

TCCCGGTTCC TACTCGACCA AGCCATCACG TCGGCTGGTC GGCATCCCGA CAGCGACATA    240

TTTCTCGACG ACGTGACCGT GAGCCGTCGC CATGCTGAAT TCCGGTTGGA AAACAACGAA    300

TTCAATGTCG TCGATGTCGG GAGTCTCAAC GGCACCTACG TCAACCGCGA GCCCGTGGAT    360

TCGGCGGTGC TGGCGAACGG CGACGAGGTC CAGATCGGCA AGCTCCGGTT GGTGTTCTTG    420

ACCGGACCCA AGCAAGGCGA GGATGACGGG AGTACCGGGG GCCCGTGAGC GCACCCGATA    480

GCCCCGCGCT GGCCGGGATG TCGATCGGGG CGGTCCTCCG ACCTGCTACG ACCGGATTTT    540

CCCTGATGTC CACCATCTCC AAGATTCGAT TCTTGGGAGG CTTGAGGGTC NGGGTGACCC    600

CCCCGCGGGC CTCATTCNGG GGTNTCGGCN GGTTTCACCC CNTACCNACT GCCNCCCGGN    660

TTGCNAATTC NTTCTTCNCT GCCCNNAAAG GGACCNTTAN CTTGCCGCTN GAAANGGTNA    720

TCCNGGGCCC NTCCTNGAAN CCCCNTCCCC CT                                  752
```

(2) INFORMATION FOR SEQ ID NO:3:

(i) SEQUENCE CHARACTERISTICS:
        (A) LENGTH: 813 base pairs
        (B) TYPE: nucleic acid
        (C) STRANDEDNESS: single
        (D) TOPOLOGY: linear (xi) SEQUENCE DESCRIPTION: SEQ ID NO:3:

```
CATATGCATC ACCATCACCA TCACACTTCT AACCGCCCAG CGCGTCGGGG GCGTCGAGCA     60

CCACGCGACA CCGGGCCCGA TCGATCTGCT AGCTTGAGTC TGGTCAGGCA TCGTCGTCAG    120

CAGCGCGATG CCCTATGTTT GTCGTCGACT CAGATATCGC GGCAATCCAA TCTCCCGCCT    180

GCGGCCGGCG GTGCTGCAAA CTACTCCCGG AGGAATTTCG ACGTGCGCAT CAAGATCTTC    240

ATGCTGGTCA CGGCTGTCGT TTTGCTCTGT TGTTCGGGTG TGGCCACGGC CGCGCCCAAG    300

ACCTACTGCG AGGAGTTGAA AGGCACCGAT ACCGGCCAGG CGTGCCAGAT TCAAATGTCC    360

GACCCGGCCT ACAACATCAA CATCAGCCTG CCCAGTTACT ACCCCGACCA GAAGTCGCTG    420

GAAAATTACA TCGCCCAGAC GCGCGACAAG TTCCTCAGCG CGGCCACATC GTCCACTCCA    480

CGCGAAGCCC CCTACGAATT GAATATCACC TCGGCCACAT ACCAGTCCGC GATACCGCCG    540

CGTGGTACGC AGGCCGTGGT GCTCAMGGTC TACCACAACG CCGGCGGCAC GCACCCAACG    600

ACCACGTACA AGGCCTTCGA TTGGGACCAG GCCTATCGCA AGCCAATCAC CTATGACACG    660

CTGTGGCAGG CTGACACCGA TCCGCTGCCA GTCGTCTTCC CCATTGTTGC AAGGTGAACT    720

GAGCAACGCA GACCGGGACA ACWGGTATCG ATAGCCGCCN AATGCCGGCT TGGAACCCNG    780
```

TGAAATTATC ACAACTTCGC AGTCACNAAA NAA                               813

(2) INFORMATION FOR SEQ ID NO:4:

(i) SEQUENCE CHARACTERISTICS:
        (A) LENGTH: 447 base pairs
        (B) TYPE: nucleic acid
        (C) STRANDEDNESS: single
        (D) TOPOLOGY: linear (xi) SEQUENCE DESCRIPTION: SEQ ID NO:4:

CGGTATGAAC ACGGCCGCGT CCGATAACTT CCAGCTGTCC CAGGGTGGGC AGGGATTCGC    60

CATTCCGATC GGGCAGGCGA TGGCGATCGC GGGCCAGATC CGATCGGGTG GGGGGTCACC   120

CACCGTTCAT ATCGGGCCTA CCGCCTTCCT CGGCTTGGGT GTTGTCGACA ACAACGGCAA   180

CGGCGCACGA GTCCAACGCG TGGTCGGGAG CGCTCCGGCG GCAAGTCTCG GCATCTCCAC   240

CGGCGACGTG ATCACCGCGG TCGACGGCGC TCCGATCAAC TCGGCCACCG CGATGGCGGA   300

CGCGCTTAAC GGGCATCATC CCGGTGACGT CATCTCGGTG AACTGGCAAA CCAAGTCGGG   360

CGGCACGCGT ACAGGGAACG TGACATTGGC CGAGGGACCC CCGGCCTGAT TCGTCGYGG    420

ATACCACCCG CCGGCCGGCC AATTGGA                                      447

(2) INFORMATION FOR SEQ ID NO:5:

(i) SEQUENCE CHARACTERISTICS:
        (A) LENGTH: 604 base pairs
        (B) TYPE: nucleic acid
        (C) STRANDEDNESS: single
        (D) TOPOLOGY: linear (xi) SEQUENCE DESCRIPTION: SEQ ID NO:5:

GTCCCACTGC GGTCGCCGAG TATGTCGCCC AGCAAATGTC TGGCAGCCGC CCAACGGAAT    60

CCGGTGATCC GACGTCGCAG GTTGTCGAAC CCGCCGCCGC GGAAGTATCG GTCCATGCCT   120

AGCCCGGCGA CGGCGAGCGC CGGAATGGCG CGAGTGAGGA GGCGGGCAAT TTGGCGGGGC   180

CCGGCGACGG NGAGCGCCGG AATGGCGCGA GTGAGGAGGT GGNCAGTCAT GCCCAGNGTG   240

ATCCAATCAA CCTGNATTCG GNCTGNGGGN CCATTTGACA ATCGAGGTAG TGAGCGCAAA   300

TGAATGATGG AAAACGGGNG GNGACGTCCG NTGTTCTGGT GGTGNTAGGT GNCTGNCTGG   360

NGTNGNGGNT ATCAGGATGT TCTTCGNCGA AANCTGATGN CGAGGAACAG GGTGTNCCCG   420

NNANNCCNAN GGGNTCCNAN CCCNNNNTCC TCGNCGANAT CANANAGNCG NTTGATGNGA   480

NAAAAGGGTG GANCAGNNNN AANTNGNGGN CCNAANAANC NNNANNGNNG NNAGNTNGNT   540

NNNTNTTNNC ANNNNNNNTG NNGNNGNNCN NNNCAANCNN NTNNNNGNAA NNGGNTTNTT   600

NAAT                                                               604

(2) INFORMATION FOR SEQ ID NO:6:

(i) SEQUENCE CHARACTERISTICS:
        (A) LENGTH: 633 base pairs
        (B) TYPE: nucleic acid
        (C) STRANDEDNESS: single
        (D) TOPOLOGY: linear (xi) SEQUENCE DESCRIPTION: SEQ ID NO:6:

TTGCANGTCG AACCACCTCA CTAAAGGGAA CAAAAGCTNG AGCTCCACCG CGGTGGCGGC    60

CGCTCTAGAA CTAGTGKATM YYYCKGGCTG CAGSAATYCG GYACGAGCAT TAGGACAGTC   120

TAACGGTCCT GTTACGGTGA TCGAATGACC GACGACATCC TGCTGATCGA CACCGACGAA   180

```
CGGGTGCGAA CCCTCACCCT CAACCGGCCG CAGTCCCGYA ACGCGCTCTC GGCGGCGCTA    240

CGGGATCGGT TTTTCGCGGY GTTGGYCGAC GCCGAGGYCG ACGACGACAT CGACGTCGTC    300

ATCCTCACCG GYGCCGATCC GGTGTTCTGC GCCGGACTGG ACCTCAAGGT AGCTGGCCGG    360

GCAGACCGCG CTGCCGGACA TCTCACCGCG GTGGGCGGCC ATGACCAAGC CGGTGATCGG    420

CGCGATCAAC GGCGCCGCGG TCACCGGCGG GCTCGAACTG GCGCTGTACT GCGACATCCT    480

GATCGCCTCC GAGCACGCCC GCTTCGNCGA CACCCACGCC CGGGTGGGGC TGCTGCCCAC    540

CTGGGGACTC AGTGTGTGCT TGCCGCAAAA GGTCGGCATC GGNCTGGGCC GGTGGATGAG    600

CCTGACCGGC GACTACCTGT CCGTGACCGA CGC                                 633
```

(2) INFORMATION FOR SEQ ID NO:7:

(i) SEQUENCE CHARACTERISTICS:
        (A) LENGTH: 1362 base pairs
        (B) TYPE: nucleic acid
        (C) STRANDEDNESS: single
        (D) TOPOLOGY: linear (xi) SEQUENCE DESCRIPTION: SEQ ID NO:7:

```
CGACGACGAC GGCGCCGGAG AGCGGGCGCG AACGGCGATC GACGCGGCCC TGGCCAGAGT     60

CGGCACCACC CAGGAGGGAG TCGAATCATG AAATTTGTCA ACCATATTGA GCCCGTCGCG    120

CCCCGCCGAG CCGGCGGCGC GGTCGCCGAG GTCTATGCCG AGGCCCGCCG CGAGTTCGGC    180

CGGCTGCCCG AGCCGCTCGC CATGCTGTCC CCGGACGAGG GACTGCTCAC CGCCGGCTGG    240

GCGACGTTGC GCGAGACACT GCTGGTGGGC CAGGTGCCGC GTGGCCGCAA GGAAGCCGTC    300

GCCGCCGCCG TCGCGGCCAG CCTGCGCTGC CCCTGGTGCG TCGACGCACA CACCACCATG    360

CTGTACGCGG CAGGCCAAAC CGACACCGCC GCGGCGATCT TGGCCGGCAC AGCACCTGCC    420

GCCGGTGACC CGAACGCGCC GTATGTGGCG TGGGCGGCAG GAACCGGGAC ACCGGCGGGA    480

CCGCCGGCAC CGTTCGGCCC GGATGTCGCC GCCGAATACC TGGGCACCGC GGTGCAATTC    540

CACTTCATCG CACGCCTGGT CCTGGTGCTG CTGGACGAAA CCTTCCTGCC GGGGGGCCCG    600

CGCGCCCAAC AGCTCATGCG CCGCGCCGGT GGACTGGTGT TCGCCCGCAA GGTGCGCGCG    660

GAGCATCGGC CGGGCCGCTC CACCCGCCGG CTCGAGCCGC GAACGCTGCC CGACGATCTG    720

GCATGGGCAA CACCGTCCGA GCCCATAGCA ACCGCGTTCG CCGCGCTCAG CCACCACCTG    780

GACACCGCGC CGCACCTGCC GCCACCGACT CGTCAGGTGG TCAGGCGGGT CGTGGGGTCG    840

TGGCACGGCG AGCCAATGCC GATGAGCAGT CGCTGGACGA ACGAGCACAC CGCCGAGCTG    900

CCCGCCGACC TGCACGCGCC CACCCGTCTT GCCCTGCTGA CCGGCCTGGC CCCGCATCAG    960

GTGACCGACG ACGACGTCGC CGCGGCCCGA TCCCTGCTCG ACACCGATGC GGCGCTGGTT   1020

GGCGCCCTGG CCTGGGCCGC CTTCACCGCC GCGCGGCGCA TCGGCACCTG GATCGGCGCC   1080

GCCGCCGAGG GCCAGGTGTC GCGGCAAAAC CCGACTGGGT GAGTGTGCGC GCCCTGTCGG   1140

TAGGGTGTCA TCGCTGGCCC GAGGGATCTC GCGGCGGCGA ACGGAGGTGG CGACACAGGT   1200

GGAAGCTGCG CCCACTGGCT TGCGCCCCAA CGCCGTCGTG GGCGTTCGGT TGGCCGCACT   1260

GGCCGATCAG GTCGGCGCCG GCCCTTGGCC GAAGGTCCAG CTCAACGTGC CGTCACCGAA   1320

GGACCGGACG GTCACCGGGG GTCACCCTGC GCGCCCAAGG AA                     1362
```

(2) INFORMATION FOR SEQ ID NO:8:

(i) SEQUENCE CHARACTERISTICS:
        (A) LENGTH: 1458 base pairs (B) TYPE: nucleic acid
        (C) STRANDEDNESS: single
        (D) TOPOLOGY: linear (xi) SEQUENCE DESCRIPTION: SEQ ID NO:8:

```
GCGACGACCC CGATATGCCG GGCACCGTAG CGAAAGCCGT CGCCGACGCA CTCGGGCGCG      60

GTATCGCTCC CGTTGAGGAC ATTCAGGACT GCGTGGAGGC CCGGCTGGGG GAAGCCGGTC     120

TGGATGACGT GGCCCGTGTT TACATCATCT ACCGGCAGCG GCGCGCCGAG CTGCGGACGG     180

CTAAGGCCTT GCTCGGCGTG CGGGACGAGT TAAAGCTGAG CTTGGCGGCC GTGACGGTAC     240

TGCGCGAGCG CTATCTGCTG CACGACGAGC AGGGCCGGCC GGCCGAGTCG ACCGGCGAGC     300

TGATGGACCG ATCGGCGCGC TGTGTCGCGG CGGCCGAGGA CCAGTATGAG CCGGGCTCGT     360

CGAGGCGGTG GGCCGAGCGG TTCGCCACGC TATTACGCAA CCTGGAATTC CTGCCGAATT     420

CGCCCACGTT GATGAACTCT GGCACCGACC TGGGACTGCT CGCCGGCTGT TTTGTTCTGC     480

CGATTGAGGA TTCGCTGCAA TCGATCTTTG CGACGCTGGG ACAGGCCGCC GAGCTGCAGC     540

GGGCTGGAGG CGGCACCGGA TATGCGTTCA GCCACCTGCG ACCCGCCGGG GATCGGGTGG     600

CCTCCACGGG CGGCACGGCC AGCGGACCGG TGTCGTTTCT ACGGCTGTAT GACAGTGCCG     660

CGGGTGTGGT CTCCATGGGC GGTCGCCGGC GTGGCGCCTG TATGGCTGTG CTTGATGTGT     720

CGCACCCGGA TATCTGTGAT TTCGTCACCG CCAAGGCCGA ATCCCCAGC GAGCTCCCGC      780

ATTTCAACCT ATCGGTTGGT GTGACCGACG CGTTCCTGCG GGCCGTCGAA CGCAACGGCC     840

TACACCGGCT GGTCAATCCG CGAACCGGCA AGATCGTCGC GCGGATGCCC GCCGCCGAGC     900

TGTTCGACGC CATCTGCAAA GCCGCGCACG CCGGTGGCGA TCCCGGGCTG GTGTTTCTCG     960

ACACGATCAA TAGGGCAAAC CCGGTGCCGG GGAGAGGCCG CATCGAGGCG ACCAACCCGT    1020

GCGGGGAGGT CCCACTGCTG CCTTACGAGT CATGTAATCT CGGCTCGATC AACCTCGCCC    1080

GGATGCTCGC CGACGGTCGC GTCGACTGGG ACCGGCTCGA GGAGGTCGCC GGTGTGGCGG    1140

TGCGGTTCCT TGATGACGTC ATCGATGTCA GCCGCTACCC CTTCCCCGAA CTGGGTGAGG    1200

CGGCCCGCGC CACCCGCAAG ATCGGGCTGG GAGTCATGGG TTTGGCGGAA CTGCTTGCCG    1260

CACTGGGTAT TCCGTACGAC AGTGAAGAAG CCGTGCGGTT AGCCACCCGG CTCATGCGTC    1320

GCATACAGCA GGCGGCGCAC ACGGCATCGC GGAGGCTGGC CGAAGAGCGG GGCGCATTCC    1380

CGGCGTTCAC CGATAGCCGG TTCGCGCGGT CGGGCCCGAG GCGCAACGCA CAGGTCACCT    1440

CCGTCGCTCC GACGGGCA                                                  1458
```

(2) INFORMATION FOR SEQ ID NO:9:

(i) SEQUENCE CHARACTERISTICS:
        (A) LENGTH: 862 base pairs
        (B) TYPE: nucleic acid
        (C) STRANDEDNESS: single
        (D) TOPOLOGY: linear (xi) SEQUENCE DESCRIPTION: SEQ ID NO:9:

```
ACGGTGTAAT CGTGCTGGAT CTGGAACCGC GTGGCCCGCT ACCTACCGAG ATCTACTGGC      60

GGCGCAGGGG GCTGGCCCTG GGCATCGCGG TCGTCGTAGT CGGGATCGCG GTGGCCATCG     120

TCATCGCCTT CGTCGACAGC AGCGCCGGTG CCAAACCGGT CAGCGCCGAC AAGCCGGCCT     180

CCGCCCAGAG CCATCCGGGC TCGCCGGCAC CCCAAGCACC CCAGCCGGCC GGGCAAACCG     240

AAGGTAACGC CGCCGCGGCC CCGCCGCAGG GCCAAAACCC CGAGACACCC ACGCCCACCG     300

CCGCGGTGCA GCCGCCGCCG GTGCTCAAGG AAGGGGACGA TTGCCCCGAT TCGACGCTGG     360
```

-continued

```
CCGTCAAAGG TTTGACCAAC GCGCCGCAGT ACTACGTCGG CGACCAGCCG AAGTTCACCA      420

TGGTGGTCAC CAACATCGGC CTGGTGTCCT GTAAACGCGA CGTTGGGGCC GCGGTGTTGG      480

CCGCCTACGT TTACTCGCTG GACAACAAGC GGTTGTGGTC CAACCTGGAC TGCGCGCCCT      540

CGAATGAGAC GCTGGTCAAG ACGTTTTCCC CCGGTGAGCA GGTAACGACC GCGGTGACCT      600

GGACCGGGAT GGGATCGGCG CCGCGCTGCC CATTGCCGCG GCCGGCGATC GGGCCGGGCA      660

CCTACAATCT CGTGGTACAA CTGGGCAATC TGCGCTCGCT GCCGGTTCCG TTCATCCTGA      720

ATCAGCCGCC GCCGCCGCCC GGGCCGGTAC CCGCTCCGGG TCCAGCGCAG GCGCCTCCGC      780

CGGAGTCTCC CGCGCAAGGC GGATAATTAT TGATCGCTGA TGGTCGATTC CGCCAGCTGT      840

GACAACCCCT CGCCTCGTGC CG                                              862
```

(2) INFORMATION FOR SEQ ID NO:10:

(i) SEQUENCE CHARACTERISTICS:
        (A) LENGTH: 622 base pairs
        (B) TYPE: nucleic acid
        (C) STRANDEDNESS: single
        (D) TOPOLOGY: linear (xi) SEQUENCE DESCRIPTION: SEQ ID NO:10:

```
TTGATCAGCA CCGGCAAGGC GTCACATGCC TCCCTGGGTG TGCAGGTGAC CAATGACAAA       60

GACACCCCGG CGCCAAGAT CGTCGAAGTA GTGGCCGGTG GTGCTGCCGC GAACGCTGGA      120

GTGCCGAAGG CGCTCGTTGT CACCAAGGTC GACGACCGCC CGATCAACAG CGCGGACGCG     180

TTGGTTGCCG CCGTGCGGTC CAAAGCGCCG GGCGCCACGG TGGCGCTAAC CTTTCAGGAT     240

CCCTCGGGCG GTAGCCGCAC AGTGCAAGTC ACCCTCGGCA AGGCGGAGCA GTGATGAAGG     300

TCGCCGCGCA GTGTTCAAAG CTCGGATATA CGGTGGCACC CATGGAACAG CGTGCGGAGT     360

TGGTGGTTGG CCGGGCACTT GTCGTCGTCG TTGACGATCG CACGGCGCAC GGCGATGAAG     420

ACCACAGCGG GCCGCTTGTC ACCGAGCTGC TCACCGAGGC CGGGTTTGTT GTCGACGGCG     480

TGGTGGCGGT GTCGGCCGAC GAGGTCGAGA TCCGAAATGC GCTGAACACA GCGGTGATCG     540

GCGGGGTGGA CCTGGTGGTG TCGGTCGGCG GGACCGGNGT GACGNCTCGC GATGTCACCC     600

CGGAAGCCAC CCGNGACATT CT                                              622
```

(2) INFORMATION FOR SEQ ID NO:11:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (xi) SEQUENCE DESCRIPTION: SEQ ID NO:11:

```
GGCGCAGCGG TAAGCCTGTT GGCCGCCGGC ACACTGGTGT TGACAGCATG CGGCGGTGGC       60

ACCAACAGCT CGTCGTCAGG CGCAGGCGGA ACGTCTGGGT CGGTGCACTG CGGCGGCAAG      120

AAGGAGCTCC ACTCCAGCGG CTCGACCGCA CAAGAAAATG CCATGGAGCA GTTCGTCTAT      180

GCCTACGTGC GATCGTGCCC GGGCTACACG TTGGACTACA ACGCCAACGG GTCCGGTGCC      240

GGGGTGACCC AGTTTCTCAA CAACGAAACC GATTTCGCCG GCTCGGATGT CCCGTTGAAT      300

CCGTCGACCG GTCAACCTGA CCGGTCGGCG GAGCGGTGCG GTTCCCCGGC ATGGGACCTG      360

CCGACGGTGT TCGGCCCGAT CGCGATCACC TACAATATCA AGGGCGTGAG CACGCTGAAT      420

CTTGACGGAC CCACTACCGC CAAGATTTTC AACGGCACCA TCACCGTGTG GAATGATCCA      480

CAGATCCAAG CCCTCAACTC CGGCACCGAC CTGCCGCCAA CACCGATTAG CGTTATCTTC      540
```

-continued

```
CGCAGCGACA AGTCCGGTAC GTCGGACAAC TTCCAGAAAT ACCTCGACGG TGTATCCAAC      600

GGGGCGTGGG GCAAAGGCGC CAGCGAAACG TTCAGCGGGG GCGTCGGCGT CGGCGCCAGC      660

GGGAACAACG GAACGTCGGC CCTACTGCAG ACGACCGACG GGTCGATCAC CTACAACGAG      720

TGGTCGTTTG CGGTGGGTAA GCAGTTGAAC ATGGCCCAGA TCATCACGTC GGCGGGTCCG      780

GATCCAGTGG CGATCACCAC CGAGTCGGTC GGTAAGACAA TCGCCGGGGC CAAGATCATG      840

GGACAAGGCA ACGACCTGGT ATTGGACACG TCGTCGTTCT ACAGACCCAC CCAGCCTGGC      900

TCTTACCCGA TCGTGCTGGC GACCTATGAG ATCGTCTGCT CGAAATACCC GGATGCGACG      960

ACCGGTACTG CGGTAAGGGC GTTTATGCAA GCCGCGATTG GTCCAGGCCA AGAAGGCCTG     1020

GACCAATACG GCTCCATTCC GTTGCCCAAA TCGTTCCAAG CAAAATTGGC GGCCGCGGTG     1080

AATGCTATTT CTTGACCTAG TGAAGGGAAT TCGACGGTGA GCGATGCCGT TCCGCAGGTA     1140

GGGTCGCAAT TTGGGCCGTA TCAGCTATTG CGGCTGCTGG GCCGAGGCGG GATGGGCGAG     1200
```

(2) INFORMATION FOR SEQ ID NO:12:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (xi) SEQUENCE DESCRIPTION: SEQ ID NO:12:

```
GCAAGCAGCT GCAGGTCGTG CTGTTCGACG AACTGGGCAT GCCGAAGACC AAACGCACCA       60

AGACCGGCTA CACCACGGAT GCCGACGCGC TGCAGTCGTT GTTCGACAAG ACCGGGCATC      120

CGTTTCTGCA ACATCTGCTC GCCCACCGCG ACGTCACCCG GCTCAAGGTC ACCGTCGACG      180

GGTTGCTCCA AGCGGTGGCC GCCGACGGCC GCATCCACAC CACGTTCAAC CAGACGATCG      240

CCGCGACCGG CCGGCTCTCC TCGACCGAAC CCAACCTGCA GAACATCCCG ATCCGCACCG      300

ACGCGGGCCG GCGGATCCGG GACGCGTTCG TGGTCGGGGA CGGTTACGCC GAGTTGATGA      360

CGGCCGACTA CAGCCAGATC GAGATGCGGA TCATGGGGCA CCTGTCCGGG GACGAGGGCC      420

TCATCGAGGC GTTCAACACC GGGGAGGACC TGTATTCGTT CGTCGCGTCC CGGGTGTTCG      480

GTGTGCCCAT CGACGAGGTC ACCGGCGAGT TGCGGCGCCG GGTCAAGGCG ATGTCCTACG      540

GGCTGGTTTA CGGGTTGAGC GCCTACGGCC TGTCGCAGCA GTTGAAAATC TCCACCGAGG      600

AAGCCAACGA GCAGATGGAC GCGTATTTCG CCCGATTCGG CGGGGTGCGC GACTACCTGC      660

GCGCCGTAGT CGAGCGGGCC CGCAAGGACG GCTACACCTC GACGGTGCTG GGCCGTCGCC      720

GCTACCTGCC CGAGCTGGAC AGCAGCAACC GTCAAGTGCG GGAGGCCGCC GAGCGGGCGG      780

CGCTGAACGC GCCGATCCAG GGCAGCGCGG CCGACATCAT CAAGGTGGCC ATGATCCAGG      840

TCGACAAGGC GCTCAACGAG GCACAGCTGG CGTCGCGCAT GCTGCTGCAG GTCCACGACG      900

AGCTGCTGTT CGAAATCGCC CCCGGTGAAC GCGAGCGGGT CGAGGCCCTG GTGCGCGACA      960

AGATGGGCGG CGCTTACCCG CTCGACGTCC CGCTGGAGGT GTCGGTGGGC TACGCCGCA     1020

GCTGGGACGC GGCGGCGCAC TGAGTGCCGA GCGTGCATCT GGGGCGGGAA TTCGGCGATT     1080

TTTCCGCCCT GAGTTCACGC TCGGCGCAAT CGGGACCGAG TTTGTCCAGC GTGTACCCGT     1140

CGAGTAGCCT CGTCA                                                      1155
```

(2) INFORMATION FOR SEQ ID NO:13:

(i) SEQUENCE CHARACTERISTICS:
        (A) LENGTH: 1771 base pairs (B) TYPE: nucleic acid
        (C) STRANDEDNESS: single
        (D) TOPOLOGY: linear (xi) SEQUENCE DESCRIPTION: SEQ ID NO:13:

```
GAGCGCCGTC TGGTGTTTGA ACGGTTTTAC CGGTCGGCAT CGGCACGGGC GTTGCCGGGT      60

TCGGGCCTCG GGTTGGCGAT CGTCAAACAG GTGGTGCTCA ACCACGGCGG ATTGCTGCGC     120

ATCGAAGACA CCGACCCAGG CGGCCAGCCC CCTGGAACGT CGATTTACGT GCTGCTCCCC     180

GGCCGTCGGA TGCCGATTCC GCAGCTTCCC GGTGCGACGG CTGGCGCTCG GAGCACGGAC     240

ATCGAGAACT CTCGGGGTTC GGCGAACGTT ATCTCAGTGG AATCTCAGTC CACGCGCGCA     300

ACCTAGTTGT GCAGTTACTG TTGAAAGCCA CACCCATGCC AGTCCACGCA TGGCCAAGTT     360

GGCCCGAGTA GTGGGCCTAG TACAGGAAGA GCAACCTAGC GACATGACGA ATCACCCACG     420

GTATTCGCCA CCGCCGCAGC AGCCGGGAAC CCCAGGTTAT GCTCAGGGGC AGCAGCAAAC     480

GTACAGCCAG CAGTTCGACT GGCGTTACCC ACCGTCCCCG CCCCCGCAGC CAACCCAGTA     540

CCGTCAACCC TACGAGGCGT TGGGTGGTAC CCGGCCGGGT CTGATACCTG GCGTGATTCC     600

GACCATGACG CCCCCTCCTG GGATGGTTCG CCAACGCCCT CGTGCAGGCA TGTTGGCCAT     660

CGGCGCGGTG ACGATAGCGG TGGTGTCCGC CGGCATCGGC GGCGCGGCCG CATCCCTGGT     720

CGGGTTCAAC CGGGCACCCG CCGGCCCCAG CGGCGGCCCA GTGGCTGCCA GCGCGGCGCC     780

AAGCATCCCC GCAGCAAACA TGCCGCCGGG GTCGGTCGAA CAGGTGGCGG CCAAGGTGGT     840

GCCCAGTGTC GTCATGTTGG AAACCGATCT GGGCCGCCAG TCGGAGGAGG GCTCCGGCAT     900

CATTCTGTCT GCCGAGGGGC TGATCTTGAC CAACAACCAC GTGATCGCGG CGGCCGCCAA     960

GCCTCCCCTG GGCAGTCCGC CGCCGAAAAC GACGGTAACC TTCTCTGACG GGCGGACCGC    1020

ACCCTTCACG GTGGTGGGGG CTGACCCCAC CAGTGATATC GCCGTCGTCC GTGTTCAGGG    1080

CGTCTCCGGG CTCACCCCGA TCTCCCTGGG TTCCTCCTCG GACCTGAGGG TCGGTCAGCC    1140

GGTGCTGGCG ATCGGGTCGC CGCTCGGTTT GGAGGGCACC GTGACCACGG GGATCGTCAG    1200

CGCTCTCAAC CGTCCAGTGT CGACGACCGG CGAGGCCGGC AACCAGAACA CCGTGCTGGA    1260

CGCCATTCAG ACCGACGCCG CGATCAACCC CGGTAACTCC GGGGGCGCGC TGGTGAACAT    1320

GAACGCTCAA CTCGTCGGAG TCAACTCGGC CATTGCCACG CTGGGCGCGG ACTCAGCCGA    1380

TGCGCAGAGC GGCTCGATCG GTCTCGGTTT TGCGATTCCA GTCGACCAGG CCAAGCGCAT    1440

CGCCGACGAG TTGATCAGCA CCGGCAAGGC GTCACATGCC TCCCTGGGTG TGCAGGTGAC    1500

CAATGACAAA GACACCCCGG GCGCCAAGAT CGTCGAAGTA GTGGCCGGTG GTGCTGCCGC    1560

GAACGCTGGA GTGCCGAAGG GCGTCGTTGT CACCAAGGTC GACGACCGCC CGATCAACAG    1620

CGCGGACGCG TTGGTTGCCG CCGTGCGGTC CAAAGCGCCG GGCGCCACGG TGGCGCTAAC    1680

CTTTCAGGAT CCCTCGGGCG GTAGCCGCAC AGTGCAAGTC ACCCTCGGCA AGGCGGAGCA    1740

GTGATGAAGG TCGCCGCGCA GTGTTCAAAG C                                    1771
```

(2) INFORMATION FOR SEQ ID NO:14:

(i) SEQUENCE CHARACTERISTICS:
        (A) LENGTH: 1058 base pairs
        (B) TYPE: nucleic acid
        (C) STRANDEDNESS: single
        (D) TOPOLOGY: linear (xi) SEQUENCE DESCRIPTION: SEQ ID NO:14:

```
CTCCACCGCG GTGGCGGCCG CTCTAGAACT AGTGGATCCC CCGGGCTGCA GGAATTCGGC      60
```

```
ACGAGGATCC GACGTCGCAG GTTGTCGAAC CCGCCGCCGC GGAAGTATCG GTCCATGCCT      120

AGCCCGGCGA CGGCGAGCGC CGGAATGGCG CGAGTGAGGA GGCGGGCAAT TTGGCGGGGC      180

CCGGCGACGG CGAGCGCCGG AATGGCGCGA GTGAGGAGGC GGGCAGTCAT GCCCAGCGTG      240

ATCCAATCAA CCTGCATTCG GCCTGCGGGC CCATTTGACA ATCGAGGTAG TGAGCGCAAA      300

TGAATGATGG AAAACGGGCG GTGACGTCCG CTGTTCTGGT GGTGCTAGGT GCCTGCCTGG      360

CGTTGTGGCT ATCAGGATGT TCTTCGCCGA AACCTGATGC CGAGGAACAG GGTGTTCCCG      420

TGAGCCCGAC GGCGTCCGAC CCCGCGCTCC TCGCCGAGAT CAGGCAGTCG CTTGATGCGA      480

CAAAAGGGTT GACCAGCGTG CACGTAGCGG TCCGAACAAC CGGGAAAGTC GACAGCTTGC      540

TGGGTATTAC CAGTGCCGAT GTCGACGTCC GGGCCAATCC GCTCGCGGCA AAGGGCGTAT      600

GCACCTACAA CGACGAGCAG GGTGTCCCGT TTCGGGTACA AGGCGACAAC ATCTCGGTGA      660

AACTGTTCGA CGACTGGAGC AATCTCGGCT CGATTTCTGA ACTGTCAACT TCACGCGTGC      720

TCGATCCTGC CGCTGGGGTG ACGCAGCTGC TGTCCGGTGT CACGAACCTC CAAGCGCAAG      780

GTACCGAAGT GATAGACGGA ATTTCGACCA CCAAAATCAC CGGGACCATC CCCGCGAGCT      840

CTGTCAAGAT GCTTGATCCT GGCGCCAAGA GTGCAAGGCC GGCGACCGTG TGGATTGCCC      900

AGGACGGCTC GCACCACCTC GTCCGAGCGA GCATCGACCT CGGATCCGGG TCGATTCAGC      960

TCACGCAGTC GAAATGGAAC GAACCCGTCA ACGTCGACTA GGCCGAAGTT GCGTCGACGC     1020

GTTGNTCGAA ACGCCCTTGT GAACGGTGTC AACGGNAC                             1058

(2) INFORMATION FOR SEQ ID NO:15:

(i) SEQUENCE CHARACTERISTICS:
        (A) LENGTH: 542 base pairs
        (B) TYPE: nucleic acid
        (C) STRANDEDNESS: single
        (D) TOPOLOGY: linear (xi) SEQUENCE DESCRIPTION: SEQ ID NO:15:

GAATTCGGCA CGAGAGGTGA TCGACATCAT CGGGACCAGC CCCACATCCT GGGAACAGGC       60

GGCGGCGGAG GCGGTCCAGC GGGCGCGGGA TAGCGTCGAT GACATCCGCG TCGCTCGGGT      120

CATTGAGCAG GACATGGCCG TGGACAGCGC CGGCAAGATC ACCTACCGCA TCAAGCTCGA      180

AGTGTCGTTC AAGATGAGGC CGGCGCAACC GCGCTAGCAC GGGCCGGCGA GCAAGACGCA      240

AAATCGCACG GTTTGCGGTT GATTCGTGCG ATTTTGTGTC TGCTCGCCGA GGCCTACCAG      300

GCGCGGCCCA GGTCCGCGTG CTGCCGTATC CAGGCGTGCA TCGCGATTCC GGCGGCCACG      360

CCGGAGTTAA TGCTTCGCGT CGACCCGAAC TGGGCGATCC GCCGGNGAGC TGATCGATGA      420

CCGTGGCCAG CCCGTCGATG CCCGAGTTGC CCGAGGAAAC GTGCTGCCAG GCCGGTAGGA      480

AGCGTCCGTA GGCGGCGGTG CTGACCGGCT CTGCCTGCGC CCTCAGTGCG GCCAGCGAGC      540

GG                                                                    542

(2) INFORMATION FOR SEQ ID NO:16:

(i) SEQUENCE CHARACTERISTICS:
        (A) LENGTH: 913 base pairs
        (B) TYPE: nucleic acid
        (C) STRANDEDNESS: single
        (D) TOPOLOGY: linear (xi) SEQUENCE DESCRIPTION: SEQ ID NO:16:

CGGTGCCGCC CGCGCCTCCG TTGCCCCCAT TGCCGCCGTC GCCGATCAGC TGCGCATCGC       60

CACCATCACC GCCTTTGCCG CCGGCACCGC CGGTGGCGCC GGGGCCGCCG ATGCCACCGC      120
```

-continued

```
TTGACCCTGG CCGCCGGCGC CGCCATTGCC ATACAGCACC CCGCCGGGGG CACCGTTACC      180

GCCGTCGCCA CCGTCGCCGC CGCTGCCGTT TCAGGCCGGG GAGGCCGAAT GAACCGCCGC      240

CAAGCCCGCC GCCGGCACCG TTGCCGCCTT TTCCGCCCGC CCCGCCGGCG CCGCCAATTG      300

CCGAACAGCC AMGCACCGTT GCCGCCAGCC CCGCCGCCGT TAACGGCGCT GCCGGGCGCC      360

GCCGCCGGAC CCGCCATTAC CGCCGTTCCC GTTCGGTGCC CCGCCGTTAC CGGCGCCGCC      420

GTTTGCCGCC AATATTCGGC GGGCACCGCC AGACCCGCCG GGGCCACCAT TGCCGCCGGG      480

CACCGAAACA ACAGCCCAAC GGTGCCGCCG GCCCCGCCGT TTGCCGCCAT CACCGGCCAT      540

TCACCGCCAG CACCGCCGTT AATGTTTATG AACCCGGTAC CGCCAGCGCG GCCCCTATTG      600

CCGGGCGCCG GAGNGCGTGC CCGCCGGCGC CGCCAACGCC CAAAAGCCCG GGGTTGCCAC      660

CGGCCCCGCC GGACCCACCG GTCCCGCCGA TCCCCCCGTT GCCGCCGGTG CCGCCGCCAT      720

TGGTGCTGCT GAAGCCGTTA GCGCCGGTTC CGCSGGTTCC GGCGGTGGCG CCNTGGCCGC      780

CGGCCCCGCC GTTGCCGTAC AGCCACCCCC CGGTGGCGCC GTTGCCGCCA TTGCCGCCAT      840

TGCCGCCGTT GCCGCCATTG CCGCCGTTCC CGCCGCCACC GCCGGNTTGG CCGCCGGCGC      900

CGCCGGCGGC CGC                                                         913

(2) INFORMATION FOR SEQ ID NO:17:

(i) SEQUENCE CHARACTERISTICS:
        (A) LENGTH: 1872 base pairs
        (B) TYPE: nucleic acid
        (C) STRANDEDNESS: single
        (D) TOPOLOGY: linear (xi) SEQUENCE DESCRIPTION: SEQ ID NO:17:

GACTACGTTG GTGTAGAAAA ATCCTGCCGC CCGGACCCTT AAGGCTGGGA CAATTTCTGA       60

TAGCTACCCC GACACAGGAG GTTACGGGAT GAGCAATTCG CGCCGCCGCT CACTCAGGTG      120

GTCATGGTTG CTGAGCGTGC TGGCTGCCGT CGGGCTGGGC CTGGCCACGG CGCCGGCCCA      180

GGCGGCCCCG CCGGCCTTGT CGCAGGACCG GTTCGCCGAC TTCCCCGCGC TGCCCCTCGA      240

CCCGTCCGCG ATGGTCGCCC AAGTGGCGCC ACAGGTGGTC AACATCAACA CCAAACTGGG      300

CTACAACAAC GCCGTGGGCG CCGGGACCGG CATCGTCATC GATCCCAACG GTGTCGTGCT      360

GACCAACAAC CACGTGATCG CGGGCGCCAC CGACATCAAT GCGTTCAGCG TCGGCTCCGG      420

CCAAACCTAC GGCGTCGATG TGGTCGGGTA TGACCGCACC CAGGATGTCG CGGTGCTGCA      480

GCTGCGCGGT GCCGGTGGCC TGCCGTCGGC GGCGATCGGT GGCGGCGTCG CGGTTGGTGA      540

GCCCGTCGTC GCGATGGGCA ACAGCGGTGG GCAGGGCGGA ACGCCCCGTG CGGTGCCTGG      600

CAGGGTGGTC GCGCTCGGCC AAACCGTGCA GGCGTCGGAT TCGCTGACCG GTGCCGAAGA      660

GACATTGAAC GGGTTGATCC AGTTCGATGC CGCAATCCAG CCCGGTGATT CGGGCGGGCC      720

CGTCGTCAAC GGCCTAGGAC AGGTGGTCGG TATGAACACG GCCGCGTCCG ATAACTTCCA      780

GCTGTCCCAG GGTGGGCAGG GATTCGCCAT TCCGATCGGG CAGGCGATGG CGATCGCGGG      840

CCAAATCCGA TCGGGTGGGG GGTCACCCAC CGTTCATATC GGGCCTACCG CCTTCCTCGG      900

CTTGGGTGTT GTCGACAACA ACGGCAACGG CGCACGAGTC CAACGCGTGG TCGGAAGCGC      960

TCCGGCGGCA AGTCTCGGCA TCTCCACCGG CGACGTGATC ACCGCGGTCG ACGGCGCTCC     1020

GATCAACTCG GCCACCGCGA TGGCGGACGC GCTTAACGGG CATCATCCCG GTGACGTCAT     1080

CTCGGTGAAC TGGCAAACCA AGTCGGGCGG CACGCGTACA GGGAACGTGA CATTGGCCGA     1140

GGGACCCCCG GCCTGATTTG TCGCGGATAC CACCCGCCGG CCGGCCAATT GGATTGGCGC     1200
```

-continued

```
CAGCCGTGAT TGCCGCGTGA GCCCCCGAGT TCCGTCTCCC GTGCGCGTGG CATTGTGGAA      1260

GCAATGAACG AGGCAGAACA CAGCGTTGAG CACCCTCCCG TGCAGGGCAG TTACGTCGAA      1320

GGCGGTGTGG TCGAGCATCC GGATGCCAAG GACTTCGGCA GCGCCGCCGC CCTGCCCGCC      1380

GATCCGACCT GGTTTAAGCA CGCCGTCTTC TACGAGGTGC TGGTCCGGGC GTTCTTCGAC      1440

GCCAGCGCGG ACGGTTCCGN CGATCTGCGT GGACTCATCG ATCGCCTCGA CTACCTGCAG      1500

TGGCTTGGCA TCGACTGCAT CTGTTGCCGC CGTTCCTACG ACTCACCGCT GCGCGACGGC      1560

GGTTACGACA TTCGCGACTT CTACAAGGTG CTGCCCGAAT TCGGCACCGT CGACGATTTC      1620

GTCGCCCTGG TCGACACCGC TCACCGGCGA GGTATCCGCA TCATCACCGA CCTGGTGATG      1680

AATCACACCT CGGAGTCGCA CCCCTGGTTT CAGGAGTCCC GCCGCGACCC AGACGGACCG      1740

TACGGTGACT ATTACGTGTG GAGCGACACC AGCGAGCGCT ACACCGACGC CCGGATCATC      1800

TTCGTCGACA CCGAAGAGTC GAACTGGTCA TTCGATCCTG TCCGCCGACA GTTNCTACTG      1860

GCACCGATTC TT                                                          1872
```

(2) INFORMATION FOR SEQ ID NO:18:

(i) SEQUENCE CHARACTERISTICS:
        (A) LENGTH: 1482 base pairs
        (B) TYPE: nucleic acid
        (C) STRANDEDNESS: single
        (D) TOPOLOGY: linear (xi) SEQUENCE DESCRIPTION: SEQ ID NO:18:

```
CTTCGCCGAA ACCTGATGCC GAGGAACAGG GTGTTCCCGT GAGCCCGACG GCGTCCGACC        60

CCGCGCTCCT CGCCGAGATC AGGCAGTCGC TTGATGCGAC AAAAGGGTTG ACCAGCGTGC       120

ACGTAGCGGT CCGAACAACC GGGAAAGTCG ACAGCTTGCT GGGTATTACC AGTGCCGATG       180

TCGACGTCCG GGCCAATCCG CTCGCGGCAA AGGGCGTATG CACCTACAAC GACGAGCAGG       240

GTGTCCCGTT TCGGGTACAA GGCGACAACA TCTCGGTGAA ACTGTTCGAC GACTGGAGCA       300

ATCTCGGCTC GATTTCTGAA CTGTCAACTT CACGCGTGCT CGATCCTGCC GCTGGGGTGA       360

CGCAGCTGCT GTCCGGTGTC ACGAACCTCC AAGCGCAAGG TACCGAAGTG ATAGACGGAA       420

TTTCGACCAC CAAAATCACC GGGACCATCC CCGCGAGCTC TGTCAAGATG CTTGATCCTG       480

GCGCCAAGAG TGCAAGGCCG GCGACCGTGT GGATTGCCCA GGACGGCTCG CACCACCTCG       540

TCCGAGCGAG CATCGACCTC GGATCCGGGT CGATTCAGCT CACGCAGTCG AAATGGAACG       600

AACCCGTCAA CGTCGACTAG GCCGAAGTTG CGTCGACGCG TTGCTCGAAA CGCCCTTGTG       660

AACGGTGTCA ACGGCACCCG AAAACTGACC CCCTGACGGC ATCTGAAAAT TGACCCCCTA       720

GACCGGGCGG TTGGTGGTTA TTCTTCGGTG GTTCCGGCTG GTGGGACGCG GCCGAGGTCG       780

CGGTCTTTGA GCCGGTAGCT GTCGCCTTTG AGGGCGACGA CTTCAGCATG GTGGACGAGG       840

CGGTCGATCA TGGCGGCAGC AACGACGTCG TCGCCGCCGA AAACCTCGCC CCACCGGCCG       900

AAGGCCTTAT TGGACGTGAC GATCAAGCTG GCCCGCTCAT ACCGGGAGGA CACCAGCTGG       960

AAGAAGAGGT TGGCGGCCTC GGGCTCAAAC GGAATGTAAC CGACTTCGTC AACCACCAGG      1020

AGCGGATAGC GGCCAAACCG GGTGAGTTCG GCGTAGATGC GCCCGGCGTG GTGAGCCTCG      1080

GCGAACCGTG CTACCCATTC GGCGGCGGTG GCGAACAGCA CCCGATGACC GGCCTGACAC      1140

GCGCGTATCG CCAGGCCGAC CGCAAGATGA GTCTTCCCGG TGCCAGGCGG GGCCCAAAAA      1200

CACGACGTTA TCGCGGGCGG TGATGAAATC CAGGGTGCCC AGATGTGCGA TGGTGTCGCG      1260

TTTGAGGCCA CGAGCATGCT CAAAGTCGAA CTCTTCCAAC GACTTCCGAA CCGGGAAGCG      1320
```

| GGCGGCGCGG ATGCGGCCCT CACCACCATG GGACTCCCGG GCTGACACTT CCCGCTGCAG | 1380 |
| GCAGGCGGCC AGGTATTCTT CGTGGCTCCA GTTCTCGGCG CGGGCGCGAT CGGCCAGCCG | 1440 |
| GGACACTGAC TCACGCAGGG TGGGAGCTTT CAATGCTCTT GT | 1482 |

(2) INFORMATION FOR SEQ ID NO:19:

(i) SEQUENCE CHARACTERISTICS:
        (A) LENGTH: 876 base pairs
        (B) TYPE: nucleic acid
        (C) STRANDEDNESS: single
        (D) TOPOLOGY: linear (xi) SEQUENCE DESCRIPTION: SEQ ID NO:19:

| GAATTCGGCA CGAGCCGGCG ATAGCTTCTG GGCCGCGGCC GACCAGATGG CTCGAGGGTT | 60 |
| CGTGCTCGGG GCCACCGCCG GGCGCACCAC CCTGACCGGT GAGGGCCTGC AACACGCCGA | 120 |
| CGGTCACTCG TTGCTGCTGG ACGCCACCAA CCCCGGCGGTG GTTGCCTACG ACCCGGCCTT | 180 |
| CGCCTACGAA ATCGGCTACA TCGNGGAAAG CGGACTGGCC AGGATGTGCG GGGAGAACCC | 240 |
| GGAGAACATC TTCTTCTACA TCACCGTCTA CAACGAGCCG TACGTGCAGC CGCCGGAGCC | 300 |
| GGAGAACTTC GATCCCGAGG GCGTGCTGGG GGGTATCTAC CGNTATCACG CGGCCACCGA | 360 |
| GCAACGCACC AACAAGGNGC AGATCCTGGC CTCCGGGGTA GCGATGCCCG CGGCGCTGCG | 420 |
| GGCAGCACAG ATGCTGGCCG CCGAGTGGGA TGTCGCCGCC GACGTGTGGT CGGTGACCAG | 480 |
| TTGGGGCGAG CTAAACCGCG ACGGGGTGGT CATCGAGACC GAGAAGCTCC GCCACCCCGA | 540 |
| TCGGCCGGCG GCGTGCCCT ACGTGACGAG AGCGCTGGAG AATGCTCGGG GCCCGGTGAT | 600 |
| CGCGGTGTCG GACTGGATGC GCGCGGTCCC CGAGCAGATC CGACCGTGGG TGCCGGGCAC | 660 |
| ATACCTCACG TTGGGCACCG ACGGGTTCGG TTTTTCCGAC ACTCGGCCCG CCGGTCGTCG | 720 |
| TTACTTCAAC ACCGACGCCG AATCCCAGGT TGGTCGCGGT TTTGGGAGGG GTTGGCCGGG | 780 |
| TCGACGGGTG AATATCGACC CATTCGGTGC CGGTCGTGGG CCGCCCGCCC AGTTACCCGG | 840 |
| ATTCGACGAA GGTGGGGGGT TGCGCCCGAN TAAGTT | 876 |

(2) INFORMATION FOR SEQ ID NO:20:

(i) SEQUENCE CHARACTERISTICS:
        (A) LENGTH: 1021 base pairs
        (B) TYPE: nucleic acid
        (C) STRANDEDNESS: single
        (D) TOPOLOGY: linear (xi) SEQUENCE DESCRIPTION: SEQ ID NO:20:

| ATCCCCCCGG GCTGCAGGAA TTCGGCACGA GAGACAAAAT TCCACGCGTT AATGCAGGAA | 60 |
| CAGATTCATA ACGAATTCAC AGCGGCACAA CAATATGTCG CGATCGCGGT TTATTTCGAC | 120 |
| AGCGAAGACC TGCCGCAGTT GGCGAAGCAT TTTTACAGCC AAGCGGTCGA GGAACGAAAC | 180 |
| CATGCAATGA TGCTCGTGCA ACACCTGCTC GACCGCGACC TTCGTGTCGA AATTCCCGGC | 240 |
| GTAGACACGG TGCGAAACCA GTTCGACAGA CCCCGCGAGG CACTGGCGCT GGCGCTCGAT | 300 |
| CAGGAACGCA CAGTCACCGA CCAGGTCGGT CGGCTGACAG CGGTGGCCCG CGACGAGGGC | 360 |
| GATTTCCTCG GCGAGCAGTT CATGCAGTGG TTCTTGCAGG AACAGATCGA AGAGGTGGCC | 420 |
| TTGATGGCAA CCCTGGTGCG GGTTGCCGAT CGGGCCGGGG CCAACCTGTT CGAGCTAGAG | 480 |
| AACTTCGTCG CACGTGAAGT GGATGTGGCG CCGGCCGCAT CAGGCGCCCC GCACGCTGCC | 540 |
| GGGGGCCGCC TCTAGATCCC TGGGGGGGAT CAGCGAGTGG TCCCGTTCGC CCGCCCGTCT | 600 |

```
TCCAGCCAGG CCTTGGTGCG GCCGGGGTGG TGAGTACCAA TCCAGGCCAC CCCGACCTCC      660

CGGNAAAAGT CGATGTCCTC GTACTCATCG ACGTTCCAGG AGTACACCGC CCGGCCCTGA      720

GCTGCCGAGC GGTCAACGAG TTGCGGATAT TCCTTTAACG CAGGCAGTGA GGGTCCCACG      780

GCGGTTGGCC CGACCGCCGT GGCCGCACTG CTGGTCAGGT ATCGGGGGT  CTTGGCGAGC      840

AACAACGTCG GCAGGAGGGG TGGAGCCCGC CGGATCCGCA GACCGGGGGG GCGAAAACGA      900

CATCAACACC GCACGGGATC GATCTGCGGA GGGGGGTGCG GGAATACCGA ACCGGTGTAG      960

GAGCGCCAGC AGTTGTTTTT CCACCAGCGA AGCGTTTTCG GGTCATCGGN GGCNNTTAAG     1020

T                                                                    1021

(2) INFORMATION FOR SEQ ID NO:21:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:21:

CGTGCCGACG AACGGAAGAA CACAACCATG AAGATGGTGA AATCGATCGC CGCAGGTCTG       60

ACCGCCGCGG CTGCAATCGG CGCCGCTGCG GCCGGTGTGA CTTCGATCAT GGCTGGCGGN      120

CCGGTCGTAT ACCAGATGCA GCCGGTCGTC TTCGGCGCGC CACTGCCGTT GGACCCGGNA      180

TCCGCCCCTG ANGTCCCGAC CGCCGCCCAG TGGACCAGNC TGCTCAACAG NCTCGNCGAT      240

CCCAACGTGT CGTTTGNGAA CAAGGGNAGT CTGGTCGAGG GNGGNATCGG NGGNANCGAG      300

GGNGNGNATC GNCGANCACA A                                                321

(2) INFORMATION FOR SEQ ID NO:22:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (xi) SEQUENCE DESCRIPTION: SEQ ID NO:22:

TCTTATCGGT TCCGGTTGGC GACGGGTTTT GGGNGCGGGT GGTTAACCCG CTCGGCCAGC       60

CGATCGACGG GCGCGGAGAC GTCGACTCCG ATACTCGGCG CGCGCTGGAG CTCCAGGCGC      120

CCTCGGTGGT GNACCGGCAA GGCGTGAAGG AGCCGTTGNA GACCGGGATC AAGGCGATTG      180

ACGCGATGAC CCCGATCGGC CGCGGGCAGC GCCAGCTGAT CATCGGGGAC CGCAAGACCG      240

GCAAAAACCG CCGTCTGTGT CGGACACCAT CCTCAAACCA GCGGGAAGAA CTGGGAGTCC      300

GGTGGATCCC AAGAAGCAGG TGCGCTTGTG TATACGTTGG CCATCGGGCA AGAAGGGGAA      360

CTTACCATCG CCG                                                         373

(2) INFORMATION FOR SEQ ID NO:23:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (xi) SEQUENCE DESCRIPTION: SEQ ID NO:23:

GTGACGCCGT GATGGGATTC CTGGGCGGGG CCGGTCCGCT GGCGGTGGTG GATCAGCAAC       60

TGGTTACCCG GGTGCCGCAA GGCTGGTCGT TTGCTCAGGC AGCCGCTGTG CCGGTGGTGT      120
```

```
TCTTGACGGC CTGGTACGGG TTGGCCGATT TAGCCGAGAT CAAGGCGGGC GAATCGGTGC      180

TGATCCATGC CGGTACCGGC GGTGTGGGCA TGGCGGCTGT GCAGCTGGCT CGCCAGTGGG      240

GCGTGGAGGT TTTCGTCACC GCCAGCCGTG GNAAGTGGGA CACGCTGCGC GCCATNGNGT      300

TTGACGACGA NCCATATCGG NGATTCCCNC ACATNCGAAG TTCCGANGGA GA             352
```

(2) INFORMATION FOR SEQ ID NO:24:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (xi) SEQUENCE DESCRIPTION: SEQ ID NO:24:

```
GAAATCCGCG TTCATTCCGT TCGACCAGCG GCTGGCGATA ATCGACGAAG TGATCAAGCC       60

GCGGTTCGCG GCGCTCATGG GTCACAGCGA GTAATCAGCA AGTTCTCTGG TATATCGCAC      120

CTAGCGTCCA GTTGCTTGCC AGATCGCTTT CGTACCGTCA TCGCATGTAC CGGTTCGCGT      180

GCCGCACGCT CATGCTGGCG GCGTGCATCC TGGCCACGGG TGTGGCGGGT CTCGGGGTCG      240

GCGCGCAGTC CGCAGCCCAA ACCGCGCCGG TGCCCGACTA CTACTGGTGC CCGGGGCAGC      300

CTTTCGACCC CGCATGGGGG CCCAACTGGG ATCCCTACAC CTGCCATGAC GACTTCCACC      360

GCGACAGCGA CGGCCCCGAC CACAGCCGCG ACTACCCCGG ACCCATCCTC GAAGGTCCCG      420

TGCTTGACGA TCCCGGTGCT GCGCCGCCGC CCCCGGCTGC CGGTGGCGGC GCATAGCGCT      480

CGTTGACCGG GCCGCATCAG CGAATACGCG TATAAACCCG GGCGTGCCCC CGGCAAGCTA      540

CGACCCCCGG CGGGGCAGAT TTACGCTCCC GTGCCGATGG ATCGCGCCGT CCGATGACAG      600

AAAATAGGCG ACGGTTTTGG CAACCGCTTG GAGGACGCTT GAAGGGAACC TGTCATGAAC      660

GGCGACAGCG CCTCCACCAT CGACATCGAC AAGGTTGTTA CCCGCACACC CGTTCGCCGG      720

ATCGTG                                                                726
```

(2) INFORMATION FOR SEQ ID NO:25:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (xi) SEQUENCE DESCRIPTION: SEQ ID NO:25:

```
CGCGACGACG ACGAACGTCG GGCCCACCAC CGCCTATGCG TTGATGCAGG CGACCGGGAT       60

GGTCGCCGAC CATATCCAAG CATGCTGGGT GCCCACTGAG CGACCTTTTG ACCAGCCGGG      120

CTGCCCGATG GCGGCCCGGT GAAGTCATTG CGCCGGGCT TGTGCACCTG ATGAACCCGA      180

ATAGGGAACA ATAGGGGGT GATTTGGCAG TTCAATGTCG GGTATGGCTG GAAATCCAAT      240

GGCGGGGCAT GCTCGGCGCC GACCAGGCTC GCGCAGGCGG GCCAGCCCGA ATCTGGAGGG      300

AGCACTCAAT GGCGGCGATG AAGCCCCGGA CCGGCGACGG TCCTTTGGAA GCAACTAAGG      360

AGGGGCGCGG CATTGTGATG CGAGTACCAC TTGAGGGTGG CGGTCGCCTG GTCGTCGAGC      420

TGACACCCGA CGAAGCCGCC GCACTGGGTG ACGAACTCAA AGGCGTTACT AGCTAAGACC      480

AGCCCAACGG CGAATGGTCG GCGTTACGCG CACACCTTCC GGTAGATGTC CAGTGTCTGC      540

TCGGCGATGT ATGCCCAGGA GAACTCTTGG ATACAGCGCT                           580
```

(2) INFORMATION FOR SEQ ID NO:26:

(i) SEQUENCE CHARACTERISTICS:
    (A) LENGTH: 160 base pairs
    (B) TYPE: nucleic acid
    (C) STRANDEDNESS: single
    (D) TOPOLOGY: linear (xi) SEQUENCE DESCRIPTION: SEQ ID NO:26:

```
AACGGAGGCG CCGGGGGTTT TGGCGGGGCC GGGGCGGTCG GCGGCAACGG CGGGGCCGGC      60
GGTACCGCCG GGTTGTTCGG TGTCGGCGGG GCCGGTGGGG CCGGAGGCAA CGGCATCGCC     120
GGTGTCACGG GTACGTCGGC CAGCACACCG GGTGGATCCG                           160
```

(2) INFORMATION FOR SEQ ID NO:27:

(i) SEQUENCE CHARACTERISTICS:
    (A) LENGTH: 272 base pairs
    (B) TYPE: nucleic acid
    (C) STRANDEDNESS: single
    (D) TOPOLOGY: linear (xi) SEQUENCE DESCRIPTION: SEQ ID NO:27:

```
GACACCGATA CGATGGTGAT GTACGCCAAC GTTGTCGACA CGCTCGAGGC GTTCACGATC      60
CAGCGCACAC CCGACGGCGT GACCATCGGC GATGCGGCCC CGTTCGCGGA GGCGGCTGCC     120
AAGGCGATGG GAATCGACAA GCTGCGGGTA ATTCATACCG GAATGGACCC CGTCGTCGCT     180
GAACGCGAAC AGTGGGACGA CGGCAACAAC ACGTTGGCGT TGGCGCCCGG TGTCGTTGTC     240
GCCTACGAGC GCAACGTACA GACCAACGCC CG                                   272
```

(2) INFORMATION FOR SEQ ID NO:28:

(i) SEQUENCE CHARACTERISTICS:
    (A) LENGTH: 317 base pairs
    (B) TYPE: nucleic acid
    (C) STRANDEDNESS: single
    (D) TOPOLOGY: linear (xi) SEQUENCE DESCRIPTION: SEQ ID NO:28:

```
GCAGCCGGTG GTTCTCGGAC TATCTGCGCA CGGTGACGCA GCGCGACGTG CGCGAGCTGA      60
AGCGGATCGA GCAGACGGAT CGCCTGCCGC GGTTCATGCG CTACCTGGCC GCTATCACCG     120
CGCAGGAGCT GAACGTGGCC GAAGCGGCGC GGGTCATCGG GGTCGACGCG GGGACGATCC     180
GTTCGGATCT GGCGTGGTTC GAGACGGTCT ATCTGGTACA TCGCCTGCCC GCCTGGTCGC     240
GGAATCTGAC CGCGAAGATC AAGAAGCGGT CAAAGATCCA CGTCGTCGAC AGTGGCTTCG     300
CGGCCTGGTT GCGCGGG                                                    317
```

(2) INFORMATION FOR SEQ ID NO:29:

(i) SEQUENCE CHARACTERISTICS:
    (A) LENGTH: 182 base pairs
    (B) TYPE: nucleic acid
    (C) STRANDEDNESS: single
    (D) TOPOLOGY: linear (xi) SEQUENCE DESCRIPTION: SEQ ID NO:29:

```
GATCGTGGAG CTGTCGATGA ACAGCGTTGC CGGACGCGCG GCGGCCAGCA CGTCGGTGTA      60
GCAGCGCCGG ACCACCTCGC CGGTGGGCAG CATGGTGATG ACCACGTCGG CCTCGGCCAC     120
CGCTTCGGGC GCGCTACGAA ACACCGCGAC ACCGTGCGCG GCGGCGCCGG ACGCCGCCGT     180
GG                                                                    182
```

(2) INFORMATION FOR SEQ ID NO:30:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (xi) SEQUENCE DESCRIPTION: SEQ ID NO:30:

GATCGCGAAG TTTGGTGAGC AGGTGGTCGA CGCGAAAGTC TGGGCGCCTG CGAAGCGGGT    60

CGGCGTTCAC GAGGCGAAGA CACGCCTGTC CGAGCTGCTG CGGCTCGTCT ACGGCGGGCA    120

GAGGTTGAGA TTGCCCGCCG CGGCGAGCCG GTAGCAAAGC TTGTGCCGCT GCATCCTCAT    180

GAGACTCGGC GGTTAGGCAT TGACCATGGC GTGTACCGCG TGCCCGACGA TTTGGACGCT    240

CCGTTGTCAG ACGACGTGCT CGAACGCTTT CACCGGTGAA GCGCTACCTC ATCGACACCC    300

ACGTTTGG    308

(2) INFORMATION FOR SEQ ID NO:31:

(i) SEQUENCE CHARACTERISTICS:
        (A) LENGTH: 267 base pairs
        (B) TYPE: nucleic acid
        (C) STRANDEDNESS: single
        (D) TOPOLOGY: linear (xi) SEQUENCE DESCRIPTION: SEQ ID NO:31:

CCGACGACGA GCAACTCACG TGGATGATGG TCGGCAGCGG CATTGAGGAC GGAGAGAATC    60

CGGCCGAAGC TGCCGCGCGG CAAGTGCTCA TAGTGACCGG CCGTAGAGGG CTCCCCCGAT    120

GGCACCGGAC TATTCTGGTG TGCCGCTGGC CGGTAAGAGC GGGTAAAAGA ATGTGAGGGG    180

ACACGATGAG CAATCACACC TACCGAGTGA TCGAGATCGT CGGGACCTCG CCCGACGGCG    240

TCGACGCGGC AATCCAGGGC GGTCTGG    267

(2) INFORMATION FOR SEQ ID NO:32:

(i) SEQUENCE CHARACTERISTICS:
        (A) LENGTH: 1539 base pairs
        (B) TYPE: nucleic acid
        (C) STRANDEDNESS: single
        (D) TOPOLOGY: linear (xi) SEQUENCE DESCRIPTION: SEQ ID NO:32:

CTCGTGCCGA AAGAATGTGA GGGGACACGA TGAGCAATCA CACCTACCGA GTGATCGAGA    60

TCGTCGGGAC CTCGCCCGAC GGCGTCGACG CGGCAATCCA GGGCGGTCTG GCCCGAGCTG    120

CGCAGACCAT GCGCGCGCTG GACTGGTTCG AAGTACAGTC AATTCGAGGC CACCTGGTCG    180

ACGGAGCGGT CGCGCACTTC CAGGTGACTA TGAAAGTCGG CTTCCGCTGG AGGATTCCTG    240

AACCTTCAAG CGCGGCCGAT AACTGAGGTG CATCATTAAG CGACTTTTCC AGAACATCCT    300

GACGCGCTCG AAACGCGGTT CAGCCGACGG TGGCTCCGCC GAGGCGCTGC CTCCAAAATC    360

CCTGCGACAA TTCGTCGGCG GCGCCTACAA GGAAGTCGGT GCTGAATTCG TCGGGTATCT    420

GGTCGACCTG TGTGGGCTGC AGCCGGACGA AGCGGTGCTC GACGTCGGCT GCGGCTCGGG    480

GCGGATGGCG TTGCCGCTCA CCGGCTATCT GAACAGCGAG GGACGCTACG CCGGCTTCGA    540

TATCTCGCAG AAAGCCATCG CGTGGTGCCA GGAGCACATC ACCTCGGCGC ACCCCAACTT    600

CCAGTTCGAG GTCTCCGACA TCTACAACTC GCTGTACAAC CCGAAAGGGA AATACCAGTC    660

ACTAGACTTT CGCTTTCCAT ATCCGGATGC GTCGTTCGAT GTGGTGTTTC TTACCTCGGT    720

GTTCACCCAC ATGTTTCCGC CGGACGTGGA GCACTATCTG GACGAGATCT CCCGCGTGCT    780

```
GAAGCCCGGC GGACGATGCC TGTGCACGTA CTTCTTGCTC AATGACGAGT CGTTAGCCCA      840

CATCGCGGAA GGAAAGAGTG CGCACAACTT CCAGCATGAG GGACCGGGTT ATCGGACAAT      900

CCACAAGAAG CGGCCCGAAG AAGCAATCGG CTTGCCGGAA CCTTCGTCA GGGATGTCTA       960

TGGCAAGTTC GGCCTCGCCG TGCACGAACC ATTGCACTAC GGCTCATGGA GTGGCCGGGA     1020

ACCACGCCTA AGCTTCCAGG ACATCGTCAT CGCGACCAAA ACCGCGAGCT AGGTCGGCAT     1080

CCGGGAAGCA TCGCGACACC GTGGCGCCGA GCGCCGCTGC CGGCAGGCCG ATTAGGCGGG     1140

CAGATTAGCC CGCCGCGGCT CCCGGCTCCG AGTACGGCGC CCCGAATGGC GTCACCGGCT     1200

GGTAACCACG CTTGCGCGCC TGGGCGGCGG CCTGCCGGAT CAGGTGGTAG ATGCCGACAA     1260

AGCCTGCGTG ATCGGTCATC ACCAACGGTG ACAGCAGCCG GTTGTGCACC AGCGCGAACG     1320

CCACCCCGGT CTCCGGGTCT GTCCAGCCGA TCGAGCCGCC CAAGCCCACA TGACCAAACC     1380

CCGGCATCAC GTTGCCGATC GGCATACCGT GATAGCCAAG ATGAAAATTT AAGGGCACCA     1440

ATAGATTTCG ATCCGGCAGA ACTTGCCGTC GGTTGCGGGT CAGGCCCGTG ACCAGCTCCC     1500

GCGACAAGAA CCGTATGCCG TCGATCTCGC CTCGTGCCG                           1539

(2) INFORMATION FOR SEQ ID NO:33:

(i) SEQUENCE CHARACTERISTICS:
        (A) LENGTH: 851 base pairs
        (B) TYPE: nucleic acid
        (C) STRANDEDNESS: single
        (D) TOPOLOGY: linear (xi) SEQUENCE DESCRIPTION: SEQ ID NO:33:

CTGCAGGGTG GCGTGGATGA GCGTCACCGC GGGGCAGGCC GAGCTGACCG CCGCCCAGGT       60

CCGGGTTGCT GCGGCGGCCT ACGAGACGGC GTATGGGCTG ACGGTGCCCC CGCCGGTGAT      120

CGCCGAGAAC CGTGCTGAAC TGATGATTCT GATAGCGACC AACCTCTTGG GGCAAAACAC      180

CCCGGCGATC GCGGTCAACG AGGCCGAATA CGGCGAGATG TGGGCCCAAG ACGCCGCCGC      240

GATGTTTGGC TACGCCGCGG CGACGGCGAC GGCGACGGCG ACGTTGCTGC CGTTCGAGGA      300

GGCGCCGGAG ATGACCAGCG CGGGTGGGCT CCTCGAGCAG GCCGCCGCGG TCGAGGAGGC      360

CTCCGACACC GCCGCGGCGA ACCAGTTGAT GAACAATGTG CCCCAGGCGC TGAAACAGTT      420

GGCCCAGCCC ACGCAGGGCA CCACGCCTTC TTCCAAGCTG GGTGGCCTGT GGAAGACGGT      480

CTCGCCGCAT CGGTCGCCGA TCAGCAACAT GGTGTCGATG GCCAACAACC ACATGTCGAT      540

GACCAACTCG GGTGTGTCGA TGACCAACAC CTTGAGCTCG ATGTTGAAGG GCTTTGCTCC      600

GGCGGCGGCC GCCCAGGCCG TGCAAACCGC GGCGCAAAAC GGGGTCCGGG CGATGAGCTC      660

GCTGGGCAGC TCGCTGGGTT CTTCGGGTCT GGGCGGTGGG GTGGCCGCCA ACTTGGGTCG      720

GGCGGCCTCG GTACGGTATG GTCACCGGGA TGGCGGAAAA TATGCANAGT CTGGTCGGCG      780

GAACGGTGGT CCGGCGTAAG GTTTACCCCC GTTTTCTGGA TGCGGTGAAC TTCGTCAACG      840

GAAACAGTTA C                                                          851

(2) INFORMATION FOR SEQ ID NO:34:

(i) SEQUENCE CHARACTERISTICS:
        (A) LENGTH: 254 base pairs
        (B) TYPE: nucleic acid
        (C) STRANDEDNESS: single
        (D) TOPOLOGY: linear (xi) SEQUENCE DESCRIPTION: SEQ ID NO:34:

GATCGATCGG GCGGAAATTT GGACCAGATT CGCCTCCGGC GATAACCCAA TCAATCGAAC       60
```

```
CTAGATTTAT TCCGTCCAGG GGCCCGAGTA ATGGCTCGCA GGAGAGGAAC CTTACTGCTG      120

CGGGCACCTG TCGTAGGTCC TCGATACGGC GGAAGGCGTC GACATTTTCC ACCGACACCC      180

CCATCCAAAC GTTCGAGGGC CACTCCAGCT TGTGAGCGAG GCGACGCAGT CGCAGGCTGC      240

GCTTGGTCAA GATC                                                       254
```

(2) INFORMATION FOR SEQ ID NO:35:

(i) SEQUENCE CHARACTERISTICS:
        (A) LENGTH: 1227 base pairs
        (B) TYPE: nucleic acid
        (C) STRANDEDNESS: single
        (D) TOPOLOGY: linear (xi) SEQUENCE DESCRIPTION: SEQ ID NO:35:

```
GATCCTGACC GAAGCGGCCG CCGCCAAGGC GAAGTCGCTG TTGGACCAGG AGGGACGGGA       60

CGATCTGGCG CTGCGGATCG CGGTTCAGCC GGGGGGGTGC GCTGGATTGC GCTATAACCT      120

TTTCTTCGAC GACCGGACGC TGGATGGTGA CCAAACCGCG GAGTTCGGTG GTGTCAGGTT      180

GATCGTGGAC CGGATGAGCG CGCCGTATGT GGAAGGCGCG TCGATCGATT TCGTCGACAC      240

TATTGAGAAG CAAGGTTCAC CATCGACAAT CCCAACGCCA CCGGCTCCTG CGCGTGCGGG      300

GATTCGTTCA ACTGATAAAA CGCTAGTACG ACCCCGCGGT GCGCAACACG TACGAGCACA      360

CCAAGACCTG ACCGCGCTGG AAAAGCAACT GAGCGATGCC TTGCACCTGA CCGCGTGGCG      420

GGCCGCCGGC GGCAGGTGTC ACCTGCATGG TGAACAGCAC CTGGGCCTGA TATTGCGACC      480

AGTACACGAT TTTGTCGATC GAGGTCACTT CGACCTGGGA GAACTGCTTG CGGAACGCGT      540

CGCTGCTCAG CTTGGCCAAG GCCTGATCGG AGCGCTTGTC GCGCACGCCG TCGTGGATAC      600

CGCACAGCGC ATTGCGAACG ATGGTGTCCA CATCGCGGTT CTCCAGCGCG TTGAGGTATC      660

CCTGAATCGC GGTTTTGGCC GGTCCCTCCG AGAATGTGCC TGCCGTGTTG GCTCCGTTGG      720

TGCGGACCCC GTATATGATC GCCGCCGTCA TAGCCGACAC CAGCGCGAGG GCTACCACAA      780

TGCCGATCAG CAGCCGCTTG TGCCGTCGCT TCGGGTAGGA CACCTGCGGC GGCACGCCGG      840

GATATGCGGC GGGCGGCAGC GCCGCGTCGT CTGCCGGTCC CGGGGCGAAG GCCGGTTCGG      900

CGGCGCCGAG GTCGTGGGGG TAGTCCAGGG CTTGGGGTTC GTGGGATGAG GGCTCGGGGT      960

ACGGCGCCGG TCCGTTGGTG CCGACACCGG GGTTCGGCGA GTGGGACCG GGCATTGTGG     1020

TTCTCCTAGG GTGGTGGACG GGACCAGCTG CTAGGGCGAC AACCGCCCGT CGCGTCAGCC     1080

GGCAGCATCG GCAATCAGGT GAGCTCCCTA GGCAGGCTAG CGCAACAGCT GCCGTCAGCT     1140

CTCAACGCGA CGGGGCGGGC CGCGGCGCCG ATAATGTTGA AGACTAGGC AACCTTAGGA      1200

ACGAAGGACG GAGATTTTGT GACGATC                                        1227
```

(2) INFORMATION FOR SEQ ID NO:36:

(i) SEQUENCE CHARACTERISTICS:
        (A) LENGTH: 181 base pairs
        (B) TYPE: nucleic acid
        (C) STRANDEDNESS: single
        (D) TOPOLOGY: linear (xi) SEQUENCE DESCRIPTION: SEQ ID NO:36:

```
GCGGTGTCGG CGGATCCGGC GGGTGGTTGA ACGGCAACGG CGGGGCCGGC GGGGCCGGCG       60

GGACCGGCGC TAACGGTGGT GCCGGCGGCA ACGCCTGGTT GTTCGGGGCC GGCGGGTCCG      120

GCGGNGCCGG CACCAATGGT GGNGTCGGCG GGTCCGGCGG ATTTGTCTAC GGCAACGGCG      180
```

G                                                                          181

(2) INFORMATION FOR SEQ ID NO:37:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (xi) SEQUENCE DESCRIPTION: SEQ ID NO:37:

GCGGTGTCGG CGGATCCGGC GGGTGGTTGA ACGGCAACGG CGGTGTCGGC GGCCGGGGCG      60

GCGACGGCGT CTTTGCCGGT GCCGGCGGCC AGGGCGGCCT CGGTGGGCAG GCGGCAATG      120

GCGGCGGCTC CACCGGCGGC AACGGCGGTC TTGGCGGCGC GGGCGGTGGC GGAGGCAACG     180

CCCCGGACGG CGGCTTCGGT GGCAACGGCG GTAAGGGTGG CCAGGGCGGN ATTGGCGGCG     240

GCACTCAGAG CGCGACCGGC CTCGGNGGTG ACGGCGGTGA CGGCGGTGAC                290

(2) INFORMATION FOR SEQ ID NO:38:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:38:

GATCCAGTGG CATGGNGGGT GTCAGTGGAA GCAT                                  34

(2) INFORMATION FOR SEQ ID NO:39:

(i) SEQUENCE CHARACTERISTICS:
        (A) LENGTH: 155 base pairs
        (B) TYPE: nucleic acid
        (C) STRANDEDNESS: single
        (D) TOPOLOGY: linear (xi) SEQUENCE DESCRIPTION: SEQ ID NO:39:

GATCGCTGCT CGTCCCCCCC TTGCCGCCGA CGCCACCGGT CCCACCGTTA CCGAACAAGC      60

TGGCGTGGTC GCCAGCACCC CCGGCACCGC CGACGCCGGA GTCGAACAAT GGCACCGTCG     120

TATCCCCACC ATTGCCGCCG GNCCCACCGG CACCG                                155

(2) INFORMATION FOR SEQ ID NO:40:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (xi) SEQUENCE DESCRIPTION: SEQ ID NO:40:

ATGGCGTTCA CGGGGCGCCG GGGACCGGGC AGCCCGGNGG GGCCGGGGGG TGG             53

(2) INFORMATION FOR SEQ ID NO:41:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (xi) SEQUENCE DESCRIPTION: SEQ ID NO:41:

GATCCACCGC GGGTGCAGAC GGTGCCCGCG GCGCCACCCC GACCAGCGGC GGCAACGGCG      60

```
GCACCGGCGG CAACGGCGCG AACGCCACCG TCGTCGGNGG GGCCGGCGGG GCCGGCGGCA        120

AGGGCGGCAA CG                                                           132
```

(2) INFORMATION FOR SEQ ID NO:42:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (xi) SEQUENCE DESCRIPTION: SEQ ID NO:42:

```
GATCGGCGGC CGGNACGGNC GGGGACGGCG GCAAGGGCGG NAACGGGGGC GCCGNAGCCA        60

CCNGCCAAGA ATCCTCCGNG TCCNCCAATG GCGCGAATGG CGGACAGGGC GGCAACGGCG        120

GCANCGGCGG CA                                                           132
```

(2) INFORMATION FOR SEQ ID NO:43:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (xi) SEQUENCE DESCRIPTION: SEQ ID NO:43:

```
CGGCACGAGG ATCGGTACCC CGCGGCATCG GCAGCTGCCG ATTCGCCGGG TTTCCCCACC        60

CGAGGAAAGC CGCTACCAGA TGGCGCTGCC GAAGTAGGGC GATCCGTTCG CGATGCCGGC        120

ATGAACGGGC GGCATCAAAT TAGTGCAGGA ACCTTTCAGT TTAGCGACGA TAATGGCTAT        180

AGCACTAAGG AGGATGATCC GATATGACGC AGTCGCAGAC CGTGACGGTG GATCAGCAAG        240

AGATTTTGAA CAGGGCCAAC GAGGTGGAGG CCCCGATGGC GGACCCACCG ACTGATGTCC        300

CCATCACACC GTGCGAACTC ACGGNGGNTA AAAACGCCGC CCAACAGNTG GTNTTGTCCG        360

CCGACAACAT GCGGGAATAC CTGGCGGCCG GTGCCAAAGA GCGGCAGCGT CTGGCGACCT        420

CGCTGCGCAA CGCGGCCAAG GNGTATGGCG AGGTTGATGA GGAGGCTGCG ACCGCGCTGG        480

ACAACGACGG CGAAGGAACT GTGCAGGCAG AATCGGCCGG GGCCGTCGGA GGGGACAGTT        540

CGGCCGAACT AACCGATACG CCGAGGGTGG CCACGGCCGG TGAACCCAAC TTCATGGATC        600

TCAAAGAAGC GGCAAGGAAG CTCGAAACGG GCGACCAAGG CGCATCGCTC GCGCACTGNG        660

GGGATGGGTG AACACTTNC ACCCTGACGC TGCAAGGCGA CG                          702
```

(2) INFORMATION FOR SEQ ID NO:44:

(i) SEQUENCE CHARACTERISTICS:
        (A) LENGTH: 298 base pairs
        (B) TYPE: nucleic acid
        (C) STRANDEDNESS: single
        (D) TOPOLOGY: linear (xi) SEQUENCE DESCRIPTION: SEQ ID NO:44:

```
GAAGCCGCAG CGCTGTCGGG CGACGTGGCG GTCAAAGCGG CATCGCTCGG TGGCGGTGGA        60

GGCGGCGGGG TGCCGTCGGC GCCGTTGGGA TCCGCGATCG GGGCGCCGA ATCGGTGCGG         120

CCCGCTGGCG CTGGTGACAT TGCCGGCTTA GGCCAGGGAA GGGCCGGCGG CGGCGCCGCG        180

CTGGGCGGCG GTGGCATGGG AATGCCGATG GGTGCCGCGC ATCAGGGACA AGGGGGCGCC        240

AAGTCCAAGG GTTCTCAGCA GGAAGACGAG GCGCTCTACA CCGAGGATCC TCGTGCCG         298
```

(2) INFORMATION FOR SEQ ID NO:45:

(i) SEQUENCE CHARACTERISTICS:
            (A) LENGTH: 1058 base pairs
            (B) TYPE: nucleic acid
            (C) STRANDEDNESS: single
            (D) TOPOLOGY: linear (xi) SEQUENCE DESCRIPTION: SEQ ID NO:45:

CGGCACGAGG ATCGAATCGC GTCGCCGGGA GCACAGCGTC GCACTGCACC AGTGGAGGAG        60

CCATGACCTA CTCGCCGGGT AACCCCGGAT ACCCGCAAGC GCAGCCCGCA GGCTCCTACG       120

GAGGCGTCAC ACCCTCGTTC GCCCACGCCG ATGAGGGTGC GAGCAAGCTA CCGATGTACC       180

TGAACATCGC GGTGGCAGTG CTCGGTCTGG CTGCGTACTT CGCCAGCTTC GGCCCAATGT       240

TCACCCTCAG TACCGAACTC GGGGGGGGTG ATGGCGCAGT GTCCGGTGAC ACTGGGCTGC       300

CGGTCGGGGT GGCTCTGCTG GCTGCGCTGC TTGCCGGGGT GGTTCTGGTG CCTAAGGCCA       360

AGAGCCATGT GACGGTAGTT GCGGTGCTCG GGGTACTCGG CGTATTTCTG ATGGTCTCGG       420

CGACGTTTAA CAAGCCCAGC GCCTATTCGA CCGGTTGGGC ATTGTGGGTT GTGTTGGCTT       480

TCATCGTGTT CCAGGCGGTT GCGGCAGTCC TGGCGCTCTT GGTGGAGACC GGCGCTATCA       540

CCGCGCCGGC GCCGCGGCCC AAGTTCGACC CGTATGGACA GTACGGGCGG TACGGGCAGT       600

ACGGGCAGTA CGGGGTGCAG CCGGGTGGGT ACTACGGTCA GCAGGGTGCT CAGCAGGCCG       660

CGGGACTGCA GTCGCCCGGC CCGCAGCAGT CTCCGCAGCC TCCCGGATAT GGGTCGCAGT       720

ACGGCGGCTA TTCGTCCAGT CCGAGCCAAT CGGGCAGTGG ATACACTGCT CAGCCCCCGG       780

CCCAGCCGCC GGCGCAGTCC GGGTCGCAAC AATCGCACCA GGGCCCATCC ACGCCACCTA       840

CCGGCTTTCC GAGCTTCAGC CCACCACCAC CGGTCAGTGC CGGGACGGGG TCGCAGGCTG       900

GTTCGGCTCC AGTCAACTAT TCAAACCCCA GCGGGGGCGA GCAGTCGTCG TCCCCCGGGG       960

GGGCGCCGGT CTAACCGGGC GTTCCCGCGT CCGGTCGCGC GTGTGCGCGA AGAGTGAACA      1020

GGGTGTCAGC AAGCGCGGAC GATCCTCGTG CCGAATTC                              1058

(2) INFORMATION FOR SEQ ID NO:46:

(i) SEQUENCE CHARACTERISTICS:
            (A) LENGTH: 327 base pairs
            (B) TYPE: nucleic acid
            (C) STRANDEDNESS: single
            (D) TOPOLOGY: linear (xi) SEQUENCE DESCRIPTION: SEQ ID NO:46:

CGGCACGAGA GACCGATGCC GCTACCCTCG CGCAGGAGGC AGGTAATTTC GAGCGGATCT        60

CCGGCGACCT GAAAACCCAG ATCGACCAGG TGGAGTCGAC GGCAGGTTCG TTGCAGGGCC       120

AGTGGCGCGG CGCGGCGGGG ACGGCCGCCC AGGCCGCGGT GGTGCGCTTC CAAGAAGCAG       180

CCAATAAGCA GAAGCAGGAA CTCGACGAGA TCTCGACGAA TATTCGTCAG GCCGGCGTCC       240

AATACTCGAG GGCCGACGAG GAGCAGCAGC AGGCGCTGTC CTCGCAAATG GGCTTCTGAC       300

CCGCTAATAC GAAAAGAAAC GGAGCAA                                          327

(2) INFORMATION FOR SEQ ID NO:47:

(i) SEQUENCE CHARACTERISTICS:
            (A) LENGTH: 170 base pairs
            (B) TYPE: nucleic acid
            (C) STRANDEDNESS: single
            (D) TOPOLOGY: linear (xi) SEQUENCE DESCRIPTION: SEQ ID NO:47:

```
CGGTCGCGAT GATGGCGTTG TCGAACGTGA CCGATTCTGT ACCGCCGTCG TTGAGATCAA      60

CCAACAACGT GTTGGCGTCG GCAAATGTGC CGNACCCGTG GATCTCGGTG ATCTTGTTCT     120

TCTTCATCAG GAAGTGCACA CCGGCCACCC TGCCCTCGGN TACCTTTCGG                170
```

(2) INFORMATION FOR SEQ ID NO:48:

(i) SEQUENCE CHARACTERISTICS:
    (A) LENGTH: 127 base pairs
    (B) TYPE: nucleic acid
    (C) STRANDEDNESS: single
    (D) TOPOLOGY: linear (xi) SEQUENCE DESCRIPTION: SEQ ID NO:48:

```
GATCCGGCGG CACGGGGGGT GCCGGCGGCA GCACCGCTGG CGCTGGCGGC AACGGCGGGG      60

CCGGGGGTGG CGGCGGAACC GGTGGGTTGC TCTTCGGCAA CGGCGGTGCC GGCGGGCACG     120

GGGCCGT                                                              127
```

(2) INFORMATION FOR SEQ ID NO:49:

(i) SEQUENCE CHARACTERISTICS:
    (A) LENGTH: 81 base pairs
    (B) TYPE: nucleic acid
    (C) STRANDEDNESS: single
    (D) TOPOLOGY: linear (xi) SEQUENCE DESCRIPTION: SEQ ID NO:49:

```
CGGCGGCAAG GGCGGCACCG CCGGCAACGG GAGCGGCGCG GCCGGCGGCA ACGGCGGCAA      60

CGGCGGCTCC GGCCTCAACG G                                               81
```

(2) INFORMATION FOR SEQ ID NO:50:

(i) SEQUENCE CHARACTERISTICS:
    (A) LENGTH: 149 base pairs
    (B) TYPE: nucleic acid
    (C) STRANDEDNESS: single
    (D) TOPOLOGY: linear (xi) SEQUENCE DESCRIPTION: SEQ ID NO:50:

```
GATCAGGGCT GGCCGGCTCC GGCCAGAAGG GCGGTAACGG AGGAGCTGCC GGATTGTTTG      60

GCAACGGCGG GGCCGGNGGT GCCGGCGCGT CCAACCAAGC CGGTAACGGC GGNGCCGGCG     120

GAAACGGTGG TGCCGGTGGG CTGATCTGG                                      149
```

(2) INFORMATION FOR SEQ ID NO:51:

(i) SEQUENCE CHARACTERISTICS:
    (A) LENGTH: 355 base pairs
    (B) TYPE: nucleic acid
    (C) STRANDEDNESS: single
    (D) TOPOLOGY: linear (xi) SEQUENCE DESCRIPTION: SEQ ID NO:51:

```
CGGCACGAGA TCACACCTAC CGAGTGATCG AGATCGTCGG GACCTCGCCC GACGGTGTCG      60

ACGCGGNAAT CCAGGGCGGT CTGGCCCGAG CTGCGCAGAC CATGCGCGCG CTGGACTGGT     120

TCGAAGTACA GTCAATTCGA GGCCACCTGG TCGACGGAGC GGTCGCGCAC TTCCAGGTGA     180

CTATGAAAGT CGGCTTCCGC CTGGAGGATT CCTGAACCTT CAAGCGCGGC CGATAACTGA     240

GGTGCATCAT TAAGCGACTT TTCCAGAACA TCCTGACGCG CTCGAAACGC GGTTCAGCCG     300

ACGGTGGCTC CGCCGAGGCG CTGCCTCCAA AATCCCTGCG ACAATTCGTC GGCGG          355
```

(2) INFORMATION FOR SEQ ID NO:52:

(i) SEQUENCE CHARACTERISTICS:
        (A) LENGTH: 999 base pairs
        (B) TYPE: nucleic acid
        (C) STRANDEDNESS: single
        (D) TOPOLOGY: linear (xi) SEQUENCE DESCRIPTION: SEQ ID NO:52:

```
ATGCATCACC ATCACCATCA CATGCATCAG GTGGACCCCA ACTTGACACG TCGCAAGGGA      60
CGATTGGCGG CACTGGCTAT CGCGGCGATG GCCAGCGCCA GCCTGGTGAC CGTTGCGGTG     120
CCCGCGACCG CCAACGCCGA TCCGGAGCCA GCGCCCCCGG TACCCACAAC GGCCGCCTCG     180
CCGCCGTCGA CCGCTGCAGC GCCACCCGCA CCGGCGACAC CTGTTGCCCC CCACCACCG      240
GCCGCCGCCA ACACGCCGAA TGCCCAGCCG GGCGATCCCA ACGCAGCACC TCCGCCGGCC     300
GACCCGAACG CACCGCCGCC ACCTGTCATT GCCCCAAACG CACCCCAACC TGTCCGGATC     360
GACAACCCGG TTGGAGGATT CAGCTTCGCG CTGCCTGCTG GCTGGGTGGA GTCTGACGCC     420
GCCCACTTCG ACTACGGTTC AGCACTCCTC AGCAAAACCA CCGGGGACCC GCCATTTCCC     480
GGACAGCCGC CGCCGGTGGC CAATGACACC CGTATCGTGC TCGGCCGGCT AGACCAAAAG     540
CTTTACGCCA GCGCCGAAGC CACCGACTCC AAGGCCGCGG CCCGGTTGGG CTCGGACATG     600
GGTGAGTTCT ATATGCCCTA CCCGGGCACC CGGATCAACC AGGAAACCGT CTCGCTCGAC     660
GCCAACGGGG TGTCTGGAAG CGCGTCGTAT TACGAAGTCA AGTTCAGCGA TCCGAGTAAG     720
CCGAACGGCC AGATCTGGAC GGGCGTAATC GGCTCGCCCG CGGCGAACGC ACCGGACGCC     780
GGGCCCCCTC AGCGCTGGTT TGTGGTATGG CTCGGGACCG CCAACAACCC GGTGGACAAG     840
GGCGCGGCCA AGGCGCTGGC CGAATCGATC CGGCCTTTGG TCGCCCCGCC GCCGGCGCCG     900
GCACCGGCTC CTGCAGAGCC CGCTCCGGCG CCGGCGCCGG CCGGGGAAGT CGCTCCTACC     960
CCGACGACAC CGACACCGCA GCGGACCTTA CCGGCCTGA                          999
```

(2) INFORMATION FOR SEQ ID NO:53:

(i) SEQUENCE CHARACTERISTICS:
        (A) LENGTH: 332 amino acids
        (B) TYPE: amino acid
        (C) STRANDEDNESS: single
        (D) TOPOLOGY: linear (xi) SEQUENCE DESCRIPTION: SEQ ID NO:53:

```
Met His His His His His His Met His Gln Val Asp Pro Asn Leu Thr
  1               5                  10                  15

Arg Arg Lys Gly Arg Leu Ala Ala Leu Ala Ile Ala Ala Met Ala Ser
             20                  25                  30

Ala Ser Leu Val Thr Val Ala Val Pro Ala Thr Ala Asn Ala Asp Pro
         35                  40                  45

Glu Pro Ala Pro Pro Val Pro Thr Thr Ala Ala Ser Pro Pro Ser Thr
     50                  55                  60

Ala Ala Ala Pro Pro Ala Pro Ala Thr Pro Val Ala Pro Pro Pro
 65                  70                  75                  80

Ala Ala Ala Asn Thr Pro Asn Ala Gln Pro Gly Asp Pro Asn Ala Ala
                 85                  90                  95

Pro Pro Pro Ala Asp Pro Asn Ala Pro Pro Pro Val Ile Ala Pro
                100                 105                 110

Asn Ala Pro Gln Pro Val Arg Ile Asp Asn Pro Val Gly Gly Phe Ser
                115                 120                 125
```

-continued

```
Phe Ala Leu Pro Ala Gly Trp Val Glu Ser Asp Ala Ala His Phe Asp
            130                 135                 140

Tyr Gly Ser Ala Leu Leu Ser Lys Thr Thr Gly Asp Pro Pro Phe Pro
145                 150                 155                 160

Gly Gln Pro Pro Val Ala Asn Asp Thr Arg Ile Val Leu Gly Arg
                165                 170                 175

Leu Asp Gln Lys Leu Tyr Ala Ser Ala Glu Ala Thr Asp Ser Lys Ala
                180                 185                 190

Ala Ala Arg Leu Gly Ser Asp Met Gly Glu Phe Tyr Met Pro Tyr Pro
            195                 200                 205

Gly Thr Arg Ile Asn Gln Glu Thr Val Ser Leu Asp Ala Asn Gly Val
            210                 215                 220

Ser Gly Ser Ala Ser Tyr Tyr Glu Val Lys Phe Ser Asp Pro Ser Lys
225                 230                 235                 240

Pro Asn Gly Gln Ile Trp Thr Gly Val Ile Gly Ser Pro Ala Ala Asn
                245                 250                 255

Ala Pro Asp Ala Gly Pro Pro Gln Arg Trp Phe Val Val Trp Leu Gly
            260                 265                 270

Thr Ala Asn Asn Pro Val Asp Lys Gly Ala Ala Lys Ala Leu Ala Glu
            275                 280                 285

Ser Ile Arg Pro Leu Val Ala Pro Pro Ala Pro Ala Pro Ala Pro
            290                 295                 300

Ala Glu Pro Ala Pro Ala Pro Ala Pro Gly Glu Val Ala Pro Thr
305                 310                 315                 320

Pro Thr Thr Pro Thr Pro Gln Arg Thr Leu Pro Ala
                325                 330
```

(2) INFORMATION FOR SEQ ID NO:54:

(i) SEQUENCE CHARACTERISTICS:
        (A) LENGTH: 20 amino acids
        (B) TYPE: amino acid
        (C) STRANDEDNESS:
        (D) TOPOLOGY: linear (xi) SEQUENCE DESCRIPTION: SEQ ID NO:54:

```
Asp Pro Val Asp Ala Val Ile Asn Thr Thr Xaa Asn Tyr Gly Gln Val
1               5                   10                  15

Val Ala Ala Leu
            20
```

(2) INFORMATION FOR SEQ ID NO:55:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:55:

```
Ala Val Glu Ser Gly Met Leu Ala Leu Gly Thr Pro Ala Pro Ser
1               5                   10                  15
```

(2) INFORMATION FOR SEQ ID NO:56:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:56:

Ala Ala Met Lys Pro Arg Thr Gly Asp Gly Pro Leu Glu Ala Ala Lys
1               5                   10                  15

Glu Gly Arg (2) INFORMATION FOR SEQ ID NO:57:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:57:

Tyr Tyr Trp Cys Pro Gly Gln Pro Phe Asp Pro Ala Trp Gly Pro
1               5                   10                  15

(2) INFORMATION FOR SEQ ID NO:58:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:58:

Asp Ile Gly Ser Glu Ser Thr Glu Asp Gln Gln Xaa Ala Val
1               5                   10

(2) INFORMATION FOR SEQ ID NO:59:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:59:

Ala Glu Glu Ser Ile Ser Thr Xaa Glu Xaa Ile Val Pro
1               5                   10

(2) INFORMATION FOR SEQ ID NO:60:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:60:

Asp Pro Glu Pro Ala Pro Pro Val Pro Thr Ala Ala Ala Pro Pro
1               5                   10                  15

Ala (2) INFORMATION FOR SEQ ID NO:61:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:61:

Ala Pro Lys Thr Tyr Xaa Glu Glu Leu Lys Gly Thr Asp Thr Gly
1               5                   10                  15

(2) INFORMATION FOR SEQ ID NO:62:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:62:

```
Asp Pro Ala Ser Ala Pro Asp Val Pro Thr Ala Ala Gln Gln Thr Ser
1               5                  10                  15

Leu Leu Asn Asn Leu Ala Asp Pro Asp Val Ser Phe Ala Asp
            20                  25                  30
```

(2) INFORMATION FOR SEQ ID NO:63:

(i) SEQUENCE CHARACTERISTICS:
        (A) LENGTH: 187 amino acids
        (B) TYPE: amino acid
        (C) STRANDEDNESS: single
        (D) TOPOLOGY: linear (xi) SEQUENCE DESCRIPTION: SEQ ID NO:63:

```
Thr Gly Ser Leu Asn Gln Thr His Asn Arg Arg Ala Asn Glu Arg Lys
1               5                  10                  15

Asn Thr Thr Met Lys Met Val Lys Ser Ile Ala Ala Gly Leu Thr Ala
            20                  25                  30

Ala Ala Ala Ile Gly Ala Ala Ala Ala Gly Val Thr Ser Ile Met Ala
        35                  40                  45

Gly Gly Pro Val Val Tyr Gln Met Gln Pro Val Val Phe Gly Ala Pro
    50                  55                  60

Leu Pro Leu Asp Pro Ala Ser Ala Pro Asp Val Pro Thr Ala Ala Gln
65                  70                  75                  80

Leu Thr Ser Leu Leu Asn Ser Leu Ala Asp Pro Asn Val Ser Phe Ala
            85                  90                  95

Asn Lys Gly Ser Leu Val Glu Gly Gly Ile Gly Gly Thr Glu Ala Arg
        100                 105                 110

Ile Ala Asp His Lys Leu Lys Lys Ala Ala Glu His Gly Asp Leu Pro
    115                 120                 125

Leu Ser Phe Ser Val Thr Asn Ile Gln Pro Ala Ala Ala Gly Ser Ala
130                 135                 140

Thr Ala Asp Val Ser Val Ser Gly Pro Lys Leu Ser Ser Pro Val Thr
145                 150                 155                 160

Gln Asn Val Thr Phe Val Asn Gln Gly Gly Trp Met Leu Ser Arg Ala
            165                 170                 175

Ser Ala Met Glu Leu Leu Gln Ala Ala Gly Xaa
        180                 185
```

(2) INFORMATION FOR SEQ ID NO:64:

(i) SEQUENCE CHARACTERISTICS:
        (A) LENGTH: 148 amino acids
        (B) TYPE: amino acid
        (C) STRANDEDNESS: single
        (D) TOPOLOGY: linear (xi) SEQUENCE DESCRIPTION: SEQ ID NO:64:

```
Asp Glu Val Thr Val Glu Thr Thr Ser Val Phe Arg Ala Asp Phe Leu
1               5                  10                  15

Ser Glu Leu Asp Ala Pro Ala Gln Ala Gly Thr Glu Ser Ala Val Ser
```

-continued

```
            20                  25                  30
Gly Val Glu Gly Leu Pro Pro Gly Ser Ala Leu Leu Val Lys Arg
             35                  40                  45

Gly Pro Asn Ala Gly Ser Arg Phe Leu Leu Asp Gln Ala Ile Thr Ser
 50                  55                  60

Ala Gly Arg His Pro Asp Ser Asp Ile Phe Leu Asp Asp Val Thr Val
 65                  70                  75                  80

Ser Arg Arg His Ala Glu Phe Arg Leu Glu Asn Asn Glu Phe Asn Val
                 85                  90                  95

Val Asp Val Gly Ser Leu Asn Gly Thr Tyr Val Asn Arg Glu Pro Val
            100                 105                 110

Asp Ser Ala Val Leu Ala Asn Gly Asp Glu Val Gln Ile Gly Lys Leu
            115                 120                 125

Arg Leu Val Phe Leu Thr Gly Pro Lys Gln Gly Glu Asp Asp Gly Ser
130                 135                 140

Thr Gly Gly Pro
145
```

(2) INFORMATION FOR SEQ ID NO:65:

(i) SEQUENCE CHARACTERISTICS:
        (A) LENGTH: 230 amino acids
        (B) TYPE: amino acid
        (C) STRANDEDNESS: single
        (D) TOPOLOGY: linear (xi) SEQUENCE DESCRIPTION: SEQ ID NO:65:

```
Thr Ser Asn Arg Pro Ala Arg Arg Gly Arg Arg Ala Pro Arg Asp Thr
 1               5                  10                  15

Gly Pro Asp Arg Ser Ala Ser Leu Ser Leu Val Arg His Arg Arg Gln
             20                  25                  30

Gln Arg Asp Ala Leu Cys Leu Ser Thr Gln Ile Ser Arg Gln Ser
             35                  40                  45

Asn Leu Pro Pro Ala Ala Gly Gly Ala Ala Asn Tyr Ser Arg Arg Asn
 50                  55                  60

Phe Asp Val Arg Ile Lys Ile Phe Met Leu Val Thr Ala Val Val Leu
 65                  70                  75                  80

Leu Cys Cys Ser Gly Val Ala Thr Ala Ala Pro Lys Thr Tyr Cys Glu
                 85                  90                  95

Glu Leu Lys Gly Thr Asp Thr Gly Gln Ala Cys Gln Ile Gln Met Ser
            100                 105                 110

Asp Pro Ala Tyr Asn Ile Asn Ile Ser Leu Pro Ser Tyr Tyr Pro Asp
            115                 120                 125

Gln Lys Ser Leu Glu Asn Tyr Ile Ala Gln Thr Arg Asp Lys Phe Leu
130                 135                 140

Ser Ala Ala Thr Ser Ser Thr Pro Arg Glu Ala Pro Tyr Glu Leu Asn
145                 150                 155                 160

Ile Thr Ser Ala Thr Tyr Gln Ser Ala Ile Pro Pro Arg Gly Thr Gln
                165                 170                 175

Ala Val Val Leu Xaa Val Tyr His Asn Ala Gly Gly Thr His Pro Thr
            180                 185                 190

Thr Thr Tyr Lys Ala Phe Asp Trp Asp Gln Ala Tyr Arg Lys Pro Ile
            195                 200                 205

Thr Tyr Asp Thr Leu Trp Gln Ala Asp Thr Asp Pro Leu Pro Val Val
            210                 215                 220
```

```
Phe Pro Ile Val Ala Arg
225                 230

(2) INFORMATION FOR SEQ ID NO:66:

(i) SEQUENCE CHARACTERISTICS:
        (A) LENGTH: 132 amino acids
        (B) TYPE: amino acid
        (C) STRANDEDNESS: single
        (D) TOPOLOGY: linear (xi) SEQUENCE DESCRIPTION: SEQ ID NO:66:

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Arg Ser
            20                  25                  30

Gly Gly Gly Ser Pro Thr Val His Ile Gly Pro Thr Ala Phe Leu Gly
        35                  40                  45

Leu Gly Val Val Asp Asn Asn Gly Asn Gly Ala Arg Val Gln Arg Val
    50                  55                  60

Val Gly Ser Ala Pro Ala Ala Ser Leu Gly Ile Ser Thr Gly Asp Val
65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Asn Trp
                100                 105                 110

Gln Thr Lys Ser Gly Gly Thr Arg Thr Gly Asn Val Thr Leu Ala Glu
            115                 120                 125

Gly Pro Pro Ala
        130

(2) INFORMATION FOR SEQ ID NO:67:

(i) SEQUENCE CHARACTERISTICS:
        (A) LENGTH: 100 amino acids
        (B) TYPE: amino acid
        (C) STRANDEDNESS: single
        (D) TOPOLOGY: linear (xi) SEQUENCE DESCRIPTION: SEQ ID NO:67:

Val Pro Leu Arg Ser Pro Ser Met Ser Pro Ser Lys Cys Leu Ala Ala
1               5                   10                  15

Ala Gln Arg Asn Pro Val Ile Arg Arg Arg Leu Ser Asn Pro Pro
            20                  25                  30

Pro Arg Lys Tyr Arg Ser Met Pro Ser Pro Ala Thr Ala Ser Ala Gly
            35                  40                  45

Met Ala Arg Val Arg Arg Arg Ala Ile Trp Arg Gly Pro Ala Thr Xaa
        50                  55                  60

Ser Ala Gly Met Ala Arg Val Arg Arg Trp Xaa Val Met Pro Xaa Val
65                  70                  75                  80

Ile Gln Ser Thr Xaa Ile Arg Xaa Xaa Gly Pro Phe Asp Asn Arg Gly
                85                  90                  95

Ser Glu Arg Lys
            100

(2) INFORMATION FOR SEQ ID NO:68:

(i) SEQUENCE CHARACTERISTICS:
        (A) LENGTH: 163 amino acids
        (B) TYPE: amino acid
```

-continued

```
        (C) STRANDEDNESS: single
        (D) TOPOLOGY: linear (xi) SEQUENCE DESCRIPTION: SEQ ID NO:68:

Met Thr Asp Asp Ile Leu Leu Ile Asp Thr Asp Glu Arg Val Arg Thr
1               5                   10                  15

Leu Thr Leu Asn Arg Pro Gln Ser Arg Asn Ala Leu Ser Ala Ala Leu
            20                  25                  30

Arg Asp Arg Phe Phe Ala Xaa Leu Xaa Asp Ala Glu Xaa Asp Asp Asp
        35                  40                  45

Ile Asp Val Val Ile Leu Thr Gly Ala Asp Pro Val Phe Cys Ala Gly
50                      55                  60

Leu Asp Leu Lys Val Ala Gly Arg Ala Asp Arg Ala Ala Gly His Leu
65                  70                  75                  80

Thr Ala Val Gly Gly His Asp Gln Ala Gly Asp Arg Arg Asp Gln Arg
                85                  90                  95

Arg Arg Gly His Arg Arg Ala Arg Thr Gly Ala Val Leu Arg His Pro
            100                 105                 110

Asp Arg Leu Arg Ala Arg Pro Leu Arg Arg His Pro Arg Pro Gly Gly
        115                 120                 125

Ala Ala Ala His Leu Gly Thr Gln Cys Val Leu Ala Ala Lys Gly Arg
130                 135                 140

His Arg Xaa Gly Pro Val Asp Glu Pro Asp Arg Arg Leu Pro Val Arg
145                 150                 155                 160

Asp Arg Arg (2) INFORMATION FOR SEQ ID NO:69:

(i) SEQUENCE CHARACTERISTICS:
        (A) LENGTH: 344 amino acids
        (B) TYPE: amino acid
        (C) STRANDEDNESS: single
        (D) TOPOLOGY: linear (xi) SEQUENCE DESCRIPTION: SEQ ID NO:69:

Met Lys Phe Val Asn His Ile Glu Pro Val Ala Pro Arg Arg Ala Gly
1               5                   10                  15

Gly Ala Val Ala Glu Val Tyr Ala Glu Ala Arg Arg Glu Phe Gly Arg
            20                  25                  30

Leu Pro Glu Pro Leu Ala Met Leu Ser Pro Asp Glu Gly Leu Leu Thr
        35                  40                  45

Ala Gly Trp Ala Thr Leu Arg Glu Thr Leu Leu Val Gly Gln Val Pro
50                  55                      60

Arg Gly Arg Lys Glu Ala Val Ala Ala Val Ala Ala Ser Leu Arg
65                  70                  75                  80

Cys Pro Trp Cys Val Asp Ala His Thr Thr Met Leu Tyr Ala Ala Gly
                85                  90                  95

Gln Thr Asp Thr Ala Ala Ala Ile Leu Ala Gly Thr Ala Pro Ala Ala
            100                 105                 110

Gly Asp Pro Asn Ala Pro Tyr Val Ala Trp Ala Ala Gly Thr Gly Thr
        115                 120                 125

Pro Ala Gly Pro Pro Ala Pro Phe Gly Pro Asp Val Ala Ala Glu Tyr
        130                 135                 140

Leu Gly Thr Ala Val Gln Phe His Phe Ile Ala Arg Leu Val Leu Val
145                 150                 155                 160

Leu Leu Asp Glu Thr Phe Leu Pro Gly Gly Pro Arg Ala Gln Gln Leu
```

```
                         165                 170                 175
Met Arg Arg Ala Gly Gly Leu Val Phe Ala Arg Lys Val Arg Ala Glu
                180                 185                 190

His Arg Pro Gly Arg Ser Thr Arg Leu Glu Pro Arg Thr Leu Pro
        195                 200                 205

Asp Asp Leu Ala Trp Ala Thr Pro Ser Glu Pro Ile Ala Thr Ala Phe
    210                 215                 220

Ala Ala Leu Ser His His Leu Asp Thr Ala Pro His Leu Pro Pro Pro
225                 230                 235                 240

Thr Arg Gln Val Val Arg Arg Val Val Gly Ser Trp His Gly Glu Pro
                245                 250                 255

Met Pro Met Ser Ser Arg Trp Thr Asn Glu His Thr Ala Glu Leu Pro
                260                 265                 270

Ala Asp Leu His Ala Pro Thr Arg Leu Ala Leu Leu Thr Gly Leu Ala
                275                 280                 285

Pro His Gln Val Thr Asp Asp Val Ala Ala Arg Ser Leu Leu
        290                 295                 300

Asp Thr Asp Ala Ala Leu Val Gly Ala Leu Ala Trp Ala Ala Phe Thr
305                 310                 315                 320

Ala Ala Arg Arg Ile Gly Thr Trp Ile Gly Ala Ala Glu Gly Gln
                325                 330                 335

Val Ser Arg Gln Asn Pro Thr Gly
                340
```

(2) INFORMATION FOR SEQ ID NO:70:

(i) SEQUENCE CHARACTERISTICS:
        (A) LENGTH: 485 amino acids
        (B) TYPE: amino acid
        (C) STRANDEDNESS: single
        (D) TOPOLOGY: linear (xi) SEQUENCE DESCRIPTION: SEQ ID NO:70:

```
Asp Asp Pro Asp Met Pro Gly Thr Val Ala Lys Ala Val Ala Asp Ala
1               5                   10                  15

Leu Gly Arg Gly Ile Ala Pro Val Glu Asp Ile Gln Asp Cys Val Glu
                20                  25                  30

Ala Arg Leu Gly Glu Ala Gly Leu Asp Asp Val Ala Arg Val Tyr Ile
                35                  40                  45

Ile Tyr Arg Gln Arg Arg Ala Glu Leu Arg Thr Ala Lys Ala Leu Leu
    50                  55                  60

Gly Val Arg Asp Glu Leu Lys Leu Ser Leu Ala Ala Val Thr Val Leu
65                  70                  75                  80

Arg Glu Arg Tyr Leu Leu His Asp Glu Gln Gly Arg Pro Ala Glu Ser
                85                  90                  95

Thr Gly Glu Leu Met Asp Arg Ser Ala Arg Cys Val Ala Ala Ala Glu
                100                 105                 110

Asp Gln Tyr Glu Pro Gly Ser Ser Arg Arg Trp Ala Glu Arg Phe Ala
                115                 120                 125

Thr Leu Leu Arg Asn Leu Glu Phe Leu Pro Asn Ser Pro Thr Leu Met
    130                 135                 140

Asn Ser Gly Thr Asp Leu Gly Leu Leu Ala Gly Cys Phe Val Leu Pro
145                 150                 155                 160

Ile Glu Asp Ser Leu Gln Ser Ile Phe Ala Thr Leu Gly Gln Ala Ala
                165                 170                 175
```

-continued

```
Glu Leu Gln Arg Ala Gly Gly Thr Gly Tyr Ala Phe Ser His Leu
            180                 185                 190

Arg Pro Ala Gly Asp Arg Val Ala Ser Thr Gly Gly Thr Ala Ser Gly
            195                 200                 205

Pro Val Ser Phe Leu Arg Leu Tyr Asp Ser Ala Ala Gly Val Val Ser
210                 215                 220

Met Gly Gly Arg Arg Gly Ala Cys Met Ala Val Leu Asp Val Ser
225                 230                 235                 240

His Pro Asp Ile Cys Asp Phe Val Thr Ala Lys Ala Glu Ser Pro Ser
                245                 250                 255

Glu Leu Pro His Phe Asn Leu Ser Val Gly Val Thr Asp Ala Phe Leu
            260                 265                 270

Arg Ala Val Glu Arg Asn Gly Leu His Arg Leu Val Asn Pro Arg Thr
            275                 280                 285

Gly Lys Ile Val Ala Arg Met Pro Ala Ala Glu Leu Phe Asp Ala Ile
            290                 295                 300

Cys Lys Ala Ala His Ala Gly Gly Asp Pro Gly Leu Val Phe Leu Asp
305                 310                 315                 320

Thr Ile Asn Arg Ala Asn Pro Val Pro Gly Arg Gly Arg Ile Glu Ala
                325                 330                 335

Thr Asn Pro Cys Gly Glu Val Pro Leu Leu Pro Tyr Glu Ser Cys Asn
            340                 345                 350

Leu Gly Ser Ile Asn Leu Ala Arg Met Leu Ala Asp Gly Arg Val Asp
            355                 360                 365

Trp Asp Arg Leu Glu Glu Val Ala Gly Val Ala Val Arg Phe Leu Asp
            370                 375                 380

Asp Val Ile Asp Val Ser Arg Tyr Pro Phe Pro Glu Leu Gly Glu Ala
385                 390                 395                 400

Ala Arg Ala Thr Arg Lys Ile Gly Leu Gly Val Met Gly Leu Ala Glu
            405                 410                 415

Leu Leu Ala Ala Leu Gly Ile Pro Tyr Asp Ser Glu Glu Ala Val Arg
            420                 425                 430

Leu Ala Thr Arg Leu Met Arg Arg Ile Gln Gln Ala Ala His Thr Ala
            435                 440                 445

Ser Arg Arg Leu Ala Glu Glu Arg Gly Ala Phe Pro Ala Phe Thr Asp
            450                 455                 460

Ser Arg Phe Ala Arg Ser Gly Pro Arg Arg Asn Ala Gln Val Thr Ser
465                 470                 475                 480

Val Ala Pro Thr Gly
                485
```

(2) INFORMATION FOR SEQ ID NO:71:

(i) SEQUENCE CHARACTERISTICS:
        (A) LENGTH: 267 amino acids
        (B) TYPE: amino acid
        (C) STRANDEDNESS: single
        (D) TOPOLOGY: linear (xi) SEQUENCE DESCRIPTION: SEQ ID NO:71:

```
Gly Val Ile Val Leu Asp Leu Glu Pro Arg Gly Pro Leu Pro Thr Glu
1               5                   10                  15

Ile Tyr Trp Arg Arg Gly Leu Ala Leu Gly Ile Ala Val Val Val
            20                  25                  30

Val Gly Ile Ala Val Ala Ile Val Ile Ala Phe Val Asp Ser Ser Ala
            35                  40                  45
```

```
Gly Ala Lys Pro Val Ser Ala Asp Lys Pro Ala Ser Ala Gln Ser His
        50                  55                  60

Pro Gly Ser Pro Ala Pro Gln Ala Pro Gln Pro Ala Gly Gln Thr Glu
 65                  70                  75                  80

Gly Asn Ala Ala Ala Pro Pro Gln Gly Gln Asn Pro Glu Thr Pro
                85                  90                  95

Thr Pro Thr Ala Ala Val Gln Pro Pro Val Leu Lys Glu Gly Asp
                100                 105                 110

Asp Cys Pro Asp Ser Thr Leu Ala Val Lys Gly Leu Thr Asn Ala Pro
            115                 120                 125

Gln Tyr Tyr Val Gly Asp Gln Pro Lys Phe Thr Met Val Val Thr Asn
    130                 135                 140

Ile Gly Leu Val Ser Cys Lys Arg Asp Val Gly Ala Ala Val Leu Ala
145                 150                 155                 160

Ala Tyr Val Tyr Ser Leu Asp Asn Lys Arg Leu Trp Ser Asn Leu Asp
                165                 170                 175

Cys Ala Pro Ser Asn Glu Thr Leu Val Lys Thr Phe Ser Pro Gly Glu
            180                 185                 190

Gln Val Thr Thr Ala Val Thr Trp Thr Gly Met Gly Ser Ala Pro Arg
        195                 200                 205

Cys Pro Leu Pro Arg Pro Ala Ile Gly Pro Gly Thr Tyr Asn Leu Val
    210                 215                 220

Val Gln Leu Gly Asn Leu Arg Ser Leu Pro Val Pro Phe Ile Leu Asn
225                 230                 235                 240

Gln Pro Pro Pro Pro Gly Pro Val Pro Ala Pro Gly Pro Ala Gln
                245                 250                 255

Ala Pro Pro Pro Glu Ser Pro Ala Gln Gly Gly
            260                 265

(2) INFORMATION FOR SEQ ID NO:72:

(i) SEQUENCE CHARACTERISTICS:
        (A) LENGTH: 97 amino acids
        (B) TYPE: amino acid
        (C) STRANDEDNESS: single
        (D) TOPOLOGY: linear (xi) SEQUENCE DESCRIPTION: SEQ ID NO:72:

Leu Ile Ser Thr Gly Lys Ala Ser His Ala Ser Leu Gly Val Gln Val
 1               5                  10                  15

Thr Asn Asp Lys Asp Thr Pro Gly Ala Lys Ile Val Glu Val Val Ala
                20                  25                  30

Gly Gly Ala Ala Ala Asn Ala Gly Val Pro Lys Gly Val Val Val Thr
                35                  40                  45

Lys Val Asp Asp Arg Pro Ile Asn Ser Ala Asp Ala Leu Val Ala Ala
    50                  55                  60

Val Arg Ser Lys Ala Pro Gly Ala Thr Val Ala Leu Thr Phe Gln Asp
 65                  70                  75                  80

Pro Ser Gly Gly Ser Arg Thr Val Gln Val Thr Leu Gly Lys Ala Glu
                85                  90                  95

Gln (2) INFORMATION FOR SEQ ID NO:73:

(i) SEQUENCE CHARACTERISTICS:
        (A) LENGTH: 364 amino acids
```

(B) TYPE: amino acid
(C) STRANDEDNESS: single
(D) TOPOLOGY: linear (xi) SEQUENCE DESCRIPTION: SEQ ID NO:73:

```
Gly Ala Ala Val Ser Leu Leu Ala Ala Gly Thr Leu Val Leu Thr Ala
1               5                   10                  15

Cys Gly Gly Thr Asn Ser Ser Ser Gly Ala Gly Gly Thr Ser
            20                  25                  30

Gly Ser Val His Cys Gly Gly Lys Lys Glu Leu His Ser Ser Gly Ser
            35                  40                  45

Thr Ala Gln Glu Asn Ala Met Glu Gln Phe Val Tyr Ala Tyr Val Arg
            50                  55                  60

Ser Cys Pro Gly Tyr Thr Leu Asp Tyr Asn Ala Asn Gly Ser Gly Ala
65                  70                  75                  80

Gly Val Thr Gln Phe Leu Asn Asn Glu Thr Asp Phe Ala Gly Ser Asp
            85                  90                  95

Val Pro Leu Asn Pro Ser Thr Gly Gln Pro Asp Arg Ser Ala Glu Arg
            100                 105                 110

Cys Gly Ser Pro Ala Trp Asp Leu Pro Thr Val Phe Gly Pro Ile Ala
            115                 120                 125

Ile Thr Tyr Asn Ile Lys Gly Val Ser Thr Leu Asn Leu Asp Gly Pro
            130                 135                 140

Thr Thr Ala Lys Ile Phe Asn Gly Thr Ile Thr Val Trp Asn Asp Pro
145                 150                 155                 160

Gln Ile Gln Ala Leu Asn Ser Gly Thr Asp Leu Pro Pro Thr Pro Ile
            165                 170                 175

Ser Val Ile Phe Arg Ser Asp Lys Ser Gly Thr Ser Asp Asn Phe Gln
            180                 185                 190

Lys Tyr Leu Asp Gly Val Ser Asn Gly Ala Trp Gly Lys Gly Ala Ser
            195                 200                 205

Glu Thr Phe Ser Gly Gly Val Gly Val Gly Ala Ser Gly Asn Asn Gly
            210                 215                 220

Thr Ser Ala Leu Leu Gln Thr Thr Asp Gly Ser Ile Thr Tyr Asn Glu
225                 230                 235                 240

Trp Ser Phe Ala Val Gly Lys Gln Leu Asn Met Ala Gln Ile Ile Thr
            245                 250                 255

Ser Ala Gly Pro Asp Pro Val Ala Ile Thr Thr Glu Ser Val Gly Lys
            260                 265                 270

Thr Ile Ala Gly Ala Lys Ile Met Gly Gln Gly Asn Asp Leu Val Leu
            275                 280                 285

Asp Thr Ser Ser Phe Tyr Arg Pro Thr Gln Pro Gly Ser Tyr Pro Ile
            290                 295                 300

Val Leu Ala Thr Tyr Glu Ile Val Cys Ser Lys Tyr Pro Asp Ala Thr
305                 310                 315                 320

Thr Gly Thr Ala Val Arg Ala Phe Met Gln Ala Ala Ile Gly Pro Gly
            325                 330                 335

Gln Glu Gly Leu Asp Gln Tyr Gly Ser Ile Pro Leu Pro Lys Ser Phe
            340                 345                 350

Gln Ala Lys Leu Ala Ala Ala Val Asn Ala Ile Ser
            355                 360
```

(2) INFORMATION FOR SEQ ID NO:74:

(i) SEQUENCE CHARACTERISTICS:

(A) LENGTH: 309 amino acids
        (B) TYPE: amino acid
        (C) STRANDEDNESS: single
        (D) TOPOLOGY: linear (xi) SEQUENCE DESCRIPTION: SEQ ID NO:74:

Gln Ala Ala Gly Arg Ala Val Arg Arg Thr Gly His Ala Glu Asp
1               5                   10                  15

Gln Thr His Gln Asp Arg Leu His His Gly Cys Arg Arg Ala Ala Val
            20                  25                  30

Val Val Arg Gln Asp Arg Ala Ser Val Ser Ala Thr Ser Ala Arg Pro
        35                  40                  45

Pro Arg Arg His Pro Ala Gln Gly His Arg Arg Val Ala Pro Ser
    50                  55                  60

Gly Gly Arg Arg Arg Pro His Pro His His Val Gln Pro Asp Asp Arg
65                  70                  75                  80

Arg Asp Arg Pro Ala Leu Leu Asp Arg Thr Gln Pro Ala Glu His Pro
                85                  90                  95

Asp Pro His Arg Arg Gly Pro Ala Asp Pro Gly Arg Val Arg Gly Arg
            100                 105                 110

Gly Arg Leu Arg Arg Val Asp Asp Gly Arg Leu Gln Pro Asp Arg Asp
        115                 120                 125

Ala Asp His Gly Ala Pro Val Arg Gly Arg Gly Pro His Arg Gly Val
    130                 135                 140

Gln His Arg Gly Gly Pro Val Phe Val Arg Arg Val Pro Gly Val Arg
145                 150                 155                 160

Cys Ala His Arg Arg Gly His Arg Arg Val Ala Ala Pro Gly Gln Gly
                165                 170                 175

Asp Val Leu Arg Ala Gly Leu Arg Val Glu Arg Leu Arg Pro Val Ala
            180                 185                 190

Ala Val Glu Asn Leu His Arg Gly Ser Gln Arg Ala Asp Gly Arg Val
        195                 200                 205

Phe Arg Pro Ile Arg Arg Gly Ala Arg Leu Pro Ala Arg Arg Ser Arg
    210                 215                 220

Ala Gly Pro Gln Gly Arg Leu His Leu Asp Gly Ala Gly Pro Ser Pro
225                 230                 235                 240

Leu Pro Ala Arg Ala Gly Gln Gln Pro Ser Ser Ala Gly Gly Arg
                245                 250                 255

Arg Ala Gly Gly Ala Glu Arg Ala Asp Pro Gly Gln Arg Gly Arg His
            260                 265                 270

His Gln Gly Gly His Asp Pro Gly Arg Gln Gly Ala Gln Arg Gly Thr
        275                 280                 285

Ala Gly Val Ala His Ala Ala Ala Gly Pro Arg Arg Ala Ala Val Arg
    290                 295                 300

Asn Arg Pro Arg Arg
305

(2) INFORMATION FOR SEQ ID NO:75:

(i) SEQUENCE CHARACTERISTICS:
        (A) LENGTH: 580 amino acids
        (B) TYPE: amino acid
        (C) STRANDEDNESS: single
        (D) TOPOLOGY: linear (xi) SEQUENCE DESCRIPTION: SEQ ID NO:75:

Ser Ala Val Trp Cys Leu Asn Gly Phe Thr Gly Arg His Arg His Gly

-continued

```
  1               5              10              15
Arg Cys Arg Val Arg Ala Ser Gly Trp Arg Ser Ser Asn Arg Trp Cys
                20              25              30
Ser Thr Thr Ala Asp Cys Ala Ser Lys Thr Pro Thr Gln Ala Ala
        35              40              45
Ser Pro Leu Glu Arg Arg Phe Thr Cys Cys Ser Pro Ala Val Gly Cys
        50              55              60
Arg Phe Arg Ser Phe Pro Val Arg Arg Leu Ala Leu Gly Ala Arg Thr
65                      70              75              80
Ser Arg Thr Leu Gly Val Arg Arg Thr Leu Ser Gln Trp Asn Leu Ser
                85              90              95
Pro Arg Ala Gln Pro Ser Cys Ala Val Thr Val Glu Ser His Thr His
                100             105             110
Ala Ser Pro Arg Met Ala Lys Leu Ala Arg Val Val Gly Leu Val Gln
                115             120             125
Glu Glu Gln Pro Ser Asp Met Thr Asn His Pro Arg Tyr Ser Pro Pro
                130             135             140
Pro Gln Gln Pro Gly Thr Pro Gly Tyr Ala Gln Gly Gln Gln Thr
145             150             155             160
Tyr Ser Gln Gln Phe Asp Trp Arg Tyr Pro Pro Ser Pro Pro Gln
                165             170             175
Pro Thr Gln Tyr Arg Gln Pro Tyr Glu Ala Leu Gly Thr Arg Pro
                180             185             190
Gly Leu Ile Pro Gly Val Ile Pro Thr Met Thr Pro Pro Gly Met
                195             200             205
Val Arg Gln Arg Pro Arg Ala Gly Met Leu Ala Ile Gly Ala Val Thr
    210             215             220
Ile Ala Val Val Ser Ala Gly Ile Gly Gly Ala Ala Ser Leu Val
225             230             235             240
Gly Phe Asn Arg Ala Pro Ala Gly Pro Ser Gly Gly Pro Val Ala Ala
                245             250             255
Ser Ala Ala Pro Ser Ile Pro Ala Ala Asn Met Pro Pro Gly Ser Val
                260             265             270
Glu Gln Val Ala Ala Lys Val Val Pro Ser Val Val Met Leu Glu Thr
                275             280             285
Asp Leu Gly Arg Gln Ser Glu Glu Gly Ser Gly Ile Ile Leu Ser Ala
    290             295             300
Glu Gly Leu Ile Leu Thr Asn Asn His Val Ile Ala Ala Ala Lys
305             310             315             320
Pro Pro Leu Gly Ser Pro Pro Lys Thr Thr Val Thr Phe Ser Asp
                325             330             335
Gly Arg Thr Ala Pro Phe Thr Val Val Gly Ala Asp Pro Thr Ser Asp
                340             345             350
Ile Ala Val Val Arg Val Gln Gly Val Ser Gly Leu Thr Pro Ile Ser
                355             360             365
Leu Gly Ser Ser Ser Asp Leu Arg Val Gly Gln Pro Val Leu Ala Ile
    370             375             380
Gly Ser Pro Leu Gly Leu Glu Gly Thr Val Thr Thr Gly Ile Val Ser
385             390             395             400
Ala Leu Asn Arg Pro Val Ser Thr Thr Gly Glu Ala Gly Asn Gln Asn
                405             410             415
Thr Val Leu Asp Ala Ile Gln Thr Asp Ala Ala Ile Asn Pro Gly Asn
                420             425             430
```

```
Ser Gly Gly Ala Leu Val Asn Met Asn Ala Gln Leu Val Gly Val Asn
        435                 440                 445

Ser Ala Ile Ala Thr Leu Gly Ala Asp Ser Ala Asp Ala Gln Ser Gly
    450                 455                 460

Ser Ile Gly Leu Gly Phe Ala Ile Pro Val Asp Gln Ala Lys Arg Ile
465                 470                 475                 480

Ala Asp Glu Leu Ile Ser Thr Gly Lys Ala Ser His Ala Ser Leu Gly
                485                 490                 495

Val Gln Val Thr Asn Asp Lys Asp Thr Pro Gly Ala Lys Ile Val Glu
            500                 505                 510

Val Val Ala Gly Gly Ala Ala Asn Ala Gly Val Pro Lys Gly Val
            515                 520                 525

Val Val Thr Lys Val Asp Asp Arg Pro Ile Asn Ser Ala Asp Ala Leu
    530                 535                 540

Val Ala Ala Val Arg Ser Lys Ala Pro Gly Ala Thr Val Ala Leu Thr
545                 550                 555                 560

Phe Gln Asp Pro Ser Gly Gly Ser Arg Thr Val Gln Val Thr Leu Gly
                565                 570                 575

Lys Ala Glu Gln
            580
```

(2) INFORMATION FOR SEQ ID NO:76:

(i) SEQUENCE CHARACTERISTICS:
        (A) LENGTH: 233 amino acids
        (B) TYPE: amino acid
        (C) STRANDEDNESS: single
        (D) TOPOLOGY: linear (xi) SEQUENCE DESCRIPTION: SEQ ID NO:76:

```
Met Asn Asp Gly Lys Arg Ala Val Thr Ser Ala Val Leu Val Val Leu
1               5                   10                  15

Gly Ala Cys Leu Ala Leu Trp Leu Ser Gly Cys Ser Ser Pro Lys Pro
            20                  25                  30

Asp Ala Glu Glu Gln Gly Val Pro Val Ser Pro Thr Ala Ser Asp Pro
                35                  40                  45

Ala Leu Leu Ala Glu Ile Arg Gln Ser Leu Asp Ala Thr Lys Gly Leu
    50                  55                  60

Thr Ser Val His Val Ala Val Arg Thr Gly Lys Val Asp Ser Leu
65                  70                  75                  80

Leu Gly Ile Thr Ser Ala Asp Val Asp Val Arg Ala Asn Pro Leu Ala
            85                  90                  95

Ala Lys Gly Val Cys Thr Tyr Asn Asp Glu Gln Gly Val Pro Phe Arg
            100                 105                 110

Val Gln Gly Asp Asn Ile Ser Val Lys Leu Phe Asp Asp Trp Ser Asn
            115                 120                 125

Leu Gly Ser Ile Ser Glu Leu Ser Thr Ser Arg Val Leu Asp Pro Ala
    130                 135                 140

Ala Gly Val Thr Gln Leu Leu Ser Gly Val Thr Asn Leu Gln Ala Gln
145                 150                 155                 160

Gly Thr Glu Val Ile Asp Gly Ile Ser Thr Thr Lys Ile Thr Gly Thr
                165                 170                 175

Ile Pro Ala Ser Ser Val Lys Met Leu Asp Pro Gly Ala Lys Ser Ala
            180                 185                 190

Arg Pro Ala Thr Val Trp Ile Ala Gln Asp Gly Ser His His Leu Val
```

```
                195                 200                 205
Arg Ala Ser Ile Asp Leu Gly Ser Gly Ser Ile Gln Leu Thr Gln Ser
    210                 215                 220

Lys Trp Asn Glu Pro Val Asn Val Asp
225                 230
```

(2) INFORMATION FOR SEQ ID NO:77:

(i) SEQUENCE CHARACTERISTICS:
        (A) LENGTH: 66 amino acids
        (B) TYPE: amino acid
        (C) STRANDEDNESS: single
        (D) TOPOLOGY: linear (xi) SEQUENCE DESCRIPTION: SEQ ID NO:77:

```
Val Ile Asp Ile Ile Gly Thr Ser Pro Thr Ser Trp Glu Gln Ala Ala
1               5                   10                  15

Ala Glu Ala Val Gln Arg Ala Arg Asp Ser Val Asp Asp Ile Arg Val
                20                  25                  30

Ala Arg Val Ile Glu Gln Asp Met Ala Val Asp Ser Ala Gly Lys Ile
            35                  40                  45

Thr Tyr Arg Ile Lys Leu Glu Val Ser Phe Lys Met Arg Pro Ala Gln
        50                  55                  60

Pro Arg
65
```

(2) INFORMATION FOR SEQ ID NO:78:

(i) SEQUENCE CHARACTERISTICS:
        (A) LENGTH: 69 amino acids
        (B) TYPE: amino acid
        (C) STRANDEDNESS: single
        (D) TOPOLOGY: linear (xi) SEQUENCE DESCRIPTION: SEQ ID NO:78:

```
Val Pro Pro Ala Pro Pro Leu Pro Pro Leu Pro Pro Ser Pro Ile Ser
1               5                   10                  15

Cys Ala Ser Pro Pro Ser Pro Pro Leu Pro Pro Ala Pro Pro Val Ala
                20                  25                  30

Pro Gly Pro Pro Met Pro Pro Leu Asp Pro Trp Pro Pro Ala Pro Pro
            35                  40                  45

Leu Pro Tyr Ser Thr Pro Pro Gly Ala Pro Leu Pro Pro Ser Pro Pro
        50                  55                  60

Ser Pro Pro Leu Pro
65
```

(2) INFORMATION FOR SEQ ID NO:79:

(i) SEQUENCE CHARACTERISTICS:
        (A) LENGTH: 355 amino acids
        (B) TYPE: amino acid
        (C) STRANDEDNESS: single
        (D) TOPOLOGY: linear (xi) SEQUENCE DESCRIPTION: SEQ ID NO:79:

```
Met Ser Asn Ser Arg Arg Arg Ser Leu Arg Trp Ser Trp Leu Leu Ser
1               5                   10                  15

Val Leu Ala Ala Val Gly Leu Gly Leu Ala Thr Ala Pro Ala Gln Ala
                20                  25                  30

Ala Pro Pro Ala Leu Ser Gln Asp Arg Phe Ala Asp Phe Pro Ala Leu
            35                  40                  45
```

```
Pro Leu Asp Pro Ser Ala Met Val Ala Gln Val Ala Pro Gln Val Val
    50                  55                  60

Asn Ile Asn Thr Lys Leu Gly Tyr Asn Asn Ala Val Gly Ala Gly Thr
65                  70                  75                  80

Gly Ile Val Ile Asp Pro Asn Gly Val Val Leu Thr Asn Asn His Val
                85                  90                  95

Ile Ala Gly Ala Thr Asp Ile Asn Ala Phe Ser Val Gly Ser Gly Gln
                100                 105                 110

Thr Tyr Gly Val Asp Val Gly Tyr Asp Arg Thr Gln Asp Val Ala
            115                 120                 125

Val Leu Gln Leu Arg Gly Ala Gly Gly Leu Pro Ser Ala Ala Ile Gly
    130                 135                 140

Gly Gly Val Ala Val Gly Glu Pro Val Val Ala Met Gly Asn Ser Gly
145                 150                 155                 160

Gly Gln Gly Gly Thr Pro Arg Ala Val Pro Gly Arg Val Val Ala Leu
                165                 170                 175

Gly Gln Thr Val Gln Ala Ser Asp Ser Leu Thr Gly Ala Glu Glu Thr
                180                 185                 190

Leu Asn Gly Leu Ile Gln Phe Asp Ala Ala Ile Gln Pro Gly Asp Ser
        195                 200                 205

Gly Gly Pro Val Val Asn Gly Leu Gly Gln Val Val Gly Met Asn Thr
    210                 215                 220

Ala Ala Ser Asp Asn Phe Gln Leu Ser Gln Gly Gly Gln Gly Phe Ala
225                 230                 235                 240

Ile Pro Ile Gly Gln Ala Met Ala Ile Ala Gly Gln Ile Arg Ser Gly
                245                 250                 255

Gly Gly Ser Pro Thr Val His Ile Gly Pro Thr Ala Phe Leu Gly Leu
                260                 265                 270

Gly Val Val Asp Asn Asn Gly Asn Gly Ala Arg Val Gln Arg Val Val
            275                 280                 285

Gly Ser Ala Pro Ala Ala Ser Leu Gly Ile Ser Thr Gly Asp Val Ile
    290                 295                 300

Thr Ala Val Asp Gly Ala Pro Ile Asn Ser Ala Thr Ala Met Ala Asp
305                 310                 315                 320

Ala Leu Asn Gly His His Pro Gly Asp Val Ile Ser Val Asn Trp Gln
                325                 330                 335

Thr Lys Ser Gly Gly Thr Arg Thr Gly Asn Val Thr Leu Ala Glu Gly
            340                 345                 350

Pro Pro Ala
    355

(2) INFORMATION FOR SEQ ID NO:80:

(i) SEQUENCE CHARACTERISTICS:
        (A) LENGTH: 205 amino acids
        (B) TYPE: amino acid
        (C) STRANDEDNESS: single
        (D) TOPOLOGY: linear (xi) SEQUENCE DESCRIPTION: SEQ ID NO:80:

Ser Pro Lys Pro Asp Ala Glu Glu Gln Gly Val Pro Val Ser Pro Thr
1               5                   10                  15

Ala Ser Asp Pro Ala Leu Leu Ala Glu Ile Arg Gln Ser Leu Asp Ala
            20                  25                  30

Thr Lys Gly Leu Thr Ser Val His Val Ala Val Arg Thr Thr Gly Lys
```

```
                35                  40                  45
Val Asp Ser Leu Leu Gly Ile Thr Ser Ala Asp Val Asp Val Arg Ala
 50                  55                  60
Asn Pro Leu Ala Ala Lys Gly Val Cys Thr Tyr Asn Asp Glu Gln Gly
 65                  70                  75                  80
Val Pro Phe Arg Val Gln Gly Asp Asn Ile Ser Val Lys Leu Phe Asp
                 85                  90                  95
Asp Trp Ser Asn Leu Gly Ser Ile Ser Glu Leu Ser Thr Ser Arg Val
                100                 105                 110
Leu Asp Pro Ala Ala Gly Val Thr Gln Leu Leu Ser Gly Val Thr Asn
                115                 120                 125
Leu Gln Ala Gln Gly Thr Glu Val Ile Asp Gly Ile Ser Thr Thr Lys
                130                 135                 140
Ile Thr Gly Thr Ile Pro Ala Ser Ser Val Lys Met Leu Asp Pro Gly
145                 150                 155                 160
Ala Lys Ser Ala Arg Pro Ala Thr Val Trp Ile Ala Gln Asp Gly Ser
                165                 170                 175
His His Leu Val Arg Ala Ser Ile Asp Leu Gly Ser Gly Ser Ile Gln
                180                 185                 190
Leu Thr Gln Ser Lys Trp Asn Glu Pro Val Asn Val Asp
                195                 200                 205

(2) INFORMATION FOR SEQ ID NO:81:

(i) SEQUENCE CHARACTERISTICS:
        (A) LENGTH: 286 amino acids
        (B) TYPE: amino acid
        (C) STRANDEDNESS: single
        (D) TOPOLOGY: linear (xi) SEQUENCE DESCRIPTION: SEQ ID NO:81:

Gly Asp Ser Phe Trp Ala Ala Asp Gln Met Ala Arg Gly Phe Val
 1               5                  10                  15
Leu Gly Ala Thr Ala Gly Arg Thr Thr Leu Thr Gly Glu Gly Leu Gln
                 20                  25                  30
His Ala Asp Gly His Ser Leu Leu Leu Asp Ala Thr Asn Pro Ala Val
                 35                  40                  45
Val Ala Tyr Asp Pro Ala Phe Ala Tyr Glu Ile Gly Tyr Ile Xaa Glu
 50                  55                  60
Ser Gly Leu Ala Arg Met Cys Gly Glu Asn Pro Glu Asn Ile Phe Phe
 65                  70                  75                  80
Tyr Ile Thr Val Tyr Asn Glu Pro Tyr Val Gln Pro Pro Glu Pro Glu
                 85                  90                  95
Asn Phe Asp Pro Glu Gly Val Leu Gly Gly Ile Tyr Arg Tyr His Ala
                100                 105                 110
Ala Thr Glu Gln Arg Thr Asn Lys Xaa Gln Ile Leu Ala Ser Gly Val
                115                 120                 125
Ala Met Pro Ala Ala Leu Arg Ala Ala Gln Met Leu Ala Ala Glu Trp
                130                 135                 140
Asp Val Ala Ala Asp Val Trp Ser Val Thr Ser Trp Gly Glu Leu Asn
145                 150                 155                 160
Arg Asp Gly Val Val Ile Glu Thr Glu Lys Leu Arg His Pro Asp Arg
                165                 170                 175
Pro Ala Gly Val Pro Tyr Val Thr Arg Ala Leu Glu Asn Ala Arg Gly
                180                 185                 190
```

```
Pro Val Ile Ala Val Ser Asp Trp Met Arg Ala Val Pro Glu Gln Ile
            195                 200                 205

Arg Pro Trp Val Pro Gly Thr Tyr Leu Thr Leu Gly Thr Asp Gly Phe
    210                 215                 220

Gly Phe Ser Asp Thr Arg Pro Ala Gly Arg Arg Tyr Phe Asn Thr Asp
225                 230                 235                 240

Ala Glu Ser Gln Val Gly Arg Gly Phe Arg Gly Trp Pro Gly Arg
                245                 250                 255

Arg Val Asn Ile Asp Pro Phe Gly Ala Gly Arg Gly Pro Pro Ala Gln
                260                 265                 270

Leu Pro Gly Phe Asp Glu Gly Gly Leu Arg Pro Xaa Lys
                275                 280                 285
```

(2) INFORMATION FOR SEQ ID NO:82:

(i) SEQUENCE CHARACTERISTICS:
        (A) LENGTH: 173 amino acids
        (B) TYPE: amino acid
        (C) STRANDEDNESS: single
        (D) TOPOLOGY: linear (xi) SEQUENCE DESCRIPTION: SEQ ID NO:82:

```
Thr Lys Phe His Ala Leu Met Gln Glu Gln Ile His Asn Glu Phe Thr
1                5                  10                  15

Ala Ala Gln Gln Tyr Val Ala Ile Ala Val Tyr Phe Asp Ser Glu Asp
                20                  25                  30

Leu Pro Gln Leu Ala Lys His Phe Tyr Ser Gln Ala Val Glu Glu Arg
                35                  40                  45

Asn His Ala Met Met Leu Val Gln His Leu Leu Asp Arg Asp Leu Arg
    50                  55                  60

Val Glu Ile Pro Gly Val Asp Thr Val Arg Asn Gln Phe Asp Arg Pro
65                  70                  75                  80

Arg Glu Ala Leu Ala Leu Ala Leu Asp Gln Glu Arg Thr Val Thr Asp
                85                  90                  95

Gln Val Gly Arg Leu Thr Ala Val Ala Arg Asp Glu Gly Asp Phe Leu
                100                 105                 110

Gly Glu Gln Phe Met Gln Trp Phe Leu Gln Glu Gln Ile Glu Glu Val
                115                 120                 125

Ala Leu Met Ala Thr Leu Val Arg Val Ala Asp Arg Ala Gly Ala Asn
    130                 135                 140

Leu Phe Glu Leu Glu Asn Phe Val Ala Arg Glu Val Asp Val Ala Pro
145                 150                 155                 160

Ala Ala Ser Gly Ala Pro His Ala Ala Gly Gly Arg Leu
                165                 170
```

(2) INFORMATION FOR SEQ ID NO:83:

(i) SEQUENCE CHARACTERISTICS:
        (A) LENGTH: 107 amino acids
        (B) TYPE: amino acid
        (C) STRANDEDNESS: single
        (D) TOPOLOGY: linear (xi) SEQUENCE DESCRIPTION: SEQ ID NO:83:

```
Arg Ala Asp Glu Arg Lys Asn Thr Thr Met Lys Met Val Lys Ser Ile
1                5                  10                  15

Ala Ala Gly Leu Thr Ala Ala Ala Ile Gly Ala Ala Ala Gly
                20                  25                  30
```

```
Val Thr Ser Ile Met Ala Gly Gly Pro Val Val Tyr Gln Met Gln Pro
        35                  40                  45

Val Val Phe Gly Ala Pro Leu Pro Leu Asp Pro Xaa Ser Ala Pro Xaa
    50                  55                  60

Val Pro Thr Ala Ala Gln Trp Thr Xaa Leu Leu Asn Xaa Leu Xaa Asp
65                  70                  75                  80

Pro Asn Val Ser Phe Xaa Asn Lys Gly Ser Leu Val Glu Gly Gly Ile
                85                  90                  95

Gly Gly Xaa Glu Gly Xaa Xaa Arg Arg Xaa Gln
            100                 105
```

(2) INFORMATION FOR SEQ ID NO:84:

(i) SEQUENCE CHARACTERISTICS:
        (A) LENGTH: 125 amino acids
        (B) TYPE: amino acid
        (C) STRANDEDNESS: single
        (D) TOPOLOGY: linear (xi) SEQUENCE DESCRIPTION: SEQ ID NO:84:

```
Val Leu Ser Val Pro Val Gly Asp Gly Phe Trp Xaa Arg Val Val Asn
1               5                   10                  15

Pro Leu Gly Gln Pro Ile Asp Gly Arg Gly Asp Val Asp Ser Asp Thr
                20                  25                  30

Arg Arg Ala Leu Glu Leu Gln Ala Pro Ser Val Val Xaa Arg Gln Gly
            35                  40                  45

Val Lys Glu Pro Leu Xaa Thr Gly Ile Lys Ala Ile Asp Ala Met Thr
    50                  55                  60

Pro Ile Gly Arg Gly Gln Arg Gln Leu Ile Ile Gly Asp Arg Lys Thr
65                  70                  75                  80

Gly Lys Asn Arg Arg Leu Cys Arg Thr Pro Ser Ser Asn Gln Arg Glu
                85                  90                  95

Glu Leu Gly Val Arg Trp Ile Pro Arg Ser Arg Cys Ala Cys Val Tyr
                100                 105                 110

Val Gly His Arg Ala Arg Arg Gly Thr Tyr His Arg Arg
            115                 120                 125
```

(2) INFORMATION FOR SEQ ID NO:85:

(i) SEQUENCE CHARACTERISTICS:
        (A) LENGTH: 117 amino acids
        (B) TYPE: amino acid
        (C) STRANDEDNESS: single
        (D) TOPOLOGY: linear (xi) SEQUENCE DESCRIPTION: SEQ ID NO:85:

```
Cys Asp Ala Val Met Gly Phe Leu Gly Gly Ala Gly Pro Leu Ala Val
1               5                   10                  15

Val Asp Gln Gln Leu Val Thr Arg Val Pro Gln Gly Trp Ser Phe Ala
                20                  25                  30

Gln Ala Ala Ala Val Pro Val Phe Leu Thr Ala Trp Tyr Gly Leu
            35                  40                  45

Ala Asp Leu Ala Glu Ile Lys Ala Gly Glu Ser Val Leu Ile His Ala
    50                  55                  60

Gly Thr Gly Gly Val Gly Met Ala Ala Val Gln Leu Ala Arg Gln Trp
65                  70                  75                  80

Gly Val Glu Val Phe Val Thr Ala Ser Arg Gly Lys Trp Asp Thr Leu
                85                  90                  95
```

```
Arg Ala Xaa Xaa Phe Asp Asp Xaa Pro Tyr Arg Xaa Phe Pro His Xaa
            100                 105                 110

Arg Ser Ser Xaa Gly
            115
```

(2) INFORMATION FOR SEQ ID NO:86:

(i) SEQUENCE CHARACTERISTICS:
        (A) LENGTH: 103 amino acids
        (B) TYPE: amino acid
        (C) STRANDEDNESS: single
        (D) TOPOLOGY: linear (xi) SEQUENCE DESCRIPTION: SEQ ID NO:86:

```
Met Tyr Arg Phe Ala Cys Arg Thr Leu Met Leu Ala Ala Cys Ile Leu
1               5                   10                  15

Ala Thr Gly Val Ala Gly Leu Gly Val Gly Ala Gln Ser Ala Ala Gln
            20                  25                  30

Thr Ala Pro Val Pro Asp Tyr Tyr Trp Cys Pro Gly Gln Pro Phe Asp
            35                  40                  45

Pro Ala Trp Gly Pro Asn Trp Asp Pro Tyr Thr Cys His Asp Asp Phe
    50                  55                  60

His Arg Asp Ser Asp Gly Pro Asp His Ser Arg Asp Tyr Pro Gly Pro
65                  70                  75                  80

Ile Leu Glu Gly Pro Val Leu Asp Asp Pro Gly Ala Ala Pro Pro Pro
                85                  90                  95

Pro Ala Ala Gly Gly Gly Ala
            100
```

(2) INFORMATION FOR SEQ ID NO:87:

(i) SEQUENCE CHARACTERISTICS:
        (A) LENGTH: 88 amino acids
        (B) TYPE: amino acid
        (C) STRANDEDNESS: single
        (D) TOPOLOGY: linear (xi) SEQUENCE DESCRIPTION: SEQ ID NO:87:

```
Val Gln Cys Arg Val Trp Leu Glu Ile Gln Trp Arg Gly Met Leu Gly
1               5                   10                  15

Ala Asp Gln Ala Arg Ala Gly Gly Pro Ala Arg Ile Trp Arg Glu His
            20                  25                  30

Ser Met Ala Ala Met Lys Pro Arg Thr Gly Asp Gly Pro Leu Glu Ala
            35                  40                  45

Thr Lys Glu Gly Arg Gly Ile Val Met Arg Val Pro Leu Glu Gly Gly
    50                  55                  60

Gly Arg Leu Val Val Glu Leu Thr Pro Asp Glu Ala Ala Ala Leu Gly
65                  70                  75                  80

Asp Glu Leu Lys Gly Val Thr Ser
                85
```

(2) INFORMATION FOR SEQ ID NO:88:

(i) SEQUENCE CHARACTERISTICS:
        (A) LENGTH: 95 amino acids
        (B) TYPE: amino acid
        (C) STRANDEDNESS: single
        (D) TOPOLOGY: linear (xi) SEQUENCE DESCRIPTION: SEQ ID NO:88:

```
Thr Asp Ala Ala Thr Leu Ala Gln Glu Ala Gly Asn Phe Glu Arg Ile
```

```
1               5                   10                  15
Ser Gly Asp Leu Lys Thr Gln Ile Asp Gln Val Glu Ser Thr Ala Gly
                    20                  25                  30

Ser Leu Gln Gly Gln Trp Arg Gly Ala Ala Gly Thr Ala Ala Gln Ala
                35                  40                  45

Ala Val Val Arg Phe Gln Glu Ala Ala Asn Lys Gln Lys Gln Glu Leu
50                      55                  60

Asp Glu Ile Ser Thr Asn Ile Arg Gln Ala Gly Val Gln Tyr Ser Arg
65                      70                  75                  80

Ala Asp Glu Glu Gln Gln Gln Ala Leu Ser Ser Gln Met Gly Phe
                85                  90                  95
```

(2) INFORMATION FOR SEQ ID NO:89:

(i) SEQUENCE CHARACTERISTICS:
        (A) LENGTH: 166 amino acids
        (B) TYPE: amino acid
        (C) STRANDEDNESS: single
        (D) TOPOLOGY: linear (xi) SEQUENCE DESCRIPTION: SEQ ID NO:89:

```
Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Pro Thr Asp Val
                20                  25                  30

Pro Ile Thr Pro Cys Glu Leu Thr Xaa Xaa Lys Asn Ala Ala Gln Gln
                35                  40                  45

Xaa Val Leu Ser Ala Asp Asn Met Arg Glu Tyr Leu Ala Ala Gly Ala
    50                  55                  60

Lys Glu Arg Gln Arg Leu Ala Thr Ser Leu Arg Asn Ala Ala Lys Xaa
65                  70                  75                  80

Tyr Gly Glu Val Asp Glu Glu Ala Ala Thr Ala Leu Asp Asn Asp Gly
                85                  90                  95

Glu Gly Thr Val Gln Ala Glu Ser Ala Gly Ala Val Gly Gly Asp Ser
                100                 105                 110

Ser Ala Glu Leu Thr Asp Thr Pro Arg Val Ala Thr Ala Gly Glu Pro
            115                 120                 125

Asn Phe Met Asp Leu Lys Glu Ala Ala Arg Lys Leu Glu Thr Gly Asp
            130                 135                 140

Gln Gly Ala Ser Leu Ala His Xaa Gly Asp Gly Trp Asn Thr Xaa Thr
145                 150                 155                 160

Leu Thr Leu Gln Gly Asp
                165
```

(2) INFORMATION FOR SEQ ID NO:90:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:90:

```
Arg Ala Glu Arg Met
1               5
```

(2) INFORMATION FOR SEQ ID NO:91:

(i) SEQUENCE CHARACTERISTICS:

-continued

```
        (A) LENGTH: 263 amino acids
        (B) TYPE: amino acid
        (C) STRANDEDNESS: single
        (D) TOPOLOGY: linear (xi) SEQUENCE DESCRIPTION: SEQ ID NO:91:

Val Ala Trp Met Ser Val Thr Ala Gly Gln Ala Glu Leu Thr Ala Ala
1               5                  10                  15

Gln Val Arg Val Ala Ala Ala Tyr Glu Thr Ala Tyr Gly Leu Thr
                20                  25                  30

Val Pro Pro Val Ile Ala Glu Asn Arg Ala Glu Leu Met Ile Leu
            35                  40                  45

Ile Ala Thr Asn Leu Leu Gly Gln Asn Thr Pro Ala Ile Ala Val Asn
    50                  55                  60

Glu Ala Glu Tyr Gly Glu Met Trp Ala Gln Asp Ala Ala Met Phe
65                  70                  75                  80

Gly Tyr Ala Ala Ala Thr Ala Thr Ala Thr Ala Thr Leu Leu Pro Phe
                85                  90                  95

Glu Glu Ala Pro Glu Met Thr Ser Ala Gly Gly Leu Leu Glu Gln Ala
                100                 105                 110

Ala Ala Val Glu Glu Ala Ser Asp Thr Ala Ala Ala Asn Gln Leu Met
            115                 120                 125

Asn Asn Val Pro Gln Ala Leu Lys Gln Leu Ala Gln Pro Thr Gln Gly
    130                 135                 140

Thr Thr Pro Ser Ser Lys Leu Gly Gly Leu Trp Lys Thr Val Ser Pro
145                 150                 155                 160

His Arg Ser Pro Ile Ser Asn Met Val Ser Met Ala Asn Asn His Met
                165                 170                 175

Ser Met Thr Asn Ser Gly Val Ser Met Thr Asn Thr Leu Ser Ser Met
                180                 185                 190

Leu Lys Gly Phe Ala Pro Ala Ala Ala Gln Ala Val Gln Thr Ala
            195                 200                 205

Ala Gln Asn Gly Val Arg Ala Met Ser Ser Leu Gly Ser Ser Leu Gly
    210                 215                 220

Ser Ser Gly Leu Gly Gly Gly Val Ala Ala Asn Leu Gly Arg Ala Ala
225                 230                 235                 240

Ser Val Arg Tyr Gly His Arg Asp Gly Lys Tyr Ala Xaa Ser Gly
                245                 250                 255

Arg Arg Asn Gly Gly Pro Ala
            260

(2) INFORMATION FOR SEQ ID NO:92:

(i) SEQUENCE CHARACTERISTICS:
        (A) LENGTH: 303 amino acids
        (B) TYPE: amino acid
        (C) STRANDEDNESS: single
        (D) TOPOLOGY: linear (xi) SEQUENCE DESCRIPTION: SEQ ID NO:92:

Met Thr Tyr Ser Pro Gly Asn Pro Gly Tyr Pro Gln Ala Gln Pro Ala
1               5                   10                  15

Gly Ser Tyr Gly Gly Val Thr Pro Ser Phe Ala His Ala Asp Glu Gly
                20                  25                  30

Ala Ser Lys Leu Pro Met Tyr Leu Asn Ile Ala Val Ala Val Leu Gly
            35                  40                  45

Leu Ala Ala Tyr Phe Ala Ser Phe Gly Pro Met Phe Thr Leu Ser Thr
```

```
                50                      55                      60
Glu Leu Gly Gly Gly Asp Gly Ala Val Ser Gly Asp Thr Gly Leu Pro
 65                      70                      75                      80

Val Gly Val Ala Leu Leu Ala Ala Leu Leu Ala Gly Val Val Leu Val
                         85                      90                      95

Pro Lys Ala Lys Ser His Val Thr Val Ala Val Leu Gly Val Leu
                        100                     105                     110

Gly Val Phe Leu Met Val Ser Ala Thr Phe Asn Lys Pro Ser Ala Tyr
                        115                     120                     125

Ser Thr Gly Trp Ala Leu Trp Val Val Leu Ala Phe Ile Val Phe Gln
                        130                     135                     140

Ala Val Ala Ala Val Leu Ala Leu Leu Val Glu Thr Gly Ala Ile Thr
145                     150                     155                     160

Ala Pro Ala Pro Arg Pro Lys Phe Asp Pro Tyr Gly Gln Tyr Gly Arg
                        165                     170                     175

Tyr Gly Gln Tyr Gly Gln Tyr Gly Val Gln Pro Gly Gly Tyr Tyr Gly
                        180                     185                     190

Gln Gln Gly Ala Gln Gln Ala Ala Gly Leu Gln Ser Pro Gly Pro Gln
                        195                     200                     205

Gln Ser Pro Gln Pro Pro Gly Tyr Gly Ser Gln Tyr Gly Gly Tyr Ser
210                     215                     220

Ser Ser Pro Ser Gln Ser Gly Ser Gly Tyr Thr Ala Gln Pro Pro Ala
225                     230                     235                     240

Gln Pro Pro Ala Gln Ser Gly Ser Gln Gln Ser His Gln Gly Pro Ser
                        245                     250                     255

Thr Pro Pro Thr Gly Phe Pro Ser Phe Ser Pro Pro Pro Val Ser
                        260                     265                     270

Ala Gly Thr Gly Ser Gln Ala Gly Ser Ala Pro Val Asn Tyr Ser Asn
                        275                     280                     285

Pro Ser Gly Gly Glu Gln Ser Ser Pro Gly Gly Ala Pro Val
                        290                     295                     300

(2) INFORMATION FOR SEQ ID NO:93:

(i) SEQUENCE CHARACTERISTICS:
         (A) LENGTH: 28 amino acids
         (B) TYPE: amino acid
         (C) STRANDEDNESS: single
         (D) TOPOLOGY: linear (xi) SEQUENCE DESCRIPTION: SEQ ID NO:93:

Gly Cys Gly Glu Thr Asp Ala Ala Thr Leu Ala Gln Glu Ala Gly Asn
 1               5                      10                      15

Phe Glu Arg Ile Ser Gly Asp Leu Lys Thr Gln Ile
                20                      25

(2) INFORMATION FOR SEQ ID NO:94:

(i) SEQUENCE CHARACTERISTICS:
         (A) LENGTH: 16 amino acids
         (B) TYPE: amino acid
         (C) STRANDEDNESS: single
         (D) TOPOLOGY: linear (xi) SEQUENCE DESCRIPTION: SEQ ID NO:94:

Asp Gln Val Glu Ser Thr Ala Gly Ser Leu Gln Gly Gln Trp Arg Gly
 1               5                      10                      15
```

(2) INFORMATION FOR SEQ ID NO:95:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO:95:

```
Gly Cys Gly Ser Thr Ala Gly Ser Leu Gln Gly Gln Trp Arg Gly Ala
1               5                   10                  15
Ala Gly Thr Ala Ala Gln Ala Ala Val Val Arg
            20                  25
```

(2) INFORMATION FOR SEQ ID NO:96:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO:96:

```
Gly Cys Gly Gly Thr Ala Ala Gln Ala Ala Val Val Arg Phe Gln Glu
1               5                   10                  15
Ala Ala Asn Lys Gln Lys Gln Glu Leu Asp Glu
            20                  25
```

(2) INFORMATION FOR SEQ ID NO:97:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO:97:

```
Gly Cys Gly Ala Asn Lys Gln Lys Gln Glu Leu Asp Glu Ile Ser Thr
1               5                   10                  15
Asn Ile Arg Gln Ala Gly Val Gln Tyr Ser Arg
            20                  25
```

(2) INFORMATION FOR SEQ ID NO:98:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO:98:

```
Gly Cys Gly Ile Arg Gln Ala Gly Val Gln Tyr Ser Arg Ala Asp Glu
1               5                   10                  15
Glu Gln Gln Gln Ala Leu Ser Ser Gln Met Gly Phe
            20                  25
```

(2) INFORMATION FOR SEQ ID NO:99:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:99:

```
ATGAAGATGG TGAAATCGAT CGCCGCAGGT CTGACCGCCG CGGCTGCAAT CGGCGCCGCT     60
```

| | |
|---|---|
| GCGGCCGGTG TGACTTCGAT CATGGCTGGC GGCCCGGTCG TATACCAGAT GCAGCCGGTC | 120 |
| GTCTTCGGCG CGCCACTGCC GTTGGACCCG GCATCCGCCC CTGACGTCCC GACCGCCGCC | 180 |
| CAGTTGACCA GCCTGCTCAA CAGCCTCGCC GATCCCAACG TGTCGTTTGC GAACAAGGGC | 240 |
| AGTCTGGTCG AGGGCGGCAT CGGGGGCACC GAGGCGCGCA TCGCCGACCA CAAGCTGAAG | 300 |
| AAGGCCGCCG AGCACGGGGA TCTGCCGCTG TCGTTCAGCG TGACGAACAT CCAGCCGGCG | 360 |
| GCCGCCGGTT CGGCCACCGC CGACGTTTCC GTCTCGGGTC CGAAGCTCTC GTCGCCGGTC | 420 |
| ACGCAGAACG TCACGTTCGT GAATCAAGGC GGCTGGATGC TGTCACGCGC ATCGGCGATG | 480 |
| GAGTTGCTGC AGGCCGCAGG GAACTGA | 507 |

(2) INFORMATION FOR SEQ ID NO:100:

(i) SEQUENCE CHARACTERISTICS:
        (A) LENGTH: 168 amino acids
        (B) TYPE: amino acid
        (C) STRANDEDNESS: single
        (D) TOPOLOGY: linear (xi) SEQUENCE DESCRIPTION: SEQ ID NO:100:

```
Met Lys Met Val Lys Ser Ile Ala Ala Gly Leu Thr Ala Ala Ala
1               5                  10                  15

Ile Gly Ala Ala Ala Ala Gly Val Thr Ser Ile Met Ala Gly Gly Pro
                20                  25                  30

Val Val Tyr Gln Met Gln Pro Val Val Phe Gly Ala Pro Leu Pro Leu
            35                  40                  45

Asp Pro Ala Ser Ala Pro Asp Val Pro Thr Ala Ala Gln Leu Thr Ser
    50                  55                  60

Leu Leu Asn Ser Leu Ala Asp Pro Asn Val Ser Phe Ala Asn Lys Gly
65                  70                  75                  80

Ser Leu Val Glu Gly Gly Ile Gly Gly Thr Glu Ala Arg Ile Ala Asp
                85                  90                  95

His Lys Leu Lys Lys Ala Ala Glu His Gly Asp Leu Pro Leu Ser Phe
                100                 105                 110

Ser Val Thr Asn Ile Gln Pro Ala Ala Ala Gly Ser Ala Thr Ala Asp
            115                 120                 125

Val Ser Val Ser Gly Pro Lys Leu Ser Ser Pro Val Thr Gln Asn Val
    130                 135                 140

Thr Phe Val Asn Gln Gly Gly Trp Met Leu Ser Arg Ala Ser Ala Met
145                 150                 155                 160

Glu Leu Leu Gln Ala Ala Gly Asn
                165
```

(2) INFORMATION FOR SEQ ID NO:101:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (xi) SEQUENCE DESCRIPTION: SEQ ID NO:101:

| | |
|---|---|
| CGTGGCAATG TCGTTGACCG TCGGGGCCGG GGTCGCCTCC GCAGATCCCG TGGACGCGGT | 60 |
| CATTAACACC ACCTGCAATT ACGGGCAGGT AGTAGCTGCG CTCAACGCGA CGGATCCGGG | 120 |
| GGCTGCCGCA CAGTTCAACG CCTCACCGGT GGCGCAGTCC TATTTGCGCA ATTTCCTCGC | 180 |
| CGCACCGCCA CCTCAGCGCG CTGCCATGGC CGCGCAATTG CAAGCTGTGC CGGGGGCGGC | 240 |

```
ACAGTACATC GGCCTTGTCG AGTCGGTTGC CGGCTCCTGC AACAACTATT AAGCCCATGC    300

GGGCCCCATC CCGCGACCCG GCATCGTCGC CGGGGCTAGG CCAGATTGCC CCGCTCCTCA    360

ACGGGCCGCA TCCCGCGACC CGGCATCGTC GCCGGGGCTA GGCCAGATTG CCCCGCTCCT    420

CAACGGGCCG CATCTCGTGC CGAATTCCTG CAGCCCGGGG GATCCACTAG TTCTAGAGCG    480

GCCGCCACCG CGGTGGAGCT                                                500
```

(2) INFORMATION FOR SEQ ID NO:102:

(i) SEQUENCE CHARACTERISTICS:
        (A) LENGTH: 96 amino acids
        (B) TYPE: amino acid
        (C) STRANDEDNESS: single
        (D) TOPOLOGY: linear (xi) SEQUENCE DESCRIPTION: SEQ ID NO:102:

```
Val Ala Met Ser Leu Thr Val Gly Ala Gly Val Ala Ser Ala Asp Pro
 1               5                  10                  15

Val Asp Ala Val Ile Asn Thr Thr Cys Asn Tyr Gly Gln Val Val Ala
                20                  25                  30

Ala Leu Asn Ala Thr Asp Pro Gly Ala Ala Ala Gln Phe Asn Ala Ser
            35                  40                  45

Pro Val Ala Gln Ser Tyr Leu Arg Asn Phe Leu Ala Ala Pro Pro Pro
    50                  55                  60

Gln Arg Ala Ala Met Ala Ala Gln Leu Gln Ala Val Pro Gly Ala Ala
65                  70                  75                  80

Gln Tyr Ile Gly Leu Val Glu Ser Val Ala Gly Ser Cys Asn Asn Tyr
                85                  90                  95
```

(2) INFORMATION FOR SEQ ID NO:103:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (xi) SEQUENCE DESCRIPTION: SEQ ID NO:103:

```
ATGACAGAGC AGCAGTGGAA TTTCGCGGGT ATCGAGGCCG CGGCAAGCGC AATCCAGGGA     60

AATGTCACGT CCATTCATTC CCTCCTTGAC GAGGGAAGC AGTCCCTGAC CAAGCTCGCA    120

GCGGCCTGGG GCGGTAGCGG TTCGGAAGCG TACC                                154
```

(2) INFORMATION FOR SEQ ID NO:104:

(i) SEQUENCE CHARACTERISTICS:
        (A) LENGTH: 51 amino acids
        (B) TYPE: amino acid
        (C) STRANDEDNESS: single
        (D) TOPOLOGY: linear (xi) SEQUENCE DESCRIPTION: SEQ ID NO:104:

```
Met Thr Glu Gln Gln Trp Asn Phe Ala Gly Ile Glu Ala Ala Ala Ser
 1               5                  10                  15

Ala Ile Gln Gly Asn Val Thr Ser Ile His Ser Leu Leu Asp Glu Gly
                20                  25                  30

Lys Gln Ser Leu Thr Lys Leu Ala Ala Ala Trp Gly Gly Ser Gly Ser
            35                  40                  45

Glu Ala Tyr
    50
```

(2) INFORMATION FOR SEQ ID NO:105:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (xi) SEQUENCE DESCRIPTION: SEQ ID NO:105:

```
CGGTCGCGCA CTTCCAGGTG ACTATGAAAG TCGGCTTCCG NCTGGAGGAT TCCTGAACCT      60
TCAAGCGCGG CCGATAACTG AGGTGCATCA TTAAGCGACT TTTCCAGAAC ATCCTGACGC     120
GCTCGAAACG CGGCACAGCC GACGGTGGCT CCGNCGAGGC GCTGNCTCCA AAATCCCTGA     180
GACAATTCGN CGGGGCGCC  TACAAGGAAG TCGGTGCTGA ATTCGNCGNG TATCTGGTCG     240
ACCTGTGTGG TCTGNAGCCG GACGAAGCGG TGCTCGACGT CG                        282
```

(2) INFORMATION FOR SEQ ID NO:106:

(i) SEQUENCE CHARACTERISTICS:
        (A) LENGTH: 3058 base pairs
        (B) TYPE: nucleic acid
        (C) STRANDEDNESS: single
        (D) TOPOLOGY: linear (xi) SEQUENCE DESCRIPTION: SEQ ID NO:106:

```
GATCGTACCC GTGCGAGTGC TCGGGCCGTT TGAGGATGGA GTGCACGTGT CTTTCGTGAT      60
GGCATACCCA GAGATGTTGG CGGCGGCGGC TGACACCCTG CAGAGCATCG GTGCTACCAC     120
TGTGGCTAGC AATGCCGCTG CGGCGGCCCC GACGACTGGG GTGGTGCCCC CCGCTGCCGA     180
TGAGGTGTCG GCGCTGACTG CGGCGCACTT CGCCGCACAT GCGGCGATGT ATCAGTCCGT     240
GAGCGCTCGG GCTGCTGCGA TTCATGACCA GTTCGTGGCC ACCCTTGCCA GCAGCGCCAG     300
CTCGTATGCG GCCACTGAAG TCGCCAATGC GGCGGCGGCC AGCTAAGCCA GGAACAGTCG     360
GCACGAGAAA CCACGAGAAA TAGGGACACG TAATGGTGGA TTTCGGGGCG TTACCACCGG     420
AGATCAACTC CGCGAGGATG TACGCCGGCC CGGGTTCGGC CTCGCTGGTG GCCGCGGCTC     480
AGATGTGGGA CAGCGTGGCG AGTGACCTGT TTTCGGCCGC GTCGGCGTTT CAGTCGGTGG     540
TCTGGGGTCT GACGGTGGGG TCGTGGATAG GTTCGTCGGC GGGTCTGATG GTGGCGGCGG     600
CCTCGCCGTA TGTGGCGTGG ATGAGCGTCA CCGCGGGGCA GGCCGAGCTG ACCGCCGCCC     660
AGGTCCGGGT TGCTGCGGCG GCCTACGAGA CGGCGTATGG GCTGACGGTG CCCCCGCCGG     720
TGATCGCCGA GAACCGTGCT GAACTGATGA TTCTGATAGC GACCAACCTC TTGGGGCAAA     780
ACACCCCGGC GATCGCGGTC AACGAGGCCG AATACGGCGA GATGTGGGCC CAAGACGCCG     840
CCGCGATGTT TGGCTACGCC GCGGCGACGG CGACGGCGAC GGCGACGTTG CTGCCGTTCG     900
AGGAGGCGCC GGAGATGACC AGCGCGGGTG GGCTCCTCGA GCAGGCCGCC GCGGTCGAGG     960
AGGCCTCCGA CACCGCCGCG GCGAACCAGT TGATGAACAA TGTGCCCCAG GCGCTGCAAC    1020
AGCTGGCCCA GCCCACGCAG GGCACCACGC CTTCTTCCAA GCTGGGTGGC CTGTGGAAGA    1080
CGGTCTCGCC GCATCGGTCG CCGATCAGCA ACATGGTGTC GATGGCCAAC AACCACATGT    1140
CGATGACCAA CTCGGGTGTG TCGATGACCA ACACCTTGAG CTCGATGTTG AAGGGCTTTG    1200
CTCCGGCGGC GGCCGCCCAG GCCGTGCAAA CCGCGGCGCA AAACGGGGTC CGGGCGATGA    1260
GCTCGCTGGG CAGCTCGCTG GGTTCTTCGG GTCTGGGCGG TGGGGTGGCC GCCAACTTGG    1320
GTCGGGCGGC CTCGGTCGGT TCGTTGTCGG TGCCGCAGGC CTGGGCCGCG GCCAACCAGG    1380
```

```
CAGTCACCCC GGCGGCGCGG GCGCTGCCGC TGACCAGCCT GACCAGCGCC GCGGAAAGAG    1440

GGCCCGGGCA GATGCTGGGC GGGCTGCCGG TGGGGCAGAT GGGCGCCAGG GCCGGTGGTG    1500

GGCTCAGTGG TGTGCTGCGT GTTCCGCCGC GACCCTATGT GATGCCGCAT TCTCCGGCGG    1560

CCGGCTAGGA GAGGGGCGC AGACTGTCGT TATTTGACCA GTGATCGGCG GTCTCGGTGT     1620

TTCCGCGGCC GGCTATGACA ACAGTCAATG TGCATGACAA GTTACAGGTA TTAGGTCCAG    1680

GTTCAACAAG GAGACAGGCA ACATGGCCTC ACGTTTTATG ACGGATCCGC ACGCGATGCG    1740

GGACATGGCG GGCCGTTTTG AGGTGCACGC CCAGACGGTG GAGGACGAGG CTCGCCGGAT    1800

GTGGGCGTCC GCGCAAAACA TTTCCGGTGC GGGCTGGAGT GGCATGGCCG AGGCGACCTC    1860

GCTAGACACC ATGGCCCAGA TGAATCAGGC GTTTCGCAAC ATCGTGAACA TGCTGCACGG    1920

GGTGCGTGAC GGGCTGGTTC GCGACGCCAA CAACTACGAG CAGCAAGAGC AGGCCTCCCA    1980

GCAGATCCTC AGCAGCTAAC GTCAGCCGCT GCAGCACAAT ACTTTTACAA GCGAAGGAGA    2040

ACAGGTTCGA TGACCATCAA CTATCAATTC GGGGATGTCG ACGCTCACGG CGCCATGATC    2100

CGCGCTCAGG CCGGGTTGCT GGAGGCCGAG CATCAGGCCA TCATTCGTGA TGTGTTGACC    2160

GCGAGTGACT TTTGGGGCGG CGCCGGTTCG GCGGCCTGCC AGGGGTTCAT TACCCAGTTG    2220

GGCCGTAACT TCCAGGTGAT CTACGAGCAG GCCAACGCCC ACGGGCAGAA GGTGCAGGCT    2280

GCCGGCAACA ACATGGCGCA AACCGACAGC GCCGTCGGCT CCAGCTGGGC CTGACACCAG    2340

GCCAAGGCCA GGGACGTGGT GTACGAGTGA AGTTCCTCGC GTGATCCTTC GGGTGGCAGT    2400

CTAAGTGGTC AGTGCTGGGG TGTTGGTGGT TTGCTGCTTG GCGGGTTCTT CGGTGCTGGT    2460

CAGTGCTGCT CGGGCTCGGG TGAGGACCTC GAGGCCCAGG TAGCGCCGTC CTTCGATCCA    2520

TTCGTCGTGT TGTTCGGCGA GGACGGCTCC GACGAGGCGA TGATCGAGG CGCGGTCGGG     2580

GAAGATGCCC ACGACGTCGG TTCGGCGTCG TACCTCTCGG TTGAGGCGTT CCTGGGGGTT    2640

GTTGGACCAG ATTTGGCGCC AGATCTGCTT GGGGAAGGCG GTGAACGCCA GCAGGTCGGT    2700

GCGGGCGGTG TCGAGGTGCT CGGCCACCGC GGGGAGTTTG TCGGTCAGAG CGTCGAGTAC    2760

CCGATCATAT TGGGCAACAA CTGATTCGGC GTCGGGCTGG TCGTAGATGG AGTGCAGCAG    2820

GGTGCGCACC CACGGCCAGG AGGGCTTCGG GGTGGCTGCC ATCAGATTGG CTGCGTAGTG    2880

GGTTCTGCAG CGCTGCCAGG CCGCTGCGGG CAGGGTGGCG CCGATCGCGG CCACCAGGCC    2940

GGCGTGGGCG TCGCTGGTGA CCAGCGCGAC CCCGGACAGG CCGCGGGCGA CCAGGTCGCG    3000

GAAGAACGCC AGCCAGCCGG CCCCGTCCTC GGCGGAGGTG ACCTGGATGC CCAGGATC     3058

(2) INFORMATION FOR SEQ ID NO:107:

(i) SEQUENCE CHARACTERISTICS:
        (A) LENGTH: 391 amino acids
        (B) TYPE: amino acid
        (C) STRANDEDNESS: single
        (D) TOPOLOGY: linear (xi) SEQUENCE DESCRIPTION: SEQ ID NO:107:

Met Val Asp Phe Gly Ala Leu Pro Pro Glu Ile Asn Ser Ala Arg Met
 1               5                  10                  15

Tyr Ala Gly Pro Gly Ser Ala Ser Leu Val Ala Ala Gln Met Trp
            20                  25                  30

Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60
```

```
Leu Met Val Ala Ala Ala Ser Pro Tyr Val Ala Trp Met Ser Val Thr
 65                  70                  75                  80

Ala Gly Gln Ala Glu Leu Thr Ala Ala Gln Val Arg Val Ala Ala Ala
                 85                  90                  95

Ala Tyr Glu Thr Ala Tyr Gly Leu Thr Val Pro Pro Val Ile Ala
                100                 105                 110

Glu Asn Arg Ala Glu Leu Met Ile Leu Ile Ala Thr Asn Leu Leu Gly
                115                 120                 125

Gln Asn Thr Pro Ala Ile Ala Val Asn Glu Ala Glu Tyr Gly Glu Met
            130                 135                 140

Trp Ala Gln Asp Ala Ala Ala Met Phe Gly Tyr Ala Ala Thr Ala
145                 150                 155                 160

Thr Ala Thr Ala Thr Leu Leu Pro Phe Glu Ala Pro Glu Met Thr
                165                 170                 175

Ser Ala Gly Gly Leu Leu Glu Gln Ala Ala Val Glu Glu Ala Ser
                180                 185                 190

Asp Thr Ala Ala Ala Asn Gln Leu Met Asn Asn Val Pro Gln Ala Leu
                195                 200                 205

Gln Gln Leu Ala Gln Pro Thr Gln Gly Thr Thr Pro Ser Ser Lys Leu
    210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
                260                 265                 270

Ala Ala Ala Gln Ala Val Gln Thr Ala Ala Gln Asn Gly Val Arg Ala
    275                 280                 285

Met Ser Ser Leu Gly Ser Ser Leu Gly Ser Ser Gly Leu Gly Gly Gly
    290                 295                 300

Val Ala Ala Asn Leu Gly Arg Ala Ala Ser Val Gly Ser Leu Ser Val
305                 310                 315                 320

Pro Gln Ala Trp Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
                340                 345                 350

Gln Met Leu Gly Gly Leu Pro Val Gly Gln Met Gly Ala Arg Ala Gly
                355                 360                 365

Gly Gly Leu Ser Gly Val Leu Arg Val Pro Pro Arg Pro Tyr Val Met
    370                 375                 380

Pro His Ser Pro Ala Ala Gly
385                 390

(2) INFORMATION FOR SEQ ID NO:108:

(i) SEQUENCE CHARACTERISTICS:
        (A) LENGTH: 1725 base pairs
        (B) TYPE: nucleic acid
        (C) STRANDEDNESS: single
        (D) TOPOLOGY: linear (xi) SEQUENCE DESCRIPTION: SEQ ID NO:108:

GACGTCAGCA CCCGCCGTGC AGGGCTGGAG CGTGGTCGGT TTTGATCTGC GGTCAAGGTG     60

ACGTCCCTCG GCGTGTCGCC GGCGTGGATG CAGAGACTCGAT GCCGCTCTTT AGTGCAACTA    120

ATTTCGTTGA AGTGCCTGCG AGGTATAGGA CTTCACGATT GGTTAATGTA GCGTTCACCC     180
```

```
CGTGTTGGGG TCGATTTGGC CGGACCAGTC GTCACCAACG CTTGGCGTGC GCGCCAGGCG      240

GGCGATCAGA TCGCTTGACT ACCAATCAAT CTTGAGCTCC CGGGCCGATG CTCGGGCTAA      300

ATGAGGAGGA GCACGCGTGT CTTTCACTGC GCAACCGGAG ATGTTGGCGG CCGCGGCTGG      360

CGAACTTCGT TCCCTGGGGG CAACGCTGAA GGCTAGCAAT GCCGCCGCAG CCGTGCCGAC      420

GACTGGGGTG GTGCCCCCGG CTGCCGACGA GGTGTCGCTG CTGCTTGCCA CACAATTCCG      480

TACGCATGCG GCGACGTATC AGACGGCCAG CGCCAAGGCC GCGGTGATCC ATGAGCAGTT      540

TGTGACCACG CTGGCCACCA GCGCTAGTTC ATATGCGGAC ACCGAGGCCG CCAACGCTGT      600

GGTCACCGGC TAGCTGACCT GACGGTATTC GAGCGGAAGG ATTATCGAAG TGGTGGATTT      660

CGGGGCGTTA CCACCGGAGA TCAACTCCGC GAGGATGTAC GCCGGCCCGG GTTCGGCCTC      720

GCTGGTGGCC GCCGCGAAGA TGTGGGACAG CGTGGCGAGT GACCTGTTTT CGGCCGCGTC      780

GGCGTTTCAG TCGGTGGTCT GGGGTCTGAC GGTGGGGTCG TGGATAGGTT CGTCGGCGGG      840

TCTGATGGCG GCGGCGGCCT CGCCGTATGT GGCGTGGATG AGCGTCACCG CGGGGCAGGC      900

CCAGCTGACC GCCGCCCAGG TCCGGGTTGC TGCGGCGGCC TACAGACAG CGTATAGGCT       960

GACGGTGCCC CCGCCGGTGA TCGCCGAGAA CCGTACCGAA CTGATGACGC TGACCGCGAC     1020

CAACCTCTTG GGGCAAAACA CGCCGGCGAT CGAGGCCAAT CAGGCCGCAT ACAGCCAGAT     1080

GTGGGGCCAA GACGCGGAGG CGATGTATGG CTACGCCGCC ACGGCGGCGA CGGCGACCGA     1140

GGCGTTGCTG CCGTTCGAGG ACGCCCCACT GATCACCAAC CCCGGCGGGC TCCTTGAGCA     1200

GGCCGTCGCG GTCGAGGAGG CCATCGACAC CGCCGCGGCG AACCAGTTGA TGAACAATGT     1260

GCCCCAAGCG CTGCAACAGC TGGCCCAGCC AGCGCAGGGC GTCGTACCTT CTTCCAAGCT     1320

GGGTGGGCTG TGGACGGCGG TCTCGCCGCA TCTGTCGCCG CTCAGCAACG TCAGTTCGAT     1380

AGCCAACAAC CACATGTCGA TGATGGGCAC GGGTGTGTCG ATGACCAACA CCTTGCACTC     1440

GATGTTGAAG GGCTTAGCTC CGGCGGCGGC TCAGGCCGTG GAAACCGCGG CGGAAAACGG     1500

GGTCTGGGCG ATGAGCTCGC TGGGCAGCCA GCTGGGTTCG TCGCTGGGTT CTTCGGGTCT     1560

GGGCGCTGGG GTGGCCGCCA ACTTGGGTCG GCGGCCTCG GTCGGTTCGT TGTCGGTGCC      1620

GCCAGCATGG GCCGCGGCCA ACCAGGCGGT CACCCCGGCG GCGCGGGCGC TGCCGCTGAC     1680

CAGCCTGACC AGCGCCGCCC AAACCGCCCC CGGACACATG CTGGG                    1725
```

(2) INFORMATION FOR SEQ ID NO:109:

(i) SEQUENCE CHARACTERISTICS:
        (A) LENGTH: 359 amino acids
        (B) TYPE: amino acid
        (C) STRANDEDNESS:
        (D) TOPOLOGY: linear (xi) SEQUENCE DESCRIPTION: SEQ ID NO:109:

```
Val Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Lys Met Trp
            20                  25                  30

Asp Ser Val Ala Ser Asp Leu Phe Ser Ala Ala Ser Ala Phe Gln Ser
            35                  40                  45

Val Val Trp Gly Leu Thr Val Gly Ser Trp Ile Gly Ser Ser Ala Gly
        50                  55                  60

Leu Met Ala Ala Ala Ala Ser Pro Tyr Val Ala Trp Met Ser Val Thr
65                  70                  75                  80
```

-continued

```
Ala Gly Gln Ala Gln Leu Thr Ala Ala Gln Val Arg Val Ala Ala Ala
                 85                  90                  95

Ala Tyr Glu Thr Ala Tyr Arg Leu Thr Val Pro Pro Val Ile Ala
            100                 105                 110

Glu Asn Arg Thr Glu Leu Met Thr Leu Thr Ala Thr Asn Leu Leu Gly
        115                 120                 125

Gln Asn Thr Pro Ala Ile Glu Ala Asn Gln Ala Ala Tyr Ser Gln Met
    130                 135                 140

Trp Gly Gln Asp Ala Glu Ala Met Tyr Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Glu Ala Ile
            180                 185                 190

Asp Thr Ala Ala Ala Asn Gln Leu Met Asn Asn Val Pro Gln Ala Leu
        195                 200                 205

Gln Gln Leu Ala Gln Pro Ala Gln Gly Val Val Pro Ser Ser Lys Leu
    210                 215                 220

Gly Gly Leu Trp Thr Ala Val Ser Pro His Leu Ser Pro Leu Ser Asn
225                 230                 235                 240

Val Ser Ser Ile Ala Asn Asn His Met Ser Met Met Gly Thr Gly Val
                245                 250                 255

Ser Met Thr Asn Thr Leu His Ser Met Leu Lys Gly Leu Ala Pro Ala
            260                 265                 270

Ala Ala Gln Ala Val Glu Thr Ala Ala Glu Asn Gly Val Trp Ala Met
        275                 280                 285

Ser Ser Leu Gly Ser Gln Leu Gly Ser Ser Leu Gly Ser Ser Gly Leu
    290                 295                 300

Gly Ala Gly Val Ala Ala Asn Leu Gly Arg Ala Ala Ser Val Gly Ser
305                 310                 315                 320

Leu Ser Val Pro Pro Ala Trp Ala Ala Ala Asn Gln Ala Val Thr Pro
                325                 330                 335

Ala Ala Arg Ala Leu Pro Leu Thr Ser Leu Thr Ser Ala Ala Gln Thr
            340                 345                 350

Ala Pro Gly His Met Leu Gly
        355
```

(2) INFORMATION FOR SEQ ID NO:110:

(i) SEQUENCE CHARACTERISTICS:
        (A) LENGTH: 3027 base pairs
        (B) TYPE: nucleic acid
        (C) STRANDEDNESS: single
        (D) TOPOLOGY: linear (xi) SEQUENCE DESCRIPTION: SEQ ID NO:110:

```
AGTTCAGTCG AGAATGATAC TGACGGGCTG TATCCACGAT GGCTGAGACA ACCGAACCAC     60

CGTCGGACGC GGGGACATCG CAAGCCGACG CGATGGCGTT GGCCGCCGAA GCCGAAGCCG    120

CCGAAGCCGA AGCGCTGGCC GCCGCGGCGC GGGCCCGTGC CCGTGCCGCC CGGTTGAAGC    180

GTGAGGCGCT GGCGATGGCC CCAGCCGAGG ACGAGAACGT CCCCGAGGAT ATGCAGACTG    240

GGAAGACGCC GAAGACTATG ACGACTATGA CGACTATGAG GCCGCAGACC AGGAGGCCGC    300

ACGGTCGGCA TCCTGGCGAC GGCGGTTGCG GGTGCGGTTA CCAAGACTGT CCACGATTGC    360

CATGGCGGCC GCAGTCGTCA TCATCTGCGG CTTCACCGGG CTCAGCGGAT ACATTGTGTG    420
```

-continued

```
GCAACACCAT GAGGCCACCG AACGCCAGCA GCGCGCCGCG GCGTTCGCCG CCGGAGCCAA    480

GCAAGGTGTC ATCAACATGA CCTCGCTGGA CTTCAACAAG GCCAAAGAAG ACGTCGCGCG    540

TGTGATCGAC AGCTCCACCG GCGAATTCAG GGATGACTTC CAGCAGCGGG CAGCCGATTT    600

CACCAAGGTT GTCGAACAGT CCAAAGTGGT CACCGAAGGC ACGGTGAACG CGACAGCCGT    660

CGAATCCATG AACGAGCATT CCGCCGTGGT GCTCGTCGCG GCGACTTCAC GGGTCACCAA    720

TTCCGCTGGG GCGAAAGACG AACCACGTGC GTGGCGGCTC AAAGTGACCG TGACCGAAGA    780

GGGGGGACAG TACAAGATGT CGAAAGTTGA GTTCGTACCG TGACCGATGA CGTACGCGAC    840

GTCAACACCG AAACCACTGA CGCCACCGAA GTCGCTGAGA TCGACTCAGC CGCAGGCGAA    900

GCCGGTGATT CGGCGACCGA GGCATTTGAC ACCGACTCTG CAACGGAATC TACCGCGCAG    960

AAGGGTCAGC GGCACCGTGA CCTGTGGCGA ATGCAGGTTA CCTTGAAACC CGTTCCGGTG   1020

ATTCTCATCC TGCTCATGTT GATCTCTGGG GGCGCGACGG GATGGCTATA CCTTGAGCAA   1080

TACGACCCGA TCAGCAGACG GACTCCGGCG CCGCCCGTGC TGCCGTCGCC GCGGCGTCTG   1140

ACGGGACAAT CGCGCTGTTG TGTATTCACC CGACACGTCG ACCAAGACTT CGCTACCGCC   1200

AGGTCGCACC TCGCCGGCGA TTTCCTGTCC TATACGACCA GTTCACGCAG CAGATCGTGG   1260

CTCCGGCGGC CAAACAGAAG TCACTGAAAA CCACCGCCAA GGTGGTGCGC GCGGCCGTGT   1320

CGGAGCTACA TCCGGATTCG GCCGTCGTTC TGGTTTTTGT CGACCAGAGC ACTACCAGTA   1380

AGGACAGCCC CAATCCGTCG ATGGCGGCCA GCAGCGTGAT GGTGACCCTA GCCAAGGTCG   1440

ACGGCAATTG GCTGATCACC AAGTTCACCC CGGTTTAGGT TGCCGTAGGC GGTCGCCAAG   1500

TCTGACGGGG GCGCGGGTGG CTGCTCGTGC GAGATACCGG CCGTTCTCCG GACAATCACG   1560

GCCCGACCTC AAACAGATCT CGGCCGCTGT CTAATCGGCC GGGTTATTTA AGATTAGTTG   1620

CCACTGTATT TACCTGATGT TCAGATTGTT CAGCTGGATT TAGCTTCGCG GCAGGGCGGC   1680

TGGTGCACTT TGCATCTGGG GTTGTGACTA CTTGAGAGAA TTTGACCTGT TGCCGACGTT   1740

GTTTGCTGTC CATCATTGGT GCTAGTTATG GCCGAGCGGA AGGATTATCG AAGTGGTGGA   1800

CTTCGGGGCG TTACCACCGG AGATCAACTC CGCGAGGATG TACGCCGGCC CGGGTTCGGC   1860

CTCGCTGGTG GCCGCCGCGA AGATGTGGGA CAGCGTGGCG AGTGACCTGT TTTCGGCCGC   1920

GTCGGCGTTT CAGTCGGTGG TCTGGGGTCT GACGACGGGA TCGTGGATAG GTTCGTCGGC   1980

GGGTCTGATG GTGGCGGCGG CCTCGCCGTA TGTGGCGTGG ATGAGCGTCA CCGCGGGGCA   2040

GGCCGAGCTG ACCGCCGCCC AGGTCCGGGT TGCTGCGGCG GCCTACGAGA CGGCGTATGG   2100

GCTGACGGTG CCCCCGCCGG TGATCGCCGA GAACCGTGCT GAACTGATGA TTCTGATAGC   2160

GACCAACCTC TTGGGGCAAA ACACCCCGGC GATCGCGGTC AACGAGGCCG AATACGGGGA   2220

GATGTGGGCC CAAGACGCCG CCGCGATGTT TGGCTACGCC GCCACGGCGG CGACGGCGAC   2280

CGAGGCGTTG CTGCCGTTCG AGGACGCCCC ACTGATCACC AACCCCGGCG GGCTCCTTGA   2340

GCAGGCCGTC GCGGTCGAGG AGGCCATCGA CACCGCCGCG GCGAACCAGT TGATGAACAA   2400

TGTGCCCCAA GCGCTGCAAC AACTGGCCCA GCCCACGAAA AGCATCTGGC CGTTCGACCA   2460

ACTGAGTGAA CTCTGGAAAG CCATCTCGCC GCATCTGTCG CCGCTCAGCA ACATCGTGTC   2520

GATGCTCAAC AACCACGTGT CGATGACCAA CTCGGGTGTG TCGATGGCCA GCACCTTGCA   2580

CTCAATGTTG AAGGGCTTTG CTCCGGCGGC GGCTCAGGCC GTGGAAACCG CGGCGCAAAA   2640

CGGGGTCCAG GCGATGAGCT CGCTGGGCAG CCAGCTGGGT TCGTCGCTGG GTTCTTCGGG   2700

TCTGGGCGCT GGGGTGGCCG CCAACTTGGG TCGGGCGGCC TCGGTCGGTT CGTTGTCGGT   2760

GCCGCAGGCC TGGGCCGCGG CCAACCAGGC GGTCACCCCG GCGGCGCGGG CGCTGCCGCT   2820
```

```
GACCAGCCTG ACCAGCGCCG CCCAAACCGC CCCCGGACAC ATGCTGGGCG GGCTACCGCT      2880

GGGGCAACTG ACCAATAGCG GCGGCGGGTT CGGCGGGGTT AGCAATGCGT TGCGGATGCC      2940

GCCGCGGGCG TACGTAATGC CCCGTGTGCC CGCCGCCGGG TAACGCCGAT CCGCACGCAA      3000

TGCGGGCCCT CTATGCGGGC AGCGATC                                          3027
```

(2) INFORMATION FOR SEQ ID NO:111:

(i) SEQUENCE CHARACTERISTICS:
      (A) LENGTH: 396 amino acids
      (B) TYPE: amino acid
      (C) STRANDEDNESS:
      (D) TOPOLOGY: linear (xi) SEQUENCE DESCRIPTION: SEQ ID NO:111:

```
Val Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Lys Met Trp
            20                  25                  30

Asp Ser Val Ala Ser Asp Leu Phe Ser Ala Ala Ser Ala Phe Gln Ser
            35                  40                  45

Val Val Trp Gly Leu Thr Thr Gly Ser Trp Ile Gly Ser Ser Ala Gly
50                  55                  60

Leu Met Val Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Val Ile Ala
            100                 105                 110

Glu Asn Arg Ala Glu Leu Met Ile Leu Ile Ala Thr Asn Leu Leu Gly
            115                 120                 125

Gln Asn Thr Pro Ala Ile Ala Val Asn Glu Ala Glu Tyr Gly Glu Met
            130                 135                 140

Trp Ala Gln Asp Ala Ala Ala Met Phe Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Glu Ala Ile
            180                 185                 190

Asp Thr Ala Ala Ala Asn Gln Leu Met Asn Asn Val Pro Gln Ala Leu
            195                 200                 205

Gln Gln Leu Ala Gln Pro Thr Lys Ser Ile Trp Pro Phe Asp Gln Leu
    210                 215                 220

Ser Glu Leu Trp Lys Ala Ile Ser Pro His Leu Ser Pro Leu Ser Asn
225                 230                 235                 240

Ile Val Ser Met Leu Asn Asn His Val Ser Met Thr Asn Ser Gly Val
                245                 250                 255

Ser Met Ala Ser Thr Leu His Ser Met Leu Lys Gly Phe Ala Pro Ala
            260                 265                 270

Ala Ala Gln Ala Val Glu Thr Ala Ala Gln Asn Gly Val Gln Ala Met
            275                 280                 285

Ser Ser Leu Gly Ser Gln Leu Gly Ser Ser Leu Gly Ser Ser Gly Leu
            290                 295                 300

Gly Ala Gly Val Ala Ala Asn Leu Gly Arg Ala Ala Ser Val Gly Ser
305                 310                 315                 320
```

```
Leu Ser Val Pro Gln Ala Trp Ala Ala Ala Asn Gln Ala Val Thr Pro
            325                 330                 335

Ala Ala Arg Ala Leu Pro Leu Thr Ser Leu Thr Ser Ala Ala Gln Thr
            340                 345                 350

Ala Pro Gly His Met Leu Gly Gly Leu Pro Leu Gly Gln Leu Thr Asn
            355                 360                 365

Ser Gly Gly Gly Phe Gly Gly Val Ser Asn Ala Leu Arg Met Pro Pro
    370                 375                 380

Arg Ala Tyr Val Met Pro Arg Val Pro Ala Ala Gly
385                 390                 395

(2) INFORMATION FOR SEQ ID NO:112:

(i) SEQUENCE CHARACTERISTICS:
        (A) LENGTH: 1616 base pairs
        (B) TYPE: nucleic acid
        (C) STRANDEDNESS: single
        (D) TOPOLOGY: linear (xi) SEQUENCE DESCRIPTION: SEQ ID NO:112:

CATCGGAGGG AGTGATCACC ATGCTGTGGC ACGCAATGCC ACCGGAGTAA ATACCGCACG      60

GCTGATGGCC GGCGCGGGTC CGGCTCCAAT GCTTGCGGCG GCCGCGGGAT GGCAGACGCT     120

TTCGGCGGCT CTGGACGCTC AGGCCGTCGA GTTGACCGCG CGCCTGAACT CTCTGGGAGA    180

AGCCTGGACT GGAGGTGGCA GCGACAAGGC GCTTGCGGCT GCAACGCCGA TGGTGGTCTG    240

GCTACAAACC GCGTCAACAC AGGCCAAGAC CCGTGCGATG CAGGCGACGG CGCAAGCCGC    300

GGCATACACC CAGGCCATGG CCACGACGCC GTCGCTGCCG GAGATCGCCG CCAACCACAT    360

CACCCAGGCC GTCCTTACGG CCACCAACTT CTTCGGTATC AACACGATCC CGATCGCGTT    420

GACCGAGATG GATTATTTCA TCCGTATGTG GAACCAGGCA GCCCTGGCAA TGGAGGTCTA    480

CCAGGCCGAG ACCGCGGTTA ACACGCTTTT CGAGAAGCTC GAGCCGATGG CGTCGATCCT    540

TGATCCCGGC GCGAGCCAGA GCACGACGAA CCCGATCTTC GGAATGCCCT CCCCTGGCAG    600

CTCAACACCG GTTGGCCAGT TGCCGCCGGC GGCTACCCAG ACCCTCGGCC AACTGGGTGA    660

GATGAGCGGC CCGATGCAGC AGCTGACCCA GCCGCTGCAG CAGGTGACGT CGTTGTTCAG    720

CCAGGTGGGC GGCACCGGCG GCGGCAACCC AGCCGACGAG GAAGCCGCGC AGATGGGCCT    780

GCTCGGCACC AGTCCGCTGT CGAACCATCC GCTGGCTGGT GGATCAGGCC CCAGCGCGGG    840

CGCGGGCCTG CTGCGCGCGG AGTCGCTACC TGGCGCAGGT GGGTCGTTGA CCCGCACGCC    900

GCTGATGTCT CAGCTGATCG AAAAGCCGGT TGCCCCCTCG GTGATGCCGG CGGCTGCTGC    960

CGGATCGTCG GCGACGGGTG GCGCCGCTCC GGTGGGTGCG GGAGCGATGG GCCAGGGTGC   1020

GCAATCCGGC GGCTCCACCA GGCCGGGTCT GGTCGCGCCG GCACCGCTCG CGCAGGAGCG   1080

TGAAGAAGAC GACGAGGACG ACTGGGACGA AGAGGACGAC TGGTGAGCTC CCGTAATGAC   1140

AACAGACTTC CCGGCCACCC GGGCCGGAAG ACTTGCCAAC ATTTTGGCGA GGAAGGTAAA   1200

GAGAGAAAGT AGTCCAGCAT GGCAGAGATG AAGACCGATG CCGCTACCCT CGCGCAGGAG   1260

GCAGGTAATT TCGAGCGGAT CTCCGGCGAC CTGAAAACCC AGATCGACCA GGTGGAGTCG   1320

ACGGCAGGTT CGTTGCAGGG CCAGTGGCGC GGCGCGGCGG GGACGGCCGC CCAGGCCGCG   1380

GTGGTGCGCT TCCAAGAAGC AGCCAATAAG CAGAAGCAGG AACTCGACGA GATCTCGACG   1440

AATATTCGTC AGGCCGGCGT CCAATACTCG AGGGCCGACG AGGAGCAGCA GCAGGCGCTG   1500

TCCTCGCAAA TGGGCTTCTG ACCCGCTAAT ACGAAAAGAA ACGGAGCAAA AACATGACAG   1560
```

-continued

```
AGCAGCAGTG GAATTTCGCG GGTATCGAGG CCGCGGCAAG CGCAATCCAG GGAAAT        1616
```

(2) INFORMATION FOR SEQ ID NO:113:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (xi) SEQUENCE DESCRIPTION: SEQ ID NO:113:

```
CTAGTGGATG GGACCATGGC CATTTTCTGC AGTCTCACTG CCTTCTGTGT TGACATTTTG      60

GCACGCCGGC GGAAACGAAG CACTGGGGTC GAAGAACGGC TGCGCTGCCA TATCGTCCGG     120

AGCTTCCATA CCTTCGTGCG GCCGGAAGAG CTTGTCGTAG TCGGCCGCCA TGACAACCTC     180

TCAGAGTGCG CTCAAACGTA TAAACACGAG AAAGGGCGAG ACCGACGGAA GGTCGAACTC     240

GCCCGATCCC GTGTTTCGCT ATTCTACGCG AACTCGGCGT TGCCCTATGC GAACATCCCA     300

GTGACGTTGC CTTCGGTCGA AGCCATTGCC TGACCGGCTT CGCTGATCGT CCGCGCCAGG     360

TTCTGCAGCC CGTTGTTCAG CTCGGTAGCC GTGGCGTCCC ATTTTTGCTG GACACCCTGG     420

TACGCCTCCG AA                                                        432
```

(2) INFORMATION FOR SEQ ID NO:114:

(i) SEQUENCE CHARACTERISTICS:
        (A) LENGTH: 368 amino acids
        (B) TYPE: amino acid
        (C) STRANDEDNESS: single
        (D) TOPOLOGY: linear (xi) SEQUENCE DESCRIPTION: SEQ ID NO:114:

```
Met Leu Trp His Ala Met Pro Pro Glu Xaa Asn Thr Ala Arg Leu Met
1               5                   10                  15

Ala Gly Ala Gly Pro Ala Pro Met Leu Ala Ala Ala Gly Trp Gln
            20                  25                  30

Thr Leu Ser Ala Ala Leu Asp Ala Gln Ala Val Glu Leu Thr Ala Arg
        35                  40                  45

Leu Asn Ser Leu Gly Glu Ala Trp Thr Gly Gly Ser Asp Lys Ala
50                  55                  60

Leu Ala Ala Thr Pro Met Val Val Trp Leu Gln Thr Ala Ser Thr
65                  70                  75                  80

Gln Ala Lys Thr Arg Ala Met Gln Ala Thr Ala Gln Ala Ala Tyr
            85                  90                  95

Thr Gln Ala Met Ala Thr Thr Pro Ser Leu Pro Glu Ile Ala Ala Asn
            100                 105                 110

His Ile Thr Gln Ala Val Leu Thr Ala Thr Asn Phe Phe Gly Ile Asn
            115                 120                 125

Thr Ile Pro Ile Ala Leu Thr Glu Met Asp Tyr Phe Ile Arg Met Trp
130                 135                 140

Asn Gln Ala Ala Leu Ala Met Glu Val Tyr Gln Ala Glu Thr Ala Val
145                 150                 155                 160

Asn Thr Leu Phe Glu Lys Leu Glu Pro Met Ala Ser Ile Leu Asp Pro
            165                 170                 175

Gly Ala Ser Gln Ser Thr Thr Asn Pro Ile Phe Gly Met Pro Ser Pro
            180                 185                 190

Gly Ser Ser Thr Pro Val Gly Gln Leu Pro Pro Ala Ala Thr Gln Thr
            195                 200                 205
```

```
Leu Gly Gln Leu Gly Glu Met Ser Gly Pro Met Gln Gln Leu Thr Gln
    210                 215                 220

Pro Leu Gln Gln Val Thr Ser Leu Phe Ser Gln Val Gly Gly Thr Gly
225                 230                 235                 240

Gly Gly Asn Pro Ala Asp Glu Ala Ala Gln Met Gly Leu Leu Gly
                245                 250                 255

Thr Ser Pro Leu Ser Asn His Pro Leu Ala Gly Ser Gly Pro Ser
                260                 265                 270

Ala Gly Ala Gly Leu Leu Arg Ala Glu Ser Leu Pro Gly Ala Gly Gly
                275                 280                 285

Ser Leu Thr Arg Thr Pro Leu Met Ser Gln Leu Ile Glu Lys Pro Val
    290                 295                 300

Ala Pro Ser Val Met Pro Ala Ala Ala Gly Ser Ser Ala Thr Gly
305                 310                 315                 320

Gly Ala Ala Pro Val Gly Ala Gly Ala Met Gly Gln Gly Ala Gln Ser
                325                 330                 335

Gly Gly Ser Thr Arg Pro Gly Leu Val Ala Pro Ala Pro Leu Ala Gln
                340                 345                 350

Glu Arg Glu Glu Asp Glu Asp Asp Trp Asp Glu Asp Asp Trp
    355                 360                 365

(2) INFORMATION FOR SEQ ID NO:115:

(i) SEQUENCE CHARACTERISTICS:
        (A) LENGTH: 100 amino acids
        (B) TYPE: amino acid
        (C) STRANDEDNESS:
        (D) TOPOLOGY: linear (xi) SEQUENCE DESCRIPTION: SEQ ID NO:115:

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

(2) INFORMATION FOR SEQ ID NO:116:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (xi) SEQUENCE DESCRIPTION: SEQ ID NO:116:

GATCTCCGGC GACCTGAAAA CCCAGATCGA CCAGGTGGAG TCGACGGCAG GTTCGTTGCA      60

GGGCCAGTGG CGCGGCGCGG CGGGGACGGC CGCCCAGGCC GCGGTGGTGC GCTTCCAAGA     120

AGCAGCCAAT AAGCAGAAGC AGGAACTCGA CGAGATCTCG ACGAATATTC GTCAGGCCGG     180
```

```
CGTCCAATAC TCGAGGGCCG ACGAGGAGCA GCAGCAGGCG CTGTCCTCGC AAATGGGCTT      240

CTGACCCGCT AATACGAAAA GAAACGGAGC AAAAACATGA CAGAGCAGCA GTGGAATTTC      300

GCGGGTATCG AGGCCGCGGC AAGCGCAATC CAGGGAAATG TCACGTCCAT TCATTCCCTC      360

CTTGACGAGG GGAAGCAGTC CCTGACCAAG CTCGCA                                396
```

(2) INFORMATION FOR SEQ ID NO:117:

(i) SEQUENCE CHARACTERISTICS:
        (A) LENGTH: 80 amino acids
        (B) TYPE: amino acid
        (C) STRANDEDNESS: single
        (D) TOPOLOGY: linear (xi) SEQUENCE DESCRIPTION: SEQ ID NO:117:

```
Ile Ser Gly Asp Leu Lys Thr Gln Ile Asp Gln Val Glu Ser Thr Ala
1               5                   10                  15

Gly Ser Leu Gln Gly Gln Trp Arg Gly Ala Ala Gly Thr Ala Ala Gln
            20                  25                  30

Ala Ala Val Val Arg Phe Gln Glu Ala Ala Asn Lys Gln Lys Gln Glu
        35                  40                  45

Leu Asp Glu Ile Ser Thr Asn Ile Arg Gln Ala Gly Val Gln Tyr Ser
    50                  55                  60

Arg Ala Asp Glu Glu Gln Gln Gln Ala Leu Ser Ser Gln Met Gly Phe
65                  70                  75                  80
```

(2) INFORMATION FOR SEQ ID NO:118:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (xi) SEQUENCE DESCRIPTION: SEQ ID NO:118:

```
GTGGATCCCG ATCCCGTGTT TCGCTATTCT ACGCGAACTC GGCGTTGCCC TATGCGAACA       60

TCCCAGTGAC GTTGCCTTCG GTCGAAGCCA TTGCCTGACC GGCTTCGCTG ATCGTCCGCG      120

CCAGGTTCTG CAGCGCGTTG TTCAGCTCGG TAGCCGTGGC GTCCCATTTT TGCTGGACAC      180

CCTGGTACGC CTCCGAACCG CTACCGCCCC AGGCCGCTGC GAGCTTGGTC AGGGACTGCT      240

TCCCCTCGTC AAGGAGGGAA TGAATGGACG TGACATTTCC CTGGATTGCG CTTGCCGCGG      300

CCTCGATACC CGCGAAATTC CACTGCTGCT CTGTCATGTT TTTGCTCCGT TTCTTTTCGT      360

ATTAGCGGGT CAGAAGCCCA TTTGCGA                                          387
```

(2) INFORMATION FOR SEQ ID NO:119:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (xi) SEQUENCE DESCRIPTION: SEQ ID NO:119:

```
CGGCACGAGG ATCTCGGTTG GCCCAACGGC GCTGGCGAGG GCTCCGTTCC GGGGGCGAGC       60

TGCGCGCCGG ATGCTTCCTC TGCCCGCAGC CGCGCCTGGA TGGATGGACC AGTTGCTACC      120

TTCCCGACGT TTCGTTCGGT GTCTGTGCGA TAGCGGTGAC CCCGGCGCGC ACGTCGGGAG      180

TGTTGGGGGG CAGGCCGGGT CGGTGGTTCG GCCGGGACG CAGACGGTCT GGACGGAACG      240

GGCGGGGGTT CGCCGATTGG CATCTTTGCC CA                                    272
```

(2) INFORMATION FOR SEQ ID NO:120:

(i) SEQUENCE CHARACTERISTICS:
        (A) LENGTH: 20 amino acids
        (B) TYPE: amino acid
        (C) STRANDEDNESS:
        (D) TOPOLOGY: linear (xi) SEQUENCE DESCRIPTION: SEQ ID NO:120:

Asp Pro Val Asp Ala Val Ile Asn Thr Thr Cys Asn Tyr Gly Gln Val
1               5                   10                  15

Val Ala Ala Leu
            20

(2) INFORMATION FOR SEQ ID NO:121:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:121:

Ala Val Glu Ser Gly Met Leu Ala Leu Gly Thr Pro Ala Pro Ser
1               5                   10                  15

(2) INFORMATION FOR SEQ ID NO:122:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:122:

Ala Ala Met Lys Pro Arg Thr Gly Asp Gly Pro Leu Glu Ala Ala Lys
1               5                   10                  15

Glu Gly Arg (2) INFORMATION FOR SEQ ID NO:123:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:123:

Tyr Tyr Trp Cys Pro Gly Gln Pro Phe Asp Pro Ala Trp Gly Pro
1               5                   10                  15

(2) INFORMATION FOR SEQ ID NO:124:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:124:

Asp Ile Gly Ser Glu Ser Thr Glu Asp Gln Gln Xaa Ala Val
1               5                   10

(2) INFORMATION FOR SEQ ID NO:125:

```
        (i) SEQUENCE CHARACTERISTICS:
            (A) LENGTH: 13 amino acids
            (B) TYPE: amino acid
            (C) STRANDEDNESS:
            (D) TOPOLOGY: linear (xi) SEQUENCE DESCRIPTION: SEQ ID NO:125:

Ala Glu Glu Ser Ile Ser Thr Xaa Glu Xaa Ile Val Pro
1               5                  10

(2) INFORMATION FOR SEQ ID NO:126:

(i) SEQUENCE CHARACTERISTICS:
            (A) LENGTH: 17 amino acids
            (B) TYPE: amino acid
            (C) STRANDEDNESS:
            (D) TOPOLOGY: linear (xi) SEQUENCE DESCRIPTION: SEQ ID NO:126:

Asp Pro Glu Pro Ala Pro Pro Val Pro Thr Thr Ala Ala Ser Pro Pro
1               5                  10                  15

Ser (2) INFORMATION FOR SEQ ID NO:127:

(i) SEQUENCE CHARACTERISTICS:
            (A) LENGTH: 15 amino acids
            (B) TYPE: amino acid
            (C) STRANDEDNESS:
            (D) TOPOLOGY: linear (xi) SEQUENCE DESCRIPTION: SEQ ID NO:127:

Ala Pro Lys Thr Tyr Xaa Glu Glu Leu Lys Gly Thr Asp Thr Gly
1               5                  10                  15

(2) INFORMATION FOR SEQ ID NO:128:

(i) SEQUENCE CHARACTERISTICS:
            (A) LENGTH: 30 amino acids
            (B) TYPE: amino acid
            (C) STRANDEDNESS:
            (D) TOPOLOGY: linear (xi) SEQUENCE DESCRIPTION: SEQ ID NO:128:

Asp Pro Ala Ser Ala Pro Asp Val Pro Thr Ala Ala Gln Leu Thr Ser
1               5                  10                  15

Leu Leu Asn Ser Leu Ala Asp Pro Asn Val Ser Phe Ala Asn
                20                  25                  30

(2) INFORMATION FOR SEQ ID NO:129:

(i) SEQUENCE CHARACTERISTICS:
            (A) LENGTH: 22 amino acids
            (B) TYPE: amino acid
            (C) STRANDEDNESS:
            (D) TOPOLOGY: linear (xi) SEQUENCE DESCRIPTION: SEQ ID NO:129:

Asp Pro Pro Asp Pro His Gln Xaa Asp Met Thr Lys Gly Tyr Tyr Pro
1               5                  10                  15

Gly Gly Arg Arg Xaa Phe
                20

(2) INFORMATION FOR SEQ ID NO:130:

(i) SEQUENCE CHARACTERISTICS:
```

```
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:130:

Asp Pro Gly Tyr Thr Pro Gly
1               5

(2) INFORMATION FOR SEQ ID NO:131:

(i) SEQUENCE CHARACTERISTICS:
        (A) LENGTH: 10 amino acids
        (B) TYPE: amino acid
        (C) STRANDEDNESS:
        (D) TOPOLOGY: linear (ix) FEATURE:
        (D) OTHER INFORMATION: /note= "The Second Residue Can Be
            Either a Pro or Thr"

(xi) SEQUENCE DESCRIPTION: SEQ ID NO:131:

Xaa Xaa Gly Phe Thr Gly Pro Gln Phe Tyr
1               5                   10

(2) INFORMATION FOR SEQ ID NO:132:

(i) SEQUENCE CHARACTERISTICS:
        (A) LENGTH: 9 amino acids
        (B) TYPE: amino acid
        (C) STRANDEDNESS:
        (D) TOPOLOGY: linear (ix) FEATURE:
        (D) OTHER INFORMATION: /note= "The Third Residue Can Be
            Either a Gln or Leu"

(xi) SEQUENCE DESCRIPTION: SEQ ID NO:132:

Xaa Pro Xaa Val Thr Ala Tyr Ala Gly
1               5

(2) INFORMATION FOR SEQ ID NO:133:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:133:

Xaa Xaa Xaa Glu Lys Pro Phe Leu Arg
1               5

(2) INFORMATION FOR SEQ ID NO:134:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:134:

Xaa Asp Ser Glu Lys Ser Ala Thr Ile Lys Val Thr Asp Ala Ser
1               5                   10                  15

(2) INFORMATION FOR SEQ ID NO:135:

(i) SEQUENCE CHARACTERISTICS:
        (A) LENGTH: 15 amino acids
```

(B) TYPE: amino acid
        (C) STRANDEDNESS:
        (D) TOPOLOGY: linear (xi) SEQUENCE DESCRIPTION: SEQ ID NO:135:

Ala Gly Asp Thr Xaa Ile Tyr Ile Val Gly Asn Leu Thr Ala Asp
1               5                   10                  15

(2) INFORMATION FOR SEQ ID NO:136:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:136:

Ala Pro Glu Ser Gly Ala Gly Leu Gly Gly Thr Val Gln Ala Gly
1               5                   10                  15

(2) INFORMATION FOR SEQ ID NO:137:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:137:

Xaa Tyr Ile Ala Tyr Xaa Thr Thr Ala Gly Ile Val Pro Gly Lys Ile
1               5                   10                  15

Asn Val His Leu Val
            20

(2) INFORMATION FOR SEQ ID NO:138:

(i) SEQUENCE CHARACTERISTICS:
        (A) LENGTH: 882 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:138:

```
GCAACGCTGT CGTGGCCTTT GCGGTGATCG GTTTCGCCTC GCTGGCGGTG GCGGTGGCGG        60

TCACCATCCG ACCGACCGCG GCCCTCAAAAC CGGTAGAGGG ACACCAAAAC GCCCAGCCAG      120

GGAAGTTCAT GCCGTTGTTG CCGACGCAAC AGCAGGCGCC GGTCCCGCCG CCTCCGCCCG       180

ATGATCCCAC CGCTGGATTC CAGGGCGGCA CCATTCCGGC TGTACAGAAC GTGGTGCCGC       240

GGCCGGGTAC CTCACCCGGG GTGGGTGGGA CGCCGGCTTC GCCTGCGCCG GAAGCGCCGG       300

CCGTGCCCGG TGTTGTGCCT GCCCCGGTGC CAATCCCGGT CCCGATCATC ATTCCCCCGT       360

TCCCGGGTTG GCAGCCTGGA ATGCCGACCA TCCCCACCGC ACCGCCGACG ACGCCGGTGA       420

CCACGTCGGC GACGACGCCG CCGACCACGC CGCCGACCAC GCCGGTGACC ACGCCGCCAA       480

CGACGCCGCC GACCACGCCG GTGACCACGC CGCCAACGAC GCCGCCGACC ACGCCGGTGA       540

CCACGCCACC AACGACCGTC GCCCCGACGA CCGTCGCCCC GACGACGGTC GCTCCGACCA       600

CCGTCGCCCC GACCACGGTC GCTCCAGCCA CCGCCACGCC GACGACCGTC GCTCCGCAGC       660

CGACGCAGCA GCCCACGCAA CAACCAACCC AACAGATGCC AACCCAGCAG CAGACCGTGG       720

CCCCGCAGAC GGTGGCGCCG GCTCCGCAGC CGCCGTCCGG TGGCCGCAAC GGCAGCGGCG       780
```

```
GGGGCGACTT ATTCGGCGGG TTCTGATCAC GGTCGCGGCT TCACTACGGT CGGAGGACAT      840

GGCCGGTGAT GCGGTGACGG TGGTGCTGCC CTGTCTCAAC GA                        882
```

(2) INFORMATION FOR SEQ ID NO:139:

(i) SEQUENCE CHARACTERISTICS:
        (A) LENGTH: 815 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:139:

```
CCATCAACCA ACCGCTCGCG CCGCCCGCGC CGCCGGATCC GCCGTCGCCG CCACGCCCGC       60

CGGTGCCTCC GGTGCCCCCG TTGCCGCCGT CGCCGCCGTC GCCGCCGACC GGCTGGGTGC      120

CTAGGGCGCT GTTACCGCCC TGGTTGGCGG GGACGCCGCC GGCACCACCG GTACCGCCGA      180

TGGCGCCGTT GCCGCCGGCG GCACCGTTGC CACCGTTGCC ACCGTTGCCA CCGTTGCCGA      240

CCAGCCACCC GCCGCGACCA CCGGCACCGC CGGCGCCGCC CGCACCGCCG GCGTGCCCGT      300

TCGTGCCCGT ACCGCCGGCA CCGCCGTTGC CGCCGTCACC GCCGACGGAA CTACCGGCGG      360

ACGCGGCCTG CCCGCCGGCG CCGCCCGCAC CGCCATTGGC ACCGCCGTCA CCGCCGGCTG      420

GGAGTGCCGC GATTAGGGCA CTGACCGGCG CAACCAGCGC AAGTACTCTC GGTCACCGAG      480

CACTTCCAGA CGACACCACA GCACGGGGTT GTCGGCGGAC TGGGTGAAAT GGCAGCCGAT      540

AGCGGCTAGC TGTCGGCTGC GGTCAACCTC GATCATGATG TCGAGGTGAC CGTGACCGCG      600

CCCCCCGAAG GAGGCGCTGA ACTCGGCGTT GAGCCGATCG GCGATCGGTT GGGGCAGTGC      660

CCAGGCCAAT ACGGGGATAC CGGGTGTCNA AGCCGCCGCG AGCGCAGCTT CGGTTGCGCG      720

ACNGTGGTCG GGGTGGCCTG TTACGCCGTT GTCNTCGAAC ACGAGTAGCA GGTCTGCTCC      780

GGCGAGGGCA TCCACCACGC GTTGCGTCAG CTCGT                                815
```

(2) INFORMATION FOR SEQ ID NO:140:

(i) SEQUENCE CHARACTERISTICS:
        (A) LENGTH: 1152 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:140:

```
ACCAGCCGCC GGCTGAGGTC TCAGATCAGA GAGTCTCCGG ACTCACCGGG GCGGTTCAGC       60

CTTCTCCCAG AACAACTGCT GAAGATCCTC GCCCGCGAAA CAGGCGCTGA TTTGACGCTC      120

TATGACCGGT TGAACGACGA GATCATCCGG CAGATTGATA TGGCACCGCT GGGCTAACAG      180

GTGCGCAAGA TGGTGCAGCT GTATGTCTCG GACTCCGTGT CGCGGATCAG CTTTGCCGAC      240

GGCCGGGTGA TCGTGTGGAG CGAGGAGCTC GGCGAGAGCC AGTATCCGAT CGAGACGCTG      300

GACGGCATCA CGCTGTTTGG GCGGCCGACG ATGACAACGC CCTTCATCGT TGAGATGCTC      360

AAGCGTGAGC GCGACATCCA GCTCTTCACG ACCGACGGCC ACTACCAGGG CCGGATCTCA      420

ACACCCGACG TGTCATACGC GCCGCGGCTC CGTCAGCAAG TTCACCGCAC CGACGATCCT      480

GCGTTCTGCC TGTCGTTAAG CAAGCGGATC GTGTCGAGGA AGATCCTGAA TCAGCAGGCC      540

TTGATTCGGG CACACACGTC GGGGCAAGAC GTTGCTGAGA GCATCCGCAC GATGAAGCAC      600

TCGCTGGCCT GGGTCGATCG ATCGGGCTCC CTGGCGGAGT TGAACGGGTT CGAGGGAAAT      660
```

```
GCCGCAAAGG CATACTTCAC CGCGCTGGGG CATCTCGTCC CGCAGGAGTT CGCATTCCAG    720

GGCCGCTCGA CTCGGCCGCC GTTGGACGCC TTCAACTCGA TGGTCAGCCT CGGCTATTCG    780

CTGCTGTACA AGAACATCAT AGGGGCGATC GAGCGTCACA GCCTGAACGC GTATATCGGT    840

TTCCTACACC AGGATTCACG AGGGCACGCA ACGTCTCGTG CCGAATTCGG CACGAGCTCC    900

GCTGAAACCG CTGGCCGGCT GCTCAGTGCC CGTACGTAAT CCGCTGCGCC CAGGCCGGCC    960

CGCCGGCCGA ATACCAGCAG ATCGGACAGC GAATTGCCGC CCAGCCGGTT GGAGCCGTGC   1020

ATACCGCCGG CACACTCACC GGCAGCGAAC AGGCCTGGCA CCGTGGCGGC GCCGGTGTCC   1080

GCGTCTACTT CGACACCGCC CATCACGTAG TGACACGTCG GCCCGACTTC CATTGCCTGC   1140

GTTCGGCACG AG                                                       1152
```

(2) INFORMATION FOR SEQ ID NO:141:

(i) SEQUENCE CHARACTERISTICS:
        (A) LENGTH: 655 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:141:

```
CTCGTGCCGA TTCGGCAGGG TGTACTTGCC GGTGGTGTAN GCCGCATGAG TGCCGACGAC     60

CAGCAATGCG GCAACAGCAC GGATCCCGGT CAACGACGCC ACCCGGTCCA CGTGGGCGAT    120

CCGCTCGAGT CCGCCCTGGG CGGCTCTTTC CTTGGGCAGG GTCATCCGAC GTGTTTCCGC    180

CGTGGTTTGC CGCCATTATG CCGGCGCGCC GCGTCGGGCG GCCGGTATGG CCGAANGTCG    240

ATCAGCACAC CCGAGATACG GGTCTGTGCA AGCTTTTTGA GCGTCGCGCG GGGCAGCTTC    300

GCCGGCAATT CTACTAGCGA GAAGTCTGGC CCGATACGGA TCTGACCGAA GTCGCTGCGG    360

TGCAGCCCAC CCTCATTGGC GATGGCGCCG ACGATGGCGC CTGGACCGAT CTTGTGCCGC    420

TTGCCGACGG CGACGCGGTA GGTGGTCAAG TCCGGTCTAC GCTTGGGCCT TTGCGGACGG    480

TCCCGACGCT GGTCGCGGTT GCGCCGCGAA AGCGGCGGGT CGGGTGCCAT CAGGAATGCC    540

TCACCGCCGC GGCACTGCAC GGCCAGTGCC GCGGCGATGT CAGCCATCGG GACATCATGC    600

TCGCGTTCAT ACTCCTCGAC CAGTCGGCGG AACAGCTCGA TTCCCGGACC GCCCA         655
```

(2) INFORMATION FOR SEQ ID NO:142:

(i) SEQUENCE CHARACTERISTICS:
        (A) LENGTH: 267 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:142:

```
Asn Ala Val Val Ala Phe Ala Val Ile Gly Phe Ala Ser Leu Ala Val
1               5                   10                  15

Ala Val Ala Val Thr Ile Arg Pro Thr Ala Ala Ser Lys Pro Val Glu
            20                  25                  30

Gly His Gln Asn Ala Gln Pro Gly Lys Phe Met Pro Leu Leu Pro Thr
        35                  40                  45

Gln Gln Gln Ala Pro Val Pro Pro Pro Pro Asp Asp Pro Thr Ala
    50                  55                  60
```

```
Gly Phe Gln Gly Gly Thr Ile Pro Ala Val Gln Asn Val Val Pro Arg
 65                  70                  75                  80

Pro Gly Thr Ser Pro Gly Val Gly Thr Pro Ala Ser Pro Ala Pro
                 85                  90                  95

Glu Ala Pro Ala Val Pro Gly Val Val Pro Ala Pro Val Pro Ile Pro
                100                 105                 110

Val Pro Ile Ile Ile Pro Pro Phe Pro Gly Trp Gln Pro Gly Met Pro
            115                 120                 125

Thr Ile Pro Thr Ala Pro Pro Thr Thr Pro Val Thr Thr Ser Ala Thr
    130                 135                 140

Thr Pro Pro Thr Thr Pro Pro Thr Thr Pro Val Thr Thr Pro Pro Thr
145                 150                 155                 160

Thr Pro Pro Thr Thr Pro Val Thr Thr Pro Pro Thr Thr Pro Pro Thr
                165                 170                 175

Thr Pro Val Thr Thr Pro Pro Thr Thr Val Ala Pro Thr Thr Val Ala
                180                 185                 190

Pro Thr Thr Val Ala Pro Thr Thr Val Ala Pro Thr Thr Val Ala Pro
                195                 200                 205

Ala Thr Ala Thr Pro Thr Thr Val Ala Pro Gln Pro Thr Gln Gln Pro
    210                 215                 220

Thr Gln Gln Pro Thr Gln Gln Met Pro Thr Gln Gln Gln Thr Val Ala
225                 230                 235                 240

Pro Gln Thr Val Ala Pro Ala Pro Gln Pro Pro Ser Gly Gly Arg Asn
                245                 250                 255

Gly Ser Gly Gly Gly Asp Leu Phe Gly Gly Phe
                260                 265

(2) INFORMATION FOR SEQ ID NO:143:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:143:

Ile Asn Gln Pro Leu Ala Pro Pro Ala Pro Pro Asp Pro Pro Ser Pro
  1              5                  10                  15

Pro Arg Pro Pro Val Pro Val Pro Pro Leu Pro Pro Ser Pro Pro
             20                  25                  30

Ser Pro Pro Thr Gly Trp Val Pro Arg Ala Leu Leu Pro Pro Trp Leu
         35                  40                  45

Ala Gly Thr Pro Pro Ala Pro Pro Val Pro Pro Met Ala Pro Leu Pro
     50                  55                  60

Pro Ala Ala Pro Leu Pro Pro Leu Pro Pro Leu Pro Pro Leu Pro Thr
 65                  70                  75                  80

Ser His Pro Pro Arg Pro Pro Ala Pro Pro Ala Pro Pro Ala Pro Pro
                 85                  90                  95

Ala Cys Pro Phe Val Pro Val Pro Pro Ala Pro Pro Leu Pro Pro Ser
                100                 105                 110

Pro Pro Thr Glu Leu Pro Ala Asp Ala Ala Cys Pro Pro Ala Pro Pro
            115                 120                 125

Ala Pro Pro Leu Ala Pro Pro Ser Pro Pro Ala Gly Ser Ala Ala Ile
    130                 135                 140
```

```
Arg Ala Leu Thr Gly Ala Thr Ser Ala Ser Thr Leu Gly His Arg Ala
145                 150                 155                 160

Leu Pro Asp Asp Thr Thr Ala Arg Gly Cys Arg Arg Thr Gly
                165                 170
```

(2) INFORMATION FOR SEQ ID NO:144:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:144:

```
Gln Pro Pro Ala Glu Val Ser Asp Gln Arg Val Ser Gly Leu Thr Gly
1               5                   10                  15

Ala Val Gln Pro Ser Pro Arg Thr Ala Glu Asp Pro Arg Pro Arg
                20                  25                  30

Asn Arg Arg
        35
```

(2) INFORMATION FOR SEQ ID NO:145:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:145:

```
Arg Ala Asp Ser Ala Gly Cys Thr Cys Arg Trp Cys Xaa Pro His Glu
1               5                   10                  15

Cys Arg Arg Pro Ala Met Arg Gln Gln His Gly Ser Arg Ser Thr Thr
                20                  25                  30

Pro Pro Gly Pro Arg Gly Arg Ser Ala Arg Val Arg Pro Gly Arg Leu
                35                  40                  45

Phe Pro Trp Ala Gly Ser Ser Asp Val Phe Pro Pro Trp Phe Ala Ala
        50                  55                  60

Ile Met Pro Ala Arg Arg Val Gly Arg Pro Val Trp Pro Xaa Val Asp
65                  70                  75                  80

Gln His Thr Arg Asp Thr Gly Leu Cys Lys Leu Phe Glu Arg Arg Ala
                85                  90                  95

Gly Gln Leu Arg Arg Gln Phe Tyr
                100
```

(2) INFORMATION FOR SEQ ID NO:146:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO:146:

GGATCCATAT GGGCCATCAT CATCATCATC ACGTGATCGA CATCATCGGG ACC        53

(2) INFORMATION FOR SEQ ID NO:147:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR Primer"

(vi) ORIGINAL SOURCE:
        (A) ORGANISM: Mycobacterium tuberculosis (xi) SEQUENCE DESCRIPTION: SEQ ID NO:147:

CCTGAATTCA GGCCTCGGTT GCGCCGGCCT CATCTTGAAC GA        42

(2) INFORMATION FOR SEQ ID NO:148:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR Primer"

(vi) ORIGINAL SOURCE:
        (A) ORGANISM: Mycobacterium tuberculosis (xi) SEQUENCE DESCRIPTION: SEQ ID NO:148:

GGATCCTGCA GGCTCGAAAC CACCGAGCGG T        31

(2) INFORMATION FOR SEQ ID NO:149:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO:149:

CTCTGAATTC AGCGCTGGAA ATCGTCGCGA T        31

(2) INFORMATION FOR SEQ ID NO:150:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO:150:

GGATCCAGCG CTGAGATGAA GACCGATGCC GCT        33

(2) INFORMATION FOR SEQ ID NO:151:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO:151:

GAGAGAATTC TCAGAAGCCC ATTTGCGAGG ACA                        33

(2) INFORMATION FOR SEQ ID NO:152:

(i) SEQUENCE CHARACTERISTICS:
        (A) LENGTH: 1993 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium tuberculosis (ix) FEATURE:
        (A) NAME/KEY: CDS
        (B) LOCATION: 152..1273

(xi) SEQUENCE DESCRIPTION: SEQ ID NO:152:

```
TGTTCTTCGA CGGCAGGCTG GTGGAGGAAG GGCCCACCGA ACAGCTGTTC TCCTCGCCGA      60

AGCATGCGGA AACCGCCCGA TACGTCGCCG GACTGTCGGG GGACGTCAAG GACGCCAAGC     120

GCGGAAATTG AAGAGCACAG AAAGGTATGG C GTG AAA ATT CGT TTG CAT ACG        172
                                 Val Lys Ile Arg Leu His Thr
                                  1               5

CTG TTG GCC GTG TTG ACC GCT GCG CCG CTG CTG CTA GCA GCG GCG GGC       220
Leu Leu Ala Val Leu Thr Ala Ala Pro Leu Leu Leu Ala Ala Ala Gly
         10                  15                  20

TGT GGC TCG AAA CCA CCG AGC GGT TCG CCT GAA ACG GGC GCC GGC GCC       268
Cys Gly Ser Lys Pro Pro Ser Gly Ser Pro Glu Thr Gly Ala Gly Ala
     25                  30                  35

GGT ACT GTC GCG ACT ACC CCC GCG TCG TCG CCG GTG ACG TTG GCG GAG       316
Gly Thr Val Ala Thr Thr Pro Ala Ser Ser Pro Val Thr Leu Ala Glu
 40                  45                  50                  55

ACC GGT AGC ACG CTG CTC TAC CCG CTG TTC AAC CTG TGG GGT CCG GCC       364
Thr Gly Ser Thr Leu Leu Tyr Pro Leu Phe Asn Leu Trp Gly Pro Ala
                 60                  65                  70

TTT CAC GAG AGG TAT CCG AAC GTC ACG ATC ACC GCT CAG GGC ACC GGT       412
Phe His Glu Arg Tyr Pro Asn Val Thr Ile Thr Ala Gln Gly Thr Gly
             75                  80                  85

TCT GGT GCC GGG ATC GCG CAG GCC GCC GCC GGG ACG GTC AAC ATT GGG       460
Ser Gly Ala Gly Ile Ala Gln Ala Ala Ala Gly Thr Val Asn Ile Gly
         90                  95                 100

GCC TCC GAC GCC TAT CTG TCG GAA GGT GAT ATG GCC GCG CAC AAG GGG       508
Ala Ser Asp Ala Tyr Leu Ser Glu Gly Asp Met Ala Ala His Lys Gly
     105                 110                 115

CTG ATG AAC ATC GCG CTA GCC ATC TCC GCT CAG CAG GTC AAC TAC AAC       556
Leu Met Asn Ile Ala Leu Ala Ile Ser Ala Gln Gln Val Asn Tyr Asn
120                 125                 130                 135

CTG CCC GGA GTG AGC GAG CAC CTC AAG CTG AAC GGA AAA GTC CTG GCG       604
```

```
Leu Pro Gly Val Ser Glu His Leu Lys Leu Asn Gly Lys Val Leu Ala
            140                 145                 150

GCC ATG TAC CAG GGC ACC ATC AAA ACC TGG GAC GAC CCG CAG ATC GCT          652
Ala Met Tyr Gln Gly Thr Ile Lys Thr Trp Asp Asp Pro Gln Ile Ala
            155                 160                 165

GCG CTC AAC CCC GGC GTG AAC CTG CCC GGC ACC GCG GTA GTT CCG CTG          700
Ala Leu Asn Pro Gly Val Asn Leu Pro Gly Thr Ala Val Val Pro Leu
            170                 175                 180

CAC CGC TCC GAC GGG TCC GGT GAC ACC TTC TTG TTC ACC CAG TAC CTG          748
His Arg Ser Asp Gly Ser Gly Asp Thr Phe Leu Phe Thr Gln Tyr Leu
        185                 190                 195

TCC AAG CAA GAT CCC GAG GGC TGG GGC AAG TCG CCC GGC TTC GGC ACC          796
Ser Lys Gln Asp Pro Glu Gly Trp Gly Lys Ser Pro Gly Phe Gly Thr
200                 205                 210                 215

ACC GTC GAC TTC CCG GCG GTG CCG GGT GCG CTG GGT GAG AAC GGC AAC          844
Thr Val Asp Phe Pro Ala Val Pro Gly Ala Leu Gly Glu Asn Gly Asn
                220                 225                 230

GGC GGC ATG GTG ACC GGT TGC GCC GAG ACA CCG GGC TGC GTG GCC TAT          892
Gly Gly Met Val Thr Gly Cys Ala Glu Thr Pro Gly Cys Val Ala Tyr
            235                 240                 245

ATC GGC ATC AGC TTC CTC GAC CAG GCC AGT CAA CGG GGA CTC GGC GAG          940
Ile Gly Ile Ser Phe Leu Asp Gln Ala Ser Gln Arg Gly Leu Gly Glu
            250                 255                 260

GCC CAA CTA GGC AAT AGC TCT GGC AAT TTC TTG TTG CCC GAC GCG CAA          988
Ala Gln Leu Gly Asn Ser Ser Gly Asn Phe Leu Leu Pro Asp Ala Gln
        265                 270                 275

AGC ATT CAG GCC GCG GCG GCT GGC TTC GCA TCG AAA ACC CCG GCG AAC         1036
Ser Ile Gln Ala Ala Ala Ala Gly Phe Ala Ser Lys Thr Pro Ala Asn
280                 285                 290                 295

CAG GCG ATT TCG ATG ATC GAC GGG CCC GCC CCG GAC GGC TAC CCG ATC         1084
Gln Ala Ile Ser Met Ile Asp Gly Pro Ala Pro Asp Gly Tyr Pro Ile
                300                 305                 310

ATC AAC TAC GAG TAC GCC ATC GTC AAC AAC CGG CAA AAG GAC GCC GCC         1132
Ile Asn Tyr Glu Tyr Ala Ile Val Asn Asn Arg Gln Lys Asp Ala Ala
            315                 320                 325

ACC GCG CAG ACC TTG CAG GCA TTT CTG CAC TGG GCG ATC ACC GAC GGC         1180
Thr Ala Gln Thr Leu Gln Ala Phe Leu His Trp Ala Ile Thr Asp Gly
            330                 335                 340

AAC AAG GCC TCG TTC CTC GAC CAG GTT CAT TTC CAG CCG CTG CCG CCC         1228
Asn Lys Ala Ser Phe Leu Asp Gln Val His Phe Gln Pro Leu Pro Pro
        345                 350                 355

GCG GTG GTG AAG TTG TCT GAC GCG TTG ATC GCG ACG ATT TCC AGC             1273
Ala Val Val Lys Leu Ser Asp Ala Leu Ile Ala Thr Ile Ser Ser
360                 365                 370

TAGCCTCGTT GACCACCACG CGACAGCAAC CTCCGTCGGG CCATCGGGCT GCTTTGCGGA       1333

GCATGCTGGC CCGTGCCGGT GAAGTCGGCC GCGCTGGCCC GGCCATCCGG TGGTTGGGTG       1393

GGATAGGTGC GGTGATCCCG CTGCTTGCGC TGGTCTTGGT GCTGGTGGTG CTGGTCATCG       1453

AGGCGATGGG TGCGATCAGG CTCAACGGGT TGCATTTCTT CACCGCCACC GAATGGAATC       1513

CAGGCAACAC CTACGGCGAA ACCGTTGTCA CCGACGCGTC GCCCATCCGG TCGGCGCCTA       1573

CTACGGGGCG TTGCCGCTGA TCGTCGGGAC GCTGGCGACC TCGGCAATCG CCCTGATCAT       1633

CGCGGTGCCG GTCTCTGTAG GAGCGGCGCT GGTGATCGTG AACGGCTGC CGAAACGGTT        1693

GGCCGAGGCT GTGGGAATAG TCCTGGAATT GCTCGCCGGA ATCCCCAGCG TGGTCGTCGG       1753

TTTGTGGGGG GCAATGACGT TCGGGCCGTT CATCGCTCAT CACATCGCTC CGGTGATCGC       1813

TCACAACGCT CCCGATGTGC CGGTGCTGAA CTACTTGCGC GGCGACCCGG GCAACGGGGA       1873
```

```
GGGCATGTTG GTGTCCGGTC TGGTGTTGGC GGTGATGGTC GTTCCCATTA TCGCCACCAC    1933

CACTCATGAC CTGTTCCGGC AGGTGCCGGT GTTGCCCCGG GAGGGCGCGA TCGGGAATTC    1993
```

(2) INFORMATION FOR SEQ ID NO:153:

(i) SEQUENCE CHARACTERISTICS:
        (A) LENGTH: 374 amino acids
        (B) TYPE: amino acid
        (D) TOPOLOGY: linear (ii) MOLECULE TYPE: protein (xi) SEQUENCE DESCRIPTION: SEQ ID NO:153:

```
Val Lys Ile Arg Leu His Thr Leu Leu Ala Val Leu Thr Ala Ala Pro
  1               5                  10                  15

Leu Leu Leu Ala Ala Ala Gly Cys Gly Ser Lys Pro Pro Ser Gly Ser
             20                  25                  30

Pro Glu Thr Gly Ala Gly Ala Gly Thr Val Ala Thr Thr Pro Ala Ser
         35                  40                  45

Ser Pro Val Thr Leu Ala Glu Thr Gly Ser Thr Leu Leu Tyr Pro Leu
 50                  55                  60

Phe Asn Leu Trp Gly Pro Ala Phe His Glu Arg Tyr Pro Asn Val Thr
 65                  70                  75                  80

Ile Thr Ala Gln Gly Thr Gly Ser Gly Ala Gly Ile Ala Gln Ala Ala
                 85                  90                  95

Ala Gly Thr Val Asn Ile Gly Ala Ser Asp Ala Tyr Leu Ser Glu Gly
                100                 105                 110

Asp Met Ala Ala His Lys Gly Leu Met Asn Ile Ala Leu Ala Ile Ser
            115                 120                 125

Ala Gln Gln Val Asn Tyr Asn Leu Pro Gly Val Ser Glu His Leu Lys
        130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
                180                 185                 190

Phe Leu Phe Thr Gln Tyr Leu Ser Lys Gln Asp Pro Glu Gly Trp Gly
            195                 200                 205

Lys Ser Pro Gly Phe Gly Thr Thr Val Asp Phe Pro Ala Val Pro Gly
        210                 215                 220

Ala Leu Gly Glu Asn Gly Asn Gly Gly Met Val Thr Gly Cys Ala Glu
225                 230                 235                 240

Thr Pro Gly Cys Val Ala Tyr Ile Gly Ile Ser Phe Leu Asp Gln Ala
                245                 250                 255

Ser Gln Arg Gly Leu Gly Glu Ala Gln Leu Gly Asn Ser Ser Gly Asn
            260                 265                 270

Phe Leu Leu Pro Asp Ala Gln Ser Ile Gln Ala Ala Ala Gly Phe
        275                 280                 285

Ala Ser Lys Thr Pro Ala Asn Gln Ala Ile Ser Met Ile Asp Gly Pro
    290                 295                 300

Ala Pro Asp Gly Tyr Pro Ile Ile Asn Tyr Glu Tyr Ala Ile Val Asn
305                 310                 315                 320

Asn Arg Gln Lys Asp Ala Ala Thr Ala Gln Thr Leu Gln Ala Phe Leu
                325                 330                 335
```

His Trp Ala Ile Thr Asp Gly Asn Lys Ala Ser Phe Leu Asp Gln Val
         340                 345                 350

His Phe Gln Pro Leu Pro Pro Ala Val Val Lys Leu Ser Asp Ala Leu
         355                 360                 365

Ile Ala Thr Ile Ser Ser
    370

(2) INFORMATION FOR SEQ ID NO:154:

(i) SEQUENCE CHARACTERISTICS:
        (A) LENGTH: 1993 base pairs
        (B) TYPE: nucleic acid
        (C) STRANDEDNESS: single
        (D) TOPOLOGY: linear (xi) SEQUENCE DESCRIPTION: SEQ ID NO:154:

| | | |
|---|---|---|
| TGTTCTTCGA CGGCAGGCTG GTGGAGGAAG GGCCCACCGA ACAGCTGTTC TCCTCGCCGA | 60 |
| AGCATGCGGA AACCGCCCGA TACGTCGCCG GACTGTCGGG GGACGTCAAG GACGCCAAGC | 120 |
| GCGGAAATTG AAGAGCACAG AAAGGTATGG CGTGAAAATT CGTTTGCATA CGCTGTTGGC | 180 |
| CGTGTTGACC GCTGCGCCGC TGCTGCTAGC AGCGGCGGGC TGTGGCTCGA AACCACCGAG | 240 |
| CGGTTCGCCT GAAACGGGCG CCGGCGCCGG TACTGTCGCG ACTACCCCCG CGTCGTCGCC | 300 |
| GGTGACGTTG GCGGAGACCG GTAGCACGCT GCTCTACCCG CTGTTCAACC TGTGGGGTCC | 360 |
| GGCCTTTCAC GAGAGGTATC CGAACGTCAC GATCACCGCT CAGGGCACCG GTTCTGGTGC | 420 |
| CGGGATCGCG CAGGCCGCCG CCGGGACGGT CAACATTGGG GCCTCCGACG CCTATCTGTC | 480 |
| GGAAGGTGAT ATGGCCGCGC ACAAGGGGCT GATGAACATC GCGCTAGCCA TCTCCGCTCA | 540 |
| GCAGGTCAAC TACAACCTGC CCGGAGTGAG CGAGCACCTC AAGCTGAACG GAAAAGTCCT | 600 |
| GGCGGCCATG TACCAGGGCA CCATCAAAAC CTGGGACGAC CCGCAGATCG CTGCGCTCAA | 660 |
| CCCCGGCGTG AACCTGCCCG GCACCGCGGT AGTTCCGCTG CACCGCTCCG ACGGGTCCGG | 720 |
| TGACACCTTC TTGTTCACCC AGTACCTGTC CAAGCAAGAT CCCGAGGGCT GGGGCAAGTC | 780 |
| GCCCGGCTTC GGCACCACCG TCGACTTCCC GGCGGTGCCG GGTGCGCTGG GTGAGAACGG | 840 |
| CAACGGCGGC ATGGTGACCG GTTGCGCCGA GACACCGGGC TGCGTGGCCT ATATCGGCAT | 900 |
| CAGCTTCCTC GACCAGGCCA GTCAACGGGG ACTCGGCGAG GCCCAACTAG GCAATAGCTC | 960 |
| TGGCAATTTC TTGTTGCCCG ACGCGCAAAG CATTCAGGCC GCGGCGGCTG GCTTCGCATC | 1020 |
| GAAACCCCG GCGAACCAGG CGATTTCGAT GATCGACGGG CCCGCCCCGG ACGGCTACCC | 1080 |
| GATCATCAAC TACGAGTACG CCATCGTCAA CAACCGGCAA AAGGACGCCG CCACCGCGCA | 1140 |
| GACCTTGCAG GCATTTCTGC ACTGGGCGAT CACCGACGGC AACAAGGCCT CGTTCCTCGA | 1200 |
| CCAGGTTCAT TTCCAGCCGC TGCCGCCCGC GGTGGTGAAG TTGTCTGACG CGTTGATCGC | 1260 |
| GACGATTTCC AGCTAGCCTC GTTGACCACC ACGCGACAGC AACCTCCGTC GGGCCATCGG | 1320 |
| GCTGCTTTGC GGAGCATGCT GGCCCGTGCC GGTGAAGTCG GCCGCGCTGG CCCGGCCATC | 1380 |
| CGGTGGTTGG GTGGGATAGG TGCGGTGATC CCGCTGCTTG CGCTGGTCTT GGTGCTGGTG | 1440 |
| GTGCTGGTCA TCGAGGCGAT GGGTGCGATC AGGCTCAACG GGTTGCATTT CTTCACCGCC | 1500 |
| ACCGAATGGA ATCCAGGCAA CACCTACGGC GAAACCGTTG TCACCGACGC GTCGCCCATC | 1560 |
| CGGTCGGCGC CTACTACGGG GCGTTGCCGC TGATCGTCGG GACGCTGGCG ACCTCGGCAA | 1620 |
| TCGCCCTGAT CATCGCGGTG CCGGTCTCTG TAGGAGCGGC GCTGGTGATC GTGGAACGGC | 1680 |
| TGCCGAAACG GTTGGCCGAG GCTGTGGGAA TAGTCCTGGA ATTGCTCGCC GGAATCCCCA | 1740 |
| GCGTGGTCGT CGGTTTGTGG GGGGCAATGA CGTTCGGGCC GTTCATCGCT CATCACATCG | 1800 |

```
CTCCGGTGAT CGCTCACAAC GCTCCCGATG TGCCGGTGCT GAACTACTTG CGCGGCGACC    1860

CGGGCAACGG GGAGGGCATG TTGGTGTCCG GTCTGGTGTT GGCGGTGATG GTCGTTCCCA    1920

TTATCGCCAC CACCACTCAT GACCTGTTCC GGCAGGTGCC GGTGTTGCCC CGGGAGGGCG    1980

CGATCGGGAA TTC                                                        1993
```

(2) INFORMATION FOR SEQ ID NO:155:

(i) SEQUENCE CHARACTERISTICS:
        (A) LENGTH: 374 amino acids
        (B) TYPE: amino acid
        (C) STRANDEDNESS:
        (D) TOPOLOGY: linear (xi) SEQUENCE DESCRIPTION: SEQ ID NO:155:

```
Met Lys Ile Arg Leu His Thr Leu Leu Ala Val Leu Thr Ala Ala Pro
1               5                   10                  15

Leu Leu Leu Ala Ala Ala Gly Cys Gly Ser Lys Pro Pro Ser Gly Ser
            20                  25                  30

Pro Glu Thr Gly Ala Gly Ala Gly Thr Val Ala Thr Thr Pro Ala Ser
        35                  40                  45

Ser Pro Val Thr Leu Ala Glu Thr Gly Ser Thr Leu Leu Tyr Pro Leu
    50                  55                  60

Phe Asn Leu Trp Gly Pro Ala Phe His Glu Arg Tyr Pro Asn Val Thr
65                  70                  75                  80

Ile Thr Ala Gln Gly Thr Gly Ser Gly Ala Gly Ile Ala Gln Ala Ala
                85                  90                  95

Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
            115                 120                 125

Ala Gln Gln Val Asn Tyr Asn Leu Pro Gly Val Ser Glu His Leu Lys
    130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
            180                 185                 190

Phe Leu Phe Thr Gln Tyr Leu Ser Lys Gln Asp Pro Glu Gly Trp Gly
        195                 200                 205

Lys Ser Pro Gly Phe Gly Thr Thr Val Asp Phe Pro Ala Val Pro Gly
    210                 215                 220

Ala Leu Gly Glu Asn Gly Asn Gly Gly Met Val Thr Gly Cys Ala Glu
225                 230                 235                 240

Thr Pro Gly Cys Val Ala Tyr Ile Gly Ile Ser Phe Leu Asp Gln Ala
                245                 250                 255

Ser Gln Arg Gly Leu Gly Glu Ala Gln Leu Gly Asn Ser Ser Gly Asn
            260                 265                 270

Phe Leu Leu Pro Asp Ala Gln Ser Ile Gln Ala Ala Ala Gly Phe
        275                 280                 285

Ala Ser Lys Thr Pro Ala Asn Gln Ala Ile Ser Met Ile Asp Gly Pro
    290                 295                 300

Ala Pro Asp Gly Tyr Pro Ile Ile Asn Tyr Glu Tyr Ala Ile Val Asn
305                 310                 315                 320
```

```
Asn Arg Gln Lys Asp Ala Ala Thr Ala Gln Thr Leu Gln Ala Phe Leu
            325                 330                 335

His Trp Ala Ile Thr Asp Gly Asn Lys Ala Ser Phe Leu Asp Gln Val
            340                 345                 350

His Phe Gln Pro Leu Pro Pro Ala Val Val Lys Leu Ser Asp Ala Leu
            355                 360                 365

Ile Ala Thr Ile Ser Ser
        370

(2) INFORMATION FOR SEQ ID NO:156:

(i) SEQUENCE CHARACTERISTICS:
        (A) LENGTH: 1777 base pairs
        (B) TYPE: nucleic acid
        (C) STRANDEDNESS: single
        (D) TOPOLOGY: linear (xi) SEQUENCE DESCRIPTION: SEQ ID NO:156:
```

| | | | | | |
|---|---|---|---|---|---|
| GGTCTTGACC | ACCACCTGGG | TGTCGAAGTC | GGTGCCCGGA | TTGAAGTCCA | GGTACTCGTG     60 |
| GGTGGGGCGG | GCGAAACAAT | AGCGACAAGC | ATGCGAGCAG | CCGCGGTAGC | CGTTGACGGT    120 |
| GTAGCGAAAC | GGCAACGCGG | CCGCGTTGGG | CACCTTGTTC | AGCGCTGATT | TGCACAACAC    180 |
| CTCGTGGAAG | GTGATGCCGT | CGAATTGTGG | CGCGCGAACG | CTGCGGACCA | GGCCGATCCG    240 |
| CTGCAACCCG | GCAGCGCCCG | TCGTCAACGG | GCATCCCGTT | CACCGCGACG | GCTTGCCGGG    300 |
| CCCAACGCAT | ACCATTATTC | GAACAACCGT | TCTATACTTT | GTCAACGCTG | GCCGCTACCG    360 |
| AGCGCCGCAC | AGGATGTGAT | ATGCCATCTC | TGCCCGCACA | GACAGGAGCC | AGGCCTTATG    420 |
| ACAGCATTCG | GCGTCGAGCC | CTACGGGCAG | CCGAAGTACC | TAGAAATCGC | CGGGAAGCGC    480 |
| ATGGCGTATA | TCGACGAAGG | CAAGGGTGAC | GCCATCGTCT | TTCAGCACGG | CAACCCCACG    540 |
| TCGTCTTACT | TGTGGCGCAA | CATCATGCCG | CACTTGGAAG | GCTGGGCCG | GCTGGTGGCC    600 |
| TGCGATCTGA | TCGGGATGGG | CGCGTCGGAC | AAGCTCAGCC | CATCGGGACC | CGACCGCTAT    660 |
| AGCTATGGCG | AGCAACGAGA | CTTTTTGTTC | GCGCTCTGGG | ATGCGCTCGA | CCTCGGCGAC    720 |
| CACGTGGTAC | TGGTGCTGCA | CGACTGGGGC | TCGGCGCTCG | GCTTCGACTG | GCTAACCAG    780 |
| CATCGCGACC | GAGTGCAGGG | GATCGCGTTC | ATGGAAGCGA | TCGTCACCCC | GATGACGTGG    840 |
| GCGGACTGGC | CGCCGGCCGT | GCGGGGTGTG | TTCCAGGGTT | CCGATCGCC | TCAAGGCGAG    900 |
| CCAATGGCGT | TGGAGCACAA | CATCTTTGTC | AACGGGTGC | TGCCCGGGC | GATCCTGCGA    960 |
| CAGCTCAGCG | ACGAGGAAAT | GAACCACTAT | CGGCGGCCAT | TCGTGAACGG | CGGCGAGGAC   1020 |
| CGTCGCCCCA | CGTTGTCGTG | GCCACGAAAC | CTTCCAATCG | ACGGTGAGCC | CGCCGAGGTC   1080 |
| GTCGCGTTGG | TCAACGAGTA | CCGGAGCTGG | CTCGAGGAAA | CCGACATGCC | GAAACTGTTC   1140 |
| ATCAACGCCG | AGCCCGGCGC | GATCATCACC | GGCCGCATCC | GTGACTATGT | CAGGAGCTGG   1200 |
| CCCAACCAGA | CCGAAATCAC | AGTGCCCGGC | GTGCATTTCG | TTCAGGAGGA | CAGCGATGGC   1260 |
| GTCGTATCGT | GGGCGGGCGC | TCGGCAGCAT | CGGCGACCTG | GGAGCGCTCT | CATTTCACGA   1320 |
| GACCAAGAAT | GTGATTTCCG | GCGAAGGCGG | CGCCCTGCTT | GTCAACTCAT | AAGACTTCCT   1380 |
| GCTCCGGGCA | GAGATTCTCA | GGGAAAAGGG | CACCAATCGC | AGCCGCTTCC | TTCGCAACGA   1440 |
| GGTCGACAAA | TATACGTGGC | AGGACAAAGG | TCTTCCTATT | TGCCCAGCGA | ATTAGTCGCT   1500 |
| GCCTTTCTAT | GGGCTCAGTT | CGAGGAAGCC | GAGCGGATCA | CGCGTATCCG | ATTGGACCTA   1560 |
| TGGAACCGGT | ATCATGAAAG | CTTCGAATCA | TTGGAACAGC | GGGGGCTCCT | GCGCCGTCCG   1620 |
| ATCATCCCAC | AGGGCTGCTC | TCACAACGCC | CACATGTACT | ACGTGTTACT | AGCGCCCAGC   1680 |

```
GCCGATCGGG AGGAGGTGCT GGCGCGTCTG ACGAGCGAAG GTATAGGCGC GGTCTTTCAT      1740

TACGTGCCGC TTCACGATTC GCCGGCCGGG CGTCGCT                              1777

(2) INFORMATION FOR SEQ ID NO:157:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (xi) SEQUENCE DESCRIPTION: SEQ ID NO:157:

GAGATTGAAT CGTACCGGTC TCCTTAGCGG CTCCGTCCCG TGAATGCCCA TATCACGCAC        60

GGCCATGTTC TGGCTGTCGA CCTTCGCCCC ATGCCCGGAC GTTGGTAAAC CCAGGGTTTG       120

ATCAGTAATT CCGGGGACG GTTGCGGGAA GGCGGCCAGG ATGTGCGTGA GCCGCGGCGC        180

CGCCGTCGCC CAGGCGACCG CTGGATGCTC AGCCCCGGTG CGGCGACGTA GCCAGCGTTT       240

GGCGCGTGTC GTCCACAGTG GTACTCCGGT GACGACGCGG CGCGGTGCCT GGGTGAAGAC       300

CGTGACCGAC GCCGCCGATT CAGA                                             324

(2) INFORMATION FOR SEQ ID NO:158:

(i) SEQUENCE CHARACTERISTICS:
        (A) LENGTH: 1338 base pairs
        (B) TYPE: nucleic acid
        (C) STRANDEDNESS: single
        (D) TOPOLOGY: linear (xi) SEQUENCE DESCRIPTION: SEQ ID NO:158:

GCGGTACCGC CGCGTTGCGC TGGCACGGGA CCTGTACGAC CTGAACCACT TCGCCTCGCG        60

AACGATTGAC GAACCGCTCG TGCGGCGGCT GTGGGTGCTC AAGGTGTGGG GTGATGTCGT       120

CGATGACCGG CGCGGCACCC GGCCACTACG CGTCGAAGAC GTCCTCGCCG CCCGCAGCGA       180

GCACGACTTC CAGCCCGACT CGATCGGCGT GCTGACCCGT CCTGTCGCTA TGGCTGCCTG       240

GGAAGCTCGC GTTCGGAAGC GATTTGCGTT CCTCACTGAC CTCGACGCCG ACGAGCAGCG       300

GTGGGCCGCC TGCGACGAAC GGCACCGCCG CGAAGTGGAG AACGCGCTGG CGGTGCTGCG       360

GTCCTGATCA ACCTGCCGGC GATCGTGCCG TTCCGCTGGC ACGGTTGCGG CTGGACGCGG       420

CTGAATCGAC TAGATGAGAG CAGTTGGGCA CGAATCCGGC TGTGGTGGTG AGCAAGACAC       480

GAGTACTGTC ATCACTATTG GATGCACTGG ATGACCGGCC TGATTCAGCA GGACCAATGG       540

AACTGCCCGG GGCAAAACGT CTCGGAGATG ATCGGCGTCC CCTCGGAACC CTGCGGTGCT       600

GGCGTCATTC GGACATCGGT CCGGCTCGCG GGATCGTGGT GACGCCAGCG CTGAAGGAGT       660

GGAGCGCGGC GGTGCACGCG CTGCTGGACG GCCGGCAGAC GGTGCTGCTG CGTAAGGGCG       720

GGATCGGCGA GAAGCGCTTC GAGGTGGCGG CCCACGAGTT CTTGTTGTTC CCGACGGTCG       780

CGCACAGCCA CGCCGAGCGG GTTCGCCCCG AGCACCGCGA CCTGCTGGGC CCGGCGGCCG       840

CCGACAGCAC CGACGAGTGT GTGCTACTGC GGGCCGCAGC GAAAGTTGTT GCCGCACTGC       900

CGGTTAACCG GCCAGAGGGT CTGGACGCCA TCGAGGATCT GCACATCTGG ACCGCCGAGT       960

CGGTGCGCGC CGACCGGCTC GACTTTCGGC CCAAGCACAA ACTGGCCGTC TTGGTGGTCT      1020

CGGCGATCCC GCTGGCCGAG CCGGTCCGGC TGGCGCGTAG GCCCGAGTAC GGCGGTTGCA      1080

CCAGCTGGGT GCAGCTGCCG GTGACGCCGA CGTTGGCGGC GCCGGTGCAC GACGAGGCCG      1140

CGCTGGCCGA GGTCGCCGCC CGGGTCCGCG AGGCCGTGGG TTGACTGGGC GGCATCGCTT      1200
```

```
GGGTCTGAGC TGTACGCCCA GTCGGCGCTG CGAGTGATCT GCTGTCGGTT CGGTCCCTGC    1260

TGGCGTCAAT TGACGGCGCG GGCAACAGCA GCATTGGCGG CGCCATCCTC CGCGCGGCCG    1320

GCGCCCACCG CTACAACC                                                  1338

(2) INFORMATION FOR SEQ ID NO:159:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:159:

CCGGCGGCAC CGGCGGCACC GGCGGTACCG GCGGCAACGG CGCTGACGCC GCTGCTGTGG      60

TGGGCTTCGG CGCGAACGGC GACCCTGGCT TCGCTGGCGG CAAAGGCGGT AACGGCGGAA    120

TAGGTGGGGC CGCGGTGACA GGCGGGGTCG CCGGCGACGG CGGCACCGGC GGCAAAGGTG    180

GCACCGGCGG TGCCGGCGGC GCCGGCAACG ACGCCGGCAG CACCGGCAAT CCCGGCGGTA    240

AGGGCGGCGA CGGCGGGATC GGCGGTGCCG GCGGGGCCGG CGGCGCGGCC GGCACCGGCA    300

ACGGCGGCCA TGCCGGCAAC C                                              321

(2) INFORMATION FOR SEQ ID NO:160:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (xi) SEQUENCE DESCRIPTION: SEQ ID NO:160:

GAAGACCCGG CCCCGCCATA TCGATCGGCT CGCCGACTAC TTTCGCCGAA CGTGCACGCG      60

GCGGCGTCGG GCTGATCATC ACCGGTGGCT ACGCGCCCAA CCGCACCGGA TGGCTGCTGC    120

CGTTCGCCTC CGAACTCGTC ACTTCGGCGC AAGCCCGACG GCACCGCCGA ATCACCAGGG    180

CGGTCCACGA TTCGGGTGCA AGATCCTGC TGCAAATCCT GCACGCCGGA CGCTACGCCT     240

ACCACCCACT TGCGGTCAGC GCCTCGCCGA TCAAGGCGCC GATCACCCCG TTTCGTCCGC    300

GAGCACTATC GGCTCGCGGG GTCGAAGCGA CCATCGCGGA TTTCGCCCGC TGCGCGCAGT    360

TGGCCCGCGA TGCCGGCTAC GACGGCGTCG AAATCATGGG CAGCGAAGGG TATCTGCTCA    420

ATCAGTTCCT GGCGCCGCGC ACCAACAAGC GCACCGACTC GTGGGGCGGC ACACCGGCCA    480

ACCGTCGCCG GT                                                        492

(2) INFORMATION FOR SEQ ID NO:161:

(i) SEQUENCE CHARACTERISTICS:
        (A) LENGTH: 536 amino acids
        (B) TYPE: amino acid
        (C) STRANDEDNESS:
        (D) TOPOLOGY: linear (xi) SEQUENCE DESCRIPTION: SEQ ID NO:161:

Phe Ala Gln His Leu Val Glu Gly Asp Ala Val Glu Leu Trp Arg Ala
1               5                   10                  15

Asn Ala Ala Asp Gln Ala Asp Pro Leu Gln Pro Gly Ser Ala Arg Arg
                20                  25                  30

Gln Arg Ala Ser Arg Ser Pro Arg Arg Leu Ala Gly Pro Asn Ala Tyr
            35                  40                  45

His Tyr Ser Asn Asn Arg Ser Ile Leu Cys Gln Arg Trp Pro Leu Pro
```

```
            50                  55                  60
Ser Ala Ala Gln Asp Val Ile Cys His Leu Cys Pro His Arg Gln Glu
 65                  70                  75                  80

Pro Gly Leu Met Thr Ala Phe Gly Val Glu Pro Tyr Gly Gln Pro Lys
                 85                  90                  95

Tyr Leu Glu Ile Ala Gly Lys Arg Met Ala Tyr Ile Asp Glu Gly Lys
                100                 105                 110

Gly Asp Ala Ile Val Phe Gln His Gly Asn Pro Thr Ser Ser Tyr Leu
                115                 120                 125

Trp Arg Asn Ile Met Pro His Leu Glu Gly Leu Gly Arg Leu Val Ala
                130                 135                 140

Cys Asp Leu Ile Gly Met Gly Ala Ser Asp Lys Leu Ser Pro Ser Gly
145                 150                 155                 160

Pro Asp Arg Tyr Ser Tyr Gly Glu Gln Arg Asp Phe Leu Phe Ala Leu
                165                 170                 175

Trp Asp Ala Leu Asp Leu Gly Asp His Val Val Leu Val Leu His Asp
                180                 185                 190

Trp Gly Ser Ala Leu Gly Phe Asp Trp Ala Asn Gln His Arg Asp Arg
                195                 200                 205

Val Gln Gly Ile Ala Phe Met Glu Ala Ile Val Thr Pro Met Thr Trp
                210                 215                 220

Ala Asp Trp Pro Pro Ala Val Arg Gly Val Phe Gln Gly Phe Arg Ser
225                 230                 235                 240

Pro Gln Gly Glu Pro Met Ala Leu Glu His Asn Ile Phe Val Glu Arg
                245                 250                 255

Val Leu Pro Gly Ala Ile Leu Arg Gln Leu Ser Asp Glu Glu Met Asn
                260                 265                 270

His Tyr Arg Arg Pro Phe Val Asn Gly Gly Glu Asp Arg Arg Pro Thr
                275                 280                 285

Leu Ser Trp Pro Arg Asn Leu Pro Ile Asp Gly Glu Pro Ala Glu Val
                290                 295                 300

Val Ala Leu Val Asn Glu Tyr Arg Ser Trp Leu Glu Glu Thr Asp Met
305                 310                 315                 320

Pro Lys Leu Phe Ile Asn Ala Glu Pro Gly Ala Ile Ile Thr Gly Arg
                325                 330                 335

Ile Arg Asp Tyr Val Arg Ser Trp Pro Asn Gln Thr Glu Ile Thr Val
                340                 345                 350

Pro Gly Val His Phe Val Gln Glu Asp Ser Asp Gly Val Val Ser Trp
                355                 360                 365

Ala Gly Ala Arg Gln His Arg Arg Pro Gly Ser Ala Leu Ile Ser Arg
                370                 375                 380

Asp Gln Glu Cys Asp Phe Arg Arg Arg Arg Pro Ala Cys Gln Leu
385                 390                 395                 400

Ile Arg Leu Pro Ala Pro Gly Arg Asp Ser Gln Gly Lys Gly His Gln
                405                 410                 415

Ser Gln Pro Leu Pro Ser Gln Arg Gly Arg Gln Ile Tyr Val Ala Gly
                420                 425                 430

Gln Arg Ser Ser Tyr Leu Pro Ser Glu Leu Val Ala Ala Phe Leu Trp
                435                 440                 445

Ala Gln Phe Glu Glu Ala Glu Arg Ile Thr Arg Ile Arg Leu Asp Leu
                450                 455                 460

Trp Asn Arg Tyr His Glu Ser Phe Glu Ser Leu Glu Gln Arg Gly Leu
465                 470                 475                 480
```

```
Leu Arg Arg Pro Ile Ile Pro Gln Gly Cys Ser His Asn Ala His Met
                485                 490                 495

Tyr Tyr Val Leu Leu Ala Pro Ser Ala Asp Arg Glu Glu Val Leu Ala
            500                 505                 510

Arg Leu Thr Ser Glu Gly Ile Gly Ala Val Phe His Tyr Val Pro Leu
            515                 520                 525

His Asp Ser Pro Ala Gly Arg Arg
    530                 535
```

(2) INFORMATION FOR SEQ ID NO:162:

(i) SEQUENCE CHARACTERISTICS:
        (A) LENGTH: 284 amino acids
        (B) TYPE: amino acid
        (C) STRANDEDNESS:
        (D) TOPOLOGY: linear (xi) SEQUENCE DESCRIPTION: SEQ ID NO:162:

```
Asn Glu Ser Ala Pro Arg Ser Pro Met Leu Pro Ser Ala Arg Pro Arg
1               5                   10                  15

Tyr Asp Ala Ile Ala Val Leu Leu Asn Glu Met His Ala Gly His Cys
            20                  25                  30

Asp Phe Gly Leu Val Gly Pro Ala Pro Asp Ile Val Thr Asp Ala Ala
        35                  40                  45

Gly Asp Asp Arg Ala Gly Leu Gly Val Asp Glu Gln Phe Arg His Val
50                  55                  60

Gly Phe Leu Glu Pro Ala Pro Val Leu Val Asp Gln Arg Asp Asp Leu
65                  70                  75                  80

Gly Gly Leu Thr Val Asp Trp Lys Val Ser Trp Pro Arg Gln Arg Gly
            85                  90                  95

Ala Thr Val Leu Ala Ala Val His Glu Trp Pro Pro Ile Val Val His
                100                 105                 110

Phe Leu Val Ala Glu Leu Ser Gln Asp Arg Pro Gly Gln His Pro Phe
            115                 120                 125

Asp Lys Asp Val Val Leu Gln Arg His Trp Leu Ala Leu Arg Arg Ser
        130                 135                 140

Glu Thr Leu Glu His Thr Pro His Gly Arg Arg Pro Val Arg Pro Arg
145                 150                 155                 160

His Arg Gly Asp Asp Arg Phe His Glu Arg Asp Pro Leu His Ser Val
                165                 170                 175

Ala Met Leu Val Ser Pro Val Glu Ala Glu Arg Arg Ala Pro Val Val
            180                 185                 190

Gln His Gln Tyr His Val Val Ala Glu Val Glu Arg Ile Pro Glu Arg
        195                 200                 205

Glu Gln Lys Val Ser Leu Leu Ala Ile Ala Ile Ala Val Gly Ser Arg
            210                 215                 220

Trp Ala Glu Leu Val Arg Arg Ala His Pro Asp Gln Ile Ala Gly His
225                 230                 235                 240

Gln Pro Ala Gln Pro Phe Gln Val Arg His Asp Val Ala Pro Gln Val
                245                 250                 255

Arg Arg Arg Gly Val Ala Val Leu Lys Asp Asp Gly Val Thr Leu Ala
            260                 265                 270

Phe Val Asp Ile Arg His Ala Leu Pro Gly Asp Phe
            275                 280
```

(2) INFORMATION FOR SEQ ID NO:163:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (xi) SEQUENCE DESCRIPTION: SEQ ID NO:163:

```
ATGAACATGT CGTCGGTGGT GGGTCGCAAG GCCTTTGCGC GATTCGCCGG CTACTCCTCC        60

GCCATGCACG CGATCGCCGG TTTCTCCGAT GCGTTGCGCC AAGAGCTGCG GGGTAGCGGA       120

ATCGCCGTCT CGGTGATCCA CCCGGCGCTG ACCCAGACAC CGCTGTTGGC CAACGTCGAC       180

CCCGCCGACA TGCCGCCGCC GTTTCGCAGC CTCACGCCCA TTCCCGTTCA CTGGGTCGCG       240

GCAGCGGTGC TTGACGGTGT GGCG                                             264
```

(2) INFORMATION FOR SEQ ID NO:164:

(i) SEQUENCE CHARACTERISTICS:
        (A) LENGTH: 1171 base pairs
        (B) TYPE: nucleic acid
        (C) STRANDEDNESS: single
        (D) TOPOLOGY: linear (xi) SEQUENCE DESCRIPTION: SEQ ID NO:164:

```
TAGTCGGCGA CGATGACGTC GCGGTCCAGG CCGACCGCTT CAAGCACCAG CGCGACCACG        60

AAGCCGGTGC GATCCTTACC CGCGAAGCAG TGGGTGAGCA CCGGGCGTCC GGCGGCAAGC       120

AGTGTGACGA CACGATGTAG CGCGCGCTGT GCTCCATTGC GCGTTGGGAA TTGGCGATAC       180

TCGTCGGTCA TGTAGCGGGT GGCCGCGTCA TTTATCGACT GGCTGGATTC GCCGGACTCG       240

CCGTTGGACC CGTCATTGGT TAGCAGCCTC TTGAATGCGG TTTCGTGCGG CGCTGAGTCG       300

TCGGCGTCAT CATCGGCGAG GTCGGGGAAC GGCAGCAGGT GGACGTCGAT GCCGTCCGGA       360

ACCCGTCCTG GACCGCGGCG GGCAACCTCC CGGGACGACC GCAGGTCGGC AACGTCGGTG       420

ATCCCCAGCC GGCGCAGCGT TGCCCCTCGT GCCGAATTCG GCACGAGGCT GGCGAGCCAC       480

CGGGCATCAC CAAGCAACGC TTGCCCAGTA CGGATCGTCA CTTCCGCATC CGGCAGACCA       540

ATCTCCTCGC CGCCCATCGT CAGATCCCGC TCGTGCGTTG ACAAGAACGG CCGCAGATGT       600

GCCAGCGGGT ATCGGAGATT GAACCGCGCA CGCAGTTCTT CAATCGCTGC GCGCTGCCGC       660

ACTATTGGCA CTTTCCGGCG GTCGCGGTAT TCAGCAAGCA TGCGAGTCTC GACGAACTCG       720

CCCCACGTAA CCCACGGCGT AGCTCCCGGC GTGACGCGGA GGATCGGCGG GTGATCTTTG       780

CCGCCACGCT CGTAGCCGTT GATCCACCGC TTCGCGGTGC CGGCGGGGAG GCCGATCAGC       840

TTATCGACCT CGGCGTATGC CGACGGCAAG CTGGGCGCGT TCGTCGAGGT CAAGAACTCC       900

ACCATCGGCA CCGGCACCAA GGTGCCGCAC CTGACCTACG TCGGCGACGC CGACATCGGC       960

GAGTACAGCA ACATCGGCGC CTCCAGCGTG TTCGTCAACT ACGACGGTAC GTCCAAACGG      1020

CGCACCACCG TCGGTTCGCA CGTACGGACC GGGTCCGACA CCATGTTCGT GGCCCCAGTA      1080

ACCATCGGCG ACGGCGCGTA TACCGGGGCC GGCACAGTGG TGCGGAGGA TGTCCCGCCG       1140

GGGGCGCTGG CAGTGTCGGC GGGTCCGCAA C                                    1171
```

(2) INFORMATION FOR SEQ ID NO:165:

(i) SEQUENCE CHARACTERISTICS:
        (A) LENGTH: 227 base pairs
        (B) TYPE: nucleic acid
        (C) STRANDEDNESS: single
        (D) TOPOLOGY: linear (xi) SEQUENCE DESCRIPTION: SEQ ID NO:165:

| | | | | | |
|---|---|---|---|---|---|
| GCAAAGGCGG | CACCGGCGGG | GCCGGCATGA | ACAGCCTCGA | CCCGCTGCTA | GCCGCCCAAG | 60
| ACGGCGGCCA | AGGCGGCACC | GGCGGCACCG | GCGGCAACGC | CGGCGCCGGC | GGCACCAGCT | 120
| TCACCCAAGG | CGCCGACGGC | AACGCCGGCA | ACGGCGGTGA | CGGCGGGGTC | GGCGGCAACG | 180
| GCGGAAACGG | CGGAAACGGC | GCAGACAACA | CCACCACCGC | CGCCGCC | | 227

(2) INFORMATION FOR SEQ ID NO:166:

(i) SEQUENCE CHARACTERISTICS:
      (A) LENGTH: 304 base pairs
      (B) TYPE: nucleic acid
      (C) STRANDEDNESS: single
      (D) TOPOLOGY: linear (xi) SEQUENCE DESCRIPTION: SEQ ID NO:166:

| | | | | | |
|---|---|---|---|---|---|
| CCTCGCCACC | ATGGGCGGGC | AGGGCGGTAG | CGGTGGCGCC | GGCTCTACCC | CAGGCGCCAA | 60
| GGGCGCCCAC | GGCTTCACTC | CAACCAGCGG | CGGCGACGGC | GGCGACGGCG | GCAACGGCGG | 120
| CAACTCCCAA | GTGGTCGGCG | GCAACGGCGG | CGACGGCGGC | AATGGCGGCA | ACGGCGGCAG | 180
| CGCCGGCACG | GGCGGCAACG | GCGGCCGCGG | CGGCGACGGC | GCGTTTGGTG | GCATGAGTGC | 240
| CAACGCCACC | AACCCTGGTG | AAAACGGGCC | AAACGGTAAC | CCCGGCGGCA | ACGGTGGCGC | 300
| CGGC | | | | | | 304

(2) INFORMATION FOR SEQ ID NO:167:

(i) SEQUENCE CHARACTERISTICS:
      (A) LENGTH: 1439 base pairs
      (B) TYPE: nucleic acid
      (C) STRANDEDNESS: single
      (D) TOPOLOGY: linear (xi) SEQUENCE DESCRIPTION: SEQ ID NO:167:

| | | | | | |
|---|---|---|---|---|---|
| GTGGGACGCT | GCCGAGGCTG | TATAACAAGG | ACAACATCGA | CCAGCGCCGG | CTCGGTGAGC | 60
| TGATCGACCT | ATTTAACAGT | GCGCGCTTCA | GCCGGCAGGG | CGAGCACCGC | GCCCGGGATC | 120
| TGATGGGTGA | GGTCTACGAA | TACTTCCTCG | GCAATTTCGC | TCGCGCGGAA | GGGAAGCGGG | 180
| GTGGCGAGTT | CTTTACCCCG | CCCAGCGTGG | TCAAGGTGAT | CGTGGAGGTG | CTGGAGCCGT | 240
| CGAGTGGGCG | GGTGTATGAC | CCGTGCTGCG | GTTCCGGAGG | CATGTTTGTG | CAGACCGAGA | 300
| AGTTCATCTA | CGAACACGAC | GGCGATCCGA | AGGATGTCTC | GATCTATGGC | CAGGAAAGCA | 360
| TTGAGGAGAC | CTGGCGGATG | GCGAAGATGA | ACCTCGCCAT | CCACGGCATC | GACAACAAGG | 420
| GGCTCGGCGC | CCGATGGAGT | GATACCTTCG | CCCGCGACCA | GCACCCGGAC | GTGCAGATGG | 480
| ACTACGTGAT | GGCCAATCCG | CCGTTCAACA | TCAAAGACTG | GGCCCGCAAC | GAGGAAGACC | 540
| CACGCTGGCG | CTTCGGTGTT | CCGCCCGCCA | ATAACGCCAA | CTACGCATGG | ATTCAGCACA | 600
| TCCTGTACAA | CTTGGCGCCG | GGAGGTCGGG | CGGGCGTGGT | GATGGCCAAC | GGGTCGATGT | 660
| CGTCGAACTC | CAACGGCAAG | GGGGATATTC | GCGCGCAAAT | CGTGGAGGCG | GATTTGGTTT | 720
| CCTGCATGGT | CGCGTTACCC | ACCCAGCTGT | TCCGCAGCAC | CGGAATCCCG | GTGTGCCTGT | 780
| GGTTTTTCGC | CAAAAACAAG | GCGGCAGGTA | AGCAAGGGTC | TATCAACCGG | TGCGGGCAGG | 840
| TGCTGTTCAT | CGACGCTCGT | GAACTGGGCG | ACCTAGTGGA | CCGGGCCGAG | CGGGCGCTGA | 900
| CCAACGAGGA | GATCGTCCGC | ATCGGGGATA | CCTTCCACGC | GAGCACGACC | ACCGGCAACG | 960
| CCGGCTCCGG | TGGTGCCGGC | GGTAATGGGG | GCACTGGCCT | CAACGGCGCG | GCGGTGCTG | 1020

-continued

```
GCGGGGCCGG CGGCAACGCG GGTGTCGCCG GCGTGTCCTT CGGCAACGCT GTGGGCGGCG    1080

ACGGCGGCAA CGGCGGCAAC GGCGGCCACG GCGGCGACGG CACGACGGGC GGCGCCGGCG    1140

GCAAGGGCGG CAACGGCAGC AGCGGTGCCG CCAGCGGCTC AGGCGTCGTC AACGTCACCG    1200

CCGGCCACGG CGGCAACGGC GGCAATGGCG GCAACGGCGG CAACGGCTCC GCGGGCGCCG    1260

GCGGCCAGGG CGGTGCCGGC GGCAGCGCCG GCAACGGCGG CCACGGCGGC GGTGCCACCG    1320

GCGGCGCCAG CGGCAAGGGC GGCAACGGCA CCAGCGGTGC CGCCAGCGGC TCAGGCGTCA    1380

TCAACGTCAC CGCCGGCCAC GGCGGCAACG GCGGCAATGG CCGCAACGGC GGCAACGGC     1439
```

(2) INFORMATION FOR SEQ ID NO:168:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (xi) SEQUENCE DESCRIPTION: SEQ ID NO:168:

```
GGGCCGGCGG GGCCGGATTT TCTCGTGCCT TGATTGTCGC TGGGGATAAC GGCGGTGATG     60

GTGGTAACGG CGGGATGGGC GGGGCTGGCG GGGCTGGCGG CCCCGGCGGG GCCGGCGGCC    120

TGATCAGCCT GCTGGGCGGC CAAGGCGCCG GCGGGGCCGG CGGGACCGGC GGGGCCGGCG    180

GTGTTGGCGG TGACGGCGGG GCCGGCGGCC CCGGCAACCA GGCCTTCAAC GCAGGTGCCG    240

GCGGGGCCGG CGGCCTGATC AGCCTGCTGG GCGGCCAAGG CGCCGGCGGG GCCGGCGGGA    300

CCGGCGGGGC CGGCGGTGTT GGCGGTGAC                                      329
```

(2) INFORMATION FOR SEQ ID NO:169:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO:169:

```
GCAACGGTGG CAACGGCGGC ACCAGCACGA CCGTGGGGAT GGCCGGAGGT AACTGTGGTG     60

CCGCCGGGCT GATCGGCAAC                                                 80
```

(2) INFORMATION FOR SEQ ID NO:170:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (xi) SEQUENCE DESCRIPTION: SEQ ID NO:170:

```
GGGCTGTGTC GCACTCACAC CGCCGCATTC GGCGACGTTG GCCGCCCAAT ATCCAGCTCA     60

AGGCCTACTA CTTACCGTCG GAGGACCGCC GCATCAAGGT GCGGGTCAGC GCCCAAGGAA    120

TCAAGGTCAT CGACCGCGAC GGGCATCGAG GCCGTCGTCG CGCGGCTCGG GCAGGATCCG    180

CCCCGGCGCA CTTCGCGCGC CAAGCGGGCT CATCGCTCCG AACGGCGGCG ATCCTGTGAG    240

CACAACTGAT GGCGCGCAAC GAGATTCGTC CAATTGTCAA GCCGTGTTCG ACCGCAGGGA    300

CCGGTTATAC GTATGTCAAC CTATGTCACT CGCAAGAACC GGCATAACGA TCCCGTGATC    360

CGCCGACAGC CCACGAGTGC AAGACCGTTA CA                                   392
```

(2) INFORMATION FOR SEQ ID NO:171:

```
    (i) SEQUENCE CHARACTERISTICS:
        (A) LENGTH: 535 base pairs
        (B) TYPE: nucleic acid
        (C) STRANDEDNESS: single
        (D) TOPOLOGY: linear (xi) SEQUENCE DESCRIPTION: SEQ ID NO:171:

ACCGGCGCCA CCGGCGGCAC CGGGTTCGCC GGTGGCGCCG GCGGGCCGG  CGGGCAGGGC      60

GGTATCAGCG GTGCCGGCGG CACCAACGGC TCTGGTGGCG CTGGCGGCAC CGGCGGACAA     120

GGCGGCGCCG GGGGCGCTGG CGGGGCCGGC GCCGATAACC CCACCGGCAT CGGCGGCGCC     180

GGCGGCACCG GCGGCACCGG CGGAGCGGCC GGAGCCGGCG GGGCCGGTGG CGCCATCGGT     240

ACCGGCGGCA CCGGCGGCGC GGTGGGCAGC GTCGGTAACG CCGGGATCGG CGGTACCGGC     300

GGTACGGGTG GTGTCGGTGG TGCTGGTGGT GCAGGTGCGG CTGCGGCCGC TGGCAGCAGC     360

GCTACCGGTG GCGCCGGGTT CGCCGGCGGC GCCGGCGGAG AAGGCGGACC GGGCGGCAAC     420

AGCGGTGTGG GCGGCACCAA CGGCTCCGGC GGCGCCGGCG GTGCAGGCGG CAAGGGCGGC     480

ACCGGAGGTG CCGGCGGGTC CGGCGCGGAC AACCCCACCG GTGCTGGTTT CGCCG          535

(2) INFORMATION FOR SEQ ID NO:172:

(i) SEQUENCE CHARACTERISTICS:
        (A) LENGTH: 690 base pairs
        (B) TYPE: nucleic acid
        (C) STRANDEDNESS: single
        (D) TOPOLOGY: linear (xi) SEQUENCE DESCRIPTION: SEQ ID NO:172:

CCGACGTCGC CGGGGCGATA CGGGGGTCAC CGACTACTAC ATCATCCGCA CCGAGAATCG      60

GCCGCTGCTG CAACCGCTGC GGGCGGTGCC GGTCATCGGA GATCCGCTGG CCGACCTGAT     120

CCAGCCGAAC CTGAAGGTGA TCGTCAACCT GGGCTACGGC GACCCGAACT ACGGCTACTC     180

GACGAGCTAC GCCGATGTGC GAACGCCGTT CGGGCTGTGG CCGAACGTGC CGCCTCAGGT     240

CATCGCCGAT GCCCTGGCCG CCGGAACACA AGAAGGCATC CTTGACTTCA CGGCCGACCT     300

GCAGGCGCTG TCCGCGCAAC CGCTCACGCT CCCGCAGATC CAGCTGCCGC AACCCGCCGA     360

TCTGGTGGCC GCGGTGGCCG CCGCACCGAC GCCGGCCGAG GTGGTGAACA CGCTCGCCAG     420

GATCATCTCA ACCAACTACG CCGTCCTGCT GCCCACCGTG GACATCGCCC TCGCCTGGTC     480

ACCACCCTGC CGCTGTACAC CACCCAACTG TTCGTCAGGC AACTCGCTGC GGGCAATCTG     540

ATCAACGCGA TCGGCTATCC CCTGGCGGCC ACCGTAGGTT TAGGCACGAT CGATAGCGGG     600

CGGCGTGGAA TTGCTCACCC TCCTCGCGGC GGCCTCGGAC ACCGTTCGAA ACATCGAGGG     660

CCTCGTCACC TAACGGATTC CCGACGGCAT                                     690

(2) INFORMATION FOR SEQ ID NO:173:

(i) SEQUENCE CHARACTERISTICS:
        (A) LENGTH: 407 base pairs
        (B) TYPE: nucleic acid
        (C) STRANDEDNESS: single
        (D) TOPOLOGY: linear (xi) SEQUENCE DESCRIPTION: SEQ ID NO:173:

ACGGTGACGG CGGTACTGGC GGCGGCCACG GCGGCAACGG CGGGAATCCC GGGTGGCTCT      60

TGGGCACAGC CGGGGGTGGC GGCAACGGTG GCGCCGGCAG CACCGGTACT GCAGGTGGCG     120

GCTCTGGGGG CACCGGCGGC GACGGCGGGA CCGGCGGGCG TGGCGGCCTG TTAATGGGCG     180
```

```
CCGGCGCCGG CGGGCACGGT GGCACTGGCG GCGCGGGCCG TGCCGGTGTC GACGGTGGCG    240

GCGCCGGCGG GGCCGGCGGG GCCGGCGGCA ACGGCGGCGC CGGGGGTCAA GCCGCCCTGC    300

TGTTCGGGCG CGGCGGCACC GGCGGAGCCG GCGGCTACGG CGGCGATGGC GGTGGCGGCG    360

GTGACGGCTT CGACGGCACG ATGGCCGGCC TGGGTGGTAC CGGTGGC                 407
```

(2) INFORMATION FOR SEQ ID NO:174:

(i) SEQUENCE CHARACTERISTICS:
       (A) LENGTH: 468 base pairs
       (B) TYPE: nucleic acid
       (C) STRANDEDNESS: single
       (D) TOPOLOGY: linear (xi) SEQUENCE DESCRIPTION: SEQ ID NO:174:

```
GATCGGTCAG CGCATCGCCC TCGGCGGCAA GCGATTCCGC GGTCTCACCG AAGAACATCG     60

TGCACGCGGC GGCGCGGACC AGCCCGCTGC GCTGCGGCGC GTCGAACGCC TCCAGCAGGC    120

ACAGCCAGTC CTTGGCGGCC TGCGAGGCGA ACACGTCGGT GTCACCGGTG TAGATCGCCG    180

GGATGCCCGC CTCCGCCAAC GCATTCCGGC ACGCCCGCGC GTCTTTGTGA TGCTCGACGA    240

TCACCGCGAT GTCTGCGGCC ACCACGGGCC GCCCGGCGAA GGTGGCCCCG CTGGCCAGTA    300

GCGCCGCGAC GTCGGCGGCC AGGTCGTCGG GGATGTGCCG GCGCAGCGCT CCGGCGCGAC    360

GCCCGAAAAA CGACCCCTCA CCCAGCTGGG TCCCGCTGGC ATATCCCTTG CCGTCCTGGG    420

CGATATTGGA CGCGCATGCC CCGACCGCGT ACAGGCCGGC CACCACCG                468
```

(2) INFORMATION FOR SEQ ID NO:175:

(i) SEQUENCE CHARACTERISTICS:
       (A) LENGTH: 219 base pairs
       (B) TYPE: nucleic acid
       (C) STRANDEDNESS: single
       (D) TOPOLOGY: linear (xi) SEQUENCE DESCRIPTION: SEQ ID NO:175:

```
GGTGGTAACG GCGGCCAGGG TGGCATCGGC GGCGCCGGCG AGAGAGGCGC CGACGGCGCC     60

GGCCCCAATG CTAACGGCGC AAACGGCGAG AACGGCGGTA GCGGTGGTAA CGGTGGCGAC    120

GGCGGCGCCG GCGGCAATGG CGGCGCGGGC GGCAACGCGC AGGCGGCCGG GTACACCGAC    180

GGCGCCACGG GCACCGGCGG CGACGGCGGC AACGGCGGC                          219
```

(2) INFORMATION FOR SEQ ID NO:176:

(i) SEQUENCE CHARACTERISTICS:
       (A) LENGTH: 494 base pairs
       (B) TYPE: nucleic acid
       (C) STRANDEDNESS: single
       (D) TOPOLOGY: linear (xi) SEQUENCE DESCRIPTION: SEQ ID NO:176:

```
TAGCTCCGGC GAGGGCGGCA AGGGCGGCGA CGGTGGCCAC GGCGGTGACG GCGTCGGCGG     60

CAACAGTTCC GTCACCCAAG GCGGCAGCGG CGGTGGCGGC GGCGCCGGCG GCGCCGGCGG    120

CAGCGGCTTT TTCGGCGGCA AGGGCGGCTT CGGCGGCGAC GGCGGTCAGG GCGGCCCCAA    180

CGGCGGCGGT ACCGTCGGCA CCGTGGCCGG TGGCGGCGGC AACGGCGGTG TCGGCGGCCG    240

GGGCGGCGAC GGCGTCTTTG CCGGTGCCGG CGGCCAGGGC GGCCTCGGTG GCAGGGCGG    300

CAATGGCGGC GGCTCCACCG GCGGCAACGG CGGCCTTGGC GGCGCGGGCG GTGGCGGAGG    360

CAACGCCCCG GCTCGTGCCG AATCCGGGCT GACCATGGAC AGCGCGGCCA AGTTCGCTGC    420
```

| | |
|---|---|
| CATCGCATCA GGCGCGTACT GCCCCGAACA CCTGGAACAT CACCCGAGTT AGCGGGGCGC | 480 |
| ATTTCCTGAT CACC | 494 |

(2) INFORMATION FOR SEQ ID NO:177:

(i) SEQUENCE CHARACTERISTICS:
        (A) LENGTH: 220 base pairs
        (B) TYPE: nucleic acid
        (C) STRANDEDNESS: single
        (D) TOPOLOGY: linear (xi) SEQUENCE DESCRIPTION: SEQ ID NO:177:

| | |
|---|---|
| GGGCCGGTGG TGCCGCGGGC CAGCTCTTCA GCGCCGGAGG CGCGGCGGGT GCCGTTGGGG | 60 |
| TTGGCGGCAC CGGCGGCCAG GGTGGGGCTG GCGGTGCCGG AGCGGCCGGC GCCGACGCCC | 120 |
| CCGCCAGCAC AGGTCTAACC GGTGGTACCG GGTTCGCTGG CGGGGCCGGC GGCGTCGGCG | 180 |
| GCCAGAGCGG CAACGCCATT GCCGGCGGCA TCAACGGCTC | 220 |

(2) INFORMATION FOR SEQ ID NO:178:

(i) SEQUENCE CHARACTERISTICS:
        (A) LENGTH: 388 base pairs
        (B) TYPE: nucleic acid
        (C) STRANDEDNESS: single
        (D) TOPOLOGY: linear (xi) SEQUENCE DESCRIPTION: SEQ ID NO:178:

| | |
|---|---|
| ATGGCGGCAA CGGGGGCCCC GGCGGTGCTG GCGGGGCCGG CGACTACAAT TTCCAACGGC | 60 |
| GGGCAGGGTG GTGCCGGCGG CCAAGGCGGC CAAGGCGGCC TGGGCGGGGC AAGCACCACC | 120 |
| TGATCGGCCT AGCCGCACCC GGGAAAGCCG ATCCAACAGG CGACGATGCC GCCTTCCTTG | 180 |
| CCGCGTTGGA CCAGGCCGGC ATCACCTACG CTGACCCAGG CCACGCCATA ACGGCCGCCA | 240 |
| AGGCGATGTG TGGGCTGTGT GCTAACGGCG TAACAGGTCT ACAGCTGGTC GCGGACCTGC | 300 |
| GGGACTACAA TCCCGGGCTG ACCATGGACA GCGCGGCCAA GTTCGCTGCC ATCGCATCAG | 360 |
| GCGCGTACTG CCCCGAACAC CTGGAACA | 388 |

(2) INFORMATION FOR SEQ ID NO:179:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (xi) SEQUENCE DESCRIPTION: SEQ ID NO:179:

| | |
|---|---|
| GCAAAGGCGG CACCGGCGGG GCCGGCATGA ACAGCCTCGA CCCGCTGCTA GCCGCCCAAG | 60 |
| ACGGCGGCCA AGGCGGCACC GGCGGCACCG GCGGCAACGC CGGCGCCGGC GGCACCAGCT | 120 |
| TCACCCAAGG CGCCGACGGC AACGCCGGCA ACGGCGGTGA CGGCGGGGTC GGCGGCAACG | 180 |
| GCGGAAACGG CGGAAACGGC GCAGACAACA CCACCACCGC CGCCGCCGGC ACCACAGGCG | 240 |
| GCGACGGCGG GGCCGGCGGG GCCGGCGGAA CCGGCGGAAC CGGCGGAGCC GCCGGCACCG | 300 |
| GCACCGGCGG CCAACAAGGC AACGGCGGCA ACGGCGGCAC CGGCGGCAAA GGCGGCACCG | 360 |
| GCGGCGACGG TGCACTCTCA GGCAGCACCG GTGGTGCCGG | 400 |

(2) INFORMATION FOR SEQ ID NO:180:

(i) SEQUENCE CHARACTERISTICS:
        (A) LENGTH: 538 base pairs
        (B) TYPE: nucleic acid (C) STRANDEDNESS: single
        (D) TOPOLOGY: linear (xi) SEQUENCE DESCRIPTION: SEQ ID NO:180:

```
GGCAACGGCG GCAACGGCGG CATCGCCGGC ATTGGGCGGC AACGGCGTTC CGGGACGGGC      60

AGCGGCAACG GCGGCCAACG GCGGCAGCGG CGGCAACGGC GGCAACGCCG GCATGGGCGG     120

CAACAGCGGC ACCGGCAGCG GCGACGGCGG TGCCGGCGGG AACGGCGGCG CGGCGGGCAC     180

GGGCGGCACC GGCGGCGACG GCGGCCTCAC CGGTACTGGC GGCACCGGCG GCAGCGGTGG     240

CACCGGCGGT GACGGCGGTA ACGGCGGCAA CGGAGCAGAT AACACCGCAA ACATGACTGC     300

GCAGGCGGGC GGTGACGGTG GCAACGGCGG CGACGGTGGC TTCGGCGGCG GGGCCGGGGC     360

CGGCGGCGGT GGCTTGACCG CTGGCGCCAA CGGCACCGGC GGGCAAGGCG GCGCCGGCGG     420

CGATGGCGGC AACGGGGCCA TCGGCGGCCA CGGCCCACTC ACTGACGACC CCGGCGGCAA     480

CGGGGGCACC GGCGGCAACG GCGGCACCGG CGGCACCGGC GGCGCGGGCA TCGGCAGC      538
```

(2) INFORMATION FOR SEQ ID NO:181:

(i) SEQUENCE CHARACTERISTICS:
        (A) LENGTH: 239 base pairs
        (B) TYPE: nucleic acid
        (C) STRANDEDNESS: single
        (D) TOPOLOGY: linear (xi) SEQUENCE DESCRIPTION: SEQ ID NO:181:

```
GGGCCGGTGG TGCCGCGGGC CAGCTCTTCA GCGCCGGAGG CGCGGCGGGT GCCGTTGGGG      60

TTGGCGGCAC CGGCGGCCAG GGTGGGGCTG GCGGTGCCGG AGCGGCCGGC GCCGACGCCC     120

CCGCCAGCAC AGGTCTAACC GGTGGTACCG GGTTCGCTGG CGGGGCCGGC GGCGTCGGCG     180

GCCACGGCGG CAACGCCATT GCCGGCGGCA TCAACGGCTC CGGTGGTGCC GGCGGCACC      239
```

(2) INFORMATION FOR SEQ ID NO:182:

(i) SEQUENCE CHARACTERISTICS:
        (A) LENGTH: 985 base pairs
        (B) TYPE: nucleic acid
        (C) STRANDEDNESS: single
        (D) TOPOLOGY: linear (xi) SEQUENCE DESCRIPTION: SEQ ID NO:182:

```
AGCAGCGCTA CCGGTGGCGC CGGGTTCGCC GGCGGCGCCG GCGGAGAAGG CGGAGCGGGC      60

GGCAACAGCG GTGTGGGCGG CACCAACGGC TCCGGCGGCG CCGGCGGTGC AGGCGGCAAG     120

GGCGGCACCG GAGGTGCCGG CGGGTCCGGC GCGGACAACC CCACCGGTGC TGGTTTCGCC     180

GGTGGCGCCG GCGGCACAGG TGGCGCGGCC GGCGCCGGCG GGGCCGGCGG GGCGACCGGT     240

ACCGGCGGCA CCGGCGGCGT TGTCGGCGCC ACCGGTAGTG CAGGCATCGG CGGGGCCGGC     300

GGCCGCGGCG GTGACGGCGG CGATGGGGCC AGCGGTCTCG GCCTGGGCCT CTCCGGCTTT     360

GACGGCGGCC AAGGCGGCCA AGGCGGGGCC GGCGGCAGCG CCGGCGCCGG CGGCATCAAC     420

GGGGCCGGCG GGGCCGGCGG CAACGGCGGC GACGGCGGGG ACGGCGCAAC CGGTGCCGCA     480

GGTCTCGGCG ACAACGGCGG GGTCGGCGGT GACGGTGGGG CCGGTGGCGC CGCCGGCAAC     540

GGCGGCAACG CGGGCGTCGG CCTGACAGCC AAGGCCGGCG ACGGCGGCGC CGCGGGCAAT     600

GGCGGCAACG GGGGCGCCGG CGGTGCTGGC GGGGCCGGCG ACAACAATTT CAACGGCGGC     660

CAGGGTGGTG CCGGCGGCCA AGGCGGCCAA GGCGGCTTGG GCGGGGCAAG CACCACCTGA     720

TCGGCCTAGC CGCACCCGGG AAAGCCGATC AACAGGCGA CGATGCCGCC TTCCTTGCCG     780
```

| | |
|---|---:|
| CGTTGGACCA GGCCGGCATC ACCTACGCTG ACCCAGGCCA CGCCATAACG GCCGCCAAGG | 840 |
| CGATGTGTGG GCTGTGTGCT AACGGCGTAA CAGGTCTACA GCTGGTCGCG GACCTGCGGG | 900 |
| AATACAATCC CGGGCTGACC ATGGACAGCG CGGCCAAGTT CGCTGCCATC GCATCAGGCG | 960 |
| CGTACTGCCC CGAACACCTG GAACA | 985 |

(2) INFORMATION FOR SEQ ID NO:183:

(i) SEQUENCE CHARACTERISTICS:
        (A) LENGTH: 2138 base pairs
        (B) TYPE: nucleic acid
        (C) STRANDEDNESS: single
        (D) TOPOLOGY: linear (xi) SEQUENCE DESCRIPTION: SEQ ID NO:183:

| | |
|---|---:|
| CGGCACGAGG ATCGGTACCC CGCGGCATCG GCAGCTGCCG ATTCGCCGGG TTTCCCCACC | 60 |
| CGAGGAAAGC CGCTACCAGA TGGCGCTGCC GAAGTAGGGC GATCCGTTCG CGATGCCGGC | 120 |
| ATGAACGGGC GGCATCAAAT TAGTGCAGGA ACCTTTCAGT TTAGCGACGA TAATGGCTAT | 180 |
| AGCACTAAGG AGGATGATCC GATATGACGC AGTCGCAGAC CGTGACGGTG GATCAGCAAG | 240 |
| AGATTTTGAA CAGGGCCAAC GAGGTGGAGG CCCCGATGGC GGACCCACCG ACTGATGTCC | 300 |
| CCATCACACC GTGCGAACTC ACGGCGGCTA AAAACGCCGC CCAACAGCTG GTATTGTCCG | 360 |
| CCGACAACAT GCGGGAATAC CTGGCGGCCG GTGCCAAAGA GCGGCAGCGT CTGGCGACCT | 420 |
| CGCTGCGCAA CGCGGCCAAG GCGTATGGCG AGGTTGATGA GGAGGCTGCG ACCGCGCTGG | 480 |
| ACAACGACGG CGAAGGAACT GTGCAGGCAG AATCGGCCGG GGCCGTCGGA GGGGACAGTT | 540 |
| CGGCCGAACT AACCGATACG CCGAGGGTGG CCACGGCCGG TGAACCCAAC TTCATGGATC | 600 |
| TCAAAGAAGC GGCAAGGAAG CTCGAAACGG GCGACCAAGG CGCATCGCTC GCGCACTTTG | 660 |
| CGGATGGGTG GAACACTTTC AACCTGACGC TGCAAGGCGA CGTCAAGCGG TTCCGGGGGT | 720 |
| TTGACAACTG GGAAGGCGAT GCGGCTACCG CTTGCGAGGC TTCGCTCGAT CAACAACGGC | 780 |
| AATGGATACT CCACATGGCC AAATTGAGCG CTGCGATGGC CAAGCAGGCT CAATATGTCG | 840 |
| CGCAGCTGCA CGTGTGGGCT AGGCGGGAAC ATCCGACTTA TGAAGACATA GTCGGGCTCG | 900 |
| AACGGCTTTA CGCGGAAAAC CCTTCGGCCC GCGACCAAAT TCTCCCGGTG TACGCGGAGT | 960 |
| ATCAGCAGAG GTCGGAGAAG GTGCTGACCG AATACAACAA CAAGGCAGCC CTGGAACCGG | 1020 |
| TAAACCCGCC GAAGCCTCCC CCCGCCATCA AGATCGACCC GCCCCGCCT CCGCAAGAGC | 1080 |
| AGGGATTGAT CCCTGGCTTC CTGATGCCGC CGTCTGACGG CTCCGGTGTG ACTCCCGGTA | 1140 |
| CCGGGATGCC AGCCGCACCG ATGGTTCCGC CTACCGGATC GCCGGGTGGT GGCCTCCCGG | 1200 |
| CTGACACGGC GGCGCAGCTG ACGTCGGCTG GGCGGGAAGC CGCAGCGCTG TCGGGCGACG | 1260 |
| TGGCGGTCAA AGCGGCATCG CTCGGTGGCG GTGGAGGCGG CGGGGTGCCG TCGGCGCCGT | 1320 |
| TGGGATCCGC GATCGGGGGC GCCGAATCGG TGCGGCCCGC TGGCGCTGGT GACATTGCCG | 1380 |
| GCTTAGGCCA GGGAAGGGCC GGCGGCGGCG CCGCGCTGGG CGGCGGTGGC ATGGGAATGC | 1440 |
| CGATGGGTGC CGCGCATCAG GGACAAGGGG CGCCAAGTC CAAGGGTTCT CAGCAGGAAG | 1500 |
| ACGAGGCGCT CTACACCGAG GATCGGGCAT GGACCGAGGC CGTCATTGGT AACCGTCGGC | 1560 |
| GCCAGGACAG TAAGGAGTCG AAGTGAGCAT GGACGAATTG GACCCGCATG TCGCCCGGGC | 1620 |
| GTTGACGCTG GCGGCGCGGT TTCAGTCGGC CCTAGACGGG ACGCTCAATC AGATGAACAA | 1680 |
| CGGATCCTTC CGCGCCACCG ACGAAGCCGA GACCGTCGAA GTGACGATCA ATGGGCACCA | 1740 |
| GTGGCTCACC GGCCTGCGCA TCGAAGATGG TTTGCTGAAG AAGCTGGGTG CCGAGGCGGT | 1800 |

```
GGCTCAGCGG GTCAACGAGG CGCTGCACAA TGCGCAGGCC GCGGCGTCCG CGTATAACGA    1860

CGCGGCGGGC GAGCAGCTGA CCGCTGCGTT ATCGGCCATG TCCCGCGCGA TGAACGAAGG    1920

AATGGCCTAA GCCCATTGTT GCGGTGGTAG CGACTACGCA CCGAATGAGC GCCGCAATGC    1980

GGTCATTCAG CGCGCCCGAC ACGGCGTGAG TACGCATTGT CAATGTTTTG ACATGGATCG    2040

GCCGGGTTCG GAGGGCGCCA TAGTCCTGGT CGCCAATATT GCCGCAGCTA GCTGGTCTTA    2100

GGTTCGGTTA CGCTGGTTAA TTATGACGTC CGTTACCA                            2138
```

(2) INFORMATION FOR SEQ ID NO:184:

(i) SEQUENCE CHARACTERISTICS:
        (A) LENGTH: 460 amino acids
        (B) TYPE: amino acid
        (C) STRANDEDNESS:
        (D) TOPOLOGY: linear (xi) SEQUENCE DESCRIPTION: SEQ ID NO:184:

```
Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Pro Thr Asp Val
            20                  25                  30

Pro Ile Thr Pro Cys Glu Leu Thr Ala Ala Lys Asn Ala Ala Gln Gln
        35                  40                  45

Leu Val Leu Ser Ala Asp Asn Met Arg Glu Tyr Leu Ala Ala Gly Ala
    50                  55                  60

Lys Glu Arg Gln Arg Leu Ala Thr Ser Leu Arg Asn Ala Ala Lys Ala
65                  70                  75                  80

Tyr Gly Glu Val Asp Glu Ala Ala Thr Ala Leu Asp Asn Asp Gly
                85                  90                  95

Glu Gly Thr Val Gln Ala Glu Ser Ala Gly Ala Val Gly Gly Asp Ser
            100                 105                 110

Ser Ala Glu Leu Thr Asp Thr Pro Arg Val Ala Thr Ala Gly Glu Pro
        115                 120                 125

Asn Phe Met Asp Leu Lys Glu Ala Ala Arg Lys Leu Glu Thr Gly Asp
    130                 135                 140

Gln Gly Ala Ser Leu Ala His Phe Ala Asp Gly Trp Asn Thr Phe Asn
145                 150                 155                 160

Leu Thr Leu Gln Gly Asp Val Lys Arg Phe Arg Gly Phe Asp Asn Trp
                165                 170                 175

Glu Gly Asp Ala Ala Thr Ala Cys Glu Ala Ser Leu Asp Gln Gln Arg
            180                 185                 190

Gln Trp Ile Leu His Met Ala Lys Leu Ser Ala Ala Met Ala Lys Gln
        195                 200                 205

Ala Gln Tyr Val Ala Gln Leu His Val Trp Ala Arg Arg Glu His Pro
    210                 215                 220

Thr Tyr Glu Asp Ile Val Gly Leu Glu Arg Leu Tyr Ala Glu Asn Pro
225                 230                 235                 240

Ser Ala Arg Asp Gln Ile Leu Pro Val Tyr Ala Glu Tyr Gln Gln Arg
                245                 250                 255

Ser Glu Lys Val Leu Thr Glu Tyr Asn Asn Lys Ala Ala Leu Glu Pro
            260                 265                 270

Val Asn Pro Pro Lys Pro Pro Ala Ile Lys Ile Asp Pro Pro
        275                 280                 285

Pro Pro Gln Glu Gln Gly Leu Ile Pro Gly Phe Leu Met Pro Pro Ser
    290                 295                 300
```

```
Asp Gly Ser Gly Val Thr Pro Gly Thr Gly Met Pro Ala Ala Pro Met
305                 310                 315                 320

Val Pro Pro Thr Gly Ser Pro Gly Gly Gly Leu Pro Ala Asp Thr Ala
                325                 330                 335

Ala Gln Leu Thr Ser Ala Gly Arg Glu Ala Ala Leu Ser Gly Asp
                340                 345                 350

Val Ala Val Lys Ala Ala Ser Leu Gly Gly Gly Gly Gly Gly Val
                355                 360                 365

Pro Ser Ala Pro Leu Gly Ser Ala Ile Gly Gly Ala Glu Ser Val Arg
    370                 375                 380

Pro Ala Gly Ala Gly Asp Ile Ala Gly Leu Gly Gln Gly Arg Ala Gly
385                 390                 395                 400

Gly Gly Ala Ala Leu Gly Gly Gly Met Gly Met Pro Met Gly Ala
                405                 410                 415

Ala His Gln Gly Gln Gly Gly Ala Lys Ser Lys Gly Ser Gln Gln Glu
                420                 425                 430

Asp Glu Ala Leu Tyr Thr Glu Asp Arg Ala Trp Thr Glu Ala Val Ile
            435                 440                 445

Gly Asn Arg Arg Arg Gln Asp Ser Lys Glu Ser Lys
    450                 455                 460

(2) INFORMATION FOR SEQ ID NO:185:

(i) SEQUENCE CHARACTERISTICS:
        (A) LENGTH: 277 amino acids
        (B) TYPE: amino acid
        (C) STRANDEDNESS:
        (D) TOPOLOGY: linear (xi) SEQUENCE DESCRIPTION: SEQ ID NO:185:

Ala Gly Asn Val Thr Ser Ala Ser Gly Pro His Arg Phe Gly Ala Pro
1               5                   10                  15

Asp Arg Gly Ser Gln Arg Arg Arg His Pro Ala Ala Ser Thr Ala
                20                  25                  30

Thr Glu Arg Cys Arg Phe Asp Arg His Val Ala Arg Gln Arg Cys Gly
            35                  40                  45

Phe Pro Pro Ser Arg Arg Gln Leu Arg Arg Val Ser Arg Glu Ala
    50                  55                  60

Thr Thr Arg Arg Ser Gly Arg Arg Asn His Arg Cys Gly Trp His Pro
65              70                  75                  80

Gly Thr Gly Ser His Thr Gly Ala Val Arg Arg Arg His Gln Glu Ala
                85                  90                  95

Arg Asp Gln Ser Leu Leu Leu Arg Arg Arg Gly Arg Val Asp Leu Asp
                100                 105                 110

Gly Gly Gly Arg Leu Arg Arg Val Tyr Arg Phe Gln Gly Cys Leu Val
            115                 120                 125

Val Val Phe Gly Gln His Leu Leu Arg Pro Leu Leu Ile Leu Arg Val
    130                 135                 140

His Arg Glu Asn Leu Val Ala Gly Arg Val Phe Arg Val Lys Pro
145                 150                 155                 160

Phe Glu Pro Asp Tyr Val Phe Ile Ser Arg Met Phe Pro Pro Ser Pro
                165                 170                 175

His Val Gln Leu Arg Asp Ile Leu Ser Leu Gly His Arg Ser Ala
                180                 185                 190

Gln Phe Gly His Val Glu Tyr Pro Leu Pro Leu Leu Ile Glu Arg Ser
```

```
                195                 200                 205
Leu Ala Ser Gly Ser Arg Ile Ala Phe Pro Val Val Lys Pro Pro Glu
    210                 215                 220

Pro Leu Asp Val Ala Leu Gln Arg Gln Val Glu Ser Val Pro Pro Ile
225                 230                 235                 240

Arg Lys Val Arg Glu Arg Cys Ala Leu Val Ala Arg Phe Glu Leu Pro
                245                 250                 255

Cys Arg Phe Phe Glu Ile His Glu Val Gly Phe Thr Gly Arg Gly His
            260                 265                 270

Pro Arg Arg Ile Gly
            275
```

(2) INFORMATION FOR SEQ ID NO:186:

(i) SEQUENCE CHARACTERISTICS:
        (A) LENGTH: 192 amino acids
        (B) TYPE: amino acid
        (C) STRANDEDNESS:
        (D) TOPOLOGY: linear (xi) SEQUENCE DESCRIPTION: SEQ ID NO:186:

```
Arg Val Ala Ala Ser Phe Ile Asp Trp Leu Asp Ser Pro Asp Ser Pro
1               5                   10                  15

Leu Asp Pro Ser Leu Val Ser Ser Leu Leu Asn Ala Val Ser Cys Gly
            20                  25                  30

Ala Glu Ser Ser Ala Ser Ser Ala Arg Ser Gly Asn Gly Ser Arg
        35                  40                  45

Trp Thr Ser Met Pro Ser Gly Thr Arg Pro Gly Pro Arg Arg Ala Thr
    50                  55                  60

Ser Arg Asp Asp Arg Arg Ser Ala Thr Ser Val Ile Pro Ser Arg Arg
65              70                  75                  80

Ser Val Ala Pro Arg Ala Glu Phe Gly Thr Arg Leu Ala Ser His Arg
                85                  90                  95

Ala Ser Pro Ser Asn Ala Cys Pro Val Arg Ile Val Thr Ser Ala Ser
            100                 105                 110

Gly Arg Pro Ile Ser Ser Pro Pro Ile Val Arg Ser Arg Ser Cys Val
        115                 120                 125

Asp Lys Asn Gly Arg Arg Cys Ala Ser Gly Tyr Arg Arg Leu Asn Arg
    130                 135                 140

Ala Arg Ser Ser Ser Ile Ala Ala Arg Cys Arg Thr Ile Gly Thr Phe
145                 150                 155                 160

Arg Arg Ser Arg Tyr Ser Ala Ser Met Arg Val Ser Thr Asn Ser Pro
                165                 170                 175

His Val Thr His Gly Val Ala Pro Gly Val Thr Arg Arg Ile Gly Gly
            180                 185                 190
```

(2) INFORMATION FOR SEQ ID NO:187:

(i) SEQUENCE CHARACTERISTICS:
        (A) LENGTH: 196 amino acids
        (B) TYPE: amino acid
        (C) STRANDEDNESS:
        (D) TOPOLOGY: linear (xi) SEQUENCE DESCRIPTION: SEQ ID NO:187:

```
Gln Glu Arg Pro Gln Met Cys Gln Arg Val Ser Glu Ile Glu Pro Arg
1               5                   10                  15

Thr Gln Phe Phe Asn Arg Cys Ala Leu Pro His Tyr Trp His Phe Pro
```

```
                  20                  25                  30
Ala Val Ala Val Phe Ser Lys His Ala Ser Leu Asp Glu Leu Ala Pro
            35                  40                  45
Arg Asn Pro Arg Arg Ser Arg Arg Asp Ala Glu Asp Arg Arg Val
     50                  55                  60
Ile Phe Ala Ala Thr Leu Val Ala Val Asp Pro Leu Arg Gly Ala
65                  70                  75                  80
Gly Gly Glu Ala Asp Gln Leu Ile Asp Leu Gly Val Cys Arg Arg Gln
                85                  90                  95
Ala Gly Arg Val Arg Arg Gly Gln Glu Leu His His Arg His Arg His
                100                 105                 110
Gln Gly Ala Ala Pro Asp Leu Arg Arg Arg Arg His Arg Arg Val
            115                 120                 125
Gln Gln His Arg Arg Leu Gln Arg Val Arg Gln Leu Arg Arg Tyr Val
        130                 135                 140
Gln Thr Ala His His Arg Arg Phe Ala Arg Thr Asp Arg Val Arg His
145                 150                 155                 160
His Val Arg Gly Pro Ser Asn His Arg Arg Arg Val Tyr Arg Gly
                165                 170                 175
Arg His Ser Gly Ala Gly Gly Cys Pro Ala Gly Gly Ala Gly Ser Val
                180                 185                 190
Gly Gly Ser Ala
        195

(2) INFORMATION FOR SEQ ID NO:188:

(i) SEQUENCE CHARACTERISTICS:
        (A) LENGTH: 311 amino acids
        (B) TYPE: amino acid
        (C) STRANDEDNESS:
        (D) TOPOLOGY: linear (xi) SEQUENCE DESCRIPTION: SEQ ID NO:188:

Val Arg Cys Gly Thr Leu Val Pro Val Pro Met Val Glu Phe Leu Thr
1               5                   10                  15
Ser Thr Asn Ala Pro Ser Leu Pro Ser Ala Tyr Ala Glu Val Asp Lys
            20                  25                  30
Leu Ile Gly Leu Pro Ala Gly Thr Ala Lys Arg Trp Ile Asn Gly Tyr
        35                  40                  45
Glu Arg Gly Gly Lys Asp His Pro Pro Ile Leu Arg Val Thr Pro Gly
    50                  55                  60
Ala Thr Pro Trp Val Thr Trp Gly Glu Phe Val Glu Thr Arg Met Leu
65                  70                  75                  80
Ala Glu Tyr Arg Asp Arg Arg Lys Val Pro Ile Val Arg Gln Arg Ala
                85                  90                  95
Ala Ile Glu Glu Leu Arg Ala Arg Phe Asn Leu Arg Tyr Pro Leu Ala
                100                 105                 110
His Leu Arg Pro Phe Leu Ser Thr His Glu Arg Asp Leu Thr Met Gly
            115                 120                 125
Gly Glu Glu Ile Gly Leu Pro Asp Ala Glu Val Thr Ile Arg Thr Gly
        130                 135                 140
Gln Ala Leu Leu Gly Asp Ala Arg Trp Leu Ala Ser Leu Val Pro Asn
145                 150                 155                 160
Ser Ala Arg Gly Ala Thr Leu Arg Arg Leu Gly Ile Thr Asp Val Ala
                165                 170                 175
```

```
Asp Leu Arg Ser Ser Arg Glu Val Ala Arg Arg Gly Pro Gly Arg Val
                180                 185                 190

Pro Asp Gly Ile Asp Val His Leu Leu Pro Phe Pro Asp Leu Ala Asp
            195                 200                 205

Asp Asp Ala Asp Ser Ala Pro His Glu Thr Ala Phe Lys Arg Leu
    210                 215                 220

Leu Thr Asn Asp Gly Ser Asn Gly Glu Ser Gly Glu Ser Ser Gln Ser
225                 230                 235                 240

Ile Asn Asp Ala Ala Thr Arg Tyr Met Thr Asp Glu Tyr Arg Gln Phe
                245                 250                 255

Pro Thr Arg Asn Gly Ala Gln Arg Ala Leu His Arg Val Val Thr Leu
            260                 265                 270

Leu Ala Ala Gly Arg Pro Val Leu Thr His Cys Phe Ala Gly Lys Asp
        275                 280                 285

Arg Thr Gly Phe Val Val Ala Leu Val Leu Glu Ala Val Gly Leu Asp
    290                 295                 300

Arg Asp Val Ile Val Ala Asp
305                 310

(2) INFORMATION FOR SEQ ID NO:189:

(i) SEQUENCE CHARACTERISTICS:
        (A) LENGTH: 2072 base pairs
        (B) TYPE: nucleic acid
        (C) STRANDEDNESS: single
        (D) TOPOLOGY: linear (xi) SEQUENCE DESCRIPTION: SEQ ID NO:189:

CTCGTGCCGA TTCGGCACGA GCTGAGCAGC CCAAGGGGCC GTTCGGCGAA GTCATCGAGG      60

CATTCGCCGA CGGGCTGGCC GGCAAGGGTA AGCAAATCAA CACCACGCTG AACAGCCTGT     120

CGCAGGCGTT GAACGCCTTG AATGAGGGCG CGGCGACTT CTTCGCGGTG GTACGCAGCC     180

TGGCGCTATT CGTCAACGCG CTACATCAGG ACGACCAACA GTTCGTCGCG TTGAACAAGA     240

ACCTTGCGGA GTTCACCGAC AGGTTGACCC ACTCCGATGC GGACCTGTCG AACGCCATCC     300

AGCAATTCGA CAGCTTGCTC GCCGTCGCGC GCCCGTTCTT CGCCAAGAAC CGCGAGGTGC     360

TGACGCATGA CGTCAATAAT CTCGCGACCG TGACCACCAC GTTGCTGCAG CCCGATCCGT     420

TGGATGGGTT GGAGACCGTC CTGCACATCT TCCCGACGCT GGCGGCGAAC ATTAACCAGC     480

TTTACCATCC GACACACGGT GGCGTGGTGT CGCTTTCCGC GTTCACGAAT TCGCCAACC     540

CGATGGAGTT CATCTGCAGC TCGATTCAGG CGGGTAGCCG GCTCGGTTAT CAAGAGTCGG     600

CCGAACTCTG TGCGCAGTAT CTGGCGCCAG TCCTCGATGC GATCAAGTTC AACTACTTTC     660

CGTTCGGCCT GAACGTGGCC AGCACCGCCT CGACACTGCC TAAAGAGATC GCGTACTCCG     720

AGCCCCGCTT GCAGCCGCCC AACGGGTACA AGGACACCAC GGTGCCCGGC ATCTGGGTGC     780

CGGATACGCC GTTGTCACAC CGCAACACGC AGCCCGGTTG GGTGGTGGCA CCCGGGATGC     840

AAGGGGTTCA GGTGGACCG ATCACGCAGG GTTTGCTGAC GCCGGAGTCC CTGGCCGAAC     900

TCATGGGTGG TCCCGATATC GCCCCTCCGT CGTCAGGGCT GCAAACCCCG CCCGGACCCC     960

CGAATGCGTA CGACGAGTAC CCCGTGCTGC CGCCGATCGG TTTACAGGCC CACAGGTGC    1020

CGATACCACC GCCGCCTCCT GGGCCCGACG TAATCCCGGG TCCGGTGCCA CCGGTCTTGG    1080

CGGCGATCGT GTTCCCAAGA GATCGCCCGG CAGCGTCGGA AAACTTCGAC TACATGGGCC    1140

TCTTGTTGCT GTCGCCGGGC CTGGCGACCT TCCTGTTCGG GGTGTCATCT AGCCCCGCCC    1200

GTGGAACGAT GGCCGATCGG CACGTGTTGA TACCGGCGAT CACCGGCCTG GCGTTGATCG    1260
```

```
CGGCATTCGT CGCACATTCG TGGTACCGCA CAGAACATCC GCTCATAGAC ATGCGCTTGT      1320

TCCAGAACCG AGCGGTCGCG CAGGCCAACA TGACGATGAC GGTGCTCTCC CTCGGGCTGT      1380

TTGGCTCCTT CTTGCTGCTC CCGAGCTACC TCCAGCAAGT GTTGCACCAA TCACCGATGC      1440

AATCGGGGGT GCATATCATC CCACAGGGCC TCGGTGCCAT GCTGGCGATG CCGATCGCCG      1500

GAGCGATGAT GGACCGACGG GGACCGGCCA AGATCGTGCT GGTTGGGATC ATGCTGATCG      1560

CTGCGGGGTT GGGCACCTTC GCCTTTGGTG TCGCGCGGCA AGCGGACTAC TTACCCATTC      1620

TGCCGACCGG GCTGGCAATC ATGGGCATGG GCATGGGCTG CTCCATGATG CCACTGTCCG      1680

GGGCGGCAGT GCAGACCCTG GCCCCACATC AGATCGCTCG CGGTTCGACG CTGATCAGCG      1740

TCAACCAGCA GGTGGGCGGT TCGATAGGGA CCGCACTGAT GTCGGTGCTG CTCACCTACC      1800

AGTTCAATCA CAGCGAAATC ATCGCTACTG CAAAGAAAGT CGCACTGACC CCAGAGAGTG      1860

GCGCCGGGCG GGGGCGGCG GTTGACCCTT CCTCGCTACC GCGCCAAACC AACTTCGCGG      1920

CCCAACTGCT GCATGACCTT TCGCACGCCT ACGCGGTGGT ATTCGTGATA GCGACCGCGC      1980

TAGTGGTCTC GACGCTGATC CCCGCGGCAT TCCTGCCGAA ACAGCAGGCT AGTCATCGAA      2040

GAGCACCGTT GCTATCCGCA TGACGTCTGC TT                                    2072

(2) INFORMATION FOR SEQ ID NO:190:

(i) SEQUENCE CHARACTERISTICS:
        (A) LENGTH: 1923 base pairs
        (B) TYPE: nucleic acid
        (C) STRANDEDNESS: single
        (D) TOPOLOGY: linear (xi) SEQUENCE DESCRIPTION: SEQ ID NO:190:

TCACCCCGGA GAAGTCGTTC GTCGACGACC TGGACATCGA CTCGCTGTCG ATGGTCGAGA       60

TCGCCGTGCA GACCGAGGAC AAGTACGGCG TCAAGATCCC CGACGAGGAC CTCGCCGGTC      120

TGCGTACCGT CGGTGACGTT GTCGCCTACA TCCAGAAGCT CGAGGAAGAA AACCCGGAGG      180

CGGCTCAGGC GTTGCGCGCG AAGATTGAGT CGGAGAACCC CGATGCGGCA CGAGCAGATC      240

GGTGCGTTTC ACCCACATCG CAAGCTCGAG ACGCCCGTCG TCCTCTTGCA CGCTCAGCCA      300

GGTTGGCGTG TCGCCGCCTT CCAGCAAGTG TTCCCACCAC ACGAAGGGAC CCTCGCGAAA      360

GGTGACTGAT CCGCGGACCA CATAGTCGAT GCCACCGTGG CTGACAATTG CGCCGGGTCC      420

GAGTTGGCGG GGGCCGAATT GCGGCATTGC GTCGAAGGCC AGCGGATCCC GGCGCCCGCC      480

CGGCGTGGCT GGTGTTTTGG GCCGCCGGAT GGCCACGACG AGAACGACGA TGGCGGCGAT      540

GAACAGCGCC ACGGCAATCA CGACCAGCAG ATTTCCCACG CATACCCTCT CGTACCGCTG      600

CGCCGCGGTT GGTCGATCGG TCGCATATCG ATGGCGCCGT TTAACGTAAC AGCTTTCGCG      660

GGACGGGGG TCACAACGGG CGAGTTGTCC GGCCGGGAAC CCGGCAGGTC TCGGCCGCGG       720

TCACCCCAGC TCACTGGTGC ACCATCCGGG TGTCGGTGAG CGTGCAACTC AAACACACTC      780

AACGGCAACG GTTTCTCAGG TCACCAGCTC AACCTCGACC CGCAATCGCT CGTACGTTTC      840

GACCGCGCGC AGGTCGCGAG TCAGCAGCTT TGCGCCGGCA GCTTTCGCCG TGAAGCCGAC      900

CAGGGCATCG TAGGTTGCGC CACCGGTGAC ATCGTGCTCG GCGAGGTGGT CGGTCAAGCC      960

GCGATATGAG CAGGCATCCA GTGCCAGGTA GTTGCTGGAG GTGATGTCCG CCAAGTAGGC     1020

GTGGACGGCA ACAGGGGCAA TACGATGCGG CGGTGGTAGC CGGGTCAAGA CCGAATAGGT     1080

TTCCACAGCC GCGTGCGCGA TCAGATGGAC GCCACGGTTG AGCGCGCGCA CGGCGGCCTC     1140

GTGCCCTTCG TGCCAGGTCG CGAATCCGGC AACCAGCACG CTGGTGTCTG GTGCGATCAC     1200
```

```
CGCCGTGTGC GATCGAGCGT TTCCCGAACG ATTTCGTCGG TCAACGGGGG CAGGGGACGT    1260

TCTGGCCGTG CGACGAGAAC CGAGCCTTCC CGAACGAGTT CGACACCGGT CGGGGCCGGC    1320

TCAATCTCGA TGCGCCCATC GCGCTCGGTG ATCTCCACCT GGTCGTTCCC GCGCAAGCCA    1380

AGGCGCTCGC GAATCCGCTT GGGAATCACC AGACGTCCTG CGACATCGAT GGTTGTTCGC    1440

ATGGTAGGAA ATTTACCATC GCACGTTCCA TAGGCGTGTC CTGCGCGGGA TGTCGGGACG    1500

ATCCGCTAGC GTATCGAACG ATTGTTTCGG AAATGGCTGA GGGAGCGTGC GGTGCGGGTG    1560

ATGGGTGTCG ATCCCGGGTT GACCCGATGC GGGCTGTCGC TCATCGAGAG TGGGCGTGGT    1620

CGGCAGCTCA CCGCGCTGGA TGTCGACGTG GTGCGCACAC CGTCGGATGC GGCCTTGGCG    1680

CAGCGCCTGT TGGCCATCAG CGATGCCGTC GAGCACTGGC TGGACACCCA TCATCCGGAG    1740

GTGGTGGCTA TCGAACGGGT GTTCTCTCAG CTCAACGTGA CCACGGTGAT GGGCACCGCG    1800

CAGGCCGGCG GCGTGATCGC CCTGGCGGCG GCCAAACGTG GTGTCGACGT GCATTTCCAT    1860

ACCCCCAGCG AGGTCAAGGC GGCGGTCACT GGCAACGGTT CCGCAGACAA GGCTCAGGTC    1920

ACC                                                                  1923

(2) INFORMATION FOR SEQ ID NO:191:

(i) SEQUENCE CHARACTERISTICS:
        (A) LENGTH: 1055 base pairs
        (B) TYPE: nucleic acid
        (C) STRANDEDNESS: single
        (D) TOPOLOGY: linear (xi) SEQUENCE DESCRIPTION: SEQ ID NO:191:

CTGGCGTGCC AGTGTCACCG GCGATATGAC GTCGGCATTC AATTTCGCGG CCCCGCCGGA     60

CCCGTCGCCA CCCAATCTGG ACCACCCGGT CCGTCAATTG CCGAAGGTCG CCAAGTGCGT    120

GCCCAATGTG GTGCTGGGTT TCTTGAACGA AGGCCTGCCG TATCGGGTGC CCTACCCCCA    180

AACAACGCCA GTCCAGGAAT CCGGTCCCGC GCGGCCGATT CCCAGCGGCA TCTGCTAGCC    240

GGGGATGGTT CAGACGTAAC GGTTGGCTAG GTCGAAACCC GCGCCAGGGC CGCTGGACGG    300

GCTCATGGCA GCGAAATTAG AAAACCCGGG ATATTGTCCG CGGATTGTCA TACGATGCTG    360

AGTGCTTGGT GGTTCGTGTT TAGCCATTGA GTGTGGATGT GTTGAGACCC TGGCCTGGAA    420

GGGGACAACG TGCTTTTGCC TCTTGGTCCG CCTTTGCCGC CCGACGCGGT GGTGGCGAAA    480

CGGGCTGAGT CGGGAATGCT CGGCGGGTTG TCGGTTCCGC TCAGCTGGGG AGTGGCTGTG    540

CCACCCGATG ATTATGACCA CTGGGCGCCT GCGCCGGAGG ACGGCGCCGA TGTCGATGTC    600

CAGGCGGCCG AAGGGGCGGA CGCAGAGGCC GCGGCCATGG ACGAGTGGGA TGAGTGGCAG    660

GCGTGGAACG AGTGGGTGGC GGAGAACGCT GAACCCCGCT TTGAGGTGCC ACGGAGTAGC    720

AGCAGCGTGA TTCCGCATTC TCCGGCGGCC GGCTAGGAGA GGGGGCGCAG ACTGTCGTTA    780

TTTGACCAGT GATCGGCGGT CTCGGTGTTC CCGCGGCCGG CTATGACAAC AGTCAATGTG    840

CATGACAAGT TACAGGTATT AGGTCCAGGT TCAACAAGGA CAGGCAAC ATGGCAACAC      900

GTTTTATGAC GGATCCGCAC GCGATGCGGG ACATGGCGGG CCGTTTTGAG GTGCACGCCC    960

AGACGGTGGA GGACGAGGCT CGCCGGATGT GGGCGTCCGC GCAAAACATC TCGGGNGCGG   1020

GCTGGAGTGG CATGGCCGAG GCGACCTCGC TAGAC                              1055

(2) INFORMATION FOR SEQ ID NO:192:

(i) SEQUENCE CHARACTERISTICS:
        (A) LENGTH: 359 base pairs
```

(B) TYPE: nucleic acid
        (C) STRANDEDNESS: single
        (D) TOPOLOGY: linear (xi) SEQUENCE DESCRIPTION: SEQ ID NO:192:

```
CCGCCTCGTT GTTGGCATAC TCCGCCGCGG CCGCCTCGAC CGCACTGGCC GTGGCGTGTG    60

TCCGGGCTGA CCACCGGGAT CGCCGAACCA TCCGAGATCA CCTCGCAATG ATCCACCTCG   120

CGCAGCTGGT CACCCAGCCA CCGGGCGGTG TGCGACAGCG CCTGCATCAC CTTGGTATAG   180

CCGTCGCGCC CCAGCCGCAG GAAGTTGTAG TACTGGCCCA CCACCTGGTT ACCGGGACGG   240

GAGAAGTTCA GGGTGAAGGT CGGCATGTCG CCGCCGAGGT AGTTGACCCG GAAAACCAGA   300

TCCTCCGGCA GGTGCTCGGG CCCGCGCCAC ACGACAAACC CGACGCCGGG ATAGGTCAG    359
```

(2) INFORMATION FOR SEQ ID NO:193:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (xi) SEQUENCE DESCRIPTION: SEQ ID NO:193:

```
AACGGGCCCG TGGGCACCGC TCCTCTAAGG GCTCTCGTTG GTCGCATGAA GTGCTGGAAG    60

GATGCATCTT GGCAGATTCC CGCCAGAGCA AACAGCCGC TAGTCCTAGT CCGAGTCGCC    120

CGCAAAGTTC CTCGAATAAC TCCGTACCCG GAGCGCCAAA CCGGGTCTCC TTCGCTAAGC   180

TGCGCGAACC ACTTGAGGTT CCGGGACTCC TTGACGTCCA GACCGATTCG TTCGAGTGGC   240

TGATCGGTTC GCCGCGCTGG CGCGAATCCG CCGCCGAGCG GGGTGATGTC AACCCAGTGG   300

GTGGCCTGGA AGAGGTGCTC TACGAGCTGT CTCCGATCGA GGACTTCTCC              350
```

(2) INFORMATION FOR SEQ ID NO:194:

(i) SEQUENCE CHARACTERISTICS:
        (A) LENGTH: 679 amino acids
        (B) TYPE: amino acid
        (C) STRANDEDNESS:
        (D) TOPOLOGY: linear (xi) SEQUENCE DESCRIPTION: SEQ ID NO:194:

```
Glu Gln Pro Lys Gly Pro Phe Gly Glu Val Ile Glu Ala Phe Ala Asp
1               5                   10                  15

Gly Leu Ala Gly Lys Gly Lys Gln Ile Asn Thr Thr Leu Asn Ser Leu
            20                  25                  30

Ser Gln Ala Leu Asn Ala Leu Asn Glu Gly Arg Gly Asp Phe Phe Ala
        35                  40                  45

Val Val Arg Ser Leu Ala Leu Phe Val Asn Ala Leu His Gln Asp Asp
    50                  55                  60

Gln Gln Phe Val Ala Leu Asn Lys Asn Leu Ala Glu Phe Thr Asp Arg
65                  70                  75                  80

Leu Thr His Ser Asp Ala Asp Leu Ser Asn Ala Ile Gln Gln Phe Asp
            85                  90                  95

Ser Leu Leu Ala Val Ala Arg Pro Phe Phe Ala Lys Asn Arg Glu Val
            100                 105                 110

Leu Thr His Asp Val Asn Asn Leu Ala Thr Val Thr Thr Leu Leu
        115                 120                 125

Gln Pro Asp Pro Leu Asp Gly Leu Glu Thr Val Leu His Ile Phe Pro
    130                 135                 140
```

```
Thr Leu Ala Ala Asn Ile Asn Gln Leu Tyr His Pro Thr His Gly Gly
145                 150                 155                 160

Val Val Ser Leu Ser Ala Phe Thr Asn Phe Ala Asn Pro Met Glu Phe
                165                 170                 175

Ile Cys Ser Ser Ile Gln Ala Gly Ser Arg Leu Gly Tyr Gln Glu Ser
                180                 185                 190

Ala Glu Leu Cys Ala Gln Tyr Leu Ala Pro Val Leu Asp Ala Ile Lys
            195                 200                 205

Phe Asn Tyr Phe Pro Phe Gly Leu Asn Val Ala Ser Thr Ala Ser Thr
210                 215                 220

Leu Pro Lys Glu Ile Ala Tyr Ser Glu Pro Arg Leu Gln Pro Pro Asn
225                 230                 235                 240

Gly Tyr Lys Asp Thr Thr Val Pro Gly Ile Trp Val Pro Asp Thr Pro
                245                 250                 255

Leu Ser His Arg Asn Thr Gln Pro Gly Trp Val Val Ala Pro Gly Met
                260                 265                 270

Gln Gly Val Gln Val Gly Pro Ile Thr Gln Gly Leu Leu Thr Pro Glu
            275                 280                 285

Ser Leu Ala Glu Leu Met Gly Gly Pro Asp Ile Ala Pro Pro Ser Ser
290                 295                 300

Gly Leu Gln Thr Pro Pro Gly Pro Pro Asn Ala Tyr Asp Glu Tyr Pro
305                 310                 315                 320

Val Leu Pro Pro Ile Gly Leu Gln Ala Pro Gln Val Pro Ile Pro Pro
                325                 330                 335

Pro Pro Pro Gly Pro Asp Val Ile Pro Gly Pro Val Pro Pro Val Leu
                340                 345                 350

Ala Ala Ile Val Phe Pro Arg Asp Arg Pro Ala Ala Ser Glu Asn Phe
            355                 360                 365

Asp Tyr Met Gly Leu Leu Leu Ser Pro Gly Leu Ala Thr Phe Leu
370                 375                 380

Phe Gly Val Ser Ser Pro Ala Arg Gly Thr Met Ala Asp Arg His
385                 390                 395                 400

Val Leu Ile Pro Ala Ile Thr Gly Leu Ala Leu Ile Ala Ala Phe Val
                405                 410                 415

Ala His Ser Trp Tyr Arg Thr Glu His Pro Leu Ile Asp Met Arg Leu
                420                 425                 430

Phe Gln Asn Arg Ala Val Ala Gln Ala Asn Met Thr Met Thr Val Leu
            435                 440                 445

Ser Leu Gly Leu Phe Gly Ser Phe Leu Leu Pro Ser Tyr Leu Gln
450                 455                 460

Gln Val Leu His Gln Ser Pro Met Gln Ser Gly Val His Ile Ile Pro
465                 470                 475                 480

Gln Gly Leu Gly Ala Met Leu Ala Met Pro Ile Ala Gly Ala Met Met
                485                 490                 495

Asp Arg Arg Gly Pro Ala Lys Ile Val Leu Val Gly Ile Met Leu Ile
            500                 505                 510

Ala Ala Gly Leu Gly Thr Phe Ala Phe Gly Val Ala Arg Gln Ala Asp
            515                 520                 525

Tyr Leu Pro Ile Leu Pro Thr Gly Leu Ala Ile Met Gly Met Gly Met
        530                 535                 540

Gly Cys Ser Met Met Pro Leu Ser Gly Ala Ala Val Gln Thr Leu Ala
545                 550                 555                 560

Pro His Gln Ile Ala Arg Gly Ser Thr Leu Ile Ser Val Asn Gln Gln
```

-continued

```
                565                 570                 575
Val Gly Gly Ser Ile Gly Thr Ala Leu Met Ser Val Leu Leu Thr Tyr
            580                 585                 590

Gln Phe Asn His Ser Glu Ile Ile Ala Thr Ala Lys Lys Val Ala Leu
        595                 600                 605

Thr Pro Glu Ser Gly Ala Gly Arg Gly Ala Ala Val Asp Pro Ser Ser
    610                 615                 620

Leu Pro Arg Gln Thr Asn Phe Ala Ala Gln Leu Leu His Asp Leu Ser
625                 630                 635                 640

His Ala Tyr Ala Val Val Phe Val Ile Ala Thr Ala Leu Val Val Ser
                645                 650                 655

Thr Leu Ile Pro Ala Ala Phe Leu Pro Lys Gln Gln Ala Ser His Arg
            660                 665                 670

Arg Ala Pro Leu Leu Ser Ala
        675
```

(2) INFORMATION FOR SEQ ID NO:195:

(i) SEQUENCE CHARACTERISTICS:
        (A) LENGTH: 120 amino acids
        (B) TYPE: amino acid
        (C) STRANDEDNESS:
        (D) TOPOLOGY: linear (xi) SEQUENCE DESCRIPTION: SEQ ID NO:195:

```
Thr Pro Glu Lys Ser Phe Val Asp Asp Leu Asp Ile Asp Ser Leu Ser
1               5                   10                  15

Met Val Glu Ile Ala Val Gln Thr Glu Asp Lys Tyr Gly Val Lys Ile
            20                  25                  30

Pro Asp Glu Asp Leu Ala Gly Leu Arg Thr Val Gly Asp Val Val Ala
        35                  40                  45

Tyr Ile Gln Lys Leu Glu Glu Glu Asn Pro Glu Ala Ala Gln Ala Leu
    50                  55                  60

Arg Ala Lys Ile Glu Ser Glu Asn Pro Asp Ala Ala Arg Ala Asp Arg
65                  70                  75                  80

Cys Val Ser Pro Thr Ser Gln Ala Arg Asp Ala Arg Arg Pro Leu Ala
                85                  90                  95

Arg Ser Ala Arg Leu Ala Cys Arg Arg Leu Pro Ala Ser Val Pro Thr
            100                 105                 110

Thr Arg Arg Asp Pro Arg Glu Arg
        115                 120
```

(2) INFORMATION FOR SEQ ID NO:196:

(i) SEQUENCE CHARACTERISTICS:
        (A) LENGTH: 89 amino acids
        (B) TYPE: amino acid
        (C) STRANDEDNESS:
        (D) TOPOLOGY: linear (xi) SEQUENCE DESCRIPTION: SEQ ID NO:196:

```
Leu Ala Cys Gln Cys His Arg Arg Tyr Asp Val Gly Ile Gln Phe Arg
1               5                   10                  15

Gly Pro Ala Gly Pro Val Ala Thr Gln Ser Gly Pro Pro Gly Pro Ser
            20                  25                  30

Ile Ala Glu Gly Arg Gln Val Arg Ala Gln Cys Gly Ala Gly Phe Leu
        35                  40                  45

Glu Arg Arg Pro Ala Val Ser Gly Ala Leu Pro Pro Asn Asn Ala Ser
```

-continued

```
                50                  55                  60
Pro Gly Ile Arg Ser Arg Ala Ala Asp Ser Gln Arg His Leu Leu Ala
65                  70                  75                  80

Gly Asp Gly Ser Asp Val Thr Val Gly
                85
```

(2) INFORMATION FOR SEQ ID NO:197:

(i) SEQUENCE CHARACTERISTICS:
        (A) LENGTH: 119 amino acids
        (B) TYPE: amino acid
        (C) STRANDEDNESS:
        (D) TOPOLOGY: linear (xi) SEQUENCE DESCRIPTION: SEQ ID NO:197:

```
Ala Ser Leu Leu Ala Tyr Ser Ala Ala Ala Ser Thr Ala Leu Ala
1               5                   10                  15

Val Ala Cys Val Arg Ala Asp His Arg Asp Arg Thr Ile Arg Asp
                20                  25                  30

His Leu Ala Met Ile His Leu Ala Gln Leu Val Thr Gln Pro Pro Gly
                35                  40                  45

Gly Val Arg Gln Arg Leu His His Leu Gly Ile Ala Val Ala Pro Gln
            50                  55                  60

Pro Gln Glu Val Val Leu Ala His His Leu Val Thr Gly Thr Gly
65                  70                  75                  80

Glu Val Gln Gly Glu Gly Arg His Val Ala Ala Glu Val Val Asp Pro
                85                  90                  95

Glu Asn Gln Ile Leu Arg Gln Val Leu Gly Pro Ala Pro His Asp Lys
                100                 105                 110

Pro Asp Ala Gly Ile Gly Gln
            115
```

(2) INFORMATION FOR SEQ ID NO:198:

(i) SEQUENCE CHARACTERISTICS:
        (A) LENGTH: 116 amino acids
        (B) TYPE: amino acid
        (C) STRANDEDNESS:
        (D) TOPOLOGY: linear (xi) SEQUENCE DESCRIPTION: SEQ ID NO:198:

```
Arg Ala Arg Gly His Arg Ser Ser Lys Gly Ser Arg Trp Ser His Glu
1               5                   10                  15

Val Leu Glu Gly Cys Ile Leu Ala Asp Ser Arg Gln Ser Lys Thr Ala
                20                  25                  30

Ala Ser Pro Ser Pro Ser Arg Pro Gln Ser Ser Ser Asn Asn Ser Val
                35                  40                  45

Pro Gly Ala Pro Asn Arg Val Ser Phe Ala Lys Leu Arg Glu Pro Leu
        50                  55                  60

Glu Val Pro Gly Leu Leu Asp Val Gln Thr Asp Ser Phe Glu Trp Leu
65                  70                  75                  80

Ile Gly Ser Pro Arg Trp Arg Glu Ser Ala Ala Glu Arg Gly Asp Val
                85                  90                  95

Asn Pro Val Gly Gly Leu Glu Glu Val Leu Tyr Glu Leu Ser Pro Ile
                100                 105                 110

Glu Asp Phe Ser
        115
```

(2) INFORMATION FOR SEQ ID NO:199:

(i) SEQUENCE CHARACTERISTICS:
        (A) LENGTH: 811 base pairs
        (B) TYPE: nucleic acid
        (C) STRANDEDNESS: single
        (D) TOPOLOGY: linear (xi) SEQUENCE DESCRIPTION: SEQ ID NO:199:

```
TGCTACGCAG CAATCGCTTT GGTGACAGAT GTGGATGCCG GCGTCGCTGC TGGCGATGGC      60

GTGAAAGCCG CCGACGTGTT CGCCGCATTC GGGGAGAACA TCGAACTGCT CAAAAGGCTG     120

GTGCGGGCCG CCATCGATCG GGTCGCCGAC GAGCGCACGT GCACGCACTG TCAACACCAC     180

GCCGGTGTTC CGTTGCCGTT CGAGCTGCCA TGAGGGTGCT GCTGACCGGC GCGGCCGGCT     240

TCATCGGGTC GCGCGTGGAT GCGGCGTTAC GGGCTGCGGG TCACGACGTG GTGGGCGTCG     300

ACGCGCTGCT GCCCGCCGCG CACGGGCCAA ACCCGGTGCT GCCACCGGGC TGCCAGCGGG     360

TCGACGTGCG CGACGCCAGC GCGCTGGCCC CGTTGTTGGC CGGTGTCGAT CTGGTGTGTC     420

ACCAGGCCGC CATGGTGGGT GCCGGCGTCA ACGCCGCCGA CGCACCCGCC TATGGCGGCC     480

ACAACGATTT CGCCACCACG GTGCTGCTGG CGCAGATGTT CGCCGCCGGG GTCCGCCGTT     540

TGGTGCTGGC GTCGTCGATG GTGGTTTACG GGCAGGGGCG CTATGACTGT CCCCAGCATG     600

GACCGGTCGA CCCGCTGCCG CGGCGGCGAG CCGACCTGGA CAATGGGGTC TTCGAGCACC     660

GTTGCCCGGG GTGCGGCGAG CCAGTCATCT GGCAATTGGT CGACGAAGAT GCCCCGTTGC     720

GCCCGCGCAG CCTGTACGCG GCAGCAAGAC CGCGCAGGAG CACTACGCGC TGGCGTGGTC     780

GGAAACGAAT GGCGGTTCCG TGGTGGCGTT G                                    811
```

(2) INFORMATION FOR SEQ ID NO:200:

(i) SEQUENCE CHARACTERISTICS:
        (A) LENGTH: 966 base pairs
        (B) TYPE: nucleic acid
        (C) STRANDEDNESS: single
        (D) TOPOLOGY: linear (xi) SEQUENCE DESCRIPTION: SEQ ID NO:200:

```
GTCCCGCGAT GTGGCCGAGC ATGACTTTCG GCAACACCGG CGTAGTAGTC GAAGATATCG      60

GACTTTGTGG TCCCGGTGGC GGGATAGAGC ACCTGTCGGC GTTGGTCAGC GTCACCCGTT     120

GCTCGGACGC CGAACCCATG CTTTCAACGT AGCCTGTCGG TCACACAAGT CGCGAGCGTA     180

ACGTCACGGT CAAATATCGC GTGGAATTTC GCCGTGACGT TCCGCTCGCG GACAATCAAG     240

GCATACTCAC TTACATGCGA GCCATTTGGA CGGGTTCGAT CGCCTTCGGG CTGGTGAACG     300

TGCCGGTCAA GGTGTACAGC GCTACCGCAG ACCACGACAT CAGGTTCCAC CAGGTGCACG     360

CCAAGGACAA CGGACGCATC CGGTACAAGC GCGTCTGCGA GGCGTGTGGC GAGGTGGTCG     420

ACTACCGCGA TCTTGCCCGG GCCTACGAGT CCGGCGACGG CCAAATGGTG GCGATCACCG     480

ACGACGACAT CGCCAGCTTG CCTGAAGAAC GCAGCCGGGA GATCGAGGTG TTGGAGTTCG     540

TCCCCGCCGC CGACGTGGAC CCGATGATGT TCGACCGCAG CTACTTTTTG GAGCCTGATT     600

CGAAGTCGTC GAAATCGTAT GTGCTGCTGG CTAAGACACT CGCCGAGACC GACCGGATGG     660

CGATCGTGGA TCGCCCCACC GGCCGTGAAT GCAGGAAAAA TAAGAGCCGC TATCCACAAT     720

TCGGCGTCGA GCTCGGCTAC CACAAACGGT AGAACGATCG AGACATTCCC GAGCTGAAGT     780

GCGGCGCTAT AGAAGCCGCT CTGCGCGATT ATCAAACGCA AAATACGCTT ACTCATGCCA     840

TCGGCGCTGC TCACCCGATG CGACGTTTTT GCCACGCTCC ACCGCCTGCC GCGCGACCTC     900
```

| | |
|---|---|
| AAGTGGGCAT GCATCCCACC CGTTCCCGGA AACCGGTTCC GGCGGGTCGG CTCATCGCTT | 960 |
| CATCCT | 966 |

(2) INFORMATION FOR SEQ ID NO:201:

(i) SEQUENCE CHARACTERISTICS:
        (A) LENGTH: 2367 base pairs
        (B) TYPE: nucleic acid
        (C) STRANDEDNESS: single
        (D) TOPOLOGY: linear (xi) SEQUENCE DESCRIPTION: SEQ ID NO:201:

| | |
|---|---|
| CCGCACCGCC GGCAATACCG CCAGCGCCAC CGTTACCGCC GTTTGCGCCG TTGCCCCCGT | 60 |
| TGCCGCCCGT CCCGCCGGCC CCGCCGATGG AGTTCTCATC GCCAAAAGTA CTGGCGTTGC | 120 |
| CACCGGAGCC GCCGTTGCCG CCGTCACCGC CAGCCCCGCC GACTCCACCG GCCCCACCGA | 180 |
| CTCCGCCGCT GCCACCGTTG CCGCCGTTGC CGATCAACAT GCCGCTGGCG CCACCCTTGC | 240 |
| CACCCACGCC ACCGGCTCCG CCCACCCCGC CGACACCAAG CGAGCTGCCG CCGGAGCCAC | 300 |
| CATCACCACC TACGCCACCG ACCGCCCAGA CACCAGCGAC CGGGTCTTCG TGAAACGTCG | 360 |
| CGGTGCCACC ACCGCCGCCG TTACCGCCAA CCCCACCGGC AACGCCGGCG CCGCCATCCC | 420 |
| CGCCGGCCCC GGCGTTGCCG CCGTTGCCGC CGTTGCCGAA CAACAACCCG CCGGCGCCGC | 480 |
| CGTTGCCGCC CGCGCCGCCG GTCCCGCCGG CGCCGCCGAC GCCAAGGCCG CTGCCGCCCT | 540 |
| TGCCGCCATC ACCACCCTTG CCGCCGACCA CATCGGGTTC TGCCTCGGGG TCTGGGCTGT | 600 |
| CAAACCTCGC GATGCCAGCG TTGCCGCCGC TTCCCCCGGG CCCCCCCGTG GCGCCGTCAC | 660 |
| CACCGATACC ACCCGCGCCA CCGGCGCCAC CGTTGCCGCC ATCACCGAAT AGCAACCCGC | 720 |
| CGGCGCCACC ATTGCCGCCA GCTCCCCCTG CGCCACCGTC GGCGCCGGAG CGGCACTGG | 780 |
| CAGCCCCGTT ACCACCGAAA CCGCCGCTAC CACCGGTAGA GGTGGCAGTG GCGATGTGTA | 840 |
| CGAAAGCGCC GCCTCCGGCG CCGCCGCTAC CACCCCCACT GCCGGCGGCT ACACCGTCGG | 900 |
| ACCCGTTGCC ACCATCACCG CCAAAGGCGC TCGCAATGTC GCCCTGCGCG ACTCCGCCGT | 960 |
| CGCCGCCGTT GCCGCCGCCG CCACCGGCAG CGGCGGTACC GCCGTCACCA CCGGCACCGC | 1020 |
| CGGTGGCCTT GCCCGAGCCT GCCGTCGCGG TGGCACCGTC GCCGCCGGTG CCACCGGTCG | 1080 |
| GCGTGCCGGC AGTGCCATGG CCGCCCGTGC CGCCGTCGCC GCCGGTTTGA TCACCGATGC | 1140 |
| CGGACACATC TGCCGGGCTG TCCCCGGTGC TGGCCGCGGG GCCGGGCGTG GGATTGACCC | 1200 |
| CGTTTGCCCC GGCGAGGCCG GCGCCGCCGG TACCACCGGC GCCGCCATGG CCGAACAGCC | 1260 |
| CGGCGTTGCC GCCGTTACCG CCCGCACCCC CGATGCCTGC GGCCACGCTG GTGCCGCCGA | 1320 |
| CACCGCCGTT GCCGCCGTTG CCCCACAACC ACCCCCGTT CCCACCGGCA CCGCCGGCCG | 1380 |
| CGCCGGTACC ACCGGCCCCG CCGTTGCCGC CGTTGCCGAT CAACCCGGCC GCGCCTCCGC | 1440 |
| TGCCGCCGGT TTGACCGAAC CCGCCAGCCG CGCCGTTGCC ACCGTTGCCA AACAGCAACC | 1500 |
| CGCCGGCCGC GCCAGGCTGC CCGGGTGCCG TCCCGTCGGC GCCGTTTCCG ATCAACGGGC | 1560 |
| GCCCAAAAG CGCCTCGGTG GGCGCATTCA CCGCACCCAG CAGACTCCGC TCAACAGCGG | 1620 |
| CTTCAGTGCT GGCATACCGA CCCGCGGCCG CAGTCAACGC CTGCACAAAC TGCTCGTGAA | 1680 |
| ACGCTGCCAC CTGTACGCTG AGCGCCTGAT ACTGCCGAGC ATGGGCCCCG AACAACCCCG | 1740 |
| CAATCGCCGC CGACACTTCA TCGGCAGCCG CAGCCACCAC TTCCGTCGTC GGGATCGCCG | 1800 |
| CGGCCGCATT AGCCGCGCTC ACCTGCGAAC CAATAGTCGA TAAATCCAAA GCCGCAGTTG | 1860 |
| CCAGCAGCTG CGGCGTCGCG ATCACCAAGG ACACCTCGCA CCTCCGGATA CCCCATATCG | 1920 |

```
CCGCACCGTG TCCCCAGCGG CCACGTGACC TTTGGTCGCT GGCTGGCGGC CCTGACTATG    1980

GCCGCGACGG CCCTCGTTCT GATTCGCCCC GGCGCGCAGC TTGTTGCGCG AGTTGAAGAC    2040

GGGAGGACAG GCCGAGCTTG GTGTAGACGT GGGTCAAGTG GGAATGCACG GTCCGCGGCG    2100

AGATGAATAG GCGGACGCCG ATCTCCTTGT TGCTGAGTCC CTCACCGACC AGTAGAGCCA    2160

CCTCAAGCTC TGTCGGTGTC AACGCGCCCC AGCCACTTGT CGGGCGTTTC CGTGCACCGC    2220

GGCCTCGTTG CGCGTACGCG ATCGCCTCAT CGATCGATAA CGCAGTTCCT TCGGCCCAGG    2280

CATCGTCGAA CTCGCTGTCA CCCATGGATT TTCGAAGGGT GGCTAGCGAC GAGTTACAGC    2340

CCGCCTGGTA GATCCCGAAG CGGACCG                                        2367
```

(2) INFORMATION FOR SEQ ID NO:202:

(i) SEQUENCE CHARACTERISTICS:
        (A) LENGTH: 376 amino acids
        (B) TYPE: amino acid
        (C) STRANDEDNESS:
        (D) TOPOLOGY: linear (xi) SEQUENCE DESCRIPTION: SEQ ID NO:202:

```
Gln Pro Ala Gly Ala Thr Ile Ala Ala Ser Ser Pro Cys Ala Thr Val
1               5                   10                  15

Gly Ala Gly Gly Gly Thr Gly Ser Pro Val Thr Thr Glu Thr Ala Ala
            20                  25                  30

Thr Thr Gly Arg Gly Gly Ser Gly Asp Val Tyr Glu Ser Ala Ala Ser
        35                  40                  45

Gly Ala Ala Ala Thr Thr Pro Thr Ala Gly Gly Tyr Thr Val Gly Pro
    50                  55                  60

Val Ala Thr Ile Thr Ala Lys Gly Ala Arg Asn Val Ala Leu Arg Asp
65                  70                  75                  80

Ser Ala Val Ala Ala Val Ala Ala Ala Thr Gly Ser Gly Gly Thr
                85                  90                  95

Ala Val Thr Thr Gly Thr Ala Gly Gly Leu Ala Arg Ala Cys Arg Arg
            100                 105                 110

Gly Gly Thr Val Ala Ala Gly Ala Thr Gly Arg Arg Ala Gly Ser Ala
        115                 120                 125

Met Ala Ala Arg Ala Ala Val Ala Ala Gly Leu Ile Thr Asp Ala Gly
    130                 135                 140

His Ile Cys Arg Ala Val Pro Gly Ala Gly Arg Gly Ala Gly Arg Gly
145                 150                 155                 160

Ile Asp Pro Val Cys Pro Gly Glu Ala Gly Ala Ala Gly Thr Thr Gly
                165                 170                 175

Ala Ala Met Ala Glu Gln Pro Gly Val Ala Ala Val Thr Ala Arg Thr
            180                 185                 190

Pro Asp Ala Cys Gly His Ala Gly Ala Ala Asp Thr Ala Val Ala Ala
        195                 200                 205

Val Ala Pro Gln Pro Pro Val Pro Thr Gly Thr Ala Gly Arg Ala
    210                 215                 220

Gly Thr Thr Gly Pro Ala Val Ala Ala Val Ala Asp Gln Pro Gly Arg
225                 230                 235                 240

Ala Ser Ala Ala Ala Gly Leu Thr Glu Pro Ala Ser Arg Ala Val Ala
                245                 250                 255

Thr Val Ala Lys Gln Gln Pro Ala Gly Arg Ala Arg Leu Pro Gly Cys
            260                 265                 270

Arg Pro Val Gly Ala Val Ser Asp Gln Arg Ala Pro Gln Lys Arg Leu
```

```
                         275                 280                 285
Gly Gly Arg Ile His Arg Thr Gln Gln Thr Pro Leu Asn Ser Gly Phe
    290                 295                 300

Ser Ala Gly Ile Pro Thr Arg Gly Arg Ser Gln Arg Leu His Lys Leu
305                 310                 315                 320

Leu Val Lys Arg Cys His Leu Tyr Ala Glu Arg Leu Ile Leu Pro Ser
                325                 330                 335

Met Gly Pro Glu Gln Pro Arg Asn Arg Arg His Phe Ile Gly Ser
            340                 345                 350

Arg Ser His His Phe Arg Arg Arg Asp Arg Arg Gly Arg Ile Ser Arg
                355                 360                 365

Ala His Leu Arg Thr Asn Ser Arg
    370                 375

(2) INFORMATION FOR SEQ ID NO:203:

(i) SEQUENCE CHARACTERISTICS:
        (A) LENGTH: 2852 base pairs
        (B) TYPE: nucleic acid
        (C) STRANDEDNESS: single
        (D) TOPOLOGY: linear (xi) SEQUENCE DESCRIPTION: SEQ ID NO:203:

GGCCAAAACG CCCCGGCGAT CGCGGCCACC GAGGCCGCCT ACGACCAGAT GTGGGCCCAG      60

GACGTGGCGG CGATGTTTGG CTACCATGCC GGGGCTTCGG CGGCCGTCTC GGCGTTGACA     120

CCGTTCGGCC AGGCGCTGCC GACCGTGGCG GGCGGCGGTG CGCTGGTCAG CGCGGCCGCG     180

GCTCAGGTGA CCACGCGGGT CTTCCGCAAC CTGGGCTTGG CGAACGTCCG CGAGGGCAAC     240

GTCCGCAACG GTAATGTCCG GAACTTCAAT CTCGGCTCGG CCAACATCGG CAACGGCAAC     300

ATCGGCAGCG GCAACATCGG CAGCTCCAAC ATCGGGTTTG GCAACGTGGG TCCTGGGTTG     360

ACCGCAGCGC TGAACAACAT CGGTTTCGGC AACACCGGCA GCAACAACAT CGGGTTTGGC     420

AACACCGGCA GCAACAACAT CGGGTTCGGC AATACCGGAG ACGGCAACCG AGGTATCGGG     480

CTCACGGGTA GCGGTTTGTT GGGGTTCGGC GGCCTGAACT CGGGCACCGG CAACATCGGT     540

CTGTTCAACT CGGGCACCGG AAACGTCGGC ATCGGCAACT CGGGTACCGG GAACTGGGGC     600

ATTGGCAACT CGGGCAACAG CTACAACACC GGTTTTGGCA ACTCCGGCGA CGCCAACACG     660

GGCTTCTTCA ACTCCGGAAT AGCCAACACC GGCGTCGGCA ACGCCGGCAA CTACAACACC     720

GGTAGCTACA ACCCGGGCAA CAGCAATACC GGCGGCTTCA ACATGGGCCA GTACAACACG     780

GGCTACCTGA ACAGCGGCAA CTACAACACC GGCTTGGCAA ACTCCGGCAA TGTCAACACC     840

GGCGCCTTCA TTACTGGCAA CTTCAACAAC GGCTTCTTGT GGCGCGGCGA CCACCAAGGC     900

CTGATTTTCG GGAGCCCCGG CTTCTTCAAC TCGACCAGTG CGCCGTCGTC GGGATTCTTC     960

AACAGCGGTG CCGGTAGCGC GTCCGGCTTC CTGAACTCCG GTGCCAACAA TTCTGGCTTC    1020

TTCAACTCTT CGTCGGGGGC CATCGGTAAC TCCGGCCTGG CAAACGCGGG CGTGCTGGTA    1080

TCGGGCGTGA TCAACTCGGG CAACACCGTA TCGGGTTTGT TCAACATGAG CCTGGTGGCC    1140

ATCACAACGC CGGCCTTGAT CTCGGGCTTC TTCAACACCG GAAGCAACAT GTCGGGATTT    1200

TTCGGTGGCC CACCGGTCTT CAATCTCGGC CTGGCAAACC GGGGCGTCGT GAACATTCTC    1260

GGCAACGCCA ACATCGGCAA TTACAACATT CTCGGCAGCG GAAACGTCGG TGACTTCAAC    1320

ATCCTTGGCA GCGGCAACCT CGGCAGCCAA AACATCTTGG CAGCGGCAA CGTCGGCAGC    1380

TTCAATATCG GCAGTGGAAA CATCGGAGTA TTCAATGTCG GTTCCGGAAG CCTGGGAAAC    1440
```

-continued

```
TACAACATCG GATCCGGAAA CCTCGGGATC TACAACATCG GTTTTGGAAA CGTCGGCGAC    1500

TACAACGTCG GCTTCGGGAA CGCGGGCGAC TTCAACCAAG GCTTTGCCAA CACCGGCAAC    1560

AACAACATCG GGTTCGCCAA CACCGGCAAC AACAACATCG GCATCGGGCT GTCCGGCGAC    1620

AACCAGCAGG GCTTCAATAT TGCTAGCGGC TGGAACTCGG GCACCGGCAA CAGCGGCCTG    1680

TTCAATTCGG GCACCAATAA CGTTGGCATC TTCAACGCGG GCACCGGAAA CGTCGGCATC    1740

GCAAACTCGG GCACCGGGAA CTGGGGTATC GGGAACCCGG GTACCGACAA TACCGGCATC    1800

CTCAATGCTG GCAGCTACAA CACGGGCATC CTCAACGCCG GCGACTTCAA CACGGGCTTC    1860

TACAACACGG GCAGCTACAA CACCGGCGGC TTCAACGTCG GTAACACCAA CACCGGCAAC    1920

TTCAACGTGG GTGACACCAA TACCGGCAGC TATAACCCGG GTGACACCAA CACCGGCTTC    1980

TTCAATCCCG GCAACGTCAA TACCGGCGCT TTCGACACGG GCGACTTCAA CAATGGCTTC    2040

TTGGTGGCGG GCGATAACCA GGGCCAGATT GCCATCGATC TCTCGGTCAC CACTCCATTC    2100

ATCCCCATAA ACGAGCAGAT GGTCATTGAC GTACACAACG TAATGACCTT CGGCGGCAAC    2160

ATGATCACGG TCACCGAGGC CTCGACCGTT TTCCCCCAAA CCTTCTATCT GAGCGGTTTG    2220

TTCTTCTTCG GCCCGGTCAA TCTCAGCGCA TCCACGCTGA CCGTTCCGAC GATCACCCTC    2280

ACCATCGGCG GACCGACGGT GACCGTCCCC ATCAGCATTG TCGGTGCTCT GGAGAGCCGC    2340

ACGATTACCT TCCTCAAGAT CGATCCGGCG CCGGGCATCG GAAATTCGAC CACCAACCCC    2400

TCGTCCGGCT TCTTCAACTC GGGCACCGGT GGCACATCTG GCTTCCAAAA CGTCGGCGGC    2460

GGCAGTTCAG GCGTCTGGAA CAGTGGTTTG AGCAGCGCGA TAGGGAATTC GGGTTTCCAG    2520

AACCTCGGCT CGCTGCAGTC AGGCTGGGCG AACCTGGGCA ACTCCGTATC GGGCTTTTTC    2580

AACACCAGTA CGGTGAACCT CTCCACGCCG GCCAATGTCT CGGGCCTGAA CAACATCGGC    2640

ACCAACCTGT CCGGCGTGTT CCGCGGTCCG ACCGGGACGA TTTTCAACGC GGGCCTTGCC    2700

AACCTGGGCC AGTTGAACAT CGGCAGCGCC TCGTGCCGAA TTCGGCACGA GTTAGATACG    2760

GTTTCAACAA TCATATCCGC GTTTTGCGGC AGTGCATCAG ACGAATCGAA CCCGGGAAGC    2820

GTAAGCGAAT AAACCGAATG GCGGCCTGTC AT                                 2852
```

(2) INFORMATION FOR SEQ ID NO:204:

(i) SEQUENCE CHARACTERISTICS:
        (A) LENGTH: 943 amino acids
        (B) TYPE: amino acid
        (C) STRANDEDNESS:
        (D) TOPOLOGY: linear (xi) SEQUENCE DESCRIPTION: SEQ ID NO:204:

```
Gly Gln Asn Ala Pro Ala Ile Ala Ala Thr Glu Ala Ala Tyr Asp Gln
  1               5                  10                  15

Met Trp Ala Gln Asp Val Ala Ala Met Phe Gly Tyr His Ala Gly Ala
             20                  25                  30

Ser Ala Ala Val Ser Ala Leu Thr Pro Phe Gly Gln Ala Leu Pro Thr
         35                  40                  45

Val Ala Gly Gly Gly Ala Leu Val Ser Ala Ala Ala Gln Val Thr
     50                  55                  60

Thr Arg Val Phe Arg Asn Leu Gly Leu Ala Asn Val Arg Glu Gly Asn
 65                  70                  75                  80

Val Arg Asn Gly Asn Val Arg Asn Phe Asn Leu Gly Ser Ala Asn Ile
                 85                  90                  95

Gly Asn Gly Asn Ile Gly Ser Gly Asn Ile Gly Ser Ser Asn Ile Gly
            100                 105                 110
```

-continued

```
Phe Gly Asn Val Gly Pro Gly Leu Thr Ala Ala Leu Asn Asn Ile Gly
            115                 120                 125

Phe Gly Asn Thr Gly Ser Asn Asn Ile Gly Phe Gly Asn Thr Gly Ser
            130                 135                 140

Asn Asn Ile Gly Phe Gly Asn Thr Gly Asp Gly Asn Arg Gly Ile Gly
145                 150                 155                 160

Leu Thr Gly Ser Gly Leu Leu Gly Phe Gly Gly Leu Asn Ser Gly Thr
                165                 170                 175

Gly Asn Ile Gly Leu Phe Asn Ser Gly Thr Gly Asn Val Gly Ile Gly
            180                 185                 190

Asn Ser Gly Thr Gly Asn Trp Gly Ile Gly Asn Ser Gly Asn Ser Tyr
            195                 200                 205

Asn Thr Gly Phe Gly Asn Ser Gly Asp Ala Asn Thr Gly Phe Phe Asn
            210                 215                 220

Ser Gly Ile Ala Asn Thr Gly Val Gly Asn Ala Gly Asn Tyr Asn Thr
225                 230                 235                 240

Gly Ser Tyr Asn Pro Gly Asn Ser Asn Thr Gly Gly Phe Asn Met Gly
                245                 250                 255

Gln Tyr Asn Thr Gly Tyr Leu Asn Ser Gly Asn Tyr Asn Thr Gly Leu
            260                 265                 270

Ala Asn Ser Gly Asn Val Asn Thr Gly Ala Phe Ile Thr Gly Asn Phe
            275                 280                 285

Asn Asn Gly Phe Leu Trp Arg Gly Asp His Gln Gly Leu Ile Phe Gly
            290                 295                 300

Ser Pro Gly Phe Phe Asn Ser Thr Ser Ala Pro Ser Ser Gly Phe Phe
305                 310                 315                 320

Asn Ser Gly Ala Gly Ser Ala Ser Gly Phe Leu Asn Ser Gly Ala Asn
                325                 330                 335

Asn Ser Gly Phe Phe Asn Ser Ser Gly Ala Ile Gly Asn Ser Gly
            340                 345                 350

Leu Ala Asn Ala Gly Val Leu Val Ser Gly Val Ile Asn Ser Gly Asn
            355                 360                 365

Thr Val Ser Gly Leu Phe Asn Met Ser Leu Val Ala Ile Thr Thr Pro
370                 375                 380

Ala Leu Ile Ser Gly Phe Phe Asn Thr Gly Ser Asn Met Ser Gly Phe
385                 390                 395                 400

Phe Gly Gly Pro Pro Val Phe Asn Leu Gly Leu Ala Asn Arg Gly Val
                405                 410                 415

Val Asn Ile Leu Gly Asn Ala Asn Ile Gly Asn Tyr Asn Ile Leu Gly
            420                 425                 430

Ser Gly Asn Val Gly Asp Phe Asn Ile Leu Gly Ser Gly Asn Leu Gly
            435                 440                 445

Ser Gln Asn Ile Leu Gly Ser Gly Asn Val Gly Ser Phe Asn Ile Gly
            450                 455                 460

Ser Gly Asn Ile Gly Val Phe Asn Val Gly Ser Gly Ser Leu Gly Asn
465                 470                 475                 480

Tyr Asn Ile Gly Ser Gly Asn Leu Gly Ile Tyr Asn Ile Gly Phe Gly
                485                 490                 495

Asn Val Gly Asp Tyr Asn Val Gly Phe Gly Asn Ala Gly Asp Phe Asn
            500                 505                 510

Gln Gly Phe Ala Asn Thr Gly Asn Asn Asn Ile Gly Phe Ala Asn Thr
            515                 520                 525
```

-continued

```
Gly Asn Asn Asn Ile Gly Ile Gly Leu Ser Gly Asp Asn Gln Gln Gly
    530                 535                 540

Phe Asn Ile Ala Ser Gly Trp Asn Ser Gly Thr Gly Asn Ser Gly Leu
545                 550                 555                 560

Phe Asn Ser Gly Thr Asn Asn Val Gly Ile Phe Asn Ala Gly Thr Gly
                565                 570                 575

Asn Val Gly Ile Ala Asn Ser Gly Thr Gly Asn Trp Gly Ile Gly Asn
            580                 585                 590

Pro Gly Thr Asp Asn Thr Gly Ile Leu Asn Ala Gly Ser Tyr Asn Thr
        595                 600                 605

Gly Ile Leu Asn Ala Gly Asp Phe Asn Thr Gly Phe Tyr Asn Thr Gly
    610                 615                 620

Ser Tyr Asn Thr Gly Gly Phe Asn Val Gly Asn Thr Asn Thr Gly Asn
625                 630                 635                 640

Phe Asn Val Gly Asp Thr Asn Thr Gly Ser Tyr Asn Pro Gly Asp Thr
                645                 650                 655

Asn Thr Gly Phe Phe Asn Pro Gly Asn Val Asn Thr Gly Ala Phe Asp
            660                 665                 670

Thr Gly Asp Phe Asn Asn Gly Phe Leu Val Ala Gly Asp Asn Gln Gly
        675                 680                 685

Gln Ile Ala Ile Asp Leu Ser Val Thr Thr Pro Phe Ile Pro Ile Asn
    690                 695                 700

Glu Gln Met Val Ile Asp Val His Asn Val Met Thr Phe Gly Gly Asn
705                 710                 715                 720

Met Ile Thr Val Thr Glu Ala Ser Thr Val Phe Pro Gln Thr Phe Tyr
                725                 730                 735

Leu Ser Gly Leu Phe Phe Gly Pro Val Asn Leu Ser Ala Ser Thr
            740                 745                 750

Leu Thr Val Pro Thr Ile Thr Leu Thr Ile Gly Gly Pro Thr Val Thr
        755                 760                 765

Val Pro Ile Ser Ile Val Gly Ala Leu Glu Ser Arg Thr Ile Thr Phe
    770                 775                 780

Leu Lys Ile Asp Pro Ala Pro Gly Ile Gly Asn Ser Thr Thr Asn Pro
785                 790                 795                 800

Ser Ser Gly Phe Phe Asn Ser Gly Thr Gly Thr Ser Gly Phe Gln
                805                 810                 815

Asn Val Gly Gly Gly Ser Ser Gly Val Trp Asn Ser Gly Leu Ser Ser
            820                 825                 830

Ala Ile Gly Asn Ser Gly Phe Gln Asn Leu Gly Ser Leu Gln Ser Gly
        835                 840                 845

Trp Ala Asn Leu Gly Asn Ser Val Ser Gly Phe Phe Asn Thr Ser Thr
    850                 855                 860

Val Asn Leu Ser Thr Pro Ala Asn Val Ser Gly Leu Asn Asn Ile Gly
865                 870                 875                 880

Thr Asn Leu Ser Gly Val Phe Arg Gly Pro Thr Gly Thr Ile Phe Asn
                885                 890                 895

Ala Gly Leu Ala Asn Leu Gly Gln Leu Asn Ile Gly Ser Ala Ser Cys
            900                 905                 910

Arg Ile Arg His Glu Leu Asp Thr Val Ser Thr Ile Ile Ser Ala Phe
        915                 920                 925

Cys Gly Ser Ala Ser Asp Glu Ser Asn Pro Gly Ser Val Ser Glu
    930                 935                 940
```

(2) INFORMATION FOR SEQ ID NO:205:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (xi) SEQUENCE DESCRIPTION: SEQ ID NO:205:

GGATCCATAT GGGCCATCAT CATCATCATC ACGTGATCGA CATCATCGGG ACC          53

(2) INFORMATION FOR SEQ ID NO:206:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:206:

CCTGAATTCA GGCCTCGGTT GCGCCGGCCT CATCTTGAAC GA                       42

(2) INFORMATION FOR SEQ ID NO:207:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:207:

GGATCCTGCA GGCTCGAAAC CACCGAGCGG T                                   31

(2) INFORMATION FOR SEQ ID NO:208:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:208:

CTCTGAATTC AGCGCTGGAA ATCGTCGCGA T                                   31

(2) INFORMATION FOR SEQ ID NO:209:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:209:

GGATCCAGCG CTGAGATGAA GACCGATGCC GCT                                 33

(2) INFORMATION FOR SEQ ID NO:210:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:210:

GGATATCTGC AGAATTCAGG TTTAAAGCCC ATTTGCGA                            38

(2) INFORMATION FOR SEQ ID NO:211:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:211:

CCGCATGCGA GCCACGTGCC CACAACGGCC                                            30

(2) INFORMATION FOR SEQ ID NO:212:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:212:

CTTCATGGAA TTCTCAGGCC GGTAAGGTCC GCTGCGG                                    37

(2) INFORMATION FOR SEQ ID NO:213:

(i) SEQUENCE CHARACTERISTICS:
        (A) LENGTH: 7676 base pairs
        (B) TYPE: nucleic acid
        (C) STRANDEDNESS: single
        (D) TOPOLOGY: linear (xi) SEQUENCE DESCRIPTION: SEQ ID NO:213:

TGGCGAATGG GACGCGCCCT GTAGCGGCGC ATTAAGCGCG GCGGGTGTGG TGGTTACGCG           60

CAGCGTGACC GCTACACTTG CCAGCGCCCT AGCGCCCGCT CCTTTCGCTT TCTTCCCTTC          120

CTTTCTCGCC ACGTTCGCCG GCTTTCCCCG TCAAGCTCTA AATCGGGGGC TCCCTTTAGG          180

GTTCCGATTT AGTGCTTTAC GGCACCTCGA CCCCAAAAAA CTTGATTAGG GTGATGGTTC          240

ACGTAGTGGG CCATCGCCCT GATAGACGGT TTTTCGCCCT TTGACGTTGG AGTCCACGTT          300

CTTTAATAGT GGACTCTTGT TCCAAACTGG AACAACACTC AACCCTATCT CGGTCTATTC          360

TTTTGATTTA TAAGGGATTT TGCCGATTTC GGCCTATTGG TTAAAAAATG AGCTGATTTA          420

ACAAAAATTT AACGCGAATT TTAACAAAAT ATTAACGTTT ACAATTTCAG GTGGCACTTT          480

TCGGGGAAAT GTGCGCGGAA CCCCTATTTG TTTATTTTTC TAAATACATT CAAATATGTA          540

TCCGCTCATG AATTAATTCT TAGAAAAACT CATCGAGCAT CAAATGAAAC TGCAATTTAT          600

TCATATCAGG ATTATCAATA CCATATTTTT GAAAAAGCCG TTTCTGTAAT GAAGGAGAAA          660

ACTCACCGAG GCAGTTCCAT AGGATGGCAA GATCCTGGTA TCGGTCTGCG ATTCCGACTC          720

GTCCAACATC AATACAACCT ATTAATTTCC CCTCGTCAAA AATAAGGTTA TCAAGTGAGA          780

AATCACCATG AGTGACGACT GAATCCGGTG AGAATGGCAA AAGTTTATGC ATTTCTTTCC          840

AGACTTGTTC AACAGGCCAG CCATTACGCT CGTCATCAAA ATCACTCGCA TCAACCAAAC          900

CGTTATTCAT TCGTGATTGC GCCTGAGCGA GACGAAATAC GCGATCGCTG TTAAAAGGAC          960

AATTACAAAC AGGAATCGAA TGCAACCGGC GCAGGAACAC TGCCAGCGCA TCAACAATAT         1020

TTTCACCTGA ATCAGGATAT CTTCTAATA CCTGGAATGC TGTTTTCCCG GGGATCGCAG          1080

TGGTGAGTAA CCATGCATCA TCAGGAGTAC GGATAAAATG CTTGATGGTC GGAAGAGGCA         1140

TAAATTCCGT CAGCCAGTTT AGTCTGACCA TCTCATCTGT AACATCATTG GCAACGCTAC         1200

CTTTGCCATG TTTCAGAAAC AACTCTGGCG CATCGGGCTT CCCATACAAT CGATAGATTG         1260

TCGCACCTGA TTGCCCGACA TTATCGCGAG CCCATTTATA CCCATATAAA TCAGCATCCA         1320

```
TGTTGGAATT TAATCGCGGC CTAGAGCAAG ACGTTTCCCG TTGAATATGG CTCATAACAC    1380

CCCTTGTATT ACTGTTTATG TAAGCAGACA GTTTTATTGT TCATGACCAA AATCCCTTAA    1440

CGTGAGTTTT CGTTCCACTG AGCGTCAGAC CCCGTAGAAA AGATCAAAGG ATCTTCTTGA    1500

GATCCTTTTT TTCTGCGCGT AATCTGCTGC TTGCAAACAA AAAAACCACC GCTACCAGCG    1560

GTGGTTTGTT TGCCGGATCA AGAGCTACCA ACTCTTTTTC CGAAGGTAAC TGGCTTCAGC    1620

AGAGCGCAGA TACCAAATAC TGTCCTTCTA GTGTAGCCGT AGTTAGGCCA CCACTTCAAG    1680

AACTCTGTAG CACCGCCTAC ATACCTCGCT CTGCTAATCC TGTTACCAGT GGCTGCTGCC    1740

AGTGGCGATA AGTCGTGTCT TACCGGGTTG GACTCAAGAC GATAGTTACC GGATAAGGCG    1800

CAGCGGTCGG GCTGAACGGG GGGTTCGTGC ACACAGCCCA GCTTGGAGCG AACGACCTAC    1860

ACCGAACTGA GATACCTACA GCGTGAGCTA TGAGAAAGCG CCACGCTTCC CGAAGGGAGA    1920

AAGGCGGACA GGTATCCGGT AAGCGGCAGG GTCGGAACAG GAGAGCGCAC GAGGGAGCTT    1980

CCAGGGGGAA ACGCCTGGTA TCTTTATAGT CCTGTCGGGT TTCGCCACCT CTGACTTGAG    2040

CGTCGATTTT TGTGATGCTC GTCAGGGGGG CGGAGCCTAT GGAAAAACGC CAGCAACGCG    2100

GCCTTTTTAC GGTTCCTGGC CTTTTGCTGG CCTTTTGCTC ACATGTTCTT TCCTGCGTTA    2160

TCCCCTGATT CTGTGGATAA CCGTATTACC GCCTTTGAGT GAGCTGATAC CGCTCGCCGC    2220

AGCCGAACGA CCGAGCGCAG CGAGTCAGTG AGCGAGGAAG CGGAAGAGCG CCTGATGCGG    2280

TATTTTCTCC TTACGCATCT GTGCGGTATT TCACACCGCA TATATGGTGC ACTCTCAGTA    2340

CAATCTGCTC TGATGCCGCA TAGTTAAGCC AGTATACACT CCGCTATCGC TACGTGACTG    2400

GGTCATGGCT GCGCCCCGAC ACCCGCCAAC ACCCGCTGAC GCGCCCTGAC GGGCTTGTCT    2460

GCTCCCGGCA TCCGCTTACA GACAAGCTGT GACCGTCTCC GGGAGCTGCA TGTGTCAGAG    2520

GTTTTCACCG TCATCACCGA AACGCGCGAG GCAGCTGCGG TAAAGCTCAT CAGCGTGGTC    2580

GTGAAGCGAT TCACAGATGT CTGCCTGTTC ATCCGCGTCC AGCTCGTTGA GTTTCTCCAG    2640

AAGCGTTAAT GTCTGGCTTC TGATAAAGCG GGCCATGTTA AGGGCGGTTT TTTCCTGTTT    2700

GGTCACTGAT GCCTCCGTGT AAGGGGGATT TCTGTTCATG GGGTAATGA TACCGATGAA     2760

ACGAGAGAGG ATGCTCACGA TACGGGTTAC TGATGATGAA CATGCCCGGT TACTGGAACG    2820

TTGTGAGGGT AAACAACTGG CGGTATGGAT GCGGCGGGAC CAGAGAAAAA TCACTCAGGG    2880

TCAATGCCAG CGCTTCGTTA ATACAGATGT AGGTGTTCCA CAGGGTAGCC AGCAGCATCC    2940

TGCGATGCAG ATCCGGAACA TAATGGTGCA GGGCGCTGAC TTCCGCGTTT CCAGACTTTA    3000

CGAAACACGG AAACCGAAGA CCATTCATGT TGTTGCTCAG GTCGCAGACG TTTTGCAGCA    3060

GCAGTCGCTT CACGTTCGCT CGCGTATCGG TGATTCATTC TGCTAACCAG TAAGGCAACC    3120

CCGCCAGCCT AGCCGGGTCC TCAACGACAG GAGCACGATC ATGCGCACCC GTGGGCCGC    3180

CATGCCGGCG ATAATGGCCT GCTTCTCGCC GAAACGTTTG GTGGCGGGAC CAGTGACGAA    3240

GGCTTGAGCG AGGGCGTGCA AGATTCCGAA TACCGCAAGC GACAGGCCGA TCATCGTCGC    3300

GCTCCAGCGA AAGCGGTCCT CGCCGAAAAT GACCCAGAGC GCTGCCGGCA CCTGTCCTAC    3360

GAGTTGCATG ATAAAGAAGA CAGTCATAAG TGCGGCGACG ATAGTCATGC CCCGCGCCCA    3420

CCGGAAGGAG CTGACTGGGT TGAAGGCTCT CAAGGGCATC GGTCGAGATC CGGTGCCTA    3480

ATGAGTGAGC TAACTTACAT TAATTGCGTT GCGCTCACTG CCCGCTTTCC AGTCGGGAAA    3540

CCTGTCGTGC CAGCTGCATT AATGAATCGG CCAACGCGCG GGGAGAGGCG GTTTGCGTAT    3600

TGGGCGCCAG GGTGGTTTTT CTTTTCACCA GTGAGACGGG CAACAGCTGA TTGCCCTTCA    3660

CCGCCTGGCC CTGAGAGAGT TGCAGCAAGC GGTCCACGCT GGTTTGCCCC AGCAGGCGAA    3720
```

```
AATCCTGTTT GATGGTGGTT AACGGCGGGA TATAACATGA GCTGTCTTCG GTATCGTCGT    3780

ATCCCACTAC CGAGATATCC GCACCAACGC GCAGCCCGGA CTCGGTAATG GCGCGCATTG    3840

CGCCCAGCGC CATCTGATCG TTGGCAACCA GCATCGCAGT GGGAACGATG CCCTCATTCA    3900

GCATTTGCAT GGTTTGTTGA AAACCGGACA TGGCACTCCA GTCGCCTTCC CGTTCCGCTA    3960

TCGGCTGAAT TTGATTGCGA GTGAGATATT TATGCCAGCC AGCCAGACGC AGACGCGCCG    4020

AGACAGAACT TAATGGGCCC GCTAACAGCG CGATTTGCTG GTGACCCAAT GCGACCAGAT    4080

GCTCCACGCC CAGTCGCGTA CCGTCTTCAT GGGAGAAAAT AATACTGTTG ATGGGTGTCT    4140

GGTCAGAGAC ATCAAGAAAT AACGCCGGAA CATTAGTGCA GGCAGCTTCC ACAGCAATGG    4200

CATCCTGGTC ATCCAGCGGA TAGTTAATGA TCAGCCCACT GACGCGTTGC GCGAGAAGAT    4260

TGTGCACCGC CGCTTTACAG GCTTCGACGC CGCTTCGTTC TACCATCGAC ACCACCACGC    4320

TGGCACCCAG TTGATCGGCG CGAGATTTAA TCGCCGCGAC AATTTGCGAC GGCGCGTGCA    4380

GGGCCAGACT GGAGGTGGCA ACGCCAATCA GCAACGACTG TTTGCCCGCC AGTTGTTGTG    4440

CCACGCGGTT GGGAATGTAA TTCAGCTCCG CCATCGCCGC TTCCACTTTT TCCCGCGTTT    4500

TCGCAGAAAC GTGGCTGGCC TGGTTCACCA CGCGGGAAAC GGTCTGATAA GAGACACCGG    4560

CATACTCTGC GACATCGTAT AACGTTACTG GTTTCACATT CACCACCCTG AATTGACTCT    4620

CTTCCGGGCG CTATCATGCC ATACCGCGAA AGGTTTTGCG CCATTCGATG GTGTCCGGGA    4680

TCTCGACGCT CTCCCTTATG CGACTCCTGC ATTAGGAAGC AGCCCAGTAG TAGGTTGAGG    4740

CCGTTGAGCA CCGCCGCCGC AAGGAATGGT GCATGCAAGG AGATGGCGCC CAACAGTCCC    4800

CCGGCCACGG GGCCTGCCAC CATACCCACG CCGAAACAAG CGCTCATGAG CCCGAAGTGG    4860

CGAGCCCGAT CTTCCCCATC GGTGATGTCG GCGATATAGG CGCCAGCAAC CGCACCTGTG    4920

GCGCGGTGA TGCCGGCCAC GATGCGTCCG GCGTAGAGGA TCGAGATCTC GATCCCGCGA    4980

AATTAATACG ACTCACTATA GGGGAATTGT GAGCGGATAA CAATTCCCCT CTAGAAATAA    5040

TTTTGTTTAA CTTTAAGAAG GAGATATACA TATGGGCCAT CATCATCATC ATCACGTGAT    5100

CGACATCATC GGGACCAGCC CCACATCCTG GAACAGGCG GCGGCGGAGG CGGTCCAGCG    5160

GGCGCGGGAT AGCGTCGATG ACATCCGCGT CGCTCGGGTC ATTGAGCAGG ACATGGCCGT    5220

GGACAGCGCC GGCAAGATCA CCTACCGCAT CAAGCTCGAA GTGTCGTTCA AGATGAGGCC    5280

GGCGCAACCG AGGGGCTCGA AACCACCGAG CGGTTCGCCT GAAACGGGCG CCGGCGCCGG    5340

TACTGTCGCG ACTACCCCCG CGTCGTCGCC GGTGACGTTG GCGGAGACCG GTAGCACGCT    5400

GCTCTACCCG CTGTTCAACC TGTGGGGTCC GGCCTTTCAC GAGAGGTATC CGAACGTCAC    5460

GATCACCGCT CAGGGCACCG GTTCTGGTGC CGGGATCGCG CAGGCCGCCG CCGGGACGGT    5520

CAACATTGGG GCCTCCGACG CCTATCTGTC GGAAGGTGAT ATGGCCGCGC ACAAGGGGCT    5580

GATGAACATC GCGCTAGCCA TCTCCGCTCA GCAGGTCAAC TACAACCTGC CCGGAGTGAG    5640

CGAGCACCTC AAGCTGAACG GAAAAGTCCT GGCGGCCATG TACCAGGGCA CCATCAAAAC    5700

CTGGGACGAC CCGCAGATCG CTGCGCTCAA CCCCGGCGTG AACCTGCCCG GCACCGCGGT    5760

AGTTCCGCTG CACCGCTCCG ACGGGTCCGG TGACACCTTC TTGTTCACCC AGTACCTGTC    5820

CAAGCAAGAT CCCGAGGGCT GGGGCAAGTC GCCCGGCTTC GGCACCACCG TCGACTTCCC    5880

GGCGGTGCCG GGTGCGCTGG GTGAGAACGG CAACGGCGGC ATGGTGACCG GTTGCGCCGA    5940

GACACCGGGC TGCGTGGCCT ATATCGGCAT CAGCTTCCTC GACCAGGCCA GTCAACGGGA    6000

ACTCGGCGAG GCCCAACTAG GCAATAGCTC TGGCAATTTC TTGTTGCCCG ACGCGCAAAG    6060
```

```
CATTCAGGCC GCGGCGGCTG GCTTCGCATC GAAAACCCCG GCGAACCAGG CGATTTCGAT      6120

GATCGACGGG CCCGCCCCGG ACGGCTACCC GATCATCAAC TACGAGTACG CCATCGTCAA      6180

CAACCGGCAA AAGGACGCCG CCACCGCGCA GACCTTGCAG GCATTTCTGC ACTGGGCGAT      6240

CACCGACGGC AACAAGGCCT CGTTCCTCGA CCAGGTTCAT TTCCAGCCGC TGCCGCCCGC      6300

GGTGGTGAAG TTGTCTGACG CGTTGATCGC GACGATTTCC AGCGCTGAGA TGAAGACCGA      6360

TGCCGCTACC CTCGCGCAGG AGGCAGGTAA TTTCGAGCGG ATCTCCGGCG ACCTGAAAAC      6420

CCAGATCGAC CAGGTGGAGT CGACGGCAGG TTCGTTGCAG GGCCAGTGGC GCGGCGCGGC      6480

GGGGACGGCC GCCCAGGCCG CGGTGGTGCG CTTCCAAGAA GCAGCCAATA AGCAGAAGCA      6540

GGAACTCGAC GAGATCTCGA CGAATATTCG TCAGGCCGGC GTCCAATACT CGAGGGCCGA      6600

CGAGGAGCAG CAGCAGGCGC TGTCCTCGCA AATGGGCTTT GTGCCCACAA CGGCCGCCTC      6660

GCCGCCGTCG ACCGCTGCAG CGCCACCCGC ACCGGCGACA CCTGTTGCCC CCCACCACC      6720

GGCCGCCGCC AACACGCCGA ATGCCCAGCC GGGCGATCCC AACGCAGCAC CTCCGCCGGC      6780

CGACCCGAAC GCACCGCCGC CACCTGTCAT TGCCCCAAAC GCACCCCAAC CTGTCCGGAT      6840

CGACAACCCG GTTGGAGGAT TCAGCTTCGC GCTGCCTGCT GGCTGGGTGG AGTCTGACGC      6900

CGCCCACTTC GACTACGGTT CAGCACTCCT CAGCAAAACC ACCGGGGACC CGCCATTTCC      6960

CGGACAGCCG CCGCCGGTGG CCAATGACAC CCGTATCGTG CTCGGCCGGC TAGACCAAAA      7020

GCTTTACGCC AGCGCCGAAG CCACCGACTC CAAGGCCGCG GCCCGGTTGG GCTCGGACAT      7080

GGGTGAGTTC TATATGCCCT ACCCGGGCAC CCGGATCAAC CAGGAAACCG TCTCGCTTGA      7140

CGCCAACGGG GTGTCTGGAA GCGCGTCGTA TTACGAAGTC AAGTTCAGCG ATCCGAGTAA      7200

GCCGAACGGC CAGATCTGGA CGGGCGTAAT CGGCTCGCCC GCGGCGAACG CACCGGACGC      7260

CGGGCCCCCT CAGCGCTGGT TTGTGGTATG GCTCGGGACC GCCAACAACC CGGTGGACAA      7320

GGGCGCGGCC AAGGCGCTGG CCGAATCGAT CCGGCCTTTG GTCGCCCCGC CGCCGGCGCC      7380

GGCACCGGCT CCTGCAGAGC CCGCTCCGGC GCCGGCGCCG GCCGGGGAAG TCGCTCCTAC      7440

CCCGACGACA CCGACACCGC AGCGGACCTT ACCGGCCTGA GAATTCTGCA GATATCCATC      7500

ACACTGGCGG CCGCTCGAGC ACCACCACCA CCACCACTGA GATCCGGCTG CTAACAAAGC      7560

CCGAAAGGAA GCTGAGTTGG CTGCTGCCAC CGCTGAGCAA TAACTAGCAT AACCCCTTGG      7620

GGCCTCTAAA CGGGTCTTGA GGGGTTTTTT GCTGAAAGGA GGAACTATAT CCGGAT          7676
```

(2) INFORMATION FOR SEQ ID NO:214:

(i) SEQUENCE CHARACTERISTICS:
  (A) LENGTH: 802 amino acids
  (B) TYPE: amino acid
  (C) STRANDEDNESS: single
  (D) TOPOLOGY: linear (xi) SEQUENCE DESCRIPTION: SEQ ID NO:214:

```
Met Gly His His His His His His Val Ile Asp Ile Ile Gly Thr Ser
1               5                   10                  15

Pro Thr Ser Trp Glu Gln Ala Ala Glu Ala Val Gln Arg Ala Arg
            20                  25                  30

Asp Ser Val Asp Ile Arg Val Ala Arg Val Ile Glu Gln Asp Met
        35                  40                  45

Ala Val Asp Ser Ala Gly Lys Ile Thr Tyr Arg Ile Lys Leu Glu Val
    50                  55                  60

Ser Phe Lys Met Arg Pro Ala Gln Pro Arg Gly Ser Lys Pro Pro Ser
65                  70                  75                  80
```

-continued

```
Gly Ser Pro Glu Thr Gly Ala Gly Thr Val Ala Thr Thr Pro
                85                  90                  95

Ala Ser Ser Pro Val Thr Leu Ala Glu Thr Gly Ser Thr Leu Leu Tyr
            100                 105                 110

Pro Leu Phe Asn Leu Trp Gly Pro Ala Phe His Glu Arg Tyr Pro Asn
            115                 120                 125

Val Thr Ile Thr Ala Gln Gly Thr Gly Ser Gly Ala Gly Ile Ala Gln
    130                 135                 140

Ala Ala Ala Gly Thr Val Asn Ile Gly Ala Ser Asp Ala Tyr Leu Ser
145                 150                 155                 160

Glu Gly Asp Met Ala Ala His Lys Gly Leu Met Asn Ile Ala Leu Ala
                165                 170                 175

Ile Ser Ala Gln Gln Val Asn Tyr Asn Leu Pro Gly Val Ser Glu His
            180                 185                 190

Leu Lys Leu Asn Gly Lys Val Leu Ala Ala Met Tyr Gln Gly Thr Ile
            195                 200                 205

Lys Thr Trp Asp Asp Pro Gln Ile Ala Ala Leu Asn Pro Gly Val Asn
    210                 215                 220

Leu Pro Gly Thr Ala Val Val Pro Leu His Arg Ser Asp Gly Ser Gly
225                 230                 235                 240

Asp Thr Phe Leu Phe Thr Gln Tyr Leu Ser Lys Gln Asp Pro Glu Gly
                245                 250                 255

Trp Gly Lys Ser Pro Gly Phe Gly Thr Thr Val Asp Phe Pro Ala Val
            260                 265                 270

Pro Gly Ala Leu Gly Glu Asn Gly Asn Gly Gly Met Val Thr Gly Cys
            275                 280                 285

Ala Glu Thr Pro Gly Cys Val Ala Tyr Ile Gly Ile Ser Phe Leu Asp
    290                 295                 300

Gln Ala Ser Gln Arg Gly Leu Gly Glu Ala Gln Leu Gly Asn Ser Ser
305                 310                 315                 320

Gly Asn Phe Leu Leu Pro Asp Ala Gln Ser Ile Gln Ala Ala Ala Ala
                325                 330                 335

Gly Phe Ala Ser Lys Thr Pro Ala Asn Gln Ala Ile Ser Met Ile Asp
            340                 345                 350

Gly Pro Ala Pro Asp Gly Tyr Pro Ile Ile Asn Tyr Glu Tyr Ala Ile
            355                 360                 365

Val Asn Asn Arg Gln Lys Asp Ala Ala Thr Ala Gln Thr Leu Gln Ala
    370                 375                 380

Phe Leu His Trp Ala Ile Thr Asp Gly Asn Lys Ala Ser Phe Leu Asp
385                 390                 395                 400

Gln Val His Phe Gln Pro Leu Pro Ala Val Val Lys Leu Ser Asp
                405                 410                 415

Ala Leu Ile Ala Thr Ile Ser Ser Ala Glu Met Lys Thr Asp Ala Ala
            420                 425                 430

Thr Leu Ala Gln Glu Ala Gly Asn Phe Glu Arg Ile Ser Gly Asp Leu
            435                 440                 445

Lys Thr Gln Ile Asp Gln Val Glu Ser Thr Ala Gly Ser Leu Gln Gly
    450                 455                 460

Gln Trp Arg Gly Ala Ala Gly Thr Ala Ala Gln Ala Ala Val Val Arg
465                 470                 475                 480

Phe Gln Glu Ala Ala Asn Lys Gln Lys Gln Glu Leu Asp Glu Ile Ser
                485                 490                 495
```

```
Thr Asn Ile Arg Gln Ala Gly Val Gln Tyr Ser Arg Ala Asp Glu Glu
            500                 505                 510

Gln Gln Gln Ala Leu Ser Ser Gln Met Gly Phe Val Pro Thr Thr Ala
            515                 520                 525

Ala Ser Pro Pro Ser Thr Ala Ala Pro Pro Ala Pro Ala Thr Pro
            530                 535                 540

Val Ala Pro Pro Pro Ala Ala Asn Thr Pro Asn Ala Gln Pro
545                 550                 555                 560

Gly Asp Pro Asn Ala Ala Pro Pro Ala Asp Pro Asn Ala Pro Pro
                565                 570                 575

Pro Pro Val Ile Ala Pro Asn Ala Pro Gln Pro Val Arg Ile Asp Asn
            580                 585                 590

Pro Val Gly Gly Phe Ser Phe Ala Leu Pro Ala Gly Trp Val Glu Ser
            595                 600                 605

Asp Ala Ala His Phe Asp Tyr Gly Ser Ala Leu Leu Ser Lys Thr Thr
            610                 615                 620

Gly Asp Pro Pro Phe Pro Gly Gln Pro Pro Val Ala Asn Asp Thr
625                 630                 635                 640

Arg Ile Val Leu Gly Arg Leu Asp Gln Lys Leu Tyr Ala Ser Ala Glu
            645                 650                 655

Ala Thr Asp Ser Lys Ala Ala Arg Leu Gly Ser Asp Met Gly Glu
            660                 665                 670

Phe Tyr Met Pro Tyr Pro Gly Thr Arg Ile Asn Gln Glu Thr Val Ser
            675                 680                 685

Leu Asp Ala Asn Gly Val Ser Gly Ser Ala Ser Tyr Tyr Glu Val Lys
            690                 695                 700

Phe Ser Asp Pro Ser Lys Pro Asn Gly Gln Ile Trp Thr Gly Val Ile
705                 710                 715                 720

Gly Ser Pro Ala Ala Asn Ala Pro Asp Ala Gly Pro Pro Gln Arg Trp
            725                 730                 735

Phe Val Val Trp Leu Gly Thr Ala Asn Asn Pro Val Asp Lys Gly Ala
            740                 745                 750

Ala Lys Ala Leu Ala Glu Ser Ile Arg Pro Leu Val Ala Pro Pro Pro
            755                 760                 765

Ala Pro Ala Pro Ala Pro Glu Pro Ala Pro Ala Pro Ala
            770                 775                 780

Gly Glu Val Ala Pro Thr Pro Thr Thr Pro Thr Pro Gln Arg Thr Leu
785                 790                 795                 800

Pro Ala (2) INFORMATION FOR SEQ ID NO:215:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:215:

GTGGCGGCGC TGCGGCCGGC CAGCAGAGCG ATGTGCATCC GTTCGCGAAC CTGATCGCGG      60

TCGACGATGA GCGCGCCGAA CGCCGCGACG ACGAAGAACG TCAGGAAGCC GTCCAGCAGC     120

GCGGTCCGCG CGGTGACGAA GCTGACCCCG TCGCAGATCA GCAGCACCCC GGCGATGGCG     180

CCGACCAATG TCGACCGGCT GATCCGCCGC ACGATCCGCA CCACCAGCGC CACCAGGACC     240
```

```
ACACCCAGCA GGGCGCCGGT GAACCGCCAG CCGAATCCGT TGTGACCGAA GATGGCCTCC      300

CCGATCGCGA TCAGCTGCTT ACCGACCGGC GGGTGAACCA CCAGGCCGTA CCCGGGGTTG      360

TCTTCCACCC CATGGTTGTT CAGCACCTGC CAGGCCTGGC GGTGCGTAAT GCTTCTCGTC      420

GAAGATGGGG GTGCCGGCAT CCGTCACCGA GCCC                                 454

(2) INFORMATION FOR SEQ ID NO:216:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:216:

TGCAGAAGTA CGGCGGATCC TCGGTGGCCG ACGCCGAACG GATTCGCCGC GTCGCCGAAC       60

GCATCGTCGC CACCAAGAAG CAAGGCAATG ACGTCGTCGT CGTCGTCTCT GCCATGGGGG      120

ATACCACCGA CGACCTGCTG GATCTGGCTC AGCAGGTGTG CCCGGCGCCG CCGCCTCGGG      180

AGCTGGACAT GCTGCTTACC GCCGGTGAAC GCATCTCGAA TGCGTTGGTG GCCATGGCCA      240

TCGAGTCGCT CGGCGCGCAT GCCCGGTCGT TCACCGGTTC GCAGGCCGGG GTGATCACCA      300

CCGGCACCCA CGGCAACGCC AAGATCATCG ACGTCACGCC GGGGCGGCTG CAAACCGCCC      360

TTGAGGAAGG GCGGGTCGTC TTGGTGGCCG GATTCCAAGG GGTCAGCCAG GACACCAAGG      420

ATGTCACGAC GTTGGGCCGC GGCGGCTCGG ACACCACCGC CGTCGCCATG                470

(2) INFORMATION FOR SEQ ID NO:217:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:217:

GGCCGGCGTA CCCGGCCGGG ACAAACAACG ATCGATTGAT ATCGATGAGA GACGGAGGAA       60

TCGTGGCCCT TCCCCAGTTG ACCGACGAGC AGCGCGCGGC CGCGTTGGAG AAGGCTGCTG      120

CCGCACGTCG AGCGCGAGCA GAGCTCAAGG ATCGGCTCAA GCGTGGCGGC ACCAACCTCA      180

CCCAGGTCCT CAAGGACGCG GAGAGCGATG AAGTCTTGGG CAAAATGAAG GTGTCTGCGC      240

TGCTTGAGGC CTTGCCAAAG GTGGGCAAGG TCCAGGCGC                            279

(2) INFORMATION FOR SEQ ID NO:218:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:218:

ACACGGTCGA ACTCGACGAG CCCCTCGTGG AGGTGTCGAC CGACAAGGTC GACACCGAAA       60

TCCCTCGCCG GCCGCGGGTG TGCTGACCAA GATCATCGCC CAAGAAGATG ACACGGTCGA      120

GGTCGGCGGC GAGCTCTCTG TCATTGGCGA CGCCCATGAT GCCGGCGAGG CCGCGGTCCC      180
```

GGCACCCCAG AAAGTCTCTG CCGGCCCAAC CCGAATCCA                                219

(2) INFORMATION FOR SEQ ID NO:219:

(i) SEQUENCE CHARACTERISTICS:
        (A) LENGTH: 342 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:219:

TCGCTGCCGA CATCGGCGCC GCGCCCGCCC CCAAGCCCGC ACCCAAGCCC GTCCCCGAGC           60

CAGCGCCGAC GCCGAAGGCC GAACCCGCAC CATCGCCGCC GGCGGCCCAG CCAGCCGGTG          120

CGGCCGAGGG CGCACCGTAC GTGACGCCGC TGGTGCGAAA GCTGGCGTCG GAAAACAACA          180

TCGACCTCGC CGGGGTGACC GGCACCGGAG TGGGTGGTCG CATCCGCAAA CAGGATGTGC          240

TGGCCGCGGC TGAACAAAAG AAGCGGGCGA AAGCACCGGC GCCGGCCGCC CAGGCCGCCG          300

CCGCGCCGGC CCCGAAAGCG CCGCCTGAAG ATCCGATGCC GC                            342

(2) INFORMATION FOR SEQ ID NO:220:

(i) SEQUENCE CHARACTERISTICS:
        (A) LENGTH: 515 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:220:

GGGTCTTGGT CAGTATCAGC GCCGACGAGG ACGCCACGGT GCCCGTCGGC GGCGAGTTGG           60

CCCGGATCGG TGTCGCTGCC GACATCGGCG CCGCGCCCGC CCCCAAGCCC GCACCCAAGC          120

CCGTCCCCGA GCCAGCGCCG ACGCCGAAGG CCGAACCCGC ACCATCGCCG CCGGCGGCCC          180

AGCCAGCCGG TGCGGCCGAG GGCGCACCGT ACGTGACGCC GCTGGTGCGA AAGCTGGCGT          240

CGGAAAACAA CATCGACCTC GCCGGGGTGA CCGGCACCGG AGTGGGTGGT CGCATCCGCA          300

AACAGGATGT GCTGGCCGCG GCTGAACAAA AGAAGCGGGC GAAAGCACCG GCGCCCTGAG          360

CGCTTCATCA CCCGGTTAAC CAGCTTGCCC CAGAAGCCGG CTTCGACCTC TTCGCGGGTC          420

TTGGTCCGCT GCAGGCGGTC GGCGAGCCAG TTCAGGTTAG GCGGCCGAAA TCTTCCAGTT          480

CGCCAGGAAG GCACCCGGA ACAGGGTCCG CACCC                                     515

(2) INFORMATION FOR SEQ ID NO:221:

(i) SEQUENCE CHARACTERISTICS:
        (A) LENGTH: 557 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:221:

CCGACCCCAA GGTGCAGATT CAACAGGCCA TTGAGGAAGC ACAGCGCACC CACCAAGCGC           60

TGACTCAACA GGCGGCGCAA GTGATCGGTA ACCAGCGTCA ATTGGAGATG CGACTCAACC          120

GACAGCTGGC GGACATCGAA AAGCTTCAGG TCAATGTGCG CCAAGCCCTG ACGCTGGCCG          180

ACCAGGCCAC CGCCGCCGGA GACGCTGCCA AGGCCACCGA ATACAACAAC GCCGCCGAGG          240

```
CGTTCGCAGC CCAGCTGGTG ACCGCCGAGC AGAGCGTCGA AGACCTCAAG ACGCTGCATG      300

ACCAGGCGCT TAGCGCCGCA GCTCAGGCCA AGAAGGCCGT CGAACGAAAT GCGATGGTGC      360

TGCAGCAGAA GATCGCCGAG CGAACCAAGC TGCTCAGCCA GCTCGAGCAG GCGAAGATGC      420

AGGAGCAGGT CAGCGCATCG TTGCGGTCGA TGAGTGAGCT CGCCGCGCCA GGCAACACGC      480

CGAGCCTCGA CGAGGTGCGC GACAAGATCG AGCGTCGCTA CGCCAACGCG ATCGGTTCGG      540

CTGAACTTGC CGAGAGT                                                    557
```

(2) INFORMATION FOR SEQ ID NO:222:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:222:

```
CAGGATAGGT TTCGACATCC ACCTGGGTTC CGCACCCGGT GCGCGACCGT GTGATAGGCC       60

AGAGGTGGAC CTGCGCCGAC CGACGATCGA TCGAGGAGTC AACAGAAATG GCCTTCTCCG      120

TCCAGATGCC GGCACTCGGT GAGAGCGTCA CCGAGGGGAC GGTTACCCGC TGGCTCAAAC      180

AGGAAGGCGA CACGGTCGAA CTCGACGAGC CCCTCGTGGA GGT                       223
```

(2) INFORMATION FOR SEQ ID NO:223:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:223:

```
AAGAAGTACA TCTGCCGGTC GATGTCGGCG AACCACGGCA GCCAACCGGC GCAGTAGCCG       60

ACCAGGACCA CCGCATAACG CCAGTCCCGG CGCACAAACA TACGCCACCC CGCGTATGCC      120

AGGACTGGCA CCGCCAGCCA CCACATCGCG GGCGTGCCGA CCAGCATCTC GGCCTTGACG      180

CACGACTGTG CGCCGCAGCC TGCAACGTCT TGCTGGTCGA TGGCGTACAG CACCGGCCGC      240

AACGACATGG GCCAGGTCCA CGGTTTGGAT TCCCAAGGGT GGTAGTTGCC TGCGGAATTC      300

GTCAGGCCCG CGTGGAAGTG GAACGCTTTG GCGGTGTATT GCCAGAGCGA GCGCACGGCG      360

TCGGGCAGCG GAACAACCGA GTTGCGACCG ACCGCTTGAC CGACCGCATG CCGATCGATC      420

GCGGTCTCGG ACGCGAACCA CGGAGCGTAG GTGGCCAGAT AGACCGCGAA CGGGATCAAC      480

CCCAGCGCAT ACCCGCTGGG AAGCACGTCA CGCCGCACTG TTCCCAGCCA CGGTCTTTGC      540

ACTTGGTATG AACGTCGCGC CGCCACGTCA ACGCCAGC                             578
```

(2) INFORMATION FOR SEQ ID NO:224:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:224:

-continued

```
ACAACGATCG ATTGATATCG ATGAGAGACG GAGGAATCGT GGCCCTTCCC CAGTTGACCG      60

ACGAGCAGCG CGCGGCCGCG TTGGAGAAGG CTGCTGCCGC ACGTCGAGCG CGAGCAGAGC     120

TCAAGGATCG GCTCAAGCGT GGCGGCACCA ACCTCACCCA GGTCCTCAAG GACGCGGAGA     180

GCGATGAAGT CTTGGGCAAA ATGAAGGTGT CTGCGCTGCT TGAGGCCTTG CCAAAGGTGG     240

GCAAGGTCAA GGCGCAGGAG ATCATGACCG AGCTGGAAAT TGCGCCCCAC CCCGCCGCCT     300

TCGTGGCCTC GGTGACCGTC AGCGCAAGGC CCTGCTGGAA AAGTTCGGCT CCGCCTAACC     360

CCGCCGGCCG ACGATGCGGG CCGGAAGGCC TGTGGTGGGC GTACCCCGC ATACGGGGA      420

GAAGCGGCCT GACAGGGCCA GCTCACAATT CAGGCCGAAC GCCCCGGTGG GGGGGAACCC     480

GCCC                                                                484
```

(2) INFORMATION FOR SEQ ID NO:225:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:225:

```
AGGACTGGCA CCGCCAGCCA CCACATCGCG GGCGTGCCGA CCAGCATCTC GGCCTTGACG      60

CACGACTGTG CGCCGCAGCC TGCAACGTCT TGCTGGTCGA TGGCGTACAG CACCGGCCGC     120

AACGACATGG GCCAGGTCCA CGGTTTGGAT TCCCAAGGGT GGTAGTTGCC TGCGGAATTC     180

GTCAGGCCCG CGTGGAAGTG GAACGCTTTG GCGGTGTAGT GCCAGAGCGA GCGCACGGCG     240

TCGGGCAGCG GAACAACCGA GTTGCGACCG ACCGCTTGAC CGACCGCATG CCGATCGATC     300

GCGGTCTCGG ACGCGAACCA CGGAGCGTAG GTGGCCAGAT AGACCGCGAA CGGGATCAAC     360

CCCAGCGCAT ACCCGCTGGG AAGCACGTCA CGCCGCACTG TCCCCAGCCA CGGTCTTTGC     420

ACTTGGTACT GACGTCGCGC CGCCACGTCG AACGCCAGCG CCATCGCGCC GAAGAACAGC     480

ACGAAGTACA CGCCGGACCA CTTGGTGGCG CAAGCCAATC CCAAGCAGCA CCCCGGC       537
```

(2) INFORMATION FOR SEQ ID NO:226:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:226:

```
Gly Gly Ala Ala Ala Gly Gln Gln Ser Asp Val His Pro Phe Ala Asn
 1               5                  10                  15

Leu Ile Ala Val Asp Asp Glu Arg Ala Glu Arg Arg Asp Asp Glu Glu
                20                  25                  30

Arg Gln Glu Ala Val Gln Gln Arg Gly Pro Arg Gly Asp Glu Ala Asp
            35                  40                  45

Pro Val Ala Asp Gln Gln His Pro Gly Asp Gly Ala Asp Gln Cys Arg
        50                  55                  60

Pro Ala Asp Pro Pro His Asp Pro His His Gln Arg His Gln Asp His
65                  70                  75                  80

Thr Gln Gln Gly Ala Gly Glu Pro Pro Ala Glu Ser Val Val Thr Glu
```

-continued

```
                    85                  90                  95
Asp Gly Leu Pro Asp Arg Asp Gln Leu Leu Thr Asp Arg Arg Val Asn
            100                 105                 110

His Gln Ala Val Pro Gly Val Val Phe His Pro Met Val Val Gln His
            115                 120                 125

Leu Pro Gly Leu Ala Val Arg
            130                 135
```

(2) INFORMATION FOR SEQ ID NO:227:

(i) SEQUENCE CHARACTERISTICS:
        (A) LENGTH: 156 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:227:

```
Gln Lys Tyr Gly Gly Ser Ser Val Ala Asp Ala Glu Arg Ile Arg Arg
1                   5                   10                  15

Val Ala Glu Arg Ile Val Ala Thr Lys Lys Gln Gly Asn Asp Val Val
            20                  25                  30

Val Val Val Ser Ala Met Gly Asp Thr Thr Asp Asp Leu Leu Asp Leu
        35                  40                  45

Ala Gln Gln Val Cys Pro Ala Pro Pro Arg Glu Leu Asp Met Leu
    50                  55                  60

Leu Thr Ala Gly Glu Arg Ile Ser Asn Ala Leu Val Ala Met Ala Ile
65                  70                  75                  80

Glu Ser Leu Gly Ala His Ala Arg Ser Phe Thr Gly Ser Gln Ala Gly
                85                  90                  95

Val Ile Thr Thr Gly Thr His Gly Asn Ala Lys Ile Ile Asp Val Thr
            100                 105                 110

Pro Gly Arg Leu Gln Thr Ala Leu Glu Glu Gly Arg Val Val Leu Val
            115                 120                 125

Ala Gly Phe Gln Gly Val Ser Gln Asp Thr Lys Asp Val Thr Thr Leu
        130                 135                 140

Gly Arg Gly Gly Ser Asp Thr Thr Ala Val Ala Met
145                 150                 155
```

(2) INFORMATION FOR SEQ ID NO:228:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:228:

```
Pro Ala Tyr Pro Ala Gly Thr Asn Asn Asp Arg Leu Ile Ser Met Arg
1                   5                   10                  15

Asp Gly Gly Ile Val Ala Leu Pro Gln Leu Thr Asp Glu Gln Arg Ala
            20                  25                  30

Ala Ala Leu Glu Lys Ala Ala Ala Arg Arg Ala Arg Ala Glu Leu
        35                  40                  45

Lys Asp Arg Leu Lys Arg Gly Thr Asn Leu Thr Gln Val Leu Lys
50                  55                  60
```

```
Asp Ala Glu Ser Asp Glu Val Leu Gly Lys Met Lys Val Ser Ala Leu
 65              70                  75                  80

Leu Glu Ala Leu Pro Lys Val Gly Lys Val Gln Ala
             85                  90
```

(2) INFORMATION FOR SEQ ID NO:229:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:229:

```
Thr Val Glu Leu Asp Glu Pro Leu Val Glu Val Ser Thr Asp Lys Val
 1               5                  10                  15

Asp Thr Glu Ile Pro Ser Pro Ala Ala Gly Val Leu Thr Lys Ile Ile
             20                  25                  30

Ala Gln Glu Asp Asp Thr Val Glu Val Gly Gly Glu Leu Ser Val Ile
         35                  40                  45

Gly Asp Ala His Asp Ala Gly Glu Ala Ala Val Pro Ala Pro Gln Lys
     50                  55                  60

Val Ser Ala Gly Pro Thr Arg Ile
 65              70
```

(2) INFORMATION FOR SEQ ID NO:230:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:230:

```
Ala Ala Asp Ile Gly Ala Ala Pro Ala Pro Lys Pro Ala Pro Lys Pro
 1               5                  10                  15

Val Pro Glu Pro Ala Pro Thr Pro Lys Ala Glu Pro Ala Pro Ser Pro
             20                  25                  30

Pro Ala Ala Gln Pro Ala Gly Ala Ala Glu Gly Ala Pro Tyr Val Thr
         35                  40                  45

Pro Leu Val Arg Lys Leu Ala Ser Glu Asn Asn Ile Asp Leu Ala Gly
     50                  55                  60

Val Thr Gly Thr Gly Val Gly Gly Arg Ile Arg Lys Gln Asp Val Leu
 65              70                  75                  80

Ala Ala Ala Glu Gln Lys Lys Arg Ala Lys Ala Pro Ala Pro Ala Ala
             85                  90                  95

Gln Ala Ala Ala Pro Ala Pro Lys Ala Pro Pro Glu Asp Pro Met
         100                 105                 110

Pro
```

(2) INFORMATION FOR SEQ ID NO:231:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:231:

| Val | Leu | Val | Ser | Ile | Ser | Ala | Asp | Glu | Asp | Ala | Thr | Val | Pro | Val | Gly |
|---|---|---|---|---|---|---|---|---|---|---|---|---|---|---|---|
| 1 |  |  |  | 5 |  |  |  |  | 10 |  |  |  |  | 15 |  |

| Gly | Glu | Leu | Ala | Arg | Ile | Gly | Val | Ala | Ala | Asp | Ile | Gly | Ala | Ala | Pro |
|---|---|---|---|---|---|---|---|---|---|---|---|---|---|---|---|
|  |  | 20 |  |  |  |  | 25 |  |  |  |  | 30 |  |  |  |

| Ala | Pro | Lys | Pro | Ala | Pro | Lys | Pro | Val | Pro | Glu | Pro | Ala | Pro | Thr | Pro |
|---|---|---|---|---|---|---|---|---|---|---|---|---|---|---|---|
|  |  | 35 |  |  |  |  | 40 |  |  |  |  | 45 |  |  |  |

| Lys | Ala | Glu | Pro | Ala | Pro | Ser | Pro | Pro | Ala | Ala | Gln | Pro | Ala | Gly | Ala |
|---|---|---|---|---|---|---|---|---|---|---|---|---|---|---|---|
| 50 |  |  |  |  | 55 |  |  |  |  | 60 |  |  |  |  |  |

| Ala | Glu | Gly | Ala | Pro | Tyr | Val | Thr | Pro | Leu | Val | Arg | Lys | Leu | Ala | Ser |
|---|---|---|---|---|---|---|---|---|---|---|---|---|---|---|---|
| 65 |  |  |  |  | 70 |  |  |  |  | 75 |  |  |  |  | 80 |

| Glu | Asn | Asn | Ile | Asp | Leu | Ala | Gly | Val | Thr | Gly | Thr | Gly | Val | Gly | Gly |
|---|---|---|---|---|---|---|---|---|---|---|---|---|---|---|---|
|  |  |  |  | 85 |  |  |  |  | 90 |  |  |  |  | 95 |  |

| Arg | Ile | Arg | Lys | Gln | Asp | Val | Leu | Ala | Ala | Ala | Glu | Gln | Lys | Lys | Arg |
|---|---|---|---|---|---|---|---|---|---|---|---|---|---|---|---|
|  |  |  | 100 |  |  |  |  | 105 |  |  |  |  | 110 |  |  |

| Ala | Lys | Ala | Pro | Ala | Pro |
|---|---|---|---|---|---|
|  |  | 115 |  |  |  |

(2) INFORMATION FOR SEQ ID NO:232:

(i) SEQUENCE CHARACTERISTICS:
      (A) LENGTH: 185 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:232:

| Asp | Pro | Lys | Val | Gln | Ile | Gln | Gln | Ala | Ile | Glu | Glu | Ala | Gln | Arg | Thr |
|---|---|---|---|---|---|---|---|---|---|---|---|---|---|---|---|
| 1 |  |  |  | 5 |  |  |  |  | 10 |  |  |  |  | 15 |  |

| His | Gln | Ala | Leu | Thr | Gln | Gln | Ala | Ala | Gln | Val | Ile | Gly | Asn | Gln | Arg |
|---|---|---|---|---|---|---|---|---|---|---|---|---|---|---|---|
|  |  |  | 20 |  |  |  |  | 25 |  |  |  |  | 30 |  |  |

| Gln | Leu | Glu | Met | Arg | Leu | Asn | Arg | Gln | Leu | Ala | Asp | Ile | Glu | Lys | Leu |
|---|---|---|---|---|---|---|---|---|---|---|---|---|---|---|---|
|  |  | 35 |  |  |  |  | 40 |  |  |  |  | 45 |  |  |  |

| Gln | Val | Asn | Val | Arg | Gln | Ala | Leu | Thr | Leu | Ala | Asp | Gln | Ala | Thr | Ala |
|---|---|---|---|---|---|---|---|---|---|---|---|---|---|---|---|
|  | 50 |  |  |  |  | 55 |  |  |  |  | 60 |  |  |  |  |

| Ala | Gly | Asp | Ala | Ala | Lys | Ala | Thr | Glu | Tyr | Asn | Asn | Ala | Ala | Glu | Ala |
|---|---|---|---|---|---|---|---|---|---|---|---|---|---|---|---|
| 65 |  |  |  |  | 70 |  |  |  |  | 75 |  |  |  |  | 80 |

| Phe | Ala | Ala | Gln | Leu | Val | Thr | Ala | Glu | Gln | Ser | Val | Glu | Asp | Leu | Lys |
|---|---|---|---|---|---|---|---|---|---|---|---|---|---|---|---|
|  |  |  | 85 |  |  |  |  | 90 |  |  |  |  | 95 |  |  |

| Thr | Leu | His | Asp | Gln | Ala | Leu | Ser | Ala | Ala | Gln | Ala | Lys | Lys | Ala |
|---|---|---|---|---|---|---|---|---|---|---|---|---|---|---|
|  |  |  | 100 |  |  |  |  | 105 |  |  |  |  | 110 |  |

| Val | Glu | Arg | Asn | Ala | Met | Val | Leu | Gln | Gln | Lys | Ile | Ala | Glu | Arg | Thr |
|---|---|---|---|---|---|---|---|---|---|---|---|---|---|---|---|
|  |  | 115 |  |  |  |  | 120 |  |  |  |  | 125 |  |  |  |

| Lys | Leu | Leu | Ser | Gln | Leu | Glu | Gln | Ala | Lys | Met | Gln | Glu | Gln | Val | Ser |
|---|---|---|---|---|---|---|---|---|---|---|---|---|---|---|---|
|  | 130 |  |  |  |  | 135 |  |  |  |  | 140 |  |  |  |  |

| Ala | Ser | Leu | Arg | Ser | Met | Ser | Glu | Leu | Ala | Ala | Pro | Gly | Asn | Thr | Pro |
|---|---|---|---|---|---|---|---|---|---|---|---|---|---|---|---|
| 145 |  |  |  |  | 150 |  |  |  |  | 155 |  |  |  |  | 160 |

| Ser | Leu | Asp | Glu | Val | Arg | Asp | Lys | Ile | Glu | Arg | Arg | Tyr | Ala | Asn | Ala |
|---|---|---|---|---|---|---|---|---|---|---|---|---|---|---|---|
|  |  |  | 165 |  |  |  |  | 170 |  |  |  |  | 175 |  |  |

| Ile | Gly | Ser | Ala | Glu | Leu | Ala | Glu | Ser |
|---|---|---|---|---|---|---|---|---|
|  |  |  | 180 |  |  |  |  | 185 |

(2) INFORMATION FOR SEQ ID NO:233:

(i) SEQUENCE CHARACTERISTICS:
    (A) LENGTH: 71 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:233:

```
Val Ser Thr Ser Thr Trp Val Pro His Pro Val Arg Asp Arg Val Ile
1               5                   10                  15

Gly Gln Arg Trp Thr Cys Ala Asp Arg Arg Ser Ile Glu Glu Ser Thr
            20                  25                  30

Glu Met Ala Phe Ser Val Gln Met Pro Ala Leu Gly Glu Ser Val Thr
            35                  40                  45

Glu Gly Thr Val Thr Arg Trp Leu Lys Gln Glu Gly Asp Thr Val Glu
        50                  55                  60

Leu Asp Glu Pro Leu Val Glu
65                  70
```

(2) INFORMATION FOR SEQ ID NO:234:

(i) SEQUENCE CHARACTERISTICS:
        (A) LENGTH: 182 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:234:

```
Glu Val His Leu Pro Val Asp Val Gly Glu Pro Arg Gln Pro Thr Gly
1               5                   10                  15

Ala Val Ala Asp Gln Asp His Arg Ile Thr Pro Val Pro Ala His Lys
            20                  25                  30

His Thr Pro Pro Arg Val Cys Gln Asp Trp His Arg Gln Pro Pro His
            35                  40                  45

Arg Gly Arg Ala Asp Gln His Leu Gly Leu Asp Ala Arg Leu Cys Ala
    50                  55                  60

Ala Ala Cys Asn Val Leu Leu Val Asp Gly Val Gln His Arg Pro Gln
65                  70                  75                  80

Arg His Gly Pro Gly Pro Arg Phe Gly Phe Pro Arg Val Val Ala
            85                  90                  95

Cys Gly Ile Arg Gln Ala Arg Val Glu Val Glu Arg Phe Gly Gly Val
            100                 105                 110

Leu Pro Glu Arg Ala His Gly Val Gly Gln Arg Asn Asn Arg Val Ala
            115                 120                 125

Thr Asp Arg Leu Thr Asp Arg Met Pro Ile Asp Arg Gly Leu Gly Arg
            130                 135                 140

Glu Pro Arg Ser Val Gly Gly Gln Ile Asp Arg Glu Arg Asp Gln Pro
145                 150                 155                 160

Gln Arg Ile Pro Ala Gly Lys His Val Thr Pro His Cys Ser Gln Pro
                165                 170                 175

Arg Ser Leu His Leu Val
            180
```

(2) INFORMATION FOR SEQ ID NO:235:

(i) SEQUENCE CHARACTERISTICS:

(A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:235:

Asn Asp Arg Leu Ile Ser Met Arg Asp Gly Gly Ile Val Ala Leu Pro
1               5                  10                  15

Gln Leu Thr Asp Glu Gln Arg Ala Ala Ala Leu Glu Lys Ala Ala Ala
            20                  25                  30

Ala Arg Arg Ala Arg Ala Glu Leu Lys Asp Arg Leu Lys Arg Gly Gly
        35                  40                  45

Thr Asn Leu Thr Gln Val Leu Lys Asp Ala Glu Ser Asp Glu Val Leu
 50                  55                  60

Gly Lys Met Lys Val Ser Ala Leu Leu Glu Ala Leu Pro Lys Val Gly
65                  70                  75                  80

Lys Val Lys Ala Gln Glu Ile Met Thr Glu Leu Glu Ile Ala Pro His
                85                  90                  95

Pro Ala Ala Phe Val Ala Ser Val Thr Val Ser Ala Arg Pro Cys Trp
            100                 105                 110

Lys Ser Ser Ala Pro Pro Asn Pro Ala Gly Arg Arg Cys Gly Pro Glu
        115                 120                 125

Gly Leu Trp Trp Ala Tyr Pro Arg Ile Arg Gly Arg Ser Gly Leu Thr
130                 135                 140

Gly Pro Ala His Asn Ser Gly Arg Thr Pro Arg Trp Gly Gly Thr Arg
145                 150                 155                 160

(2) INFORMATION FOR SEQ ID NO:236:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:236:

Asp Trp His Arg Gln Pro Pro His Arg Gly Arg Ala Asp Gln His Leu
1               5                   10                  15

Gly Leu Asp Ala Arg Leu Cys Ala Ala Ala Cys Asn Val Leu Leu Val
            20                  25                  30

Asp Gly Val Gln His Arg Pro Gln Arg His Gly Pro Gly Pro Arg Phe
        35                  40                  45

Gly Phe Pro Arg Val Val Val Ala Cys Gly Ile Arg Gln Ala Arg Val
 50                  55                  60

Glu Val Glu Arg Phe Gly Gly Val Val Pro Glu Arg Ala His Gly Val
65                  70                  75                  80

Gly Gln Arg Asn Asn Arg Val Ala Thr Asp Arg Leu Thr Asp Arg Met
                85                  90                  95

Pro Ile Asp Arg Gly Leu Gly Arg Glu Pro Ser Val Gly Gly Gln
            100                 105                 110

Ile Asp Arg Glu Arg Asp Gln Pro Gln Arg Ile Pro Ala Gly Lys His
        115                 120                 125

Val Thr Pro His Cys Pro Gln Pro Arg Ser Leu His Leu Val Leu Thr
130                 135                 140

-continued

```
Ser Arg Arg His Val Glu Arg Gln Arg His Ala Glu Glu Gln His
145                 150                 155                 160

Glu Val His Ala Gly Pro Leu Gly Gly Ala Ser Gln Ser Gln Ala Ala
                165                 170                 175

Pro Arg
```

(2) INFORMATION FOR SEQ ID NO:237:

(i) SEQUENCE CHARACTERISTICS:
        (A) LENGTH: 271 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:237:

```
ATGCCAAGCC GGTGCTGATG CCCGAGCTCG GCGAATCGGT GACCGAGGGG ACCGTCATTC    60

GTTGGCTGAA GAAGATCGGG GATTCGGTTC AGGTTGACGA GCCACTCGTG GAGGTGTCCA   120

CCGACAAGGT GGACACCGAG ATCCCGTCCC CGGTGGCTGG GGTCTTGGTC AGTATCAGCG   180

CCGACGAGGA CGCCACGGTG CCCGTCGGCG GCGAGTTGGC CCGGATCGGT GTCGCTGCCG   240

AGATCGGCGC CGCGCCCGCC CCCAAGCCCC C                                  271
```

(2) INFORMATION FOR SEQ ID NO:238:

(i) SEQUENCE CHARACTERISTICS:
        (A) LENGTH: 89 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:238:

```
Ala Lys Pro Val Leu Met Pro Glu Leu Gly Glu Ser Val Thr Glu Gly
1                 5                  10                  15

Thr Val Ile Arg Trp Leu Lys Lys Ile Gly Asp Ser Val Gln Val Asp
                20                  25                  30

Glu Pro Leu Val Glu Val Ser Thr Asp Lys Val Asp Thr Glu Ile Pro
            35                  40                  45

Ser Pro Val Ala Gly Val Leu Val Ser Ile Ser Ala Asp Glu Asp Ala
        50                  55                  60

Thr Val Pro Val Gly Gly Glu Leu Ala Arg Ile Gly Val Ala Ala Glu
65                  70                  75                  80

Ile Gly Ala Ala Pro Ala Pro Lys Pro
                85
```

(2) INFORMATION FOR SEQ ID NO:239:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:239:

```
GAGGTAGCGG ATGGCCGGAG GAGCACCCCA GGACCGCGCC CGAACCGCGG GTGCCGGTCA    60

TCGATATGTG GGCACCGTTC GTTCCGTCCG CCGAGGTCAT TGACGAT               107
```

(2) INFORMATION FOR SEQ ID NO:240:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:240:

```
ATGAAGTTGA AGTTTGCTCG CCTGAGTACT GCGATACTGG GTTGTGCAGC GGCGCTTGTG    60

TTTCCTGCCT CGGTTGCCAG CGCAGATCCA CCTGACCCGC ATCAGCCGGA CATGACGAAA   120

GGCTATTGCC CGGGTGGCCG ATGGGGTTTT GGCGACTTGG CCGTGTGCGA CGGCGAGAAG   180

TACCCCGACG GCTCGTTTTG GCACCAGTGG ATGCAAACGT GGTTTACCGG CCCACAGTTT   240

TACTTCGATT GTGTCAGCGG CGGTGAGCCC CTCCCCGGCC CGCCGCCACC GGGTGGTTGC   300

GGTGGGGCAA TTCCGTCCGA GCAGCCCAAC GCTCCCTGA                         339
```

(2) INFORMATION FOR SEQ ID NO:241:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:241:

```
Met Lys Leu Lys Phe Ala Arg Leu Ser Thr Ala Ile Leu Gly Cys Ala
 1               5                  10                  15

Ala Ala Leu Val Phe Pro Ala Ser Val Ala Ser Ala Asp Pro Pro Asp
            20                  25                  30

Pro His Gln Pro Asp Met Thr Lys Gly Tyr Cys Pro Gly Gly Arg Trp
        35                  40                  45

Gly Phe Gly Asp Leu Ala Val Cys Asp Gly Glu Lys Tyr Pro Asp Gly
     50                  55                  60

Ser Phe Trp His Gln Trp Met Gln Thr Trp Phe Thr Gly Pro Gln Phe
65                  70                  75                  80

Tyr Phe Asp Cys Val Ser Gly Gly Glu Pro Leu Pro Gly Pro Pro Pro
                85                  90                  95

Pro Gly Gly Cys Gly Gly Ala Ile Pro Ser Glu Gln Pro Asn Ala Pro
            100                 105                 110
```

(2) INFORMATION FOR SEQ ID NO:242:

(i) SEQUENCE CHARACTERISTICS:
        (A) LENGTH: 371 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:242:

```
GTGACCACGG TGGGCCTGCC ACCAACCCGG GCAGCGGCAG CCGCGGCGGC GCCGGCGGCT    60

CCGGCGGCAA CGGTGGCGCC GGGGGTAACG CCACCGGCTC AGGCGGCAAG GCGGCGCCCG   120

GTGGCAATGG CGGTGATGGG AGCTTCGGCG CTACCAGCGG CCCCGCCTCC ATCGGGGTCA   180

CGGGCGCCCC CGGCGGCAAC GGCGGCAAGG GCGGCGCCGG TGGCAGCAAC CCCAACGGCT   240
```

| | |
|---|---|
| CAGGTGGCGA CGGCGGCAAA GGCGGCAACG GCGGTGCCGG CGGCAACGGG GGCTCGATCG | 300 |
| GCGCCAACAG CGGCATCGTC GGCGGTTCCG GTGGGGCCGG TGGCGCTGGC GGCGCCGGCG | 360 |
| GAAACGGCAG C | 371 |

(2) INFORMATION FOR SEQ ID NO:243:

(i) SEQUENCE CHARACTERISTICS:
        (A) LENGTH: 424 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:243:

| | |
|---|---|
| GTCCGGGTCC CACCACCGCG CCGGCGCGCC CCTAGCGGCC GGGCGCACCA GCCCCTTTTC | 60 |
| TTGACTCGTT CAAGAAAAGG GCCTTCTGTT TGGTCGGCCA TGTTGGCATG ATCGTGACCC | 120 |
| ATGGGCAACA TCGACGTCGA CATCTCGGCC AAGGTCTAGC TCCATGCGAA TCGCCGCCGC | 180 |
| GGTGGTGAGC ATCGGTCTAG CCGTCATAGC AGGGTTCGCG GTACCTGTTG CCGACGCACA | 240 |
| CCCGTCGGAG CCCGGGGTTG TGTCCTACGC GGTGCTCGGA AAGGGGTCGG TCGGCAACAT | 300 |
| CGTCGGCGCC CCAATGGGGT GGGAGGCGGT GTTCACCAAG CCGTTCCAGG CGTTTTGGGT | 360 |
| CGAACTACCG GCGTGCAACA ACTGGGTGGA CATCGGGCTG CCCGAGGTGT ACGACGATCC | 420 |
| CGAC | 424 |

(2) INFORMATION FOR SEQ ID NO:244:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:244:

| | |
|---|---|
| GCGATGGCGG CCGCGGGTAC CACCGCCAAT GTGGAACGGT TTCCCAACCC CAACGATCCT | 60 |
| TTGCATCTGG CGTCAATTGA CTTCAGCCCG GCCGATTTCG TCACCGAGGG CCACCGTCTA | 120 |
| AGGGCGGATG CGATCCTACT GCGCCGTACC GACCGGCTGC CTTTCGCCGA GCCGCCGGAT | 180 |
| TGGGACTTGG TGGAGTCGCA GTTGCGCACG ACCGTCACCG CCGACACGGT GCGCATCGAC | 240 |
| GTCATCGCCG ACGATATGCG TCCCGAACTG GCGGCGGCGT CCAAACTCAC CGAATCGCTG | 300 |
| CGGCTCTACG ATTCGTC | 317 |

(2) INFORMATION FOR SEQ ID NO:245:

(i) SEQUENCE CHARACTERISTICS:
        (A) LENGTH: 422 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:245:

| | |
|---|---|
| TGGCGTATGC GCTTCGCAGC CGGTGCCGCG TCAACGCGCC GGAGGCAATC GCTTCGCTGC | 60 |
| CGAGGAATGG TTCGATCACG ATCGCAGTGT GCCGTCGTGC ACCGACACCG CCGTCCAACG | 120 |
| TGAACTGAGG GCGGAAAATC GGCCGAAATC TCGCCCTCAG TTCACGCTCG GCGCCTAACG | 180 |

```
GTTCTGGAAG TTGGGTGCGC GCTTCTCGGC GAACGCGCGC GGGCCTTCCT TGGCGTCGTC      240

GGACAGGAAG ACCTTGATGC CGATCTGGGT GTCGATCTTG AACGCCTCGT TTTCGGGCAT      300

GCACTCGGTC TCGCGGATGG ACCGCAAGAT GGCCTGCACG GCCAGGGGTC CGTTAGCCGA      360

GATGGCGTCG GCAAGTTCTA GAACCTTGGT CAACGCCTGG CCGTCGGGCA CACGTGGCCG      420

AT                                                                   422
```

(2) INFORMATION FOR SEQ ID NO:246:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:246:

```
GCGTGCCGCT GAACACCAGC CCGCGGCTGC CAGATCTCCC GGACTCGGTA GTGCCGCCGG      60

TGGCGTCGTT GCTCTCCTGA CGGGGCGCGG CGACCATAAG GTCGCTAATG CCCAGGTAGC     120

GGCCCAGGTG CATGGAGTCG ATGATGATGC GACTCTCCAG CTCGCCGACC GGGAGCTTGG     180

CATCGGGCCT GATCAGCCAG GACGCGTAGG ACAAGTCGAT CGAATGCATA GTGGCCTCCA     240

GAGTGGCCGT GCCACTTCCG GCGTGCTCCA CGGCAAATGC CTTGATTTCT AGCTCCGCGT     300

AGTGTTCCCG CATCGCCTGC GGGATGAATG GGAACCGCAG GATGGCGACA AACGGGTCTG     360

ACCTCAGGTT TGCCGCTTTG CGCACAGTGG TCGACAGCCG GTACTCGGCA TAAATGCTGG     420

CCCCGA                                                               426
```

(2) INFORMATION FOR SEQ ID NO:247:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:247:

```
AGACCGGCGA GGGTGTGGTC GCTGCCCGCG GCATTGTCGA TAATCTGCGC TGGGTCGACG      60

CGCCGATCAA CTAGTGAGGC GCAACGCTAG GCTTTGGGAT ACCCACAGCT AAAAAGTTTA     120

TCAAAGAAAC GAAGAAGGTT GCCATGAGCA CTGTTGCCGC CTACGCCGCC ATGTCGGCGA     180

CCGAACCCCT GACCAAGACC ACGATCACCC GTCGCGACCC GGGCCCGCAC GACATGGCGA     240

TCGACATCAA ATTCGCCGGA ATCTGTCGCT CGGACATCCA TACCGTCCAA ACCGAATGGG     300

GGCAACCGAA TTTACCTGTG GTCCCTG                                        327
```

(2) INFORMATION FOR SEQ ID NO:248:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:248:

Asp His Gly Gly Pro Ala Thr Asn Pro Gly Ser Gly Ser Arg Gly Gly

```
  1               5                  10                 15
Ala Gly Gly Ser Gly Gly Asn Gly Gly Ala Gly Gly Asn Ala Thr Gly
                20                 25                 30
Ser Gly Gly Lys Gly Gly Ala Gly Gly Asn Gly Gly Asp Gly Ser Phe
                35                 40                 45
Gly Ala Thr Ser Gly Pro Ala Ser Ile Gly Val Thr Gly Ala Pro Gly
 50                 55                 60
Gly Asn Gly Gly Lys Gly Gly Ala Gly Gly Ser Asn Pro Asn Gly Ser
 65                 70                 75                 80
Gly Gly Asp Gly Gly Lys Gly Gly Asn Gly Gly Ala Gly Gly Asn Gly
                85                 90                 95
Gly Ser Ile Gly Ala Asn Ser Gly Ile Val Gly Gly Ser Gly Gly Ala
               100                105                110
Gly Gly Ala Gly Gly Ala Gly Gly Asn Gly Ser
               115                120
```

(2) INFORMATION FOR SEQ ID NO:249:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:249:

```
Met Ala Ala Ala Gly Thr Thr Ala Asn Val Glu Arg Phe Pro Asn Pro
 1                  5                 10                 15
Asn Asp Pro Leu His Leu Ala Ser Ile Asp Phe Ser Pro Ala Asp Phe
                20                 25                 30
Val Thr Glu Gly His Arg Leu Arg Ala Asp Ala Ile Leu Leu Arg Arg
                35                 40                 45
Thr Asp Arg Leu Pro Phe Ala Glu Pro Pro Asp Trp Asp Leu Val Glu
 50                 55                 60
Ser Gln Leu Arg Thr Thr Val Thr Ala Asp Thr Val Arg Ile Asp Val
 65                 70                 75                 80
Ile Ala Asp Asp Met Arg Pro Glu Leu Ala Ala Ser Lys Leu Thr
                85                 90                 95
Glu Ser Leu Arg Leu Tyr Asp Ser
               100
```

(2) INFORMATION FOR SEQ ID NO:250:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:250:

```
Ala Tyr Ala Leu Arg Ser Arg Cys Arg Val Asn Ala Pro Glu Ala Ile
 1                  5                 10                 15
Ala Ser Leu Pro Arg Asn Gly Ser Ile Thr Ile Ala Val Cys Arg Arg
                20                 25                 30
Ala Pro Thr Pro Pro Ser Asn Val Asn
                35                 40
```

(2) INFORMATION FOR SEQ ID NO:251:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:251:

```
Val Pro Leu Asn Thr Ser Pro Arg Leu Pro Asp Leu Pro Asp Ser Val
 1               5                  10                  15
Val Pro Pro Val Ala Ser Leu Leu Ser
            20                  25
```

(2) INFORMATION FOR SEQ ID NO:252:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:252:

```
Met Ser Thr Val Ala Ala Tyr Ala Ala Met Ser Ala Thr Glu Pro Leu
 1               5                  10                  15
Thr Lys Thr Thr Ile Thr Arg Arg Asp Pro Gly Pro His Asp Met Ala
            20                  25                  30
Ile Asp Ile Lys Phe Ala Gly Ile Cys Arg Ser Asp Ile His Thr Val
            35                  40                  45
Gln Thr Glu Trp Gly Gln Pro Asn Leu Pro Val Val Pro
         50                  55                  60
```

(2) INFORMATION FOR SEQ ID NO:253:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:253:

```
GCTTGGAGCC CTGGAGCGAC GGTGTGGGTC TGGGGGTCGA TTCGTTCTCG GCGAAAGTCA      60
ACTAAAGACC ACGTTGACAC CCAACCGGCG GCCCGGCATG GGCCGTCGCG GCGTAGAAGC     120
TTTGACCGCG GCGCGAAACG TTCGCTGCTG CGGCCCATGC AGATCGCACA CGCTTGCTTG     180
AACATCGGGT GGAGCCGGTG GTAACGCCAG GCT                                  213
```

(2) INFORMATION FOR SEQ ID NO:254:

(i) SEQUENCE CHARACTERISTICS:
        (A) LENGTH: 367 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:254:

```
CCGAGCTGCT GTTCGGCGCC GGCGGTGCGG GCGGCGCGGG TGGGGCGGGC ACCGACGGCG      60
```

```
GGCCCGGTGC TACCGGCGGG ACCGGCGGAC ACGGCGGAGT CGGCGGCGAC GGCGGATGGC        120

TGGCACCCGG CGGGGCCGGC GGGGCCGGCG GGCAAGGCGG GGCAGGTGGT GCCCGCAGCG        180

ATGGTGGCGC GTTGGGTGGT ACCGGCGGGA CGGGCGGTAC CGGCGGCGCC GGTGGCGCCG        240

GCGGTCGCGG CACACTGCTG CTGGGCGCTG GCGGACAGGG CGGCCTCGGC GGCGCCGGCG        300

GACAAGGCGG CACCGGCGGG GGCCGGCGGA GATGGCGTTC TGGGGGGTGT CAGTGGCACT        360

GGTGGTA                                                                 367

(2) INFORMATION FOR SEQ ID NO:255:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:255:

AAGGCGTGAT TGGCAAGGCG ACCGCGCAGC GGCCCGTAGC CGCGGGACGG CCCAGGCCCC         60

GACCGCAGCG GCCGGTGTCT GACCGGGTCA GCGACCAGCG GCGCTGACCG TGCCGCTCGT        120

CTACTTCGAC GCCAGCGCCT TCGTCAAACT TCTCACCACC GAGACAGGGA GCTCGCTGGC        180

GTCCGCTCTA TGGGACGGCT GCGACGCCGC ATTGTCCAAC CGCCTGGCCT ACCCCGAAGT        240

CCGCGCCGCA CTCGCTGCAA CGGGCCGCAA TCACGACCTA ACCGAATCCG AGCTCGCCGA        300

CGCCGAGCGT GACTGGGAGG ACTTCTGGGC CGCACCCGCC CAGTCGAACT CACCGCGACG        360

GTTGAACAGC ACGCCGGGCA CCTCGCCCGA ACACATGCCT TACGCGGAGC CGACACCGTT        420

(2) INFORMATION FOR SEQ ID NO:256:

(i) SEQUENCE CHARACTERISTICS:
        (A) LENGTH: 299 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:256:

CTCTTGTCGG TGGCATCGGC GGTACCGGCG GAACCGGCGG CAACGCCGGT ATGCTCGCCG         60

GCGCCGCCGG GGCCGGCGGT GCCGGCGGGT TCAGCTTCAG CACTGCCGGT GGGGCTGGCG        120

GCGCCGGCGG GGCCGGTGGG CTGTTCACCA CCGGCGGTGT CGGCGGCGCC GGTGGGCAGG        180

GTCACACGGG CGGGGCGGGC GGCGCCGGCG GGGCCGGCGG GTTGTTTGGT GCCGGCGGCA        240

TGGGCGGGGC GGGCGGATTC GGGGATCACG GAACGCTCGG CACCGGCGGG GCCGGCGGG         299

(2) INFORMATION FOR SEQ ID NO:257:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:257:

Leu Glu Pro Trp Ser Asp Gly Val Gly Leu Gly Val Asp Ser Phe Ser
 1               5                  10                  15
```

Ala Lys Val Asn
        20

(2) INFORMATION FOR SEQ ID NO:258:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:258:

Glu Leu Leu Phe Gly Ala Gly Gly Ala Gly Gly Ala Gly Gly Ala Gly
 1               5                  10                  15

Thr Asp Gly Gly Pro Gly Ala Thr Gly Gly Thr Gly Gly His Gly Gly
            20                  25                  30

Val Gly Gly Asp Gly Gly Trp Leu Ala Pro Gly Gly Ala Gly Gly Ala
        35                  40                  45

Gly Gly Gln Gly Gly Ala Gly Gly Ala Arg Ser Asp Gly Gly Ala Leu
    50                  55                  60

Gly Gly Thr Gly Gly Thr Gly Gly Thr Gly Gly Ala Gly Gly Ala Gly
65                  70                  75                  80

Gly Arg Gly Thr Leu Leu Leu Gly Ala Gly Gly Gln Gly Gly Leu Gly
                85                  90                  95

Gly Ala Gly Gly Gln Gly Gly Thr Gly Gly Gly Arg Arg Arg Trp Arg
                100                 105                 110

Ser Gly Gly Cys Gln Trp His Trp Trp
            115                 120

(2) INFORMATION FOR SEQ ID NO:259:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:259:

Gly Val Ile Gly Lys Ala Thr Ala Gln Arg Pro Val Ala Ala Gly Arg
 1               5                  10                  15

Pro Arg Pro Arg Pro Gln Arg Pro Val Ser Asp Arg Val Ser Asp Gln
            20                  25                  30

Arg Arg (2) INFORMATION FOR SEQ ID NO:260:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:260:

Leu Val Gly Gly Ile Gly Gly Thr Gly Gly Thr Gly Gly Asn Ala Gly
 1               5                  10                  15

Met Leu Ala Gly Ala Ala Gly Ala Gly Gly Ala Gly Gly Phe Ser Phe
            20                  25                  30

```
Ser Thr Ala Gly Gly Ala Gly Gly Ala Gly Gly Ala Gly Gly Leu Phe
        35                  40                  45

Thr Thr Gly Gly Val Gly Gly Ala Gly Gly Gln Gly His Thr Gly Gly
        50                  55                  60

Ala Gly Gly Ala Gly Gly Ala Gly Gly Leu Phe Gly Ala Gly Gly Met
65                  70                  75                  80

Gly Gly Ala Gly Gly Phe Gly Asp His Gly Thr Leu Gly Thr Gly Gly
                85                  90                  95

Ala Gly Gly (2) INFORMATION FOR SEQ ID NO:261:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:261:

TCCTGTTCGG CGCCGGCGGG GTGGGCGGTG TTGGCGGTGA CGGTGTGGCA TTCCTGGGCA        60

CCGCCCCCGG CGGGCCCGGT GGTGCCGGCG GGCCGGTGG GCTGTTCAGC GTCGGTGGGG       120

CCGGCGGCGC CGGCGGAATC GGATTGGTCG GGAACAGCGG TGCCGGGGGG TCCGGCGGGT       180

CCGCCCTGCT CTGGGCGAC GGCGGTGCCG GCGGCGCGGG TGGGGTCGGG TCCACTACCG        240

GCGGTGCCGG CGGGGCGGGC GGCAACGCCA GCCTGCTGGT AA                         282

(2) INFORMATION FOR SEQ ID NO:262:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:262:

CGGCACGAGC CGTGCTACTG GTCAACTGAT GCCCTGATTG TGACCTTCCC GGCGCCGGAT       60

CAGTGCTTCT CAGGACCGAC GTAATATTCG AAAACCAATC CGGCCGCCGA GGCGAGGATG      120

AATGCCACAC CGGCGGCGAT CAGCCACGGG AGCCACAACG CGATGCCGAC CGCTGCCACC      180

GAGCCGGACA ACGCGACCAT GATCGGCCAC CAGCTATGCG GACTGAAGAA TCCAAGTTCT      240

CCTGCGCCGT CGCTGATTTC AGCGCCTTCG TAGTCCTCGG GCCGGGAATC TAACCGGCGG      300

GCCACAAACC GGAAGAAGGT GGCGACGATC AACGCCATGC CGCCGGTGAG CGCCAACGCA      360

ATGGTGCCAG CCCACTCGAC ACCACCGGTG GCGAACATCG AGGTCAACAC GCCGT           415

(2) INFORMATION FOR SEQ ID NO:263:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:263:

TCACCGCGTG AACGGTTCGT AACACTGATA CGTATGCTTG TCAGCGAGCA GATCAAGTCC       60
```

```
AGTCCGACCA ATGCCAGGAG ATCATCGGCT AGGCTCACGG TTTCGCCTGG GACGAGACGG      120

TATTGAGTTC TGGCGTTGGA CGGTCCGTGG CGTGGTGGGA AGTCTGACGC GGCATCAGAA      180

CGGTTGTCAA TACCAGTCTT TGGGGGATAT GGCCTATTTG GTGTCGTCGG GCCGCTCCAC      240

CGGATCCCTT TTCGAACGTT GCGCAAGCGC GGTCCAGTTA CGGCCTGTTC ACTGCGCGCT      300

GGCGTAGCTG CGCGGCCTCG ATCGGTTTGA ACGTCATCGC AATTCCCGCA ATGGGTGAGT      360

ACCTGACGCT CCT                                                         373

(2) INFORMATION FOR SEQ ID NO:264:

(i) SEQUENCE CHARACTERISTICS:
        (A) LENGTH: 423 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:264:

CCAAACCGGA CAGGCCGGCA GCGACGGTCG GAAGTTGCAC CACGGTGCGC GCTCCATGTA       60

GCCAACCGGT GACCACGGCG TAGACAGCAG ATCCGTGGAT CGCGCGTTCG GTGTCGTCCG      120

GGCCGAGTAC CCGCGGGCCG AACCGCAGCG ACCAAAGCAA CGCGATCGAT ACGGGGATCG      180

CCACTCGTGC CGAATTCGAG CTCCGTCGAC AAGCTTGCGG CCGCACTCGA ACCCGGGTGA      240

ATGATTGAGT TTAAACCGCT TAGCAATAAC TAGCATAACC CCTTGGGGCC TCTAAACGGG      300

TCTTGAGGGG TTTTTTGCTG AAAGGAGGAA CTATATCCGG ATAACCTGGC GTAGTAGCGA      360

AGAGGCCCGC ACCGATCGCC CTTCCCAACA GTTGCGCAGC CTGAATGGCG AATGGACGCG      420

CCC                                                                    423

(2) INFORMATION FOR SEQ ID NO:265:

(i) SEQUENCE CHARACTERISTICS:
        (A) LENGTH: 404 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:265:

AGTGGCCAGC CGGTCGGCCA ATGCATCCAG CTCCCGGTAC GTCAGCTGAC CATCCGCCCA       60

ACTGACCGCC ACCGAGTCAG GCTGTGCCGC AGCGATTTCG GCGAACCGGG TATGCACCGC      120

GGGTGCCGAC GTCGTCACAT CCGGCAGGCC GGGTGCGGTC GGATCGTGCT CGCCGTCCAG      180

CAGAATGTCG ACGTCGCGCA GCGGCCGATC CCACCGGCTG ACCAAGCGCT GTAACACAGC      240

CAGCACCCGC CTGCCGAGGC TTTCGGGCGC CATCGTGCCC AGCGCACCGT CGAGCACCTC      300

CACTAGCAGC GTGAGCTCAC CGGTGCTGCG GTGCGCGGCG ACGGTCACCG GAAAGTGCGA      360

CAAACTCTCT AGCGCCACCG GACGGAACGT CACCCCGTTT GCGA                       404

(2) INFORMATION FOR SEQ ID NO:266:

(i) SEQUENCE CHARACTERISTICS:
        (A) LENGTH: 421 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:266:

| | |
|---|---|
| GTCCTGGTCG CAGGCTGTTC TTCGAACCCG CTGGCTAACT TCGCACCCGG GTATCCGCCC | 60 |
| ACCATCGAAC CCGCCCAACC GGCGGTGTCA CCGCCTACTT CGCAAGACCC GGCCGGTGCA | 120 |
| GTGCGACCAC TGAGCGGCCA CCCCCGGGCG GCACTATTCG ACAACGGCAC CCGCCAATTG | 180 |
| GTGGCTCTGC GCCCGGGCGC CGATTCGGCG GCACCCGCCA GCATCATGGT CTTCGATGAC | 240 |
| ATGCACGTTG CACCGCGCGT CATTTTTCTG CCGGGCCCGG CAGCCGCGTT GACCAGCGAC | 300 |
| GACCACGGCA CGGCCTTCCT TGCCGCCCGC GGCGGCTACT TCGTGGCCGA CCTGTCCTCC | 360 |
| GGTCACACCG CACGAGTGAA TGTCGCTGAC GCAGCGCACA CCGATTTCAC CGCGATCGCC | 420 |
| C | 421 |

(2) INFORMATION FOR SEQ ID NO:267:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:267:

| | |
|---|---|
| ATGCATATCA CGCTCAACGC CATCCTGCGT GCGATCTTCG GGGCCGGCGG CAGTGAACTA | 60 |
| GACGAGCTGC GCCGCCTCAT TCCGCCGTGG GTCACGCTGG GCTCGCGCCT GGCGGCGCTA | 120 |
| CCGAAACCCA AACGCGACTA TGGCCGCCTT AGCCCGTGGG GCCGGCTGGC CGAGTGGCGG | 180 |
| CGCCAGTACG ACACTGTCAT CGACGAGCTC ATCGAAGCCG AGCGGGCCGA CCCGAACTTC | 240 |
| GCCGATCGGA CCGACGTTTT GGCGTTGATG CTGCGCAGCA CTTACGACGA CGGTTCCATC | 300 |
| ATGTCGCGCA AGGACATTGG CGACGAACTG CTCACGCTGC TTGCCGCCGG GCACGAAACC | 360 |
| ACGGCGGCGA CATGGGCTGG GCGTTCGAAC GGCTCAACCG GCACCCCGAC GTGCTCGCGG | 420 |
| CTCTGG | 426 |

(2) INFORMATION FOR SEQ ID NO:268:

(i) SEQUENCE CHARACTERISTICS:
        (A) LENGTH: 522 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:268:

| | |
|---|---|
| GTCCTGGTCG CAGGCTGTTC TTCGAACCCG CTGGCTAACT TCGCACCCGG GTATCCGCCC | 60 |
| ACCATCGAAC CCGCCCAACC GGCGGTGTCA CCGCCTACTT CGCAAGACCC GGCCGGTGCA | 120 |
| GTGCGACCAC TGAGCGGCCA CCCCCGGGCG GCACTATTCG ACAACGGCAC CCGCCAATTG | 180 |
| GTGGCTCTGC GCCCGGGCGC CGATTCGGCG GCACCCGCCA GCATCATGGT CTTCGATGAC | 240 |
| GTGCACGTTG CACCGCGCGT CATTTTTCTG CCGGGCCCGG CAGCCGCGTT GACCAGCGAC | 300 |
| GACCACGGCA CGGCCTTCCT TGCCGCCCGC GGCGGCTACT TCGTGGCCGA CCTGTCCTCC | 360 |
| GGTCACACCG CACGAGTGAA TGTCGCTGAC GCAGCGCACA CCGATTTCAC CGCGATCGCC | 420 |
| CGCCGCTCCG ACGGCAAGCT GGTGCTGGGC AGCCAGATG GCGCCGTCTA CACGCTTGCC | 480 |
| AAGAACCCGC AGTTGACCGG CGTCGGCGCC GCCACCGTAG CC | 522 |

(2) INFORMATION FOR SEQ ID NO:269:

(i) SEQUENCE CHARACTERISTICS:
        (A) LENGTH: 739 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:269:

```
GCTGGGGCGC ACCGCCGTCC GGCGGCCCCA GCCCCTGGGC CCAGACCCCG CGCAAAACCA      60

ACCCGTGGCC CTTAGTGGCC GGCGCCGCCG CCGTCGTGCT CGTCCTCGTG TTGGGCGCCA     120

TCGGCATCTG GATCGCCATC CGGCCCAAGC CGGTACAGCC GCCTCAGCCG GTTGCGGAGG     180

AGCGCCTTAG CGCCCTACTG CTGAACTCCT CAGAAGTCAA CGCCGTGATG GGCTCGTCGT     240

CCATGCAGCC GGGCAAACCG ATCACATCGA TGGACTCTTC GCCGGTGACG GTGTCCCTGC     300

CGGACTGCCA GGGCGCGCTG TATACCAGCC AGGATCCGGT GTATGCCGGC ACCGGCTACA     360

CCGCCATCAA CGGCTTGATT TCATCCGAGC CGGGCGACAA CTACGAACAT GGGTGAACC      420

AAGCCGTCGT CGCCTTTCCG ACCGCCGACA AGCCCGCGC GTTCGTGCAG ACTTCGGCCG     480

ACAAATGGAA GAACTGCGCA GGCAAGACGG TCACCGTCAC GAATAAGGCC AAGACCTACC     540

GGTGGACGTT TGCCGACGTC AAAGGCAGCC CGCCGACGAT CACGGTGATA GACACCCAAG     600

AAGGCGCTGA GGGCTGGGAA TGCCAACGCG CGATGAGCGT GGCCAACAAT GTGGTTGTCG     660

ACGTCAACGC ATGCGGGTAC CAGATCACCA ATCAAGCAGG CCAGATCGCC GCCAAGATCT     720

GTTGACAAAG TCAACAAGG                                                  739
```

(2) INFORMATION FOR SEQ ID NO:270:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:270:

```
AGACGTCGTC GAGGCCGCCA TCGCCCGCGC CGAAGCCGTT AACCCGGCAC TGAACGCGTT      60

GGCGTATGC                                                              69
```

(2) INFORMATION FOR SEQ ID NO:271:

(i) SEQUENCE CHARACTERISTICS:
        (A) LENGTH: 523 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:271:

```
ACTGCACCCG GCAGGCGCGA CCAACGGATC GGGTCAACTA GCACTGCCGG TGGAGGCGCC      60

CCCGCGGTCT GTGCCTTCCC ACGGGGAACC CTTGGGCAGC GCGGCTCCAG AAGGGTTGGA     120

GGGAGAGTTC GACGACCGTA TCGACGAGCG GTTCCCGGTC TTCAGCTCGG CCAGTCTCGC     180

CGAAGCGCTG CCGGGTCCGC TGACCCCGAT GACGCTGGAT GTCCAGTTGA GTGGACTGCG     240

CGCGGCCGGT CGGGCGATGG GTCGGGTACT GGCGCTTGGC GGTGTCGTTG CCGATGAGTG     300
```

-continued

```
GGAGAGAAGA GCCATCGCGG TGTTCGGTCA CCGCCCGTAT ATCGGAGTGT CGGCCAATAT    360

TGTGGCCGCC GCCCAACTGC CGGGGTGGGA CGCGCAGGCC GTAACCCGGC GGGCACTGGG    420

CGAGCAACCG CAGGTCACTG AGCTGCTTCC GTTTGGTCGA CCGCAACTTG CGGGCGGACC    480

GCTCGGCTCG GTCGCGAAGG TGGTCGTGAC GGCACGGTCG CTG                      523
```

(2) INFORMATION FOR SEQ ID NO:272:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:272:

```
GTGTCGGTGT CGTCGGGGTA GGAGCGACTT CCCCGGCCGG CGCCGGCGCC GGAGCGGGCT     60

CTGCAGGAAC CGGTGCCGGC GCCGGCGGCG GGGCGACCAA AGGCCGGATC GATTCGGCCA    120

GCGCCTTGGC CGCGCCCTTG TCCACCGGGT TGTTGGCGGT CCCGAGCCAT ACCACAAACC    180

AACGCTGAAG GGGCCCGGCG TCCGGTGCGT TCGCCGCGGG CGAC                     224
```

(2) INFORMATION FOR SEQ ID NO:273:

(i) SEQUENCE CHARACTERISTICS:
        (A) LENGTH: 521 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:273:

```
TGAACTGACT GCCCCGCTCG ATCGGCGGCG GCGGCGTGTC ATAGCTGCGC CGCCAGGCCA     60

TGAACTGCTC TTCGCCATAG CGGGCCTTGG TCTCGGCCTT GTCCAAACCC TGCAGCGCGC    120

CGTAGTGGCG TTCGTTGAGC CGCCAGCTAC GCCGCACGGG AATCCAGAGC CGATCGGCGC    180

TGTCCAACGC CAGATGCGCG GTGGTGATCG CGCGCCGCAG CAACGAGGTG TAGAGCACGT    240

CGGGCAATAG GTCGTGTTCC GCGATCAGCT CGCCGCTTCG AACCGCCTCT GCCTGGCCCT    300

TGTCCGTCAG GCCGACATCG ACCCAGCCGG TGAACAGGTT GAGGGCATTC CAGTCGCTCT    360

CGCCGTGGCG CAGCAACACC AGGCTGCCAG TGTTTGCCAT ACCGGCAAGT CTCTCACGCA    420

CTCCCGCACT CCTCATCGTG GACCAAAATG CCCGAATTCT CCTCGGTCCG CTGCGCAGCG    480

CGTTCATACC GCCGAGGTGG TCGGCACCGT AACGGCCGGT T                        521
```

(2) INFORMATION FOR SEQ ID NO:274:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:274:

```
CTCCAGGCTC ATTCGCTCGA ACAAAGCCAC CCGGCCGTAC AGCGGACGCC CCCATTCGTT     60

GTCGTGATAG TCGCGGTACA GCTGGGCATC GGGCCCTGGA CGAACCTCCG CCCAGGGGCA    120

GCGAACCAGC CCGTCGCCGC TCACGCGGGG TCAGAACGGT AGTGCACGAC AGTCTCGCCG    180

CGCGAAGGGT TTGACGCGTC AGACTCGGCC TCGGCGTCTT CCGACGAGGC GTGGATCGCC    240
```

CCGAGCTGAG AGCGTAGCGC CTCGAGCTCA CGGCCGAGCC GTTCCAGCAC CCAGTCCACC   300

TCGCTGGTCT TGTTCCCGCG CAGCACCTGC GTGAACTTGA CCGCGTCGAC ATCGGCGCGG   360

GTGACCCCGA ACGCCGGCAG CGTCGTCGCC GTCGTCGCCC GCGGCAGGGG CGGCAACTGC   420

TCGCCA                                                             426

(2) INFORMATION FOR SEQ ID NO:275:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:275:

GCGGACACGG CGGACAAAGC GCAATCGGCC TCGGCGGCGG CGCCGGCGGC GACGGGGGCC    60

AGGGCGGCGC CGGCCGCGGA CTGTGGGGTA CTGGCGGCGC CGGCGGACAC GGCGGGGCAA   120

GGCGGTGGTA CCGGGGGCCC ACCGCTGCCC GGTCAGGCAG GCATGGGCGC CGCGGGTGGC   180

GCCGGTGGGC TGATCGGCAA CGGCGGGGCC GGCGGCGAC                         219

(2) INFORMATION FOR SEQ ID NO:276:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:276:

AAGATCATCG GCGCCGCTCC TTAGCATCGC TGCGCTCTGC ATCGTCGCCG GCGCGGATCA    60

CGGAGGTCCG GCCTTGTACC CCACTCCTCG AACGGTCAGC ACCACAGTCG GGTTCTCGGG   120

ATCCTTTTCG ACCTTGGCCC GCAGACGCTG GACATGCACG TTCACCAGCC TGGTATCGGC   180

TGGGTGCCGG TAACCCCATA CCTGTTCGAG CAGCACATCA CGAGTAAACA CCTGGCGCGG   240

CTTGCGCGCC AATGCGACCA ACAGGTCGAA TTCCAGCGGT GTCAACGAGA TCTGCTCACC   300

GTTGCGAGTG ACCTTGTGCG CCGGTACGTC GATTTCTACG TCGGCGATGG ACAGCATCTC   360

GGCGGGTTCG TCGTCGTTGC GGCGCAGCCG CGCCCGCACC CGCGCAACCA GCTCCTTGGG   420

CTTGAACGGC TTCATGATGT AGTCGTCGGC GCCCGACTCC AGACCCAGCA CCACATCCAC   480

GGTGTCGGTC TTTGCGGTGA GCATCACGAT CGGAACACCG GAATCGGCGC GCAACACCCG   540

GCACACGTCG ATGCCGTTCA TACCGGGGCA A                                 571

(2) INFORMATION FOR SEQ ID NO:277:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:277:

Leu Phe Gly Ala Gly Gly Val Gly Gly Val Gly Gly Asp Gly Val Ala
 1               5                  10                  15

Phe Leu Gly Thr Ala Pro Gly Gly Pro Gly Gly Ala Gly Gly Ala Gly

```
            20                  25                  30
Gly Leu Phe Ser Val Gly Gly Ala Gly Gly Ile Gly Leu
             35                  40                  45
Val Gly Asn Ser Gly Ala Gly Ser Gly Gly Ser Ala Leu Leu Trp
 50                  55                  60
Gly Asp Gly Gly Ala Gly Ala Gly Gly Val Gly Ser Thr Thr Gly
 65                  70                  75                  80
Gly Ala Gly Gly Ala Gly Gly Asn Ala Ser Leu Leu Val
                 85                  90
```

(2) INFORMATION FOR SEQ ID NO:278:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:278:

```
Met Pro Pro Val Ser Ala Asn Ala Met Val Pro Ala His Ser Thr Pro
 1               5                  10                  15
Pro Val Ala Asn Ile Glu Val Asn Thr Pro
             20                  25
```

(2) INFORMATION FOR SEQ ID NO:279:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:279:

```
Lys Pro Asp Arg Pro Ala Ala Thr Val Gly Ser Cys Thr Thr Val Arg
 1               5                  10                  15
Ala Pro Cys Ser Gln Pro Val Thr Thr Ala
             20                  25
```

(2) INFORMATION FOR SEQ ID NO:280:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:280:

```
Trp Pro Ala Gly Arg Pro Met His Pro Ala Pro Gly Thr Ser Ala Asp
 1               5                  10                  15
His Pro Pro Asn
             20
```

(2) INFORMATION FOR SEQ ID NO:281:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:281:

| Val | Leu | Val | Ala | Gly | Cys | Ser | Ser | Asn | Pro | Leu | Ala | Asn | Phe | Ala | Pro |
|---|---|---|---|---|---|---|---|---|---|---|---|---|---|---|---|
| 1 | | | | 5 | | | | | 10 | | | | | 15 | |

| Gly | Tyr | Pro | Pro | Thr | Ile | Glu | Pro | Ala | Gln | Pro | Ala | Val | Ser | Pro | Pro |
|---|---|---|---|---|---|---|---|---|---|---|---|---|---|---|---|
| | | | 20 | | | | | 25 | | | | | 30 | | |

| Thr | Ser | Gln | Asp | Pro | Ala | Gly | Ala | Val | Arg | Pro | Leu | Ser | Gly | His | Pro |
|---|---|---|---|---|---|---|---|---|---|---|---|---|---|---|---|
| | | | 35 | | | | | 40 | | | | | 45 | | |

| Arg | Ala | Ala | Leu | Phe | Asp | Asn | Gly | Thr | Arg | Gln | Leu | Val | Ala | Leu | Arg |
|---|---|---|---|---|---|---|---|---|---|---|---|---|---|---|---|
| | 50 | | | | | 55 | | | | | 60 | | | | |

| Pro | Gly | Ala | Asp | Ser | Ala | Ala | Pro | Ala | Ser | Ile | Met | Val | Phe | Asp | Asp |
|---|---|---|---|---|---|---|---|---|---|---|---|---|---|---|---|
| 65 | | | | | 70 | | | | | 75 | | | | | 80 |

| Met | His | Val | Ala | Pro | Arg | Val | Ile | Phe | Leu | Pro | Gly | Pro | Ala | Ala | Ala |
|---|---|---|---|---|---|---|---|---|---|---|---|---|---|---|---|
| | | | | 85 | | | | | 90 | | | | | 95 | |

| Leu | Thr | Ser | Asp | Asp | His | Gly | Thr | Ala | Phe | Leu | Ala | Ala | Arg | Gly | Gly |
|---|---|---|---|---|---|---|---|---|---|---|---|---|---|---|---|
| | | | | 100 | | | | | 105 | | | | | 110 | |

| Tyr | Phe | Val | Ala | Asp | Leu | Ser | Ser | Gly | His | Thr | Ala | Arg | Val | Asn | Val |
|---|---|---|---|---|---|---|---|---|---|---|---|---|---|---|---|
| | | | | 115 | | | | | 120 | | | | | 125 | |

| Ala | Asp | Ala | Ala | His | Thr | Asp | Phe | Thr | Ala | Ile | Ala |
|---|---|---|---|---|---|---|---|---|---|---|---|
| | 130 | | | | | 135 | | | | | 140 |

(2) INFORMATION FOR SEQ ID NO:282:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:282:

| Met | His | Ile | Thr | Leu | Asn | Ala | Ile | Leu | Arg | Ala | Ile | Phe | Gly | Ala | Gly |
|---|---|---|---|---|---|---|---|---|---|---|---|---|---|---|---|
| 1 | | | | 5 | | | | | 10 | | | | | 15 | |

| Gly | Ser | Glu | Leu | Asp | Glu | Leu | Arg | Arg | Leu | Ile | Pro | Pro | Trp | Val | Thr |
|---|---|---|---|---|---|---|---|---|---|---|---|---|---|---|---|
| | | | 20 | | | | | 25 | | | | | 30 | | |

| Leu | Gly | Ser | Arg | Leu | Ala | Ala | Leu | Pro | Lys | Pro | Lys | Arg | Asp | Tyr | Gly |
|---|---|---|---|---|---|---|---|---|---|---|---|---|---|---|---|
| | | | 35 | | | | | 40 | | | | | 45 | | |

| Arg | Leu | Ser | Pro | Trp | Gly | Arg | Leu | Ala | Glu | Trp | Arg | Arg | Gln | Tyr | Asp |
|---|---|---|---|---|---|---|---|---|---|---|---|---|---|---|---|
| | 50 | | | | | 55 | | | | | 60 | | | | |

| Thr | Val | Ile | Asp | Glu | Leu | Ile | Glu | Ala | Glu | Arg | Ala | Asp | Pro | Asn | Phe |
|---|---|---|---|---|---|---|---|---|---|---|---|---|---|---|---|
| 65 | | | | | 70 | | | | | 75 | | | | | 80 |

| Ala | Asp | Arg | Thr | Asp | Val | Leu | Ala | Leu | Met | Leu | Arg | Ser | Thr | Tyr | Asp |
|---|---|---|---|---|---|---|---|---|---|---|---|---|---|---|---|
| | | | | 85 | | | | | 90 | | | | | 95 | |

| Asp | Gly | Ser | Ile | Met | Ser | Arg | Lys | Asp | Ile | Gly | Asp | Glu | Leu | Leu | Thr |
|---|---|---|---|---|---|---|---|---|---|---|---|---|---|---|---|
| | | | | 100 | | | | | 105 | | | | | 110 | |

| Leu | Leu | Ala | Ala | Gly | His | Glu | Thr | Thr | Ala | Ala | Thr | Trp | Ala | Gly | Arg |
|---|---|---|---|---|---|---|---|---|---|---|---|---|---|---|---|
| | | | | 115 | | | | | 120 | | | | | 125 | |

| Ser | Asn | Gly | Ser | Thr | Gly | Thr | Pro | Thr | Cys | Ser | Arg | Leu | Trp |
|---|---|---|---|---|---|---|---|---|---|---|---|---|---|
| | 130 | | | | | 135 | | | | | 140 | | |

(2) INFORMATION FOR SEQ ID NO:283:

(i) SEQUENCE CHARACTERISTICS:
        (A) LENGTH: 163 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:283:

Val Leu Val Ala Gly Cys Ser Ser Asn Pro Leu Ala Asn Phe Ala Pro
1               5                   10                  15

Gly Tyr Pro Pro Thr Ile Glu Pro Ala Gln Pro Ala Val Ser Pro Pro
            20                  25                  30

Thr Ser Gln Asp Pro Ala Gly Ala Val Arg Pro Leu Ser Gly His Pro
        35                  40                  45

Arg Ala Ala Leu Phe Asp Asn Gly Thr Arg Gln Leu Val Ala Leu Arg
    50                  55                  60

Pro Gly Ala Asp Ser Ala Ala Pro Ala Ser Ile Met Val Phe Asp Asp
65                  70                  75                  80

Val His Val Ala Pro Arg Val Ile Phe Leu Pro Gly Pro Ala Ala Ala
                85                  90                  95

Leu Thr Ser Asp Asp His Gly Thr Ala Phe Leu Ala Ala Arg Gly Gly
            100                 105                 110

Tyr Phe Val Ala Asp Leu Ser Ser Gly His Thr Ala Arg Val Asn Val
        115                 120                 125

Ala Asp Ala Ala His Thr Asp Phe Thr Ala Ile Ala Arg Arg Ser Asp
130                 135                 140

Gly Lys Leu Val Leu Gly Ser Ala Asp Gly Ala Val Tyr Thr Leu Ala
145                 150                 155                 160

Lys Asn Pro (2) INFORMATION FOR SEQ ID NO:284:

(i) SEQUENCE CHARACTERISTICS:
        (A) LENGTH: 240 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:284:

Trp Gly Ala Pro Pro Ser Gly Gly Pro Ser Pro Trp Ala Gln Thr Pro
1               5                   10                  15

Arg Lys Thr Asn Pro Trp Pro Leu Val Ala Gly Ala Ala Ala Val Val
            20                  25                  30

Leu Val Leu Val Leu Gly Ala Ile Gly Ile Trp Ile Ala Ile Arg Pro
        35                  40                  45

Lys Pro Val Gln Pro Pro Gln Pro Val Ala Glu Glu Arg Leu Ser Ala
    50                  55                  60

Leu Leu Leu Asn Ser Ser Glu Val Asn Ala Val Met Gly Ser Ser Ser
65                  70                  75                  80

Met Gln Pro Gly Lys Pro Ile Thr Ser Met Asp Ser Ser Pro Val Thr
                85                  90                  95

Val Ser Leu Pro Asp Cys Gln Gly Ala Leu Tyr Thr Ser Gln Asp Pro
            100                 105                 110

Val Tyr Ala Gly Thr Gly Tyr Thr Ala Ile Asn Gly Leu Ile Ser Ser
        115                 120                 125

Glu Pro Gly Asp Asn Tyr Glu His Trp Val Asn Gln Ala Val Val Ala
    130                 135                 140

Phe Pro Thr Ala Asp Lys Ala Arg Ala Phe Val Gln Thr Ser Ala Asp

```
145                 150                 155                 160
Lys Trp Lys Asn Cys Ala Gly Lys Thr Val Thr Val Thr Asn Lys Ala
                165                 170                 175
Lys Thr Tyr Arg Trp Thr Phe Ala Asp Val Lys Gly Ser Pro Pro Thr
            180                 185                 190
Ile Thr Val Ile Asp Thr Gln Glu Gly Ala Glu Gly Trp Glu Cys Gln
        195                 200                 205
Arg Ala Met Ser Val Ala Asn Asn Val Val Asp Val Asn Ala Cys
    210                 215                 220
Gly Tyr Gln Ile Thr Asn Gln Ala Gly Gln Ile Ala Ala Lys Ile Cys
225                 230                 235                 240

(2) INFORMATION FOR SEQ ID NO:285:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:285:

Asp Val Val Glu Ala Ala Ile Ala Arg Ala Glu Ala Val Asn Pro Ala
1               5                   10                  15
Leu Asn Ala Leu Ala Tyr
            20

(2) INFORMATION FOR SEQ ID NO:286:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:286:

Leu His Pro Ala Gly Ala Thr Asn Gly Ser Gly Gln Leu Ala Leu Pro
1               5                   10                  15
Val Glu Ala Pro Pro Arg Ser Val Pro Ser His Gly Glu Pro Leu Gly
            20                  25                  30
Ser Ala Ala Pro Glu Gly Leu Glu Gly Glu Phe Asp Asp Arg Ile Asp
        35                  40                  45
Glu Arg Phe Pro Val Phe Ser Ser Ala Ser Leu Ala Glu Ala Leu Pro
    50                  55                  60
Gly Pro Leu Thr Pro Met Thr Leu Asp Val Gln Leu Ser Gly Leu Arg
65                  70                  75                  80
Ala Ala Gly Arg Ala Met Gly Arg Val Leu Ala Leu Gly Gly Val Val
                85                  90                  95
Ala Asp Glu Trp Glu Arg Arg Ala Ile Ala Val Phe Gly His Arg Pro
            100                 105                 110
Tyr Ile Gly Val Ser Ala Asn Ile Val Ala Ala Gln Leu Pro Gly
        115                 120                 125
Trp Asp Ala Gln Ala Val Thr Arg Arg Ala Leu Gly Glu Gln Pro Gln
    130                 135                 140
Val Thr Glu Leu Leu Pro Phe Gly Arg Pro Gln Leu Ala Gly Gly Pro
145                 150                 155                 160
```

```
Leu Gly Ser Val Ala Lys Val Val Thr Ala Arg Ser Leu
            165                 170
```

(2) INFORMATION FOR SEQ ID NO:287:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:287:

```
Val Gly Val Val Gly Val Gly Ala Thr Ser Pro Ala Gly Ala Gly Ala
 1               5                  10                  15

Gly Ala Gly Ser Ala Gly Thr Gly Ala Gly Ala Gly Gly Ala Thr
            20                  25                  30

Lys Gly Arg Ile Asp Ser Ala Ser Ala Leu Ala Ala Pro Leu Ser Thr
            35                  40                  45

Gly Leu Leu Ala Val Pro Ser His Thr Thr Asn Gln Arg
            50                  55                  60
```

(2) INFORMATION FOR SEQ ID NO:288:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:288:

```
Met Ala Asn Thr Gly Ser Leu Val Leu Leu Arg His Gly Glu Ser Asp
 1               5                  10                  15

Trp Asn Ala Leu Asn Leu Phe Thr Gly Trp Val Asp Val Gly Leu Thr
            20                  25                  30

Asp Lys Gly Gln Ala Glu Ala Val Arg Ser Gly Glu Leu Ile Ala Glu
            35                  40                  45

His Asp Leu Leu Pro Asp Val Leu Tyr Thr Ser Leu Leu Arg Arg Ala
            50                  55                  60

Ile Thr Thr Ala His Leu Ala Leu Asp Ser Ala Asp Arg Leu Trp Ile
65                  70                  75                  80

Pro Val Arg Arg Ser Trp Arg Leu Asn Glu Arg His Tyr Gly Ala Leu
                85                  90                  95

Gln Gly Leu Asp Lys Ala Glu Thr Lys Ala Arg Tyr Gly Glu Glu Gln
            100                 105                 110

Phe Met Ala Trp Arg Arg Ser Tyr Asp Thr Pro Pro Pro Ile Glu
            115                 120                 125

Arg Gly Ser Gln Phe
            130
```

(2) INFORMATION FOR SEQ ID NO:289:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:289:

```
Pro Gly Ser Phe Ala Arg Thr Lys Pro Pro Gly Arg Thr Ala Asp Ala
1               5                   10                  15

Pro Ile Arg Cys Arg Asp Ser Arg Gly Thr Ala Gly His Arg Ala Leu
            20                  25                  30

Asp Glu Pro Pro Pro Arg Gly Ser Glu Pro Ala Arg Arg Arg Ser Arg
            35                  40                  45

Gly Val Arg Thr Val Val His Asp Ser Leu Ala Ala Arg Arg Val
            50                  55                  60
```

(2) INFORMATION FOR SEQ ID NO:290:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:290:

```
Gly His Gly Gly Gln Ser Ala Ile Gly Leu Gly Gly Ala Gly Gly
1               5                   10                  15

Asp Gly Gly Gln Gly Gly Ala Gly Arg Gly Leu Trp Gly Thr Gly Gly
            20                  25                  30

Ala Gly Gly His Gly Gly Ala Arg Arg Trp Tyr Arg Gly Pro Thr Ala
            35                  40                  45

Ala Arg Ser Gly Arg His Gly Arg Arg Gly Trp Arg Arg Trp Ala Asp
            50                  55                  60

Arg Gln Arg Arg Gly Arg Arg Arg
65                  70
```

(2) INFORMATION FOR SEQ ID NO:291:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:291:

```
Asp His Arg Arg Arg Ser Leu Ala Ser Leu Arg Ser Ala Ser Ser Pro
1               5                   10                  15

Ala Arg Ile Thr Glu Val Arg Pro Cys Thr Pro Leu Leu Glu Arg Ser
            20                  25                  30

Ala Pro Gln Ser Gly Ser Arg Asp Pro Phe Arg Pro Trp Pro Ala Asp
            35                  40                  45

Ala Gly His Ala Arg Ser Pro Ala Trp Tyr Arg Leu Gly Ala Gly Asn
            50                  55                  60

Pro Ile Pro Val Arg Ala Ala His His Glu
65                  70
```

(2) INFORMATION FOR SEQ ID NO:292:

(i) SEQUENCE CHARACTERISTICS:
        (A) LENGTH: 174 base pairs
        (B) TYPE: nucleic acid
        (C) STRANDEDNESS: single
        (D) TOPOLOGY: linear -continued (ii) MOLECULE TYPE: cDNA (xi) SEQUENCE DESCRIPTION: SEQ ID NO:292:

| | | | | |
|---|---|---|---|---|
| CCGCACGTAA CACCGTGAAT TGAAGGGAGC CGCTGGTCAT GGGCCGATTC TATCCGTGGG | 60 |
| CGAACGGTTA TTGACGGCCC GGAGGCCACT CCGCTGCCAC CAAGTGGTGA CTCAGCGCGT | 120 |
| TTTCACGGCA ACGAACGGCG GACACACCAC TTGACATTCG ACAGCACGGC CGCG | 174 |

(2) INFORMATION FOR SEQ ID NO:293:

(i) SEQUENCE CHARACTERISTICS:
        (A) LENGTH: 404 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:293:

| | |
|---|---|
| TCGCAAACGG GGTGACGTTC CGTCCGGTGG CGCTAGAGAG TTTGTCGCAC TTTCCGGTGA | 60 |
| CCGTCGCCGC GCACCGCAGC ACCGGTGAGC TCACGCTGCT AGTGGAGGTG CTCGACGGTG | 120 |
| CGCTGGGCAC GATGGCGCCC GAAAGCCTCG GCAGGCGGGT GCTGGCTGTG TTACAGCGCT | 180 |
| TGGTCAGCCG GTGGGATCGG CCGCTGCGCG ACGTCGACAT TCTGCTGGAC GGCGAGCACG | 240 |
| ATCCGACCGC ACCCGGCCTG CCGGATGTGA CGACGTCGGC ACCCGCGGTG CATACCCGGT | 300 |
| TCGCCGAAAT CGCTGCGGCA CAGCCTGACT CGGTGGCGGT CAGTTGGGCG GATGGTCAGC | 360 |
| TGACGTACCG GGAGCTGGAT GCATTGGCCG ACCGGCTGGC CACT | 404 |

(2) INFORMATION FOR SEQ ID NO:294:

(i) SEQUENCE CHARACTERISTICS:
        (A) LENGTH: 134 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:294:

Ala Asn Gly Val Thr Phe Arg Pro Val Ala Leu Glu Ser Leu Ser His
1                  5                    10                  15

Phe Pro Val Thr Val Ala Ala His Arg Ser Thr Gly Glu Leu Thr Leu
                20                    25                    30

Leu Val Glu Val Leu Asp Gly Ala Leu Gly Thr Met Ala Pro Glu Ser
                35                    40                    45

Leu Gly Arg Arg Val Leu Ala Val Leu Gln Arg Leu Val Ser Arg Trp
50                  55                    60

Asp Arg Pro Leu Arg Asp Val Asp Ile Leu Leu Asp Gly Glu His Asp
65                  70                    75                    80

Pro Thr Ala Pro Gly Leu Pro Asp Val Thr Thr Ser Ala Pro Ala Val
                85                    90                    95

His Thr Arg Phe Ala Glu Ile Ala Ala Gln Pro Asp Ser Val Ala
                100                   105                  110

Val Ser Trp Ala Asp Gly Gln Leu Thr Tyr Arg Glu Leu Asp Ala Leu
                115                   120                  125

Ala Asp Arg Leu Ala Thr
                130

(2) INFORMATION FOR SEQ ID NO:295:

(i) SEQUENCE CHARACTERISTICS:
    (A) LENGTH: 526 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:295:

| | | | | | |
|---|---|---|---|---|---|
| GCTTCGACGG | CTACGAGTAC | CTGTTCTGGG | TGGGTTGTGC | GGGCGCCTAC | GACGACAAGG | 60 |
| CCAAGAAGAC | CACCAAGGCC | GTCGCCGAGC | TGTTCGCCGT | CGCCGGGGTG | AAATACTTGG | 120 |
| TGCTGGGCGC | TGGGGAAACC | TGCAACGGCG | ACTCGGCGCG | CCGCTCCGGC | AACGAGTTCC | 180 |
| TCTTCCAGCA | GCTGGCACAA | CAGGCCGTCG | AGACCCTGGA | CGGTTTGTTC | GAGGGTGTGG | 240 |
| AGACCGTCGA | CCGCAAGATC | GTTGTCACCT | GCCCGCACTG | CTTCAACACC | ATCGGCAAGG | 300 |
| AATATCGGCA | GCTGGGCGCC | AACTACACCG | TGCTGCACCA | CACCCAGCTG | CTCAATCGGT | 360 |
| TGGTGCGCGA | CAAGAGGCTG | GTCCCTGTCA | CTCCGGTTTC | TCAGGACATC | ACCTACCACG | 420 |
| ACCCGTGCTA | CCTGGGTCGG | CACAACAAGG | TCTACGAGGC | ACCACGGGAG | CTGATCGGTG | 480 |
| CCGCGGGGGC | CACCTGAGCC | GAGATGCCGC | GCCATGCCGA | CCGCAG | | 526 |

(2) INFORMATION FOR SEQ ID NO:296:

(i) SEQUENCE CHARACTERISTICS:
    (A) LENGTH: 487 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:296:

| | | | | | |
|---|---|---|---|---|---|
| CTCGCCGCCG | TGATCTGGCC | GGCGAACTTC | GTCAGTGCAT | CCAGACCCCA | ACGATCATCG | 60 |
| ATCAGGCCGA | TGCCCATGAT | CACCGCACCG | GCCACCAGCA | CCGCGGGCAT | GCCGGTGGAA | 120 |
| TAGACGAACC | CCCGGGTGAG | TGCCGGAAGC | TGGGAGGCAA | GAAAGACGGC | GCCGACAATG | 180 |
| CCCAGGAACA | TCGCCAACCC | ACCCATCCGA | GGGGTAGGCG | TGACGTGCAC | ATCTCGCTCC | 240 |
| CGCGGGTAGG | CGACGGCTCC | CAGGCGACTG | GCCAGCATCC | GCACCGGACC | GGTCGCAAAA | 300 |
| TAGGTGATGA | TCGCCGCGGT | CAGCCCGACC | AGCGCAAGCT | CACGCAGCGG | GACACCGGCG | 360 |
| CCGCGATAGG | ACAGGGCGAG | CAAGCCACCG | GCAACGCCGG | CCACATCGCT | GGACACCTCG | 420 |
| AGACCGTACT | GCACCAACCT | GAAGAGCTGA | ACACTCGCCG | AACGTGCAAC | AGCTGCGAAC | 480 |
| AATTGGG | | | | | | 487 |

(2) INFORMATION FOR SEQ ID NO:297:

(i) SEQUENCE CHARACTERISTICS:
    (A) LENGTH: 528 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:297:

| | | | | | |
|---|---|---|---|---|---|
| ACGAAGCGCG | AGAATATGAG | CCGGGGCAAC | CCGGCATGTA | CGAGCTTGAG | TTCCCGGCGC | 60 |
| CTCAGCTGTC | GTCGTCCGAC | GGCCGTGGTC | CGGTGTTGGT | GCACGCTTTG | GAAGGTTTCT | 120 |
| CCGACGCCGG | CCATGCGATC | CGGCTGGCCG | CCGCCCACCT | CAAGGCGGCC | CTGGACACAG | 180 |

```
AGCTGGTCGC GTCCTTCGCG ATCGATGAAC TACTGGACTA CCGCTCGCGG CGGCCATTAA    240

TGACTTTCAA GACCGATCAT TTCACCCACT CCGATGATCC TGAGCTAAGC CTGTATGCGC    300

TGCGCGACAG CATCGGCACC CCATTTCTGC TGCTGGCGGG TTTGGAGCCG GACCTGAAGT    360

GGGAGCGGTT CATCACCGCC GTCCGATTGC TGGCCGAGCG CCTGGGTGTA CGGCAGAACC    420

ATCGGCCTGG GCACCGTCCC GATGGCCGTT CCGCACACAC GACCGATCAC GATGACCGCT    480

CATTCCAACA ACCGGGAGCT ATCTCCGATT TTCAACCGTT CGATCTCC                528

(2) INFORMATION FOR SEQ ID NO:298:

(i) SEQUENCE CHARACTERISTICS:
        (A) LENGTH: 610 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:298:

CCAAGCCCGT CAAGGAGCCG GTGCCGGCCT TGCCTCCGGT GCCGCCGACG CCGGCGTTGC     60

CGCCGTTGCC GCCGTTGCCG CCGGTACCGG GGTTTCCTAC GGTGCCGCCG CCCGGCAGCA    120

TGGCCCCGCT GTTTAGGCCG TTTTCGCCGG CCCCGCCGTC ACCGGCTTTG CCGCCATCGC    180

CGCCGTTGCC GCCGCTGGTG GGGGTGGCGG CCTGGTTGAC GTATTGTTCC ACCGGCCCGG    240

CCCTTGACCC TTTGGCGGTG TCGATCGCGG CGTCGATGGA TCCGCCGACC ACGACGTGCG    300

AAGCCTCGCC TGCCGCCGCA GCCGCCCAAC TGTGTCGCGG CTCCTGCGAT TTGGCCCCGG    360

CCGACGAGAT GATGGGCACC ACCGGAGCCT GCGGCCGTCT GGGGGAGGCC AGCGCGGGTT    420

CGCGGTCACG CCATACGCGA CGGTGCGCCG CCGCTTCGGA GATTTGCAGG CTGCGTTGCA    480

CCAGATCGAG CAGCGGTGTG CCCAGGGACT GGGTTAGCCC GTTGGCGCCG CCGTTGTAGC    540

GGCGAGCGCA ATATCGGTGC CCACTCGACC CAACCGCGAC TCCATAAGCG ACACCATTCG    600

CGGTTGATGC                                                          610

(2) INFORMATION FOR SEQ ID NO:299:

(i) SEQUENCE CHARACTERISTICS:
        (A) LENGTH: 164 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:299:

Phe Asp Gly Tyr Glu Tyr Leu Phe Trp Val Gly Cys Ala Gly Ala Tyr
 1               5                  10                  15

Asp Asp Lys Ala Lys Lys Thr Thr Lys Ala Val Ala Glu Leu Phe Ala
                20                  25                  30

Val Ala Gly Val Lys Tyr Leu Val Leu Gly Ala Gly Glu Thr Cys Asn
            35                  40                  45

Gly Asp Ser Ala Arg Arg Ser Gly Asn Glu Phe Leu Phe Gln Gln Leu
        50                  55                  60

Ala Gln Gln Ala Val Glu Thr Leu Asp Gly Leu Phe Glu Gly Val Glu
65                  70                  75                  80

Thr Val Asp Arg Lys Ile Val Val Thr Cys Pro His Cys Phe Asn Thr
                85                  90                  95

Ile Gly Lys Glu Tyr Arg Gln Leu Gly Ala Asn Tyr Thr Val Leu His
```

```
                100             105             110
His Thr Gln Leu Leu Asn Arg Leu Val Arg Asp Lys Arg Leu Val Pro
            115                 120             125

Val Thr Pro Val Ser Gln Asp Ile Thr Tyr His Asp Pro Cys Tyr Leu
        130                 135             140

Gly Arg His Asn Lys Val Tyr Glu Ala Pro Arg Glu Leu Ile Gly Ala
145                 150                 155                 160

Ala Gly Ala Thr (2) INFORMATION FOR SEQ ID NO:300:

(i) SEQUENCE CHARACTERISTICS:
        (A) LENGTH: 161 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:300:

Arg Arg Arg Asp Leu Ala Gly Glu Leu Arg Gln Cys Ile Gln Thr Pro
1               5                   10                  15

Thr Ile Ile Asp Gln Ala Asp Ala His Asp His Arg Thr Gly His Gln
            20                  25                  30

His Arg Gly His Ala Gly Gly Ile Asp Glu Pro Pro Gly Glu Cys Arg
        35                  40                  45

Lys Leu Gly Gly Lys Lys Asp Gly Ala Asp Asn Ala Gln Glu His Arg
    50                  55                  60

Gln Pro Thr His Pro Arg Gly Arg Arg Asp Val His Ile Ser Leu Pro
65              70                  75                  80

Arg Val Gly Asp Gly Ser Gln Ala Thr Gly Gln His Pro His Arg Thr
                85                  90                  95

Gly Arg Lys Ile Gly Asp Asp Arg Arg Gly Gln Pro Asp Gln Arg Lys
            100                 105                 110

Leu Thr Gln Arg Asp Thr Gly Ala Ala Ile Gly Gln Gly Glu Gln Ala
        115                 120                 125

Thr Gly Asn Ala Gly His Ile Ala Gly His Leu Glu Thr Val Leu His
    130                 135                 140

Gln Pro Glu Glu Leu Asn Thr Arg Arg Thr Cys Asn Ser Cys Glu Gln
145                 150                 155                 160

Leu (2) INFORMATION FOR SEQ ID NO:301:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:301:

Glu Ala Arg Glu Tyr Glu Pro Gly Gln Pro Gly Met Tyr Glu Leu Glu
1               5                   10                  15

Phe Pro Ala Pro Gln Leu Ser Ser Asp Gly Arg Gly Pro Val Leu
            20                  25                  30

Val His Ala Leu Glu Gly Phe Ser Asp Ala Gly His Ala Ile Arg Leu
        35                  40                  45
```

```
Ala Ala Ala His Leu Lys Ala Leu Asp Thr Glu Leu Val Ala Ser
     50                  55                  60

Phe Ala Ile Asp Glu Leu Leu Asp Tyr Arg Ser Arg Arg Pro Leu Met
 65                  70                  75                  80

Thr Phe Lys Thr Asp His Phe Thr His Ser Asp Asp Pro Glu Leu Ser
                 85                  90                  95

Leu Tyr Ala Leu Arg Asp Ser Ile Gly Thr Pro Phe Leu Leu Leu Ala
            100                 105                 110

Gly Leu Glu Pro Asp Leu Lys Trp Glu Arg Phe Ile Thr Ala Val Arg
        115                 120                 125

Leu Leu Ala Glu Arg Leu Gly Val Arg Gln Asn His Arg Pro Gly His
    130                 135                 140

Arg Pro Asp Gly Arg Ser Ala His Thr Thr Asp His Asp Asp Arg Ser
145                 150                 155                 160

Phe Gln Gln Pro Gly Ala Ile Ser Asp Phe Gln Pro Phe Asp Leu
                165                 170                 175
```

(2) INFORMATION FOR SEQ ID NO:302:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:302:

```
Lys Pro Val Lys Glu Pro Val Pro Ala Leu Pro Pro Val Pro Pro Thr
 1               5                  10                  15

Pro Ala Leu Pro Pro Leu Pro Pro Leu Pro Pro Val Pro Gly Phe Pro
             20                  25                  30

Thr Val Pro Pro Pro Gly Ser Met Ala Pro Leu Phe Arg Pro Phe Ser
         35                  40                  45

Pro Ala Pro Pro Ser Pro Ala Leu Pro Pro Ser Pro Leu Pro Pro
 50                  55                  60

Leu Val Gly Val Ala Ala Trp Leu Thr Tyr Cys Ser Thr Gly Pro Ala
 65                  70                  75                  80

Leu Asp Pro Leu Ala Val Ser Ile Ala Ala Ser Met Asp Pro Pro Thr
                 85                  90                  95

Thr Thr Cys Glu Ala Ser Pro Ala Ala Ala Ala Gln Leu Cys Arg
            100                 105                 110

Gly Ser Cys Asp Leu Ala Pro Ala Asp Glu Met Met Gly Thr Thr Gly
        115                 120                 125

Ala Cys Gly Arg Leu Gly Glu Ala Ser Ala Gly Ser Arg Ser Arg His
    130                 135                 140

Thr Arg Arg Cys Ala Ala Ala Ser Glu Ile Cys Arg Leu Arg Cys Thr
145                 150                 155                 160

Arg Ser Ser Ser Gly Val Pro Arg Asp Trp Val Ser Pro Leu Ala Pro
                165                 170                 175

Pro Leu
```

(2) INFORMATION FOR SEQ ID NO:303:

(i) SEQUENCE CHARACTERISTICS:
        (A) LENGTH: 921 base pairs
        (B) TYPE: nucleic acid (C) STRANDEDNESS: single
            (D) TOPOLOGY: linear (ii) MOLECULE TYPE: Genomic DNA (xi) SEQUENCE DESCRIPTION: SEQ ID NO:303:

| | | | | | |
|---|---|---|---|---|---|
| AATTCGGCAC | GARCAGCACC | AACACCGGCT | TCTTCAACTC | CGGCGACGTC | AATACCGGTA | 60 |
| TCGGCAACAC | CGGCAGCTTC | AACACCGGCA | GCTTCAATCC | GGGCGATTCC | AACACCGGGG | 120 |
| ATTTCAACCC | ANGCAGCTAC | CACACGGGGA | CTCGGAAACA | CCGGCGATTT | TACACCGGCS | 180 |
| CCTTCATCTC | CGGCAGCTAC | AGCAACGGGT | CTTGTGGAGT | GGAAATTATC | AGGGCTCATT | 240 |
| GGNTGCACCC | GGSCTTRCGA | ATCCCTCGKG | CCAATTCAAC | TCCTCNACAA | GCTTGCGGCC | 300 |
| GCACTCSAGC | CCGGGTGAAT | GATTGAGTTT | AACCGCTNAN | CAATAACTAG | CATAACCCCT | 360 |
| TKGGGCCTCT | AAACGGGTCT | TGAAGGGTTT | TTTGCTGAAA | GGANGAACTA | TATCCGGATA | 420 |
| ACTGGCGTAN | TACGAAAAGC | CGCACCGATC | GCCTTCCCAA | CAGTTGCGCA | CCKGAATGGC | 480 |
| AATGGACCNC | CCTKTTACCG | GSCATTAACN | CGGGGGTGTN | GGKGTTACCC | CCACGTNACC | 540 |
| GCTACCTTGC | CANNSSCCTN | RSGCCGTCTT | TCSTTTCTTC | CTTCCTTCTC | CCMCTTCGCC | 600 |
| GGTTCCCNTC | AGCTCTAAAT | CGGGGNNCCC | TTTMGGGTTC | CAATTATTGC | TTACNGSCCC | 660 |
| CCACCCCAAA | AAYTNATTNG | GGTTAATGTC | CCTTMTTGGG | CNTCCCCCTA | WTNANNGTTT | 720 |
| TCCCCCTTNA | CTTTGRSTCC | CTTCYTTATW | NTGAMNCTNT | TTCCACYGGA | AAAMNCTCCA | 780 |
| CCNTTYSSGS | TTTCCTTTGA | WTTATMRGGR | AATTSCAATY | CCGCYTTKGG | TTMAANTTAA | 840 |
| CYTATTTCNA | ATTTTCCCGM | TTTTMMNATR | TTNSNCKCGM | KNCTCCNRKA | SSGNTTTCCT | 900 |
| CCCCCYTTSS | GKTYCCCCRN | G | | | | 921 |

(2) INFORMATION FOR SEQ ID NO:304:

(i) SEQUENCE CHARACTERISTICS:
            (A) LENGTH: 1082 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:304:

| | | | | | |
|---|---|---|---|---|---|
| AATTCGGCAC | GAGATANGGG | CGCACCGGGG | TCCGCAGCCG | GCGGGACCGT | CGCCAGCACC | 60 |
| ACCGGGGTCA | ACAGCACCAC | GGTGGCGTCC | ANGCAGAGCG | CCGCGGTGAT | GGCGGCCGAG | 120 |
| ACGGCRAACA | CCTGCCGTAG | CAGTCGGTGC | GACTCCGCGC | TCGCTCGANC | CATGGCCGCG | 180 |
| CCGGCTGCCT | CGAACANGCC | TTCGTCGTCC | ACAGCTTAGC | CAGCANCCAA | ACCGCACCCA | 240 |
| GAAACCCACA | CGCCCGCCGC | CCCGGANACC | TGCGCCATCG | KCTGCTGGGG | CGANATCCCC | 300 |
| CGATCGCTNA | CANGATGACC | GCTGCCGGAA | CGCCGCCGCT | GCCTCCGGGC | AGCCGCGTGG | 360 |
| GCSGGGCAAC | CGCGAACCCA | NGAACACGGC | AAGCAGTATC | ANCGCAACAG | CAATTGTCAA | 420 |
| GGGCTAAACG | CTTCACATCC | AGGGATCTCG | CGGCGCCACA | CCGTCGGMTC | TGCAGSGCGA | 480 |
| CCCCNTCCTN | GGGCGGNCAC | TCNTCAAAGA | TGCNGATCNA | CAGKCTAGGT | CTTCGGCCGA | 540 |
| TATGSAAGGN | CCCAACGGNT | TTAAAGCGGC | SAAAAAASTC | TCCCANTGGA | TAAAATCAGC | 600 |
| CGGGGANCCC | CCCGTGSCMM | NGTCYCGGKC | ATTNTTCAAC | MGGTTTNACG | GCGGKTGCNG | 660 |
| GCCAACTKGC | CAAAMTTAAG | KTNGGGGNTY | CGGGGCGGTA | ACCGGCNNTK | NGCCCCTTAA | 720 |
| AAAACCGGNC | YTTTCTKGAT | TAMMACCGGN | CCCCCAWTGG | CGGKTGKTCC | CANGNTYAAC | 780 |
| AMCCYCCCSS | MNGGGKTGGS | SAACCCTTCC | CGNGGGGTTC | NTKGTTSCYT | AWMCCCCCGG | 840 |

```
AAACCSGKYG GGKTGGCRTN WASSAMNCCC CMNGYYTCTT TAAAGGCCAN KNRAAWGKYT      900

CCTTGGGAAW CCTNCAATYC GAAAAYYCTC CTYMMGSSCN CTTKCWRTYN NRNGGGAACS      960

AMWTNYCCNC GWTTCAWTCG GGTCCGASMN AAACKCTTTY TTTTYCGSSC STCCMGGSNC     1020

SGGTKNANAN AAASATTTMC YYCNNNANKK YYYCSSGCTT CYKMGRRNRR GMGAACCCGR     1080

GS                                                                   1082
```

(2) INFORMATION FOR SEQ ID NO:305:

(i) SEQUENCE CHARACTERISTICS:
        (A) LENGTH: 990 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:305:

```
AATTGGCACG AGTGATCGCG CTGAAGCCGG TAGCGCGGGT GGCTCGGGTG GTTTGCGAAC       60

RAAATCCGCT CGANGTGGTC TCGGTAGGCG GTGTCCANAA CGGTGGCGCG GTGCCGGCGG      120

ATCTGATCGG CGCGGCCGTA GTGCACGTCG GCGGGCGTGT GCAGTCCGAT GCCGGAATGC      180

TTGTGTTCGT GGTTGTACCA GCCGAAGAAC CGGTCGCAGT GCACCCGGGC CGCCTCGATC      240

GACTCGAACC GTTTCGGGAA ATCGGGCCGG TACTTGAAGG TCTYGAACTG GGCCTCAGAC      300

AACGGGTTGT CTTGCTGGTG TGCGGGCGTG AGTGCGACTT GGTGACACCG AAGTCGGCCA      360

NCANCAATGC CACCGGTTTG GAACTCATCC ACAACCCCCG TCCGCGTCMA GGTCACTTGT      420

NCGGCGCTAA TTTNYTGGGC GGCAAGGGTT TGCCGAYCAN KCCGCTCGGC CAAAACTTCG      480

ANTCNCSCCA AGGCCNCCAT CCNCCCAAAC AMGTTACGGG ANAAAANATY CAAAGAYCAC      540

CYTCCGGKTN TTATANCTYC CCYTTTGSTY GGGCCCCCCN CYYTGKKNAT ACCCCTNCCA      600

AWTCCCAACN CCCKCCAANA RCYKGGGGCC CCCNCCAACC CGGGKGAAKA WTAATTTAAA      660

CCCYAACMAW ACTWMMNACC CNNGGGSCCY AAMCGTYYNR AGGTTTTSCT NAAAGAAASA      720

ANTCGGAAMC CGGNTSTACC AAAAASCCCK CCNWTCCCTC CRASATTGSC NCCSAAWKSA      780

AKGCCCCCNY TCSGCNWNNC CSGCGGKKKT KKGTTNCCCT WMRCWMWYTS GGCCNASCCN      840

CKYYSSMYCC CCCCTCCCCM CTCCGNKTCC CCAMCCYANC MGGCCCCYTM GKKCCCWKNT      900

YKGCCCCCCC AMMNNNGGGG WGACCCTNGG CCCCMKRRGM TCCCNANTGA MCCTCWGNRA      960

MKCYCCNRAR ANMCCSCNCC NGCNCRCKNN                                      990
```

(2) INFORMATION FOR SEQ ID NO:306:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:306:

```
AATTCGGGTG GCAACGCGGG CCTGTTCGGC AACGGCGGCG CCGGTGGTGC CGGTGGGGCT       60

GGTGGTGGCG CCGGCGGCGC GGGCGGTAAC GCGGGGTGGT TTGGTCATGG GGGCGCTGGC      120

GGCGTGGGTG GTGTANGTGC GGCCGGGGCC AACGGTGCTA CGCCCGGTCA GGATGGGGCG      180

GCTGGTGTTG CCGGGTCGGA CRACRCTCGT GCCGCTCGTG CCG                       223
```

(2) INFORMATION FOR SEQ ID NO:307:

(i) SEQUENCE CHARACTERISTICS:
        (A) LENGTH: 418 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:307:

```
AATTCGGCAC GANGCGGCAA CGGTGGCAGC GGCGGCACGT CNGTTGCCAC CGGGGGGGCC      60

GGGAACGGCG GTGCCGGCGG CGCCGGCGGC GGGGCCGGGC TGATCGGCAA CGGCSGCAAC     120

GGCGGCAGTG GCGGAATGGG CGATGCCCCG GGCGGCACCG GCGTCNGCGG CATCRGTGGG     180

CTGTTGTTGG GTTTGGACRG CGCCAACGCC CCGGCCAGCA CCAACCCGCT GCACACCGCG     240

CAGCACAGGC GTTGGCCGCA GTCAACGCGC CCATCCAGGC CGTGACCGGG CGCCCCTGAT     300

CGGCAACGCG CCAACGGCGC CCCGGGCAAC GGGGCCCCCG GCRGGCACGG CGGGTGGTTG     360

TTCGGCGGCG GAAGGAACGG CGGGTCCGGC GTCANCRGCG GGGCGGGCGG AAATGCCG      418
```

(2) INFORMATION FOR SEQ ID NO:308:

(i) SEQUENCE CHARACTERISTICS:
        (A) LENGTH: 1049 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:308:

```
AATTCGGCAC GAGGGGCACG ATCGCATACA GCGCTCGCGG CAGACCCGCC CGATACAGCA      60

GCTCGGCACA CGCGAGCGCA CAATACGGCG TCTGGCTGTC CGGCTTGARC ACCACCGCGT     120

TACCGGCCAC CAGCGCGGGC ACCGAGTCCG ACACCGTAAG CGTCATGGGG TAGTTCCACG     180

GCGAGATCAC CCCCACCACG CCCTTCGGTT GATAGCACAC CGTGGTCTTG CCTATCCCGG     240

GCAGCAGCGG CTGTGCCTTA CGGGGCTTCA GCAGGTCCAC ACAGACTCGT GCSTTATAAT     300

TNCGCSTTCC GCGATCAGAT CGACAATTTC CTCTTGCGCC GCCCATCGGG CCTTGCCCGC     360

CTCGGCTTGC AGGAAGTCCA TGAAGAACTC GCGGTTCTCG ATNAACAGGT CGCGATAGCG     420

GCSGATGACT GCAGCTCGCT CGATNACGGG ACCTTCGCCA GTCGGTCTGC GCCGCGCGAN     480

CTTCCGCGAA TGCCGCTTCG ACTTCCGCGG NCGTGCCAAC GGAATCNTAT CACGGGTTGC     540

CGGTTAAAAC TCCTCAATST NCYGGTCGAA ATTCGGCAAC TTCTTATCCC GGCAGGTRCC     600

AACSANNCAA ACCTCGGCAA GGTTAGGMTT TCCCCCNCTT YCAAAAATNC GGKTTTTGGN     660

CMAATTTCGC CKCNATGKTG MCAAGGMTCT CKAANAAKCS GGGTCYTCTN NTCNGKGGAK     720

CCAAAMGGKT TTGGGGMAGC GKNMNCCAAN CCTWACCCTG KTKAANGGNW TTCCCCCCGG     780

GGGAKKGNGA ATYCYCCSNA NCCCRGGGGG GNMCARATTC TYCCGGMCTC CTCKGGAWTC     840

WGMGSTTTCC CAAAAAACSC CCCAAATTMM TTTTTCCRCN TRTTGANACW CTTTTKARCA     900

MMCSSAARNS ANMCNCTCYC CKCTKTGKTK AAAAAGNAYW CCCCMAAATT TYTAWTTSSC     960

CCSCGCGGGN CCCNCTNTTT TSCNMTWCTM WNYTNCRMCC MMMSNCKSNG KKGGNRCCNN    1020

CRCCSNCCCM AAWYNTKGYN KNTATMAGC                                     1049
```

(2) INFORMATION FOR SEQ ID NO:309:

```
     (i) SEQUENCE CHARACTERISTICS:
         (A) LENGTH: 1036 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:309:

AATTCGGCAC GAGGGAATCG AGAATCCCGG AATGGTGAAG CCTCGGTGCC TGCCGTTACG        60

CCAAGAKTCA GGGTGAGCGG CCCCCCGGTG GGAATGCTGA SGCCAACCGG GAAAAGGGTG       120

AGGGCTGGGG TGGAATAACT GAANGTTACT GGGATGGAAA ACCCGGTATT GATATGTATT       180

GGGCCGATCA ANGTTGTGGG AATGGGGGAA GGCTGAGGGC GACCTGTTGG ATTTGGGGAA       240

TTGTYRTGGA CRAKACWGGC CAGCCMGCGT GATGGTTTGG TTSAANTTTT GTGCCGSCCA       300

CANGGTGATG GGATTGATTT TGATGGGGCC SATCGAAATA TTGGGTATGC CNACGCCSAA       360

CGAGATYGCC GGGACGTTCA TGGGCGGGAC AACCMASGGT CCSANGTAAK GGTTTCCTTN       420

ATNTTGATCG GGATTCCGGA ACTMTSTCGA TGSGCTCSAY MTSATSGCCC NACNCCWCCG       480

YTTATTTCMS GCTNAYGGGA ATBAMRGGAA CAAYNTCCCT CCCMGGAAAA ACCAACMSGC       540

CCTGGTNSYC CNCCCRCCNC AKAACCCRTT KCTGTRSTMC CCSMAAATNA CSCCCSCTTS       600

NACTCCNCSG AANTNSCCCC CCCSCKNNTT ATSTYCCCGK GTTCCCCCMC CCCTTNAAMC       660

TCCCCGGTTA ACCCCCWTNT SNCNCCCCCS YTAAKMNCRG GCTTSTTNCT CCCCCYTRMK       720

CNCCCCCTCK SAMCWNCCNC CTCKAACNAC CCCKCYKGSM TNCCCAATNT WCMWCKCCNS       780

KTTNTMCTKC CCAAYTNCRC CCNCRCTCCC CCKSTSTCAM WTATAAAACC WCWYAWYNNK       840

KCNCWMAWTA MGACWCTCNY NCCCCNCNCK NTTKTAMWCC CKMCCCKCSW TWCYCKCSCC       900

CCMTCTMNAC YCCCCCKKTY NKWMCCCTTC CCCCCCTCCC MCNMBMKTCT YCSGKTWCWC       960

NCYNTTMTCN CYNANMCKCK KTCTCTTCCN CRNTCTCCCC CCWCCCCCCV KKCTCTSKCC      1020

CNCNCTCCSC MMKGSC                                                    1036

(2) INFORMATION FOR SEQ ID NO:310:

(i) SEQUENCE CHARACTERISTICS:
         (A) LENGTH: 1036 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:310:

AATTCGGCAC GAGATCATGA ATAGCGGGCT GGTCAGCACC GAAGTGGTCG GCGATCTCGC        60

GAGCAAGTCT CGTCTGCTCG CCCAGCAGGA GGTCGGCATC GATGCGGACA CCTGCGATGT       120

CTTGGATGGT GTTCAGTTGC AGGTAAGGCC GACGCCGCAG CTTTGCTAGC AGGGTGTCTT       180

GGCTCTTCGC ACGTGAGGTA ACCAATAACT CCGACGCAGA CCAACTCCGG CCCTCGATCC       240

GGGTACCAGG CTCCGCCGGA GCCAGCCGTT GTGCCCCTG GCCGAAGGT CAGCTGCTGT        300

GCGATCGAAG TAAGAAACCG CGCCATGCCC GTCGCCAAGT ACGACTGACC GAGCAAACGA       360

ACGATCGTCG TCCTTTCCGT GGGGGTAATC GANCCCAGCA ACCGCACGAG CCACCAATCA       420

TTGGGATTCG GCCACTGACC GACCAACCGC CTGTGCGACA CCCCAGCGGA ATTGGTGGTC       480

TTCCGCGGGG CCGCNAACGG AATCANCGSG ACGCGCTCGC CGAASCANCC GCATANCCNT       540

ACATANCAAC GGNNTCTGCG CCCACATTTC GGGSTTMTGC CCCTCNGCAA CSSNAAYNCC       600
```

| | | | | | |
|---|---|---|---|---|---|
| CCCAATTCYG | AACNAAAAAA | TTGGYCCATY | ARNGTYCTCM | CCAAAAACCN | AWTCCCCKTA | 660
| TCCCCCGGGG | GGGRCCCCYY | NMNAAAACGG | CCCWWAANCC | CCSGGGCSCC | CGGGTTRWTN | 720
| CCCCTTGTCG | GCCCNCCSGG | TTTGGTCMCM | GGSCMMTNWN | GGGNTGCSCC | CCCNCNAAAA | 780
| AAAAAYCKNG | NCAAATYAAA | CCCKYCMAAA | ASKTGGGSSC | CCCMARCCGG | GGKAAKKWWA | 840
| ANTTAANCCN | KAAAAAAAWW | NCANNMCCCC | NGGGNCCTAA | GGKYTTAGGG | GTTSTTNANG | 900
| ARAAAATMTC | CANATMNSSK | TTNNAAAAAA | ASCCSWAKCC | CCCNNNKKNN | CCAAWKAARR | 960
| SRCCTTCGGG | TNWNSGGGGG | KKKKKTNCMS | KMNMMTTWGR | CCCNCCGCCN | NNTWKCCTTN | 1020
| TCCNYGGNGC | RNCAGN | | | | | 1036

(2) INFORMATION FOR SEQ ID NO:311:

(i) SEQUENCE CHARACTERISTICS:
        (A) LENGTH: 1060 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:311:

| | | | | | |
|---|---|---|---|---|---|
| AATTCGGCAC | GAGTCGATTC | GATCGAACAC | GCCCGCACCT | GGCCAGGCCA | CATGGGCGCG | 60
| GCCATGGCCA | ACGCCTACTC | GGCCAACCCG | AATCCATTCG | GCGTCTCACC | GCAACCCCCG | 120
| AAACCGGCGA | CCGCGGCATG | GATCAACCCG | CCCACCCCAG | ATCCGAAATA | GCGTCCACAT | 180
| AATGAGACAC | TGGCGCAAAG | AGCTTGACAG | GCGCCGCACC | ACGCAAGCTG | TTAGACGTGT | 240
| CGGTCTTGCA | AGAAGCGGGT | TGGCCACCCA | AGATACGCC | GCCCAAGGGC | ATCGAGTCAA | 300
| CGTTGCGGTG | GTATCGCGCT | AACGTCGGCG | CCGCCAAGAA | ATGACGGTGC | GCATTACCAT | 360
| GGCCCTGCTG | ATCACCTTTG | GCCACCTGCG | CACCANAACT | ATGANCAGCC | TTATGCCGAG | 420
| TCTCGTGGAC | ATCGGCAGCC | GCTTCAAAAA | CTCCTTGTCG | ACAATSGTAT | TGCTGANCCG | 480
| CCGAATTCTT | NTRCTTGCAA | SAACACTNCA | TGTTNCSGGT | NAACAACCYT | GGTTNGAAAA | 540
| ACANCCAATA | TTGAANTCCC | ANTCGGGCAM | GAACCNGTTM | CGGAAGKTGK | TGGGAACGAA | 600
| TGKTGCCCAA | AAATCCCGGG | NGGTRAAAWW | CCCNSNATGG | MSAATTTTSC | CTNGAACAAM | 660
| AAAAGGTCCA | AGKYCAAAGG | NGCCCCCCCC | SGNAAATTGG | TGAACSCAKA | WYANRTTCCC | 720
| WWWTNCAAAT | MTTNGGGTCC | KNNTCCCCWT | AAANGGGSCN | CCCCNCCRGG | GMGTYTCCCC | 780
| NWNMGGGMGN | CYYCSCCCCA | AAAAAAMMM | MTTTCSGKGG | SMGGKKCCCC | CCSGGTYWGG | 840
| GKKYTTAAAC | CCGGKGGGTN | CAAAAAANAN | ACCCCCCAMS | NGGGGGGAAA | ATTTGNAAWT | 900
| AAGGKKKTKC | SCMACCCCAA | AAANMMNNCN | AWNCCCGMGK | SARGGGGRNY | TTMKAGGGMG | 960
| GNYCCCCCCW | YCGGGGGGNA | NAAYAAAAGK | NGSNGRGAAT | NTTNTTTTGK | RSSSRNKTTT | 1020
| TYNTCCTYCN | CCNMGNRWWG | SRAMNTGKTS | NSSGGGSGGC | | | 1060

(2) INFORMATION FOR SEQ ID NO:312:

(i) SEQUENCE CHARACTERISTICS:
        (A) LENGTH: 1040 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:312:

| | | | | | |
|---|---|---|---|---|---|
| AATTCGGCAC | GAGCTTCACC | AAAGAGCTGA | CATGCCGGGT | GATGCGACAT | CGCATCGAGG | 60

```
GCAATACGGG CATGGATGAN CCGAANGGAN TCTGGCGTTC GCTCAACTGG ATTACGGTTC     120

CCAAGGTGAA ACGCTTTGCG GCGAAAGATG CGACGCTTAA CTTGCGCTTC CACCGTGCAA     180

TGTTNGTATG GATGCTGGAA CCGCGCTGAC NGATAANGAA TTCGCTGGTC GCCGGGCACN     240

ATGGATGGTC CKSTTTTCNC TCCGCSGTTA AATTGCSTGT GCATCATCTG GCAGGCTATG     300

TTCCCGCTAC RCTGCAGCCC ATCATGGATG TGCGGCTAAC GAANAAGTTA TGACATGGCG     360

CAAGCGAMTC GGGCATSCNC GCGGCAMTTT CGCAACCTGC TGTGTNTGAA GCGTMTCAAC     420

CGAATGCGGC GCTYAAAAGC NGGCTTGCGT TGATTMMAAC CNAACCCNTN CNATYCTTTG     480

CCGNGNMNTG CGTTCTCTCC AACTCCGKKG SYTGCCNCCG TGAAACCCMA CTNCCCCCCC     540

GTTGGACTTA MRTNTTCAAA AAMCGGMTNA ACCSGAATNN SAACCTNCCR TCAAANTAMM    600

SAANTCGGGC TTYGGGNRCC CCCCNGAAYW TTCKNCNGGG GMNNTYCTCN GGTTYNGGCG     660

SAAACNTTTG CCRTNCYMNN TTTACAMGGC NCMTNMTTGM GGGSCSNNAS GWCCCGGGKK     720

TNTTTNCAAW TCNCNSKTTT TTKGGGGGGG GGCYGRTRMC NCGGGCCCCC GGCCCKKMAA     780

AAAAMCMSA RRCCNCYGGG KKCCCCCCCM NNATNGGGCG YKCRAAACAA ACCCCAANRA     840

TNGNGMGGGC SMACCSGNGN GYNAAAKGGT TSNSCTMANM MKGMANNNCT SGMSCCMNSN    900

NCTGMGGGKT TTKGNNGARN AANAMKMGGM RCGGNCGCNN GAAAGGGSMS GSCKSCNNGN    960

NGASNGWMGN CRNNGANRCC NCNGYGNMRN NNGNNNGNNN GGGRKNNACN NMKMCAWSMC    1020

NSNMMGNNNS CGYMTNKCGC                                                1040

(2) INFORMATION FOR SEQ ID NO:313:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:313:

AATTCGGCAC GAGACAANGG CGTGAAATGG GATCCGGCCG AGCTGGGGCC CGTCGTCAGC     60

GACCTGTTGG CCAAGTCGCG GCCGCCGGTT CCGGTCTATG GGGCCTAGTT ATCTGCGCCG    120

AGCGTGAACT CAGGGCGAGA TTTCGGCCGT TTTCTCGCCC TGGCTTCACG TTCGGCGAAG    180

TKGGGAACGG TCAGGGTTCG CAAACCACGA TCGGGATCGT GCGGTCGGTC CAGGACTGGT    240

ANTCCTGATA CTTKGGTACA TCGTGACCAA CTGTGGNCAA TATTCGGCGC GCTCCTCGTC    300

NGTCGCGTCC CGCGCGGTAA GGTCCANCAC TTCCTTTTTC TCGTGCCG                 348

(2) INFORMATION FOR SEQ ID NO:314:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:314:

AATTCGGCAC GAGAGACCGG GTCGTTGACC AACGGACGCT TGGGCGCGGG CCCCTTGCGT     60

GGCATCAGCC CTTCTCCTTC TTAGCGCCGT AACGGCTGCG TGCCTGTTTG CGGTTCTTGA    120

CACCCTGCGT ATCCAGCGAA CCGCGGATGA TCTTGTAGCG CACACCAGGC AGGTCCTTCA    180
```

```
CCCGGCCGCC GCGCACCAGC ACCATCGAGT GCTCCTGCAG GTTGTGGCCC TCGCGGGAA      240

TGTACGCCGT GACCTCGAAC TGACTCGTCA CTTCACGCGG GCAACCTTCC GAAGCGCCGA      300

GTTCGGCTTC TTCGGAGTGG TGGCTCGTGC CG                                   332

(2) INFORMATION FOR SEQ ID NO:315:

(i) SEQUENCE CHARACTERISTICS:
        (A) LENGTH: 962 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:315:

AATTCGGCAC RAGTCGGTCT AGACGGATTC AATGCTCCCG CGAGCACCTC GCCACTGCAC       60

ACCCTGCAGC AAAATGTGCT CAATGTGGTG AACGAGCCCT TCCAGACGCT CACCGGCCGC      120

CCGCTGATCG GCAACGGCGC CAACGGGACT CCTGGAACCG GGCTGACGC GGGGCCGGCG       180

GGTGGCTGTT CGGCAACGGC GGCAACGGCG GGTCCGGGGC GAACGGAACC AACGGCGGGG      240

ACGTGGGGAC GCGCCCGGCG GGATTTCTTC GCACCGGSGC ACCGGCGGGG CCGGCGGCGT      300

CGCACAACGG CACCGGCGGG GACGCNGCGC CCGTNGGGCG GCTTCTKGAT GGGCTCCGGC      360

GGTNACGCGG CACGGCGGCG CCCGGCTCAC CGCCNGTTGG GACGCGGGGA CGCGTNACCC      420

CGATCTTCTT CCGCNCCCCG GAAACCGCGG GGCCGGCCCC ACATTAKACC CGGCGGNACC      480

GCGGMCCCGG CGGAACGGNG GGYNTTTTCC AACGGCGGGG CCGCGGAACC GNMGGSTGTT      540

CCTTNGGSGA AGGNCCAAKT CCCGKCTANC YYAATCCCCG ANGGKTGAMC CTSATGSNCA      600

MYTTMAGGAA CYTNCCCANT KTTSGRACCW CRCCNGGAAA ASRAWNKNGT KGGCAAACNA      660

NNTNCYTTKN NATTKGGNNA AAAANCCCTY CCWCSGRACT NCCCCCCNGM GRGMCNNTNN      720

NTTTYGNCNN CCCGGSNAAM RNTTKATTTC NGGGGGNTCN GGGTKMNNNA AACCCCAAAM      780

MNRNNKCSCA ANGGGKSNGC NKNNMMNSGT TTTYCKNMRA MRNWTYKNKN NTCNGARSRN      840

NAAMCNNSNK NGKKKNNKAA ARNNTTWKTN KNSCNNNCNN GRRNGVRGGC CKMKGSNMNG      900

MCWHNAWRNG NNGSNCNCKC NNKMNAAAAA AASGGVNCKS NSMKNKKKKG NRGGGGGGGG      960

GG                                                                    962

(2) INFORMATION FOR SEQ ID NO:316:

(i) SEQUENCE CHARACTERISTICS:
        (A) LENGTH: 323 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:316:

AATTCGGCAC RAGAAGACGC CCGAANGTTT GCGCTGGCTC TACAACTTCA TCAARGCGCA       60

GGGGGAACGC AACTTCGGCA AGATCTACGT TCGCTTCCCC GAAGCGGTCT CGATGCGCCA      120

GTACCTCGGC GCACCGCACG GCGAGCTGAC CCAGGATCCG GCCGCGAAAC GGCTTGCGTT      180

GCAGAAGATG TCGTTCGAGG TGGCCTGGAG GATTTTGCAN GCGACGCCNG TGACCGCGAC      240

GGGTTTKGTG TCCGCACTGC TGCTCACCAC CCGCGGCACC GCGTTGACCT CGACCAGCTG      300

CACCACTCGT GCCGCTCGTG CCG                                             323
```

(2) INFORMATION FOR SEQ ID NO:317:

(i) SEQUENCE CHARACTERISTICS:
        (A) LENGTH: 1034 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:317:

```
AATTCGCAGT GTGTGTGGCG GCGTCCAGAA GAAGATGATC GCGAACATCG CCAGCGCCGG      60
CCAGGCTATG GTGCCGGTGA TGGCCGACCA GCCGATCATC ACCGGCATAC AGCCGGCCGC     120
CCCACCCCAC ACCACGTTCT GTGACGTGCG TCGCTTGAGC CAAAGCGTGT AGACRAACAC     180
ATAAAACGCG ACGGTGACCA GGGCCAGCAC CCCCGCCAGC AGGTTCGTGG CGCACCATAG     240
CCAGAAGAAC GAGATCACCG TCNACGTCAC CCGAGTGCCA ACGCGTTTCG GGTCGGCACC     300
GCTTCCCGCG CCAAGGGCCG GCGCGCGGTT CGCTTCATCA CCTTGTCGAT ATCGGCGTCG     360
GCNACCAGTT GAGCGTGTTG GCGCCGGCGG CSGCCATCAT CCCGCCGACN ANCGTGTTGA     420
GCATGANCAG CGGATGAATG GCGCCGCGGC TCGTGCCGCT CGTGCCGAAT TCAACTCCGT     480
CNACAACTTG CGGNCGCACT CGAACCCGGG TGAATGAWTG AATTTAAACC GSTSAACANT     540
AACTACATAA CCCTTGGGGG CTCTTAACCG GTYYTGAANG GGTTTTTTGC TTAAAGGAAG     600
AACYATTTCC GGATANCTGG CSTTNWTARC GAAAAGGCCC CRCCCATNGC CCTCCACAGT     660
TTSCCCCTGA ATGGSAATGG MNCNCCYKNR CNGGGNCTTT AACRCSGGCG GGNTTTTGKT     720
MCCCNNCTKA CNTTMMMTGC ARNNCNGGCC SKCCCTTCCK TNTYCCCTCC NTCCCCCNST     780
TNCNGKTCCC CNNAMNYTNW ACGGGGGGCC YTNGGGKCRM TWTKKTTTGG GCCCCMCCCC     840
MAAANASAAN GGGGKRNGTY CSTTTGGCNC CCCAMAARGG NYCCCCCCAM YTNRRKMCSY     900
CNNTNKGGNN CTGTNCKNCG GAARAMAMCC KCCCCGNSTS STTNGTYWAG GNRWKGNSRG     960
CCSCCCCGGY MNNNAAYAWN WMNATNCNNS STNANMAKKN NNNNNNNSCN WNGNGNNTCN    1020
SCNSNGGKBC CSCC                                                      1034
```

(2) INFORMATION FOR SEQ ID NO:318:

(i) SEQUENCE CHARACTERISTICS:
        (A) LENGTH: 331 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:318:

```
AATTCGGCAC GAGCCCACAT CCGGGGCCGC TCGTTGCATG ACTCGTTCGT CATCGTCGAC      60
RAGGCACAGT CGCTGGAGCG CAATGTGTTG CTGACCGTGC TGTCCCGGTT GGGGACCGGT     120
TCCCGGGTGG TGTTGACCCA CGACATCGCC CAGCGCGACA ACCTGCGGGT CGGCCGCCAC     180
GACGGGTCGC CGCGGTGATC GAGAAGCTCA AAGGTCATCC GTTGTTCGCC CACATCACCT     240
TGCTGCGCAG TGAGCGCTCG CCGATCGCCG CGCTGGTCAC GAGATGCTCG ANGAGATCAC     300
CGGGCCGCGC TGAGTGCGCC TCCCGCGAGC A                                    331
```

(2) INFORMATION FOR SEQ ID NO:319:

(i) SEQUENCE CHARACTERISTICS:
        (A) LENGTH: 1026 base pairs
        (B) TYPE: nucleic acid

```
        (C) STRANDEDNESS: single
        (D) TOPOLOGY: linear (ii) MOLECULE TYPE: Genomic DNA (xi) SEQUENCE DESCRIPTION: SEQ ID NO:319:

AATTCGGCAC GAGATCGTCA CCCTGGCGAC CAGTGCACCC AGGCCACGCC ACCAGTTACG      60

GCTGATGGGC CAGAAGATGG ACCAGGTGCT GCCCATCCCG CCCACCGCAC TGCAGCTGAG     120

CACCGGGATC GCGGTCCTCA GCTACGGCGA TRAGCTGGTG TTCGGCATCA CCGCTGACTA     180

TGACGCCGCG TCCGAAATGC AGCAGCTGGT CAACGGTATC GAACTGGGTG TGGCGCGTCT     240

GGTGGCGCTC ANCGACAATT CCGTGCTGCT GTTTACAAGG ATCGGCSTAA GCGTTCATCC     300

CGCGCACTCC CCANCGCCGC GCGGCSGGGG CGGCCCTCTG TGCCGACCGC CCGAGCGCGT     360

CACTGACGCC ATCTCCGTCG GCGTTAACCC CGTGAGAAGG TGGGTCGTGC GCAAGTTGGG     420

CCCGGTCACC ATCNATCCGC GCCGCCATGA CGCNGTGCTG TTCCACACCA CNTSNGACNC     480

CCCCCAGGAA CTGGTCCGGC AMTNCAGGAA NTYCGTGTGG GCACCNGCTT CTTCCGKTRT     540

GGCYTAAACT TCCNATSTTN CSGCSGGCCT CTGGCGTTNC GNCCGGGCCG NTCTTNCCAA     600

ATCGGSMMAA ATCCCCANMC AAACCCCCCG GGTCTTGSGG GCSGGGNGGC GGCCNAWNCC     660

AAACCCCCCC NTTAAANTCT TTGKTNCCNN CNCSGGCNCC NCNAANSCAN CCCTTTKGGC     720

NCTTCCCCCC CCCAWTTTAA CCGAKCGSCN AAYCCCAAGY TMMGKCCYCY KNAAAAAAAA     780

AATTTGSCSG CCCCAANTAA ATTCCCNGGC CCYTTGGGGG CGRANCNYNT TTTMCCSNSS     840

TKGNNNAAMC NGGANCCSGG KAAYTMMTKG NAAYCGCCSN AAMBNTTTTC TAANNCCCCN     900

YNCCCSGAAA ATTNNAMAAM CMNNKTGSNG GGGGKTTSNC SGKKGRAGGM AAAAAANRSN     960

SKTTNMCNNN SANMNCNSNN SGGNSNNNNN NNNCNCGYKC CSNAANMCCC CGCGGGGGGG    1020

CCMMCC                                                              1026

(2) INFORMATION FOR SEQ ID NO:320:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:320:

AATTCGGCAC GAGAAGACGC CCGARNGTST GCGCTGGCTC TACAACTTCA TCAARGCGCA      60

NGGGGAACGC AACTTCGGCA AGATCTACGT TCGCTTCCCC GAAGCGGTCT CGATGCGCCA     120

GTACCTCGGC GCACCGCACG GCGAGCTGAC CCAGGATCCG GCCGCGAAAC GGCTTGCGTT     180

GCAGAAGATG TCGTTCGAGG TGGCCTGGAN GATTTTGCAN GCGACGCCNG TNACCGCGAC     240

GGGTTTKGTG TCCGCACTGC TGCTCACCAC CCGCSGCACC GCGTTGACGC TCGACCAGCT     300

GCACCACTCG TGCCGCTCGT GCCG                                           324

(2) INFORMATION FOR SEQ ID NO:321:

(i) SEQUENCE CHARACTERISTICS:
        (A) LENGTH: 1010 base pairs
        (B) TYPE: nucleic acid
        (C) STRANDEDNESS: single
        (D) TOPOLOGY: linear (ii) MOLECULE TYPE: Genomic DNA
```

(xi) SEQUENCE DESCRIPTION: SEQ ID NO:321:

```
AATTCGGCAC GANGCGTGCC GCTNAACACC AGCCCGCGGC TGCCAGATAT CCCGGACTCG        60

GTAGTGCCGC CGGTGGCGTC GTTGCTCTCC TGACGGGGCG CGGCGACCAT AAGGTCGCTM       120

ATGCCCAGGT AGCGGCCCAG GTGCATGGAG TCGATGATGA TGCGACTCTC CAGCTCGCCG       180

ACCGGGAGCT TGGCATCGGG CCTGATCAGC CAGGACGCGT AGGACAAGTC GATCGAATGC       240

ATAGTGGCCT CCAGAGTGGC CGTGCAMTTC CNGCGTGCTC CACGGCAAAT GCCTTGATTT       300

CTACTCCGCG TANTGTTCCC GCATCGCCTG CGGGATGAAT GGGAACCGCA SGATGGCGAC       360

GAACGGGTCT GANCTCAGGT TTGCCGCTTT GCGCACAGTG GTCNACANCC GGTACTCGGC       420

ATANATCTGG CCCNAAATCG GCGCCGACGG CGCCCACNAT AANAACGGGC ACNACAATCG       480

CCGCCCCGGT CACCCNAACA ACANCTTGSC ATCGGATTTT GTCCCCANCG CTCAANCCGT       540

CCCGAACGCC TCNTCCGGCG NACTTTTCTT NNAWTAACTG CCGCTTCCGK CCCTGGNGCA       600

WTAAATGGGA AACCCTTNCC CCACCTTGAA GGGGTTGTTG NATTTTTACT GSTAACCCCG       660

AATTNTTCCG GANTCGGTCN KCCGGGSTTT YSTNTTCCCC ACCTTNGNAN GGGCCGGCCA       720

AGSTTTTCTT SYTGAAGGGG GAAACCCAAC TTTNTYTYYN AACCSCMNAA MYMTTTYCSG       780

MNAASCCNKT CCCCTTTAAC CAMGGSGGTN AACCGKTMNG NGGKTAAAAA GGGSKNNKTG       840

NCCCCYMANG GGGGGRAAAA TSTKTCNNCG GGGCCKAAAW ACCMMMMYGN GTGKKKNKSS       900

GCSAAATTTT NMMRAACTKN GGGGCCSSGA NNTTTNAAAG MSCCCCCSNN GSTGKCCCNN       960

NTTTCCNNAA WMKKGKNWNM SNMNSCSNGG GKYNSGGSNN NNAAGMGGGG                 1010
```

(2) INFORMATION FOR SEQ ID NO:322:

(i) SEQUENCE CHARACTERISTICS:
        (A) LENGTH: 1010 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:322:

```
AATTCGGCAC GANGCGTGCC GCTNAACACC AGCCCGCGGC TGCCAGATAT CCCGGACTCG        60

GTAGTGCCGC CGGTGGCGTC GTTGCTCTCC TGACGGGGCG CGGCGACCAT AAGGTCGCTM       120

ATGCCCAGGT AGCGGCCCAG GTGCATGGAG TCGATGATGA TGCGACTCTC CAGCTCGCCG       180

ACCGGGAGCT TGGCATCGGG CCTGATCAGC CAGGACGCGT AGGACAAGTC GATCGAATGC       240

ATAGTGGCCT CCAGAGTGGC CGTGCAMTTC CNGCGTGCTC CACGGCAAAT GCCTTGATTT       300

CTACTCCGCG TANTGTTCCC GCATCGCCTG CGGGATGAAT GGGAACCGCA SGATGGCGAC       360

GAACGGGTCT GANCTCAGGT TTGCCGCTTT GCGCACAGTG GTCNACANCC GGTACTCGGC       420

ATANATCTGG CCCNAAATCG GCGCCGACGG CGCCCACNAT AANAACGGGC ACNACAATCG       480

CCGCCCCGGT CACCCNAACA ACANCTTGSC ATCGGATTTT GTCCCCANCG CTCAANCCGT       540

CCCGAACGCC TCNTCCGGCG NACTTTTCTT NNAWTAACTG CCGCTTCCGK CCCTGGNGCA       600

WTAAATGGGA AACCCTTNCC CCACCTTGAA GGGGTTGTTG NATTTTTACT GSTAACCCCG       660

AATTNTTCCG GANTCGGTCN KCCGGGSTTT YSTNTTCCCC ACCTTNGNAN GGGCCGGCCA       720

AGSTTTTCTT SYTGAAGGGG GAAACCCAAC TTTNTYTYYN AACCSCMNAA MYMTTTYCSG       780

MNAASCCNKT CCCCTTTAAC CAMGGSGGTN AACCGKTMNG NGGKTAAAAA GGGSKNNKTG       840

NCCCCYMANG GGGGGRAAAA TSTKTCNNCG GGGCCKAAAW ACCMMMMYGN GTGKKKNKSS       900
```

```
GCSAAATTTT NMMRAACTKN GGGGCCSSGA NNTTTNAAAG MSCCCCCSNN GSTGKCCCNN      960

NTTTCCNNAA WMKKGKNWNM SNMNSCSNGG GKYNSGGSNN NNAAGMGGGG               1010
```

(2) INFORMATION FOR SEQ ID NO:323:

(i) SEQUENCE CHARACTERISTICS:
        (A) LENGTH: 1092 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:323:

```
NGNGGGGWNS NTCAYCAYCA YCACSGGGYW CWATTGCGGC CGCAWCTTGT MAASAGATCT      60

CGAAYTCGGC AMGAGGGAMT CKCTMGCNCC GCTGTGCAAN CCAATRAGGC CTRATAATTY    120

CCACTCCACA AAAAACCGTT GTGTGTAYYT SCCGRAAATR AAGGCGCCGG TNTCAACWYC    180

GCCGGTKTTY CCRATYCCCG TKTTGTAMCT GCCKGGGTSR AAAYCCCCGG TGTTGGAYCC    240

CCGGATTGAA ACTGCCGGKT TGAAACTGCC GKTTTSGCSA TCCGGKWATT GAMSTCRCGG    300

ATTAAAAAAC CGGKKTTGGN GCTGSNCGTG CCAAATNCGR AYCCRATAYC CCATGGCCTG    360

KYCTYCTCCK YCGGTACCCA AAYCTGGGTA TCCTATACTG GYCCCTAAAK GCAAWYCKGG    420

GCTGYCMMTK TTGCKGGSGT CCNAATTTAS CACCASCGGT TCCTTCCATA CCNAAACNCG    480

CKTGGGCWCC AGMCCGRAAA AAAKAATAAT RAKAAKGGTG CATNYCCAAA ACCNCCGCCN    540

CCCNANTNCN ATCCGNTNCC MSCNCCCCCA GCGGTNAAGK TKSGGAAYTT CTMMAACCCC    600

CAAANCCCCA TAACNTNCGR GAASAAACCC CTYCNCGGGG GYCNWNCAAA ACASCNTTAT    660

TTGCTKSTTT CGGGMWCCGT GCCGCCNAAA YCCCAAASTA CTTTYTGGGT CCNAGAKAAA    720

ACCNCGGGCN CCMCCCSNAA NWTATYTCTT KGGCAANCCC CSAAACCTTR TCMNACCNCK    780

ATRMTCCCTT CCCCVSCAAT TGGYCGGRAT NCGSNCCYTY TCAAAKKKSC CAKWWNNGNG    840

GRRNNACCMA ACCCCAAGTY CCMNAAAATN GKCCCCGCTC CNAACACGNK TYYTCCSAAA    900

ASCCCWCCCC CCCCCCCRAA AACCCCCCNA RKANTNCCCA AAAACNYNGK GGCCCCCCCC    960

CAAACMAAAA AMCCCCCSGM RMACSGGGGN NMCCCCGKKK KKTTTTCTTT TKCCMRSCCC   1020

AAMGCAMWSY KSKTNMAAAA GGAAGRANCN TYCCSANANM TCCCNYWRSW CCGSWGMGNA   1080

GAASMCCCCC CS                                                       1092
```

(2) INFORMATION FOR SEQ ID NO:324:

(i) SEQUENCE CHARACTERISTICS:
        (A) LENGTH: 1251 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:324:

```
GGGGGGGNNN NATACATCWT CYGTGYACCG GGGMTCTAKT GGCGGCCGC AATCTNGTCA      60

ASAGATCTCT NAMTTCGGGC ACAAAAACTW GACAAASYMT CGNGCNMTCC GTGTCCTNKA    120

TCGCAAAACG NGTRACASAC ASACACRTAT GTGTGCCCAC CASCAAYTCK TTGGGACCTC    180

GCTRACCGGY TGCCCRNACG CCACGYTGCS CWTCTATCCC RACGCCGGCC ACGGGYGGGG    240

ATATTCCAGG CACCACGCCC AGTTTGGTGG ACAATGCCCT GGCAKTTTCC TCRAANTTCG    300

TGAAACCGAA TTCNSMTTGA ACCNCCAARG CCCCSNCCNR AACARTTGGG WTCCGCGGTT    360
```

```
CTCCCCACCG KTTTCCGGGG GTNTCGGCAN AANCGCACCC WTGGWTTCTM TCNCCGCACC      420

GGGCGGACAA NTCGGGTTGC AATTTTGCRA AYCGGGGCCG GGATTCCSCA AACGGGTGCC      480

GAAACTGTTY YCRAAMACCG GGAKCCGCAA TTTCCGGGCR ANAAATTTCN YCNCACCACT      540

GCTTRTACTT CCCCGACCGT AACMANTTTC ATCGTCNTNN CCTCTGCCCT TGGGGCAGGG      600

CKAAAYACCG CMTTKGGTTT CGCAACCTGC GGCCCAANTC CCNAMCCRCA CTTTCNATTT      660

GGNTCGAATT SCCCCCCGGT RANAACCSCC NTGGCCNNYT CGGASSAAAA NGGGCCCTNT      720

KGGCNSCCCC AGTAANACCC TACCNNAYTS CAWTCTTTGC CAAASTTKGG ACGAANSKTG      780

GGNTTCCGGK ATTTYYTTGS GGNCNCCCTN TATNGGSNTN GGGCCKCYNC NCSTKTGKCA      840

NASSKAYCCS NGNKGGGGGT ACCCCCCTMG GGGGGTTTTT NSSGCCCCCC AWAYGNKSTG      900

GCCCCCNNGG GGAAKAATWT MWWTMCNSGG GGGAAWTTTT NTSTGGAMCS SGGACYCCCR      960

GGGGGKTTTT TCCCCCNCSA NNAWANGGGG GGGGGANAYT NTGNSGNGGG KWNTTTATTT     1020

YTYYCYCCTM TKACMSGGGG GTTTKKAKNG GGGGGAGAAA ANAAAAAAAA RAKGGYKNTT     1080

TSKNCACNCT GKWNWNWANR NAGAGKTCCT CKCKCCNCSG SNTTTCTTTT MGNSGSYGGG     1140

GNNGNNNAAA ACNKSRMMAC KCSYTYCCCG CGYCTCCTCC NCNGGGGYGS NGSCGNSTYN     1200

GNNKGRKWTA TNTMGNCGTN SCCTCCNCCC GCKNKNTGTC TMTCNMYGSG C             1251

(2) INFORMATION FOR SEQ ID NO:325:

(i) SEQUENCE CHARACTERISTICS:
        (A) LENGTH: 1099 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:325:

AAYTCGGCAC MGAGTATCAC CAAKCTGYGT GGCCCAGCAA AGTGGAGCTA TTACTACCTG       60

TATGTGATCC TCRACATCTY CTCCCGCTAC KTGGTCGGGT GGATGGTGGC CTCGCKTGAK     120

TCRAAGGTCT TGGCCRAACG GCTGATCGCG CAAACCCTTG CGCCCAGCAC ATCAKCGCCG     180

AACAGCTGAC CTGCMCGCCG ACCGGGGGYC GNCAATAACT CCAAACCGGT GGCMCTGCTG     240

CTGGCCNACY CCGTGTCCCA ANTCGAACTC ASCCSGCNMA CCAKMAACKA NAACCGTTGT     300

CTGAAGCCCA GTTCAAAAAC CTCAAGTWCC GGCCCRACTT CCCGAAACGG TNCGAGTCKA     360

TCRSAGGSGG CCGGGTGCMC TGCAACCGGT TCTTCGGNTG GTRCAMCCCN AAAMCAAGCA     420

TTCCGGGMTC CGMMTGCCCA CGCCGCCAAS TTTMCTACGG GCSGSCCNAT CAAATTCGCC     480

GGGAACSGSN CCMCCKTCNK GGAMACGCCC TWCCAAAACC CYCGAACGGK ATCCTTCKGY     540

NAACNCCCGA RCNCCCKSKT TCCGGGCTTN NMSGCGAATA CCCKNSCMNT CCGAATCCAA     600

TTCCCMKYGG CTTTTYYYCC CCCCGGCCCC AAAYNGGGYC CCTASSNMKC KNCCAMNANT     660

CCNWATCTGG NGGTCCCNAN KYYGGCGTTC NMAATSAMNA NMNRGGGTYT TSCYACCMMN     720

AACCGKNNKG KCCCCMKCTK MANAAAKATT RATCAMKWNG GGNKCKCNCN NAAMACCSCN     780

CNCYNCWYTC TMYCSSKWGC GCSMYNANCA SNGGGGAGGW GGSGRMKMCT CTMTCTCNCT     840

MGCGCCKNTN TYCKSGAKAT ACASMNKTCC GCGCNGCGCN MAAMANRAKA CTAKCCGYGN     900

CCSNSTMTYN CTSNNMKMNN TCCWMWNATC NTYYGKKCNN KCTMKATNWC CSCTSKCNCK     960

MRAMTCKTYG SNMTCCTCCA TCNCTCKKSC SNMSKNTCKC KSCNCCNCWN CNKCNMKCWN    1020

GGNSTCRCCY TCTMNNNTCS AGCKCGSKNC WACNCACACK NGWCTYTTCC WKNNMKCNKM    1080
```

TCKCKCACRG MTMTCWCCS                                                    1099

(2) INFORMATION FOR SEQ ID NO:326:

(i) SEQUENCE CHARACTERISTICS:
        (A) LENGTH: 296 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:326:

GNGNTATACA TCWCTGTGYA CCSAGGATCW ANTGCGGCCG MAAKCTWSTM CASAGATCTC          60

AAAYTCTGCA MGAGCGGCAC AKAKYSTCGT CCMRACCCGG CAYACWCCWG CNCGCCCCWT         120

CTTRGACCGG GGCKATASMC ACCGTTGGCC CCGGCNCGCA CCTACACCAC CCACGCCGCC         180

AGCGCCCCCW TRAMCAAACC ACCCCGCKTT TACCGCCCGC GCCGCCGGGG CCACCACCAG         240

CCCCACCGGC ACCACCGGCG CCGCCGTTGC CAAAACAGGC CCGCKTTTGC CACCRA            296

(2) INFORMATION FOR SEQ ID NO:327:

(i) SEQUENCE CHARACTERISTICS:
        (A) LENGTH: 1073 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:327:

NGNGSGNKMY ATCATCWTTC TGCACCSNGG MTCWATTGCG GCCGCAATCT TSTMNASAGA          60

TCTCGAAYTC GGCAMGARCA TCTGCGCGGN GAATGTCCAA AWGTCWKTAA CGGCMATCGG         120

TTTGCCGYCA ACCACKCTRT SCAKATGCGG GCCAMWTYCA AACCRATTAT TTGGGYCGAG         180

AAAATTTMCG CKTGTRASCA ACCTGCAGCG GGTCAASCAA CAGCCTCTRA ACCGTAAATY         240

CKTAGGTNKT YCCGGCAACA ASCYCRATAA TSCGGCCCGC AMCCACAAAA CCTGANTNGT         300

TNTTCNCRAA NCCGGTYCCC GRAGGGGTSA ACTGCSGTAR GCTTNTCWYC NCCTTRACAT         360

TAAACCCCCC CGGNTCWTCG CCGCGCCCAA ATYCYTGCCC WTKGCNACCA YCCCANCCTG         420

CSGTATGGTS RAANCASTSG GCRAACGGTM MCCSTACCKC TGGCTGATYC KTCGGNTCCS         480

SNAATTCGGG GATTTACGGS CAMGGTTAAY CCAGGYCCCC TNTGCYTCKY CNACAACCSG         540

ATCMWCNCCG TACCTKTTAA AATTCTTTGT GGTGGAACCC AWYCKAAAAA NMTNTYCCCN         600

TCCAMMGGGG CYCGGAAKKT CNACNTGGKT NACCCCTNCC YTTGAASTTT TCYTGNCCCC         660

GGCCCKAAAS ANACCSGAKC CCCGGAAYCS WTAGGCYTCN TGCCCCSTTA AATTKGNCYC         720

AATCCKCCAA CGCTCCCCGG GGTCSSCCMT TAAAMTTCCC CCCKSCASNG GAATYCYKSG         780

GCWGTMATTW CCNCCCNTTT CYYGKNAAAC SCCCCCWKGN GSCTYCCCCN SNTTSSGCCS         840

GGTTSGAMYC AAAAWTNGGG MMCNRAGNCG SGNAMCCSCN GKKGGGSATW TKAAYYCYGG         900

GGGGGTCNYC CCCCRCSNAA AAGYGTKGGC KCCSSSCCYC CCMARTTTYT CNGGMRCMAM         960

ACCANGGGNG CTCCCGTNCW WGGCTCCCSN SNSMAMAAAN NKCKCCKGGS CKGARRNMNA        1020

MCTCSNGNGG WTCCCKNKTC NSCNSGNCGS YGGNSASWCC YNYCNCCACA ANC              1073

(2) INFORMATION FOR SEQ ID NO:328:

(i) SEQUENCE CHARACTERISTICS:

(A) LENGTH: 1166 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:328:

```
CGCCCCGTTC TTMMMTTCAY TCATTCACCG GGMTCTAGTG CGGCCGCAAK CTTGTCKACA         60

GATCTCGAAY TCGGCAMGAS ACAATSTCGG GTKGGGCAAT GTCNGGTGGG GCAACTTTGG        120

GCTCGGRAAT YCGGGGTTAA CGCCGGGTCT RATGGGTSTG GGTAATATCG GGTTTGGTAA        180

TGCCGGCAGC TACAATTTCG GTTTGGCAAA ATATGGGTGT GGGCAATATN GGGTYCGCTA        240

ACACCGSCAS TGGRAATTYC GGTATTSGGT NACCGGTRAY AAYCTGACCG GGTNCGGTGG        300

TTYCAATACC GGTAACGGGA ATGTSGGTTS YYYACYCCGS GSAACGGNWW YTTNGKTCCT        360

TMMCNCTSSM CCKSAAMTSM KMGGTSTYCT MTYCNNGGAS TAMTYNMCCC CCGWAYCKSC        420

WAYCCCTCGT CATYCCMCMC SGSGYCCTCA MNCCACCYTG NGYYCCCTCC MKMTCYCAYT        480

CMNTCCGGTW CCTNTMMNCC CSCNCRYCTC AMCNCTKSGK CACCNATMYC CSACKCHTCT        540

MCYMCSCAKN MTTCCCCTCN CCTYTNNCCA MCMCSCTCTM TCMAACTCKC CCGGYCKCNC        600

MYCTCTCKCC AYNMAACCKK TYCYWCNWYC YMYCKCKCAG WYKNMCTCCW ACTCTMYNTT        660

TCTCTCNKCC CMKACCKNTT CTCWCSCCCC CCACAKAYMC YAWCMTMTCC MCTCKACSCC        720

CYYCNNYCCM NMCWCMTCWC TWNAKCANCN TTCTTCTCTC MMYMTMACKC WCNNTCNCCK        780

SGACCYTCTC ACTKMKCCKM TCTCCTTMCK CCYMWCNTCC MKYNCCCTCC NMTCMTCKYT        840

CCTCNCNMRY CYYYAKCAKC NMCTCCCCAN KMCAKCTKCT CCCCCAKMKS ACNCKCCCWC        900

CCTCCTATCC WCTCTCWCTY ATCTCKCTCW CNYCMYMKMC ACNCKCYAYT CNACTMNMWN        960

CCANCNCTCT CTNYCTCWCK ACGTYCKCCK CTMCKCNYMC NRWCTYRCCT CKKCCNCCRN       1020

CKNMCMKCTM CTCTCCWMKM TCCCWCCCAT CTMMKSTCTC WCNCMTCCCT CNKCCYNYNT       1080

KCYTYCCMYG CTTCKNTCMT MCCWCCYATC TCTMKCCTCT CWCACYMCAC WMTTACWNCC       1140

ACTCTCTRCW CKCCKCMCCR MTCTCB                                            1166
```

(2) INFORMATION FOR SEQ ID NO:329:

(i) SEQUENCE CHARACTERISTICS:
        (A) LENGTH: 1230 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:329:

```
NGNGGNNNNT CWTACATCWN TCTNCACCSG NGMTCWATTG CGCGCCGCAW NCTTGTMNAS         60

AGAATCTCNN AAYTCGGCAC ANATGTCTTT TSTMTAKTGT GGCGGGGNGC CACGCCKTAT        120

GTGYGCCTGG GYTRACCCAA CCCCGCGGCS CGGGCCRACC AGGCGGGGRA TSCAGGCCGC        180

GGCGGCCGCG GCGGYTATAT RAAGCGCCGY TTTTKTRATA ACGGTCCGC CGCCGGGTRA        240

TTACGGGCAA AAYCGGKKTT TGGGTRTAT AACGCTAATT GCAACCAWTT TTTYCGGGTC        300

AAAAACYCGG CGWGCANATC NCGGGYCNCT RAGGCGCATT YMCGCCAAAA WTNTGGGCGC        360

AAAACCCCKT TSYTATTTTN TGGGCTATSC GGYTGCTTCG GCAAACGCTY CCCGGGTTAA       420

TCCCKTCCGC GGCGCCGCCN AAAAACCACC AATYCCGYTG GGGGTGKYCC CMCAGGCSGT       480

TGCTYCGNGY CACCTGGCCA AAYYCCCAWT AKATTGGGTG SCYCKTSCGG TTSYTGGGCY       540
```

```
CAATTACCCC CNCGGGNAAA GRRAAAANAA ATCNTCCNTT TGCTCGGYCA YCTTTMTTGG      600

SAAAAGGGGC ATGGCSCGGT TYYTTTACCT CAAYCCCCNA NCANTWACCT YTCCSCCCGG      660

GGGGNCANAA CGSTTNGCTC CGSGGNAKCC TKGTMCCCGN ATCNAAAGGC CNGAATTTGG      720

TYYSSTYCNA ATTWTWKKKY CCCCWCNTTG YAAAAAKCCA AAASAKCCCK YCNCAMMYKT      780

NGGGGTYSSG GCCKNYCTTK SNMTTAAACC CYCCCCAAAA YYNSGGGKKT TCCGCYNSAT      840

KCCACCNCCK GNGGGGGNA SAAAAAAAAY TTTYCCSAAA ATCCCACCYY TCYKTKSTRY       900

AMACCCCCTT TYYMKKAYTC CKYSCNATTC SGMTTCWAAA TYCCGYGGCT TNTTCCCCCK      960

CSGGNGCCCC AAWTTTGKTT YNCNANTTYC CCCNAAMNCM AWTMGGGGKS KCCATTCTGG     1020

SCYTMAANTA AAANAANGGG NKTTTYYCTY MANAAACACN GTGKCNCNCN CNAAMAAASN     1080

AKMAAAKAGN KKKMTKNNSA AANCCNCCCC CTSTYTNYTT NKTNMNCKCC CYGGKKNKGM     1140

SWSWYNTTCT NCCCRCCCCC YNYNKTGANA AAMMNCYCCS GGSTMCRNAN ASNMNTTTCK     1200

STSTNGMGCC KMBASNANAN MCAMWKWYCC                                      1230

(2) INFORMATION FOR SEQ ID NO:330:

(i) SEQUENCE CHARACTERISTICS:
        (A) LENGTH: 1022 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:330:

NGNGGGKNNA TMAYCWTCTC ACSSGGTCTA TGCGGCGCAW CTMGTMAASA GATCTCNAAY       60

TCGGCAMNAN GCATMTCMMC CATATATAAC CATTGCGTCS GYWTGCAWCT CRAAWCTGTC     120

CTTCSKGCCG TTKTACRAAG GTGGMWTGYT CWTYCCTRAA SCCCTCRATC TCKTKTATYC     180

CTKGGGCTYC ACTTTAACSG RATKSCTGCC TTKTAYCATT RATGCAAWTA WTGGYCRAWT     240

KTTGCAGGCC RACGGCWYCT TTTYCCGCRA GRACAATNGA TTGGAWYCGC TYCGCRAGGC     300

CCGGCACCAR ACCGGGCNCC AAAGGYCCGC GCAAWTSCCT GGKTCAAAAA TGGTGCAAAC     360

AAAMCNATCC CCGGYTTRAC CGCAGYTAMC ACAAKAAAAT TCCCWTGGCC GCACCAWNNT     420

TTYCRATCWY CWYCCCCACC TTRAACTTGK YTGCSGTATT GCCTKCCTGC CTCRACAGCM     480

YCNCCCKTCA AACCTGCGGT GACTCCAACT GGTCTGGYCG AASGGGGGYT CAMCGGACAA     540

AACCCCRANN TCGCCAAATT TTCNCCCCCC CYCGGGAAAN GKTGATMTTC TCSNAACCSA     600

CMGGGNNYTW NAACCCTGAA CSSSGSNKGA MYNSCCSGGA ANTTTTCCCT TYNGGGCGRN     660

AAANCCTTTT AAGGTACCCC KGGNGGGGKG CCCYYTTGGG AAAACAACCC CKATTGGKTT     720

TGGAAATNTT TKCNCCCCCA TTCNSGGGGG GGGCCCCAMC CCMMCTTTTN TCMSCNMTYY     780

YCYYGGGAAT TNYTCGCCSG GAAYYCGGSM CCKGYCCTAA NCCCCMNWGG GKYSTGSNAR     840

GGRATMAWWT TYSTTTYYMC CCGGCNNCCC CCCKAKMCNT KGNTAACMA AAAKCSGGGG      900

GSCNMYMWYY YCNNNGNRTT TNRGGSSNMT TYMAAAMMAN GGGGKYWTYY CKCCNGSCNN     960

GKTYSGGGST TTTCCNTTTS GGGSSATYKG MACCCCKTMT AYCCGGGGGT NTKTKYCCCC    1020

SC                                                                  1022

(2) INFORMATION FOR SEQ ID NO:331:

(i) SEQUENCE CHARACTERISTICS:
        (A) LENGTH: 1083 base pairs
```

(B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:331:

| | | | | | |
|---|---|---|---|---|---|
| NNCGNNKNTA | TAMAYCWYCT | NCACCSGGGA | TCWATTGCGG | CCGCAATCTT | STMAASAGAT | 60
| CTCKAAYTCG | GCAMGANCCG | CAWCTATTTG | KGTGRASCGC | ACCAGCGRGA | CCTCGCSGKT | 120
| CKTTYCTTGC | AGRGAGGCCK | TGGGTGGCRC | CGGTGGCAAT | GCCAACCGCC | CCCCAAAACN | 180
| CCGCAAATMY | CRAAAAACAA | CCCSGGGGTA | GKTCCSGGCC | GCCAAATMAA | TAACCGTKTT | 240
| AACKCAGGCN | ACGGCCAACC | GGYCCCGCCC | AACCAAGCNA | CCTCCCCSCC | NATAGGYCCG | 300
| GTGGGGGCTG | CCKTATYKCC | AASTCGTCAY | CTCNACGGGM | CGGYCCMCWT | TCCGCCTCAT | 360
| CCGTCTCTCC | TTMMATTTTC | CRTCCACYKG | GCGGGGAACY | TTTTTNYCNC | CCTTGSCMAN | 420
| CACCNAAGGY | CNAAAATTNC | CCMTGCCKYG | SNNCAAAYGR | GATTGGGGTY | CGKKTTTTNT | 480
| TCNMCCMAAC | CCCCNTTTNA | CGCCCCMATC | CCYTWATACC | CCCWWMCMNS | ANGKTTGNSA | 540
| AAKTNNCCCC | AAATRCCAAA | MTTCTTCGCC | NTTTMTWMCY | YYCCTTTCCC | CMCCCWNAAA | 600
| GGSCCRCCYY | TCGGGAANTY | TCCCCNCAAA | AWTCAMWCCM | TTTCCCNCCA | AGAAWTTCSG | 660
| SACTCCTTTN | TTCNGGGNAM | ATANATYYTT | YCKTNGGGSK | TTCCGMTCNC | AMMAATNTCC | 720
| RGGGKAAMCC | AGKNTNNTCC | YYYYCCCCAA | NNTYCCYKGG | RMCYNNYYCY | TTAAANRASR | 780
| SAACCCKSGG | GKCYNCNCSS | TARCCCCCAM | KAAAATTTCC | CCCSSKTTTC | TYYNNKKMRW | 840
| GCCCCCSAAM | ACTMTWAYTT | TCCCKCGNNN | TTTSYCCKCS | KCAMWMWMTG | KKNCTTTTTT | 900
| YCSCMATAMA | CTTNGGKCCT | NTCNYGSGCG | CMAAANAAGG | CGCGSTTCTN | TTCWMAMACA | 960
| YNTSGNMMMA | SAAKAKWATA | AWNNTRKKYK | TKNNCCCNCC | CKCKCTTSNN | TNKCCMCSKS | 1020
| GGGKNWNKKR | GWCTCCWCNC | CKCCCNCKNK | CCKWATMCCC | CCCCSKCCGM | NCMMNTTTKT | 1080
| CCC | | | | | | 1083

(2) INFORMATION FOR SEQ ID NO:332:

(i) SEQUENCE CHARACTERISTICS:
        (A) LENGTH: 1069 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:332:

| | | | | | |
|---|---|---|---|---|---|
| GGGGNNKYAT | MCAYCWTCTS | YACSGGGMNC | TATTGCGGCC | GCAWYTNGTM | GASAGATCTC | 60
| GAAYTCGGCA | MGAAAAAAGW | GATGTGCTGG | ACCTTMCCGC | GCGGGACGCR | ACCRACAAAG | 120
| RAASCGCGCC | ANAATATTGG | CCACAKTTGG | TCACATATTT | ACCCAATTMT | AYCAGGGAYT | 180
| MCCATTCCKG | GGACCRACCG | CACAATCCCR | ATSKTGGTTT | GCRAACCCTR | ACCGTCCCCA | 240
| MYTYCGCCRA | STTGAACCAG | GGCRAAAAAA | CGGCCRAAWY | CTCGCCCTGA | NTCCCGCTCS | 300
| GCGCNAATAA | CTAGGCCCAT | TKAACGGAAC | CGGNGGCCSC | NANTTGGCCA | ACAGGTCCTR | 360
| ACAAAGGGGC | CCCASYYCGG | CCGGWTCCCW | TTYCACNCCC | TNKTCTCKTG | CCGAATYCGG | 420
| WTCCRATNYC | CCWTGGGCCT | TKTCKYCKYC | KYCGGTNCCA | AWTCTNGGTA | TNCTATRGKG | 480
| TCCCCTAAAT | SCANATCTGG | GCKYCCATTT | NCTGGSNTTC | NATTTAMMAN | SRRCGGTTCT | 540
| TTCWTTCCRA | AACCGSNTGG | GCCCNNMCCA | AAAAATGATN | ATAATAATGK | YGSCTTTCAA | 600

-continued

| | |
|---|---|
| ACCCCGCCCC CCCCATTCRWT CSGTTCCANC CCCCNGNGGT TAAGKTGGGA ATTTYTNAMC | 660 |
| YCNARGCCCT NATTTSGGNA AAAACCYCYC GGGYCTCAAA CMNYTTTTTT GSKSSNTCGG | 720 |
| GCTCRTTCSC CAAAACCCAA ATTNTYNYGG GGYCCKTNAA ACMCGGYCRC RCCGGAAATT | 780 |
| TTTYTGGTTC AACCCCAACC TTTTCAASCC NTTTTYTYYT TRCCSSCSMN TNGSSGGGNT | 840 |
| KSSCCNTTCY RARKKCCNMN GGGGGWYCYN CCCCRMNTTT CTTTTTTTTT CCGTNNMAAM | 900 |
| NGKTTCTTCA AASMCCCCCC SCCCCCNSAA ACCCCCTNAR GTTTTYCMMA AANNWYNNGN | 960 |
| KNCCCCCCCC MMNAAAAAAY YCSCCCGNRN ACSMSNGGGA MCCCCCGGSN NTTRKTTTTT | 1020 |
| TNCMSGYCCC CSRMASYYTT TKAMAMANRR GAMNSMTTTY TNNRGNWNK | 1069 |

(2) INFORMATION FOR SEQ ID NO:333:

(i) SEQUENCE CHARACTERISTICS:
        (A) LENGTH: 1210 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:333:

| | |
|---|---|
| NGNGGGGKWK MATACATCWT TCTTCACGSG GGATCWATTG CGGGCCGCAW TCTNGTMCAA | 60 |
| SAGATCTCGA TYTCGGGCAM NACCCACCWC TCCRAAAAAA ACCCRAAWCT CGGGSKCTYC | 120 |
| GARAAGTGTT GCCCGCKTTR AATTTAACAA ATTCAGTGTC ANAGTGTCAC GGCKTTACWT | 180 |
| YCCCGGCAAA GGGGCCACAA CCTGCAGRGA SCACYCRATG GKTGYTGKTS CNCGGGCGGG | 240 |
| CCGGKTNAAG GGACCTGCCT GGGTKTGCSC TMCAAANATC WYCCGCGGGT YCGCTGGRAT | 300 |
| MCNCAGGGGT GTCAAAAAAC CGCAAACAGG CACSCCANCC NTTTACGGGS CTTAAAANGA | 360 |
| AAAAGGGCTG ATGCCCCCAA GGGGGCCCGC NCCCAACCTT CCGTTGGTCA ACAACCCGGT | 420 |
| CTCTCKTGCC RAATCCGRWT CCRATNYCNC CWTGGCCTTK TCKYCTYCTY CGGTACCCAA | 480 |
| ATCTGGGTAT CCTATASTGT CCCCTAAWTT CCAAATCTGG GCTGTCCATT TSCTTGGCNT | 540 |
| TCCAAATTTA CCANCAACGG TTTCTTNCAT NCCAAAAACC GNTKGGCKCC NRACCCRAAA | 600 |
| AAATGAATAA TAATAANNGG KCNNTTYCNA ACCNCCCCCC CCCNATTCCA TYSNGTTCCA | 660 |
| NMCCCCCAG NGGKTAGGTK GGGAAANYYC TCMACCYYCA ANCCCTWARS TTTTNGRAAT | 720 |
| KAAACCCTYC YCNGGGTCWW TYMAAAAAMA NTTATTTGGN NGNTTTCGGG MWNCKRKNST | 780 |
| SCCAAAATCC MAAATANTTT YYTGGTYCNA TWAAAAAMCG YGNCCMNCCC GGAAAAWTTT | 840 |
| TTNTGKTTSA ACCCCAAAAC YTTTTCMNAA NCSSKTTTTY CYTTCCCCCC AMNWTGGGYS | 900 |
| GGGNATKGYG SCYTNTCTTA TKTKYTYMTW CMGGGGGGNN MKMTCMMCCC CCMTTTYYCY | 960 |
| NYWRTTTTTN KCCCCKTNMR NNRAANNGGN YTCSYNANAA AAGCNCCCCC SCCKNCCCNA | 1020 |
| AAAAWCCCCN NNNARAKTNT TTMKANNRMN SCKCNKNGKY YCCCCCCCWC YNMNNAAAAA | 1080 |
| AATMYCCNCC RASANMCASM NMGGRGNRSC CCCCCCCSTT NNNNTMTTNT TTTTTTCSRA | 1140 |
| GAGCKCCSCG MNNANMKNCK CTTTTTKCNC NNGNNGNGNN GGNGMNCKCC CCNAGAAMWK | 1200 |
| CTKSTCCCKS | 1210 |

(2) INFORMATION FOR SEQ ID NO:334:

(i) SEQUENCE CHARACTERISTICS:
        (A) LENGTH: 1105 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:334:

| | | | | | | |
|---|---|---|---|---|---|---|
| NGSSSNGNNA | TMCATCWYCT | GYACSGGGMT | CWATTGCGGC | CGCAACTNGT | MAASAGATCT | 60 |
| CGAAYTCGGC | AAKANACACC | ACCGCCGTGT | MTATACACCG | CAAATGTTCT | GTKTGCCAAA | 120 |
| ACCGAGACGC | GCCGGCCGCG | GGGYTCCAAC | GCKTTACYTR | ACCCGCCAGY | TCAGTGTTRA | 180 |
| AACCGGTGYT | RAGGGCCGCA | CCCAACWTAA | ACGCTTTAKC | CAAGRAWYTG | GKTGGCCCGC | 240 |
| AGCCACCTGY | TGTGGYTGCC | CTCWYCGGTG | GTAGCGCCGG | TTANCGCCGG | TTGCGCGYTC | 300 |
| AMCASCSCGC | CGGTRATCCC | AKCNWTCCCC | CGGCCMRACC | CACCGGGCAC | TTTGRACGGT | 360 |
| GCCGCCAATT | CAAAYCKYCT | GRWTCCTTCM | AAACACCACR | AAGGCCACCM | CCMSCACCNA | 420 |
| ATMGGGRACT | TTAAGGCCCA | GGCAAAACCT | NTRAKCNCCT | CCCGGGCRAA | GGTCCSGCAA | 480 |
| SCRATCCMAA | AAAAKCKNAT | TTCCCCCAGC | AKCAACCCAA | MMCGSTTTGC | TGCTTCCGGA | 540 |
| TTCGAAMCCA | ATTMCWGGKT | NCNWGGGAAA | AACASCNNCC | NWTAKCCMGG | CCCMCGGGCA | 600 |
| ATTTCSGRAA | SAACCCCTNY | CCCGGGTTTT | YCCTGCTCMG | GCCCAANACC | CCCGGGAATC | 660 |
| AAAAASGGTC | GGNCAAANGG | GCMAAACCCS | SACCCMACTT | WTTCCRCTTN | GGGGGGSCWN | 720 |
| CCKNGTTTAA | AWKSCCTCYY | CTSCCCAAAY | TCGGKCMAAA | NNGRKTTGGK | TTNGGCNACC | 780 |
| NTTTCCGGKC | CCGGGKGKGK | WGKYCTMNMA | CSTTTNTTTT | SCCCCYKAAA | NYSCCCCCCC | 840 |
| CGGSSCCCCG | CCCGGGGGGA | NNTTTTTAMA | GKKTYCCCCT | CCCCAMAAAA | ANACCCCNYC | 900 |
| CCSGGSCCCT | TTKRWAAAMN | KCTSCCCCNG | GNNGGGGKCM | GGKTTATTMT | NNNCCSCCCC | 960 |
| TCCGCGSAAA | AAATAKMTTT | SYCCCCCCNC | CTCCKNCKNR | GKAMSMSCGC | TCCCYCTCNC | 1020 |
| GCNKNTWAAN | ARSNCCKKNN | CCNCYKCCGS | NSNGKCNWCD | NCCSTSSNCT | NKGCNCKNCN | 1080 |
| KAAANAAYNC | NGSMSTSSMN | CNKCC | | | | 1105 |

(2) INFORMATION FOR SEQ ID NO:335:

(i) SEQUENCE CHARACTERISTICS:
        (A) LENGTH: 936 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:335:

| | | | | | | |
|---|---|---|---|---|---|---|
| NGSNSNKNNN | TAMAYCWYYC | TSCACSNGGA | ACWANTGCGG | CCRMAWCTNS | TMKASAGATC | 60 |
| TMGAAYTCGG | CAAGAGCGGC | AAGAGTGTGT | GCATCTGGTC | ANAGTSTMMA | CRCGGTGCCG | 120 |
| CSGGTGKGTR | GASCACMCAT | NTGCGRACAC | CAAACCCKTC | GCGGGYCACC | GGCKTCGCCT | 180 |
| GCAAAWYCCT | CCAGGCCACC | TCRAACAAYW | YCTYCTGCAA | CGCARGCCGT | TYCGCGGCCG | 240 |
| RATCCTGGKT | CASYYCGCCK | TGCGGTGCCC | AAGKTACTGG | CSCAYCAAAA | CCGCTCCGGG | 300 |
| RAACRAACKT | AAWTYTGCCG | AATTTCNTTC | CCCTGCGCCT | TGATAAATTT | NTNAAGCCAC | 360 |
| CGCAAMCCTY | CGGGCKTCTC | CTCKTGCCRA | ATYCGRWTCC | RATAYCGCCA | TGGCCTNKTC | 420 |
| KYCTYCKYCS | GTACCCAAAT | CTTGGGTATC | CTATANTKYC | CCWAAANRCA | AWTCTGGGCK | 480 |
| KTCCATKTSC | TGGSKTCCRA | ATTTAMMACA | NCGGTTTCTT | TCWTACCAAA | AACCSNTGGG | 540 |
| CCCCRACCRA | AAAAKGATAA | TAATAAKGTG | CWWWCAAAAC | CCCGCCCCCC | RRTTCAAYCG | 600 |
| GTCCARCACC | CCANGNGGTN | AGGTNGGAAT | TYTMAACCCC | CAGCCCATAA | SNTTNSGNAA | 660 |
| AAACCCCCCN | GGGYMYCAAA | AMMCTTTTTG | GGGMTTCSGS | CCATKGYKCC | AAAACCAAAA | 720 |

```
TMTTTCYGGT CRWAAAAACC GGCCCNCCCG NAAATTTTTT GKCAACCCCA AACCTTTMAM      780

CCNNNTTCYY YCCCNSACAA TNGGSGGNKN NGSSCNTTYT TWTTTYYNNA GGGGGGRRWC      840

SNCCCCNAAN YYCCNAANKG NKCCCGSNMA AAAGAGANTT YCMKAAAAAC CCCCNCNCCC      900

NAAAYACCCC MAAAKWTTCM AAASMSCNNG YCCCCC                                936

(2) INFORMATION FOR SEQ ID NO:336:

(i) SEQUENCE CHARACTERISTICS:
        (A) LENGTH: 1042 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:336:

NNNGNKNNNY ATMMAYTCWY YCTSCACCSG GGNNWCWATT GCGGCCRMAW KCTTGTMAAS       60

AGATCTMNAA YTCGGCACAG ASSSGCACAG ASCCGCGGCG CTATYCMYCC GYTGCTCATG      120

CTCAACACGC TCKTCGGCGW GRATAATGGC NCGCCGCCGG CGCCAACACG YTCAAYTGCT     180

TCGCCAACGC CATATNTCAA CAAGGTRATA AAASCAAAAC CGCSCGCCGY GCCCTTGGGC      240

SCGGRAASCG GTGCCAACCC RAAACNCKTT GGGCACYCGG KTSRACTTTA AASGGTAATC      300

TCKTCCTCCT GGGCTATGGT GCGCCACAAA CCTSYTGGCG WGGGTCTGGC CCTGGGYCAC      360

CGYCRCNTTT TATNTNTCCK YCTACACNCT TKGGTYCAAC CAACCCACTT CACMAAATTG      420

TTTTGGGKTG GGGSSGCCGG YTGTNNCCGK TAATAATCSG NTGKTCSGCC MYCACCGGWA      480

CCATANCCTG GCCGGCSCTG GCAAATTTCC SAAATCATYT CCTTCTGRAC CCCCACAMRC      540

CTNSAAATCC GRATCAATNC CCCNKGGCTT NTCYCTCTCN GTRCCCAATY TGGTTTCTAT      600

RKTNCCCYAA TSCAATTGGS TTYCCRTTSC YGSTTCCAAN TTNACAAMAS GGTTTYTCMT      660

ACCAAAACCC NTGGSCCNNA CMNAAAAKNA RAAAANAKGG KCTTTYAAAC CCCCCCCTAT      720

TCAWYCGGTN CMRNWCCCCG NGKAAGGKGN GAAAYTTHRA CCCAANCCMT ARSTTSGNAK      780

AAACCCYYCG GGGTSMCAAA MKNTWTTSSC CTTCGGMCTT YCCAAATMSA AAATYYTCKK      840

KRMNAAAAMC YGNCCCCSAA ANATTTTTGT NAAMCCCKMA YYTRTTWMCC WTTTTCCYCC      900

CCMCNNSNSG GNTNCCCTTY TYATTTCYMM MCRNNSGACN CCCCMNTYTT TWTTCKCWCN      960

MMARGSNNYT RGRMMNMNCC CCNCCCCNAK MTCCNCAAAK NTTTNAACNN NNKYCKCCCC     1020

CCCMWMNKNC CCCCMNCMTT TM                                             1042

(2) INFORMATION FOR SEQ ID NO:337:

(i) SEQUENCE CHARACTERISTICS:
        (A) LENGTH: 1073 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:337:

NNSGSGMKKK ATAMATCWCT CTSYACCSNG GMTCWATTGC GGCCGMAWTC TNGTMAASAG       60

ATCTCGAAYT CGGCAAANAK ACGCMAYGTC AAGTGTRAYY CGGTCACATA TCMTCGCGNG      120

TCAACMCCAA AGCCGNGTCA CCGYCTCCCT GGGGCGCCAC CCCCATCGGT RATGCAACYT      180

CGCGCGCCAC CGYCAAAAGG KTCWTTRAGG CGCTAAAGGT CAMCAATTCC TRAGGTYMCN      240
```

```
CACCGTTNTT TGGCCCGCCC RAWTYCTRAC CCGCAATWTC GGTAATCGGR AATTTGGGCW      300

YCGGCTTGGG CAATAAGKTN TTGGGCAACG GCGGRWTCYC NCTGGCCGRA ATTCCCNCAT      360

TCCKTTAACG GKTGRACCGT TTYCCCGGYT GCCGTAAYTG YTYCNTGGGC GCCYTCGGCC      420

CRNAGCASYY CRCTAACGGY CMCCAGGCAA TACCKTTGGC TTTRAACCAC CGGRATNAAY      480

TGKTACCCAC YTCAASSGTS CTGRANTTRK TNTCNTGRAA AANMCCACCN AACCCGGNTT      540

RATCTGCTTC MTCANCWTTT SCCGGGTTCT GCCGTTTTGR AAYCTTNATC CMTYCAAAAG      600

GTTTAMTTTC CCAANRAATT CGGYTTGCCA CCTTGGCCGS GGCTGGTTTM CGMWCCTTRR      660

AMATCCNCCS GCGGGSAAAN AMTTSGGNTT SGSCCGGTCC CCCGNAATAT YCNTGGNCCT      720

GNAAATTGSS GGGATCCCCN GSGNAYCCGG CCWTKGGGGK TNCCCAGTTG GWACAATTYC      780

WKCCGTTCCA AACCCGGGNC CGGGGGGTGG GSCCCNTTTT CCTMYNNAAA AAGKGTTTGN      840

NYYTTTTCCG CNRAANTTCA CCSKCNKTNT GGNCCNAACY YYYCAANTTC CANACCTTTA      900

AASAAANCYK YGKTYYCCCC TTTTMCCSGS SANCCCCCCM NMSSKNCGGG AAAAAAAGNK      960

TYNGCCTTAN CNSNKTKTTT TNKTYCCCCC NMWNNSNMCY NCBKKCNKRY NGNSNMNCCT     1020

MKYSKCNNNN SNNNNNKCGN GSNCSGMKYM CMNNCNGMYK NGNKSNNCCC MSC            1073

(2) INFORMATION FOR SEQ ID NO:338:

(i) SEQUENCE CHARACTERISTICS:
         (A) LENGTH: 1061 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:338:

GNSNGNKNTN TMCAYCWYCT SCACSGGGTC TATTGCGGCC GCAATYTNGT CKASAGATCT       60

CGATYTCGGC AMNANAARTG TCGTCGTCAA TTTCAGKKTG GTCKTCAAAY GGGCCAGGCC      120

GNGACCRACA CCCTGNGTCA CCCAAAANAC CAACAGCWTC AAATWTCAAG GCCRAGGCSC      180

TRTCAATYCC CRASCAKTTA ACCGTKTCCW TCRAAGGTGC CRAACCAGGC ACCCAGYTCA      240

CCGCCSGGCA AWTCGCGCTG CCGGCCGGTN TCAGCCTGAT TYCTGACCCT RWTCTGTSGG      300

TGGYCAMCNT GGTGAAGGCC CWWCCGCCNA AGAACTGGAG GGCRAATTCC CAGGANCCNA      360

GRAACCCNAG GAACCCGCGG TAKAANCCGG CRAAACCRAG GCCGYTGGCN ATTCCNATTA      420

NAMSGGTTTG CRACNTGGCC RAACCGTTTY CTTGGTCGGC CTCGGCAACC CTGGACCANT      480

TACCCCKTNC CCGGNMCMAC CYCGGGTNCT TGKYCCCAAT NTGCYCCCGC GNRANTNGGC      540

CNAATTCCAG GGCNCCANCT TTCCGGCCCN AATTCCCYTG GTTAATCACC GGGCNCNCCT      600

GGTTTTGGGC AACCCCNCYS CTTMTTTAAA CATTCCGSCC CAAATGGGNC STTGGSAAAT      660

TCTNTYCGGT GGGGCSGGCR ANMYTTCTCT YCCCNAASAN CTTAMYCCAN TTCGSSNTCC      720

CGGKCAAAWS NGGGGGGGNA AAGGGCCCCC CGGNTSCKCC GGGGKKGCCC CYGGKTTCAA      780

AANTTTCSGG GKTSTMSCGG NVTCSCCCCC CSGCCAAGRA CCGNGGTTTT TTTTTGAACC      840

KCMANTCSSA AMCCGCCSSC CCCMAAAGGS GCCTNAAWGR RAYTTNKSCC CNNAAACSGG      900

CCCCCAKYTY SGGKTTCNNC CNCCSGKKGT CCMTSTTTMM MRCCCTTTGN GNKTTTTAN      960

MGSCCTTNNC CACCCCCYCK GGGKCSMNNA GAAKTMYWKC CNGGGGNNAN RSCCCCCCNN     1020

GSGKGGGGKG MGAGYSCCKT CTKGCGNCNN YKNTTTCCCC C                         1061

(2) INFORMATION FOR SEQ ID NO:339:
```

```
       (i) SEQUENCE CHARACTERISTICS:
           (A) LENGTH: 986 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO:339:

GNNGNNNKWN ATMCAYCWYY CTSCACCSGG GMTCWATTGC GGCCGCAWKY TNGTMAASAG     60

ATCTMGAAYT CGGCACANAG CGGCACAGAG TGTGTGCATC TGTGTCANAG CTGTCAACGC    120

GGTGCCGCSG GTGGTRASCA CMCATTGCGR AACACCAAAC CCGTCCGCGG GYCACCGGCK    180

TCGCCTGCAA AAYCCTCCAG GCCACCYCRA ACAAYWYCT CCTGCAACSC ARSCCGTTYC     240

GCGGCCGRAT CCTGGKYCAS YTCGCCKTGC GGTGCGCCAA GGTACTGGCS CWYCRANACC    300

GCTYCGGGRA ACCNAACGTA AATCTTGCCN AATTTGCNTT CCCCCTSCCC TTRATNAATT    360

TGTTAAACCA CGCAAACCTY CGGGCKTCTC CTCKTGCCRA WTCCGRWTCC RATNYCGCCA    420

TGGCCTNKTC KYCTYCKYCS GTMCCCAAAT CTTGGTATCC TATATTGTCC CTAAATGCAA    480

ATCTKGGCTG TCCATNTGCT GGCGTTCAAA TTWAMANCAG NGGTTTCTTY CTTCCNAAAC    540

CCSTTGGCCC CAAACCNAAA AATGATNATA ATAATGGTGC TNTCAAACCC CGCNCCCATY    600

CNATCSGKCC AMMCCCCRGN GGKTANKKGG GNAATTCTMM AACCCCAAGC CATAASNTTG    660

SGANAAACCY NCNCMGGYCA CCAAAACANY NTTNTTGGNY SSNTTCGGMN YCATGGCTNN    720

CMAAAACCCA AATACTNYYG GGYCCAATAA AAMMMSGGYC SAMCCGGAAA WTTTTYTTGN    780

KYNAAACCNA AAKCCTTTTT CNAACCCDAN WNTYCCTNCC RCRCMANTGG CNSGGARTKT    840

SSSCTTNCCA ATGKYCCMAA AGNGGGRANA CCARCCCCAA TTCCTNNNTN KNKNCCCNST    900

TRNAAAAGGG GKNTYNCMAA AASCNCCNCC NCNCTCCCAA AAKAMCCCCN AAAGAKNTCN    960

NAANASKYSN NNNSCCCCCC CCMMMN                                         986

(2) INFORMATION FOR SEQ ID NO:340:

(i) SEQUENCE CHARACTERISTICS:
           (A) LENGTH: 1074 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO:340:

NGNGGGNKRN ATMMAYCWCT SATYYACCSN GGMNMWATTG CGGCCRMAWT CTNGTMKASA     60

GATCTMGAAA YTCGGCAAAG AGYATKCTCG GGGGCCAGAT TTNTGGCCCG CAACCGCCGC    120

ACTTTGCAYW TCAACAKTCC SGGTGCCCCA AAAAAWTCWT ACCCCCATMC TYCKTGCASM    180

ASYTGCGCCC RATTRAACAC CCGGCCGGCW TGCTGCGCCA GGTATTYCAS CAGYTCAAAY    240

YCTTTKTAGK TAAAATCCAG CSGGCGGCCA CNCAGCCGGG CGGTKTAGGT GCCTYCRTCA    300

ATMACCAGCY CGCCCAGGGY CACCTTGCCC AAAAYCTCCT GGGTCAGCCA AATTYCCGCS    360

CCGGCCAACM ACCANCCGCA TYCTGGCNTC AATCYCACCG GCCCGGTGY TAAAMMANMA     420

GRATCTCKTC MANCCCCCAN TCAGCSYTNA CNGCMACAGC CCGCCTTCTT CAMACCGCCA    480

RTACCGGGWT CAACCGGCCS GTCAAACTCA ACAGGCGGNC AGGCCTCCCC CGGANSAAAG    540

GTCTTACSCC NNYAANAAAA MAAGNTCTGT TTTCCCCCTC CASAASNAAA AANCCCCSGC    600

CGGGCCTTCN NMMGGGTTTG GGGMANANAA AARCNCCGGN GGAACGNATC CGAAAMCTCC    660
```

```
CAAGTCNCMT TWAWAACYCN NNAACCCCCC ANTTTTGGGA AAGGNTCCCC NTTMYCCCCC      720

TTTTASGKTS GGGMMYYCTY TAAAAAAATT CCCCAAAAAG CCCCGGGAAG GGTCMAMCTG      780

GGNAAATTTC CAAMCCNWGK TTNTTYNGGT TMCGGGGRA AATTYCNCTC CCYYNNNGGG      840

CSSGSNNNAT TAYGGMSNMT TTTNNAAWTM NSGKKTSAMM YNNKCCMNNN SNNMSMANNK      900

TNAMCKCCCN CCTCNGNGKY CSCYNCCCSG GNAGNGGRAS MKCCNANMAA AYASGNTTNK      960

CGGAAMMCNN AATKGNNNSC CCGGASMCMN NNNMAAATMT CNCNKCNSNN AANRGMRACN     1020

CCCNSNSGMN RRGAARMTNY YCCCCCGSKM GKGNKAAAAW GKYCCCCCCM AAAG          1074

(2) INFORMATION FOR SEQ ID NO:341:

(i) SEQUENCE CHARACTERISTICS:
        (A) LENGTH: 1195 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:341:

NGNGNCNKNT MTACATCWTT CTGCACCSGG GNTCWANTGC GGCCGCAWKY TTGTCGASAG       60

ATCTCGAAYT CGGCAMGAGG ACWCTCGCRA CGCCCCCACA NACTCTGGCG TGTGTACCCC      120

ATTGNGCGCK TCACGCGCCC AYTGANCCAK TNCACTGGGG TGCCGTYCGC CKTGCGCGGC      180

GGCCTCACGG CKCTSCWTCT RAAGGCWTGG CGCACCGCAT TCGGTTTTCT RAACGCTGGG      240

AAAWTGGCCA GCCGTCTGGC TCATGGGNTC TACGCAACGC CNGCCCCCAA CRCTTTCTTA      300

AATCCGGYCC NTCCTGANCS CTTTGAAYCC CGGGGSAAGA ACTGGTTGCS CNCGAYCTGC      360

TCGAACTTRK TCNAAATCCC GCANAKTGTT TCNTAMGYCC CNCCGGAAGG NGAACCTACT      420

TTCNGGWANG TCGGCNKCCG GCGCTTATCA STCCTGATCA ACGGGGAACT GGYKNNSTTG      480

KGGGAAAAAG RRCCTCAATG MTYGGTCCKC GCTGCGKANC CGCSCCCTGK GYCGCNAATG      540

GAAGGCSMAG GGTTAANGCC MTTYCNYCCR RSCCGTSTGA SGKWTTYCGG MGGANKAMNN      600

NNKMAMWTTK TCRGNGGCCW ATSTSCCGGG CKSTTAKAGA ANACTYCCKW WCCGTNTYSC      660

SAAAGNTKCS GCGMGTTTTS SCCKMGANGN YCTGATTTSA GGGGGKYKCC CCCGGGGTYC      720

CGAAWKWRKY CCYAGGGGGM GNYCSAGCSC CGMNNATNAG AGNAAGGKTT RYGSTSKNCC      780

TYTNKGGACC WSCNNCWSAK ANAACNNKKT TGCSCCNTMS AGNKTNKGRT YCCNKTSTTC      840

TAAGAGGAGC TATKMKCGCC CKTGGANGMM GAGWGMGCGC KYCCCSNKRT TCNTNGWAAA      900

TATKSAGMGG TKCCGMAGMK CCSCGTTTKT TKTGANAAMN MSMRKNKKTG CGMGYTCTSC      960

GGGNTTTGTA GAGTAKTCGS CSCSSMWGAC WCSGMCMGNG AGKNKTNNTS YANTGARCGY     1020

MNNSKTMKMT MSCSCGCGNA GGAGNGCCCC CSANGMSTGY NKGGNMSSNG ARAKGATGGS     1080

GGCCNCGMNN MGMGGANMGA SANNGMGGMR GGGGGKTGKC TCKCSCCGNS CSANGRAGAA     1140

GKTCNGSCGC CGMGGKYGKT KTKTKNKTGG YSTCMSSMMM NAGAAAAGAG AGGGC          1195

(2) INFORMATION FOR SEQ ID NO:342:

(i) SEQUENCE CHARACTERISTICS:
        (A) LENGTH: 3572 base pairs
        (B) TYPE: nucleic acid
        (C) STRANDEDNESS: single
        (D) TOPOLOGY: linear (ii) MOLECULE TYPE: Genomic DNA
```

(xi) SEQUENCE DESCRIPTION: SEQ ID NO:342:

```
CCATCTGATC GTTGGCAACC AGCATCGCAG TGGGAACGAT GCCCTCATTC AGCATTTGCA      60
TGGTTTGTTG AAAACCGGAC ATGGCACTCC AGTCGCCTTC CCGTTCCGCT ATCGGCTGAA     120
TTTGATTGCG AGTGAGATAT TTATGCCAGC CAGCCAGACG CAGACGCGCC GAGACAGAAC     180
TTAATGGGCC CGCTAACAGC GCGATTTGCT GGTGACCCAA TGCGACCAGA TGCTCCACGC     240
CCAGTCGCGT ACCGTCTTCA TGGGAGAAAA TAATACTGTT GATGGGTGTC TGGTCAGAGA     300
CATCAAGAAA TAACGCCGGA ACATTAGTGC AGGCAGCTTC CACAGCAATG GCATCCTGGT     360
CATCCAGCGG ATAGTTAATG ATCAGCCCAC TGACGCGTTG CGCGAGAAGA TTGTGCACCG     420
CCGCTTTACA GGCTTCGACG CCGCTTCGTT CTACCATCGA CACCACCACG CTGGCACCCA     480
GTTGATCGGC GCGAGATTTA ATCGCCGCGA CAATTTGCGA CGGCGCGTGC AGGGCCAGAC     540
TGGAGGTGGC AACGCCAATC AGCAACGACT GTTTGCCCGC CAGTTGTTGT GCCACGCGGT     600
TGGGAATGTA ATTCAGCTCC GCCATCGCCG CTTCCACTTT TTCCCGCGTT TTCGCAGAAA     660
CGTGGCTGGC CTGGTTCACC ACGCGGGAAA CGGTCTGATA AGAGACACCG GCATACTCTG     720
CGACATCGTA TAACGTTACT GGTTTCACAT TCACCACCCT GAATTGACTC TCTTCCGGGC     780
GCTATCATGC CATACCGCGA AAGGTTTTGC GCCATTCGAT GGTGTCCGGG ATCTCGACGC     840
TCTCCCTTAT GCGACTCCTG CATTAGGAAG CAGCCCAGTA GTAGGTTGAG GCCGTTGAGC     900
ACCGCCGCCG CAAGGAATGG TGCATGCAAG GAGATGGCGC CAACAGTCC CCCGGCCACG      960
GGGCCTGCCA CCATACCCAC GCCGAAACAA GCGCTCATGA GCCCGAAGTG GCGAGCCCGA    1020
TCTTCCCCAT CGGTGATGTC GGCGATATAG GCGCCAGCAA CCGCACCTGT GGCGCCGGTG    1080
ATGCCGGCCA CGATGCGTCC GGCGTAGAGG ATCGAGATCT CGATCCCGCG AAATTAATAC    1140
GACTCACTAT AGGGGAATTG TGAGCGGATA ACAATTCCCC TCTAGAAATA ATTTTGTTTA    1200
ACTTTAAGAA GGAGATATAC ATATGGGCCA TCATCATCAT CATCACGTGA TCGACATCAT    1260
CGGGACCAGC CCCACATCCT GGGAACAGGC GGCGGCGGAG GCGGTCCAGC GGGCGCGGGA    1320
TAGCGTCGAT GACATCCGCG TCGCTCGGGT CATTGAGCAG GACATGGCCG TGGACAGCGC    1380
CGGCAAGATC ACCTACCGCA TCAAGCTCGA AGTGTCGTTC AAGATGAGGC CGGCGCAACC    1440
GAGGGGCTCG AAACCACCGA GCGGTTCGCC TGAAACGGGC GCCGGCGCCG GTACTGTCGC    1500
GACTACCCCC GCGTCGTCGC CGGTGACGTT GGCGGAGACC GGTAGCACGC TGCTCTACCC    1560
GCTGTTCAAC CTGTGGGGTC CGGCCTTTCA CGAGAGGTAT CCGAACGTCA CGATCACCGC    1620
TCAGGGCACC GGTTCTGGTG CCGGGATCGC GCAGGCCGCC GCCGGGACGG TCAACATTGG    1680
GGCCTCCGAC GCCTATCTGT CGGAAGGTGA TATGGCCGCG CACAAGGGGC TGATGAACAT    1740
CGCGCTAGCC ATCTCCGCTC AGCAGGTCAA CTACAACCTG CCCGGAGTGA GCGAGCACCT    1800
CAAGCTGAAC GGAAAAGTCC TGGCGGCCAT GTACCAGGGC ACCATCAAAA CCTGGGACGA    1860
CCCGCAGATC GCTGCGCTCA ACCCCGGCGT GAACCTGCCC GGCACCGCGG TAGTTCCGCT    1920
GCACCGCTCC GACGGGTCCG GTGACACCTT CTTGTTCACC CAGTACCTGT CCAAGCAAGA    1980
TCCCGAGGGC TGGGGCAAGT CGCCCGGCTT CGGCACCACC GTCGACTTCC CGGCGGTGCC    2040
GGGTGCGCTG GGTGAGAACG GCAACGGCGG CATGGTGACC GGTTGCGCCG AGACACCGGG    2100
CTGCGTGGCC TATATCGGCA TCAGCTTCCT CGACCAGGCC AGTCAACGGG GACTCGGCGA    2160
GGCCCAACTA GGCAATAGCT CTGGCAATTT CTTGTTGCCC GACGCGCAAA GCATTCAGGC    2220
CGCGGCGGCT GGCTTCGCAT CGAAAACCCC GGCGAACCAG GCGATTTCGA TGATCGACGG    2280
GCCCGCCCCG GACGGCTACC CGATCATCAA CTACGAGTAC GCCATCGTCA ACAACCGGCA    2340
```

```
AAAGGACGCC GCCACCGCGC AGACCTTGCA GGCATTTCTG CACTGGGCGA TCACCGACGG    2400

CAACAAGGCC TCGTTCCTCG ACCAGGTTCA TTTCCAGCCG CTGCCGCCCG CGGTGGTGAA    2460

GTTGTCTGAC GCGTTGATCG CGACGATTTC CAGCGCTGAG ATGAAGACCG ATGCCGCTAC    2520

CCTCGCGCAG GAGGCAGGTA ATTTCGAGCG GATCTCCGGC GACCTGAAAA CCCAGATCGA    2580

CCAGGTGGAG TCGACGGCAG GTTCGTTGCA GGGCCAGTGG CGCGGCGCGG CGGGGACGGC    2640

CGCCCAGGCC GCGGTGGTGC GCTTCCAAGA AGCAGCCAAT AAGCAGAAGC AGGAACTCGA    2700

CGAGATCTCG ACGAATATTC GTCAGGCCGG CGTCCAATAC TCGAGGGCCG ACGAGGAGCA    2760

GCAGCAGGCG CTGTCCTCGC AAATGGGCTT TGGATTCAGC TTCGCGCTGC CTGCTGGCTG    2820

GGTGGAGTCT GACGCCGCCC ACTTCGACTA CGGTTCAGCA CTCCTCAGCA AAACCACCGG    2880

GGACCCGCCA TTTCCCGGAC AGCCGCCGCC GGTGGCCAAT GACACCCGTA TCGTGCTCGG    2940

CCGGCTAGAC CAAAAGCTTT ACGCCAGCGC CGAAGCCACC GACTCCAAGG CCGCGGCCCG    3000

GTTGGGCTCG GACATGGGTG AGTTCTATAT GCCCTACCCG GGCACCCGGA TCAACCAGGA    3060

AACCGTCTCG CTYGACGCCA ACGGGGTGTC TGGAAGCGCG TCGTATTACG AAGTCAAGTT    3120

CAGCGATCCG AGTAAGCCGA ACGGCCAGAT CTGGACGGGC GTAATCGGCT CGCCCGCGGC    3180

GAACGCACCG GACGCCGGGC CCCCTCAGCG CTGGTTTGTG GTATGGCTCG GACCGCCAA    3240

CAACCCGGTG GACAAGGGCG CGGCCAAGGC GCTGGCCGAA TCGATCCGGC CTTTGGTCGC    3300

CCCGCCGCCG GCGCCGGCCG GGGAAGTCGC TCCTACCCCG ACGACACCGA CACCGCAGCG    3360

GACCTTACCG GCCTGAGAAT TCTGCAGATA TCCATCACAC TGGCGGCCGC TCGAGCACCA    3420

CCACCACCAC CACTGAGATC CGGCTGCTAA CAAAGCCCGA AAGGAAGCTG AGTTGGCTGC    3480

TGCCACCGCT GAGCAATAAC TAGCATAACC CCTTGGGGCC TCTAAACGGG TCTTGAGGGG    3540

TTTTTTGCTG AAAGGAGGAA CTATATCCGG AT                                  3572
```

(2) INFORMATION FOR SEQ ID NO:343:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:343:

```
Val Gln Phe Gln Ser Gly Gly Asp Asn Ser Pro Ala Val Tyr Xaa Xaa
 1               5                  10                  15

Asp Gly Xaa Arg
            20
```

(2) INFORMATION FOR SEQ ID NO:344:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:344:

```
Thr Thr Val Pro Xaa Val Thr Glu Ala Arg
 1               5                  10
```

(2) INFORMATION FOR SEQ ID NO:345:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:345:

```
Thr Thr Pro Ser Xaa Val Ala Phe Ala Arg
 1               5                  10
```

(2) INFORMATION FOR SEQ ID NO:346:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:346:

```
Asp Ala Gly Lys Xaa Ala Gly Xaa Asp Val Xaa Arg
 1               5                  10
```

(2) INFORMATION FOR SEQ ID NO:347:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:347:

```
Thr Xaa Glu Glu Xaa Gln Glu Ser Phe Asn Ser Ala Ala Pro Gly Asn
 1               5                  10                  15
Xaa Lys
```

(2) INFORMATION FOR SEQ ID NO:348:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:348:

CTAGTTAGTA CTCAGTCGCA GACCGTG                                27

(2) INFORMATION FOR SEQ ID NO:349:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:349:

GCAGTGACGA ATTCACTTCG ACTCC                                  25

(2) INFORMATION FOR SEQ ID NO:350:

(i) SEQUENCE CHARACTERISTICS:
        (A) LENGTH: 2412 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:350:

```
CATATGGGCC ATCATCATCA TCATCACGTG ATCGACATCA TCGGGACCAG CCCCACATCC        60

TGGGAACAGG CGGCGGCGGA GGCGGTCCAG CGGGCGCGGG ATAGCGTCGA TGACATCCGC       120

GTCGCTCGGG TCATTGAGCA GGACATGGCC GTGGACAGCG CCGGCAAGAT CACCTACCGC       180

ATCAAGCTCG AAGTGTCGTT CAAGATGAGG CCGGCGCAAC CGAGGGGCTC GAAACCACCG       240

AGCGGTTCGC CTGAAACGGG CGCCGGCGCC GGTACTGTCG CGACTACCCC CGCGTCGTCG       300

CCGGTGACGT TGGCGGAGAC CGGTAGCACG CTGCTCTACC CGCTGTTCAA CCTGTGGGGT       360

CCGGCCTTTC ACGAGAGGTA TCCGAACGTC ACGATCACCG CTCAGGGCAC CGGTTCTGGT       420

GCCGGGATCG CGCAGGCCGC CGCCGGGACG GTCAACATTG GGCCTCCGA CGCCTATCTG       480

TCGGAAGGTG ATATGGCCGC GCACAAGGGG CTGATGAACA TCGCGCTAGC CATCTCCGCT       540

CAGCAGGTCA ACTACAACCT GCCCGGAGTG AGCGAGCACC TCAAGCTGAA CGGAAAAGTC       600

CTGGCGGCCA TGTACCAGGG CACCATCAAA ACCTGGACG ACCCGCAGAT CGCTGCGCTC       660

AACCCCGGCG TGAACCTGCC CGGCACCGCG GTAGTTCCGC TGCACCGCTC CGACGGGTCC       720

GGTGACACCT TCTTGTTCAC CCAGTACCTG TCCAAGCAAG ATCCCGAGGG CTGGGGCAAG       780

TCGCCCGGCT TCGGCACCAC CGTCGACTTC CCGGCGGTGC CGGGTGCGCT GGGTGAGAAC       840

GGCAACGGCG GCATGGTGAC CGGTTGCGCC GAGACACCGG GCTGCGTGGC CTATATCGGC       900

ATCAGCTTCC TCGACCAGGC CAGTCAACGG GGACTCGGCG AGGCCCAACT AGGCAATAGC       960

TCTGGCAATT TCTTGTTGCC CGACGCGCAA AGCATTCAGG CCGCGGCGGC TGGCTTCGCA      1020

TCGAAAACCC CGGCGAACCA GGCGATTTCG ATGATCGACG GGCCCGCCCC GGACGGCTAC      1080

CCGATCATCA ACTACGAGTA CGCCATCGTC AACAACCGGC AAAAGGACGC CGCCACCGCG      1140

CAGACCTTGC AGGCATTTCT GCACTGGGCG ATCACCGACG GCAACAAGGC CTCGTTCCTC      1200

GACCAGGTTC ATTTCCAGCC GCTGCCGCCC GCGGTGGTGA AGTTGTCTGA CGCGTTGATC      1260

GCGACGATTT CCAGCGCTGA GATGAAGACC GATGCCGCTA CCCTCGCGCA GGAGGCAGGT      1320

AATTTCGAGC GGATCTCCGG CGACCTGAAA ACCCAGATCG ACCAGGTGGA GTCGACGGCA      1380

GGTTCGTTGC AGGGCCAGTG GCGCGGCGCG GCGGGGACGG CCGCCCAGGC CGCGGTGGTG      1440

CGCTTCCAAG AAGCAGCCAA TAAGCAGAAG CAGGAACTCG ACGAGATCTC GACGAATATT      1500

CGTCAGGCCG GCGTCCAATA CTCGAGGGCC GACGAGGAGC AGCAGCAGGC GCTGTCCTCG      1560

CAAATGGGCT TTGTGCCCAC AACGGCCGCC TCGCCGCCGT CGACCGCTGC AGCGCCACCC      1620

GCACCGGCGA CACCTGTTGC CCCCCCACCA CCGGCCGCCG CCAACACGCC GAATGCCCAG      1680

CCGGGCGATC CCAACGCAGC ACCTCCGCCG GCCGACCCGA ACGCACCGCC GCCACCTGTC      1740

ATTGCCCCAA ACGCACCCCA ACCTGTCCGG ATCGACAACC CGGTTGGAGG ATTCAGCTTC      1800

GCGCTGCCTG CTGGCTGGGT GGAGTCTGAC GCCGCCCACT TCGACTACGG TTCAGCACTC      1860

CTCAGCAAAA CCACCGGGGA CCCGCCATTT CCCGGACAGC CGCCGCCGGT GGCCAATGAC      1920

ACCCGTATCG TGCTCGGCCG GCTAGACCAA AAGCTTTACG CCAGCGCCGA AGCCACCGAC      1980
```

```
TCCAAGGCCG CGGCCCGGTT GGGCTCGGAC ATGGGTGAGT CTATATGCC CTACCCGGGC     2040

ACCCGGATCA ACCAGGAAAC CGTCTCGCTC GACGCCAACG GGGTGTCTGG AAGCGCGTCG    2100

TATTACGAAG TCAAGTTCAG CGATCCGAGT AAGCCGAACG GCCAGATCTG GACGGGCGTA    2160

ATCGGCTCGC CCGCGGCGAA CGCACCGGAC GCCGGGCCCC CTCAGCGCTG GTTTGTGGTA    2220

TGGCTCGGGA CCGCCAACAA CCCGGTGGAC AAGGGCGCGG CCAAGGCGCT GGCCGAATCG    2280

ATCCGGCCTT TGGTCGCCCC GCCGCCGGCG CCGGCACCGG CTCCTGCAGA GCCCGCTCCG    2340

GCGCCGGCGC CGGCCGGGGA AGTCGCTCCT ACCCCGACGA CACCGACACC GCAGCGGACC    2400

TTACCGGCCT GA                                                        2412

(2) INFORMATION FOR SEQ ID NO:351:

(i) SEQUENCE CHARACTERISTICS:
        (A) LENGTH: 802 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:351:

Met Gly His His His His His His Val Ile Asp Ile Ile Gly Thr Ser
1               5                   10                  15

Pro Thr Ser Trp Glu Gln Ala Ala Glu Ala Val Gln Arg Ala Arg
            20                  25                  30

Asp Ser Val Asp Asp Ile Arg Val Ala Arg Val Ile Glu Gln Asp Met
        35                  40                  45

Ala Val Asp Ser Ala Gly Lys Ile Thr Tyr Arg Ile Lys Leu Glu Val
    50                  55                  60

Ser Phe Lys Met Arg Pro Ala Gln Pro Arg Gly Ser Lys Pro Pro Ser
65                  70                  75                  80

Gly Ser Pro Glu Thr Gly Ala Gly Ala Gly Thr Val Ala Thr Thr Pro
                85                  90                  95

Ala Ser Ser Pro Val Thr Leu Ala Glu Thr Gly Ser Thr Leu Leu Tyr
            100                 105                 110

Pro Leu Phe Asn Leu Trp Gly Pro Ala Phe His Glu Arg Tyr Pro Asn
        115                 120                 125

Val Thr Ile Thr Ala Gln Gly Thr Gly Ser Gly Ala Gly Ile Ala Gln
    130                 135                 140

Ala Ala Ala Gly Thr Val Asn Ile Gly Ala Ser Asp Ala Tyr Leu Ser
145                 150                 155                 160

Glu Gly Asp Met Ala Ala His Lys Gly Leu Met Asn Ile Ala Leu Ala
                165                 170                 175

Ile Ser Ala Gln Gln Val Asn Tyr Asn Leu Pro Gly Val Ser Glu His
            180                 185                 190

Leu Lys Leu Asn Gly Lys Val Leu Ala Ala Met Tyr Gln Gly Thr Ile
        195                 200                 205

Lys Thr Trp Asp Asp Pro Gln Ile Ala Ala Leu Asn Pro Gly Val Asn
    210                 215                 220

Leu Pro Gly Thr Ala Val Val Pro Leu His Arg Ser Asp Gly Ser Gly
225                 230                 235                 240

Asp Thr Phe Leu Phe Thr Gln Tyr Leu Ser Lys Gln Asp Pro Glu Gly
                245                 250                 255

Trp Gly Lys Ser Pro Gly Phe Gly Thr Thr Val Asp Phe Pro Ala Val
            260                 265                 270
```

-continued

```
Pro Gly Ala Leu Gly Glu Asn Gly Asn Gly Met Val Thr Gly Cys
            275                 280                 285
Ala Glu Thr Pro Gly Cys Val Ala Tyr Ile Gly Ile Ser Phe Leu Asp
        290                 295                 300
Gln Ala Ser Gln Arg Gly Leu Gly Glu Ala Gln Leu Gly Asn Ser Ser
305                 310                 315                 320
Gly Asn Phe Leu Leu Pro Asp Ala Gln Ser Ile Gln Ala Ala Ala Ala
                325                 330                 335
Gly Phe Ala Ser Lys Thr Pro Ala Asn Gln Ala Ile Ser Met Ile Asp
            340                 345                 350
Gly Pro Ala Pro Asp Gly Tyr Pro Ile Ile Asn Tyr Glu Tyr Ala Ile
            355                 360                 365
Val Asn Asn Arg Gln Lys Asp Ala Ala Thr Ala Gln Thr Leu Gln Ala
370                 375                 380
Phe Leu His Trp Ala Ile Thr Asp Gly Asn Lys Ala Ser Phe Leu Asp
385                 390                 395                 400
Gln Val His Phe Gln Pro Leu Pro Pro Ala Val Val Lys Leu Ser Asp
            405                 410                 415
Ala Leu Ile Ala Thr Ile Ser Ser Ala Glu Met Lys Thr Asp Ala Ala
            420                 425                 430
Thr Leu Ala Gln Glu Ala Gly Asn Phe Glu Arg Ile Ser Gly Asp Leu
        435                 440                 445
Lys Thr Gln Ile Asp Gln Val Glu Ser Thr Ala Gly Ser Leu Gln Gly
        450                 455                 460
Gln Trp Arg Gly Ala Ala Gly Thr Ala Ala Gln Ala Ala Val Val Arg
465                 470                 475                 480
Phe Gln Glu Ala Ala Asn Lys Gln Lys Gln Glu Leu Asp Glu Ile Ser
            485                 490                 495
Thr Asn Ile Arg Gln Ala Gly Val Gln Tyr Ser Arg Ala Asp Glu Glu
            500                 505                 510
Gln Gln Gln Ala Leu Ser Ser Gln Met Gly Phe Val Pro Thr Thr Ala
        515                 520                 525
Ala Ser Pro Pro Ser Thr Ala Ala Pro Pro Ala Pro Ala Thr Pro
        530                 535                 540
Val Ala Pro Pro Pro Ala Ala Ala Asn Thr Pro Asn Ala Gln Pro
545                 550                 555                 560
Gly Asp Pro Asn Ala Ala Pro Pro Ala Asp Pro Asn Ala Pro Pro
            565                 570                 575
Pro Pro Val Ile Ala Pro Asn Ala Pro Gln Pro Val Arg Ile Asp Asn
            580                 585                 590
Pro Val Gly Gly Phe Ser Phe Ala Leu Pro Ala Gly Trp Val Glu Ser
            595                 600                 605
Asp Ala Ala His Phe Asp Tyr Gly Ser Ala Leu Leu Ser Lys Thr Thr
            610                 615                 620
Gly Asp Pro Pro Phe Pro Gly Gln Pro Pro Val Ala Asn Asp Thr
625                 630                 635                 640
Arg Ile Val Leu Gly Arg Leu Asp Gln Lys Leu Tyr Ala Ser Ala Glu
                645                 650                 655
Ala Thr Asp Ser Lys Ala Ala Ala Arg Leu Gly Ser Asp Met Gly Glu
            660                 665                 670
Phe Tyr Met Pro Tyr Pro Gly Thr Arg Ile Asn Gln Glu Thr Val Ser
            675                 680                 685
```

-continued

```
Leu Asp Ala Asn Gly Val Ser Gly Ser Ala Ser Tyr Tyr Glu Val Lys
    690                 695                 700
Phe Ser Asp Pro Ser Lys Pro Asn Gly Gln Ile Trp Thr Gly Val Ile
705                 710                 715                 720
Gly Ser Pro Ala Ala Asn Ala Pro Asp Ala Gly Pro Pro Gln Arg Trp
                725                 730                 735
Phe Val Val Trp Leu Gly Thr Ala Asn Asn Pro Val Asp Lys Gly Ala
            740                 745                 750
Ala Lys Ala Leu Ala Glu Ser Ile Arg Pro Leu Val Ala Pro Pro Pro
        755                 760                 765
Ala Pro Ala Pro Ala Pro Ala Glu Pro Ala Pro Ala Pro Ala Pro Ala
    770                 775                 780
Gly Glu Val Ala Pro Thr Pro Thr Thr Pro Thr Pro Gln Arg Thr Leu
785                 790                 795                 800
Pro Ala
```

(2) INFORMATION FOR SEQ ID NO:352:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:352:

GGATCCAAAC CACCGAGCGG TTCGCCTGAA ACGG                                34

(2) INFORMATION FOR SEQ ID NO:353:

(i) SEQUENCE CHARACTERISTICS:
       (A) LENGTH: 37 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:353:

CGCTGCGAAT TCACCTCCGG AGGAAATCGT CGCGATC                             37

(2) INFORMATION FOR SEQ ID NO:354:

(i) SEQUENCE CHARACTERISTICS:
       (A) LENGTH: 1962 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:354:

CATATGGGCC ATCATCATCA TCATCACGGA TCCAAACCAC CGAGCGGTTC GCCTGAAACG      60

GGCGCCGGCG CCGGTACTGT CGCGACTACC CCCGCGTCGT CGCCGGTGAC GTTGGCGGAG     120

ACCGGTAGCA CGCTGCTCTA CCCGCTGTTC AACCTGTGGG GTCCGGCCTT TCACGAGAGG     180

TATCCGAACG TCACGATCAC CGCTCAGGGC ACCGGTTCTG GTGCCGGGAT CGCGCAGGCC     240

GCCGCCGGGA CGGTCAACAT TGGGGCCTCC GACGCCTATC TGTCGGAAGG TGATATGGCC     300

GCGCACAAGG GGCTGATGAA CATCGCGCTA GCCATCTCCC CTCAGCAGGT CAACTACAAC     360

CTGCCCGGAG TGAGCGAGCA CCTCAAGCTG AACGGAAAAG TCCTGGCGGC CATGTACCAG     420
```

```
GGCACCATCA AAACCTGGGA CGACCCGCAG ATCGCTGCGC TCAACCCCGG CGTGAACCTG    480

CCCGGCACCG CGGTAGTTCC GCTGCACCGC TCCGACGGGT CCGGTGACAC CTTCTTGTTC    540

ACCCAGTACC TGTCCAAGCA AGATCCCGAG GGCTGGGGCA AGTCGCCCGG CTTCGGCACC    600

ACCGTCGACT TCCCGGCGGT GCCGGGTGCG CTGGGTGAGA ACGGCAACGG CGGCATGGTG    660

ACCGGTTGCG CCGAGACACC GGGCTGCGTG GCCTATATCG GCATCAGCTT CCTCGACCAG    720

GCCAGTCAAC GGGGACTCGG CGAGGCCCAA CTAGGCAATA GCTCTGGCAA TTTCTTGTTG    780

CCCGACGCGC AAAGCATTCA GGCCGCGGCG GCTGGCTTCG CATCGAAAAC CCCGGCGAAC    840

CAGGCGATTT CGATGATCGA CGGGCCCGCC CCGGACGGCT ACCCGATCAT CAACTACGAG    900

TACGCCATCG TCAACAACCG GCAAAAGGAC GCCGCCACCG CGCAGACCTT GCAGGCATTT    960

CTGCACTGGG CGATCACCGA CGGCAACAAG GCCTCGTTCC TCGACCAGGT TCATTTCCAG   1020

CCGCTGCCGC CCGCGGTGGT GAAGTTGTCT GACGCGTTGA TCGCGACGAT TTCCTCCGGA   1080

GGTGGCAGTG GGGGAGGCTC AGGTGGAGGT TCTGGCGGGA GCGTGCCCAC AACGGCCGCC   1140

TCGCCGCCGT CGACCGCTGC AGCGCCACCC GCACCGGCGA CACCTGTTGC CCCCCCACCA   1200

CCGGCCGCCG CCAACACGCC GAATGCCCAG CCGGGCGATC CCAACGCAGC ACCTCCGCCG   1260

GCCGACCCGA ACGACCGCC GCCACCTGTC ATTGCCCCAA ACGCACCCCA ACCTGTCCGG   1320

ATCGACAACC CGGTTGGAGG ATTCAGCTTC GCGCTGCCTG CTGGCTGGGT GGAGTCTGAC   1380

GCCGCCCACT TCGACTACGG TTCAGCACTC CTCAGCAAAA CCACCGGGGA CCCGCCATTT   1440

CCCGGACAGC CGCCGCCGGT GGCCAATGAC ACCCGTATCG TGCTCGGCCG GCTAGACCAA   1500

AAGCTTTACG CCAGCGCCGA AGCCACCGAC TCCAAGGCCG CGGCCCGGTT GGGCTCGGAC   1560

ATGGGTGAGT CTATATGCC CTACCCGGGC ACCCGGATCA ACCAGGAAAC CGTCTCGCTC   1620

GACGCCAACG GGGTGTCTGG AAGCGCGTCG TATTACGAAG TCAAGTTCAG CGATCCGAGT   1680

AAGCCGAACG GCCAGATCTG GACGGGCGTA ATCGGCTCGC CCGCGGCGAA CGCACCGGAC   1740

GCCGGGCCCC CTCAGCGCTG GTTTGTGGTA TGGCTCGGGA CCGCCAACAA CCCGGTGGAC   1800

AAGGGCGCGG CCAAGGCGCT GGCCGAATCG ATCCGGCCTT TGGTCGCCCC GCCGCCGGCG   1860

CCGGCACCGG CTCCTGCAGA GCCCGCTCCG GCGCCGGCGC CGGCCGGGGA AGTCGCTCCT   1920

ACCCCGACGA CACCGACACC GCAGCGGACC TTACCGGCCT GA                     1962
```

(2) INFORMATION FOR SEQ ID NO:355:

(i) SEQUENCE CHARACTERISTICS:
        (A) LENGTH: 652 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:355:

```
Met Gly His His His His His Gly Ser Lys Pro Pro Ser Gly Ser
 1               5                  10                  15

Pro Glu Thr Gly Ala Gly Ala Gly Thr Val Ala Thr Pro Ala Ser
            20                  25                  30

Ser Pro Val Thr Leu Ala Glu Thr Gly Ser Thr Leu Leu Tyr Pro Leu
            35                  40                  45

Phe Asn Leu Trp Gly Pro Ala Phe His Glu Arg Tyr Pro Asn Val Thr
        50                  55                  60

Ile Thr Ala Gln Gly Thr Gly Ser Gly Ala Gly Ile Ala Gln Ala Ala
```

-continued

```
65                  70                  75                  80
Ala Gly Thr Val Asn Ile Gly Ala Ser Asp Ala Tyr Leu Ser Glu Gly
                85                  90                  95
Asp Met Ala Ala His Lys Gly Leu Met Asn Ile Ala Leu Ala Ile Ser
                100                 105                 110
Ala Gln Gln Val Asn Tyr Asn Leu Pro Gly Val Ser Glu His Leu Lys
                115                 120                 125
Leu Asn Gly Lys Val Leu Ala Ala Met Tyr Gln Gly Thr Ile Lys Thr
                130                 135                 140
Trp Asp Asp Pro Gln Ile Ala Ala Leu Asn Pro Gly Val Asn Leu Pro
145                 150                 155                 160
Gly Thr Ala Val Val Pro Leu His Arg Ser Asp Gly Ser Gly Asp Thr
                165                 170                 175
Phe Leu Phe Thr Gln Tyr Leu Ser Lys Gln Asp Pro Glu Gly Trp Gly
                180                 185                 190
Lys Ser Pro Gly Phe Gly Thr Thr Val Asp Phe Pro Ala Val Pro Gly
                195                 200                 205
Ala Leu Gly Glu Asn Gly Asn Gly Gly Met Val Thr Gly Cys Ala Glu
                210                 215                 220
Thr Pro Gly Cys Val Ala Tyr Ile Gly Ile Ser Phe Leu Asp Gln Ala
225                 230                 235                 240
Ser Gln Arg Gly Leu Gly Glu Ala Gln Leu Gly Asn Ser Ser Gly Asn
                245                 250                 255
Phe Leu Leu Pro Asp Ala Gln Ser Ile Gln Ala Ala Ala Gly Phe
                260                 265                 270
Ala Ser Lys Thr Pro Ala Asn Gln Ala Ile Ser Met Ile Asp Gly Pro
                275                 280                 285
Ala Pro Asp Gly Tyr Pro Ile Ile Asn Tyr Glu Tyr Ala Ile Val Asn
                290                 295                 300
Asn Arg Gln Lys Asp Ala Ala Thr Ala Gln Thr Leu Gln Ala Phe Leu
305                 310                 315                 320
His Trp Ala Ile Thr Asp Gly Asn Lys Ala Ser Phe Leu Asp Gln Val
                325                 330                 335
His Phe Gln Pro Leu Pro Pro Ala Val Val Lys Leu Ser Asp Ala Leu
                340                 345                 350
Ile Ala Thr Ile Ser Ser Gly Gly Ser Gly Gly Ser Gly Gly
                355                 360                 365
Gly Ser Gly Gly Ser Val Pro Thr Thr Ala Ala Ser Pro Pro Ser Thr
                370                 375                 380
Ala Ala Ala Pro Pro Ala Pro Ala Thr Pro Val Ala Pro Pro Pro
385                 390                 395                 400
Ala Ala Ala Asn Thr Pro Asn Ala Gln Pro Gly Asp Pro Asn Ala Ala
                405                 410                 415
Pro Pro Pro Ala Asp Pro Asn Ala Pro Pro Pro Val Ile Ala Pro
                420                 425                 430
Asn Ala Pro Gln Pro Val Arg Ile Asp Asn Pro Val Gly Gly Phe Ser
                435                 440                 445
Phe Ala Leu Pro Ala Gly Trp Val Glu Ser Asp Ala Ala His Phe Asp
                450                 455                 460
Tyr Gly Ser Ala Leu Leu Ser Lys Thr Thr Gly Asp Pro Pro Phe Pro
465                 470                 475                 480
Gly Gln Pro Pro Pro Val Ala Asn Asp Thr Arg Ile Val Leu Gly Arg
                485                 490                 495
```

-continued

```
Leu Asp Gln Lys Leu Tyr Ala Ser Ala Glu Ala Thr Asp Ser Lys Ala
            500                 505                 510

Ala Ala Arg Leu Gly Ser Asp Met Gly Glu Phe Tyr Met Pro Tyr Pro
            515                 520                 525

Gly Thr Arg Ile Asn Gln Glu Thr Val Ser Leu Asp Ala Asn Gly Val
        530                 535                 540

Ser Gly Ser Ala Ser Tyr Tyr Glu Val Lys Phe Ser Asp Pro Ser Lys
545                 550                 555                 560

Pro Asn Gly Gln Ile Trp Thr Gly Val Ile Gly Ser Pro Ala Ala Asn
                565                 570                 575

Ala Pro Asp Ala Gly Pro Pro Gln Arg Trp Phe Val Val Trp Leu Gly
            580                 585                 590

Thr Ala Asn Asn Pro Val Asp Lys Gly Ala Ala Lys Ala Leu Ala Glu
            595                 600                 605

Ser Ile Arg Pro Leu Val Ala Pro Pro Ala Pro Ala Pro
        610                 615                 620

Ala Glu Pro Ala Pro Ala Pro Ala Pro Ala Gly Glu Val Ala Pro Thr
625                 630                 635                 640

Pro Thr Thr Pro Thr Pro Gln Arg Thr Leu Pro Ala
                645                 650
```